(12) United States Patent
Mullick et al.

(10) Patent No.: US 10,912,792 B2
(45) Date of Patent: Feb. 9, 2021

(54) COMPOUNDS AND METHODS FOR MODULATING ANGIOTENSINOGEN EXPRESSION

(71) Applicant: Ionis Pharmaceuticals, Inc., Carlsbad, CA (US)

(72) Inventors: Adam Mullick, Carlsbad, CA (US); Mark J. Graham, San Clemente, CA (US); Punit P. Seth, Carlsbad, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/763,942

(22) PCT Filed: Oct. 7, 2016

(86) PCT No.: PCT/US2016/056068
§ 371 (c)(1),
(2) Date: Mar. 28, 2018

(87) PCT Pub. No.: WO2017/062816
PCT Pub. Date: Apr. 13, 2017

(65) Prior Publication Data
US 2019/0160090 A1   May 30, 2019

Related U.S. Application Data

(60) Provisional application No. 62/238,831, filed on Oct. 8, 2015.

(51) Int. Cl.
| | |
|---|---|
| *A61K 31/712* | (2006.01) |
| *A61K 31/7125* | (2006.01) |
| *C07H 21/00* | (2006.01) |
| *C12N 15/113* | (2010.01) |
| *C07H 21/02* | (2006.01) |
| *C07H 21/04* | (2006.01) |
| *A61P 9/12* | (2006.01) |

(52) U.S. Cl.
CPC .............. *A61K 31/712* (2013.01); *A61P 9/12* (2018.01); *C07H 21/00* (2013.01); *C07H 21/02* (2013.01); *C07H 21/04* (2013.01); *C12N 15/113* (2013.01)

(58) Field of Classification Search
None
See application file for complete search history.

(56) References Cited

U.S. PATENT DOCUMENTS

| 4,981,957 A | 1/1991 | Lableu et al. |
|---|---|---|
| 5,034,506 A | 7/1991 | Summerton et al. |
| 5,118,800 A | 6/1992 | Smith et al. |
| 5,166,315 A | 11/1992 | Summerton et al. |
| 5,185,444 A | 2/1993 | Summerton et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,466,786 A | 11/1995 | Buhr et al. |
| 5,514,785 A | 5/1996 | Van Ness et al. |
| 5,519,134 A | 5/1996 | Acevedo et al. |
| 5,567,811 A | 10/1996 | Misturn et al. |
| 5,576,427 A | 11/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,670,633 A | 9/1997 | Cook et al. |
| 5,698,685 A | 12/1997 | Summerton et al. |
| 5,700,920 A | 12/1997 | Altmann et al. |
| 5,792,847 A | 8/1998 | Buhr et al. |
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,670,461 B1 | 12/2003 | Wengel et al. |
| 6,770,748 B2 | 8/2004 | Imanishi et al. |

(Continued)

FOREIGN PATENT DOCUMENTS

| WO | WO 1997/33623 | 9/1997 |
|---|---|---|
| WO | WO 1998/39352 | 9/1998 |

(Continued)

OTHER PUBLICATIONS

Acelajado et al., "Refractory Hypertension: Definition, Prevalence, and Patient Characteristics." J. Clin. Hypertens (2012) 14(1):7-12.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals" Chimia. (1996) 50(4):168-176.

(Continued)

*Primary Examiner* — Tracy Vivlemore
(74) *Attorney, Agent, or Firm* — Knobbe, Martens, Olson & Bear, LLP

(57) ABSTRACT

Disclosed herein are compositions and compounds comprising modified oligonucleotides for modulating AGT and modulating a RAAS pathway related disease, disorder and/or condition in an individual in need thereof. A RAAS pathway related disease, disorder and/or condition in an individual such as hypertension can be treated, ameliorated, delayed or prevented with the administration of antisense compounds targeted to AGT.

11 Claims, No Drawings
Specification includes a Sequence Listing.

(56) References Cited

U.S. PATENT DOCUMENTS

| | | |
|---|---|---|
| 6,794,499 B2 | 9/2004 | Wengel et al. |
| 6,902,888 B1 | 6/2005 | McGrail et al. |
| 7,034,133 B2 | 4/2006 | Wengel et al. |
| 7,053,207 B2 | 5/2006 | Wengel |
| 7,374,884 B2 | 5/2008 | McGrail et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 2001/0053519 A1 | 12/2001 | Fodor et al. |
| 2003/0228597 A1 | 12/2003 | Cowsert et al. |
| 2004/0077611 A1 | 4/2004 | Alexander et al. |
| 2004/0171570 A1 | 9/2004 | Allerson et al. |
| 2005/0130923 A1 | 6/2005 | Bhat et al. |
| 2006/0063730 A1 | 3/2006 | Monia et al. |
| 2007/0031844 A1 | 2/2007 | Khvorova et al. |
| 2008/0039618 A1 | 2/2008 | Allerson et al. |
| 2008/0261231 A1 | 10/2008 | McGrail et al. |
| 2009/0012281 A1 | 1/2009 | Swayze et al. |
| 2009/0105177 A1 | 4/2009 | Monia et al. |
| 2010/0130595 A1 | 5/2010 | Dean et al. |
| 2015/0031130 A1 | 1/2015 | Bhat |
| 2017/0189541 A1* | 7/2017 | Foster .................. C12N 15/113 |
| 2018/0169129 A1* | 6/2018 | Hinkle ...................... A61P 9/12 |

FOREIGN PATENT DOCUMENTS

| | | |
|---|---|---|
| WO | WO 1999/014226 | 3/1999 |
| WO | WO 2000/071751 | 11/2000 |
| WO | WO 2001/049687 | 7/2001 |
| WO | WO 2003/004602 | 1/2003 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2011/041545 | 4/2011 |
| WO | WO 2012/007327 | 1/2012 |
| WO | WO 2014/018930 | 1/2014 |

OTHER PUBLICATIONS

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cowley et al., "Genetically defined risk of salt sensitivity in an intercross of Brown Norway and Dahl S rats" Physiol Genomics (2000) 2(3):107-115.

Crooke et al., "Basic Principles of Antisense Therapeutics" Antisense Research and Application (1998) Chapter 1:1-50.

Eide et al., "Low-renin status in therapy-resistant hypertension: a clue to efficient treatment" Journ of Hypertension (2004) 22: 2217-2226.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a novel bcl-2/bcl-xLbispecific antisense oligonucleotide against tumors of diverse histologic origins" J. Natl. Cancer Inst. (2001) 93:463-471.

Gu et al., "Base pairing properties of D- and L-cyclohexene nucleic acids (CeNA)" Oligonucleotides (2003) 13(6):479-489.

Gu et al., "Enzymatic resolution and base pairing properties of D- and L-cyclohexenyl nucleic acids (CeNA)" Nucleosides Nucleotides Nucleic Acids (2005) 24(5-7):993-998.

Gu et al., "Synthesis of enantiomeric-pure cyclohexenyl nucleoside building blocks for oligonucleotide synthesis" Tetrahedron (2004) 60(9):2111-2123.

Gyurko et al., "Antisense inhibition of AT1 receptor mRNA and angiotensinogen mRNA in the brain of spontaneously hypertensive rats reduces hypertension of neurogenic origin" Reg. Pep. (1993) 49:167-174.

Horvath et al., "Stereoselective synthesis of (−)-ara-cyclohexenyl-adenine" Tetrahedron Letters (2007) 48:3621-3623.

Jones et al., "RNA quantitation by fluorescence-based solution assay: RiboGreen reagent characterization" Anal. Biochem. (1998) 265(2):368-374.

Judd et al., "Apparent and true resistant hypertension: definition, prevalence and outcomes." J. Hum. Hypertens. (2014) 28(8):463-468.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Leumann et al., "DNA Analogues: From Supramolecular Principles to Biological Properties" Bioorganic & Medicinal Chemistry (2002) 10:841-854.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Maher et al. "Synthesis of Antisense Oligonucleotides Conjugated to a Multivalent Carbohydrate Cluster for Cellular Targeting" Bioconjugate Chemistry (2003) 14: 18-29.

Martin, "New acces to 2'-O-alkylated ribonucleosides and properties of 2'-O-alkylated oligoribonucleotides" Helv. Chim. Acta. (1995) 78:486-504.

Nauwelaerts et al., "Cyclohexenyl nucleic acids: conformationally flexible oligonucleotides" Nucleic Acids Res. (2005) 33(8):2452-2463.

Nauwelaerts et al., "Structural characterization and biological evaluation of small interfering RNAs containing cyclohexenyl nucleosides" J. Am. Chem. Soc. (2007) 129(30):9340-9348.

New England Biolabs 1998/99 Catalog (cover page and pp. 121 and 284).

Nguyen et al., "The biology of the (pro)renin receptor" J. Am. Soc. Nephrol. (2010) 21(1):18-23.

Nobakht et al., "Limitations of angiotensin inhibition" Nat. Rev. Nephrol. (2011) 7(6):356-359.

Okamoto et al., "Development of a strain of spontaneously hypertensive rats" Jpn. Circ. J. (1963) 27:282-293.

(56) References Cited

OTHER PUBLICATIONS

Orum et al., "Locked nucleic acids: A promising molecular family for gene-function analysis and antisense drug development" Curr. Opinion Mol. Ther. (2001) 3:239-243.
Paulis et al., "Key advances in antihypertensive treatment" Nat. Rev. Cardiol. (2012) 9(5):276-285.
Phillips et al., "Antisense inhibition of hypertension: A new strategy for renin-angiotensin candidate genes" Kidney International (1994) 46:1554-1556.
Pilla et al., "Resistant Hypertension: An Incurable Disease or Just a Challenge For Our Medical Skill?" High Blood Press Cardiovasc Pre. (2016) 23(4);347-353.
Raasch et al., "Combined blockade of AT1-receptors and ACE synergistically potentiates antihypertensive effects in SHR" Journal of Hypertension (2004) 22:611-618.
Rensen et al., "Design and Synthesis of Novel N-Acetylgalactosamine-Terminated Glycolipids for Targeting of Lipoproteins to the Hepatic Asiaglycoprotein Receptor" J. Med. Chem. (2004) 47: 5798-5808.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Sander et al., "Resistant hypertension: concepts and approach to management" Current Hypertension Reports (2011) 13: 347-355.
Sanghvi et al., "Heterocyclic Base Modifications in Nucleic Acids and Their Applications in Antisense Oligonucleotides" Antisense Research and Applications (1993) pp. 273-288.
Sarafidis et al., "Resistant hypertension—its identification and epidemiology." Nat. Rev. Nephrol. (2013) 9(1):51-58.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of biosequences" Adv. Appl. Math. (1981) 2(4):482-489.
Smith et al., "Epidemiology, Prognosis, and Treatment of Resistant Hypertension." Pharmacotherapy (2013) 33(10):1071-1086.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Tang et al., "Intravaneous angiotensingogen antisense in AAV-based vector decreases hypertension" American Jour of Physiology (1999) 277: H2392-H2399.
Tomita et al., "Effect of angiotensinogen on blood pressure regulation in normotensive rats: application of a loss of function approach" J. Hypertens. (1995) 13:1767-1774.
Tomita et al., "Transient decrease in high blood pressure by in vivo transfer of antisense oligodeoxynucleotides against rat angiotensinogen" Hypertension (1995) 26:131-136.
Van De Wal et al., "Determinants of increased angiotensin II levels in severe chronic heart failure patients despite ACE inhibition" International Journal of Cardiology (2006) 106: 367-372.
Verbeure et al., "RNase H mediated cleavage of RNA by cyclohexene nucleic acid (CeNA)" Nucleic Acids Res. (2001) 29(24):4941-4947.
Viera, Aj, "Resistant Hypertension." J. Am. Board Fam. Med. (2012) 25(4):487-495.
Wahlestedt et al., "Potent and nontoxic antisense oligonucleotide containing locked nucleic acids" Proc. Natl. Acad. Sci. USA (2000) 97: 5633-5638.
Wang et al., "A straightforward stereoselective synthesis of D- and L-5-hydroxy-4-hydroxymethyl-2-cyclohexenylguanine" J. Org. Chem. (2001) 66(25):8478-8482.
Wang et al., "Cyclohexene nucleic acids (CeNA) form stable duplexes with RNA and induce RNase H activity" Nucleosides Nucleotides Nucleic Acids (2001) 20(4-7):785-788.
Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.
Wang et al., "Stereocontrolled synthesis of ara-type cyclohexenyl nucleosides" J. Org. Chem. (2003) 68(11):4499-4505.
Wielbo et al., "Antisense inhibition of angiotensinogen in hepatoma cell culture is enhanced by cationic liposome delivery" Biochem. Biophys. Res. Commun. (1997) 232(3):794-799.
Wielbo et al., "Antisense inhibition of hypertension in the spontaneously hypertensive rat" Hypertension (1995) 25:314-319.
Wielbo et al., "Inhibition of hypertension by peripheral administration of antisense oligodeoxynucleotides" Hypertension (1996) 28:147-151.
Woolf et al., "Specificity of antisense oligonucleotides in vivo" Proc. Natl. Acad. Sci. (1992) 89(16):7305-7309.
Yoshitomi et al., "Effectiveness of the Direct Renin Inhibitor, Aliskiren, in Patients With Resistant Hypertension." Int Heart J. (2013) 54(2):88-92.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Serch Report for PCT/US2016/056068 dated Apr. 4, 2017.
International Search Report for PCT/US13/52399 dated Dec. 20, 2013.
European search report for 13823783.9 dated Feb. 12, 2016.
Makino et al., "Chronic antisense therapy for angiotensinogen on cardiac hypertrophy in spontaneously hypertensive rats" Cardiovasc Res (1999) 44: 543-548.
Schinke et al., "Permanent inhibition of angiotensinogen synthesis by antisense RNA expression" Hypertension (1996) 27: 508-513.
Extended European Search Report dated Jun. 19, 2020, issued in European Patent Application No. 19216534.8.

* cited by examiner

COMPOUNDS AND METHODS FOR MODULATING ANGIOTENSINOGEN EXPRESSION

SEQUENCE LISTING

The present application is being filed along with a Sequence Listing in electronic format. The Sequence Listing is provided as a file entitled BIOL0270USASEQ_ST25.txt created Mar. 27, 2018, which is 456 kb in size. The information in the electronic format of the sequence listing is incorporated herein by reference in its entirety.

FIELD OF THE INVENTION

The present invention provides compounds, compositions and methods for modulating angiotensinogen (AGT) expression for the purpose of modulating a RAAS pathway related disease, disorder or condition in an animal. The present invention also provides compounds, compositions and methods for reducing hypertension and organ damage by administering an AGT inhibitor to an animal

BACKGROUND OF THE INVENTION

Angiotensinogen (AGT), also known as SERPINA8 or ANHU, is a member of the serpin family and is a component of the renin-angiotensin-aldosterone system (RAAS). It is primarily produced in the liver and is released into the circulation where renin converts it into angiotensin I. Angiotensin I is subsequently converted into angiotensin II by angiotension converting enzyme (ACE). Angiotensin II is a peptide hormone which causes vasoconstriction which, in turn, can increase blood pressure. Angiotensin II also stimulates secretion of the hormone aldosterone from the adrenal cortex. Aldosterone causes the kidneys to increase reabsorption of sodium and water leading to an increase of the fluid volume in a body which, in turn, can increase blood pressure. Over stimulation or activity of the RAAS pathway can lead to high blood pressure. Chronic high blood pressure is known as hypertension. The high blood pressure in a hypertensive subject requires the heart to work harder to circulate blood through the blood vessels.

The World Health Organization (WHO) has identified hypertension as a leading cause of cardiovascular morbidity. Hypertension is a major risk factor for various disease, disorders and conditions such as shortened life expectancy, chronic kidney disease, stroke, myocardial infarction, heart failure, aneurysms of the blood vessels (e.g. aortic aneurysm), peripheral artery disease, heart damage (e.g., heart enlargement or hypertrophy) and other cardiovascular related diseases, disorders and/or conditions.

The prevelance of resistant hypertension (RHTN), hypertension resistant to drug treatment, has steadily increased in number likely due to an ageing population and an ever increasing incidence of obesity. The current projection of approximately 10 million RHTN adults in the United States is expected to continue to rise.

Anti-hypertensive drugs, renal denervation, baroreceptor activation therapy, diet changes and lifestyle changes may reduce hypertension and reduce the diseases, disorders and/or conditions associated with hypertension (Paulis et al., Nat Rev Cardiol, 2012, 9:276-285). However, there are limitations to the therapies currently approved for treating hypertension as a significant subset of all hypertensive patients do not achieve adequate blood pressure control. For example, drugs such as ACE inhibitors and angiotensin receptor blockers (ARBs) that target parts of the renin-angiotensin system (RAS) pathway are limited in their ability to inhibit the RAAS pathway (Nobakht et al., Nat Rev Nephrol, 2011, 7:356-359). Additionally, certain anti-hypertensive drugs such as ACE inhibitors are contra-indicated in hypertensive patients with renal disease due to their potential to compromise renal function in patients.

Accordingly, there is a need to find alternative treatments to inhibit the RAAS pathway and treat hypertension. Antisense technology is emerging as an effective means for reducing the expression of certain gene products. However, early antisense oligonucleotides targeting AGT provided limited benefit (WO 1997/33623) or targeted non-human AGT (WO 2014/018930). The compounds and compositions herein provide novel, highly potent and tolerable compounds to inhibit human AGT and are suitable for use in human subjects. Additionally, compounds disclosed herein, by using a conjugate strategy that delivers antisense compounds to the liver and limits their renal distribution and activity, are predicted to mitigate the tolerability issues of traditional RAS blockers in patients at risk for hyperkalemia and/or renal disease.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY OF THE INVENTION

Provided herein are compositions, compounds and methods for lowering the levels of AGT mRNA and/or protein in an animal.

Certain embodiments disclosed herein provide a compound comprising a modified oligonucleotide targeting a nucleic acid sequence encoding AGT. In certain embodiments, the compound targets an AGT sequence as shown in the nucleobase sequences of any of SEQ ID NOs: 1-6.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2250 to 2337 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2281 to 2300 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides and having a nucleobase sequence comprising at least 8 contiguous nucleobases of any of the nucleobase sequences of SEQ ID NOs: 46, 53-54, 61, 68, 76, 83, 85, 93, 96-97, 109, 127, 129-130, 132, 134-15, 137-39, 142, 163-172, 180-184, 186, 189, 234, 236, 238-239, 267, 313, 411, 452, 463-470, 475-478, 480, 500-503, 512, 517-518, 524-526, 654, 689, 702, 725-726, 728, 738, 779, 786-787, 800, 808, 810-811, 825, 865, 868, 889, 894, 903, 905, 909, 954, 966, 1011, 1015, 1021, 1024, 1080, 1085, 1258-1259, 1261-1262, 1293-1294, 1299, 1325, 1470, 1472-1473, 1522, 1542, 1604, 1623-1624, 1667, 1670, 1682-1683, 1687, 1700, 1703-1704, 1708, 1714, 1716, 1719-1720, 1724-1726, 1729-1730, 1827, 1936, 1843-1844, 1846, 1886, 1893-1894, 1914, 1923, 1925, 1932, 1979, 1986, 1988, 1990, 2003, 2015, 2018, 2020, 2027-2028, 2035, 2037, 2039, 2044.

Certain embodiments disclosed herein provide a compound comprising a modified oligonucleotide according to the following formula: mCes Aes mCes Aes Aes Ads mCds Ads Ads Gds mCds Tds Gds Gds Tds mCes Ges Ges Tes Te (SEQ ID NO: 1914); wherein, A is an adenine, mC is a 5'-methylcytosine, G is a guanine, T is a thymine, e is a 2'-O-methoxyethyl modified nucleoside, d is a 2'-deoxynucleoside, and s is a phosphorothioate internucleoside linkage. In certain embodiments, the modified oligonucleotide further comprises a GalNAc conjugate. In certain embodiments, the conjugate is a 5'-Trishexylamino-(THA)-C6 GalNAc₃ conjugate. In certain embodiments, the modified oligonucleotide is linked to the 5'-Trishexylamino-(THA)-C6 GalNAc₃ conjugate by a cleavable moiety. In certain embodiments, the cleavable moiety is a phosphate group.

Certain embodiments disclosed herein provide a compound comprising a modified oligonucleotide with the following formula:

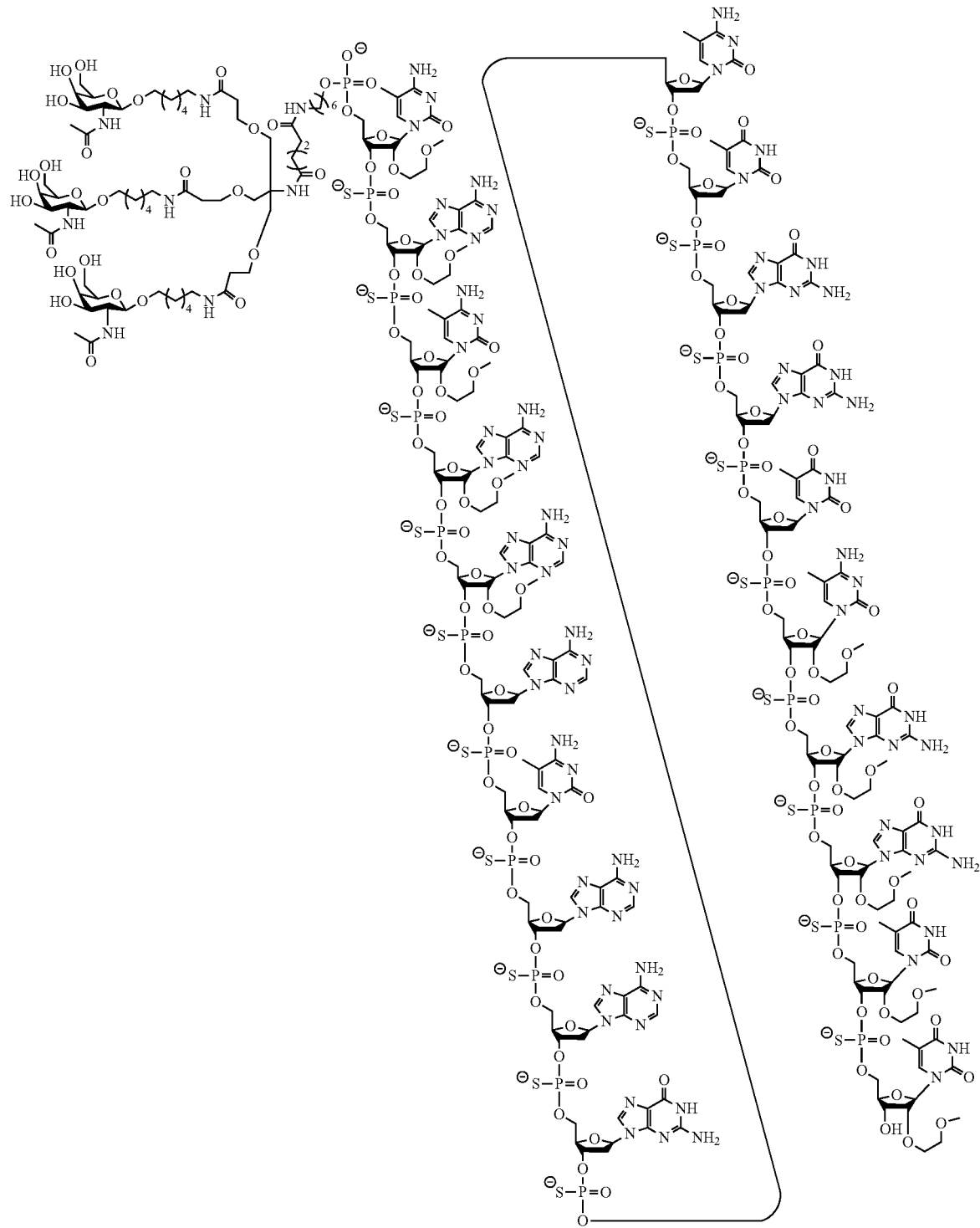

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"About" means within +10% of a value. For example, if it is stated, "a marker may be increased by about 50%", it is implied that the marker may be increased between 45%-55%.

"ACE escape", also known as angiotensin II reactivation, refers to the inability of currently available ACE inhibitor treatment to reliably suppress plasma angiotensin II levels. The increase in plasma angiotensin II levels during ACE inhibition occurs via other enzymes converting angiotensin I to angiotensin. This incomplete blockage of angiotensin II levels prevents the ACE inhibitors from effectively treating some hypertensive subjects. Angiotensin Receptor Blockers (ARBs) may also be susceptible to ACE escape as other receptors besides the AT1 receptor engage angiotensin metabolites.

"Active pharmaceutical agent" or "Pharmaceutical agent" means the substance or substances in a pharmaceutical composition that provide a therapeutic benefit when administered to an individual. For example, in certain embodiments, an antisense oligonucleotide targeted to AGT is an active pharmaceutical agent.

"Active target region" or "target region" means a region to which one or more active antisense compounds is targeted.

"Active antisense compounds" means antisense compounds that reduce target nucleic acid levels or protein levels.

"Administered concomitantly" refers to the co-administration of two agents in any manner in which the pharmacological effects of both are manifest in the patient time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Aldosterone escape" or "aldosterone breakthrough" refers to the inability of currently available ACE inhibitor Angiotensin Receptor Blocker (ARB) and/or Direct Renin Inhibitor (DRI) treatment to reliably suppress aldosterone release in some treated subjects. This incomplete blockage of aldosterone prevents the ACE inhibitors, DRIs and ARBs from effectively treating some hypertensive subjects.

"Agent" means an active substance that can provide a therapeutic benefit when administered to an animal. "First Agent" means a therapeutic compound provided herein. For example, a first agent is an antisense oligonucleotide targeting AGT. "Second agent" means a second therapeutic compound described herein. For example, a second agent can be a second antisense oligonucleotide targeting AGT or a non-AGT target. Alternatively, a second agent can be a compound other than an antisense oligonucleotide.

"Amelioration" or "ameliorate" refers to a lessening of at least one indicator, marker, sign, or symptom of an associated disease, disorder and/or condition. In certain embodiments, amelioration includes a delay or slowing in the progression of one or more indicators of a condition, disorder and/or disease. The severity of indicators may be determined by subjective or objective measures, which are known to those skilled in the art.

"Angiotensinogen" and "AGT" is used interchangeably herein. Angiotensinogen is also known as SERPINA8 and ANHU.

"Angiotensinogen nucleic acid" or "AGT nucleic acid" means any nucleic acid encoding AGT. For example, in certain embodiments, an AGT nucleic acid includes a DNA sequence encoding AGT, an RNA sequence transcribed from DNA encoding AGT (including genomic DNA comprising introns and exons), and an mRNA sequence encoding AGT. "AGT mRNA" means an mRNA encoding an AGT protein.

"AGT specific inhibitor" refers to any agent capable of specifically inhibiting the expression of AGT mRNA and/or AGT protein. For example, AGT specific inhibitors include nucleic acids (including antisense compounds such as RNasH, siRNA and blockmer antisense compounds), peptides, antibodies, small molecules, and other agents capable of specifically inhibiting the expression of AGT mRNA and/or AGT protein. In certain embodiments, by specifically modulating AGT mRNA level and/or AGT protein expression, AGT specific inhibitors can affect components of the renin-angiotensin-aldosterone system (RAAS) pathway. In certain embodiments, by specifically modulating AGT mRNA level and/or AGT protein expression, AGT specific inhibitors can affect RAAS pathway related diseases, disorders and/or conditions such as blood pressure. Similarly, in certain embodiments, AGT specific inhibitors can affect other molecular processes in an animal.

"Animal" refers to a human or non-human animal, including, but not limited to, mice, rats, rabbits, dogs, cats, pigs, and non-human primates, including, but not limited to, monkeys and chimpanzees.

"Anti-hypertensive drug" refers to a drug capable of lowering blood pressure. Examples of such drugs include, but are not limited to, RAAS inhibitors, diuretics, calcium channel blockers, adrenergic receptor antagonists, adrenergic agonists and vasodilators. In one example, the anti-hypertensive drug captopril can be used in combination with the AGT compound described herein to treat an animal having or at risk of having a RAAS pathway related disease, disorder and/or condition.

"Anti-hypertensive procedure" refers to a medical procedure performed on a subject to reduce hypertension. Examples of such procedures include renal denervation and baroreceptor activation therapy.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Blood pressure" refers to the pressure of the blood in the circulatory system against the walls of the blood vessel. The blood pressure is due mainly to the beating of the heart in an animal. During each heartbeat, the blood pressure varies between a maximum (systolic) blood pressure (SBP) and minimum (diastolic) blood pressure (DBP). The mean arterial pressure (MAP) is the average arterial pressure during a heartbeat cycle. Blood pressure can be measure by a blood pressure meter (i.e., a sphygmomanometer). Normal blood pressure at rest is within the range of 100-140 mmHg systolic and 60-90 mmHg diastolic and is commonly expressed as the systolic pressure (top reading)/diastolic pressure (bottom reading) mmHg.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses concomitant, parallel or sequential administration.

"Complementarity" means the capacity for pairing between nucleobases of a first nucleic acid and a second nucleic acid. In certain embodiments, the first nucleic acid is an antisense compound and the second nucleic acid is a target nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diluent" means an ingredient in a composition that lacks pharmacological activity, but is pharmaceutically necessary or desirable. For example, the diluent in an injected composition may be a liquid, e.g. phosphate buffered saline (PBS) or water.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors. In an example, an effective amount of an AGT antisense oligonucleotide decreases blood pressure and/or ameliorates organ damage due to hypertension.

"Fully complementary" or "100% complementary" means that each nucleobase of a nucleobase sequence of a first nucleic acid has a complementary nucleobase in a second nucleobase sequence of a second nucleic acid. In certain embodiments, the first nucleic acid is an antisense compound and the second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxynucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Hypertension" or "HTN" refers to a chronic medical condition where the blood pressure in an animal is elevated. The elevated blood pressure requires the heart to work harder to circulate blood through the blood vessels. High blood pressure is said to be present if it is persistently at or above 140/90 mmHg. Hypertension is classified as primary (essential) or secondary. Primary hypertension has no clear cause and is thought to be linked to genetics, diet, lack of exercise and obesity. Secondary hypertension is caused by another medical condition. Hypertension is a major risk factor for shortened life expectancy, chronic kidney disease, stroke, myocardial infarction, heart failure, aneurysms of the blood vessels (e.g. aortic aneurysm), peripheral artery disease, organ damage (e.g., heart enlargement or hypertrophy) and other cardiovascular diseases, disorders and/or conditions or symptoms thereof. Anti-hypertensive drugs, diet changes and lifestyle changes may reduce hypertension and reduce the diseases, disorders and/or conditions associated with hypertension. Hypertension can be nonresistant to drug intervention (i.e., controllable by commercially available drug therapies) or resistant to drug intervention.

"Identifying an animal having, or at risk for, a RAAS related disease, disorder and/or condition" means identifying an animal having been diagnosed with a RAAS related disease, disorder and/or condition or identifying an animal predisposed to develop a RAAS related disease, disorder and/or condition. Individuals predisposed to develop a RAAS related disease, disorder and/or condition include, for example, individuals with a familial history a RAAS related disease such as hypertension. Such identification may be accomplished by any method including evaluating an individual's medical history and standard clinical tests or assessments.

"Immediately adjacent" means that there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Internucleoside linkage" refers to the chemical bond between nucleosides.

"Intravenous administration" means administration into a vein.

"Linked nucleosides" means adjacent nucleosides which are bonded together.

"Marker" or "biomarker" is any measurable and quantifiable biological parameter that serves as an index for health- or physiology-related assessments. For example, an increase in blood pressure, or a decrease in organ damage (e.g., fibrosis) can be considered markers of an RAAS related disease, disorder and/or condition.

"Mismatch" or "non-complementary nucleobase" or "MM" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. For example, a modified nucleobase can be 5'-methylcytosine. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising a modified internucleoside linkage, a modified sugar, and/or a modified nucleobase.

"Modified sugar" refers to a substitution or change from a natural sugar. For example, a modified sugar can be 2'-MOE.

"Modulating" refers to changing or adjusting a feature in a cell, tissue, organ or organism. For example, modulating AGT mRNA can mean to increase or decrease the level of AGT mRNA and/or AGT protein in a cell, tissue, organ or organism. Modulating AGT mRNA and/or protein can lead to an increase or decrease in a RAAS related disease, disorder and/or condition in a cell, tissue, organ or organism. A "modulator" effects the change in the cell, tissue, organ or organism. For example, an AGT antisense compound can be a modulator that increases or decreases the amount of AGT mRNA and/or AGT protein in a cell, tissue, organ or organism.

"Monomer" refers to a single unit of an oligomer. Monomers include, but are not limited to, nucleosides and nucleotides, whether naturally occurring or modified.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nonresistant hypertension", "nonrefractory hypertension" or "controlled hypertension" is defined as hypertension that responds to treatment resulting in, for example, blood pressure<140 mmHg SBP or <90 mmHg DBP with concurrent use of up to 3 anti-hypertensive agents.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound; such as, for example, nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound; such as, for example, peptide nucleic acids or morpholinos (morpholinos linked by —N(H)—C(=O)—O— or other non-phosphodiester linkage).

"Organ damage" or "end organ damage" refers to damage occurring in major organs fed by the circulatory system such as the heart (e.g., heart muscle hypertrophy, reduced heart function and/or heart failure), kidney (e.g., albuminurea, proteinurea, reduced renal function and/or renal failure), eyes (e.g., hypertensive retinopathy), brain (e.g., stroke) and the like. The organs can be damaged by hypertension in an animal. In certain embodiments, the heart damage is fibrosis, heart cell and/or muscle hypertrophy leading to heart enlargement.

"Oligomeric compound" or "oligomer" refers to a polymeric structure comprising two or more sub-structures (monomers) and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intra-arterial administration, intraperitoneal administration, or intracranial administration, e.g., intrathecal or intracerebroventricular administration. Administration can be continuous, or chronic, or short or intermittent.

"Peptide" refers to a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable carrier" means a medium or diluent that does not interfere with the structure of the oligonucleotide. Certain of such carriers enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution, such as sterile water or PBS.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset, development, or progression of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Renin-angiotensin-aldosterone system", "Renin-angiotensin-aldosterone system pathway", "RAAS pathway" or "RAAS" refer to a multi-component enzymatic pathway where a precursor component (angiotensinogen) is converted by various enzymes such as renin and enzyme angiotensin-converting-enzyme (ACE) into downstream components such as angiotensin I and angiotensin II. Angiotensin I stimulates secretion of the steroid aldosterone in the pathway. The RAAS pathway regulates blood pressure and fluid balance in a body.

"Renin-angiotensin System", or "RAS" or "RAS pathway" refer to a portion of the RAAS pathway. Various components of this pathway have been targeted by agonists or antagonists to block the production of the components. For example renin inhibitors, ACE inhibitors, angiotensin-receptor blockers (ARBs) and the like have been developed to inhibit or block the RAS pathway. However, commercially available therapies targeting various RAS pathway components have been ineffective in completely inhibiting or blocking the RAS pathway due to various mechanisms (Nobakht et al., Nat Rev Nephrol, 2011, 7:356-359).

"RAAS related disease, disorder and/or condition" or "RAAS pathway related disease, disorder and/or condition" refers to any disease, disorder or condition related to RAAS in an animal. Examples of RAAS related diseases, disorders and/or conditions include shortened life expectancy, hypertension (e.g. nonresistant hypertension, resistant hypertension), kidney disease (e.g., chronic kidney disease, polycystic kidney disease), stroke, heart disease (e.g., myocardial infarction, heart failure, valvular heart disease), aneurysms of the blood vessels (e.g. aortic aneurysm), peripheral artery disease, organ damage (e.g., heart damage or hypertrophy), tissue fibrosis and other cardiovascular diseases, disorders and/or conditions or symptoms thereof. In certain embodiments, RAAS related disease, disorder and/or condition does not include hypertension.

"Resistant hypertension" or "RHTN" is defined as (1) blood pressure≥140 mmHg SBP or ≥90 mmHg DBP despite concurrent use of 3 anti-hypertensive agents from different drug classes or (2) use of ≥4 anti-hypertensive drugs regardless of blood pressure.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, e.g., under physiological conditions in the case of in vivo assays and therapeutic treatments. In an example, an antisense compound is specifically hybridizable to a target when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an animal.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleotide) or a DNA nucleotide (i.e. β-D-deoxyribonucleotide).

CERTAIN EMBODIMENTS

Certain embodiments provide compounds specifically modulating AGT. In certain embodiments, the AGT specific modulators are AGT specific inhibitors, for use in treating, preventing, or ameliorating a RAAS related disease, disorder and/or condition. In certain embodiments, AGT specific inhibitors are nucleic acid compounds capable of inhibiting the expression of AGT mRNA and/or AGT protein. In certain embodiments, the nucleic acid compounds are oligomeric compounds. In certain embodiments, the oligomeric compounds are antisense oligonucleotides. In certain embodiments, the antisense oligonucleotides are modified antisense oligonucleotides. In certain embodiments, the modified antisense oligonucleotides are chimeric antisense oligonucleotides.

In certain embodiments, the compounds target an AGT nucleic acid. In certain embodiments, the AGT nucleic acid is any of the human sequences set forth in GENBANK Accession No. NM_000029.3 (incorporated herein as SEQ ID NO: 1), the complement of the nucleotides 24354000 to 24370100 of GENBANK Accession No. NT_167186.1 (incorporated herein as SEQ ID NO: 2), GENBANK Accession No. AK307978.1 (incorporated herein as SEQ ID NO: 3), GENBANK Accession No. AK303755.1 (incorporated herein as SEQ ID NO: 4), GENBANK Accession No. AK293507.1 (incorporated herein as SEQ ID NO: 5), and GENBANK Accession No. CR606672.1 (incorporated herein as SEQ ID NO: 6).

Certain embodiments disclosed herein provide a compound comprising a modified oligonucleotide targeting a nucleic acid sequence encoding AGT. In certain embodiments, the compound targets an AGT sequence as shown in the nucleobase sequences of any of SEQ ID NOs: 1-6.

Certain embodiments disclosed herein provide a compound comprising a modified oligonucleotide consisting of 12 to 30 linked nucleosides having a nucleobase sequence comprising at least 8, least 9, least 10, least 11, at least 12, least 13, at least 14, at least 15, at least 16, least 17, least 18, least 19, or 20 contiguous nucleobases complementary to an equal length portion of SEQ ID NOs: 1-6.

In certain embodiments, the nucleobase sequence of the modified oligonucleotide is at least 70%, at least 75%, at least 80%, at least 85%, at least 90%, at least 95%, at least 96%, at least 97%, at least 98%, or at least 99% complementary to an equal length portion of any of SEQ ID NOs: 1-6. In certain embodiments, the modified oligonucleotide comprises a nucleobase sequence 100% complementary to an equal length portion of any of SEQ ID NOs: 1-6.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2027-2068 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 2027 to 2068 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2250 to 2337 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 2250 to 2337 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2266 to 2337 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 2266 to 2337 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2281 to 2300 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 2281 to 2300 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8 contiguous nucleobases complementary to an equal length portion of nucleobases 2324 to 2346 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 2324 to 2346 of SEQ ID NO: 1, wherein the nucleobase sequence of the modified oligonucleotide is at least 80% complementary to SEQ ID NO: 1.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14-2051.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 40, 42, 46, 47, 49, 53 to 55, 61, 62, 68, 71, 76, 82, 84, 85, 89, 93, 96 to 98, 102, 109, 114, 119, 127, 129, 130 to 135, 137 to 140, 142, 143, 160, 162 to 207, 209, 210, 223, 225 to 227, 230 to 243, 252 to 254, 257, 258, 262 to 273, 276, 278, 279, 281, 284, 452, 463, 464, 466, 467, 470, 477, 480, 500, 502, 512, 517, 525, 526, 726, 728, 868, 905, 906, 954, 961, 962, 963, 965, 966, 971, 973, 986, 987, 989, 990, 991, 994, 997, 998, 1000, 1001, 1011, 1015, 1021, 1024, 1035, 1080, 1085, 1150, 1258, 1259 to 1262, 1293, 1294, 1299, 1325, 1326, 1354, 1355 to 1357, 1370, 1384, 1391, 1393 to 1395, 1406 to 1408, 1431, 1467, 1468, 1470, 1472 to 1474, 1476, 1488, 1489, 1500, 1503, 1504, 1522, 1524, 1526, 1528, 1535, 1536, 1539, 1542, 1543, 1545, 1585, 1592, 1594, 1595, 1599, 1604, 1610 to 1612, 1615, 1618, 1619 to 1624, 1626, 1628, 1629, 1631, 1632, 1635 to 1637, 1640, 1658, 1662, 1665 to 1671, 1673, 1676 to 1679, 1681 to 1683, 1686, 1687, 1699 to 1710, 1712, 1714 to 1721, 1724 to 1726, 1728 to 1731, 1735, 1736, 1739 to 1741, 1751, 1755, 1771, 1778, 1781 to 1783, 1827, 1834, 1836, 1843 to 1846, 1872, 1874, 1875 to 1888, 1890 to 1895, 1897, 1898, 1900, 1904 to 1927, 1931 to 1933, 1937, 1939, 1940, 1943, 1950, 1951, 1953, 1955 to 1959, 1962, 1964 to 1967, 1969 to 1971, 1973, 1977 to 1981, 1984 to 1991, 1993 to 1996, 2000 to 2005, 2007 to 2012, 2014 to 2025, 2027, 2028, 2030, 2032 to 2037, 2039-2045, 2047, 2051.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 46, 53, 54, 68, 76, 85, 96, 97, 114, 127, 129 to 132, 134, 135, 137 to 139, 142, 162 to 207, 225, 226, 230 to 243, 252, 264, 266 to 270, 284, 464, 467, 962, 963, 965, 966, 973, 990, 991, 997, 1000, 1001, 1011, 1261, 1299, 1355, 1356, 1470, 1472, 1473, 1503, 1504, 1522, 1526, 1535, 1536, 1542, 1543, 1545, 1595, 1599, 1604, 1620, 1623, 1624, 1626, 1640, 1662, 1666, 1667, 1669, 1670, 1673, 1682, 1683, 1687, 1699 to 1706, 1708, 1712, 1714 to 1716, 1719 to 1721, 1724 to 1726, 1729, 1730, 1736, 1778, 1783, 1836, 1843, 1875 to 1888, 1893 to 1895, 1897, 1900, 1904 to 1908, 1911, 1914 to 1918, 1920, 1922, 1923, 1925, 1926, 1931 to 1933, 1937, 1939, 1955, 1958, 1959, 1962, 1966, 1967, 1970, 1971, 1973, 1977, 1978 to 1981, 1985, 1986, 1987, 1988, 1990, 1991, 1994, 1996, 2000, 2002 to 2005, 2010, 2011, 2014 to 2025, 2027, 2028, 2035 to 2037, 2039, 2041 to 2045.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 96, 127, 129 to 132, 139, 162 to 169, 171 to 189, 191 to 193, 195, 196, 198 to 206, 234, 236, 238 to 240, 267 to 270, 966, 1000, 1522, 1542, 1623, 1624, 1667, 1682, 1683, 1700, 1703, 1704, 1708, 1714, 1719, 1720, 1724 to 1726, 1729, 1875, 1876, 1878, 1884 to 1886, 1893, 1894, 1906, 1908, 1914, 1917, 1918, 1922, 1923, 1925, 1926, 1932, 1933, 1967, 1970, 1978 to 1981, 1985, 1986, 1988, 1990, 1991, 2003, 2010, 2015, 2016, 2018, 2020, 2021, 2024, 2025, 2027, 2028, 2035, 2037, 2039, 2044.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 129, 130, 132, 163 to 168, 171, 172, 175 to 186, 188, 189, 192, 193, 195, 198 to 206, 238, 239, 966, 1703, 1720, 1726, 1923, 1925, 2003, 2015.

Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 46, 53-54, 61, 68, 76, 83, 85, 93, 96-97, 109, 127, 129-130, 132, 134-15, 137-39, 142, 163-172, 180-184, 186, 189, 234, 236, 238-239, 267, 313, 411, 452, 463-470, 475-478, 480, 500-503, 512, 517-518, 524-526, 654, 689, 702, 725-726, 728, 738, 779, 786-787, 800, 808, 810-811, 825, 865, 868, 889, 894, 903, 905, 909, 954, 966, 1011, 1015, 1021, 1024, 1080, 1085, 1258-1259, 1261-1262, 1293-1294, 1299, 1325, 1470, 1472-1473, 1522, 1542, 1604, 1623-1624, 1667, 1670, 1682-1683, 1687, 1700, 1703-1704, 1708, 1714, 1716, 1719-1720, 1724-1726, 1729-1730, 1827, 1936, 1843-1844, 1846, 1886, 1893-1894, 1914, 1923, 1925, 1932, 1979, 1986, 1988, 1990, 2003, 2015, 2018, 2020, 2027-2028, 2035, 2037, 2039, 2044. Certain embodiments disclosed herein provide a compound comprising a modified oligonucleotide consisting of 12 to 30 linked nucleosides having a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 238, 1714, 1719, 1893-1894, 1914, 1923, 1925, 2003.

In certain embodiments, the compound comprises a modified oligonucleotide consisting of 8 to 80, 20 to 80, 10 to 50, 20 to 35, 10 to 30, 12 to 30, 15 to 30, 16 to 30, 20 to 30, 20 to 29, 20 to 28, 20 to 27, 20 to 26, 20 to 25, 20 to 24, 20 to 23, 20 to 22, 20 to 21, 15 to 25, 16 to 25, 15 to 24, 16 to 24, 17 to 24, 18 to 24, 19 to 24, 19 to 22, 16 to 21, 18 to 21 or 16 to 20 linked nucleobases. In certain embodiments, the compound comprises a modified oligonucleotide consisting of 16 linked nucleosides. In certain embodiments, the compound comprises a modified oligonucleotide consisting of 20 linked nucleosides.

In certain embodiments, the compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the modified oligonucleotide is single-stranded.

In certain embodiments, the modified oligonucleotide comprises at least one modified internucleoside linkage. In certain embodiments, the modified internucleoside linkage is a phosphorothioate internucleoside linkage. In certain embodiments, at least one modified internucleoside linkage is a phosphorothioate internucleoside linkage. In certain embodiments, each modified internucleoside linkage is a phosphorothioate internucleoside linkage.

In certain embodiments, the modified oligonucleotide comprises at least one nucleoside comprising a modified sugar. In certain embodiments, at least one modified sugar comprises a bicyclic sugar. In certain embodiments, at least one modified sugar comprises a 2'-O-methoxyethyl, a constrained ethyl, a 3'-fluoro-HNA or a 4'-$(CH_2)_n$—O-2' bridge, wherein n is 1 or 2.

In certain embodiments, the modified oligonucleotide comprises at least one nucleoside comprising a modified nucleobase. In certain embodiments, the modified nucleobase is a 5-methylcytosine.

In certain embodiments, the modified oligonucleotide comprises a conjugate group. In certain embodiments, the conjugate is a carbohydrate moiety. In certain embodiments, the conjugate is a GalNAc moiety. In certain embodiments, the GalNAc is 5'-Trishexylamino-(THA)-C6 $GalNAc_3$. In certain embodiments, the 5'-Trishexylamino-(THA)-C6 $GalNAc_3$ conjugate has the formula

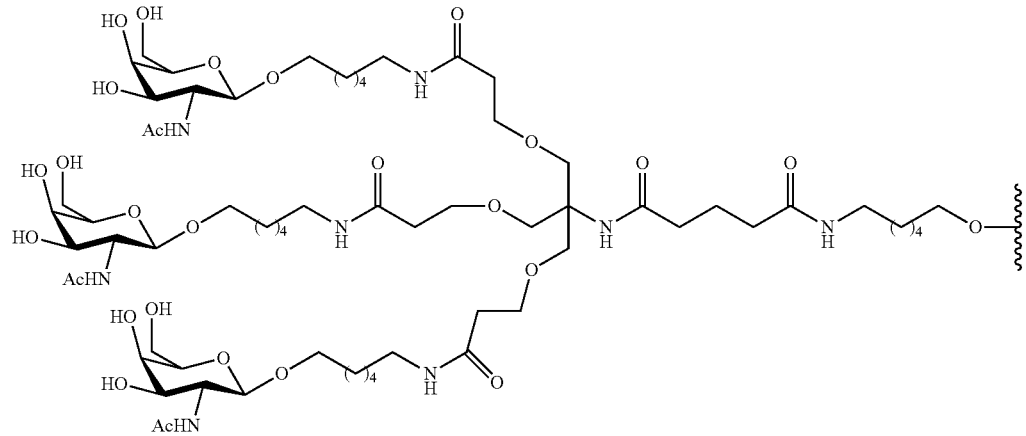

In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprises a modified oligonucleotide consisting of 12 to 30 linked nucleosides and targeted to or complementary to an equal length portion of region 2250 to 2337 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprises a modified oligonucleotide consisting of 12 to 30 linked nucleosides and targeted to or complementary to an equal length portion of region 2266 to 2337 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprises a modified oligonucleotide consisting of 12 to 30 linked nucleosides and targeted to or complementary to an equal length portion of region 2281 to 2300 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprises a modified oligonucleotide consisting of 20 linked nucleosides and targeted to or complementary to an equal length portion of region 2027 to 2068 of SEQ ID NO: 1, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 14-2051, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group. In certain embodiments, the compound comprising a modified oligonucleotide consisting of 16 to 20 linked nucleosides and having a nucleobase sequence comprising at least 8 contiguous nucleobases of SEQ ID NOs: 40, 42, 46, 47, 49, 53 to 55, 61, 62, 68, 71, 76, 82, 84, 85, 89, 93, 96 to 98, 102, 109, 114, 119, 127, 129, 130 to 135, 137 to 140, 142, 143, 160, 162 to 207, 209, 210, 223, 225 to 227, 230 to 243, 252 to 254, 257, 258, 262 to 273, 276, 278, 279, 281, 284, 452, 463, 464, 466, 467, 470, 477, 480, 500, 502, 512, 517, 525, 526, 726, 728, 868, 905, 906, 954, 961, 962, 963, 965, 966, 971, 973, 986, 987, 989, 990, 991, 994, 997, 998, 1000, 1001, 1011, 1015, 1021, 1024, 1035, 1080, 1085, 1150, 1258, 1259 to 1262, 1293, 1294, 1299, 1325, 1326, 1354, 1355 to 1357, 1370, 1384, 1391, 1393 to 1395, 1406 to 1408, 1431, 1467, 1468, 1470, 1472 to 1474, 1476, 1488, 1489, 1500, 1503, 1504, 1522, 1524, 1526, 1528, 1535, 1536, 1539, 1542, 1543, 1545, 1585, 1592, 1594, 1595, 1599, 1604, 1610 to 1612, 1615, 1618, 1619 to 1624, 1626, 1628, 1629, 1631, 1632, 1635 to 1637, 1640, 1658, 1662, 1665 to 1671, 1673, 1676 to 1679, 1681 to 1683, 1686, 1687, 1699 to 1710, 1712, 1714 to 1721, 1724 to 1726, 1728 to 1731, 1735, 1736, 1739 to 1741, 1751, 1755, 1771, 1778, 1781 to 1783, 1827, 1834, 1836, 1843 to 1846, 1872, 1874, 1875 to 1888, 1890 to 1895, 1897, 1898, 1900, 1904 to 1927, 1931 to 1933, 1937, 1939, 1940, 1943, 1950, 1951, 1953, 1955 to 1959, 1962, 1964 to 1967, 1969 to 1971, 1973, 1977 to 1981, 1984 to 1991, 1993 to 1996, 2000 to 2005, 2007 to 2012, 2014 to 2025, 2027, 2028, 2030, 2032 to 2037, 2039-2045, 2047, 2051, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 46, 53, 54, 68, 76, 85, 96, 97, 114, 127, 129 to 132, 134, 135, 137 to 139, 142, 162 to 207, 225, 226, 230 to 243, 252, 264, 266 to 270, 284, 464, 467, 962, 963, 965, 966, 973, 990, 991, 997, 1000, 1001, 1011, 1261, 1299, 1355, 1356, 1470, 1472, 1473, 1503, 1504, 1522, 1526, 1535, 1536, 1542, 1543, 1545, 1595, 1599, 1604, 1620, 1623, 1624, 1626, 1640, 1662, 1666, 1667, 1669, 1670, 1673, 1682, 1683, 1687, 1699 to 1706, 1708, 1712, 1714 to 1716, 1719 to 1721, 1724 to 1726, 1729, 1730, 1736, 1778, 1783, 1836, 1843, 1875 to 1888, 1893 to 1895, 1897, 1900, 1904 to 1908, 1911, 1914 to 1918, 1920, 1922, 1923, 1925, 1926, 1931 to 1933, 1937, 1939, 1955, 1958, 1959, 1962, 1966, 1967, 1970, 1971, 1973, 1977, 1978 to 1981, 1985, 1986, 1987, 1988, 1990, 1991, 1994, 1996, 2000, 2002 to 2005, 2010, 2011, 2014 to 2025, 2027, 2028, 2035 to 2037, 2039, 2041 to 2045, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 96, 127, 129 to 132, 139, 162 to 169, 171 to 189, 191 to 193, 195, 196, 198 to 206, 234, 236, 238 to 240, 267 to 270, 966, 1000, 1522, 1542, 1623, 1624, 1667, 1682, 1683, 1700, 1703, 1704, 1708, 1714, 1719, 1720, 1724 to 1726, 1729, 1875, 1876, 1878, 1884 to 1886, 1893, 1894, 1906, 1908, 1914, 1917, 1918, 1922, 1923, 1925, 1926, 1932, 1933, 1967, 1970, 1978 to 1981, 1985, 1986, 1988, 1990, 1991, 2003, 2010, 2015, 2016, 2018, 2020, 2021, 2024, 2025, 2027, 2028, 2035, 2037, 2039, 2044, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 129, 130, 132, 163 to 168, 171, 172, 175 to 186, 188, 189, 192, 193, 195, 198 to 206, 238, 239, 966, 1703, 1720, 1726, 1923, 1925, 2003, 2015, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 46, 53-54, 61, 68, 76, 83, 85, 93, 96-97, 109, 127, 129-130, 132, 134-15, 137-39, 142, 163-172, 180-184, 186, 189, 234, 236, 238-239, 267, 313, 411, 452, 463-470, 475-478, 480, 500-503, 512, 517-518, 524-526, 654, 689, 702, 725-726, 728, 738, 779, 786-787, 800, 808, 810-811, 825, 865, 868, 889, 894, 903, 905, 909, 954, 966, 1011, 1015, 1021, 1024, 1080, 1085, 1258-1259, 1261-1262, 1293-1294, 1299, 1325, 1470, 1472-1473, 1522, 1542, 1604, 1623-1624, 1667, 1670, 1682-1683, 1687, 1700, 1703-1704, 1708, 1714, 1716, 1719-1720, 1724-1726, 1729-1730, 1827, 1936, 1843-1844, 1846, 1886, 1893-1894, 1914, 1923, 1925, 1932, 1979, 1986, 1988, 1990, 2003, 2015, 2018, 2020, 2027-2028, 2035, 2037, 2039, 2044, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 16 to 20 linked nucleosides and having a nucleobase sequence comprising at least 8 contiguous nucleobases of SEQ ID NOs: 238, 1714, 1719, 1893-1894, 1914, 1923, 1925, 2003, wherein the modified oligonucleotide comprises: (a) a gap segment consisting of linked deoxynucleosides; (b) a 5' wing segment consisting of linked nucleosides; and (c) a 3' wing segment consisting of linked nucleosides; wherein the gap segment is positioned immediately adjacent to and between the 5' wing segment and the 3' wing segment, wherein each nucleoside of each wing segment comprises a modified sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

In certain embodiments, the compound comprising a modified oligonucleotide consisting of 20 linked nucleosides and having a nucleobase sequence comprising at least 8 contiguous nucleobases of SEQ ID NO: 1914, wherein the modified oligonucleotide comprises: (a) a gap segment consisting often linked deoxynucleosides; (b) a 5' wing segment consisting of five linked nucleosides; and (c) a 3' wing segment consisting of five linked nucleosides; wherein the gap segment is positioned immediately adjacent to and between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine. In certain embodiments, each internucleoside linkage is a phosphorothioate linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

Certain embodiments disclosed herein provide a compound comprising a modified oligonucleotide according to the following formula: mCes Aes mCes Aes Aes Ads mCds Ads Ads Gds mCds Tds Gds Gds Tds mCes Ges Ges Tes Te (SEQ ID NO: 1914); wherein, A is an adenine, mC is a 5'-methylcytosine, G is a guanine, T is a thymine, e is a 2'-O-methoxyethyl modified nucleoside, d is a 2'-deoxynucleoside, and s is a phosphorothioate internucleoside linkage. In certain embodiments, the modified oligonucleotide further comprises a GalNAc conjugate. In certain embodiments, the conjugate is a 5'-Trishexylamino-(THA)-C6 GalNAc$_3$ conjugate. In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

Certain embodiments disclosed herein provide a compound comprising a modified oligonucleotide with the following formula:

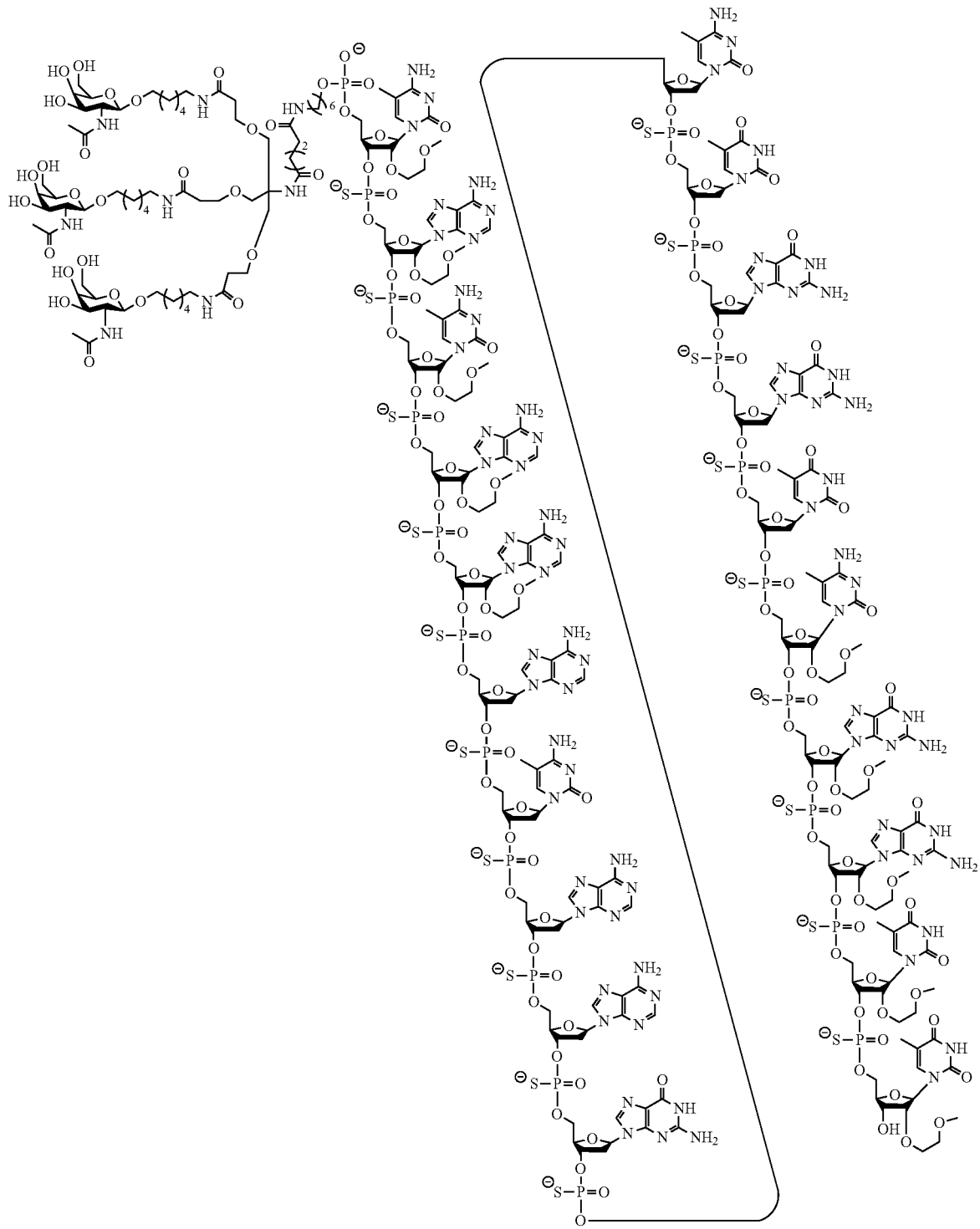

In certain embodiments, the compounds or compositions disclosed herein comprise a salt of the modified oligonucleotide.

In certain embodiments, the compounds or compositions disclosed herein further comprise a pharmaceutically acceptable carrier or diluent.

In certain embodiments, the animal is a human.

Certain embodiments provide a composition or compound comprising a modified oligonucleotide as described herein, wherein the viscosity level is less than 40 cP. In certain embodiments, the composition has a viscosity level less than 15 cP. In certain embodiments, the composition has a viscosity level less than 12 cP. In certain embodiments, the composition has a viscosity level less than 10 cP.

Certain embodiments disclosed herein provide compounds and compositions comprising a modified oligonucleotide targeting AGT for use in reducing AGT in a cell, tissue, organ or animal. In certain embodiments, reducing AGT treats, prevents, slows the progression, delays the onset of, and/or reduces a RAAS pathway related disease, disorder and/or condition, or symptom thereof. In certain embodiments, reducing AGT decreases hypertension. In certain embodiments, reducing AGT decreases or prevents fibrosis. In certain embodiments, reducing AGT modulates a symptom or marker of a RAAS pathway related disease, disorder and/or condition. In certain embodiments, the marker can be selected from one or more of shortened life expectancy, hypertension, chronic kidney disease, stroke, myocardial infarction, heart failure, valvular heart disease, aneurysms of the blood vessels, peripheral artery disease, organ damage and other cardiovascular diseases, disorders and/or conditions or symptoms thereof.

In certain embodiments, provided are compounds and compositions comprising a modified oligonucleotide targeting AGT for use in therapy. In certain embodiments, the compounds and compositions comprising a modified oligonucleotide targeting AGT are administered to an animal in a therapeutically effective amount.

In certain embodiments, provided are compounds and compositions comprising a modified oligonucleotide targeting AGT for use in the preparation of a medicament. In certain embodiments, the medicament is used for treating, preventing, slowing the progression, delaying the onset of, and/or reducing a RAAS pathway related disease, disorder and/or condition, or symptom thereof.

In certain embodiments, provided is a kit for treating, preventing, or ameliorating a RAAS pathway related disease and/or condition, disease, disorder or condition, wherein the kit comprises: (i) an AGT specific inhibitor as described herein; and optionally (ii) an additional agent or therapy as described herein. A kit of the present invention may further include instructions for using the kit to treat, prevent, or ameliorate a RAAS pathway related disease, disorder or condition as described herein.

In certain embodiments, the RAAS pathway related disease, disorder or condition is shortened life expectancy, hypertension, kidney disease (e.g., chronic kidney disease), stroke, cardiac disease (e.g., myocardial infarction, heart failure, valvular heart disease), aneurysms of the blood vessels, peripheral artery disease, organ damage and other RAAS related diseases, disorders and/or conditions or symptoms thereof. In certain embodiments, the hypertension is nonresistant hypertension or resistant hypertension. In certain embodiments, the aneurysm of the blood vessels is aortic aneurysm. In certain embodiments, the organ damage is heart muscle hypertrophy or fibrosis in an organ or tissue. In certain embodiments, the organ is heart, liver or kidney and the tissue is derived from the heart, liver or kidney.

The compound can be used in combination therapy with one or more additional agent or therapy as described herein. Agents or therapies can be administered concomitantly or sequentially to an animal. In certain embodiments, the composition or compound comprising a modified oligonucleotide targeting AGT is co-administered with one or more second agent(s). In certain embodiments the second agent includes procedures to reduce hypertension, diet changes, lifestyle changes, anti-fibrotic drugs and anti-hypertensive drugs such as RAS or RAAS inhibitors, diuretics, calcium channel blockers, adrenergic receptor antagonists, adrenergic agonists and vasodilators. In certain embodiments, the second agent is a second antisense compound. In further embodiments, the second antisense compound targets AGT. In other embodiments, the second antisense compound targets a non-AGT compound.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to AGT nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have a single nucleoside deleted from the 5' end (5' truncation), the central portion or alternatively from the 3' end (3' truncation). A shortened or truncated oligonucleotide can have two or more nucleosides deleted from the 5' end, two or more nucleosides deleted from the central portion or alternatively can have two or more nucleosides deleted from the 3' end. Alternatively, the deleted nucleosides can be dispersed throughout the modified oligonucleotide, for example, in an antisense compound having one or more nucleoside deleted from the 5' end, one or more nucleoside deleted from the central portion and/or one or more nucleoside deleted from the 3' end.

When a single additional nucleoside is present in a lengthened oligonucleotide, the additional nucleoside can be located at the 5' end, 3' end or central portion of the oligonucleotide. When two or more additional nucleosides are present, the added nucleosides can be adjacent to each other, for example, in an oligonucleotide having two nucleosides added to the 5' end (5' addition), to the 3' end (3' addition) or the central portion, of the oligonucleotide. Alternatively, the added nucleoside can be dispersed throughout the antisense compound, for example, in an oligonucleotide having one or more nucleoside added to the 5' end, one or more nucleoside added to the 3' end, and/or one or more nucleoside added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl (cEt) or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an AGT nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m(B)_n(J)_p\text{-}(B)_r\text{-}(A)_t\text{-}(D)_g\text{-}(A)_v\text{-}(B)_w\text{-}(J)_x\text{-}(B)_y\text{-}(J)_z$ wherein:

each A is independently a 2'-substituted nucleoside;

each B is independently a bicyclic nucleoside;

each J is independently either a 2'-substituted nucleoside or a 2'-deoxynucleoside;

each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:

at least one of m, n, and r is other than 0;

at least one of w and y is other than 0;

the sum of m, n, p, r, and t is from 2 to 5; and the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO 2011/139702.

In certain embodiments, the 5'-nucleoside of an ssRNA compound has Formula IIc:

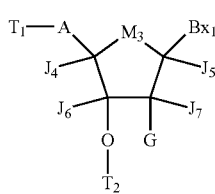

IIc wherein:

$T_1$ is an optionally protected phosphorus moiety;

$T_2$ is an internucleoside linking group linking the compound of Formula IIc to the oligomeric compound;

A has one of the formulas:

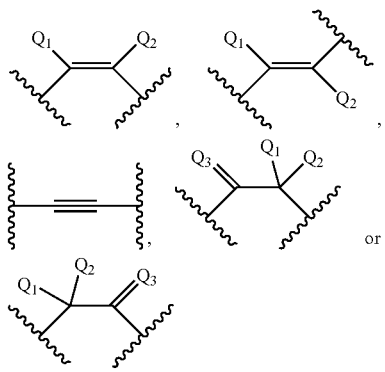

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_7)(R_{15})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{15}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O-[C(R_8)(R_9)]_n-[(C=O)_m-X_1]_j-Z$;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

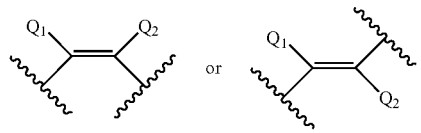

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

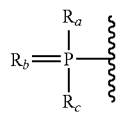

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$.
In certain embodiments, G is F, $OCH_3$ or $O(CH_2)_2$—$OCH_3$.
In certain embodiments, G is $O(CH_2)_2$—$OCH_3$.

In certain embodiments, the 5'-terminal nucleoside has Formula IIe:

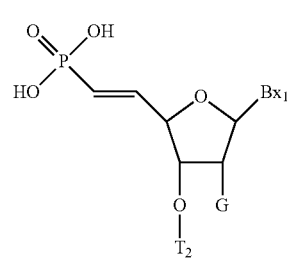

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$, wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

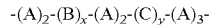
-(A)$_2$-(B)$_x$-(A)$_2$-(C)$_y$-(A)$_3$- wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

5'-(Q)-(AB)$_x$A$_y$-(D)$_z$ wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:

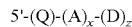
5'-(Q)-(A)$_x$-(D)$_z$ wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is AGT. In certain embodiment, the degradation of the targeted AGT is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target AGT by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode AGT include, without limitation, the following: GENBANK Accession No. NM_000029.3 (incorporated herein as SEQ ID NO: 1), the complement of the nucleotides 24354000 to 24370100 of GENBANK Accession No. NT_167186.1 (incorporated herein as SEQ ID NO: 2), GENBANK Accession No. AK307978.1 (incorporated herein as SEQ ID NO: 3), GENBANK Accession No. AK303755.1 (incorporated herein as SEQ ID NO: 4), GENBANK Accession No. AK293507.1 (incorporated herein as SEQ ID NO: 5), and GENBANK Accession No. CR606672.1 (incorporated herein as SEQ ID NO: 6). In certain embodiments, an antisense compound described herein targets a nucleic acid sequence encoding AGT. In certain embodiments, an antisense compound described herein targets the sequence of any of SEQ ID NOs: 1-6.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for AGT can be obtained by accession number from sequence databases such as NCBI and such information is incorporated herein by reference. In certain embodiments, a target region may encompass the sequence from a 5' target site of one target segment within the target region to a 3' target site of another target segment within the target region. In certain embodiments, a target region may encompass at least 8 consecutive nucleobases selected from within an antisense compound at least 8 consecutive nucleobases from the 5'-terminus of the antisense compound (the remaining nucleobases being a consecutive stretch the beginning immediately upstream of the 5'-terminus of the antisense compound which is specifically hybridizable to the target nucleic acid and continuing until the region contains about 8 to about 80 nucleobases). In certain embodiments, a target region may encompass at least 8 consecutive nucleobases selected from within an antisense compound at least 8 consecutive nucleobases from the 3'-terminus of the antisense compound (the remaining nucleobases being a consecutive stretch beginning immediately downstream of the 3'-terminus of the antisense compound which is specifically hybridizable to the target nucleic acid and continuing until the region contains about 8 to about 80 nucleobases). In certain embodiments, the target region comprises at least 8 consecutive nucleobases selected from any of SEQ ID NOs: 14-2051 and continues up to 80 nucleobases 5' or 3' of the 8 consecutive nucleobase sequence.

In certain embodiments, a "target segment" is a smaller, sub-portion of a target region within a nucleic acid. For example, a target segment can be the sequence of nucleotides of a target nucleic acid to which one or more antisense compound is targeted. "5' target site" refers to the 5'-most nucleotide of a target segment. "3' target site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in AGT mRNA levels are indicative of inhibition of AGT expression. Reductions in levels of an AGT protein are also indicative of inhibition of AGT expression. Further, phenotypic changes are indicative of inhibition of AGT expression. For example, a decrease in fibrosis in tissues can be indicative of inhibition of AGT expression. In another example, an decrease in hypertension can be indicative of inhibition of AGT expression.

Hybridization

In some embodiments, hybridization occurs between an antisense compound disclosed herein and an AGT nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001). In certain embodiments, the antisense compounds provided herein are specifically hybridizable with an AGT nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an AGT nucleic acid).

Non-complementary nucleobases between an antisense compound and an AGT nucleic acid may be tolerated provided that the antisense compound remains able to specifically hybridize to the AGT nucleic acid. Moreover, an antisense compound may hybridize over one or more segments of an AGT nucleic acid such that intervening or adjacent segments are not involved in the hybridization event (e.g., a loop structure, mismatch or hairpin structure).

In certain embodiments, the antisense compounds provided herein, or a specified portion thereof, are, or are at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to an AGT nucleic acid, a target region, target segment, or specified portion thereof. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to an AGT nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an AGT nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an AGT nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, at least a 10, at least an 11, at least a 12, at least a 13, at least a 14, at least a 15, at least a 16, at least a 17, at least an 18, at least a 19, at least a 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, at least 75%, at least 80%, at least 85%, at least 90%, at least 95%, at least 96%, at least 97%, at least 98%, at least 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an AGT nucleic acid comprise one or more modified internucleoside linkages. In certain embodiments, at least one of the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Zhou et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. Patent Applications, Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 99/14226; and PCT International Applications Nos.: PCT/US2008/068922; PCT/US-2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-CH$_2$—(CH$_2$)$_3$-2', wherein R is H, a protecting group or C$_1$-C$_{12}$ alkyl.

In certain embodiment, bicyclic nucleosides have the formula:

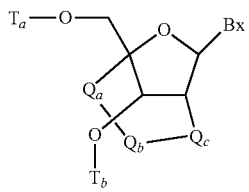

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and
T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

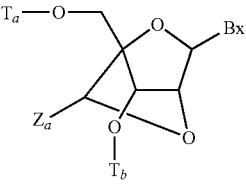

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_e$J$_d$, SJ$_c$, N$_3$, OC(=X)J$_c$, and NJ$_e$C(=X)NJ$_c$J$_d$, wherein each J$_c$, J$_d$ and J$_e$ is, independently, H, C$_1$-C$_6$ alkyl, or substituted C$_1$-C$_6$ alkyl and X is O or NJ$_c$.

In certain embodiments, bicyclic nucleosides have the formula:

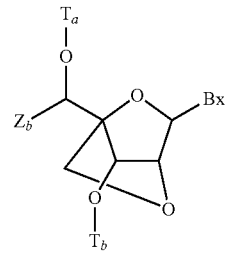

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_b$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl or substituted acyl (C(=O)—).

In certain embodiments, bicyclic nucleosides have the formula:

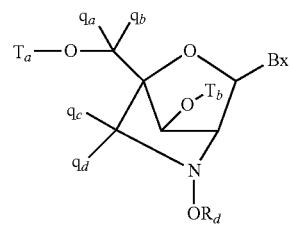

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

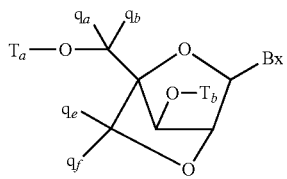

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

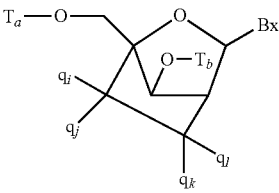

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Frier et al., *Nucleic Acids Research*, 1997, 25(22), 4429-4443 and Albaek et al., *J Org. Chem.*, 2006, 71, 7731-7740). The synthesis and preparation of carbocyclic bicyclic nucleosides along with their oligomerization and biochemical studies have also been described (Srivastava et al., *J Am. Chem. Soc.* 2007, 129(26), 8362-8379).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-($CH_2$)$_3$-2') BNA, and (K) vinyl BNA as depicted below.

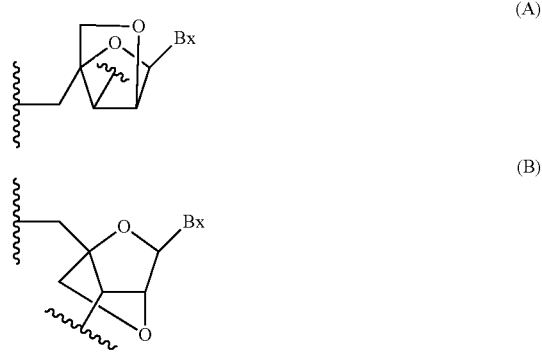

-continued (C) 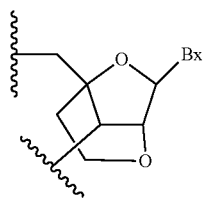

(D) 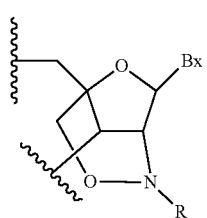

(E) 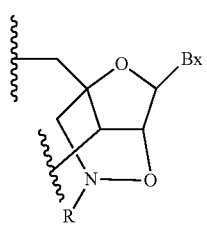

(F) 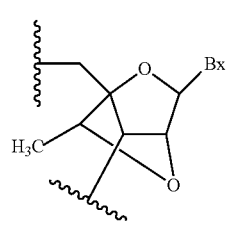

(G) 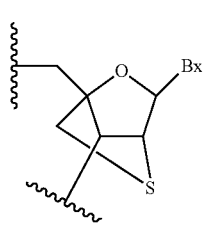

(H) 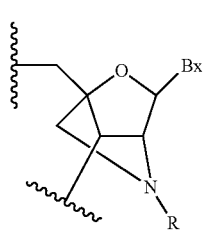

(I) 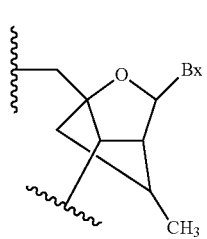

-continued (J) 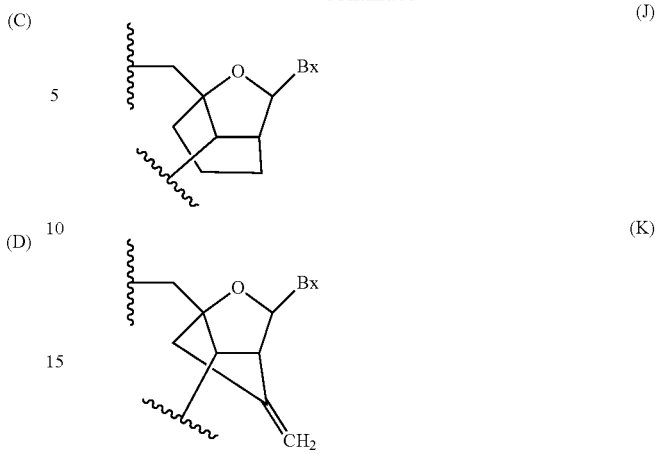

(K)

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyranyl ring system as illustrated below.

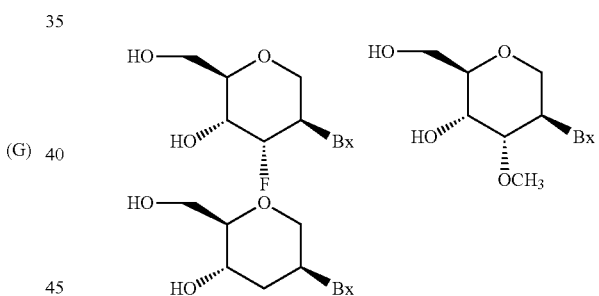

In certain embodiment, sugar surrogates are selected having the formula:

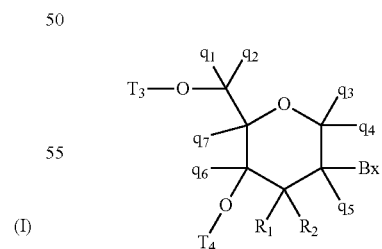

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

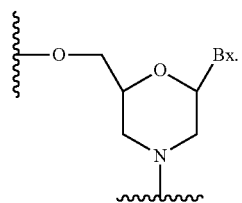

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

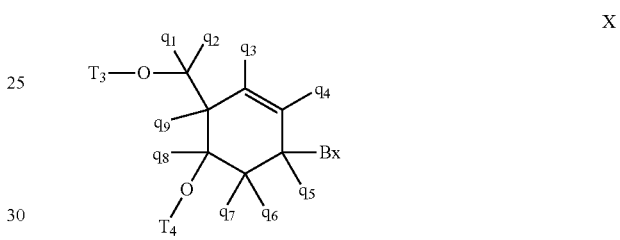

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O $(CH_2)_2SCH_3$, O—$(CH_2)_2$—O—N($R_m$)($R_n$), or O—$CH_2$—C (=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118, 800; 5,319,080; 5,359,044; 5,393,878; 5,446,137; 5,466, 786; 5,514,785; 5,519,134; 5,567,811; 5,576,427; 5,591, 722; 5,597,909; 5,610,300; 5,627,053; 5,639,873; 5,646, 265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications,* CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to an AGT nucleic acid comprise one or more modified nucleobases. In certain embodiments, gap-widened antisense oligonucleotides targeted to an AGT nucleic acid comprise one or more modified nucleobases. In certain embodiments, at least one of the modified nucleobases is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an AGT nucleic acid can be utilized in pharmaceutical compositions by combining the antisense compound with a suitable pharmaceutically acceptable diluent or carrier. A pharmaceutically acceptable diluent includes water e.g., water-for-injection (WFI). A pharmaceutically acceptable diluent includes saline e.g., phosphate-buffered saline (PBS). Water or saline is a diluent suitable for use in compositions to be delivered parenterally. Accordingly, in one embodiment, employed in the methods described herein is a pharmaceutical composition comprising an antisense compound targeted to an AGT nucleic acid and a pharmaceutically acceptable diluent. In certain embodiments, the pharmaceutically acceptable diluent is water or saline. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure herein is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of AGT or the prevention, reduction, amelioration or slowing the progression of a disease, disorder or condition associated with AGT.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 μg to 100 mg per kg of body weight, or within a range of 0.001 mg to 1000 mg dosing, and may be given once or more daily, weekly, biweekly, monthly, quarterly, semi-annually or yearly, or even once every 2 to 20 years. Following successful treatment, it may be desirable to have the patient undergo maintenance therapy to prevent the recurrence of the disease state, wherein the oligonucleotide is administered in maintenance doses, ranging from 0.01 μg to 100 mg per kg of body weight, once or more daily, to once every 20 years or ranging from 0.001 mg to 1000 mg dosing.

Administration

The compounds or pharmaceutical compositions of the present invention can be administered in a number of ways depending upon whether local or systemic treatment is desired and upon the area to be treated. Administration can be inhaled (i.e., pulmonary), enteral (i.e., enteric), parenteral or topical.

In certain embodiments, the compounds and compositions as described herein are administered parenterally. Parenteral administration includes, but is not limited to, intravenous, intra-arterial, subcutaneous, intraperitoneal, intraocular, intramuscular, intracranial, intrathecal, intramedullary, intraventricular or intratumoral injection or infusion. Parenteral administration also includes intranasal administration.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, formulations for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, the compounds and compositions as described herein are administered enterally. Enteric administration includes, but is not limited to, oral, transmucosal, intestinal or rectal (e.g., suppository, enema). In certain embodiments, formulations for enteral administration of the compounds or compositions can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, enteral formulations are those in which compounds provided herein are administered in conjunction with one or more penetration enhancers, surfactants and chelators.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Conjugated Antisense Compounds

In certain embodiments, the oligonucleotides or oligomeric compounds as provided herein are modified by covalent attachment of one or more conjugate groups. In general, conjugate groups modify one or more properties of the attached oligonucleotide or oligomeric compound including but not limited to pharmacodynamics, pharmacokinetics, stability, binding, absorption, cellular distribution, cellular uptake, charge and clearance. As used herein, "conjugate group" means a radical group comprising a group of atoms that are attached to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligonucleotide or oligomeric compound. In certain embodiments, conjugate groups include a cleavable moiety that covalently links the conjugate group to an oligonucleotide or oligomeric compound. In certain embodiments, conjugate groups include a conjugate linker and a cleavable moiety to covalently link the conjugate group to an oligonucleotide or oligomeric compound. In certain embodiments, a conjugate group has the general formula:

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligo-

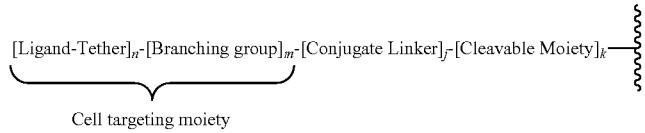

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

meric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3, 4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry,* 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

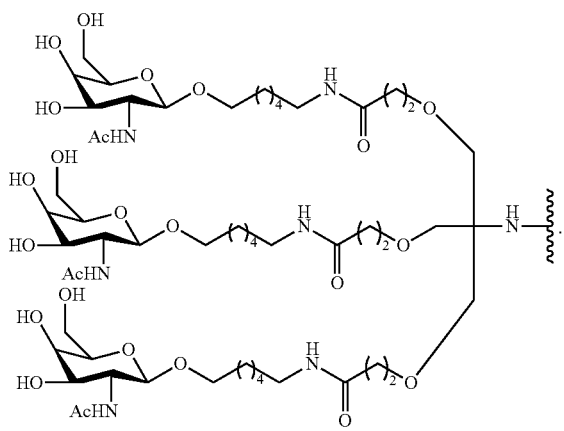

In certain embodiments, conjugate groups are provided wherein the cell-targeting moiety has the formula:

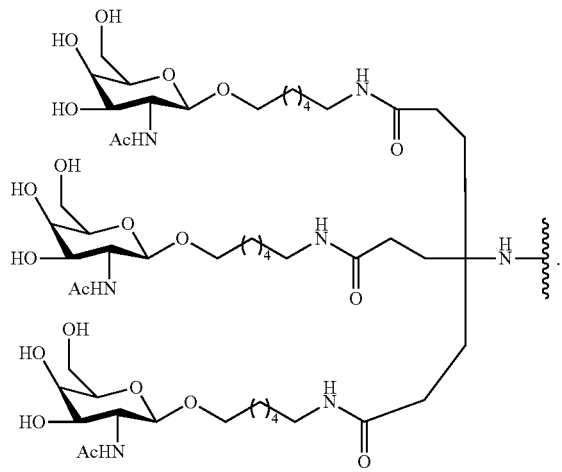

In certain embodiments, conjugate groups are provided wherein the cell-targeting moiety has the formula:

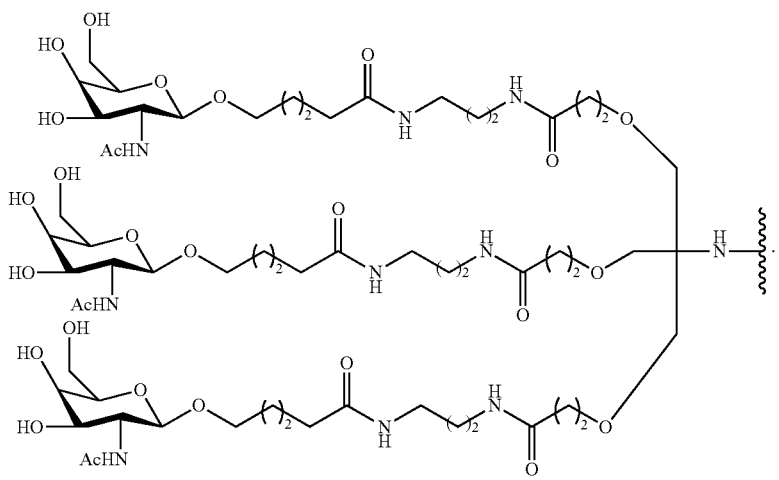

In certain embodiments, conjugate groups have the formula:

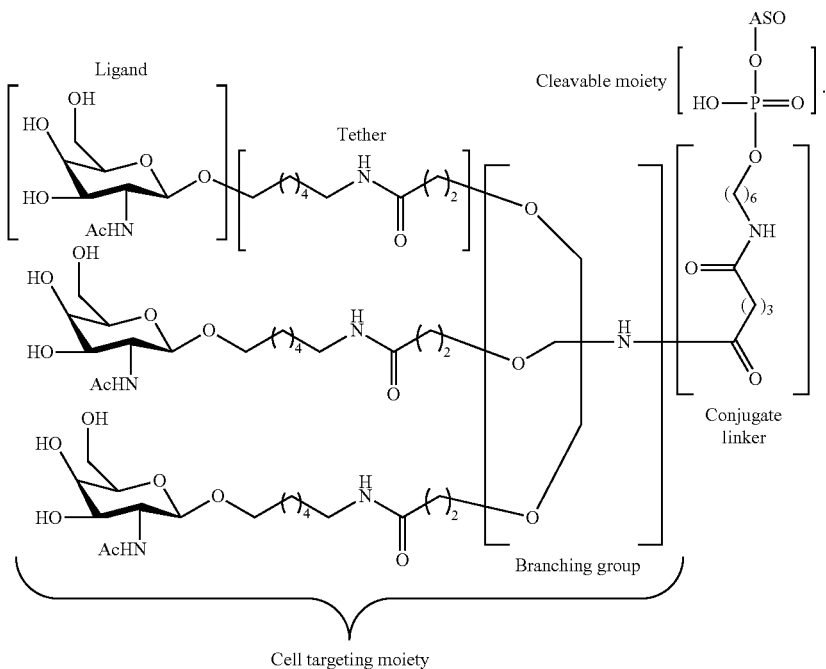

In certain embodiments, an antisense oligonucleotide linked to the conjugate group shown in the formula above has the nucleobase sequence of SEQ ID NO: 1914.

Representative United States patents, United States patent application publications, and international patent application publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230, WO 2014/179620 and WO 2012/037254, each of which is incorporated by reference herein in its entirety.

Representative publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

Some nonlimiting examples of conjugate linkers include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, conjugate groups are at the 5'-end of an oligonucleotide of an oligomeric compound. In certain embodiments, conjugate groups are near the 5'-end.

In certain embodiments, a modified oligonucleotide targeting AGT described herein further comprises a GalNAc conjugate group. In certain embodiments, the GalNAc conjugate group is 5'-Trishexylamino-(THA)-C6 GalNAc$_3$. In certain embodiments, the 5'-Trishexylamino-(THA)-C6 GalNAc$_3$ conjugate has the formula

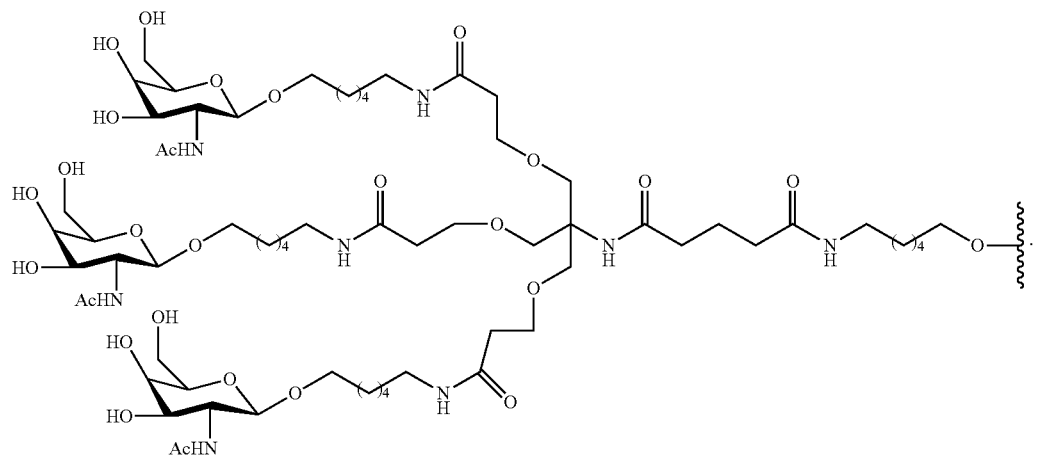

In certain embodiments, the modified oligonucleotide is linked to the 5'-Trishexylamino-(THA)-C6 GalNAc$_3$ conjugate by a cleavable moiety. In certain embodiments, the cleavable moiety is a phosphate group.

Cell Culture and Antisense Compounds Treatment

The effects of antisense compounds on the level, activity or expression of AGT nucleic acids can be tested in vitro in a variety of cell types. Cell types used for such analyses are available from commercial vendors (e.g., American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g., Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell in *Molecular Cloning. A Laboratory Manual*. Third Edition. Cold Spring Harbor laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrook and Russell in *Molecular Cloning. A Laboratory Manual*. Third Edition. Cold Spring Harbor laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrook and Russell in *Molecular Cloning. A Laboratory Manual*. Third Edition. Cold Spring Harbor laboratory Press, Cold Spring Harbor, N.Y. 2001). Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrook and Russell, Molecular Cloning: A Laboratory Manual, 3'd Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an AGT nucleic acid can be assayed in a variety of ways known in the art (Sambrook and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to an AGT nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of AGT nucleic acids can be assessed by measuring AGT protein levels. Protein levels of AGT can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell, Molecular Cloning: A Laboratory Manual, $3^{rd}$ Ed., 2001). Antibodies directed to a target can be identified and obtained from a variety of commercially available sources, or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of AGT and produce phenotypic changes, such as, reduced hypertension in the body. Testing can be performed in normal animals, or in experimental disease models. For administration to animals, antisense oligonucleotides are formulated in a pharmaceutically acceptable diluent, such as sterile water-for-injection or phosphate-buffered saline. Administration includes parenteral routes of administration, such as intraperitoneal, intravenous, and subcutaneous. Calculation of antisense oligonucleotide dosage and dosing frequency depends upon factors such as route of administration and animal body weight. In one embodiment, following a period of treatment with antisense oligonucleotides, RNA is isolated from liver tissue and changes in AGT nucleic acid expression are measured. Changes in AGT protein levels can be directly measured. Changes in AGT expression can also be measured by determining the level of inhibition of the RAAS pathway. RAAS pathway related diseases, disorders and/or conditions may be used as markers for determining the level of AGT inhibition.

Certain Indications

Certain embodiments of the invention provide compounds, compositions and methods of using the compounds and compositions to reduce AGT levels. In certain embodiments, the invention provides compounds, compositions and methods of using the compounds and compositions to treat a subject comprising administering a therapeutically effective amount of the compounds or compositions to the subject. In certain embodiments, the subject has, or is at risk for, a RAAS pathway related disease, disorder or condition. In certain embodiments, the compound or composition comprises and antisense compound.

In certain embodiments, administration of a therapeutically effective amount of an antisense compound targeted to an AGT nucleic acid is accompanied by monitoring of AGT levels in the serum or tissue of a subject to determine a subject's response to the antisense compound. A subject's response to administration of the antisense compound is used by a physician to determine the amount and duration of therapeutic intervention.

In certain embodiments, administration of an antisense compound targeted to an AGT nucleic acid results in reduction of AGT expression by at least 15, 20, 25, 30, 35, 40, 45, 50, 55, 60, 65, 70, 75, 80, 85, 90, 95, 99% or 100% or a range defined by any two of these values. In certain embodiments, administration of an antisense compound targeted to an AGT nucleic acid results in inhibition of the RAAS pathway by at least 15, 20, 25, 30, 35, 40, 45, 50, 55, 60, 65, 70, 75, 80, 85, 90, 95, 99% or 100% or a range defined by any two of these values. In certain embodiments, administration of an antisense compound targeted to an AGT nucleic acid results in a change the RAAS pathway related disease, disorder, condition, symptom or marker (e.g., hypertension or organ damage). In certain embodiments, administration of an AGT antisense compound increases or decreases the RAAS related disease, disorder, condition, symptom or marker by at least 15, 20, 25, 30, 35, 40, 45, 50, 55, 60, 65, 70, 75, 80, 85, 90, 95, 99% or 100% or a range defined by any two of these values.

In certain embodiments, pharmaceutical compositions comprising an antisense compound targeted to AGT are used in the preparation of a medicament for reducing AGT levels. In certain embodiments, pharmaceutical compositions comprising an antisense compound targeted to AGT are used in the preparation of a medicament for treating a subject suffering from, or susceptible to, a RAAS related disease, disorder or condition.

In certain embodiments, reducing AGT levels in a subject treats, ameliorates, prevents, slows the progression, or delays the onset of a disease, condition or disorder. In certain embodiments, the disease, condition or disorder is shortened life expectancy, hypertension, hypertensive emergency (i.e. malignant hypertension), kidney disease (e.g., chronic kidney disease, polycystic kidney disease), pre-eclampsia, Marfan Syndrome, stroke, cardiac disease (e.g., myocardial infarction, heart failure, congestive heart failure, valvular heart disease), aneurysms of the blood vessels, abdominal aneurysm, peripheral artery disease, organ damage, pulmonary arterial hypertension, obesity, metabolic syndrome, non-alcoholic steatohepatitis (NASH), non-alcoholic fatty liver disease (NAFLD) and RAAS related diseases, disorders and/or conditions or symptoms thereof. In certain embodiments, the hypertension is nonresistant hypertension or resistant hypertension. In certain embodiments, the aneurysm of the blood vessels is aortic aneurysm. In certain embodiments, the organ damage is heart muscle hypertrophy or fibrosis in an organ or tissue. In certain embodiments, the organ is heart, liver or kidney and the tissue is derived from the heart, liver or kidney.

In certain embodiments, reducing AGT levels in a subject treats, ameliorates, prevents, slows the progression, or delays the onset of a RAAS pathway related disease, disorder or condition. In certain embodiments, the RAAS pathway related disease, disorder or condition is shortened life expectancy, hypertension, hypertensive emergency (i.e. malignant hypertension), kidney disease (e.g., chronic kidney disease, polycystic kidney disease), pre-eclampsia, Marfan Syndrome, stroke, cardiac disease (e.g., myocardial infarction, heart failure, congestive heart failure, valvular heart disease), aneurysms of the blood vessels, abdominal aneurysm, peripheral artery disease, organ damage, pulmonary arterial hypertension, obesity, metabolic syndrome, NASH, NAFLD and other RAAS related diseases, disorders and/or conditions or symptoms thereof. In certain embodiments, the hypertension is nonresistant hypertension or resistant hypertension. In certain embodiments, the aneurysm of the blood vessels is aortic aneurysm. In certain embodiments, the organ damage is heart muscle hypertrophy or fibrosis in an organ or tissue. In certain embodiments, the organ is heart, liver or kidney and the tissue is derived from the heart, liver or kidney.

In certain embodiments, provided are compounds, compositions and methods for modulating a symptom or marker of a disease, disorder and/or condition. In certain embodiments, the marker can be selected from one or more of shortened life expectancy, hypertension, hypertensive emergency (i.e. malignant hypertension), kidney disease (e.g., chronic kidney disease, polycystic kidney disease), preeclampsia, Marfan Syndrome, stroke, cardiac disease (e.g., myocardial infarction, heart failure, congestive heart failure, valvular heart disease), aneurysms of the blood vessels, abdominal aneurysm, peripheral artery disease, organ damage and other RAAS related diseases, disorders and/or conditions or symptoms thereof.

Certain Combination Therapies

In certain embodiments, a first agent comprising an antisense compound provided herein is co-administered with one or more secondary agents. In certain embodiments, the antisense compound is an antisense oligonucleotide. In certain embodiments, the antisense oligonucleotide is a modified oligonucleotide.

In certain embodiments, such second agents are designed to treat the same RAAS pathway related disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, such first agents are designed to treat an undesired side effect of a second agent. In certain embodiments, second agents are co-administered with the first agent to treat an undesired effect of the first agent. In certain embodiments, second agents are co-administered with the first agent to produce a combinational or additive effect. In certain embodiments, second agents are co-administered with the first agent to produce a synergistic effect.

In certain embodiments, the co-administration of the first and second agents permits use of lower dosages than would be required to achieve a therapeutic or prophylactic effect if the agents were administered as independent therapy. In certain embodiments the dose of a co-administered second agent is the same as the dose that would be administered if the second agent was administered alone. In certain embodiments the dose of a co-administered second agent is greater than the dose that would be administered if the second agent was administered alone.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to, certain procedures to reduce hypertension, diet changes, lifestyle changes, anti-fibrotic drugs and anti-hypertensive drugs such as RAAS inhibitors, endothelin receptor antagonists, neprilysin inhibitors, diuretics, calcium channel blockers, adrenergic receptor antagonists, adrenergic agonists and vasodilators.

Examples of procedures that can reduce hypertension include, but are not limited to, renal denervation and baroreceptor activation therapy.

Examples of RAS or RAAS inhibitors include, but are not limited to ACE inhibitors (e.g., captopril, enalapril, fosinopril, lisinopril, perindopril, quinapril, ramipril, trandolapril and benazepril), angiotensin II receptor antagonists (e.g., candesartan, eprosartan, irbesartan, losartan, olmesartan, telmisartan and valsartan), renin inhibitors (e.g., aliskiren), aldosterone receptor antagonists (e.g., eplerenone, spironolactone and finerenone).

Examples of endothelin receptor antagonists include ambrisentan, sitaxentan, atrasentan, BQ-123, zibotentan, bosentan, macitentan and tezosentan.

Examples of neprilysin inhibitors include sacubitril and omapatrilat.

Examples of diuretics include loop diuretics (e.g., bumetanide, ethacrynic acid, furosemide, torsemide), thiazide diuretics (e.g., epitizide, hydrochlorothiazide, chlorothiazide and bendroflumethiazide), thiazide-like diuretics (e.g., indapamide, chlorthalidone and metolazone) and potassium-sparing diuretics (e.g., amiloride, triamterene and spironolactone).

Examples of calcium channel blockers include dihydropyridines (e.g., amlodipine, felodipine, isradipine, lercanidipine, nicardipine, nifedipine, nimodipine and nitrendipine) and non-dihydropyridines (e.g., diltiazem and verapamil).

Examples of adrenergic receptor antagonists include Beta blockers (e.g., atenolol, metoprolol, nadolol, oxprenolol, pindolol, propranolol and timolol), Alpha blockers (e.g., doxazosin, phentolamine, indoramin, phenoxybenzamine, prazosin, terazosin and tolazoline) and mixed Alpha+Beta blockers (e.g., bucindolol, carvedilol and labetalol).

Examples of vasodilators include sodium nitroprusside and hydralazine and its derivatives.

Examples of adrenergic agonists include alpha-2 agonists (e.g., clonidine, guanabenz, methyldopa and moxonidine).

Additional examples of anti-hypertensive drugs include guanethidine, reserpine and the like.

The second agents can be used in combination with the therapeutic compounds described herein to decrease a disease, disorder and/or condition such as hypertension, organ damage and the like.

Certain Compounds

Preferred antisense compounds with beneficial properties that enhance their use as therapeutic treatments in humans are demonstrated in the examples herein. For brevity, only the studies that contributed to the selection of the preferred antisense compounds are described. A non-exhaustive summary of the examples is provided below for ease of reference.

Over 2000 antisense compounds with a MOE containing and/or a cEt containing gapmer motif targeting human AGT were designed. Example 1 shows representative single dose inhibition data for the over 2000 potent antisense compounds tested in HepG2 cells for their effect on human AGT mRNA.

Of the over 2000 antisense compounds tested with a single dose in vitro, over 160 antisense compounds were chosen for testing in dose-dependent inhibition studies to determine their half maximal inhibitory concentration ($IC_{50}$) in HepG2 cells (Example 2).

Base on the in vitro dose response studies, over 50 antisense compounds were selected for single dose potency and tolerability testing in human AGT transgenic (huAGT tg) mice as described in the exemplary studies in Example 3. Of the over 50 antisense compounds, about 14 antisense compounds were further selected for dose response and tolerability studies in huAGT tg mice (Example 4).

Nine antisense compounds exhibiting significant potency and tolerability in huAGT mice were chosen for further studies: in a viscosity assay (Example 5); in CD1 mice (Example 6) and Sprague-Dawlay rats (Example 7) to assess tolerability of the antisense compounds; in monkey hepatocytes to test cross-species potency in inhibiting monkey AGT (Example 8); and in cynomolgus monkeys to assess potency and tolerability (Example 9). Although the antisense compounds in the studies described in Example 9 were tested in cynomolgus monkeys, the cynomolgus monkey AGT sequence was not available for comparison to the sequences of the antisense compounds, therefore the sequences of the antisense compounds were compared to that of the closely related rhesus monkey (Example 8).

Based on the extensive characterization of the 9 antisense compounds, the sequence of antisense compound ISIS 654472 (parent compound) was selected for further study (Example 10). Six antisense compounds were designed with the sequence of parent compound ISIS 654472 but with different chemical modifications and a GalNAc conjugate. The 6 newly designed compounds were administered to CD1 mice (Example 10) and Sprague-Dawley rats (Example 11) to test their tolerability in these animal models. Of the 6 GalNAc conjugated antisense compounds, compound ISIS 757456 was selected to test in huAGT mice compared to the parent antisense compound ISIS 654472. ISIS 757456 showed an 8× improvement in potency compared to unconjugated compound ISIS 654472.

Accordingly, provided herein are antisense compounds with any one or more characteristics that are beneficial for their use as a therapeutic agent. In certain embodiments, provided herein are antisense compounds comprising a modified oligonucleotide as described herein targeted to, or specifically hybridizable with, a region of nucleotides selected from any of SEQ ID NOs: 1-6.

In certain embodiments, certain antisense compounds as described herein are efficacious by virtue of their potency in inhibiting AGT expression. In certain embodiments, the compounds or compositions inhibit AGT by at least 40%, at least 45%, at least 50%, at least 55%, at least 60%, at least 65%, at least 70%, at least 75%, at least 80%, at least 85%, at least 90% or at least 95%.

In certain embodiments, certain antisense compounds as described herein are efficacious by virtue of an in vitro $IC_{50}$ of less than 20 μM, less than 10 μM, less than 8 μM, less than 5 μM, less than 2 μM, less than 1 μM, less than 0.9 μM, less than 0.8 μM, less than 0.7 μM, less than 0.6 μM, or less than 0.5 μM when tested in human cells, for example, in the Hep3B cell line (as described in Example 2).

In certain embodiments, certain antisense compounds as described herein are efficacious by virtue of a median effective dose ($ED_{50}$) of ≤10 mpk/wk, ≤9 mpk/wk, ≤8 mpk/wk, ≤7 mpk/wk, ≤6 mpk/wk, ≤5 mpk/wk, ≤4 mpk/wk, ≤3 mpk/wk, ≤2 mpk/wk, or ≤1 mpk/wk in vivo as shown in Example 4. In certain embodiments, a preferred antisense compound such as antisense compound ISIS 757456 has an $ED_{50}$≤3 mpk/wk as shown in Example 12.

In certain embodiments, certain antisense compounds as described herein are efficacious by virtue of having a viscosity of less than 40 cP, less than 35 cP, less than 30 cP, less than 25 cP, less than 20 cP, less than 15 cP, or less than 12 cP as described in Example 5. Oligonucleotides having a viscosity greater than 40 cP would have less than optimal viscosity.

In certain embodiments, certain antisense compounds as described herein are highly tolerable, as demonstrated by the in vivo tolerability measurements described in the examples.

In certain embodiments, the certain antisense compounds as described herein are highly tolerable, as demonstrated by having an increase in ALT and/or AST value of no more than 3 fold, 2 fold or 1.5 fold over saline treated animals.

In certain embodiments, certain antisense compounds as described herein are efficacious by virtue of having one or more of an inhibition potency of greater than 50%, an $ED_{50}$≤5 mpk/wk, a viscosity of less than 40 cP, and no more than a 3 fold increase in ALT and/or AST in transgenic mice.

In certain embodiments, ISIS 757456 (SEQ ID NO: 1914) is preferred. This compound was found to be a potent inhibitor in AGT transgenic mice and a very tolerable antisense compound in CD-1 mice. In mice it had less than a 3 fold increase in ALT and/or AST levels over saline treated animals. It had an $ED_{50}$≤3 mpk/wk in huAGT transgenic mice.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Angiotensinogen (AGT) in HepG2 Cells Over 2000 antisense oligonucleotides were designed targeting human AGT nucleic acid and were tested for their effects on AGT mRNA in vitro in a series of experiments that had similar culture conditions. The results for representative antisense oligonucleotides are presented in tables shown below.

The newly designed chimeric antisense oligonucleotides in the Tables below were designed as MOE and/or cEt containing gapmers. The MOE containing oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a 2'-MOE sugar modification. The cEt containing oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a cEt sugar modification. In some instances oligonucleotides were designed to contain both a MOE and a cEt. The MOE and cEt containing oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a MOE and/or cEt sugar modification.

The "Chemistry" column describes the sugar modifications of each oligonucleotide. "k" indicates an cEt sugar modification; "d" indicates deoxyribose; and "e" indicates a MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human AGT mRNA, designated herein as SEQ ID NO: 1 (GENBANK Accession NM_000029.3) and/or the human AGT genomic sequence, designated herein as SEQ ID NO: 2 (GENBANK Accession NT_167186.1 truncated from nucleotides 24354000 to 24370100).

Table 1 shows inhibition of AGT mRNA in HepG2 cells cultured at a density of 20,000 cells per well which were transfected using electroporation with 4500 nM antisense oligonucleotide. After a treatment period of approximately 24 hours, RNA was isolated from the cells and AGT mRNA levels were measured by quantitative real-time PCR. Human primer probe set RTS3721 (forward sequence CCCTGATGGGAGCCAGTGT, designated herein as SEQ ID NO: 8; reverse sequence AGCAGGGAGAAGCCCTTCA, designated herein as SEQ ID NO: 9; and probe sequence CCCTGGCTTTCAACACCTACGTCCACTX, where X is a fluorescent label, designated herein as SEQ ID NO: 10) was used to measure mRNA levels. AGT mRNA levels were adjusted according to total RNA content, as measured by RIBOGREEN®. Results are presented as percent inhibition of AGT, relative to untreated control cells.

TABLE 1

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568518 | 1 | 16 | TGCCCGCTCATGGGAT | eekddddddddddkke | 26 | 1986 | 2001 | 14 |
| 568519 | 20 | 35 | GGGCCACTTCTGACCC | eekddddddddddkke | 34 | 2005 | 2020 | 15 |
| 568520 | 35 | 50 | GCTTAGGCAACACGGG | eekddddddddddkke | 20 | 2020 | 2035 | 16 |
| 568521 | 45 | 60 | GGAGAGTCTTGCTTAG | eekddddddddddkke | 26 | 2030 | 2045 | 17 |
| 568522 | 80 | 95 | CATGCAGGCCGGAGGT | eekddddddddddkke | 25 | 2065 | 2080 | 18 |
| 568523 | 90 | 105 | GCCACAGGGACATGCA | eekddddddddddkke | 30 | 2075 | 2090 | 19 |
| 568524 | 122 | 137 | TGACCCAGCCCCGGGA | eekddddddddddkke | 40 | 2107 | 2122 | 20 |
| 568525 | 155 | 170 | TGTGACAGCCTGAGGC | eekddddddddddkke | 25 | 2140 | 2155 | 21 |
| 568526 | 165 | 180 | TCCCTAGGTGTGTGAC | eekddddddddddkke | 34 | 2150 | 2165 | 22 |
| 568527 | 179 | 194 | GAAACGGGAGCATCTC | eekddddddddddkke | 9 | 2164 | 2179 | 23 |
| 568528 | 189 | 204 | AAGGTTCCCAGAAACG | eekddddddddddkke | 19 | 2174 | 2189 | 24 |
| 568529 | 209 | 224 | AGTTTGCAGGAGTCGG | eekddddddddddkke | 26 | 2194 | 2209 | 25 |
| 568530 | 229 | 244 | TCGAGTTACACATTTA | eekddddddddddkke | 24 | 2214 | 2229 | 26 |
| 568531 | 248 | 263 | AGAGTGAGCCGGTGCA | eekddddddddddkke | 21 | 2233 | 2248 | 27 |
| 568532 | 258 | 273 | ACTGCTGAACAGAGTG | eekddddddddddkke | 19 | 2243 | 2258 | 28 |
| 568533 | 268 | 283 | GCAGAGTTTCACTGCT | eekddddddddddkke | 16 | 2253 | 2268 | 29 |
| 568534 | 278 | 293 | AGTGATCGATGCAGAG | eekddddddddddkke | 32 | 2263 | 2278 | 30 |
| 568535 | 288 | 303 | AGGAAGTCTTAGTGAT | eekddddddddddkke | 15 | 2273 | 2288 | 31 |
| 568536 | 301 | 316 | TGGGACCTCTTCCAGG | eekddddddddddkke | 31 | 2286 | 2301 | 32 |
| 568537 | 353 | 368 | GGCCAGACCACAGGCT | eekddddddddddkke | 16 | 2338 | 2353 | 33 |
| 568538 | 363 | 378 | TACATCACTTGGCCAG | eekddddddddddkke | 30 | 2348 | 2363 | 34 |
| 568539 | 373 | 388 | AGAGGAGGGTTACATC | eekddddddddddkke | 24 | 2358 | 2373 | 35 |
| 568540 | 386 | 401 | GTGCACAGGCTGGAGA | eekddddddddddkke | 43 | 2371 | 2386 | 36 |
| 568541 | 431 | 446 | TATTTATAGCTGAGGG | eekddddddddddkke | 29 | 2416 | 2431 | 37 |
| 568542 | 441 | 456 | CACGATGCCCTATTTA | eekddddddddddkke | 34 | 2426 | 2441 | 38 |
| 568543 | 478 | 493 | TACCCAGAACAACGGC | eekddddddddddkke | 28 | 2463 | 2478 | 39 |
| 568544 | 525 | 540 | GCCATCTCAGACTGGG | eekddddddddddkke | 69 | 5742 | 5757 | 40 |
| 568545 | 535 | 550 | ACCGGCAGGAGCCATC | eekddddddddddkke | 42 | 5752 | 5767 | 41 |

TABLE 1-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568546 | 545 | 560 | TCAGGCTCACACCGGC | eekddddddddddkke | 67 | 5762 | 5777 | 42 |
| 568547 | 555 | 570 | ATGGTGGCCCTCAGGC | eekddddddddddkke | 39 | 5772 | 5787 | 43 |
| 568548 | 596 | 611 | GGTCACCTGCAGCCAG | eekddddddddddkke | 59 | 5813 | 5828 | 44 |
| 568549 | 606 | 621 | ATGTACACCCGGTCAC | eekddddddddddkke | 25 | 5823 | 5838 | 45 |
| 568550 | 643 | 658 | GGTACTCTCATTGTGG | eekddddddddddkke | 76 | 5860 | 5875 | 46 |
| 568551 | 654 | 669 | AGCTGCTCACAGGTAC | eekddddddddddkke | 60 | 5871 | 5886 | 47 |
| 568552 | 676 | 691 | CTTCCCGGCATTGGCC | eekddddddddddkke | 50 | 5893 | 5908 | 48 |
| 568553 | 703 | 718 | AGCAGGTATGAAGGTG | eekddddddddddkke | 62 | 5920 | 5935 | 49 |
| 568554 | 713 | 728 | CCTGAATTGGAGCAGG | eekddddddddddkke | 43 | 5930 | 5945 | 50 |
| 568555 | 723 | 738 | GATGTCTTGGCCTGAA | eekddddddddddkke | 21 | 5940 | 5955 | 51 |
| 568556 | 739 | 754 | CTTTTCATCCACAGGG | eekddddddddddkke | 39 | 5956 | 5971 | 52 |
| 568557 | 762 | 777 | AGCACCAGCTGGTCCT | eekddddddddddkke | 71 | 5979 | 5994 | 53 |
| 568558 | 772 | 787 | TGCAGCGACTAGCACC | eekddddddddddkke | 71 | 5989 | 6004 | 54 |
| 568559 | 782 | 797 | TGTCAAGTTTTGCAGC | eekddddddddddkke | 61 | 5999 | 6014 | 55 |
| 568560 | 803 | 818 | CGGCCCTCAACTTGTC | eekddddddddddkke | 45 | 6020 | 6035 | 56 |
| 568561 | 815 | 830 | TCCCGACCATTGCGGC | eekddddddddddkke | 25 | 6032 | 6047 | 57 |
| 568562 | 825 | 840 | TTGGCCAGCATCCCGA | eekddddddddddkke | 51 | 6042 | 6057 | 58 |
| 568563 | 835 | 850 | GCCCAAGAAGTTGGCC | eekddddddddddkke | 13 | 6052 | 6067 | 59 |
| 568564 | 845 | 860 | ATATACGGAAGCCCAA | eekddddddddddkke | 52 | 6062 | 6077 | 60 |
| 568565 | 855 | 870 | TGCATGCCATATATAC | eekddddddddddkke | 64 | 6072 | 6087 | 61 |
| 568566 | 871 | 886 | GCCCCATAGCTCACTG | eekddddddddddkke | 64 | 6088 | 6103 | 62 |
| 568567 | 886 | 901 | GGCCCCATGGACCACG | eekddddddddddkke | 38 | 6103 | 6118 | 63 |
| 568568 | 913 | 928 | AAAGACAGCCGTTGGG | eekddddddddddkke | 58 | 6130 | 6145 | 64 |
| 568569 | 923 | 938 | CCAGGGTGCCAAAGAC | eekddddddddddkke | 36 | 6140 | 6155 | 65 |
| 568570 | 937 | 952 | CAGATAGAGAGAGGCC | eekddddddddddkke | 59 | 6154 | 6169 | 66 |
| 568571 | 954 | 969 | GTGTGGTCCAAGGCTC | eekddddddddddkke | 37 | 6171 | 6186 | 67 |
| 568572 | 983 | 998 | CACCCAGGATTGCCTG | eekddddddddddkke | 72 | 6200 | 6215 | 68 |
| 568573 | 993 | 1008 | TTCCAAGGAACACCCA | eekddddddddddkke | 35 | 6210 | 6225 | 69 |
| 568574 | 1017 | 1032 | AGCCGGGAGGTGCAGT | eekddddddddddkke | 53 | 6234 | 6249 | 70 |
| 568575 | 1020 | 1035 | TCCAGCCGGGAGGTGC | eekddddddddddkke | 62 | 6237 | 6252 | 71 |
| 568576 | 1053 | 1068 | ACAGCCTGCAGGGCAG | eekddddddddddkke | 47 | 6270 | 6285 | 72 |
| 568577 | 1070 | 1085 | CCACTAGCAGGCCCTG | eekddddddddddkke | 33 | 6287 | 6302 | 73 |
| 568578 | 1088 | 1103 | TATCAGCCCTGCCCTG | eekddddddddddkke | 37 | 6305 | 6320 | 74 |
| 568579 | 1098 | 1113 | TGGGCCTGGCTATCAG | eekddddddddddkke | 42 | 6315 | 6330 | 75 |
| 568580 | 1114 | 1129 | CGTGGACAGCAGCAGC | eekddddddddddkke | 70 | 6331 | 6346 | 76 |
| 568581 | 1131 | 1146 | GTGAACACGCCCACCA | eekddddddddddkke | 48 | 6348 | 6363 | 77 |

TABLE 1-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568582 | 1151 | 1166 | TCAGGTGCAGGCCTGG | eekddddddddddkke | 36 | 6368 | 6383 | 78 |
| 568583 | 1171 | 1186 | GCCCTGCACAAACGGC | eekddddddddddkke | 16 | 6388 | 6403 | 79 |
| 568584 | 1182 | 1197 | TAGAGAGCCAGGCCCT | eekddddddddddkke | 52 | 6399 | 6414 | 80 |
| 568585 | 1203 | 1218 | CGTGGGAGGACCACAG | eekddddddddddkke | 47 | 6420 | 6435 | 81 |
| 568586 | 1217 | 1232 | TGAAGTCCAGAGAGCG | eekddddddddddkke | 60 | 6434 | 6449 | 82 |
| 568587 | 1233 | 1248 | GCAACATCCAGTTCTG | eekddddddddddkke | 50 | 6450 | 6465 | 83 |
| 568588 | 1244 | 1259 | TCTTCTCAGCAGCAAC | eekddddddddddkke | 54 | 6461 | 6476 | 84 |
| 568589 | 1272 | 1287 | CCTGTCACAGCCTGCA | eekddddddddddkke | 77 | 6489 | 6504 | 85 |
| 568590 | 1278 | 1293 | TTCCATCCTGTCACAG | eekddddddddddkke | 51 | 6495 | 6510 | 86 |
| 568595 | 1403 | 1418 | TGTCCACCCAGAACTC | eekddddddddddkke | 33 | 10414 | 10429 | 87 |
| 568596 | 1406 | 1421 | TGTTGTCCACCCAGAA | eekddddddddddkke | 59 | 10417 | 10432 | 88 |
| 568597 | 1409 | 1424 | TGCTGTTGTCCACCCA | eekddddddddddkke | 60 | 10420 | 10435 | 89 |
| 568598 | 1412 | 1427 | AGGTGCTGTTGTCCAC | eekddddddddddkke | 57 | 10423 | 10438 | 90 |
| 568599 | 1415 | 1430 | CTGAGGTGCTGTTGTC | eekddddddddddkke | 56 | 10426 | 10441 | 91 |
| 568600 | 1418 | 1433 | ACACTGAGGTGCTGTT | eekddddddddddkke | 28 | 10429 | 10444 | 92 |
| 568601 | 1421 | 1436 | CAGACACTGAGGTGCT | eekddddddddddkke | 67 | 10432 | 10447 | 93 |
| 568602 | 1431 | 1446 | AGCATGGGAACAGACA | eekddddddddddkke | 27 | 10442 | 10457 | 94 |
| 568603 | 1443 | 1458 | CCCATGCCAGAGAGCA | eekddddddddddkke | 30 | 10454 | 10469 | 95 |
| 568604 | 1462 | 1477 | ACTCCAGTGCTGGAAG | eekddddddddddkke | 41 | 10473 | 10488 | 96 |
| 568605 | 1465 | 1480 | GTCACTCCAGTGCTGG | eekddddddddddkke | 73 | 10476 | 10491 | 97 |
| 568606 | 1474 | 1489 | GTCCTGGATGTCACTC | eekddddddddddkke | 68 | 10485 | 10500 | 98 |
| 568607 | 1484 | 1499 | CCGAGAAGTTGTCCTG | eekddddddddddkke | 47 | 10495 | 10510 | 99 |
| 568608 | 1494 | 1509 | ACTTGAGTCACCGAGA | eekddddddddddkke | 39 | 10505 | 10520 | 100 |
| 568609 | 1504 | 1519 | AGTGAAGGGCACTTGA | eekddddddddddkke | 28 | 10515 | 10530 | 101 |
| 568610 | 1531 | 1546 | CTGGATCAGCAGCAGG | eekddddddddddkke | 69 | 10542 | 10557 | 102 |
| 568611 | 1550 | 1565 | GGTCAGAGGCATAGTG | eekddddddddddkke | 43 | 10561 | 10576 | 103 |
| 568612 | 1578 | 1593 | TGGAAAGTGAGACCCT | eekddddddddddkke | 45 | 10589 | 10604 | 104 |
| 568613 | 1588 | 1603 | GGAGTTTTGCTGGAAA | eekddddddddddkke | 53 | 10599 | 10614 | 105 |
| 568614 | 1598 | 1613 | TCCAGTTGAGGGAGTT | eekddddddddddkke | 38 | 10609 | 10624 | 106 |
| 568615 | 1614 | 1629 | GGAGATAGTTTCTTCA | eekddddddddddkke | 24 | 10625 | 10640 | 107 |
| 568616 | 1631 | 1646 | TCAGGTGGATGGTCCG | eekddddddddddkke | 34 | N/A | N/A | 108 |
| 568617 | 1653 | 1668 | TGCAGCACCAGTTGGG | eekddddddddddkke | 65 | 12259 | 12274 | 109 |
| 568618 | 1663 | 1678 | ATAAGATCCTTGCAGC | eekddddddddddkke | 21 | 12269 | 12284 | 110 |
| 568619 | 1680 | 1695 | AGCAGGTCCTGCAGGT | eekddddddddddkke | 50 | 12286 | 12301 | 111 |
| 568620 | 1700 | 1715 | CGGGCAGCTCAGCCTG | eekddddddddddkke | 39 | 12306 | 12321 | 112 |
| 568621 | 1710 | 1725 | TGCAGAATGGCGGGCA | eekddddddddddkke | 57 | 12316 | 12331 | 113 |

TABLE 1-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568622 | 1720 | 1735 | CAGCTCGGTGTGCAGA | eekddddddddddkke | 70 | 12326 | 12341 | 114 |
| 568623 | 1730 | 1745 | TTTGCAGGTTCAGCTC | eekddddddddddkke | 44 | 12336 | 12351 | 115 |
| 568624 | 1745 | 1760 | GGTCATTGCTCAATTT | eekddddddddddkke | 45 | 12351 | 12366 | 116 |
| 568625 | 1755 | 1770 | ACCCTGATGCGGTCAT | eekddddddddddkke | 43 | 12361 | 12376 | 117 |
| 568626 | 1794 | 1809 | GCTTCAAGCTCAAAAA | eekddddddddddkke | 56 | 13263 | 13278 | 118 |
| 568627 | 1827 | 1842 | TGTTGGGTAGACTCTG | eekddddddddddkke | 61 | 13296 | 13311 | 119 |
| 568628 | 1841 | 1856 | CAGGCTTGTTAAGCTG | eekddddddddddkke | 53 | 13310 | 13325 | 120 |
| 568629 | 1851 | 1866 | TCCAAGACCTCAGGCT | eekddddddddddkke | 46 | 13320 | 13335 | 121 |
| 568630 | 1875 | 1890 | AGGAATGGGCGGTTCA | eekddddddddddkke | 58 | 13344 | 13359 | 122 |
| 568631 | 1923 | 1938 | CGGCCCAGGAAGTGCA | eekddddddddddkke | 30 | 13392 | 13407 | 123 |
| 568632 | 1933 | 1948 | GTTGGCCACGCGGCCC | eekddddddddddkke | 11 | 13402 | 13417 | 124 |
| 568633 | 1943 | 1958 | TGCTCAGCGGGTTGGC | eekddddddddddkke | 49 | 13412 | 13427 | 125 |
| 568634 | 1961 | 1976 | GGCCCTGGCCTCATGC | eekddddddddddkke | 44 | 13430 | 13445 | 126 |
| 568635 | 1986 | 2001 | GGCCTTGCCAGGCACT | eekddddddddddkke | 86 | 13455 | 13470 | 127 |
| 568636 | 2007 | 2022 | GCCTCAAAGGCCAGGG | eekddddddddddkke | 49 | 13476 | 13491 | 128 |
| 568637 | 2046 | 2061 | CGCTGATTTGTCCGGG | eekddddddddddkke | 92 | 13515 | 13530 | 129 |
| 568638 | 2056 | 2071 | GGTGACACATCGCTGA | eekddddddddddkke | 86 | 13525 | 13540 | 130 |
| 568639 | 2075 | 2090 | GAAAAGGTGGGAGACT | eekddddddddddkke | 39 | 13544 | 13559 | 131 |
| 568640 | 2088 | 2103 | CGACTCATTAGAAGAA | eekddddddddddkke | 87 | 13557 | 13572 | 132 |
| 568641 | 2111 | 2126 | ACGGCTGCTTTCCAGC | eekddddddddddkke | 64 | 13580 | 13595 | 133 |
| 568642 | 2121 | 2136 | CCAAGGAGAAACGGCT | eekddddddddddkke | 79 | 13590 | 13605 | 134 |
| 568643 | 2131 | 2146 | CACACTTAGACCAAGG | eekddddddddddkke | 78 | 13600 | 13615 | 135 |
| 568644 | 2166 | 2181 | TGCCGCTGCAGGCTTC | eekddddddddddkke | 57 | 13635 | 13650 | 136 |
| 568645 | 2176 | 2191 | GGTGCATTTGTGCCGC | eekddddddddddkke | 75 | 13645 | 13660 | 137 |
| 568646 | 2274 | 2289 | TGGTCGGTTGGAATTC | eekddddddddddkke | 77 | 13743 | 13758 | 138 |
| 568647 | 2284 | 2299 | ACAAACAAGCTGGTCG | eekddddddddddkke | 84 | 13753 | 13768 | 139 |
| 568648 | 2311 | 2326 | CTTGAAAAGGGAACAC | eekddddddddddkke | 62 | 13780 | 13795 | 140 |
| 568649 | 2331 | 2346 | AACCCAATTTTTGTTC | eekddddddddddkke | 56 | 13800 | 13815 | 141 |
| 568650 | 2362 | 2377 | GGCAATGCAAAAATGT | eekddddddddddkke | 78 | 13831 | 13846 | 142 |
| 568651 | 2391 | 2406 | TACATTCAAGACACTA | eekddddddddddkke | 60 | 13860 | 13875 | 143 |
| 568652 | 2402 | 2417 | GGTCATGTTCTTACAT | eekddddddddddkke | 55 | 13871 | 13886 | 144 |
| 568653 | 2412 | 2427 | ACTACACGGAGGTCAT | eekddddddddddkke | 55 | 13881 | 13896 | 145 |
| 568654 | 2422 | 2437 | TATTACAGACACTACA | eekddddddddddkke | 35 | 13891 | 13906 | 146 |
| 568655 | 2482 | 2497 | GGTGCTTGCATCTTTC | eekddddddddddkke | 58 | 13951 | 13966 | 147 |
| 568656 | 2492 | 2507 | CAGAAATTCAGGTGCT | eekddddddddddkke | 47 | 13961 | 13976 | 148 |
| 568657 | 2503 | 2518 | CCGCATTCAAACAGAA | eekddddddddddkke | 38 | 13972 | 13987 | 149 |

TABLE 1-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568658 | 2513 | 2528 | AGCTATGGTTCCGCAT | eekddddddddddkke | 55 | 13982 | 13997 | 150 |
| 568659 | 2537 | 2552 | TACTAACACAAGGGAG | eekddddddddddkke | 37 | 14006 | 14021 | 151 |
| 568660 | 2558 | 2573 | TTATTGTGGCAAGACG | eekddddddddddkke | 48 | 14027 | 14042 | 152 |
| 568661 | N/A | N/A | TTACTAATACAGCCCA | eekddddddddddkke | 31 | 3322 | 3337 | 153 |
| 568662 | N/A | N/A | GGTTTCCCTGATGCAG | eekddddddddddkke | 34 | 3516 | 3531 | 154 |
| 568663 | N/A | N/A | TGATAGTTGGATTCCT | eekddddddddddkke | 21 | 4783 | 4798 | 155 |
| 568664 | N/A | N/A | TGTGGTCCCAACATGC | eekddddddddddkke | 41 | 4944 | 4959 | 156 |
| 568665 | N/A | N/A | TTGAAGTCCTCAACCC | eekddddddddddkke | 26 | 5460 | 5475 | 157 |
| 568670 | N/A | N/A | CTCTTGGATGTCACAG | eekddddddddddkke | 56 | 10997 | 11012 | 158 |
| 568671 | N/A | N/A | GATGGCAAATTTTGTT | eekddddddddddkke | 23 | 11321 | 11336 | 159 |
| 568672 | N/A | N/A | TGTGTTACTTGGGTAA | eekddddddddddkke | 68 | 11933 | 11948 | 160 |
| 568673 | N/A | N/A | GCCACACAGTGAGGGC | eekddddddddddkke | 22 | 12189 | 12204 | 161 |

Table 2 shows the percent inhibition of AGT mRNA by additional gapmer oligonucleotides. Cultured HepG2 cells at a density of about 20,000 cells per well were transfected using electroporation with 4,000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 2

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 92 | 13515 | 13530 | 129 |
| 568637 | 2046 | 2061 | CGCTGATTTGTCCGGG | eekddddddddddkke | 91 | 13515 | 13530 | 129 |
| 568637 | 2046 | 2061 | CGCTGATTTGTCCGGG | eekddddddddddkke | 97 | 13515 | 13530 | 129 |
| 568637 | 2046 | 2061 | CGCTGATTTGTCCGGG | eekddddddddddkke | 94 | 13515 | 13530 | 129 |
| 568637 | 2046 | 2061 | CGCTGATTTGTCCGGG | eekddddddddddkke | 92 | 13515 | 13530 | 129 |
| 568638 | 2056 | 2071 | GGTGACACATCGCTGA | eekddddddddddkke | 82 | 13525 | 13540 | 130 |
| 594621 | 2022 | 2037 | CTGCTGCTGGCCTTTG | kkkddddddddddkkk | 87 | 13491 | 13506 | 162 |
| 594622 | 2027 | 2042 | GTTATCTGCTGCTGGC | kkkddddddddddkkk | 97 | 13496 | 13511 | 163 |
| 594622 | 2027 | 2042 | GTTATCTGCTGCTGGC | kkkddddddddddkkk | 99 | 13496 | 13511 | 163 |
| 594623 | 2032 | 2047 | GGGTTGTTATCTGCTG | kkkddddddddddkkk | 90 | 13501 | 13516 | 164 |
| 594624 | 2046 | 2061 | CGCTGATTTGTCCGGG | kkkddddddddddkkk | 94 | 13515 | 13530 | 129 |
| 594625 | 2047 | 2062 | TCGCTGATTTGTCCGG | kkkddddddddddkkk | 91 | 13516 | 13531 | 165 |
| 594625 | 2047 | 2062 | TCGCTGATTTGTCCGG | kkkddddddddddkkk | 97 | 13516 | 13531 | 165 |
| 594626 | 2049 | 2064 | CATCGCTGATTTGTCC | kkkddddddddddkkk | 0 | 13518 | 13533 | 166 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 594627 | 2053 | 2068 | GACACATCGCTGATTT | kkkddddddddddkkk | 92 | 13522 | 13537 | 167 |
| 594628 | 2073 | 2088 | AAAGGTGGGAGACTGG | kkkddddddddddkkk | 81 | 13542 | 13557 | 168 |
| 594629 | 2082 | 2097 | ATTAGAAGAAAAGGTG | kkkddddddddddkkk | 84 | 13551 | 13566 | 169 |
| 594630 | 2090 | 2105 | GTCGACTCATTAGAAG | kkkddddddddddkkk | 79 | 13559 | 13574 | 170 |
| 594631 | 2095 | 2110 | TCAAAGTCGACTCATT | kkkddddddddddkkk | 91 | 13564 | 13579 | 171 |
| 594632 | 2099 | 2114 | CAGCTCAAAGTCGACT | kkkddddddddddkkk | 96 | 13568 | 13583 | 172 |
| 594641 | 2022 | 2037 | CTGCTGCTGGCCTTTG | eekddddddddddkke | 61 | 13491 | 13506 | 162 |
| 594642 | 2027 | 2042 | GTTATCTGCTGCTGGC | eekddddddddddkke | 91 | 13496 | 13511 | 163 |
| 594643 | 2032 | 2047 | GGGTTGTTATCTGCTG | eekddddddddddkke | 91 | 13501 | 13516 | 164 |
| 594644 | 2047 | 2062 | TCGCTGATTTGTCCGG | eekddddddddddkke | 87 | 13516 | 13531 | 165 |
| 594645 | 2049 | 2064 | CATCGCTGATTTGTCC | eekddddddddddkke | 79 | 13518 | 13533 | 166 |
| 594646 | 2053 | 2068 | GACACATCGCTGATTT | eekddddddddddkke | 80 | 13522 | 13537 | 167 |
| 594647 | 2073 | 2088 | AAAGGTGGGAGACTGG | eekddddddddddkke | 62 | 13542 | 13557 | 168 |
| 609078 | 2020 | 2035 | GCTGCTGGCCTTTGCC | kkkddddddddddkkk | 73 | 13489 | 13504 | 173 |
| 609079 | 2021 | 2036 | TGCTGCTGGCCTTTGC | kkkddddddddddkkk | 69 | 13490 | 13505 | 174 |
| 609080 | 2023 | 2038 | TCTGCTGCTGGCCTTT | kkkddddddddddkkk | 91 | 13492 | 13507 | 175 |
| 609081 | 2024 | 2039 | ATCTGCTGCTGGCCTT | kkkddddddddddkkk | 90 | 13493 | 13508 | 176 |
| 609082 | 2025 | 2040 | TATCTGCTGCTGGCCT | kkkddddddddddkkk | 84 | 13494 | 13509 | 177 |
| 609083 | 2026 | 2041 | TTATCTGCTGCTGGCC | kkkddddddddddkkk | 91 | 13495 | 13510 | 178 |
| 609084 | 2028 | 2043 | TGTTATCTGCTGCTGG | kkkddddddddddkkk | 89 | 13497 | 13512 | 179 |
| 609085 | 2029 | 2044 | TTGTTATCTGCTGCTG | kkkddddddddddkkk | 91 | 13498 | 13513 | 180 |
| 609086 | 2030 | 2045 | GTTGTTATCTGCTGCT | kkkddddddddddkkk | 98 | 13499 | 13514 | 181 |
| 609087 | 2031 | 2046 | GGTTGTTATCTGCTGC | kkkddddddddddkkk | 97 | 13500 | 13515 | 182 |
| 609088 | 2048 | 2063 | ATCGCTGATTTGTCCG | kkkddddddddddkkk | 98 | 13517 | 13532 | 183 |
| 609089 | 2050 | 2065 | ACATCGCTGATTTGTC | kkkddddddddddkkk | 92 | 13519 | 13534 | 184 |
| 609090 | 2051 | 2066 | CACATCGCTGATTTGT | kkkddddddddddkkk | 91 | 13520 | 13535 | 185 |
| 609091 | 2052 | 2067 | ACACATCGCTGATTTG | kkkddddddddddkkk | 96 | 13521 | 13536 | 186 |
| 609092 | 2054 | 2069 | TGACACATCGCTGATT | kkkddddddddddkkk | 34 | 13523 | 13538 | 187 |
| 609093 | 2055 | 2070 | GTGACACATCGCTGAT | kkkddddddddddkkk | 78 | 13524 | 13539 | 188 |
| 609094 | 2056 | 2071 | GGTGACACATCGCTGA | kkkddddddddddkkk | 93 | 13525 | 13540 | 130 |
| 609095 | 2057 | 2072 | GGGTGACACATCGCTG | kkkddddddddddkkk | 96 | 13526 | 13541 | 189 |
| 609096 | 2074 | 2089 | AAAAGGTGGGAGACTG | kkkddddddddddkkk | 70 | 13543 | 13558 | 190 |
| 609097 | 2075 | 2090 | GAAAAGGTGGGAGACT | kkkddddddddddkkk | 80 | 13544 | 13559 | 131 |
| 609098 | 2076 | 2091 | AGAAAAGGTGGGAGAC | kkkddddddddddkkk | 85 | 13545 | 13560 | 191 |
| 609099 | 2080 | 2095 | TAGAAGAAAAGGTGGG | kkkddddddddddkkk | 90 | 13549 | 13564 | 192 |
| 609100 | 2081 | 2096 | TTAGAAGAAAAGGTGG | kkkddddddddddkkk | 95 | 13550 | 13565 | 193 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 609101 | 2083 | 2098 | CATTAGAAGAAAAGGT | kkkddddddddddkkk | 76 | 13552 | 13567 | 194 |
| 609102 | 2084 | 2099 | TCATTAGAAGAAAAGG | kkkddddddddddkkk | 97 | 13553 | 13568 | 195 |
| 609103 | 2085 | 2100 | CTCATTAGAAGAAAAG | kkkddddddddddkkk | 87 | 13554 | 13569 | 196 |
| 609104 | 2086 | 2101 | ACTCATTAGAAGAAAA | kkkddddddddddkkk | 70 | 13555 | 13570 | 197 |
| 609105 | 2087 | 2102 | GACTCATTAGAAGAAA | kkkddddddddddkkk | 93 | 13556 | 13571 | 198 |
| 609106 | 2088 | 2103 | CGACTCATTAGAAGAA | kkkddddddddddkkk | 98 | 13557 | 13572 | 132 |
| 609107 | 2089 | 2104 | TCGACTCATTAGAAGA | kkkddddddddddkkk | 97 | 13558 | 13573 | 199 |
| 609108 | 2091 | 2106 | AGTCGACTCATTAGAA | kkkddddddddddkkk | 97 | 13560 | 13575 | 200 |
| 609109 | 2092 | 2107 | AAGTCGACTCATTAGA | kkkddddddddddkkk | 96 | 13561 | 13576 | 201 |
| 609110 | 2093 | 2108 | AAAGTCGACTCATTAG | kkkddddddddddkkk | 96 | 13562 | 13577 | 202 |
| 609111 | 2094 | 2109 | CAAAGTCGACTCATTA | kkkddddddddddkkk | 92 | 13563 | 13578 | 203 |
| 609112 | 2096 | 2111 | CTCAAAGTCGACTCAT | kkkddddddddddkkk | 93 | 13565 | 13580 | 204 |
| 609113 | 2097 | 2112 | GCTCAAAGTCGACTCA | kkkddddddddddkkk | 97 | 13566 | 13581 | 205 |
| 609114 | 2098 | 2113 | AGCTCAAAGTCGACTC | kkkddddddddddkkk | 95 | 13567 | 13582 | 206 |
| 609115 | 2020 | 2035 | GCTGCTGGCCTTTGCC | eekddddddddddkke | 71 | 13489 | 13504 | 173 |
| 609116 | 2021 | 2036 | TGCTGCTGGCCTTTGC | eekddddddddddkke | 47 | 13490 | 13505 | 174 |
| 609117 | 2023 | 2038 | TCTGCTGCTGGCCTTT | eekddddddddddkke | 74 | 13492 | 13507 | 175 |
| 609118 | 2024 | 2039 | ATCTGCTGCTGGCCTT | eekddddddddddkke | 81 | 13493 | 13508 | 176 |
| 609119 | 2025 | 2040 | TATCTGCTGCTGGCCT | eekddddddddddkke | 76 | 13494 | 13509 | 177 |
| 609120 | 2026 | 2041 | TTATCTGCTGCTGGCC | eekddddddddddkke | 56 | 13495 | 13510 | 178 |
| 609121 | 2028 | 2043 | TGTTATCTGCTGCTGG | eekddddddddddkke | 73 | 13497 | 13512 | 179 |
| 609122 | 2029 | 2044 | TTGTTATCTGCTGCTG | eekddddddddddkke | 87 | 13498 | 13513 | 180 |
| 609123 | 2030 | 2045 | GTTGTTATCTGCTGCT | eekddddddddddkke | 92 | 13499 | 13514 | 181 |
| 609124 | 2031 | 2046 | GGTTGTTATCTGCTGC | eekddddddddddkke | 90 | 13500 | 13515 | 182 |
| 609125 | 2048 | 2063 | ATCGCTGATTTGTCCG | eekddddddddddkke | 91 | 13517 | 13532 | 183 |
| 609126 | 2050 | 2065 | ACATCGCTGATTTGTC | eekddddddddddkke | 66 | 13519 | 13534 | 184 |
| 609127 | 2051 | 2066 | CACATCGCTGATTTGT | eekddddddddddkke | 79 | 13520 | 13535 | 185 |
| 609128 | 2052 | 2067 | ACACATCGCTGATTTG | eekddddddddddkke | 72 | 13521 | 13536 | 186 |
| 609129 | 2054 | 2069 | TGACACATCGCTGATT | eekddddddddddkke | 60 | 13523 | 13538 | 187 |
| 609130 | 2055 | 2070 | GTGACACATCGCTGAT | eekddddddddddkke | 77 | 13524 | 13539 | 188 |
| 609131 | 2057 | 2072 | GGGTGACACATCGCTG | eekddddddddddkke | 85 | 13526 | 13541 | 189 |
| 609132 | 2020 | 2035 | GCTGCTGGCCTTTGCC | eekkddddddkkeee | 47 | 13489 | 13504 | 173 |
| 609133 | 2021 | 2036 | TGCTGCTGGCCTTTGC | eekkddddddkkeee | 44 | 13490 | 13505 | 174 |
| 609134 | 2022 | 2037 | CTGCTGCTGGCCTTTG | eekkddddddkkeee | 62 | 13491 | 13506 | 162 |
| 609135 | 2023 | 2038 | TCTGCTGCTGGCCTTT | eekkddddddkkeee | 59 | 13492 | 13507 | 175 |
| 609136 | 2024 | 2039 | ATCTGCTGCTGGCCTT | eekkddddddkkeee | 70 | 13493 | 13508 | 176 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 609137 | 2025 | 2040 | TATCTGCTGCTGGCCT | eekkddddddddkkeee | 59 | 13494 | 13509 | 177 |
| 609138 | 2026 | 2041 | TTATCTGCTGCTGGCC | eekkddddddddkkeee | 78 | 13495 | 13510 | 178 |
| 609139 | 2027 | 2042 | GTTATCTGCTGCTGGC | eekkddddddddkkeee | 79 | 13496 | 13511 | 163 |
| 609140 | 2028 | 2043 | TGTTATCTGCTGCTGG | eekkddddddddkkeee | 83 | 13497 | 13512 | 179 |
| 609141 | 2029 | 2044 | TTGTTATCTGCTGCTG | eekkddddddddkkeee | 67 | 13498 | 13513 | 180 |
| 609142 | 2030 | 2045 | GTTGTTATCTGCTGCT | eekkddddddddkkeee | 68 | 13499 | 13514 | 181 |
| 609143 | 2031 | 2046 | GGTTGTTATCTGCTGC | eekkddddddddkkeee | 81 | 13500 | 13515 | 182 |
| 609144 | 2032 | 2047 | GGGTTGTTATCTGCTG | eekkddddddddkkeee | 81 | 13501 | 13516 | 164 |
| 609145 | 2046 | 2061 | CGCTGATTTGTCCGGG | eekkddddddddkkeee | 53 | 13515 | 13530 | 129 |
| 609146 | 2047 | 2062 | TCGCTGATTTGTCCGG | eekkddddddddkkeee | 80 | 13516 | 13531 | 165 |
| 609147 | 2048 | 2063 | ATCGCTGATTTGTCCG | eekkddddddddkkeee | 88 | 13517 | 13532 | 183 |
| 609148 | 2049 | 2064 | CATCGCTGATTTGTCC | eekkddddddddkkeee | 75 | 13518 | 13533 | 166 |
| 609149 | 2050 | 2065 | ACATCGCTGATTTGTC | eekkddddddddkkeee | 64 | 13519 | 13534 | 184 |
| 609150 | 2051 | 2066 | CACATCGCTGATTTGT | eekkddddddddkkeee | 77 | 13520 | 13535 | 185 |
| 609151 | 2052 | 2067 | ACACATCGCTGATTTG | eekkddddddddkkeee | 57 | 13521 | 13536 | 186 |
| 609152 | 2053 | 2068 | GACACATCGCTGATTT | eekkddddddddkkeee | 52 | 13522 | 13537 | 167 |
| 609153 | 2054 | 2069 | TGACACATCGCTGATT | eekkddddddddkkeee | 37 | 13523 | 13538 | 187 |
| 609154 | 2055 | 2070 | GTGACACATCGCTGAT | eekkddddddddkkeee | 50 | 13524 | 13539 | 188 |
| 609155 | 2056 | 2071 | GGTGACACATCGCTGA | eekkddddddddkkeee | 60 | 13525 | 13540 | 130 |
| 609156 | 2057 | 2072 | GGGTGACACATCGCTG | eekkddddddddkkeee | 54 | 13526 | 13541 | 189 |
| 609157 | 2073 | 2088 | AAAGGTGGGAGACTGG | eekkddddddddkkeee | 40 | 13542 | 13557 | 168 |
| 609158 | 2020 | 2035 | GCTGCTGGCCTTTGCC | eekkddddddddkkee | 77 | 13489 | 13504 | 173 |
| 609159 | 2021 | 2036 | TGCTGCTGGCCTTTGC | eekkddddddddkkee | 85 | 13490 | 13505 | 174 |
| 609160 | 2022 | 2037 | CTGCTGCTGGCCTTTG | eekkddddddddkkee | 81 | 13491 | 13506 | 162 |
| 609161 | 2023 | 2038 | TCTGCTGCTGGCCTTT | eekkddddddddkkee | 91 | 13492 | 13507 | 175 |
| 609162 | 2024 | 2039 | ATCTGCTGCTGGCCTT | eekkddddddddkkee | 92 | 13493 | 13508 | 176 |
| 609163 | 2025 | 2040 | TATCTGCTGCTGGCCT | eekkddddddddkkee | 83 | 13494 | 13509 | 177 |
| 609164 | 2026 | 2041 | TTATCTGCTGCTGGCC | eekkddddddddkkee | 93 | 13495 | 13510 | 178 |
| 609165 | 2027 | 2042 | GTTATCTGCTGCTGGC | eekkddddddddkkee | 93 | 13496 | 13511 | 163 |
| 609166 | 2028 | 2043 | TGTTATCTGCTGCTGG | eekkddddddddkkee | 98 | 13497 | 13512 | 179 |
| 609167 | 2029 | 2044 | TTGTTATCTGCTGCTG | eekkddddddddkkee | 95 | 13498 | 13513 | 180 |
| 609168 | 2030 | 2045 | GTTGTTATCTGCTGCT | eekkddddddddkkee | 95 | 13499 | 13514 | 181 |
| 609169 | 2031 | 2046 | GGTTGTTATCTGCTGC | eekkddddddddkkee | 95 | 13500 | 13515 | 182 |
| 609170 | 2032 | 2047 | GGGTTGTTATCTGCTG | eekkddddddddkkee | 96 | 13501 | 13516 | 164 |
| 609171 | 2046 | 2061 | CGCTGATTTGTCCGGG | eekkddddddddkkee | 90 | 13515 | 13530 | 129 |
| 609172 | 2047 | 2062 | TCGCTGATTTGTCCGG | eekkddddddddkkee | 92 | 13516 | 13531 | 165 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 609173 | 2048 | 2063 | ATCGCTGATTTGTCCG | eekkddddddddkkee | 94 | 13517 | 13532 | 183 |
| 609174 | 2049 | 2064 | CATCGCTGATTTGTCC | eekkddddddddkkee | 96 | 13518 | 13533 | 166 |
| 609175 | 2050 | 2065 | ACATCGCTGATTTGTC | eekkddddddddkkee | 91 | 13519 | 13534 | 184 |
| 609176 | 2051 | 2066 | CACATCGCTGATTTGT | eekkddddddddkkee | 94 | 13520 | 13535 | 185 |
| 609177 | 2052 | 2067 | ACACATCGCTGATTTG | eekkddddddddkkee | 96 | 13521 | 13536 | 186 |
| 609178 | 2053 | 2068 | GACACATCGCTGATTT | eekkddddddddkkee | 88 | 13522 | 13537 | 167 |
| 609179 | 2054 | 2069 | TGACACATCGCTGATT | eekkddddddddkkee | 84 | 13523 | 13538 | 187 |
| 609180 | 2055 | 2070 | GTGACACATCGCTGAT | eekkddddddddkkee | 83 | 13524 | 13539 | 188 |
| 609181 | 2056 | 2071 | GGTGACACATCGCTGA | eekkddddddddkkee | 87 | 13525 | 13540 | 130 |
| 609182 | 2057 | 2072 | GGGTGACACATCGCTG | eekkddddddddkkee | 90 | 13526 | 13541 | 189 |
| 609183 | 2073 | 2088 | AAAGGTGGGAGACTGG | eekkddddddddkkee | 82 | 13542 | 13557 | 168 |
| 609184 | 2020 | 2035 | GCTGCTGGCCTTTGCC | ekkddddddddkkee | 84 | 13489 | 13504 | 173 |
| 609185 | 2021 | 2036 | TGCTGCTGGCCTTTGC | ekkddddddddkkee | 88 | 13490 | 13505 | 174 |
| 609186 | 2022 | 2037 | CTGCTGCTGGCCTTTG | ekkddddddddkkee | 88 | 13491 | 13506 | 162 |
| 609187 | 2023 | 2038 | TCTGCTGCTGGCCTTT | ekkddddddddkkee | 74 | 13492 | 13507 | 175 |
| 609188 | 2024 | 2039 | ATCTGCTGCTGGCCTT | ekkddddddddkkee | 90 | 13493 | 13508 | 176 |
| 609189 | 2025 | 2040 | TATCTGCTGCTGGCCT | ekkddddddddkkee | 91 | 13494 | 13509 | 177 |
| 609190 | 2026 | 2041 | TTATCTGCTGCTGGCC | ekkddddddddkkee | 87 | 13495 | 13510 | 178 |
| 609191 | 2027 | 2042 | GTTATCTGCTGCTGGC | ekkddddddddkkee | 97 | 13496 | 13511 | 163 |
| 609192 | 2028 | 2043 | TGTTATCTGCTGCTGG | ekkddddddddkkee | 95 | 13497 | 13512 | 179 |
| 609193 | 2029 | 2044 | TTGTTATCTGCTGCTG | ekkddddddddkkee | 96 | 13498 | 13513 | 180 |
| 609194 | 2030 | 2045 | GTTGTTATCTGCTGCT | ekkddddddddkkee | 97 | 13499 | 13514 | 181 |
| 609195 | 2031 | 2046 | GGTTGTTATCTGCTGC | ekkddddddddkkee | 97 | 13500 | 13515 | 182 |
| 609196 | 2032 | 2047 | GGGTTGTTATCTGCTG | ekkddddddddkkee | 98 | 13501 | 13516 | 164 |
| 609197 | 2046 | 2061 | CGCTGATTTGTCCGGG | ekkddddddddkkee | 96 | 13515 | 13530 | 129 |
| 609198 | 2047 | 2062 | TCGCTGATTTGTCCGG | ekkddddddddkkee | 95 | 13516 | 13531 | 165 |
| 609199 | 2048 | 2063 | ATCGCTGATTTGTCCG | ekkddddddddkkee | 96 | 13517 | 13532 | 183 |
| 609200 | 2049 | 2064 | CATCGCTGATTTGTCC | ekkddddddddkkee | 94 | 13518 | 13533 | 166 |
| 609201 | 2050 | 2065 | ACATCGCTGATTTGTC | ekkddddddddkkee | 94 | 13519 | 13534 | 184 |
| 609202 | 2051 | 2066 | CACATCGCTGATTTGT | ekkddddddddkkee | 94 | 13520 | 13535 | 185 |
| 609203 | 2052 | 2067 | ACACATCGCTGATTTG | ekkddddddddkkee | 91 | 13521 | 13536 | 186 |
| 609204 | 2053 | 2068 | GACACATCGCTGATTT | ekkddddddddkkee | 94 | 13522 | 13537 | 167 |
| 609205 | 2054 | 2069 | TGACACATCGCTGATT | ekkddddddddkkee | 87 | 13523 | 13538 | 187 |
| 609206 | 2055 | 2070 | GTGACACATCGCTGAT | ekkddddddddkkee | 91 | 13524 | 13539 | 188 |
| 609207 | 2056 | 2071 | GGTGACACATCGCTGA | ekkddddddddkkee | 93 | 13525 | 13540 | 130 |
| 609208 | 2057 | 2072 | GGGTGACACATCGCTG | ekkddddddddkkee | 97 | 13526 | 13541 | 189 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 609209 | 2073 | 2088 | AAAGGTGGGAGACTGG | ekkddddddddkkee | 95 | 13542 | 13557 | 168 |
| 609983 | 1983 | 2002 | AGGCCTTGCCAGGCACTGTG | eeeeddddddddddeeeee | 75 | 13452 | 13471 | 207 |
| 609984 | 1984 | 2003 | GAGGCCTTGCCAGGCACTGT | eeeeddddddddddeeeee | 54 | 13453 | 13472 | 208 |
| 609985 | 1985 | 2004 | AGAGGCCTTGCCAGGCACTG | eeeeddddddddddeeeee | 63 | 13454 | 13473 | 209 |
| 609986 | 1986 | 2005 | CAGAGGCCTTGCCAGGCACT | eeeeddddddddddeeeee | 63 | 13455 | 13474 | 210 |
| 609987 | 1987 | 2006 | GCAGAGGCCTTGCCAGGCAC | eeeeddddddddddeeeee | 36 | 13456 | 13475 | 211 |
| 609988 | 1988 | 2007 | GGCAGAGGCCTTGCCAGGCA | eeeeddddddddddeeeee | 48 | 13457 | 13476 | 212 |
| 609989 | 1989 | 2008 | GGGCAGAGGCCTTGCCAGGC | eeeeddddddddddeeeee | 55 | 13458 | 13477 | 213 |
| 609990 | 2007 | 2026 | CTTTGCCTCAAAGGCCAGGG | eeeeddddddddddeeeee | 38 | 13476 | 13495 | 214 |
| 609991 | 2008 | 2027 | CCTTTGCCTCAAAGGCCAGG | eeeeddddddddddeeeee | 12 | 13477 | 13496 | 215 |
| 609992 | 2009 | 2028 | GCCTTTGCCTCAAAGGCCAG | eeeeddddddddddeeeee | 11 | 13478 | 13497 | 216 |
| 609993 | 2010 | 2029 | GGCCTTTGCCTCAAAGGCCA | eeeeddddddddddeeeee | 16 | 13479 | 13498 | 217 |
| 609994 | 2011 | 2030 | TGGCCTTTGCCTCAAAGGCC | eeeeddddddddddeeeee | 13 | 13480 | 13499 | 218 |
| 609995 | 2012 | 2031 | CTGGCCTTTGCCTCAAAGGC | eeeeddddddddddeeeee | 13 | 13481 | 13500 | 219 |
| 609996 | 2013 | 2032 | GCTGGCCTTTGCCTCAAAGG | eeeeddddddddddeeeee | 35 | 13482 | 13501 | 220 |
| 609997 | 2014 | 2033 | TGCTGGCCTTTGCCTCAAAG | eeeeddddddddddeeeee | 20 | 13483 | 13502 | 221 |
| 609998 | 2015 | 2034 | CTGCTGGCCTTTGCCTCAAA | eeeeddddddddddeeeee | 33 | 13484 | 13503 | 222 |
| 609999 | 2016 | 2035 | GCTGCTGGCCTTTGCCTCAA | eeeeddddddddddeeeee | 69 | 13485 | 13504 | 223 |
| 610000 | 2017 | 2036 | TGCTGCTGGCCTTTGCCTCA | eeeeddddddddddeeeee | 55 | 13486 | 13505 | 224 |
| 610001 | 2018 | 2037 | CTGCTGCTGGCCTTTGCCTC | eeeeddddddddddeeeee | 73 | 13487 | 13506 | 225 |
| 610002 | 2019 | 2038 | TCTGCTGCTGGCCTTTGCCT | eeeeddddddddddeeeee | 72 | 13488 | 13507 | 226 |
| 610003 | 2020 | 2039 | ATCTGCTGCTGGCCTTTGCC | eeeeddddddddddeeeee | 69 | 13489 | 13508 | 227 |
| 610004 | 2021 | 2040 | TATCTGCTGCTGGCCTTTGC | eeeeddddddddddeeeee | 56 | 13490 | 13509 | 228 |
| 610005 | 2022 | 2041 | TTATCTGCTGCTGGCCTTTG | eeeeddddddddddeeeee | 29 | 13491 | 13510 | 229 |
| 610006 | 2023 | 2042 | GTTATCTGCTGCTGGCCTTT | eeeeddddddddddeeeee | 74 | 13492 | 13511 | 230 |
| 610007 | 2024 | 2043 | TGTTATCTGCTGCTGGCCTT | eeeeddddddddddeeeee | 74 | 13493 | 13512 | 231 |
| 610008 | 2025 | 2044 | TTGTTATCTGCTGCTGGCCT | eeeeddddddddddeeeee | 72 | 13494 | 13513 | 232 |
| 610009 | 2026 | 2045 | GTTGTTATCTGCTGCTGGCC | eeeeddddddddddeeeee | 73 | 13495 | 13514 | 233 |
| 610010 | 2027 | 2046 | GGTTGTTATCTGCTGCTGGC | eeeeddddddddddeeeee | 83 | 13496 | 13515 | 234 |
| 610011 | 2028 | 2047 | GGGTTGTTATCTGCTGCTGG | eeeeddddddddddeeeee | 76 | 13497 | 13516 | 235 |
| 610012 | 2046 | 2065 | ACATCGCTGATTTGTCCGGG | eeeeddddddddddeeeee | 79 | 13515 | 13534 | 236 |
| 610013 | 2047 | 2066 | CACATCGCTGATTTGTCCGG | eeeeddddddddddeeeee | 79 | 13516 | 13535 | 237 |
| 610014 | 2048 | 2067 | ACACATCGCTGATTTGTCCG | eeeeddddddddddeeeee | 77 | 13517 | 13536 | 238 |
| 610015 | 2049 | 2068 | GACACATCGCTGATTTGTCC | eeeeddddddddddeeeee | 89 | 13518 | 13537 | 239 |
| 610016 | 2050 | 2069 | TGACACATCGCTGATTTGTC | eeeeddddddddddeeeee | 83 | 13519 | 13538 | 240 |
| 610017 | 2051 | 2070 | GTGACACATCGCTGATTTGT | eeeeddddddddddeeeee | 74 | 13520 | 13539 | 241 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610018 | 2052 | 2071 | GGTGACACATCGCTGATTTG | eeeeedddddddddddeeeee | 74 | 13521 | 13540 | 242 |
| 610019 | 2053 | 2072 | GGGTGACACATCGCTGATTT | eeeeedddddddddddeeeee | 76 | 13522 | 13541 | 243 |
| 610020 | 2073 | 2092 | AAGAAAAGGTGGGAGACTGG | eeeeedddddddddddeeeee | 24 | 13542 | 13561 | 244 |
| 610021 | 2074 | 2093 | GAAGAAAAGGTGGGAGACTG | eeeeedddddddddddeeeee | 23 | 13543 | 13562 | 245 |
| 610022 | 2075 | 2094 | AGAAGAAAAGGTGGGAGACT | eeeeedddddddddddeeeee | 26 | 13544 | 13563 | 246 |
| 610023 | 2076 | 2095 | TAGAAGAAAAGGTGGGAGAC | eeeeedddddddddddeeeee | 24 | 13545 | 13564 | 247 |
| 610024 | 2077 | 2096 | TTAGAAGAAAAGGTGGGAGA | eeeeedddddddddddeeeee | 19 | 13546 | 13565 | 248 |
| 610025 | 2078 | 2097 | ATTAGAAGAAAAGGTGGGAG | eeeeedddddddddddeeeee | 30 | 13547 | 13566 | 249 |
| 610026 | 2079 | 2098 | CATTAGAAGAAAAGGTGGGA | eeeeedddddddddddeeeee | 40 | 13548 | 13567 | 250 |
| 610027 | 2080 | 2099 | TCATTAGAAGAAAAGGTGGG | eeeeedddddddddddeeeee | 56 | 13549 | 13568 | 251 |
| 610028 | 2081 | 2100 | CTCATTAGAAGAAAAGGTGG | eeeeedddddddddddeeeee | 74 | 13550 | 13569 | 252 |
| 610029 | 2082 | 2101 | ACTCATTAGAAGAAAAGGTG | eeeeedddddddddddeeeee | 62 | 13551 | 13570 | 253 |
| 610030 | 2083 | 2102 | GACTCATTAGAAGAAAAGGT | eeeeedddddddddddeeeee | 69 | 13552 | 13571 | 254 |
| 610031 | 2084 | 2103 | CGACTCATTAGAAGAAAAGG | eeeeedddddddddddeeeee | 59 | 13553 | 13572 | 255 |
| 610032 | 2085 | 2104 | TCGACTCATTAGAAGAAAAG | eeeeedddddddddddeeeee | 50 | 13554 | 13573 | 256 |
| 610033 | 2086 | 2105 | GTCGACTCATTAGAAGAAAA | eeeeedddddddddddeeeee | 67 | 13555 | 13574 | 257 |
| 610034 | 2087 | 2106 | AGTCGACTCATTAGAAGAAA | eeeeedddddddddddeeeee | 62 | 13556 | 13575 | 258 |
| 610035 | 2088 | 2107 | AAGTCGACTCATTAGAAGAA | eeeeedddddddddddeeeee | 45 | 13557 | 13576 | 259 |
| 610036 | 2089 | 2108 | AAAGTCGACTCATTAGAAGA | eeeeedddddddddddeeeee | 43 | 13558 | 13577 | 260 |
| 610037 | 2090 | 2109 | CAAAGTCGACTCATTAGAAG | eeeeedddddddddddeeeee | 46 | 13559 | 13578 | 261 |
| 610038 | 2091 | 2110 | TCAAAGTCGACTCATTAGAA | eeeeedddddddddddeeeee | 67 | 13560 | 13579 | 262 |
| 610039 | 2092 | 2111 | CTCAAAGTCGACTCATTAGA | eeeeedddddddddddeeeee | 65 | 13561 | 13580 | 263 |
| 610040 | 2093 | 2112 | GCTCAAAGTCGACTCATTAG | eeeeedddddddddddeeeee | 74 | 13562 | 13581 | 264 |
| 610041 | 2094 | 2113 | AGCTCAAAGTCGACTCATTA | eeeeedddddddddddeeeee | 61 | 13563 | 13582 | 265 |
| 610042 | 2095 | 2114 | CAGCTCAAAGTCGACTCATT | eeeeedddddddddddeeeee | 71 | 13564 | 13583 | 266 |
| 610043 | 2096 | 2115 | CCAGCTCAAAGTCGACTCAT | eeeeedddddddddddeeeee | 77 | 13565 | 13584 | 267 |
| 610044 | 2097 | 2116 | TCCAGCTCAAAGTCGACTCA | eeeeedddddddddddeeeee | 82 | 13566 | 13585 | 268 |
| 610045 | 2098 | 2117 | TTCCAGCTCAAAGTCGACTC | eeeeedddddddddddeeeee | 80 | 13567 | 13586 | 269 |
| 610046 | 2099 | 2118 | TTTCCAGCTCAAAGTCGACT | eeeeedddddddddddeeeee | 84 | 13568 | 13587 | 270 |
| 610047 | 2100 | 2119 | CTTTCCAGCTCAAAGTCGAC | eeeeedddddddddddeeeee | 65 | 13569 | 13588 | 271 |
| 610048 | 2101 | 2120 | GCTTTCCAGCTCAAAGTCGA | eeeeedddddddddddeeeee | 61 | 13570 | 13589 | 272 |
| 610049 | 2102 | 2121 | TGCTTTCCAGCTCAAAGTCG | eeeeedddddddddddeeeee | 69 | 13571 | 13590 | 273 |
| 610050 | 2103 | 2122 | CTGCTTTCCAGCTCAAAGTC | eeeeedddddddddddeeeee | 54 | 13572 | 13591 | 274 |
| 610051 | 2104 | 2123 | GCTGCTTTCCAGCTCAAAGT | eeeeedddddddddddeeeee | 57 | 13573 | 13592 | 275 |
| 610052 | 2105 | 2124 | GGCTGCTTTCCAGCTCAAAG | eeeeedddddddddddeeeee | 63 | 13574 | 13593 | 276 |
| 610053 | 2106 | 2125 | CGGCTGCTTTCCAGCTCAAA | eeeeedddddddddddeeeee | 40 | 13575 | 13594 | 277 |

TABLE 2-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610054 | 2107 | 2126 | ACGGCTGCTTTCCAGCTCAA | eeeedddddddddeeeee | 62 | 13576 | 13595 | 278 |
| 610055 | 2108 | 2127 | AACGGCTGCTTTCCAGCTCA | eeeedddddddddeeeee | 69 | 13577 | 13596 | 279 |
| 610056 | 2109 | 2128 | AAACGGCTGCTTTCCAGCTC | eeeedddddddddeeeee | 54 | 13578 | 13597 | 280 |
| 610057 | 2110 | 2129 | GAAACGGCTGCTTTCCAGCT | eeeedddddddddeeeee | 64 | 13579 | 13598 | 281 |
| 610058 | 2111 | 2130 | AGAAACGGCTGCTTTCCAGC | eeeedddddddddeeeee | 57 | 13580 | 13599 | 282 |
| 610059 | 2112 | 2131 | GAGAAACGGCTGCTTTCCAG | eeeedddddddddeeeee | 56 | 13581 | 13600 | 283 |
| 610060 | 2113 | 2132 | GGAGAAACGGCTGCTTTCCA | eeeedddddddddeeeee | 73 | 13582 | 13601 | 284 |

Table 3 shows inhibition of AGT mRNA in HepG2 cells cultured at a density of 20,000 cells per well which were transfected using electroporation with 500 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 3

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 65 | 13515 | 13530 | 129 |
| 568637 | 2046 | 2061 | CGCTGATTTGTCCGGG | eekddddddddddkke | 75 | 13515 | 13530 | 129 |
| 568637 | 2046 | 2061 | CGCTGATTTGTCCGGG | eekddddddddddkke | 0 | 13515 | 13530 | 129 |
| 568637 | 2046 | 2061 | CGCTGATTTGTCCGGG | eekddddddddddkke | 72 | 13515 | 13530 | 129 |
| 568637 | 2046 | 2061 | CGCTGATTTGTCCGGG | eekddddddddddkke | 65 | 13515 | 13530 | 129 |
| 594622 | 2027 | 2042 | GTTATCTGCTGCTGGC | kkkddddddddddkkk | 80 | 13496 | 13511 | 163 |
| 594622 | 2027 | 2042 | GTTATCTGCTGCTGGC | kkkddddddddddkkk | 81 | 13496 | 13511 | 163 |
| 594622 | 2027 | 2042 | GTTATCTGCTGCTGGC | kkkddddddddddkkk | 81 | 13496 | 13511 | 163 |
| 594622 | 2027 | 2042 | GTTATCTGCTGCTGGC | kkkddddddddddkkk | 76 | 13496 | 13511 | 163 |
| 594622 | 2027 | 2042 | GTTATCTGCTGCTGGC | kkkddddddddddkkk | 88 | 13496 | 13511 | 163 |
| 594625 | 2047 | 2062 | TCGCTGATTTGTCCGG | kkkddddddddddkkk | 68 | 13516 | 13531 | 165 |
| 594625 | 2047 | 2062 | TCGCTGATTTGTCCGG | kkkddddddddddkkk | 75 | 13516 | 13531 | 165 |
| 594625 | 2047 | 2062 | TCGCTGATTTGTCCGG | kkkddddddddddkkk | 62 | 13516 | 13531 | 165 |
| 594625 | 2047 | 2062 | TCGCTGATTTGTCCGG | kkkddddddddddkkk | 54 | 13516 | 13531 | 165 |
| 594625 | 2047 | 2062 | TCGCTGATTTGTCCGG | kkkddddddddddkkk | 81 | 13516 | 13531 | 165 |
| 611901 | 1 | 16 | TGCCCGCTCATGGGAT | ekkddddddddddkke | 13 | 1986 | 2001 | 14 |
| 611902 | 6 | 21 | CCTGCTGCCCGCTCAT | ekkddddddddddkke | 19 | 1991 | 2006 | 285 |
| 611903 | 11 | 26 | CTGACCCTGCTGCCCG | ekkddddddddddkke | 19 | 1996 | 2011 | 286 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 611904 | 16 | 31 | CACTTCTGACCCTGCT | ekkdddddddddddkke | 0 | 2001 | 2016 | 287 |
| 611905 | 35 | 50 | GCTTAGGCAACACGGG | ekkdddddddddddkke | 0 | 2020 | 2035 | 16 |
| 611906 | 40 | 55 | GTCTTGCTTAGGCAAC | ekkdddddddddddkke | 27 | 2025 | 2040 | 288 |
| 611907 | 45 | 60 | GGAGAGTCTTGCTTAG | ekkdddddddddddkke | 0 | 2030 | 2045 | 17 |
| 611908 | 67 | 82 | GGTGCAGAGGGCAGAG | ekkdddddddddddkke | 0 | 2052 | 2067 | 289 |
| 611909 | 72 | 87 | CCGGAGGTGCAGAGGG | ekkdddddddddddkke | 17 | 2057 | 2072 | 290 |
| 611910 | 77 | 92 | GCAGGCCGGAGGTGCA | ekkdddddddddddkke | 10 | 2062 | 2077 | 291 |
| 611911 | 82 | 97 | GACATGCAGGCCGGAG | ekkdddddddddddkke | 16 | 2067 | 2082 | 292 |
| 611912 | 87 | 102 | ACAGGGACATGCAGGC | ekkdddddddddddkke | 20 | 2072 | 2087 | 293 |
| 611913 | 92 | 107 | AGGCCACAGGGACATG | ekkdddddddddddkke | 5 | 2077 | 2092 | 294 |
| 611914 | 97 | 112 | CCAAGAGGCCACAGGG | ekkdddddddddddkke | 0 | 2082 | 2097 | 295 |
| 611915 | 102 | 117 | TACCCCAAGAGGCCA | ekkdddddddddddkke | 0 | 2087 | 2102 | 296 |
| 611916 | 107 | 122 | AGATGTACCCCAAGA | ekkdddddddddddkke | 8 | 2092 | 2107 | 297 |
| 611917 | 112 | 127 | CCGGAGATGTACCCC | ekkdddddddddddkke | 16 | 2097 | 2112 | 298 |
| 611918 | 117 | 132 | CAGCCCCGGGAGATGT | ekkdddddddddddkke | 15 | 2102 | 2117 | 299 |
| 611919 | 122 | 137 | TGACCCAGCCCCGGGA | ekkdddddddddddkke | 4 | 2107 | 2122 | 20 |
| 611920 | 127 | 142 | CCTTCTGACCCAGCCC | ekkdddddddddddkke | 23 | 2112 | 2127 | 300 |
| 611921 | 132 | 147 | CCAGGCCTTCTGACCC | ekkdddddddddddkke | 20 | 2117 | 2132 | 301 |
| 611922 | 137 | 152 | ACCACCCAGGCCTTCT | ekkdddddddddddkke | 15 | 2122 | 2137 | 302 |
| 611923 | 142 | 157 | GGCCAACCACCCAGGC | ekkdddddddddddkke | 11 | 2127 | 2142 | 303 |
| 611924 | 147 | 162 | CCTGAGGCCAACCACC | ekkdddddddddddkke | 0 | 2132 | 2147 | 304 |
| 611925 | 152 | 167 | GACAGCCTGAGGCCAA | ekkdddddddddddkke | 18 | 2137 | 2152 | 305 |
| 611926 | 157 | 172 | TGTGTGACAGCCTGAG | ekkdddddddddddkke | 12 | 2142 | 2157 | 306 |
| 611927 | 162 | 177 | CTAGGTGTGTGACAGC | ekkdddddddddddkke | 23 | 2147 | 2162 | 307 |
| 611928 | 167 | 182 | TCTCCCTAGGTGTGTG | ekkdddddddddddkke | 9 | 2152 | 2167 | 308 |
| 611929 | 172 | 187 | GAGCATCTCCCTAGGT | ekkdddddddddddkke | 12 | 2157 | 2172 | 309 |
| 611930 | 177 | 192 | AACGGGAGCATCTCCC | ekkdddddddddddkke | 8 | 2162 | 2177 | 310 |
| 611931 | 182 | 197 | CCAGAAACGGGAGCAT | ekkdddddddddddkke | 9 | 2167 | 2182 | 311 |
| 611932 | 187 | 202 | GGTTCCCAGAAACGGG | ekkdddddddddddkke | 13 | 2172 | 2187 | 312 |
| 611933 | 192 | 207 | GCCAAGGTTCCCAGAA | ekkdddddddddddkke | 33 | 2177 | 2192 | 313 |
| 611934 | 208 | 223 | GTTTGCAGGAGTCGGG | ekkdddddddddddkke | 17 | 2193 | 2208 | 314 |
| 611935 | 213 | 228 | CCGAAGTTTGCAGGAG | ekkdddddddddddkke | 27 | 2198 | 2213 | 315 |
| 611936 | 218 | 233 | ATTTACCGAAGTTTGC | ekkdddddddddddkke | 7 | 2203 | 2218 | 316 |
| 611937 | 223 | 238 | TACACATTTACCGAAG | ekkdddddddddddkke | 14 | 2208 | 2223 | 317 |
| 611938 | 228 | 243 | CGAGTTACACATTTAC | ekkdddddddddddkke | 12 | 2213 | 2228 | 318 |
| 611939 | 233 | 248 | AGGGTCGAGTTACACA | ekkdddddddddddkke | 9 | 2218 | 2233 | 319 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 611940 | 238 | 253 | GGTGCAGGGTCGAGTT | ekkdddddddddddkke | 28 | 2223 | 2238 | 320 |
| 611941 | 243 | 258 | GAGCCGGTGCAGGGTC | ekkdddddddddddkke | 26 | 2228 | 2243 | 321 |
| 611942 | 248 | 263 | AGAGTGAGCCGGTGCA | ekkdddddddddddkke | 8 | 2233 | 2248 | 27 |
| 611943 | 253 | 268 | TGAACAGAGTGAGCCG | ekkdddddddddddkke | 16 | 2238 | 2253 | 322 |
| 611944 | 258 | 273 | ACTGCTGAACAGAGTG | ekkdddddddddddkke | 17 | 2243 | 2258 | 28 |
| 611945 | 263 | 278 | GTTTCACTGCTGAACA | ekkdddddddddddkke | 17 | 2248 | 2263 | 323 |
| 611946 | 268 | 283 | GCAGAGTTTCACTGCT | ekkdddddddddddkke | 0 | 2253 | 2268 | 29 |
| 611947 | 273 | 288 | TCGATGCAGAGTTTCA | ekkdddddddddddkke | 2 | 2258 | 2273 | 324 |
| 611948 | 278 | 293 | AGTGATCGATGCAGAG | ekkdddddddddddkke | 12 | 2263 | 2278 | 30 |
| 611949 | 283 | 298 | GTCTTAGTGATCGATG | ekkdddddddddddkke | 0 | 2268 | 2283 | 325 |
| 611950 | 288 | 303 | AGGAAGTCTTAGTGAT | ekkdddddddddddkke | 3 | 2273 | 2288 | 31 |
| 611951 | 293 | 308 | CTTCCAGGAAGTCTTA | ekkdddddddddddkke | 10 | 2278 | 2293 | 326 |
| 611952 | 299 | 314 | GGACCTCTTCCAGGAA | ekkdddddddddddkke | 21 | 2284 | 2299 | 327 |
| 611953 | 304 | 319 | CGCTGGGACCTCTTCC | ekkdddddddddddkke | 20 | 2289 | 2304 | 328 |
| 611954 | 309 | 324 | ACTCACGCTGGGACCT | ekkdddddddddddkke | 0 | 2294 | 2309 | 329 |
| 611955 | 314 | 329 | GCGACACTCACGCTGG | ekkdddddddddddkke | 21 | 2299 | 2314 | 330 |
| 611956 | 319 | 334 | CAGAAGCGACACTCAC | ekkdddddddddddkke | 18 | 2304 | 2319 | 331 |
| 611957 | 324 | 339 | GATGCCAGAAGCGACA | ekkdddddddddddkke | 1 | 2309 | 2324 | 332 |
| 611958 | 329 | 344 | GGACAGATGCCAGAAG | ekkdddddddddddkke | 16 | 2314 | 2329 | 333 |
| 611959 | 334 | 349 | CAGAAGGACAGATGCC | ekkdddddddddddkke | 0 | 2319 | 2334 | 334 |
| 611960 | 339 | 354 | CTGGCCAGAAGGACAG | ekkdddddddddddkke | 13 | 2324 | 2339 | 335 |
| 611961 | 344 | 359 | ACAGGCTGGCCAGAAG | ekkdddddddddddkke | 15 | 2329 | 2344 | 336 |
| 611962 | 349 | 364 | AGACCACAGGCTGGCC | ekkdddddddddddkke | 17 | 2334 | 2349 | 337 |
| 611963 | 354 | 369 | TGGCCAGACCACAGGC | ekkdddddddddddkke | 21 | 2339 | 2354 | 338 |
| 611964 | 359 | 374 | TCACTTGGCCAGACCA | ekkdddddddddddkke | 7 | 2344 | 2359 | 339 |
| 611965 | 364 | 379 | TTACATCACTTGGCCA | ekkdddddddddddkke | 21 | 2349 | 2364 | 340 |
| 611966 | 369 | 384 | GAGGGTTACATCACTT | ekkdddddddddddkke | 20 | 2354 | 2369 | 341 |
| 611967 | 374 | 389 | GAGAGGAGGGTTACAT | ekkdddddddddddkke | 18 | 2359 | 2374 | 342 |
| 611968 | 386 | 401 | GTGCACAGGCTGGAGA | ekkdddddddddddkke | 4 | 2371 | 2386 | 36 |
| 611969 | 391 | 406 | TGCCTGTGCACAGGCT | ekkdddddddddddkke | 10 | 2376 | 2391 | 343 |
| 611970 | 396 | 411 | CAGGCTGCCTGTGCAC | ekkdddddddddddkke | 26 | 2381 | 2396 | 344 |
| 611971 | 401 | 416 | GTTCCCAGGCTGCCTG | ekkdddddddddddkke | 30 | 2386 | 2401 | 345 |
| 611972 | 406 | 421 | GAGCTGTTCCCAGGCT | ekkdddddddddddkke | 15 | 2391 | 2406 | 346 |
| 611973 | 411 | 426 | GGATGGAGCTGTTCCC | ekkdddddddddddkke | 19 | 2396 | 2411 | 347 |
| 611974 | 431 | 446 | TATTTATAGCTGAGGG | ekkdddddddddddkke | 11 | 2416 | 2431 | 37 |
| 611975 | 436 | 451 | TGCCCTATTTATAGCT | ekkdddddddddddkke | 20 | 2421 | 2436 | 348 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 611976 | 441 | 456 | CACGATGCCCTATTTA | ekkddddddddddkke | 11 | 2426 | 2441 | 38 |
| 612381 | 1852 | 1867 | CTCCAAGACCTCAGGC | ekkddddddddddkke | 4 | 13321 | 13336 | 349 |
| 612382 | 1855 | 1870 | CACCTCCAAGACCTCA | ekkddddddddddkke | 18 | 13324 | 13339 | 350 |
| 612383 | 1858 | 1873 | GGTCACCTCCAAGACC | ekkddddddddddkke | 0 | 13327 | 13342 | 351 |
| 612384 | 1861 | 1876 | CAGGGTCACCTCCAAG | ekkddddddddddkke | 16 | 13330 | 13345 | 352 |
| 612385 | 1864 | 1879 | GTTCAGGGTCACCTCC | ekkddddddddddkke | 28 | 13333 | 13348 | 353 |
| 612386 | 1867 | 1882 | GCGGTTCAGGGTCACC | ekkddddddddddkke | 18 | 13336 | 13351 | 354 |
| 612387 | 1873 | 1888 | GAATGGGCGGTTCAGG | ekkddddddddddkke | 6 | 13342 | 13357 | 355 |
| 612388 | 1876 | 1891 | CAGGAATGGGCGGTTC | ekkddddddddddkke | 13 | 13345 | 13360 | 356 |
| 612389 | 1879 | 1894 | AAACAGGAATGGGCGG | ekkddddddddddkke | 16 | 13348 | 13363 | 357 |
| 612390 | 1883 | 1898 | CAGCAAACAGGAATGG | ekkddddddddddkke | 11 | 13352 | 13367 | 358 |
| 612391 | 1887 | 1902 | TACACAGCAAACAGGA | ekkddddddddddkke | 8 | 13356 | 13371 | 359 |
| 612392 | 1892 | 1907 | GATCATACACAGCAAA | ekkddddddddddkke | 6 | 13361 | 13376 | 360 |
| 612393 | 1895 | 1910 | TTTGATCATACACAGC | ekkddddddddddkke | 15 | 13364 | 13379 | 361 |
| 612394 | 1898 | 1913 | CGCTTTGATCATACAC | ekkddddddddddkke | 16 | 13367 | 13382 | 362 |
| 612395 | 1916 | 1931 | GGAAGTGCAGGGCAGT | ekkddddddddddkke | 8 | 13385 | 13400 | 363 |
| 612396 | 1923 | 1938 | CGGCCCAGGAAGTGCA | ekkddddddddddkke | 0 | 13392 | 13407 | 123 |
| 612397 | 1926 | 1941 | ACGCGGCCCAGGAAGT | ekkddddddddddkke | 1 | 13395 | 13410 | 364 |
| 612398 | 1929 | 1944 | GCCACGCGGCCCAGGA | ekkddddddddddkke | 6 | 13398 | 13413 | 365 |
| 612399 | 1932 | 1947 | TTGGCCACGCGGCCCA | ekkddddddddddkke | 7 | 13401 | 13416 | 366 |
| 612400 | 1935 | 1950 | GGGTTGGCCACGCGGC | ekkddddddddddkke | 29 | 13404 | 13419 | 367 |
| 612401 | 1938 | 1953 | AGCGGGTTGGCCACGC | ekkddddddddddkke | 13 | 13407 | 13422 | 368 |
| 612402 | 1941 | 1956 | CTCAGCGGGTTGGCCA | ekkddddddddddkke | 0 | 13410 | 13425 | 369 |
| 612403 | 1944 | 1959 | GTGCTCAGCGGGTTGG | ekkddddddddddkke | 13 | 13413 | 13428 | 370 |
| 612404 | 1947 | 1962 | GCTGTGCTCAGCGGGT | ekkddddddddddkke | 39 | 13416 | 13431 | 371 |
| 612405 | 1949 | 1964 | ATGCTGTGCTCAGCGG | ekkddddddddddkke | 13 | 13418 | 13433 | 372 |
| 612406 | 1950 | 1965 | CATGCTGTGCTCAGCG | ekkddddddddddkke | 20 | 13419 | 13434 | 373 |
| 612407 | 1951 | 1966 | TCATGCTGTGCTCAGC | ekkddddddddddkke | 23 | 13420 | 13435 | 374 |
| 612408 | 1952 | 1967 | CTCATGCTGTGCTCAG | ekkddddddddddkke | 29 | 13421 | 13436 | 375 |
| 612409 | 1954 | 1969 | GCCTCATGCTGTGCTC | ekkddddddddddkke | 36 | 13423 | 13438 | 376 |
| 612410 | 1956 | 1971 | TGGCCTCATGCTGTGC | ekkddddddddddkke | 0 | 13425 | 13440 | 377 |
| 612411 | 1957 | 1972 | CTGGCCTCATGCTGTG | ekkddddddddddkke | 2 | 13426 | 13441 | 378 |
| 612412 | 1959 | 1974 | CCCTGGCCTCATGCTG | ekkddddddddddkke | 5 | 13428 | 13443 | 379 |
| 612413 | 1960 | 1975 | GCCCTGGCCTCATGCT | ekkddddddddddkke | 6 | 13429 | 13444 | 380 |
| 612414 | 1961 | 1976 | GGCCCTGGCCTCATGC | ekkddddddddddkke | 0 | 13430 | 13445 | 126 |
| 612415 | 1976 | 1991 | GGCACTGTGTTCTGGG | ekkddddddddddkke | 45 | 13445 | 13460 | 381 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612416 | 1987 | 2002 | AGGCCTTGCCAGGCAC | ekkdddddddddddkke | 35 | 13456 | 13471 | 382 |
| 612417 | 1992 | 2007 | GGCAGAGGCCTTGCCA | ekkdddddddddddkke | 14 | 13461 | 13476 | 383 |
| 612418 | 2007 | 2022 | GCCTCAAAGGCCAGGG | ekkdddddddddddkke | 0 | 13476 | 13491 | 128 |
| 612419 | 2008 | 2023 | TGCCTCAAAGGCCAGG | ekkdddddddddddkke | 10 | 13477 | 13492 | 384 |
| 612420 | 2009 | 2024 | TTGCCTCAAAGGCCAG | ekkdddddddddddkke | 7 | 13478 | 13493 | 385 |
| 612421 | 2010 | 2025 | TTTGCCTCAAAGGCCA | ekkdddddddddddkke | 13 | 13479 | 13494 | 386 |
| 612422 | 2011 | 2026 | CTTTGCCTCAAAGGCC | ekkdddddddddddkke | 0 | 13480 | 13495 | 387 |
| 612423 | 2012 | 2027 | CCTTTGCCTCAAAGGC | ekkdddddddddddkke | 14 | 13481 | 13496 | 388 |
| 612424 | 2013 | 2028 | GCCTTTGCCTCAAAGG | ekkdddddddddddkke | 3 | 13482 | 13497 | 389 |
| 612425 | 2014 | 2029 | GGCCTTTGCCTCAAAG | ekkdddddddddddkke | 15 | 13483 | 13498 | 390 |
| 612426 | 2015 | 2030 | TGGCCTTTGCCTCAAA | ekkdddddddddddkke | 0 | 13484 | 13499 | 391 |
| 612427 | 2016 | 2031 | CTGGCCTTTGCCTCAA | ekkdddddddddddkke | 0 | 13485 | 13500 | 392 |
| 612428 | 2017 | 2032 | GCTGGCCTTTGCCTCA | ekkdddddddddddkke | 5 | 13486 | 13501 | 393 |
| 612429 | 2100 | 2115 | CCAGCTCAAAGTCGAC | ekkdddddddddddkke | 46 | 13569 | 13584 | 394 |
| 612430 | 2101 | 2116 | TCCAGCTCAAAGTCGA | ekkdddddddddddkke | 34 | 13570 | 13585 | 395 |
| 612431 | 2102 | 2117 | TTCCAGCTCAAAGTCG | ekkdddddddddddkke | 16 | 13571 | 13586 | 396 |
| 612432 | 2103 | 2118 | TTTCCAGCTCAAAGTC | ekkdddddddddddkke | 5 | 13572 | 13587 | 397 |
| 612433 | 2105 | 2120 | GCTTTCCAGCTCAAAG | ekkdddddddddddkke | 9 | 13574 | 13589 | 398 |
| 612434 | 2110 | 2125 | CGGCTGCTTTCCAGCT | ekkdddddddddddkke | 0 | 13579 | 13594 | 399 |
| 612435 | 2111 | 2126 | ACGGCTGCTTTCCAGC | ekkdddddddddddkke | 24 | 13580 | 13595 | 133 |
| 612436 | 2112 | 2127 | AACGGCTGCTTTCCAG | ekkdddddddddddkke | 14 | 13581 | 13596 | 400 |
| 612437 | 2113 | 2128 | AAACGGCTGCTTTCCA | ekkdddddddddddkke | 14 | 13582 | 13597 | 401 |
| 612438 | 2114 | 2129 | GAAACGGCTGCTTTCC | ekkdddddddddddkke | 13 | 13583 | 13598 | 402 |
| 612439 | 2115 | 2130 | AGAAACGGCTGCTTTC | ekkdddddddddddkke | 15 | 13584 | 13599 | 403 |
| 612440 | 2116 | 2131 | GAGAAACGGCTGCTTT | ekkdddddddddddkke | 33 | 13585 | 13600 | 404 |
| 612441 | 2117 | 2132 | GGAGAAACGGCTGCTT | ekkdddddddddddkke | 26 | 13586 | 13601 | 405 |
| 612442 | 2118 | 2133 | AGGAGAAACGGCTGCT | ekkdddddddddddkke | 50 | 13587 | 13602 | 406 |
| 612443 | 2119 | 2134 | AAGGAGAAACGGCTGC | ekkdddddddddddkke | 21 | 13588 | 13603 | 407 |
| 612444 | 2120 | 2135 | CAAGGAGAAACGGCTG | ekkdddddddddddkke | 30 | 13589 | 13604 | 408 |
| 612445 | 2121 | 2136 | CCAAGGAGAAACGGCT | ekkdddddddddddkke | 43 | 13590 | 13605 | 134 |
| 612446 | 2122 | 2137 | ACCAAGGAGAAACGGC | ekkdddddddddddkke | 32 | 13591 | 13606 | 409 |
| 612447 | 2123 | 2138 | GACCAAGGAGAAACGG | ekkdddddddddddkke | 33 | 13592 | 13607 | 410 |
| 612448 | 2124 | 2139 | AGACCAAGGAGAAACG | ekkdddddddddddkke | 55 | 13593 | 13608 | 411 |
| 612449 | 2125 | 2140 | TAGACCAAGGAGAAAC | ekkdddddddddddkke | 15 | 13594 | 13609 | 412 |
| 612450 | 2126 | 2141 | TTAGACCAAGGAGAAA | ekkdddddddddddkke | 17 | 13595 | 13610 | 413 |
| 612451 | 2128 | 2143 | ACTTAGACCAAGGAGA | ekkdddddddddddkke | 32 | 13597 | 13612 | 414 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612452 | 2129 | 2144 | CACTTAGACCAAGGAG | ekkddddddddddkke | 38 | 13598 | 13613 | 415 |
| 612453 | 2130 | 2145 | ACACTTAGACCAAGGA | ekkddddddddddkke | 48 | 13599 | 13614 | 416 |
| 612454 | 2133 | 2148 | AGCACACTTAGACCAA | ekkddddddddddkke | 29 | 13602 | 13617 | 417 |
| 612455 | 2134 | 2149 | CAGCACACTTAGACCA | ekkddddddddddkke | 31 | 13603 | 13618 | 418 |
| 612456 | 2135 | 2150 | GCAGCACACTTAGACC | ekkddddddddddkke | 13 | 13604 | 13619 | 419 |
| 612457 | 2136 | 2151 | TGCAGCACACTTAGAC | ekkddddddddddkke | 18 | 13605 | 13620 | 420 |
| 612458 | 2137 | 2152 | ATGCAGCACACTTAGA | ekkddddddddddkke | 0 | 13606 | 13621 | 421 |
| 612459 | 2138 | 2153 | CATGCAGCACACTTAG | ekkddddddddddkke | 0 | 13607 | 13622 | 422 |
| 612460 | 2139 | 2154 | CCATGCAGCACACTTA | ekkddddddddddkke | 0 | 13608 | 13623 | 423 |
| 612461 | 2140 | 2155 | TCCATGCAGCACACTT | ekkddddddddddkke | 24 | 13609 | 13624 | 424 |
| 612462 | 2141 | 2156 | CTCCATGCAGCACACT | ekkddddddddddkke | 40 | 13610 | 13625 | 425 |
| 612463 | 2142 | 2157 | ACTCCATGCAGCACAC | ekkddddddddddkke | 0 | 13611 | 13626 | 426 |
| 612464 | 2143 | 2158 | CACTCCATGCAGCACA | ekkddddddddddkke | 18 | 13612 | 13627 | 427 |
| 612465 | 2144 | 2159 | TCACTCCATGCAGCAC | ekkddddddddddkke | 14 | 13613 | 13628 | 428 |
| 612466 | 2162 | 2177 | GCTGCAGGCTTCTACT | ekkddddddddddkke | 12 | 13631 | 13646 | 429 |
| 612467 | 2163 | 2178 | CGCTGCAGGCTTCTAC | ekkddddddddddkke | 2 | 13632 | 13647 | 430 |
| 612468 | 2164 | 2179 | CCGCTGCAGGCTTCTA | ekkddddddddddkke | 2 | 13633 | 13648 | 431 |
| 612469 | 2165 | 2180 | GCCGCTGCAGGCTTCT | ekkddddddddddkke | 12 | 13634 | 13649 | 432 |
| 612470 | 2166 | 2181 | TGCCGCTGCAGGCTTC | ekkddddddddddkke | 1 | 13635 | 13650 | 136 |
| 612471 | 2167 | 2182 | GTGCCGCTGCAGGCTT | ekkddddddddddkke | 12 | 13636 | 13651 | 433 |
| 612472 | 2168 | 2183 | TGTGCCGCTGCAGGCT | ekkddddddddddkke | 31 | 13637 | 13652 | 434 |
| 612473 | 2169 | 2184 | TTGTGCCGCTGCAGGC | ekkddddddddddkke | 20 | 13638 | 13653 | 435 |
| 612474 | 2170 | 2185 | TTTGTGCCGCTGCAGG | ekkddddddddddkke | 27 | 13639 | 13654 | 436 |
| 612475 | 2171 | 2186 | ATTTGTGCCGCTGCAG | ekkddddddddddkke | 29 | 13640 | 13655 | 437 |
| 612476 | 2172 | 2187 | CATTTGTGCCGCTGCA | ekkddddddddddkke | 33 | 13641 | 13656 | 438 |
| 612477 | 2173 | 2188 | GCATTTGTGCCGCTGC | ekkddddddddddkke | 48 | 13642 | 13657 | 439 |
| 612478 | 2174 | 2189 | TGCATTTGTGCCGCTG | ekkddddddddddkke | 13 | 13643 | 13658 | 440 |
| 612479 | 2175 | 2190 | GTGCATTTGTGCCGCT | ekkddddddddddkke | 49 | 13644 | 13659 | 441 |
| 612480 | 2176 | 2191 | GGTGCATTTGTGCCGC | ekkddddddddddkke | 32 | 13645 | 13660 | 137 |
| 612481 | 2177 | 2192 | AGGTGCATTTGTGCCG | ekkddddddddddkke | 40 | 13646 | 13661 | 442 |
| 612482 | 2178 | 2193 | GAGGTGCATTTGTGCC | ekkddddddddddkke | 48 | 13647 | 13662 | 443 |
| 612483 | 2179 | 2194 | GGAGGTGCATTTGTGC | ekkddddddddddkke | 17 | 13648 | 13663 | 444 |
| 612484 | 2180 | 2195 | GGGAGGTGCATTTGTG | ekkddddddddddkke | 15 | 13649 | 13664 | 445 |
| 612485 | 2181 | 2196 | TGGGAGGTGCATTTGT | ekkddddddddddkke | 25 | 13650 | 13665 | 446 |
| 612486 | 2182 | 2197 | CTGGGAGGTGCATTTG | ekkddddddddddkke | 25 | 13651 | 13666 | 447 |
| 612487 | 2183 | 2198 | ACTGGGAGGTGCATTT | ekkddddddddddkke | 19 | 13652 | 13667 | 448 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612488 | 2184 | 2199 | AACTGGGAGGTGCATT | ekkdddddddddddkke | 0 | 13653 | 13668 | 449 |
| 612489 | 2185 | 2200 | AAACTGGGAGGTGCAT | ekkdddddddddddkke | 14 | 13654 | 13669 | 450 |
| 612490 | 2186 | 2201 | CAAACTGGGAGGTGCA | ekkdddddddddddkke | 53 | 13655 | 13670 | 451 |
| 612491 | 2187 | 2202 | GCAAACTGGGAGGTGC | ekkdddddddddddkke | 63 | 13656 | 13671 | 452 |
| 612492 | 2188 | 2203 | AGCAAACTGGGAGGTG | ekkdddddddddddkke | 26 | 13657 | 13672 | 453 |
| 612493 | 2192 | 2207 | ACCCAGCAAACTGGGA | ekkdddddddddddkke | 0 | 13661 | 13676 | 454 |
| 612494 | 2193 | 2208 | AACCCAGCAAACTGGG | ekkdddddddddddkke | 0 | 13662 | 13677 | 455 |
| 612495 | 2195 | 2210 | TAAACCCAGCAAACTG | ekkdddddddddddkke | 8 | 13664 | 13679 | 456 |
| 612496 | 2196 | 2211 | ATAAACCCAGCAAACT | ekkdddddddddddkke | 4 | 13665 | 13680 | 457 |
| 612497 | 2210 | 2225 | CCCCATTCTCTAAAAT | ekkdddddddddddkke | 24 | 13679 | 13694 | 458 |
| 612498 | 2211 | 2226 | CCCCCATTCTCTAAAA | ekkdddddddddddkke | 0 | 13680 | 13695 | 459 |
| 612499 | 2212 | 2227 | ACCCCCATTCTCTAAA | ekkdddddddddddkke | 0 | 13681 | 13696 | 460 |
| 612500 | 2213 | 2228 | CACCCCCATTCTCTAA | ekkdddddddddddkke | 6 | 13682 | 13697 | 461 |
| 612501 | 2214 | 2229 | CCACCCCCATTCTCTA | ekkdddddddddddkke | 39 | 13683 | 13698 | 462 |
| 612502 | 2226 | 2241 | GTTCTTGCCTCCCCAC | ekkdddddddddddkke | 61 | 13695 | 13710 | 463 |
| 612503 | 2227 | 2242 | GGTTCTTGCCTCCCCA | ekkdddddddddddkke | 76 | 13696 | 13711 | 464 |
| 612504 | 2228 | 2243 | TGGTTCTTGCCTCCCC | ekkdddddddddddkke | 59 | 13697 | 13712 | 465 |
| 612505 | 2229 | 2244 | CTGGTTCTTGCCTCCC | ekkdddddddddddkke | 66 | 13698 | 13713 | 466 |
| 612506 | 2230 | 2245 | ACTGGTTCTTGCCTCC | ekkdddddddddddkke | 70 | 13699 | 13714 | 467 |
| 612507 | 2231 | 2246 | CACTGGTTCTTGCCTC | ekkdddddddddddkke | 57 | 13700 | 13715 | 468 |
| 612508 | 2232 | 2247 | ACACTGGTTCTTGCCT | ekkdddddddddddkke | 45 | 13701 | 13716 | 469 |
| 612509 | 2233 | 2248 | AACACTGGTTCTTGCC | ekkdddddddddddkke | 66 | 13702 | 13717 | 470 |
| 612510 | 2234 | 2249 | AAACACTGGTTCTTGC | ekkdddddddddddkke | 52 | 13703 | 13718 | 471 |
| 612511 | 2235 | 2250 | TAAACACTGGTTCTTG | ekkdddddddddddkke | 17 | 13704 | 13719 | 472 |
| 612512 | 2236 | 2251 | CTAAACACTGGTTCTT | ekkdddddddddddkke | 35 | 13705 | 13720 | 473 |
| 612513 | 2237 | 2252 | GCTAAACACTGGTTCT | ekkdddddddddddkke | 53 | 13706 | 13721 | 474 |
| 612514 | 2238 | 2253 | CGCTAAACACTGGTTC | ekkdddddddddddkke | 56 | 13707 | 13722 | 475 |
| 612515 | 2239 | 2254 | GCGCTAAACACTGGTT | ekkdddddddddddkke | 59 | 13708 | 13723 | 476 |
| 612516 | 2240 | 2255 | CGCGCTAAACACTGGT | ekkdddddddddddkke | 66 | 13709 | 13724 | 477 |
| 612517 | 2241 | 2256 | CCGCGCTAAACACTGG | ekkdddddddddddkke | 57 | 13710 | 13725 | 478 |
| 612518 | 2242 | 2257 | CCCGCGCTAAACACTG | ekkdddddddddddkke | 35 | 13711 | 13726 | 479 |
| 612519 | 2243 | 2258 | TCCCGCGCTAAACACT | ekkdddddddddddkke | 60 | 13712 | 13727 | 480 |
| 612520 | 2244 | 2259 | GTCCCGCGCTAAACAC | ekkdddddddddddkke | 38 | 13713 | 13728 | 481 |
| 612521 | 2245 | 2260 | AGTCCCGCGCTAAACA | ekkdddddddddddkke | 35 | 13714 | 13729 | 482 |
| 612522 | 2246 | 2261 | TAGTCCCGCGCTAAAC | ekkdddddddddddkke | 1 | 13715 | 13730 | 483 |
| 612524 | 2248 | 2263 | AGTAGTCCCGCGCTAA | ekkdddddddddddkke | 47 | 13717 | 13732 | 484 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612525 | 2249 | 2264 | CAGTAGTCCCGCGCTA | ekkddddddddddkke | 13 | 13718 | 13733 | 485 |
| 612526 | 2250 | 2265 | ACAGTAGTCCCGCGCT | ekkddddddddddkke | 32 | 13719 | 13734 | 486 |
| 612527 | 2251 | 2266 | AACAGTAGTCCCGCGC | ekkddddddddddkke | 46 | 13720 | 13735 | 487 |
| 612528 | 2252 | 2267 | GAACAGTAGTCCCGCG | ekkddddddddddkke | 27 | 13721 | 13736 | 488 |
| 612529 | 2253 | 2268 | GGAACAGTAGTCCCGC | ekkddddddddddkke | 46 | 13722 | 13737 | 489 |
| 612530 | 2254 | 2269 | TGGAACAGTAGTCCCG | ekkddddddddddkke | 17 | 13723 | 13738 | 490 |
| 612531 | 2255 | 2270 | TTGGAACAGTAGTCCC | ekkddddddddddkke | 42 | 13724 | 13739 | 491 |
| 612532 | 2256 | 2271 | TTTGGAACAGTAGTCC | ekkddddddddddkke | 14 | 13725 | 13740 | 492 |
| 612533 | 2257 | 2272 | TTTTGGAACAGTAGTC | ekkddddddddddkke | 7 | 13726 | 13741 | 493 |
| 612534 | 2258 | 2273 | TTTTTGGAACAGTAGT | ekkddddddddddkke | 4 | 13727 | 13742 | 494 |
| 612535 | 2259 | 2274 | CTTTTTGGAACAGTAG | ekkddddddddddkke | 31 | 13728 | 13743 | 495 |
| 612536 | 2264 | 2279 | GAATTCTTTTTGGAAC | ekkddddddddddkke | 6 | 13733 | 13748 | 496 |
| 612537 | 2265 | 2280 | GGAATTCTTTTTGGAA | ekkddddddddddkke | 45 | 13734 | 13749 | 497 |
| 612538 | 2266 | 2281 | TGGAATTCTTTTTGGA | ekkddddddddddkke | 42 | 13735 | 13750 | 498 |
| 612539 | 2267 | 2282 | TTGGAATTCTTTTTGG | ekkddddddddddkke | 26 | 13736 | 13751 | 499 |
| 612540 | 2270 | 2285 | CGGTTGGAATTCTTTT | ekkddddddddddkke | 61 | 13739 | 13754 | 500 |
| 612541 | 2271 | 2286 | TCGGTTGGAATTCTTT | ekkddddddddddkke | 58 | 13740 | 13755 | 501 |
| 612542 | 2272 | 2287 | GTCGGTTGGAATTCTT | ekkddddddddddkke | 60 | 13741 | 13756 | 502 |
| 612543 | 2273 | 2288 | GGTCGGTTGGAATTCT | ekkddddddddddkke | 58 | 13742 | 13757 | 503 |
| 612544 | 2274 | 2289 | TGGTCGGTTGGAATTC | ekkddddddddddkke | 46 | 13743 | 13758 | 138 |
| 612545 | 2275 | 2290 | CTGGTCGGTTGGAATT | ekkddddddddddkke | 0 | 13744 | 13759 | 504 |
| 612546 | 2276 | 2291 | GCTGGTCGGTTGGAAT | ekkddddddddddkke | 27 | 13745 | 13760 | 505 |
| 612547 | 2277 | 2292 | AGCTGGTCGGTTGGAA | ekkddddddddddkke | 33 | 13746 | 13761 | 506 |
| 612548 | 2278 | 2293 | AAGCTGGTCGGTTGGA | ekkddddddddddkke | 51 | 13747 | 13762 | 507 |
| 612549 | 2279 | 2294 | CAAGCTGGTCGGTTGG | ekkddddddddddkke | 32 | 13748 | 13763 | 508 |
| 612550 | 2280 | 2295 | ACAAGCTGGTCGGTTG | ekkddddddddddkke | 19 | 13749 | 13764 | 509 |
| 612551 | 2281 | 2296 | AACAAGCTGGTCGGTT | ekkddddddddddkke | 39 | 13750 | 13765 | 510 |
| 612552 | 2282 | 2297 | AAACAAGCTGGTCGGT | ekkddddddddddkke | 49 | 13751 | 13766 | 511 |
| 612553 | 2283 | 2298 | CAAACAAGCTGGTCGG | ekkddddddddddkke | 63 | 13752 | 13767 | 512 |
| 612554 | 2284 | 2299 | ACAAACAAGCTGGTCG | ekkddddddddddkke | 48 | 13753 | 13768 | 139 |
| 612555 | 2285 | 2300 | CACAAACAAGCTGGTC | ekkddddddddddkke | 37 | 13754 | 13769 | 513 |
| 612556 | 2286 | 2301 | TCACAAACAAGCTGGT | ekkddddddddddkke | 28 | 13755 | 13770 | 514 |
| 612557 | 2287 | 2302 | TTCACAAACAAGCTGG | ekkddddddddddkke | 52 | 13756 | 13771 | 515 |
| 612558 | 2288 | 2303 | TTTCACAAACAAGCTG | ekkddddddddddkke | 14 | 13757 | 13772 | 516 |
| 612559 | 2289 | 2304 | GTTTCACAAACAAGCT | ekkddddddddddkke | 65 | 13758 | 13773 | 517 |
| 612560 | 2290 | 2305 | TGTTTCACAAACAAGC | ekkddddddddddkke | 58 | 13759 | 13774 | 518 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612561 | 2291 | 2306 | TTGTTTCACAAACAAG | ekkddddddddddkke | 8 | 13760 | 13775 | 519 |
| 612562 | 2304 | 2319 | AGGGAACACTTTTTTG | ekkddddddddddkke | 26 | 13773 | 13788 | 520 |
| 612563 | 2311 | 2326 | CTTGAAAAGGGAACAC | ekkddddddddddkke | 29 | 13780 | 13795 | 140 |
| 612564 | 2312 | 2327 | ACTTGAAAAGGGAACA | ekkddddddddddkke | 19 | 13781 | 13796 | 521 |
| 612565 | 2313 | 2328 | AACTTGAAAAGGGAAC | ekkddddddddddkke | 2 | 13782 | 13797 | 522 |
| 612566 | 2316 | 2331 | CTCAACTTGAAAAGGG | ekkddddddddddkke | 49 | 13785 | 13800 | 523 |
| 612567 | 2321 | 2336 | TTGTTCTCAACTTGAA | ekkddddddddddkke | 58 | 13790 | 13805 | 524 |
| 612568 | 2322 | 2337 | TTTGTTCTCAACTTGA | ekkddddddddddkke | 63 | 13791 | 13806 | 525 |
| 612569 | 2329 | 2344 | CCCAATTTTGTTCTC | ekkddddddddddkke | 65 | 13798 | 13813 | 526 |
| 612570 | 2330 | 2345 | ACCCAATTTTTGTTCT | ekkddddddddddkke | 37 | 13799 | 13814 | 527 |
| 612571 | 2331 | 2346 | AACCCAATTTTTGTTC | ekkddddddddddkke | 30 | 13800 | 13815 | 141 |
| 612572 | 2362 | 2377 | GGCAATGCAAAAATGT | ekkddddddddddkke | 53 | 13831 | 13846 | 142 |
| 612573 | 2366 | 2381 | CGAAGGCAATGCAAAA | ekkddddddddddkke | 7 | 13835 | 13850 | 528 |
| 612574 | 2367 | 2382 | CCGAAGGCAATGCAAA | ekkddddddddddkke | 25 | 13836 | 13851 | 529 |
| 612575 | 2368 | 2383 | ACCGAAGGCAATGCAA | ekkddddddddddkke | 36 | 13837 | 13852 | 530 |
| 612576 | 2369 | 2384 | AACCGAAGGCAATGCA | ekkddddddddddkke | 36 | 13838 | 13853 | 531 |
| 612577 | 2370 | 2385 | AAACCGAAGGCAATGC | ekkddddddddddkke | 29 | 13839 | 13854 | 532 |
| 612578 | 2371 | 2386 | CAAACCGAAGGCAATG | ekkddddddddddkke | 6 | 13840 | 13855 | 533 |
| 612579 | 2372 | 2387 | ACAAACCGAAGGCAAT | ekkddddddddddkke | 0 | 13841 | 13856 | 534 |
| 612580 | 2373 | 2388 | TACAAACCGAAGGCAA | ekkddddddddddkke | 27 | 13842 | 13857 | 535 |
| 612581 | 2374 | 2389 | ATACAAACCGAAGGCA | ekkddddddddddkke | 13 | 13843 | 13858 | 536 |
| 612582 | 2375 | 2390 | AATACAAACCGAAGGC | ekkddddddddddkke | 0 | 13844 | 13859 | 537 |
| 612583 | 2376 | 2391 | AAATACAAACCGAAGG | ekkddddddddddkke | 0 | 13845 | 13860 | 538 |
| 612584 | 2377 | 2392 | TAAATACAAACCGAAG | ekkddddddddddkke | 25 | 13846 | 13861 | 539 |
| 612585 | 2378 | 2393 | CTAAATACAAACCGAA | ekkddddddddddkke | 0 | 13847 | 13862 | 540 |
| 612586 | 2379 | 2394 | ACTAAATACAAACCGA | ekkddddddddddkke | 19 | 13848 | 13863 | 541 |
| 612587 | 2380 | 2395 | CACTAAATACAAACCG | ekkddddddddddkke | 15 | 13849 | 13864 | 542 |
| 612588 | 2382 | 2397 | GACACTAAATACAAAC | ekkddddddddddkke | 0 | 13851 | 13866 | 543 |
| 612589 | 2385 | 2400 | CAAGACACTAAATACA | ekkddddddddddkke | 9 | 13854 | 13869 | 544 |
| 612590 | 2386 | 2401 | TCAAGACACTAAATAC | ekkddddddddddkke | 19 | 13855 | 13870 | 545 |
| 612591 | 2387 | 2402 | TTCAAGACACTAAATA | ekkddddddddddkke | 0 | 13856 | 13871 | 546 |
| 612592 | 2388 | 2403 | ATTCAAGACACTAAAT | ekkddddddddddkke | 2 | 13857 | 13872 | 547 |
| 612593 | 2389 | 2404 | CATTCAAGACACTAAA | ekkddddddddddkke | 0 | 13858 | 13873 | 548 |
| 612594 | 2390 | 2405 | ACATTCAAGACACTAA | ekkddddddddddkke | 8 | 13859 | 13874 | 549 |
| 612595 | 2391 | 2406 | TACATTCAAGACACTA | ekkddddddddddkke | 1 | 13860 | 13875 | 143 |
| 612596 | 2392 | 2407 | TTACATTCAAGACACT | ekkddddddddddkke | 3 | 13861 | 13876 | 550 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612597 | 2393 | 2408 | CTTACATTCAAGACAC | ekkddddddddddkke | 0 | 13862 | 13877 | 551 |
| 612598 | 2394 | 2409 | TCTTACATTCAAGACA | ekkddddddddddkke | 0 | 13863 | 13878 | 552 |
| 612599 | 2395 | 2410 | TTCTTACATTCAAGAC | ekkddddddddddkke | 0 | 13864 | 13879 | 553 |
| 612600 | 2398 | 2413 | ATGTTCTTACATTCAA | ekkddddddddddkke | 10 | 13867 | 13882 | 554 |
| 612601 | 2401 | 2416 | GTCATGTTCTTACATT | ekkddddddddddkke | 0 | 13870 | 13885 | 555 |
| 612602 | 2402 | 2417 | GGTCATGTTCTTACAT | ekkddddddddddkke | 34 | 13871 | 13886 | 144 |
| 612603 | 2403 | 2418 | AGGTCATGTTCTTACA | ekkddddddddddkke | 35 | 13872 | 13887 | 556 |
| 612604 | 2404 | 2419 | GAGGTCATGTTCTTAC | ekkddddddddddkke | 37 | 13873 | 13888 | 557 |
| 612605 | 2405 | 2420 | GGAGGTCATGTTCTTA | ekkddddddddddkke | 25 | 13874 | 13889 | 558 |
| 612606 | 2406 | 2421 | CGGAGGTCATGTTCTT | ekkddddddddddkke | 31 | 13875 | 13890 | 559 |
| 612607 | 2407 | 2422 | ACGGAGGTCATGTTCT | ekkddddddddddkke | 23 | 13876 | 13891 | 560 |
| 612608 | 2408 | 2423 | CACGGAGGTCATGTTC | ekkddddddddddkke | 24 | 13877 | 13892 | 561 |
| 612685 | 2565 | 2580 | TGGAGGCTTATTGTGG | ekkddddddddddkke | 25 | 14034 | 14049 | 562 |
| 612686 | 2566 | 2581 | TTGGAGGCTTATTGTG | ekkddddddddddkke | 30 | 14035 | 14050 | 563 |
| 612687 | 2567 | 2582 | TTTGGAGGCTTATTGT | ekkddddddddddkke | 20 | 14036 | 14051 | 564 |
| 612688 | N/A | N/A | CGGCTTACCTTCTGCT | ekkddddddddddkke | 30 | 2483 | 2498 | 565 |
| 612689 | N/A | N/A | CCTCCCGGCCTTTTCC | ekkddddddddddkke | 23 | 2562 | 2577 | 566 |
| 612690 | N/A | N/A | TAGGGTGACCACTCTG | ekkddddddddddkke | 26 | 2897 | 2912 | 567 |
| 612691 | N/A | N/A | AGCAAATCGAGGTTCA | ekkddddddddddkke | 25 | 2970 | 2985 | 568 |
| 612692 | N/A | N/A | TATTAGTTCTCTTCAG | ekkddddddddddkke | 9 | 3047 | 3062 | 569 |
| 612693 | N/A | N/A | CCTTTTAGCTTATCCC | ekkddddddddddkke | 24 | 3089 | 3104 | 570 |
| 612694 | N/A | N/A | AATCTGCCTTTTAGCT | ekkddddddddddkke | 20 | 3095 | 3110 | 571 |
| 612695 | N/A | N/A | CAATCTACGCTGCCCT | ekkddddddddddkke | 27 | 3124 | 3139 | 572 |
| 612696 | N/A | N/A | AGCACCAATCTACGCT | ekkddddddddddkke | 16 | 3129 | 3144 | 573 |
| 612697 | N/A | N/A | CATCCTGGAGAAGTAG | ekkddddddddddkke | 9 | 3276 | 3291 | 574 |
| 612698 | N/A | N/A | GCATCCTGGAGAAGTA | ekkddddddddddkke | 13 | 3277 | 3292 | 575 |
| 612699 | N/A | N/A | ATACAGCCCACATTCC | ekkddddddddddkke | 17 | 3316 | 3331 | 576 |
| 612700 | N/A | N/A | CTGTACCATGTAGTTA | ekkddddddddddkke | 32 | 3418 | 3433 | 577 |
| 612701 | N/A | N/A | CCACACCGGGCACTCT | ekkddddddddddkke | 12 | 3476 | 3491 | 578 |
| 612702 | N/A | N/A | CCCACCACACCGGGCA | ekkddddddddddkke | 22 | 3480 | 3495 | 579 |
| 612703 | N/A | N/A | TTCCCCACCACACCGG | ekkddddddddddkke | 19 | 3483 | 3498 | 580 |
| 612704 | N/A | N/A | TTCACCCTGCAGCTTT | ekkddddddddddkke | 13 | 3497 | 3512 | 581 |
| 612705 | N/A | N/A | CATAGTCCTCACCTTC | ekkddddddddddkke | 16 | 3537 | 3552 | 582 |
| 612706 | N/A | N/A | GTGAAGATGACGGCTC | ekkddddddddddkke | 24 | 3615 | 3630 | 583 |
| 612707 | N/A | N/A | TATGTCTCCCTACTTC | ekkddddddddddkke | 25 | 3651 | 3666 | 584 |
| 612708 | N/A | N/A | GGGAGTAATGGTGCTC | ekkddddddddddkke | 33 | 3755 | 3770 | 585 |

TABLE 3-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612709 | N/A | N/A | GTCCTGGGAGTAATGG | ekkddddddddddkke | 24 | 3760 | 3775 | 586 |
| 612710 | N/A | N/A | GGGAACCGACTGCTGG | ekkddddddddddkke | 24 | 3977 | 3992 | 587 |
| 612711 | N/A | N/A | CCTGTGGGAACCGACT | ekkddddddddddkke | 14 | 3982 | 3997 | 588 |
| 612712 | N/A | N/A | CCTAATCTAGACAGTC | ekkddddddddddkke | 5 | 4024 | 4039 | 589 |
| 612713 | N/A | N/A | CATCCGCTGTTCTCAG | ekkddddddddddkke | 2 | 4133 | 4148 | 590 |
| 612714 | N/A | N/A | CTCCATCCGCTGTTCT | ekkddddddddddkke | 28 | 4136 | 4151 | 591 |
| 612715 | N/A | N/A | GACTCCATCCGCTGTT | ekkddddddddddkke | 30 | 4138 | 4153 | 592 |
| 612716 | N/A | N/A | TGACTCCATCCGCTGT | ekkddddddddddkke | 25 | 4139 | 4154 | 593 |
| 612717 | N/A | N/A | GCTGAAGTACCTGGTG | ekkddddddddddkke | 34 | 4230 | 4245 | 594 |
| 612718 | N/A | N/A | GCCCTCAACACGGTGC | ekkddddddddddkke | 25 | 4250 | 4265 | 595 |
| 612719 | N/A | N/A | TGCCCTCAACACGGTG | ekkddddddddddkke | 20 | 4251 | 4266 | 596 |
| 612720 | N/A | N/A | GTCATTCTTCTTACAT | ekkddddddddddkke | 14 | 4307 | 4322 | 597 |
| 612721 | N/A | N/A | GCTTCCTTGGAGCTGT | ekkddddddddddkke | 5 | 4390 | 4405 | 598 |
| 612722 | N/A | N/A | GTGTACTGCAATATCG | ekkddddddddddkke | 39 | 4446 | 4461 | 599 |
| 612723 | N/A | N/A | CACTCATTTCTTGTGG | ekkddddddddddkke | 8 | 4468 | 4483 | 600 |
| 612724 | N/A | N/A | TTGTACCACATCTCAC | ekkddddddddddkke | 21 | 4481 | 4496 | 601 |
| 612725 | N/A | N/A | GTTCTCTCAAAGGCCT | ekkddddddddddkke | 32 | 4651 | 4666 | 602 |
| 612726 | N/A | N/A | GCAGGGTTTAGAACCC | ekkddddddddddkke | 18 | 4694 | 4709 | 603 |
| 612727 | N/A | N/A | TATGTAAGCAGGGTTT | ekkddddddddddkke | 11 | 4701 | 4716 | 604 |
| 612728 | N/A | N/A | AAACCAGCTCTCAACC | ekkddddddddddkke | 5 | 4864 | 4879 | 605 |
| 612729 | N/A | N/A | TAAGACATGCTCCTGC | ekkddddddddddkke | 12 | 5094 | 5109 | 606 |
| 612730 | N/A | N/A | ACTTATGGCAGCCCAA | ekkddddddddddkke | 20 | 5116 | 5131 | 607 |
| 612731 | N/A | N/A | TACTTATGGCAGCCCA | ekkddddddddddkke | 12 | 5117 | 5132 | 608 |
| 612732 | N/A | N/A | CCATTATTTGGAGACA | ekkddddddddddkke | 9 | 5426 | 5441 | 609 |
| 612733 | N/A | N/A | TGCCATCTAACCAGAT | ekkddddddddddkke | 15 | 5655 | 5670 | 610 |
| 612745 | N/A | N/A | GTTTTCAGTAATGCCC | ekkddddddddddkke | 21 | 7085 | 7100 | 611 |

Table 4 shows inhibition of AGT mRNA in HepG2 cells cultured at a density of 20,000 cells per well which were transfected using electroporation with 1000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 4

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 43 | 13515 | 13530 | 129 |
| 568637 | 2046 | 2061 | CGCTGATTTGTCCGGG | eekddddddddddkke | 36 | 13515 | 13530 | 129 |
| 568637 | 2046 | 2061 | CGCTGATTTGTCCGGG | eekddddddddddkke | 20 | 13515 | 13530 | 129 |
| 568637 | 2046 | 2061 | CGCTGATTTGTCCGGG | eekddddddddddkke | 51 | 13515 | 13530 | 129 |
| 594622 | 2027 | 2042 | GTTATCTGCTGCTGGC | kkkddddddddddkkk | 92 | 13496 | 13511 | 163 |
| 594622 | 2027 | 2042 | GTTATCTGCTGCTGGC | kkkddddddddddkkk | 91 | 13496 | 13511 | 163 |
| 594622 | 2027 | 2042 | GTTATCTGCTGCTGGC | kkkddddddddddkkk | 92 | 13496 | 13511 | 163 |
| 594622 | 2027 | 2042 | GTTATCTGCTGCTGGC | kkkddddddddddkkk | 90 | 13496 | 13511 | 163 |
| 594625 | 2047 | 2062 | TCGCTGATTTGTCCGG | kkkddddddddddkkk | 79 | 13516 | 13531 | 165 |
| 594625 | 2047 | 2062 | TCGCTGATTTGTCCGG | kkkddddddddddkkk | 88 | 13516 | 13531 | 165 |
| 594625 | 2047 | 2062 | TCGCTGATTTGTCCGG | kkkddddddddddkkk | 80 | 13516 | 13531 | 165 |
| 594625 | 2047 | 2062 | TCGCTGATTTGTCCGG | kkkddddddddddkkk | 73 | 13516 | 13531 | 165 |
| 611977 | 446 | 461 | CGGGTCACGATGCCCT | ekkddddddddddkke | 13 | 2431 | 2446 | 612 |
| 611978 | 451 | 466 | CCGGCCGGGTCACGAT | ekkddddddddddkke | 20 | 2436 | 2451 | 613 |
| 611979 | 454 | 469 | CCCCCGGCCGGGTCAC | ekkddddddddddkke | 26 | 2439 | 2454 | 614 |
| 611980 | 457 | 472 | CTTCCCCCGGCCGGGT | ekkddddddddddkke | 20 | 2442 | 2457 | 615 |
| 611981 | 460 | 475 | CTTCTTCCCCCGGCCG | ekkddddddddddkke | 24 | 2445 | 2460 | 616 |
| 611982 | 463 | 478 | CAGCTTCTTCCCCCGG | ekkddddddddddkke | 41 | 2448 | 2463 | 617 |
| 611983 | 466 | 481 | CGGCAGCTTCTTCCCC | ekkddddddddddkke | 15 | 2451 | 2466 | 618 |
| 611984 | 469 | 484 | CAACGGCAGCTTCTTC | ekkddddddddddkke | 20 | 2454 | 2469 | 619 |
| 611985 | 472 | 487 | GAACAACGGCAGCTTC | ekkddddddddddkke | 27 | 2457 | 2472 | 620 |
| 611986 | 475 | 490 | CCAGAACAACGGCAGC | ekkddddddddddkke | 23 | 2460 | 2475 | 621 |
| 611987 | 478 | 493 | TACCCAGAACAACGGC | ekkddddddddddkke | 40 | 2463 | 2478 | 39 |
| 611988 | 481 | 496 | TAGTACCCAGAACAAC | ekkddddddddddkke | 10 | 2466 | 2481 | 622 |
| 611989 | 484 | 499 | CTGTAGTACCCAGAAC | ekkddddddddddkke | 21 | 2469 | 2484 | 623 |
| 611990 | 487 | 502 | CTGCTGTAGTACCCAG | ekkddddddddddkke | 28 | 2472 | 2487 | 624 |
| 611991 | 490 | 505 | CTTCTGCTGTAGTACC | ekkddddddddddkke | 33 | 2475 | 2490 | 625 |
| 611992 | 493 | 508 | ACCCTTCTGCTGTAGT | ekkddddddddddkke | 39 | N/A | N/A | 626 |
| 611993 | 496 | 511 | CATACCCTTCTGCTGT | ekkddddddddddkke | 19 | N/A | N/A | 627 |
| 611994 | 499 | 514 | CCGCATACCCTTCTGC | ekkddddddddddkke | 11 | N/A | N/A | 628 |
| 611995 | 502 | 517 | CTTCCGCATACCCTTC | ekkddddddddddkke | 21 | N/A | N/A | 629 |
| 611996 | 505 | 520 | TCGCTTCCGCATACCC | ekkddddddddddkke | 53 | 5722 | 5737 | 630 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 611997 | 508 | 523 | TGCTCGCTTCCGCATA | ekkddddddddddkke | 6 | 5725 | 5740 | 631 |
| 611998 | 511 | 526 | GGGTGCTCGCTTCCGC | ekkddddddddddkke | 38 | 5728 | 5743 | 632 |
| 611999 | 525 | 540 | GCCATCTCAGACTGGG | ekkddddddddddkke | 31 | 5742 | 5757 | 40 |
| 612000 | 533 | 548 | CGGCAGGAGCCATCTC | ekkddddddddddkke | 31 | 5750 | 5765 | 633 |
| 612001 | 536 | 551 | CACCGGCAGGAGCCAT | ekkddddddddddkke | 19 | 5753 | 5768 | 634 |
| 612002 | 539 | 554 | TCACACCGGCAGGAGC | ekkddddddddddkke | 19 | 5756 | 5771 | 635 |
| 612003 | 542 | 557 | GGCTCACACCGGCAGG | ekkddddddddddkke | 41 | 5759 | 5774 | 636 |
| 612004 | 545 | 560 | TCAGGCTCACACCGGC | ekkddddddddddkke | 46 | 5762 | 5777 | 42 |
| 612005 | 549 | 564 | GCCCTCAGGCTCACAC | ekkddddddddddkke | 18 | 5766 | 5781 | 637 |
| 612006 | 552 | 567 | GTGGCCCTCAGGCTCA | ekkddddddddddkke | 29 | 5769 | 5784 | 638 |
| 612007 | 555 | 570 | ATGGTGGCCCTCAGGC | ekkddddddddddkke | 32 | 5772 | 5787 | 43 |
| 612008 | 561 | 576 | CAGAGGATGGTGGCCC | ekkddddddddddkke | 33 | 5778 | 5793 | 639 |
| 612009 | 596 | 611 | GGTCACCTGCAGCCAG | ekkddddddddddkke | 38 | 5813 | 5828 | 44 |
| 612010 | 599 | 614 | CCCGGTCACCTGCAGC | ekkddddddddddkke | 47 | 5816 | 5831 | 640 |
| 612011 | 602 | 617 | ACACCCGGTCACCTGC | ekkddddddddddkke | 29 | 5819 | 5834 | 641 |
| 612012 | 605 | 620 | TGTACACCCGGTCACC | ekkddddddddddkke | 22 | 5822 | 5837 | 642 |
| 612013 | 608 | 623 | GTATGTACACCCGGTC | ekkddddddddddkke | 5 | 5825 | 5840 | 643 |
| 612014 | 611 | 626 | GGTGTATGTACACCCG | ekkddddddddddkke | 0 | 5828 | 5843 | 644 |
| 612015 | 626 | 641 | TGACGAGGTGGAAGGG | ekkddddddddddkke | 21 | 5843 | 5858 | 645 |
| 612016 | 629 | 644 | GGATGACGAGGTGGAA | ekkddddddddddkke | 32 | 5846 | 5861 | 646 |
| 612017 | 632 | 647 | TGTGGATGACGAGGTG | ekkddddddddddkke | 48 | 5849 | 5864 | 647 |
| 612018 | 635 | 650 | CATTGTGGATGACGAG | ekkddddddddddkke | 28 | 5852 | 5867 | 648 |
| 612019 | 638 | 653 | TCTCATTGTGGATGAC | ekkddddddddddkke | 34 | 5855 | 5870 | 649 |
| 612020 | 639 | 654 | CTCTCATTGTGGATGA | ekkddddddddddkke | 38 | 5856 | 5871 | 650 |
| 612021 | 640 | 655 | ACTCTCATTGTGGATG | ekkddddddddddkke | 45 | 5857 | 5872 | 651 |
| 612022 | 641 | 656 | TACTCTCATTGTGGAT | ekkddddddddddkke | 29 | 5858 | 5873 | 652 |
| 612023 | 642 | 657 | GTACTCTCATTGTGGA | ekkddddddddddkke | 46 | 5859 | 5874 | 653 |
| 612024 | 643 | 658 | GGTACTCTCATTGTGG | ekkddddddddddkke | 58 | 5860 | 5875 | 46 |
| 612025 | 645 | 660 | CAGGTACTCTCATTGT | ekkddddddddddkke | 59 | 5862 | 5877 | 654 |
| 612026 | 646 | 661 | ACAGGTACTCTCATTG | ekkddddddddddkke | 50 | 5863 | 5878 | 655 |
| 612027 | 647 | 662 | CACAGGTACTCTCATT | ekkddddddddddkke | 37 | 5864 | 5879 | 656 |
| 612028 | 648 | 663 | TCACAGGTACTCTCAT | ekkddddddddddkke | 31 | 5865 | 5880 | 657 |
| 612029 | 649 | 664 | CTCACAGGTACTCTCA | ekkddddddddddkke | 22 | 5866 | 5881 | 658 |
| 612030 | 652 | 667 | CTGCTCACAGGTACTC | ekkddddddddddkke | 4 | 5869 | 5884 | 659 |
| 612031 | 659 | 674 | TTGCCAGCTGCTCACA | ekkddddddddddkke | 39 | 5876 | 5891 | 660 |
| 612032 | 662 | 677 | CCTTTGCCAGCTGCTC | ekkddddddddddkke | 45 | 5879 | 5894 | 661 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612033 | 665 | 680 | TGGCCTTTGCCAGCTG | ekkddddddddddkke | 30 | 5882 | 5897 | 662 |
| 612034 | 668 | 683 | CATTGGCCTTTGCCAG | ekkddddddddddkke | 18 | 5885 | 5900 | 663 |
| 612035 | 671 | 686 | CGGCATTGGCCTTTGC | ekkddddddddddkke | 18 | 5888 | 5903 | 664 |
| 612036 | 674 | 689 | TCCCGGCATTGGCCTT | ekkddddddddddkke | 27 | 5891 | 5906 | 665 |
| 612037 | 677 | 692 | GCTTCCCGGCATTGGC | ekkddddddddddkke | 15 | 5894 | 5909 | 666 |
| 612038 | 680 | 695 | TGGGCTTCCCGGCATT | ekkddddddddddkke | 2 | 5897 | 5912 | 667 |
| 612039 | 683 | 698 | CTTTGGGCTTCCCGGC | ekkddddddddddkke | 44 | 5900 | 5915 | 668 |
| 612040 | 686 | 701 | GGTCTTTGGGCTTCCC | ekkddddddddddkke | 36 | 5903 | 5918 | 669 |
| 612041 | 701 | 716 | CAGGTATGAAGGTGGG | ekkddddddddddkke | 42 | 5918 | 5933 | 670 |
| 612042 | 704 | 719 | GAGCAGGTATGAAGGT | ekkddddddddddkke | 39 | 5921 | 5936 | 671 |
| 612043 | 707 | 722 | TTGGAGCAGGTATGAA | ekkddddddddddkke | 28 | 5924 | 5939 | 672 |
| 612044 | 710 | 725 | GAATTGGAGCAGGTAT | ekkddddddddddkke | 20 | 5927 | 5942 | 673 |
| 612045 | 713 | 728 | CCTGAATTGGAGCAGG | ekkddddddddddkke | 7 | 5930 | 5945 | 50 |
| 612046 | 716 | 731 | TGGCCTGAATTGGAGC | ekkddddddddddkke | 23 | 5933 | 5948 | 674 |
| 612047 | 719 | 734 | TCTTGGCCTGAATTGG | ekkddddddddddkke | 29 | 5936 | 5951 | 675 |
| 612048 | 722 | 737 | ATGTCTTGGCCTGAAT | ekkddddddddddkke | 22 | 5939 | 5954 | 676 |
| 612049 | 725 | 740 | GGGATGTCTTGGCCTG | ekkddddddddddkke | 35 | 5942 | 5957 | 677 |
| 612050 | 739 | 754 | CTTTTCATCCACAGGG | ekkddddddddddkke | 21 | 5956 | 5971 | 52 |
| 612051 | 742 | 757 | GGCCTTTTCATCCACA | ekkddddddddddkke | 3 | 5959 | 5974 | 678 |
| 612052 | 745 | 760 | TAGGGCCTTTTCATCC | ekkddddddddddkke | 10 | 5962 | 5977 | 679 |
| 612053 | 748 | 763 | CTGTAGGGCCTTTTCA | ekkddddddddddkke | 5 | 5965 | 5980 | 680 |
| 612054 | 751 | 766 | GTCCTGTAGGGCCTTT | ekkddddddddddkke | 6 | 5968 | 5983 | 681 |
| 612055 | 754 | 769 | CTGGTCCTGTAGGGCC | ekkddddddddddkke | 19 | 5971 | 5986 | 682 |
| 612056 | 758 | 773 | CCAGCTGGTCCTGTAG | ekkddddddddddkke | 34 | 5975 | 5990 | 683 |
| 612057 | 759 | 774 | ACCAGCTGGTCCTGTA | ekkddddddddddkke | 31 | 5976 | 5991 | 684 |
| 612058 | 762 | 777 | AGCACCAGCTGGTCCT | ekkddddddddddkke | 56 | 5979 | 5994 | 53 |
| 612059 | 763 | 778 | TAGCACCAGCTGGTCC | ekkddddddddddkke | 35 | 5980 | 5995 | 685 |
| 612060 | 764 | 779 | CTAGCACCAGCTGGTC | ekkddddddddddkke | 18 | 5981 | 5996 | 686 |
| 612061 | 765 | 780 | ACTAGCACCAGCTGGT | ekkddddddddddkke | 10 | 5982 | 5997 | 687 |
| 612062 | 766 | 781 | GACTAGCACCAGCTGG | ekkddddddddddkke | 32 | 5983 | 5998 | 688 |
| 612063 | 767 | 782 | CGACTAGCACCAGCTG | ekkddddddddddkke | 49 | 5984 | 5999 | 689 |
| 612064 | 768 | 783 | GCGACTAGCACCAGCT | ekkddddddddddkke | 39 | 5985 | 6000 | 690 |
| 612065 | 769 | 784 | AGCGACTAGCACCAGC | ekkddddddddddkke | 29 | 5986 | 6001 | 691 |
| 612066 | 770 | 785 | CAGCGACTAGCACCAG | ekkddddddddddkke | 38 | 5987 | 6002 | 692 |
| 612067 | 771 | 786 | GCAGCGACTAGCACCA | ekkddddddddddkke | 39 | 5988 | 6003 | 693 |
| 612068 | 772 | 787 | TGCAGCGACTAGCACC | ekkddddddddddkke | 31 | 5989 | 6004 | 54 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612069 | 773 | 788 | TTGCAGCGACTAGCAC | ekkddddddddddkke | 28 | 5990 | 6005 | 694 |
| 612070 | 774 | 789 | TTTGCAGCGACTAGCA | ekkddddddddddkke | 31 | 5991 | 6006 | 695 |
| 612071 | 775 | 790 | TTTTGCAGCGACTAGC | ekkddddddddddkke | 28 | 5992 | 6007 | 696 |
| 612072 | 776 | 791 | GTTTTGCAGCGACTAG | ekkddddddddddkke | 11 | 5993 | 6008 | 697 |
| 612073 | 777 | 792 | AGTTTTGCAGCGACTA | ekkddddddddddkke | 7 | 5994 | 6009 | 698 |
| 612074 | 778 | 793 | AAGTTTTGCAGCGACT | ekkddddddddddkke | 10 | 5995 | 6010 | 699 |
| 612075 | 781 | 796 | GTCAAGTTTTGCAGCG | ekkddddddddddkke | 49 | 5998 | 6013 | 700 |
| 612076 | 784 | 799 | GGTGTCAAGTTTTGCA | ekkddddddddddkke | 39 | 6001 | 6016 | 701 |
| 612077 | 787 | 802 | TTCGGTGTCAAGTTTT | ekkddddddddddkke | 53 | 6004 | 6019 | 702 |
| 612078 | 790 | 805 | GTCTTCGGTGTCAAGT | ekkddddddddddkke | 39 | 6007 | 6022 | 703 |
| 612079 | 793 | 808 | CTTGTCTTCGGTGTCA | ekkddddddddddkke | 35 | 6010 | 6025 | 704 |
| 612080 | 796 | 811 | CAACTTGTCTTCGGTG | ekkddddddddddkke | 42 | 6013 | 6028 | 705 |
| 612081 | 799 | 814 | CCTCAACTTGTCTTCG | ekkddddddddddkke | 1 | 6016 | 6031 | 706 |
| 612082 | 802 | 817 | GGCCCTCAACTTGTCT | ekkddddddddddkke | 0 | 6019 | 6034 | 707 |
| 612083 | 805 | 820 | TGCGGCCCTCAACTTG | ekkddddddddddkke | 13 | 6022 | 6037 | 708 |
| 612084 | 808 | 823 | CATTGCGGCCCTCAAC | ekkddddddddddkke | 0 | 6025 | 6040 | 709 |
| 612085 | 811 | 826 | GACCATTGCGGCCCTC | ekkddddddddddkke | 30 | 6028 | 6043 | 710 |
| 612086 | 814 | 829 | CCCGACCATTGCGGCC | ekkddddddddddkke | 32 | 6031 | 6046 | 711 |
| 612087 | 817 | 832 | CATCCCGACCATTGCG | ekkddddddddddkke | 49 | 6034 | 6049 | 712 |
| 612088 | 820 | 835 | CAGCATCCCGACCATT | ekkddddddddddkke | 17 | 6037 | 6052 | 713 |
| 612089 | 823 | 838 | GGCCAGCATCCCGACC | ekkddddddddddkke | 46 | 6040 | 6055 | 714 |
| 612090 | 826 | 841 | GTTGGCCAGCATCCCG | ekkddddddddddkke | 10 | 6043 | 6058 | 715 |
| 612091 | 829 | 844 | GAAGTTGGCCAGCATC | ekkddddddddddkke | 0 | 6046 | 6061 | 716 |
| 612092 | 832 | 847 | CAAGAAGTTGGCCAGC | ekkddddddddddkke | 0 | 6049 | 6064 | 717 |
| 612093 | 835 | 850 | GCCCAAGAAGTTGGCC | ekkddddddddddkke | 0 | 6052 | 6067 | 59 |
| 612094 | 838 | 853 | GAAGCCCAAGAAGTTG | ekkddddddddddkke | 28 | 6055 | 6070 | 718 |
| 612095 | 841 | 856 | ACGGAAGCCCAAGAAG | ekkddddddddddkke | 13 | 6058 | 6073 | 719 |
| 612096 | 844 | 859 | TATACGGAAGCCCAAG | ekkddddddddddkke | 18 | 6061 | 6076 | 720 |
| 612097 | 847 | 862 | ATATATACGGAAGCCC | ekkddddddddddkke | 0 | 6064 | 6079 | 721 |
| 612098 | 850 | 865 | GCCATATATACGGAAG | ekkddddddddddkke | 42 | 6067 | 6082 | 722 |
| 612099 | 853 | 868 | CATGCCATATATACGG | ekkddddddddddkke | 20 | 6070 | 6085 | 723 |
| 612100 | 856 | 871 | GTGCATGCCATATATA | ekkddddddddddkke | 47 | 6073 | 6088 | 724 |
| 612101 | 859 | 874 | ACTGTGCATGCCATAT | ekkddddddddddkke | 52 | 6076 | 6091 | 725 |
| 612102 | 862 | 877 | CTCACTGTGCATGCCA | ekkddddddddddkke | 62 | 6079 | 6094 | 726 |
| 612103 | 865 | 880 | TAGCTCACTGTGCATG | ekkddddddddddkke | 45 | 6082 | 6097 | 727 |
| 612104 | 868 | 883 | CCATAGCTCACTGTGC | ekkddddddddddkke | 66 | 6085 | 6100 | 728 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612105 | 871 | 886 | GCCCCATAGCTCACTG | ekkddddddddddkke | 16 | 6088 | 6103 | 62 |
| 612107 | 877 | 892 | GACCACGCCCCATAGC | ekkddddddddddkke | 0 | 6094 | 6109 | 729 |
| 612108 | 880 | 895 | ATGGACCACGCCCCAT | ekkddddddddddkke | 0 | 6097 | 6112 | 730 |
| 612109 | 884 | 899 | CCCCATGGACCACGCC | ekkddddddddddkke | 0 | 6101 | 6116 | 731 |
| 612110 | 887 | 902 | TGGCCCCATGGACCAC | ekkddddddddddkke | 24 | 6104 | 6119 | 732 |
| 612111 | 890 | 905 | CGGTGGCCCCATGGAC | ekkddddddddddkke | 1 | 6107 | 6122 | 733 |
| 612112 | 893 | 908 | GGACGGTGGCCCCATG | ekkddddddddddkke | 4 | 6110 | 6125 | 734 |
| 612113 | 896 | 911 | AGAGGACGGTGGCCCC | ekkddddddddddkke | 7 | 6113 | 6128 | 735 |
| 612114 | 899 | 914 | GGGAGAGGACGGTGGC | ekkddddddddddkke | 28 | 6116 | 6131 | 736 |
| 612115 | 913 | 928 | AAAGACAGCCGTTGGG | ekkddddddddddkke | 30 | 6130 | 6145 | 64 |
| 612116 | 916 | 931 | GCCAAAGACAGCCGTT | ekkddddddddddkke | 45 | 6133 | 6148 | 737 |
| 612117 | 919 | 934 | GGTGCCAAAGACAGCC | ekkddddddddddkke | 52 | 6136 | 6151 | 738 |
| 612118 | 922 | 937 | CAGGGTGCCAAAGACA | ekkddddddddddkke | 20 | 6139 | 6154 | 739 |
| 612119 | 926 | 941 | AGGCCAGGGTGCCAAA | ekkddddddddddkke | 20 | 6143 | 6158 | 740 |
| 612120 | 937 | 952 | CAGATAGAGAGAGGCC | ekkddddddddddkke | 0 | 6154 | 6169 | 66 |
| 612121 | 940 | 955 | TCCCAGATAGAGAGAG | ekkddddddddddkke | 0 | 6157 | 6172 | 741 |
| 612122 | 943 | 958 | GGCTCCCAGATAGAGA | ekkddddddddddkke | 11 | 6160 | 6175 | 742 |
| 612123 | 946 | 961 | CAAGGCTCCCAGATAG | ekkddddddddddkke | 5 | 6163 | 6178 | 743 |
| 612124 | 949 | 964 | GTCCAAGGCTCCCAGA | ekkddddddddddkke | 14 | 6166 | 6181 | 744 |
| 612125 | 952 | 967 | GTGGTCCAAGGCTCCC | ekkddddddddddkke | 19 | 6169 | 6184 | 745 |
| 612126 | 955 | 970 | TGTGTGGTCCAAGGCT | ekkddddddddddkke | 25 | 6172 | 6187 | 746 |
| 612127 | 958 | 973 | AGCTGTGTGGTCCAAG | ekkddddddddddkke | 40 | 6175 | 6190 | 747 |
| 612128 | 961 | 976 | GTCAGCTGTGTGGTCC | ekkddddddddddkke | 22 | 6178 | 6193 | 748 |
| 612281 | 1547 | 1562 | CAGAGGCATAGTGAGG | ekkddddddddddkke | 25 | 10558 | 10573 | 749 |
| 612282 | 1550 | 1565 | GGTCAGAGGCATAGTG | ekkddddddddddkke | 20 | 10561 | 10576 | 103 |
| 612283 | 1553 | 1568 | CCAGGTCAGAGGCATA | ekkddddddddddkke | 36 | 10564 | 10579 | 750 |
| 612284 | 1557 | 1572 | TTGTCCAGGTCAGAGG | ekkddddddddddkke | 24 | 10568 | 10583 | 751 |
| 612285 | 1560 | 1575 | ACCTTGTCCAGGTCAG | ekkddddddddddkke | 37 | 10571 | 10586 | 752 |
| 612286 | 1566 | 1581 | CCCTCCACCTTGTCCA | ekkddddddddddkke | 9 | 10577 | 10592 | 753 |
| 612287 | 1570 | 1585 | GAGACCCTCCACCTTG | ekkddddddddddkke | 31 | 10581 | 10596 | 754 |
| 612288 | 1574 | 1589 | AAGTGAGACCCTCCAC | ekkddddddddddkke | 5 | 10585 | 10600 | 755 |
| 612289 | 1578 | 1593 | TGGAAAGTGAGACCCT | ekkddddddddddkke | 13 | 10589 | 10604 | 104 |
| 612290 | 1581 | 1596 | TGCTGGAAAGTGAGAC | ekkddddddddddkke | 27 | 10592 | 10607 | 756 |
| 612291 | 1584 | 1599 | TTTTGCTGGAAAGTGA | ekkddddddddddkke | 0 | 10595 | 10610 | 757 |
| 612292 | 1587 | 1602 | GAGTTTTGCTGGAAAG | ekkddddddddddkke | 15 | 10598 | 10613 | 758 |
| 612293 | 1590 | 1605 | AGGGAGTTTTGCTGGA | ekkddddddddddkke | 27 | 10601 | 10616 | 759 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612294 | 1594 | 1609 | GTTGAGGGAGTTTTGC | ekkddddddddddkke | 0 | 10605 | 10620 | 760 |
| 612295 | 1597 | 1612 | CCAGTTGAGGGAGTTT | ekkddddddddddkke | 6 | 10608 | 10623 | 761 |
| 612296 | 1600 | 1615 | CATCCAGTTGAGGGAG | ekkddddddddddkke | 8 | 10611 | 10626 | 762 |
| 612297 | 1603 | 1618 | CTTCATCCAGTTGAGG | ekkddddddddddkke | 11 | 10614 | 10629 | 763 |
| 612298 | 1612 | 1627 | AGATAGTTTCTTCATC | ekkddddddddddkke | 0 | 10623 | 10638 | 764 |
| 612299 | 1629 | 1644 | AGGTGGATGGTCCGGG | ekkddddddddddkke | 36 | N/A | N/A | 765 |
| 612300 | 1632 | 1647 | GTCAGGTGGATGGTCC | ekkddddddddddkke | 25 | 12238 | 12253 | 766 |
| 612301 | 1636 | 1651 | CATGGTCAGGTGGATG | ekkddddddddddkke | 26 | 12242 | 12257 | 767 |
| 612302 | 1639 | 1654 | GGGCATGGTCAGGTGG | ekkddddddddddkke | 40 | 12245 | 12260 | 768 |
| 612303 | 1653 | 1668 | TGCAGCACCAGTTGGG | ekkddddddddddkke | 33 | 12259 | 12274 | 109 |
| 612304 | 1656 | 1671 | CCTTGCAGCACCAGTT | ekkddddddddddkke | 3 | 12262 | 12277 | 769 |
| 612305 | 1659 | 1674 | GATCCTTGCAGCACCA | ekkddddddddddkke | 12 | 12265 | 12280 | 770 |
| 612306 | 1662 | 1677 | TAAGATCCTTGCAGCA | ekkddddddddddkke | 8 | 12268 | 12283 | 771 |
| 612307 | 1665 | 1680 | TCATAAGATCCTTGCA | ekkddddddddddkke | 8 | 12271 | 12286 | 772 |
| 612308 | 1669 | 1684 | CAGGTCATAAGATCCT | ekkddddddddddkke | 8 | 12275 | 12290 | 773 |
| 612309 | 1672 | 1687 | CTGCAGGTCATAAGAT | ekkddddddddddkke | 0 | 12278 | 12293 | 774 |
| 612310 | 1675 | 1690 | GTCCTGCAGGTCATAA | ekkddddddddddkke | 10 | 12281 | 12296 | 775 |
| 612311 | 1682 | 1697 | CGAGCAGGTCCTGCAG | ekkddddddddddkke | 32 | 12288 | 12303 | 776 |
| 612312 | 1685 | 1700 | GGGCGAGCAGGTCCTG | ekkddddddddddkke | 11 | 12291 | 12306 | 777 |
| 612313 | 1688 | 1703 | CCTGGGCGAGCAGGTC | ekkddddddddddkke | 22 | 12294 | 12309 | 778 |
| 612314 | 1700 | 1715 | CGGGCAGCTCAGCCTG | ekkddddddddddkke | 0 | 12306 | 12321 | 112 |
| 612315 | 1703 | 1718 | TGGCGGGCAGCTCAGC | ekkddddddddddkke | 55 | 12309 | 12324 | 779 |
| 612316 | 1706 | 1721 | GAATGGCGGGCAGCTC | ekkddddddddddkke | 16 | 12312 | 12327 | 780 |
| 612317 | 1709 | 1724 | GCAGAATGGCGGGCAG | ekkddddddddddkke | 16 | 12315 | 12330 | 781 |
| 612318 | 1712 | 1727 | TGTGCAGAATGGCGGG | ekkddddddddddkke | 24 | 12318 | 12333 | 782 |
| 612319 | 1715 | 1730 | CGGTGTGCAGAATGGC | ekkddddddddddkke | 35 | 12321 | 12336 | 783 |
| 612320 | 1718 | 1733 | GCTCGGTGTGCAGAAT | ekkddddddddddkke | 13 | 12324 | 12339 | 784 |
| 612321 | 1721 | 1736 | TCAGCTCGGTGTGCAG | ekkddddddddddkke | 28 | 12327 | 12342 | 785 |
| 612322 | 1724 | 1739 | GGTTCAGCTCGGTGTG | ekkddddddddddkke | 49 | 12330 | 12345 | 786 |
| 612323 | 1727 | 1742 | GCAGGTTCAGCTCGGT | ekkddddddddddkke | 53 | 12333 | 12348 | 787 |
| 612324 | 1732 | 1747 | TTTTGCAGGTTCAGC | ekkddddddddddkke | 8 | 12338 | 12353 | 788 |
| 612325 | 1735 | 1750 | CAATTTTTGCAGGTTC | ekkddddddddddkke | 14 | 12341 | 12356 | 789 |
| 612326 | 1738 | 1753 | GCTCAATTTTTGCAGG | ekkddddddddddkke | 38 | 12344 | 12359 | 790 |
| 612327 | 1741 | 1756 | ATTGCTCAATTTTTGC | ekkddddddddddkke | 2 | 12347 | 12362 | 791 |
| 612328 | 1744 | 1759 | GTCATTGCTCAATTTT | ekkddddddddddkke | 38 | 12350 | 12365 | 792 |
| 612329 | 1747 | 1762 | GCGGTCATTGCTCAAT | ekkddddddddddkke | 32 | 12353 | 12368 | 793 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612330 | 1750 | 1765 | GATGCGGTCATTGCTC | ekkddddddddddkke | 27 | 12356 | 12371 | 794 |
| 612331 | 1753 | 1768 | CCTGATGCGGTCATTG | ekkddddddddddkke | 15 | 12359 | 12374 | 795 |
| 612332 | 1756 | 1771 | CACCCTGATGCGGTCA | ekkddddddddddkke | 1 | 12362 | 12377 | 796 |
| 612333 | 1759 | 1774 | CCCCACCCTGATGCGG | ekkddddddddddkke | 11 | 12365 | 12380 | 797 |
| 612334 | 1762 | 1777 | CTCCCCCACCCTGATG | ekkddddddddddkke | 0 | 12368 | 12383 | 798 |
| 612335 | 1771 | 1786 | GTTCAGCACCTCCCCC | ekkddddddddddkke | 12 | N/A | N/A | 799 |
| 612336 | 1774 | 1789 | GCTGTTCAGCACCTCC | ekkddddddddddkke | 57 | N/A | N/A | 800 |
| 612337 | 1777 | 1792 | AATGCTGTTCAGCACC | ekkddddddddddkke | 29 | 13246 | 13261 | 801 |
| 612338 | 1780 | 1795 | AAAAATGCTGTTCAGC | ekkddddddddddkke | 38 | 13249 | 13264 | 802 |
| 612339 | 1793 | 1808 | CTTCAAGCTCAAAAAA | ekkddddddddddkke | 0 | 13262 | 13277 | 803 |
| 612340 | 1796 | 1811 | CCGCTTCAAGCTCAAA | ekkddddddddddkke | 41 | 13265 | 13280 | 804 |
| 612341 | 1799 | 1814 | CATCCGCTTCAAGCTC | ekkddddddddddkke | 27 | 13268 | 13283 | 805 |
| 612342 | 1802 | 1817 | TCTCATCCGCTTCAAG | ekkddddddddddkke | 32 | 13271 | 13286 | 806 |
| 612343 | 1805 | 1820 | CTCTCTCATCCGCTTC | ekkddddddddddkke | 26 | 13274 | 13289 | 807 |
| 612344 | 1808 | 1823 | GCTCTCTCTCATCCGC | ekkddddddddddkke | 44 | 13277 | 13292 | 808 |
| 612345 | 1812 | 1827 | GTGGGCTCTCTCTCAT | ekkddddddddddkke | 15 | 13281 | 13296 | 809 |
| 612346 | 1817 | 1832 | ACTCTGTGGGCTCTCT | ekkddddddddddkke | 42 | 13286 | 13301 | 810 |
| 612347 | 1820 | 1835 | TAGACTCTGTGGGCTC | ekkddddddddddkke | 55 | 13289 | 13304 | 811 |
| 612348 | 1824 | 1839 | TGGGTAGACTCTGTGG | ekkddddddddddkke | 23 | 13293 | 13308 | 812 |
| 612349 | 1827 | 1842 | TGTTGGGTAGACTCTG | ekkddddddddddkke | 30 | 13296 | 13311 | 119 |
| 612350 | 1830 | 1845 | AGCTGTTGGGTAGACT | ekkddddddddddkke | 34 | 13299 | 13314 | 813 |
| 612351 | 1833 | 1848 | TTAAGCTGTTGGGTAG | ekkddddddddddkke | 13 | 13302 | 13317 | 814 |
| 612352 | 1836 | 1851 | TTGTTAAGCTGTTGGG | ekkddddddddddkke | 33 | 13305 | 13320 | 815 |
| 612353 | 1839 | 1854 | GGCTTGTTAAGCTGTT | ekkddddddddddkke | 30 | 13308 | 13323 | 816 |
| 612354 | 1842 | 1857 | TCAGGCTTGTTAAGCT | ekkddddddddddkke | 10 | 13311 | 13326 | 817 |
| 612355 | 1845 | 1860 | ACCTCAGGCTTGTTAA | ekkddddddddddkke | 17 | 13314 | 13329 | 818 |
| 612356 | 1848 | 1863 | AAGACCTCAGGCTTGT | ekkddddddddddkke | 33 | 13317 | 13332 | 819 |
| 612609 | 2409 | 2424 | ACACGGAGGTCATGTT | ekkddddddddddkke | 20 | 13878 | 13893 | 820 |
| 612610 | 2410 | 2425 | TACACGGAGGTCATGT | ekkddddddddddkke | 25 | 13879 | 13894 | 821 |
| 612611 | 2411 | 2426 | CTACACGGAGGTCATG | ekkddddddddddkke | 24 | 13880 | 13895 | 822 |
| 612612 | 2412 | 2427 | ACTACACGGAGGTCAT | ekkddddddddddkke | 26 | 13881 | 13896 | 145 |
| 612613 | 2413 | 2428 | CACTACACGGAGGTCA | ekkddddddddddkke | 30 | 13882 | 13897 | 823 |
| 612614 | 2414 | 2429 | ACACTACACGGAGGTC | ekkddddddddddkke | 49 | 13883 | 13898 | 824 |
| 612615 | 2415 | 2430 | DACACTACACGGAGGT | ekkddddddddddkke | 56 | 13884 | 13899 | 825 |
| 612616 | 2416 | 2431 | AGACACTACACGGAGG | ekkddddddddddkke | 40 | 13885 | 13900 | 826 |
| 612617 | 2417 | 2432 | CAGACACTACACGGAG | ekkddddddddddkke | 48 | 13886 | 13901 | 827 |

TABLE 4-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612618 | 2418 | 2433 | ACAGACACTACACGGA | ekkddddddddddkke | 44 | 13887 | 13902 | 828 |
| 612619 | 2419 | 2434 | TACAGACACTACACGG | ekkddddddddddkke | 39 | 13888 | 13903 | 829 |
| 612620 | 2420 | 2435 | TTACAGACACTACACG | ekkddddddddddkke | 28 | 13889 | 13904 | 830 |
| 612621 | 2421 | 2436 | ATTACAGACACTACAC | ekkddddddddddkke | 21 | 13890 | 13905 | 831 |
| 612622 | 2422 | 2437 | TATTACAGACACTACA | ekkddddddddddkke | 0 | 13891 | 13906 | 146 |
| 612623 | 2423 | 2438 | GTATTACAGACACTAC | ekkddddddddddkke | 35 | 13892 | 13907 | 832 |
| 612624 | 2428 | 2443 | CTAAGGTATTACAGAC | ekkddddddddddkke | 8 | 13897 | 13912 | 833 |
| 612625 | 2429 | 2444 | ACTAAGGTATTACAGA | ekkddddddddddkke | 14 | 13898 | 13913 | 834 |
| 612626 | 2430 | 2445 | AACTAAGGTATTACAG | ekkddddddddddkke | 14 | 13899 | 13914 | 835 |
| 612627 | 2431 | 2446 | AAACTAAGGTATTACA | ekkddddddddddkke | 12 | 13900 | 13915 | 836 |
| 612628 | 2432 | 2447 | AAAACTAAGGTATTAC | ekkddddddddddkke | 3 | 13901 | 13916 | 837 |
| 612629 | 2438 | 2453 | GTGGAAAAAACTAAGG | ekkddddddddddkke | 0 | 13907 | 13922 | 838 |
| 612630 | 2447 | 2462 | CAAGCATCTGTGGAAA | ekkddddddddddkke | 0 | 13916 | 13931 | 839 |
| 612631 | 2449 | 2464 | CACAAGCATCTGTGGA | ekkddddddddddkke | 20 | 13918 | 13933 | 840 |
| 612632 | 2450 | 2465 | TCACAAGCATCTGTGG | ekkddddddddddkke | 1 | 13919 | 13934 | 841 |
| 612633 | 2451 | 2466 | ATCACAAGCATCTGTG | ekkddddddddddkke | 20 | 13920 | 13935 | 842 |
| 612634 | 2452 | 2467 | AATCACAAGCATCTGT | ekkddddddddddkke | 2 | 13921 | 13936 | 843 |
| 612635 | 2464 | 2479 | GTATTGTTCAAAAATC | ekkddddddddddkke | 16 | 13933 | 13948 | 844 |
| 612636 | 2465 | 2480 | CGTATTGTTCAAAAAT | ekkddddddddddkke | 0 | 13934 | 13949 | 845 |
| 612637 | 2482 | 2497 | GGTGCTTGCATCTTTC | ekkddddddddddkke | 21 | 13951 | 13966 | 147 |
| 612638 | 2483 | 2498 | AGGTGCTTGCATCTTT | ekkddddddddddkke | 13 | 13952 | 13967 | 846 |
| 612639 | 2484 | 2499 | CAGGTGCTTGCATCTT | ekkddddddddddkke | 19 | 13953 | 13968 | 847 |
| 612640 | 2485 | 2500 | TCAGGTGCTTGCATCT | ekkddddddddddkke | 38 | 13954 | 13969 | 848 |
| 612641 | 2486 | 2501 | TTCAGGTGCTTGCATC | ekkddddddddddkke | 29 | 13955 | 13970 | 849 |
| 612642 | 2487 | 2502 | ATTCAGGTGCTTGCAT | ekkddddddddddkke | 19 | 13956 | 13971 | 850 |
| 612643 | 2488 | 2503 | AATTCAGGTGCTTGCA | ekkddddddddddkke | 34 | 13957 | 13972 | 851 |
| 612644 | 2489 | 2504 | AAATTCAGGTGCTTGC | ekkddddddddddkke | 24 | 13958 | 13973 | 852 |
| 612645 | 2490 | 2505 | GAAATTCAGGTGCTTG | ekkddddddddddkke | 2 | 13959 | 13974 | 853 |
| 612646 | 2491 | 2506 | AGAAATTCAGGTGCTT | ekkddddddddddkke | 5 | 13960 | 13975 | 854 |
| 612647 | 2493 | 2508 | ACAGAAATTCAGGTGC | ekkddddddddddkke | 0 | 13962 | 13977 | 855 |
| 612648 | 2502 | 2517 | CGCATTCAAACAGAAA | ekkddddddddddkke | 22 | 13971 | 13986 | 856 |
| 612649 | 2503 | 2518 | CCGCATTCAAACAGAA | ekkddddddddddkke | 50 | 13972 | 13987 | 149 |
| 612650 | 2504 | 2519 | TCCGCATTCAAACAGA | ekkddddddddddkke | 35 | 13973 | 13988 | 857 |
| 612651 | 2505 | 2520 | TTCCGCATTCAAACAG | ekkddddddddddkke | 29 | 13974 | 13989 | 858 |
| 612652 | 2506 | 2521 | GTTCCGCATTCAAACA | ekkddddddddddkke | 25 | 13975 | 13990 | 859 |
| 612653 | 2507 | 2522 | GGTTCCGCATTCAAAC | ekkddddddddddkke | 28 | 13976 | 13991 | 860 |

TABLE 4-continued

Inhibition of AGT mRNA by MOE and/or cEt containing
gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612654 | 2508 | 2523 | TGGTTCCGCATTCAAA | ekkddddddddddkke | 38 | 13977 | 13992 | 861 |
| 612655 | 2509 | 2524 | ATGGTTCCGCATTCAA | ekkddddddddddkke | 45 | 13978 | 13993 | 862 |
| 612656 | 2510 | 2525 | TATGGTTCCGCATTCA | ekkddddddddddkke | 42 | 13979 | 13994 | 863 |
| 612657 | 2511 | 2526 | CTATGGTTCCGCATTC | ekkddddddddddkke | 41 | 13980 | 13995 | 864 |
| 612658 | 2512 | 2527 | GCTATGGTTCCGCATT | ekkddddddddddkke | 58 | 13981 | 13996 | 865 |
| 612659 | 2513 | 2528 | AGCTATGGTTCCGCAT | ekkddddddddddkke | 32 | 13982 | 13997 | 150 |
| 612660 | 2514 | 2529 | CAGCTATGGTTCCGCA | ekkddddddddddkke | 46 | 13983 | 13998 | 866 |
| 612661 | 2515 | 2530 | CCAGCTATGGTTCCGC | ekkddddddddddkke | 47 | 13984 | 13999 | 867 |
| 612662 | 2516 | 2531 | ACCAGCTATGGTTCCG | ekkddddddddddkke | 60 | 13985 | 14000 | 868 |
| 612663 | 2517 | 2532 | AACCAGCTATGGTTCC | ekkddddddddddkke | 36 | 13986 | 14001 | 869 |
| 612664 | 2518 | 2533 | TAACCAGCTATGGTTC | ekkddddddddddkke | 0 | 13987 | 14002 | 870 |
| 612665 | 2519 | 2534 | ATAACCAGCTATGGTT | ekkddddddddddkke | 17 | 13988 | 14003 | 871 |
| 612666 | 2521 | 2536 | AAATAACCAGCTATGG | ekkddddddddddkke | 3 | 13990 | 14005 | 872 |
| 612667 | 2522 | 2537 | GAAATAACCAGCTATG | ekkddddddddddkke | 2 | 13991 | 14006 | 873 |
| 612668 | 2523 | 2538 | AGAAATAACCAGCTAT | ekkddddddddddkke | 4 | 13992 | 14007 | 874 |
| 612669 | 2535 | 2550 | CTAACACAAGGGAGAA | ekkddddddddddkke | 23 | 14004 | 14019 | 875 |
| 612670 | 2536 | 2551 | ACTAACACAAGGGAGA | ekkddddddddddkke | 13 | 14005 | 14020 | 876 |
| 612671 | 2537 | 2552 | TACTAACACAAGGGAG | ekkddddddddddkke | 9 | 14006 | 14021 | 151 |
| 612672 | 2538 | 2553 | TTACTAACACAAGGGA | ekkddddddddddkke | 51 | 14007 | 14022 | 877 |
| 612673 | 2539 | 2554 | ATTACTAACACAAGGG | ekkddddddddddkke | 47 | 14008 | 14023 | 878 |
| 612674 | 2540 | 2555 | TATTACTAACACAAGG | ekkddddddddddkke | 16 | 14009 | 14024 | 879 |
| 612675 | 2541 | 2556 | TTATTACTAACACAAG | ekkddddddddddkke | 0 | 14010 | 14025 | 880 |
| 612676 | 2543 | 2558 | GTTTATTACTAACACA | ekkddddddddddkke | 0 | 14012 | 14027 | 881 |
| 612677 | 2544 | 2559 | CGTTTATTACTAACAC | ekkddddddddddkke | 35 | 14013 | 14028 | 882 |
| 612678 | 2558 | 2573 | TTATTGTGGCAAGACG | ekkddddddddddkke | 28 | 14027 | 14042 | 152 |
| 612679 | 2559 | 2574 | CTTATTGTGGCAAGAC | ekkddddddddddkke | 21 | 14028 | 14043 | 883 |
| 612680 | 2560 | 2575 | GCTTATTGTGGCAAGA | ekkddddddddddkke | 16 | 14029 | 14044 | 884 |
| 612681 | 2561 | 2576 | GGCTTATTGTGGCAAG | ekkddddddddddkke | 35 | 14030 | 14045 | 885 |
| 612682 | 2562 | 2577 | AGGCTTATTGTGGCAA | ekkddddddddddkke | 34 | 14031 | 14046 | 886 |
| 612683 | 2563 | 2578 | GAGGCTTATTGTGGCA | ekkddddddddddkke | 23 | 14032 | 14047 | 887 |
| 612684 | 2564 | 2579 | GGAGGCTTATTGTGGC | ekkddddddddddkke | 0 | 14033 | 14048 | 888 |

Table 5 shows inhibition of AGT mRNA in HepG2 cells cultured at a density of 20,000 cells per well which were transfected using electroporation with 1000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 5

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568637 | 2046 | 2061 | CGCTGATTTGTCCGGG | eekddddddddddkke | 87 | 13515 | 13530 | 129 |
| 568637 | 2046 | 2061 | CGCTGATTTGTCCGGG | eekddddddddddkke | 90 | 13515 | 13530 | 129 |
| 568637 | 2046 | 2061 | CGCTGATTTGTCCGGG | eekddddddddddkke | 95 | 13515 | 13530 | 129 |
| 568637 | 2046 | 2061 | CGCTGATTTGTCCGGG | eekddddddddddkke | 94 | 13515 | 13530 | 129 |
| 594622 | 2027 | 2042 | GTTATCTGCTGCTGGC | kkkddddddddddkkk | 6 | 13496 | 13511 | 163 |
| 594622 | 2027 | 2042 | GTTATCTGCTGCTGGC | kkkddddddddddkkk | 83 | 13496 | 13511 | 163 |
| 594622 | 2027 | 2042 | GTTATCTGCTGCTGGC | kkkddddddddddkkk | 86 | 13496 | 13511 | 163 |
| 594622 | 2027 | 2042 | GTTATCTGCTGCTGGC | kkkddddddddddkkk | 85 | 13496 | 13511 | 163 |
| 594625 | 2047 | 2062 | TCGCTGATTTGTCCGG | kkkddddddddddkkk | 0 | 13516 | 13531 | 165 |
| 594625 | 2047 | 2062 | TCGCTGATTTGTCCGG | kkkddddddddddkkk | 64 | 13516 | 13531 | 165 |
| 594625 | 2047 | 2062 | TCGCTGATTTGTCCGG | kkkddddddddddkkk | 74 | 13516 | 13531 | 165 |
| 594625 | 2047 | 2062 | TCGCTGATTTGTCCGG | kkkddddddddddkkk | 70 | 13516 | 13531 | 165 |
| 612129 | 965 | 980 | GCCTGTCAGCTGTGTG | ekkddddddddddkke | 29 | 6182 | 6197 | 889 |
| 612130 | 968 | 983 | GTAGCCTGTCAGCTGT | ekkddddddddddkke | 44 | 6185 | 6200 | 890 |
| 612131 | 971 | 986 | CCTGTAGCCTGTCAGC | ekkddddddddddkke | 21 | 6188 | 6203 | 891 |
| 612132 | 974 | 989 | TTGCCTGTAGCCTGTC | ekkddddddddddkke | 38 | 6191 | 6206 | 892 |
| 612133 | 977 | 992 | GGATTGCCTGTAGCCT | ekkddddddddddkke | 14 | 6194 | 6209 | 893 |
| 612134 | 980 | 995 | CCAGGATTGCCTGTAG | ekkddddddddddkke | 46 | 6197 | 6212 | 894 |
| 612135 | 983 | 998 | CACCCAGGATTGCCTG | ekkddddddddddkke | 23 | 6200 | 6215 | 68 |
| 612136 | 986 | 1001 | GAACACCCAGGATTGC | ekkddddddddddkke | 16 | 6203 | 6218 | 895 |
| 612137 | 993 | 1008 | TTCCAAGGAACACCCA | ekkddddddddddkke | 26 | 6210 | 6225 | 69 |
| 612138 | 997 | 1012 | GTCCTTCCAAGGAACA | ekkddddddddddkke | 27 | 6214 | 6229 | 896 |
| 612139 | 1000 | 1015 | CTTGTCCTTCCAAGGA | ekkddddddddddkke | 57 | 6217 | 6232 | 897 |
| 612140 | 1003 | 1018 | GTTCTTGTCCTTCCAA | ekkddddddddddkke | 22 | 6220 | 6235 | 898 |
| 612141 | 1006 | 1021 | GCAGTTCTTGTCCTTC | ekkddddddddddkke | 42 | 6223 | 6238 | 899 |
| 612142 | 1009 | 1024 | GGTGCAGTTCTTGTCC | ekkddddddddddkke | 0 | 6226 | 6241 | 900 |
| 612143 | 1012 | 1027 | GGAGGTGCAGTTCTTG | ekkddddddddddkke | 0 | 6229 | 6244 | 901 |
| 612144 | 1015 | 1030 | CCGGGAGGTGCAGTTC | ekkddddddddddkke | 34 | 6232 | 6247 | 902 |
| 612145 | 1018 | 1033 | CAGCCGGGAGGTGCAG | ekkddddddddddkke | 30 | 6235 | 6250 | 903 |
| 612146 | 1021 | 1036 | ATCCAGCCGGGAGGTG | ekkddddddddddkke | 43 | 6238 | 6253 | 904 |
| 612147 | 1024 | 1039 | CGCATCCAGCCGGGAG | ekkddddddddddkke | 63 | 6241 | 6256 | 905 |
| 612148 | 1027 | 1042 | GTGCGCATCCAGCCGG | ekkddddddddddkke | 64 | 6244 | 6259 | 906 |
| 612149 | 1030 | 1045 | CTTGTGCGCATCCAGC | ekkddddddddddkke | 4 | 6247 | 6262 | 907 |
| 612150 | 1033 | 1048 | GACCTTGTGCGCATCC | ekkddddddddddkke | 0 | 6250 | 6265 | 908 |
| 612151 | 1036 | 1051 | CAGGACCTTGTGCGCA | ekkddddddddddkke | 46 | 6253 | 6268 | 909 |
| 612152 | 1039 | 1054 | AGACAGGACCTTGTGC | ekkddddddddddkke | 12 | 6256 | 6271 | 910 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612153 | 1042 | 1057 | GGCAGACAGGACCTTG | ekkddddddddddkke | 24 | 6259 | 6274 | 911 |
| 612154 | 1060 | 1075 | GCCCTGTACAGCCTGC | ekkddddddddddkke | 36 | 6277 | 6292 | 912 |
| 612155 | 1064 | 1079 | GCAGGCCCTGTACAGC | ekkddddddddddkke | 19 | 6281 | 6296 | 913 |
| 612156 | 1067 | 1082 | CTAGCAGGCCCTGTAC | ekkddddddddddkke | 1 | 6284 | 6299 | 914 |
| 612157 | 1071 | 1086 | GCCACTAGCAGGCCCT | ekkddddddddddkke | 0 | 6288 | 6303 | 915 |
| 612158 | 1074 | 1089 | TGGGCCACTAGCAGGC | ekkddddddddddkke | 0 | 6291 | 6306 | 916 |
| 612159 | 1077 | 1092 | CCCTGGGCCACTAGCA | ekkddddddddddkke | 27 | 6294 | 6309 | 917 |
| 612160 | 1080 | 1095 | CTGCCCTGGGCCACTA | ekkddddddddddkke | 42 | 6297 | 6312 | 918 |
| 612161 | 1088 | 1103 | TATCAGCCCTGCCCTG | ekkddddddddddkke | 28 | 6305 | 6320 | 74 |
| 612162 | 1091 | 1106 | GGCTATCAGCCCTGCC | ekkddddddddddkke | 38 | 6308 | 6323 | 919 |
| 612163 | 1094 | 1109 | CCTGGCTATCAGCCCT | ekkddddddddddkke | 38 | 6311 | 6326 | 920 |
| 612164 | 1097 | 1112 | GGGCCTGGCTATCAGC | ekkddddddddddkke | 24 | 6314 | 6329 | 921 |
| 612165 | 1100 | 1115 | GCTGGGCCTGGCTATC | ekkddddddddddkke | 0 | 6317 | 6332 | 922 |
| 612166 | 1115 | 1130 | CCGTGGACAGCAGCAG | ekkddddddddddkke | 0 | 6332 | 6347 | 923 |
| 612167 | 1118 | 1133 | CCACCGTGGACAGCAG | ekkddddddddddkke | 28 | 6335 | 6350 | 924 |
| 612168 | 1121 | 1136 | CCACCACCGTGGACAG | ekkddddddddddkke | 27 | 6338 | 6353 | 925 |
| 612169 | 1124 | 1139 | CGCCCACCACCGTGGA | ekkddddddddddkke | 11 | 6341 | 6356 | 926 |
| 612170 | 1127 | 1142 | ACACGCCCACCACCGT | ekkddddddddddkke | 18 | 6344 | 6359 | 927 |
| 612171 | 1130 | 1145 | TGAACACGCCCACCAC | ekkddddddddddkke | 34 | 6347 | 6362 | 928 |
| 612172 | 1133 | 1148 | CTGTGAACACGCCCAC | ekkddddddddddkke | 37 | 6350 | 6365 | 929 |
| 612173 | 1136 | 1151 | GGGCTGTGAACACGCC | ekkddddddddddkke | 0 | 6353 | 6368 | 930 |
| 612174 | 1151 | 1166 | TCAGGTGCAGGCCTGG | ekkddddddddddkke | 5 | 6368 | 6383 | 78 |
| 612175 | 1154 | 1169 | GCTTCAGGTGCAGGCC | ekkddddddddddkke | 45 | 6371 | 6386 | 931 |
| 612176 | 1157 | 1172 | GCTGCTTCAGGTGCAG | ekkddddddddddkke | 30 | 6374 | 6389 | 932 |
| 612177 | 1160 | 1175 | ACGGCTGCTTCAGGTG | ekkddddddddddkke | 45 | 6377 | 6392 | 933 |
| 612178 | 1163 | 1178 | CAAACGGCTGCTTCAG | ekkddddddddddkke | 17 | 6380 | 6395 | 934 |
| 612179 | 1166 | 1181 | GCACAAACGGCTGCTT | ekkddddddddddkke | 34 | 6383 | 6398 | 935 |
| 612180 | 1169 | 1184 | CCTGCACAAACGGCTG | ekkddddddddddkke | 0 | 6386 | 6401 | 936 |
| 612181 | 1172 | 1187 | GGCCCTGCACAAACGG | ekkddddddddddkke | 0 | 6389 | 6404 | 937 |
| 612182 | 1182 | 1197 | TAGAGAGCCAGGCCCT | ekkddddddddddkke | 38 | 6399 | 6414 | 80 |
| 612183 | 1185 | 1200 | GTATAGAGAGCCAGGC | ekkddddddddddkke | 19 | 6402 | 6417 | 938 |
| 612184 | 1203 | 1218 | CGTGGGAGGACCACAG | ekkddddddddddkke | 26 | 6420 | 6435 | 81 |
| 612185 | 1217 | 1232 | TGAAGTCCAGAGAGCG | ekkddddddddddkke | 5 | 6434 | 6449 | 82 |
| 612186 | 1220 | 1235 | CTGTGAAGTCCAGAGA | ekkddddddddddkke | 45 | 6437 | 6452 | 939 |
| 612187 | 1223 | 1238 | GTTCTGTGAAGTCCAG | ekkddddddddddkke | 49 | 6440 | 6455 | 940 |
| 612188 | 1226 | 1241 | CCAGTTCTGTGAAGTC | ekkddddddddddkke | 23 | 6443 | 6458 | 941 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612189 | 1229 | 1244 | CATCCAGTTCTGTGAA | ekkddddddddddkke | 31 | 6446 | 6461 | 942 |
| 612190 | 1232 | 1247 | CAACATCCAGTTCTGT | ekkddddddddddkke | 30 | 6449 | 6464 | 943 |
| 612191 | 1235 | 1250 | CAGCAACATCCAGTTC | ekkddddddddddkke | 35 | 6452 | 6467 | 944 |
| 612192 | 1244 | 1259 | TCTTCTCAGCAGCAAC | ekkddddddddddkke | 61 | 6461 | 6476 | 84 |
| 612193 | 1247 | 1262 | CAATCTTCTCAGCAGC | ekkddddddddddkke | 34 | 6464 | 6479 | 945 |
| 612194 | 1250 | 1265 | TGTCAATCTTCTCAGC | ekkddddddddddkke | 44 | 6467 | 6482 | 946 |
| 612195 | 1253 | 1268 | ACCTGTCAATCTTCTC | ekkddddddddddkke | 47 | 6470 | 6485 | 947 |
| 612196 | 1256 | 1271 | TGAACCTGTCAATCTT | ekkddddddddddkke | 18 | 6473 | 6488 | 948 |
| 612197 | 1259 | 1274 | GCATGAACCTGTCAAT | ekkddddddddddkke | 39 | 6476 | 6491 | 949 |
| 612198 | 1262 | 1277 | CCTGCATGAACCTGTC | ekkddddddddddkke | 35 | 6479 | 6494 | 950 |
| 612199 | 1265 | 1280 | CAGCCTGCATGAACCT | ekkddddddddddkke | 47 | 6482 | 6497 | 951 |
| 612200 | 1267 | 1282 | CACAGCCTGCATGAAC | ekkddddddddddkke | 26 | 6484 | 6499 | 952 |
| 612201 | 1268 | 1283 | TCACAGCCTGCATGAA | ekkddddddddddkke | 36 | 6485 | 6500 | 953 |
| 612202 | 1274 | 1289 | ATCCTGTCACAGCCTG | ekkddddddddddkke | 68 | 6491 | 6506 | 954 |
| 612203 | 1276 | 1291 | CCATCCTGTCACAGCC | ekkddddddddddkke | 50 | 6493 | 6508 | 955 |
| 612204 | 1277 | 1292 | TCCATCCTGTCACAGC | ekkddddddddddkke | 7 | 6494 | 6509 | 956 |
| 612205 | 1279 | 1294 | CTTCCATCCTGTCACA | ekkddddddddddkke | 33 | 6496 | 6511 | 957 |
| 612206 | 1282 | 1297 | AGTCTTCCATCCTGTC | ekkddddddddddkke | 54 | 6499 | 6514 | 958 |
| 612207 | 1286 | 1301 | AGCCAGTCTTCCATCC | ekkddddddddddkke | 58 | 6503 | 6518 | 959 |
| 612233 | 1399 | 1414 | CACCCAGAACTCCTGG | ekkddddddddddkke | 7 | 10410 | 10425 | 960 |
| 612234 | 1402 | 1417 | GTCCACCCAGAACTCC | ekkddddddddddkke | 66 | 10413 | 10428 | 961 |
| 612235 | 1405 | 1420 | GTTGTCCACCCAGAAC | ekkddddddddddkke | 73 | 10416 | 10431 | 962 |
| 612236 | 1408 | 1423 | GCTGTTGTCCACCCAG | ekkddddddddddkke | 76 | 10419 | 10434 | 963 |
| 612237 | 1411 | 1426 | GGTGCTGTTGTCCACC | ekkddddddddddkke | 25 | 10422 | 10437 | 964 |
| 612238 | 1414 | 1429 | TGAGGTGCTGTTGTCC | ekkddddddddddkke | 77 | 10425 | 10440 | 965 |
| 612239 | 1417 | 1432 | CACTGAGGTGCTGTTG | ekkddddddddddkke | 92 | 10428 | 10443 | 966 |
| 612240 | 1421 | 1436 | CAGACACTGAGGTGCT | ekkddddddddddkke | 50 | 10432 | 10447 | 93 |
| 612241 | 1429 | 1444 | CATGGGAACAGACACT | ekkddddddddddkke | 0 | 10440 | 10455 | 967 |
| 612242 | 1432 | 1447 | GAGCATGGGAACAGAC | ekkddddddddddkke | 0 | 10443 | 10458 | 968 |
| 612243 | 1435 | 1450 | AGAGAGCATGGGAACA | ekkddddddddddkke | 6 | 10446 | 10461 | 969 |
| 612244 | 1438 | 1453 | GCCAGAGAGCATGGGA | ekkddddddddddkke | 52 | 10449 | 10464 | 970 |
| 612245 | 1441 | 1456 | CATGCCAGAGAGCATG | ekkddddddddddkke | 63 | 10452 | 10467 | 971 |
| 612246 | 1444 | 1459 | GCCCATGCCAGAGAGC | ekkddddddddddkke | 59 | 10455 | 10470 | 972 |
| 612247 | 1447 | 1462 | GGTGCCCATGCCAGAG | ekkddddddddddkke | 76 | 10458 | 10473 | 973 |
| 612248 | 1450 | 1465 | GAAGGTGCCCATGCCA | ekkddddddddddkke | 0 | 10461 | 10476 | 974 |
| 612249 | 1453 | 1468 | CTGGAAGGTGCCCATG | ekkddddddddddkke | 47 | 10464 | 10479 | 975 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612250 | 1457 | 1472 | AGTGCTGGAAGGTGCC | ekkdddddddddddkke | 0 | 10468 | 10483 | 976 |
| 612251 | 1460 | 1475 | TCCAGTGCTGGAAGGT | ekkdddddddddddkke | 11 | 10471 | 10486 | 977 |
| 612252 | 1462 | 1477 | ACTCCAGTGCTGGAAG | ekkdddddddddddkke | 85 | 10473 | 10488 | 96 |
| 612253 | 1463 | 1478 | CACTCCAGTGCTGGAA | ekkdddddddddddkke | 31 | 10474 | 10489 | 978 |
| 612254 | 1465 | 1480 | GTCACTCCAGTGCTGG | ekkdddddddddddkke | 77 | 10476 | 10491 | 97 |
| 612255 | 1466 | 1481 | TGTCACTCCAGTGCTG | ekkdddddddddddkke | 58 | 10477 | 10492 | 979 |
| 612256 | 1467 | 1482 | ATGTCACTCCAGTGCT | ekkdddddddddddkke | 8 | 10478 | 10493 | 980 |
| 612257 | 1468 | 1483 | GATGTCACTCCAGTGC | ekkdddddddddddkke | 35 | 10479 | 10494 | 981 |
| 612258 | 1469 | 1484 | GGATGTCACTCCAGTG | ekkdddddddddddkke | 2 | 10480 | 10495 | 982 |
| 612259 | 1470 | 1485 | TGGATGTCACTCCAGT | ekkdddddddddddkke | 15 | 10481 | 10496 | 983 |
| 612260 | 1472 | 1487 | CCTGGATGTCACTCCA | ekkdddddddddddkke | 40 | 10483 | 10498 | 984 |
| 612261 | 1475 | 1490 | TGTCCTGGATGTCACT | ekkdddddddddddkke | 46 | 10486 | 10501 | 985 |
| 612262 | 1478 | 1493 | AGTTGTCCTGGATGTC | ekkdddddddddddkke | 63 | 10489 | 10504 | 986 |
| 612263 | 1481 | 1496 | AGAAGTTGTCCTGGAT | ekkdddddddddddkke | 65 | 10492 | 10507 | 987 |
| 612264 | 1484 | 1499 | CCGAGAAGTTGTCCTG | ekkdddddddddddkke | 59 | 10495 | 10510 | 99 |
| 612265 | 1487 | 1502 | TCACCGAGAAGTTGTC | ekkdddddddddddkke | 0 | 10498 | 10513 | 988 |
| 612266 | 1490 | 1505 | GAGTCACCGAGAAGTT | ekkdddddddddddkke | 68 | 10501 | 10516 | 989 |
| 612267 | 1493 | 1508 | CTTGAGTCACCGAGAA | ekkdddddddddddkke | 76 | 10504 | 10519 | 990 |
| 612268 | 1496 | 1511 | GCACTTGAGTCACCGA | ekkdddddddddddkke | 77 | 10507 | 10522 | 991 |
| 612269 | 1499 | 1514 | AGGGCACTTGAGTCAC | ekkdddddddddddkke | 43 | 10510 | 10525 | 992 |
| 612270 | 1502 | 1517 | TGAAGGGCACTTGAGT | ekkdddddddddddkke | 42 | 10513 | 10528 | 993 |
| 612271 | 1505 | 1520 | CAGTGAAGGGCACTTG | ekkdddddddddddkke | 65 | 10516 | 10531 | 994 |
| 612272 | 1508 | 1523 | TCTCAGTGAAGGGCAC | ekkdddddddddddkke | 0 | 10519 | 10534 | 995 |
| 612273 | 1511 | 1526 | CGCTCTCAGTGAAGGG | ekkdddddddddddkke | 35 | 10522 | 10537 | 996 |
| 612274 | 1524 | 1539 | AGCAGCAGGCAGGCGC | ekkdddddddddddkke | 77 | 10535 | 10550 | 997 |
| 612275 | 1528 | 1543 | GATCAGCAGCAGGCAG | ekkdddddddddddkke | 64 | 10539 | 10554 | 998 |
| 612276 | 1532 | 1547 | GCTGGATCAGCAGCAG | ekkdddddddddddkke | 33 | 10543 | 10558 | 999 |
| 612277 | 1535 | 1550 | GAGGCTGGATCAGCAG | ekkdddddddddddkke | 81 | 10546 | 10561 | 1000 |
| 612278 | 1538 | 1553 | AGTGAGGCTGGATCAG | ekkdddddddddddkke | 79 | 10549 | 10564 | 1001 |
| 612279 | 1541 | 1556 | CATAGTGAGGCTGGAT | ekkdddddddddddkke | 58 | 10552 | 10567 | 1002 |
| 612280 | 1544 | 1559 | AGGCATAGTGAGGCTG | ekkdddddddddddkke | 20 | 10555 | 10570 | 1003 |
| 612688 | N/A | N/A | CGGCTTACCTTCTGCT | ekkdddddddddddkke | 0 | 2483 | 2498 | 565 |
| 612799 | N/A | N/A | AGACACACAGGCCGCC | ekkdddddddddddkke | 0 | 10783 | 10798 | 1004 |
| 612800 | N/A | N/A | ACACTAACTGGAGAGC | ekkdddddddddddkke | 29 | 10830 | 10845 | 1005 |
| 612801 | N/A | N/A | AGAGGGCGGATTGCAA | ekkdddddddddddkke | 39 | 10939 | 10954 | 1006 |
| 612802 | N/A | N/A | CAGAGGGCGGATTGCA | ekkdddddddddddkke | 37 | 10940 | 10955 | 1007 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612803 | N/A | N/A | TCTCAGAGGGCGGATT | ekkddddddddddkke | 36 | 10943 | 10958 | 1008 |
| 612804 | N/A | N/A | CTCTCAGAGGGCGGAT | ekkddddddddddkke | 55 | 10944 | 10959 | 1009 |
| 612805 | N/A | N/A | TCTCTCAGAGGGCGGA | ekkddddddddddkke | 34 | 10945 | 10960 | 1010 |
| 612806 | N/A | N/A | GCTGTGTGTCAGGTGT | ekkddddddddddkke | 71 | 10977 | 10992 | 1011 |
| 612807 | N/A | N/A | AAGAAGCTCTTGGATG | ekkddddddddddkke | 0 | 11003 | 11018 | 1012 |
| 612808 | N/A | N/A | TCCAAGAAGCTCTTGG | ekkddddddddddkke | 52 | 11006 | 11021 | 1013 |
| 612809 | N/A | N/A | CCAGCCGCCAGCCGCC | ekkddddddddddkke | 28 | 11109 | 11124 | 1014 |
| 612810 | N/A | N/A | TTAGTGTTTCAGCAGG | ekkddddddddddkke | 69 | 11451 | 11466 | 1015 |
| 612811 | N/A | N/A | AGTTAGTGTTTCAGCA | ekkddddddddddkke | 35 | 11453 | 11468 | 1016 |
| 612812 | N/A | N/A | AACCTCGAGGACATCG | ekkddddddddddkke | 37 | 11506 | 11521 | 1017 |
| 612813 | N/A | N/A | ACTTATAAGAGCTGAC | ekkddddddddddkke | 7 | 11696 | 11711 | 1018 |
| 612814 | N/A | N/A | AGCACTTATAAGAGCT | ekkddddddddddkke | 21 | 11699 | 11714 | 1019 |
| 612815 | N/A | N/A | GCAGTGTTCTTGATGA | ekkddddddddddkke | 27 | 11866 | 11881 | 1020 |
| 612816 | N/A | N/A | ACAGCAGTGTTCTTGA | ekkddddddddddkke | 67 | 11869 | 11884 | 1021 |
| 612817 | N/A | N/A | ATAATGCACTGTGTCT | ekkddddddddddkke | 57 | 11895 | 11910 | 1022 |
| 612818 | N/A | N/A | GATGAGGACCTAGGAA | ekkddddddddddkke | 48 | 11996 | 12011 | 1023 |
| 612819 | N/A | N/A | CCGATGAGGACCTAGG | ekkddddddddddkke | 67 | 11998 | 12013 | 1024 |
| 612820 | N/A | N/A | ACGACAGGGATGTTTG | ekkddddddddddkke | 21 | 12128 | 12143 | 1025 |
| 612821 | N/A | N/A | GGTCAGGCACAGACAC | ekkddddddddddkke | 0 | 12398 | 12413 | 1026 |
| 612822 | N/A | N/A | ATCCCGGTTTCAACTC | ekkddddddddddkke | 45 | 12671 | 12686 | 1027 |
| 612823 | N/A | N/A | TCCCGCTGGCCCCCGT | ekkddddddddddkke | 21 | 12866 | 12881 | 1028 |
| 612824 | N/A | N/A | CTAACTTAGCACAGAG | ekkddddddddddkke | 13 | 12888 | 12903 | 1029 |
| 612825 | N/A | N/A | CCATGGCCCACCAGTG | ekkddddddddddkke | 44 | 12915 | 12930 | 1030 |
| 612826 | N/A | N/A | TTGGCCATGGCCCACC | ekkddddddddddkke | 30 | 12919 | 12934 | 1031 |
| 612827 | N/A | N/A | GGCAGAATTCCTGGCT | ekkddddddddddkke | 0 | 12938 | 12953 | 1032 |
| 612828 | N/A | N/A | GCAAGGGTGTGTCTGT | ekkddddddddddkke | 13 | 13059 | 13074 | 1033 |
| 612829 | N/A | N/A | GGCAAGGGTGTGTCTG | ekkddddddddddkke | 23 | 13060 | 13075 | 1034 |
| 612830 | N/A | N/A | CTCAGTGTAGGCAAGG | ekkddddddddddkke | 60 | 13069 | 13084 | 1035 |
| 612831 | N/A | N/A | GAGGATGCACAGTGTA | ekkddddddddddkke | 12 | 13094 | 13109 | 1036 |
| 612832 | N/A | N/A | GCTCAGGACCTCTGTG | ekkddddddddddkke | 22 | 13151 | 13166 | 1037 |
| 612833 | N/A | N/A | GGCTCAGGACCTCTGT | ekkddddddddddkke | 34 | 13152 | 13167 | 1038 |
| 612834 | N/A | N/A | GGCGCACTGGGTGACC | ekkddddddddddkke | 38 | 13198 | 13213 | 1039 |
| 612835 | N/A | N/A | TCTGAGGGCGCACTGG | ekkddddddddddkke | 9 | 13204 | 13219 | 1040 |
| 612836 | N/A | N/A | TCATTCTGAGGGCGCA | ekkddddddddddkke | 1 | 13208 | 13223 | 1041 |
| 612838 | N/A | N/A | GCTCCTACCGGGGAGA | ekkddddddddddkke | 33 | 10636 | 10651 | 1042 |
| 612839 | N/A | N/A | ACACATACCTCCCCCA | ekkddddddddddkke | 0 | 12376 | 12391 | 1043 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612840 | N/A | N/A | CGCATACCCTGAAATA | ekkddddddddddkke | 0 | 5715 | 5730 | 1044 |
| 612842 | N/A | N/A | GGATGGTCCTGGGGAG | ekkddddddddddkke | 13 | 12231 | 12246 | 1045 |
| 612843 | N/A | N/A | TTCAGCACCTGCAAAG | ekkddddddddddkke | 0 | 13239 | 13254 | 1046 |
| 612844 | N/A | N/A | CCGGCTTACCTTCTGC | ekkddddddddddkke | 9 | 2484 | 2499 | 1047 |
| 612845 | N/A | N/A | CCCCCGGCTTACCTTC | ekkddddddddddkke | 0 | 2487 | 2502 | 1048 |
| 612846 | N/A | N/A | GGGCCCCCGGCTTACC | ekkddddddddddkke | 0 | 2490 | 2505 | 1049 |
| 612847 | N/A | N/A | GTGAATGTGAGCCCCG | ekkddddddddddkke | 14 | 3361 | 3376 | 1050 |
| 612848 | N/A | N/A | TCCCTCCTTATAACCC | ekkddddddddddkke | 0 | 3435 | 3450 | 1051 |
| 612849 | N/A | N/A | CCGGGCACTCTCAACT | ekkddddddddddkke | 4 | 3471 | 3486 | 1052 |
| 612850 | N/A | N/A | AGTAATGGTGCTCTGG | ekkddddddddddkke | 4 | 3752 | 3767 | 1053 |
| 612851 | N/A | N/A | TCCTGGGAGTAATGGT | ekkddddddddddkke | 30 | 3759 | 3774 | 1054 |
| 612852 | N/A | N/A | TCTCAGTTGTGATCTG | ekkddddddddddkke | 31 | 3817 | 3832 | 1055 |
| 612853 | N/A | N/A | TCCAGAGACGCAATTC | ekkddddddddddkke | 0 | 3868 | 3883 | 1056 |
| 612854 | N/A | N/A | TCTCCAGAGACGCAAT | ekkddddddddddkke | 11 | 3870 | 3885 | 1057 |
| 612855 | N/A | N/A | ACCTGTGGGAACCGAC | ekkddddddddddkke | 4 | 3983 | 3998 | 1058 |
| 612856 | N/A | N/A | AAACCTGTGGGAACCG | ekkddddddddddkke | 0 | 3985 | 4000 | 1059 |
| 612857 | N/A | N/A | CCTAGATTTTTCTGCT | ekkddddddddddkke | 27 | 4340 | 4355 | 1060 |
| 612858 | N/A | N/A | GCCTTTTCTGTCCCCC | ekkddddddddddkke | 57 | 4420 | 4435 | 1061 |
| 612859 | N/A | N/A | CATTTCTTGTGGAGGG | ekkddddddddddkke | 12 | 4464 | 4479 | 1062 |
| 612860 | N/A | N/A | TGGGCTGGCCCTGCTA | ekkddddddddddkke | 2 | 4569 | 4584 | 1063 |
| 612861 | N/A | N/A | GAGCCCCAAAGGCATG | ekkddddddddddkke | 33 | 4822 | 4837 | 1064 |
| 612862 | N/A | N/A | TCTAATATGACCTGTG | ekkddddddddddkke | 43 | 5357 | 5372 | 1065 |
| 612863 | N/A | N/A | TGATCTAATATGACCT | ekkddddddddddkke | 13 | 5360 | 5375 | 1066 |
| 612864 | N/A | N/A | GTCCTCAACCCCAGGA | ekkddddddddddkke | 0 | 5455 | 5470 | 1067 |
| 612865 | N/A | N/A | GCTCCATGGAAAATAT | ekkddddddddddkke | 4 | 5553 | 5568 | 1068 |
| 612866 | N/A | N/A | TCCATTCATGTCTACA | ekkddddddddddkke | 19 | 5593 | 5608 | 1069 |
| 612867 | N/A | N/A | TTAAGTGCCATCTAAC | ekkddddddddddkke | 17 | 5660 | 5675 | 1070 |
| 612868 | N/A | N/A | GCATACCCTGAAATAT | ekkddddddddddkke | 0 | 5714 | 5729 | 1071 |
| 612893 | N/A | N/A | TGTCTACTCCCCACCC | ekkddddddddddkke | 42 | 10707 | 10722 | 1072 |
| 612894 | N/A | N/A | ACAGACACTAACTGGA | ekkddddddddddkke | 28 | 10834 | 10849 | 1073 |
| 612895 | N/A | N/A | GTGTGTCAGGTGTGGG | ekkddddddddddkke | 37 | 10974 | 10989 | 1074 |
| 612896 | N/A | N/A | GCAAGTCAGTTCCAAG | ekkddddddddddkke | 35 | 11016 | 11031 | 1075 |
| 612897 | N/A | N/A | CTCGAAAATGGTTACG | ekkddddddddddkke | 55 | 11336 | 11351 | 1076 |
| 612898 | N/A | N/A | GGTGGTAACCACATGC | ekkddddddddddkke | 53 | 11583 | 11598 | 1077 |
| 612899 | N/A | N/A | ATGCACTGTGTCTTAC | ekkddddddddddkke | 31 | 11892 | 11907 | 1078 |
| 612900 | N/A | N/A | AATAATGCACTGTGTC | ekkddddddddddkke | 39 | 11896 | 11911 | 1079 |

TABLE 5-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612901 | N/A | N/A | GTTACTTGGGTAATTT | ekkddddddddddkke | 68 | 11930 | 11945 | 1080 |
| 612902 | N/A | N/A | TCCTTTGGTGCATTCT | ekkddddddddddkke | 19 | 11974 | 11989 | 1081 |
| 612903 | N/A | N/A | CTAGGAATGGTTGTCC | ekkddddddddddkke | 0 | 11987 | 12002 | 1082 |
| 612904 | N/A | N/A | GACGACAGGGATGTTT | ekkddddddddddkke | 20 | 12129 | 12144 | 1083 |
| 612905 | N/A | N/A | CTGACGACAGGGATGT | ekkddddddddddkke | 25 | 12131 | 12146 | 1084 |
| 612906 | N/A | N/A | GCACAGTTAGGAAGGC | ekkddddddddddkke | 60 | 12210 | 12225 | 1085 |
| 612907 | N/A | N/A | TTAGCTAACTTAGCAC | ekkddddddddddkke | 8 | 12892 | 12907 | 1086 |
| 612908 | N/A | N/A | CATGGCCCACCAGTGC | ekkddddddddddkke | 41 | 12914 | 12929 | 1087 |
| 612909 | N/A | N/A | CACAGTGTATGCCTGC | ekkddddddddddkke | 52 | 13087 | 13102 | 1088 |
| 612910 | N/A | N/A | GCACTGGGTGACCCAG | ekkddddddddddkke | 0 | 13195 | 13210 | 1089 |
| 612911 | N/A | N/A | TCAGCACCTGCAAAGC | ekkddddddddddkke | 0 | 13238 | 13253 | 1090 |

Table 6 shows inhibition of AGT mRNA in HepG2 cells cultured at a density of 20,000 cells per well which were transfected using electroporation with 1000 nM antisense oligonucleotide. After a treatment period of approximately 24 hours, RNA was isolated from the cells and AGT mRNA levels were measured by quantitative real-time PCR. Human primer probe set RTS4039 (forward sequence GGACAAGGTGGAGGGTCTCA, designated herein as SEQ ID NO: 11; reverse sequence AGATCCTTGCAGCACCAGTTG, designated herein as SEQ ID NO: 12; and probe sequence ATGAAGAAAC-TATCTCCCCGGACCATCCAX, where X is a fluorescent label, designated herein as SEQ ID NO: 13) was used to measure mRNA levels. AGT mRNA levels were adjusted according to total RNA content, as measured by RIBOGREEN®. Results are presented as percent inhibition of AGT, relative to untreated control cells.

TABLE 6

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 74 | 13515 | 13530 | 129 |
| 594622 | 2027 | 2042 | GTTATCTGCTGCTGGC | kkkddddddddddkkk | 64 | 13496 | 13511 | 163 |
| 594625 | 2047 | 2062 | TCGCTGATTTGTCCGG | kkkddddddddddkkk | 57 | 13516 | 13531 | 165 |
| 612205 | 1279 | 1294 | CTTCCATCCTGTCACA | ekkddddddddddkke | 0 | 6496 | 6511 | 957 |
| 612206 | 1282 | 1297 | AGTCTTCCATCCTGTC | ekkddddddddddkke | 9 | 6499 | 6514 | 958 |
| 612207 | 1286 | 1301 | AGCCAGTCTTCCATCC | ekkddddddddddkke | 0 | 6503 | 6518 | 959 |
| 612208 | 1290 | 1305 | GAGCAGCCAGTCTTCC | ekkddddddddddkke | 0 | 6507 | 6522 | 1091 |
| 612209 | 1293 | 1308 | AGGGAGCAGCCAGTCT | ekkddddddddddkke | 0 | 6510 | 6525 | 1092 |
| 612210 | 1296 | 1311 | ATCAGGGAGCAGCCAG | ekkddddddddddkke | 0 | 6513 | 6528 | 1093 |
| 612211 | 1300 | 1315 | TCCCATCAGGGAGCAG | ekkddddddddddkke | 0 | 6517 | 6532 | 1094 |
| 612212 | 1303 | 1318 | GGCTCCCATCAGGGAG | ekkddddddddddkke | 0 | 6520 | 6535 | 1095 |
| 612213 | 1306 | 1321 | ACTGGCTCCCATCAGG | ekkddddddddddkke | 16 | 6523 | 6538 | 1096 |
| 612214 | 1310 | 1325 | CCACACTGGCTCCCAT | ekkddddddddddkke | 0 | 6527 | 6542 | 1097 |

TABLE 6-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612215 | 1315 | 1330 | GCTGTCCACACTGGCT | ekkddddddddddkke | 13 | 6532 | 6547 | 1098 |
| 612216 | 1318 | 1333 | GGTGCTGTCCACACTG | ekkddddddddddkke | 20 | 6535 | 6550 | 1099 |
| 612217 | 1321 | 1336 | CAGGGTGCTGTCCACA | ekkddddddddddkke | 0 | 6538 | 6553 | 1100 |
| 612218 | 1324 | 1339 | AGCCAGGGTGCTGTCC | ekkddddddddddkke | 14 | 6541 | 6556 | 1101 |
| 612219 | 1327 | 1342 | GAAAGCCAGGGTGCTG | ekkddddddddddkke | 0 | 6544 | 6559 | 1102 |
| 612220 | 1330 | 1345 | GTTGAAAGCCAGGGTG | ekkddddddddddkke | 6 | 6547 | 6562 | 1103 |
| 612221 | 1333 | 1348 | GGTGTTGAAAGCCAGG | ekkddddddddddkke | 34 | 6550 | 6565 | 1104 |
| 612222 | 1336 | 1351 | GTAGGTGTTGAAAGCC | ekkddddddddddkke | 9 | 6553 | 6568 | 1105 |
| 612223 | 1351 | 1366 | CCCTTGGAAGTGGACG | ekkddddddddddkke | 0 | N/A | N/A | 1106 |
| 612224 | 1354 | 1369 | CTTCCCTTGGAAGTGG | ekkddddddddddkke | 17 | N/A | N/A | 1107 |
| 612225 | 1357 | 1372 | CATCTTCCCTTGGAAG | ekkddddddddddkke | 11 | N/A | N/A | 1108 |
| 612226 | 1360 | 1375 | CTTCATCTTCCCTTGG | ekkddddddddddkke | 0 | N/A | N/A | 1109 |
| 612227 | 1364 | 1379 | AGCCCTTCATCTTCCC | ekkddddddddddkke | 5 | 10375 | 10390 | 1110 |
| 612228 | 1367 | 1382 | AGAAGCCCTTCATCTT | ekkddddddddddkke | 0 | 10378 | 10393 | 1111 |
| 612229 | 1370 | 1385 | GGGAGAAGCCCTTCAT | ekkddddddddddkke | 0 | 10381 | 10396 | 1112 |
| 612230 | 1373 | 1388 | GCAGGGAGAAGCCCTT | ekkddddddddddkke | 25 | 10384 | 10399 | 1113 |
| 612231 | 1380 | 1395 | TCGGCCAGCAGGGAGA | ekkddddddddddkke | 32 | 10391 | 10406 | 1114 |
| 612232 | 1383 | 1398 | GGCTCGGCCAGCAGGG | ekkddddddddddkke | 24 | 10394 | 10409 | 1115 |
| 612233 | 1399 | 1414 | CACCCAGAACTCCTGG | ekkddddddddddkke | 5 | 10410 | 10425 | 960 |
| 612234 | 1402 | 1417 | GTCCACCCAGAACTCC | ekkddddddddddkke | 0 | 10413 | 10428 | 961 |
| 612235 | 1405 | 1420 | GTTGTCCACCCAGAAC | ekkddddddddddkke | 0 | 10416 | 10431 | 962 |
| 612236 | 1408 | 1423 | GCTGTTGTCCACCCAG | ekkddddddddddkke | 14 | 10419 | 10434 | 963 |
| 612237 | 1411 | 1426 | GGTGCTGTTGTCCACC | ekkddddddddddkke | 20 | 10422 | 10437 | 964 |
| 612238 | 1414 | 1429 | TGAGGTGCTGTTGTCC | ekkddddddddddkke | 32 | 10425 | 10440 | 965 |
| 612239 | 1417 | 1432 | CACTGAGGTGCTGTTG | ekkddddddddddkke | 36 | 10428 | 10443 | 966 |
| 612240 | 1421 | 1436 | CAGACACTGAGGTGCT | ekkddddddddddkke | 1 | 10432 | 10447 | 93 |
| 612241 | 1429 | 1444 | CATGGGAACAGACACT | ekkddddddddddkke | 9 | 10440 | 10455 | 967 |
| 612242 | 1432 | 1447 | GAGCATGGGAACAGAC | ekkddddddddddkke | 0 | 10443 | 10458 | 968 |
| 612243 | 1435 | 1450 | AGAGAGCATGGGAACA | ekkddddddddddkke | 0 | 10446 | 10461 | 969 |
| 612244 | 1438 | 1453 | GCCAGAGAGCATGGGA | ekkddddddddddkke | 5 | 10449 | 10464 | 970 |
| 612245 | 1441 | 1456 | CATGCCAGAGAGCATG | ekkddddddddddkke | 27 | 10452 | 10467 | 971 |
| 612246 | 1444 | 1459 | GCCCATGCCAGAGAGC | ekkddddddddddkke | 0 | 10455 | 10470 | 972 |
| 612247 | 1447 | 1462 | GGTGCCCATGCCAGAG | ekkddddddddddkke | 36 | 10458 | 10473 | 973 |
| 612248 | 1450 | 1465 | GAAGGTGCCCATGCCA | ekkddddddddddkke | 0 | 10461 | 10476 | 974 |
| 612249 | 1453 | 1468 | CTGGAAGGTGCCCATG | ekkddddddddddkke | 24 | 10464 | 10479 | 975 |
| 612250 | 1457 | 1472 | AGTGCTGGAAGGTGCC | ekkddddddddddkke | 0 | 10468 | 10483 | 976 |

TABLE 6-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612251 | 1460 | 1475 | TCCAGTGCTGGAAGGT | ekkddddddddddkke | 3 | 10471 | 10486 | 977 |
| 612252 | 1462 | 1477 | ACTCCAGTGCTGGAAG | ekkddddddddddkke | 72 | 10473 | 10488 | 96 |
| 612253 | 1463 | 1478 | CACTCCAGTGCTGGAA | ekkddddddddddkke | 19 | 10474 | 10489 | 978 |
| 612254 | 1465 | 1480 | GTCACTCCAGTGCTGG | ekkddddddddddkke | 45 | 10476 | 10491 | 97 |
| 612255 | 1466 | 1481 | TGTCACTCCAGTGCTG | ekkddddddddddkke | 15 | 10477 | 10492 | 979 |
| 612256 | 1467 | 1482 | ATGTCACTCCAGTGCT | ekkddddddddddkke | 0 | 10478 | 10493 | 980 |
| 612257 | 1468 | 1483 | GATGTCACTCCAGTGC | ekkddddddddddkke | 16 | 10479 | 10494 | 981 |
| 612258 | 1469 | 1484 | GGATGTCACTCCAGTG | ekkddddddddddkke | 0 | 10480 | 10495 | 982 |
| 612259 | 1470 | 1485 | TGGATGTCACTCCAGT | ekkddddddddddkke | 3 | 10481 | 10496 | 983 |
| 612260 | 1472 | 1487 | CCTGGATGTCACTCCA | ekkddddddddddkke | 10 | 10483 | 10498 | 984 |
| 612261 | 1475 | 1490 | TGTCCTGGATGTCACT | ekkddddddddddkke | 8 | 10486 | 10501 | 985 |
| 612262 | 1478 | 1493 | AGTTGTCCTGGATGTC | ekkddddddddddkke | 0 | 10489 | 10504 | 986 |
| 612263 | 1481 | 1496 | AGAAGTTGTCCTGGAT | ekkddddddddddkke | 14 | 10492 | 10507 | 987 |
| 612264 | 1484 | 1499 | CCGAGAAGTTGTCCTG | ekkddddddddddkke | 10 | 10495 | 10510 | 99 |
| 612265 | 1487 | 1502 | TCACCGAGAAGTTGTC | ekkddddddddddkke | 0 | 10498 | 10513 | 988 |
| 612266 | 1490 | 1505 | GAGTCACCGAGAAGTT | ekkddddddddddkke | 33 | 10501 | 10516 | 989 |
| 612267 | 1493 | 1508 | CTTGAGTCACCGAGAA | ekkddddddddddkke | 35 | 10504 | 10519 | 990 |
| 612268 | 1496 | 1511 | GCACTTGAGTCACCGA | ekkddddddddddkke | 37 | 10507 | 10522 | 991 |
| 612269 | 1499 | 1514 | AGGGCACTTGAGTCAC | ekkddddddddddkke | 0 | 10510 | 10525 | 992 |
| 612270 | 1502 | 1517 | TGAAGGGCACTTGAGT | ekkddddddddddkke | 8 | 10513 | 10528 | 993 |
| 612271 | 1505 | 1520 | CAGTGAAGGGCACTTG | ekkddddddddddkke | 8 | 10516 | 10531 | 994 |
| 612272 | 1508 | 1523 | TCTCAGTGAAGGGCAC | ekkddddddddddkke | 0 | 10519 | 10534 | 995 |
| 612273 | 1511 | 1526 | CGCTCTCAGTGAAGGG | ekkddddddddddkke | 18 | 10522 | 10537 | 996 |
| 612274 | 1524 | 1539 | AGCAGCAGGCAGGCGC | ekkddddddddddkke | 27 | 10535 | 10550 | 997 |
| 612275 | 1528 | 1543 | GATCAGCAGCAGGCAG | ekkddddddddddkke | 39 | 10539 | 10554 | 998 |
| 612276 | 1532 | 1547 | GCTGGATCAGCAGCAG | ekkddddddddddkke | 21 | 10543 | 10558 | 999 |
| 612277 | 1535 | 1550 | GAGGCTGGATCAGCAG | ekkddddddddddkke | 34 | 10546 | 10561 | 1000 |
| 612278 | 1538 | 1553 | AGTGAGGCTGGATCAG | ekkddddddddddkke | 28 | 10549 | 10564 | 1001 |
| 612279 | 1541 | 1556 | CATAGTGAGGCTGGAT | ekkddddddddddkke | 13 | 10552 | 10567 | 1002 |
| 612280 | 1544 | 1559 | AGGCATAGTGAGGCTG | ekkddddddddddkke | 0 | 10555 | 10570 | 1003 |

Table 7 shows inhibition of AGT mRNA in HepG2 cells cultured at a density of 20,000 cells per well which were transfected using electroporation with 1000 nM antisense oligonucleotide. After a treatment period of approximately 24 hours, RNA was isolated from the cells and AGT mRNA levels were measured by quantitative real-time PCR. Human primer probe set RTS4039 was used to measure mRNA levels. AGT mRNA levels were adjusted according to total RNA content, as measured by RIBOGREEN®. Results are presented as percent inhibition of AGT, relative to untreated control cells.

TABLE 7

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568637 | 2046 | 2061 | CGCTGATTTGTCCGGG | eekddddddddddkke | 93 | 13515 | 13530 | 129 |
| 568637 | 2046 | 2061 | CGCTGATTTGTCCGGG | eekddddddddddkke | 90 | 13515 | 13530 | 129 |
| 568637 | 2046 | 2061 | CGCTGATTTGTCCGGG | eekddddddddddkke | 84 | 13515 | 13530 | 129 |
| 594622 | 2027 | 2042 | GTTATCTGCTGCTGGC | kkkddddddddddkkk | 86 | 13496 | 13511 | 163 |
| 594622 | 2027 | 2042 | GTTATCTGCTGCTGGC | kkkddddddddddkkk | 85 | 13496 | 13511 | 163 |
| 594622 | 2027 | 2042 | GTTATCTGCTGCTGGC | kkkddddddddddkkk | 5 | 13496 | 13511 | 163 |
| 594625 | 2047 | 2062 | TCGCTGATTTGTCCGG | kkkddddddddddkkk | 75 | 13516 | 13531 | 165 |
| 594625 | 2047 | 2062 | TCGCTGATTTGTCCGG | kkkddddddddddkkk | 70 | 13516 | 13531 | 165 |
| 594625 | 2047 | 2062 | TCGCTGATTTGTCCGG | kkkddddddddddkkk | 0 | 13516 | 13531 | 165 |
| 612129 | 965 | 980 | GCCTGTCAGCTGTGTG | ekkddddddddddkke | 35 | 6182 | 6197 | 889 |
| 612130 | 968 | 983 | GTAGCCTGTCAGCTGT | ekkddddddddddkke | 35 | 6185 | 6200 | 890 |
| 612131 | 971 | 986 | CCTGTAGCCTGTCAGC | ekkddddddddddkke | 30 | 6188 | 6203 | 891 |
| 612132 | 974 | 989 | TTGCCTGTAGCCTGTC | ekkddddddddddkke | 37 | 6191 | 6206 | 892 |
| 612133 | 977 | 992 | GGATTGCCTGTAGCCT | ekkddddddddddkke | 30 | 6194 | 6209 | 893 |
| 612134 | 980 | 995 | CCAGGATTGCCTGTAG | ekkddddddddddkke | 56 | 6197 | 6212 | 894 |
| 612135 | 983 | 998 | CACCCAGGATTGCCTG | ekkddddddddddkke | 0 | 6200 | 6215 | 68 |
| 612136 | 986 | 1001 | GAACACCCAGGATTGC | ekkddddddddddkke | 8 | 6203 | 6218 | 895 |
| 612137 | 993 | 1008 | TTCCAAGGAACACCCA | ekkddddddddddkke | 27 | 6210 | 6225 | 69 |
| 612138 | 997 | 1012 | GTCCTTCCAAGGAACA | ekkddddddddddkke | 26 | 6214 | 6229 | 896 |
| 612139 | 1000 | 1015 | CTTGTCCTTCCAAGGA | ekkddddddddddkke | 47 | 6217 | 6232 | 897 |
| 612140 | 1003 | 1018 | GTTCTTGTCCTTCCAA | ekkddddddddddkke | 36 | 6220 | 6235 | 898 |
| 612141 | 1006 | 1021 | GCAGTTCTTGTCCTTC | ekkddddddddddkke | 28 | 6223 | 6238 | 899 |
| 612142 | 1009 | 1024 | GGTGCAGTTCTTGTCC | ekkddddddddddkke | 13 | 6226 | 6241 | 900 |
| 612143 | 1012 | 1027 | GGAGGTGCAGTTCTTG | ekkddddddddddkke | 0 | 6229 | 6244 | 901 |
| 612144 | 1015 | 1030 | CCGGGAGGTGCAGTTC | ekkddddddddddkke | 27 | 6232 | 6247 | 902 |
| 612145 | 1018 | 1033 | CAGCCGGGAGGTGCAG | ekkddddddddddkke | 39 | 6235 | 6250 | 903 |
| 612146 | 1021 | 1036 | ATCCAGCCGGGAGGTG | ekkddddddddddkke | 24 | 6238 | 6253 | 904 |
| 612147 | 1024 | 1039 | CGCATCCAGCCGGGAG | ekkddddddddddkke | 55 | 6241 | 6256 | 905 |
| 612148 | 1027 | 1042 | GTGCGCATCCAGCCGG | ekkddddddddddkke | 37 | 6244 | 6259 | 906 |
| 612149 | 1030 | 1045 | CTTGTGCGCATCCAGC | ekkddddddddddkke | 11 | 6247 | 6262 | 907 |
| 612150 | 1033 | 1048 | GACCTTGTGCGCATCC | ekkddddddddddkke | 12 | 6250 | 6265 | 908 |
| 612151 | 1036 | 1051 | CAGGACCTTGTGCGCA | ekkddddddddddkke | 41 | 6253 | 6268 | 909 |
| 612152 | 1039 | 1054 | AGACAGGACCTTGTGC | ekkddddddddddkke | 9 | 6256 | 6271 | 910 |
| 612153 | 1042 | 1057 | GGCAGACAGGACCTTG | ekkddddddddddkke | 30 | 6259 | 6274 | 911 |
| 612154 | 1060 | 1075 | GCCCTGTACAGCCTGC | ekkddddddddddkke | 19 | 6277 | 6292 | 912 |
| 612155 | 1064 | 1079 | GCAGGCCCTGTACAGC | ekkddddddddddkke | 0 | 6281 | 6296 | 913 |

TABLE 7-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612156 | 1067 | 1082 | CTAGCAGGCCCTGTAC | ekkddddddddddkke | 21 | 6284 | 6299 | 914 |
| 612157 | 1071 | 1086 | GCCACTAGCAGGCCCT | ekkddddddddddkke | 0 | 6288 | 6303 | 915 |
| 612158 | 1074 | 1089 | TGGGCCACTAGCAGGC | ekkddddddddddkke | 13 | 6291 | 6306 | 916 |
| 612159 | 1077 | 1092 | CCCTGGGCCACTAGCA | ekkddddddddddkke | 23 | 6294 | 6309 | 917 |
| 612160 | 1080 | 1095 | CTGCCCTGGGCCACTA | ekkddddddddddkke | 28 | 6297 | 6312 | 918 |
| 612161 | 1088 | 1103 | TATCAGCCCTGCCCTG | ekkddddddddddkke | 0 | 6305 | 6320 | 74 |
| 612162 | 1091 | 1106 | GGCTATCAGCCCTGCC | ekkddddddddddkke | 27 | 6308 | 6323 | 919 |
| 612163 | 1094 | 1109 | CCTGGCTATCAGCCCT | ekkddddddddddkke | 13 | 6311 | 6326 | 920 |
| 612164 | 1097 | 1112 | GGGCCTGGCTATCAGC | ekkddddddddddkke | 3 | 6314 | 6329 | 921 |
| 612165 | 1100 | 1115 | GCTGGGCCTGGCTATC | ekkddddddddddkke | 10 | 6317 | 6332 | 922 |
| 612166 | 1115 | 1130 | CCGTGGACAGCAGCAG | ekkddddddddddkke | 12 | 6332 | 6347 | 923 |
| 612167 | 1118 | 1133 | CCACCGTGGACAGCAG | ekkddddddddddkke | 42 | 6335 | 6350 | 924 |
| 612168 | 1121 | 1136 | CCACCACCGTGGACAG | ekkddddddddddkke | 27 | 6338 | 6353 | 925 |
| 612169 | 1124 | 1139 | CGCCCACCACCGTGGA | ekkddddddddddkke | 29 | 6341 | 6356 | 926 |
| 612170 | 1127 | 1142 | ACACGCCCACCACCGT | ekkddddddddddkke | 9 | 6344 | 6359 | 927 |
| 612171 | 1130 | 1145 | TGAACACGCCCACCAC | ekkddddddddddkke | 25 | 6347 | 6362 | 928 |
| 612172 | 1133 | 1148 | CTGTGAACACGCCCAC | ekkddddddddddkke | 32 | 6350 | 6365 | 929 |
| 612173 | 1136 | 1151 | GGGCTGTGAACACGCC | ekkddddddddddkke | 0 | 6353 | 6368 | 930 |
| 612174 | 1151 | 1166 | TCAGGTGCAGGCCTGG | ekkddddddddddkke | 8 | 6368 | 6383 | 78 |
| 612175 | 1154 | 1169 | GCTTCAGGTGCAGGCC | ekkddddddddddkke | 30 | 6371 | 6386 | 931 |
| 612176 | 1157 | 1172 | GCTGCTTCAGGTGCAG | ekkddddddddddkke | 21 | 6374 | 6389 | 932 |
| 612177 | 1160 | 1175 | ACGGCTGCTTCAGGTG | ekkddddddddddkke | 46 | 6377 | 6392 | 933 |
| 612178 | 1163 | 1178 | CAAACGGCTGCTTCAG | ekkddddddddddkke | 7 | 6380 | 6395 | 934 |
| 612179 | 1166 | 1181 | GCACAAACGGCTGCTT | ekkddddddddddkke | 31 | 6383 | 6398 | 935 |
| 612180 | 1169 | 1184 | CCTGCACAAACGGCTG | ekkddddddddddkke | 10 | 6386 | 6401 | 936 |
| 612181 | 1172 | 1187 | GGCCCTGCACAAACGG | ekkddddddddddkke | 5 | 6389 | 6404 | 937 |
| 612182 | 1182 | 1197 | TAGAGAGCCAGGCCCT | ekkddddddddddkke | 29 | 6399 | 6414 | 80 |
| 612183 | 1185 | 1200 | GTATAGAGAGCCAGGC | ekkddddddddddkke | 0 | 6402 | 6417 | 938 |
| 612184 | 1203 | 1218 | CGTGGGAGGACCACAG | ekkddddddddddkke | 16 | 6420 | 6435 | 81 |
| 612185 | 1217 | 1232 | TGAAGTCCAGAGAGCG | ekkddddddddddkke | 27 | 6434 | 6449 | 82 |
| 612186 | 1220 | 1235 | CTGTGAAGTCCAGAGA | ekkddddddddddkke | 26 | 6437 | 6452 | 939 |
| 612187 | 1223 | 1238 | GTTCTGTGAAGTCCAG | ekkddddddddddkke | 44 | 6440 | 6455 | 940 |
| 612188 | 1226 | 1241 | CCAGTTCTGTGAAGTC | ekkddddddddddkke | 29 | 6443 | 6458 | 941 |
| 612189 | 1229 | 1244 | CATCCAGTTCTGTGAA | ekkddddddddddkke | 14 | 6446 | 6461 | 942 |
| 612190 | 1232 | 1247 | CAACATCCAGTTCTGT | ekkddddddddddkke | 0 | 6449 | 6464 | 943 |
| 612191 | 1235 | 1250 | CAGCAACATCCAGTTC | ekkddddddddddkke | 24 | 6452 | 6467 | 944 |

TABLE 7-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID 2: Start Site | SEQ ID 2: Stop Site | SEQ ID NO |
|---|---|---|---|---|---|---|---|---|
| 612192 | 1244 | 1259 | TCTTCTCAGCAGCAAC | ekkddddddddddkke | 62 | 6461 | 6476 | 84 |
| 612193 | 1247 | 1262 | CAATCTTCTCAGCAGC | ekkddddddddddkke | 27 | 6464 | 6479 | 945 |
| 612194 | 1250 | 1265 | TGTCAATCTTCTCAGC | ekkddddddddddkke | 18 | 6467 | 6482 | 946 |
| 612195 | 1253 | 1268 | ACCTGTCAATCTTCTC | ekkddddddddddkke | 33 | 6470 | 6485 | 947 |
| 612196 | 1256 | 1271 | TGAACCTGTCAATCTT | ekkddddddddddkke | 25 | 6473 | 6488 | 948 |
| 612197 | 1259 | 1274 | GCATGAACCTGTCAAT | ekkddddddddddkke | 27 | 6476 | 6491 | 949 |
| 612198 | 1262 | 1277 | CCTGCATGAACCTGTC | ekkddddddddddkke | 15 | 6479 | 6494 | 950 |
| 612199 | 1265 | 1280 | CAGCCTGCATGAACCT | ekkddddddddddkke | 42 | 6482 | 6497 | 951 |
| 612200 | 1267 | 1282 | CACAGCCTGCATGAAC | ekkddddddddddkke | 39 | 6484 | 6499 | 952 |
| 612201 | 1268 | 1283 | TCACAGCCTGCATGAA | ekkddddddddddkke | 27 | 6485 | 6500 | 953 |
| 612202 | 1274 | 1289 | ATCCTGTCACAGCCTG | ekkddddddddddkke | 44 | 6491 | 6506 | 954 |
| 612203 | 1276 | 1291 | CCATCCTGTCACAGCC | ekkddddddddddkke | 39 | 6493 | 6508 | 955 |
| 612204 | 1277 | 1292 | TCCATCCTGTCACAGC | ekkddddddddddkke | 27 | 6494 | 6509 | 956 |
| 612688 | N/A | N/A | CGGCTTACCTTCTGCT | ekkddddddddddkke | 7 | 2483 | 2498 | 565 |
| 612761 | N/A | N/A | CGAAGGGAGACCCATT | ekkddddddddddkke | 24 | 8270 | 8285 | 1116 |
| 612762 | N/A | N/A | TTCGAAGGGAGACCCA | ekkddddddddddkke | 9 | 8272 | 8287 | 1117 |
| 612763 | N/A | N/A | CTTTCGAAGGGAGACC | ekkddddddddddkke | 12 | 8274 | 8289 | 1118 |
| 612764 | N/A | N/A | CCGATCTCCTCACTGG | ekkddddddddddkke | 9 | 8497 | 8512 | 1119 |
| 612765 | N/A | N/A | CCCCGATCTCCTCACT | ekkddddddddddkke | 6 | 8499 | 8514 | 1120 |
| 612766 | N/A | N/A | ACAGCCCCGATCTCC | ekkddddddddddkke | 35 | 8504 | 8519 | 1121 |
| 612767 | N/A | N/A | GAGACAGCCCCCGATC | ekkddddddddddkke | 3 | 8507 | 8522 | 1122 |
| 612768 | N/A | N/A | CCGAGACAGCCCCCGA | ekkddddddddddkke | 7 | 8509 | 8524 | 1123 |
| 612769 | N/A | N/A | CTAGCTGCCTGCTGAG | ekkddddddddddkke | 27 | 8569 | 8584 | 1124 |
| 612770 | N/A | N/A | TCTAGCTGCCTGCTGA | ekkddddddddddkke | 22 | 8570 | 8585 | 1125 |
| 612771 | N/A | N/A | GTGGGACACATCTAGC | ekkddddddddddkke | 16 | 8580 | 8595 | 1126 |
| 612772 | N/A | N/A | TCTAGTGGGACACATC | ekkddddddddddkke | 27 | 8584 | 8599 | 1127 |
| 612773 | N/A | N/A | TCTCTAGTGGGACACA | ekkddddddddddkke | 17 | 8586 | 8601 | 1128 |
| 612774 | N/A | N/A | CATGAGAGTGGCTGCC | ekkddddddddddkke | 29 | 8789 | 8804 | 1129 |
| 612775 | N/A | N/A | CTTTTAGTTTAGAGGG | ekkddddddddddkke | 25 | 8883 | 8898 | 1130 |
| 612776 | N/A | N/A | ATGTGAGCGGGAAACT | ekkddddddddddkke | 16 | 8961 | 8976 | 1131 |
| 612777 | N/A | N/A | CATGTGAGCGGGAAAC | ekkddddddddddkke | 38 | 8962 | 8977 | 1132 |
| 612778 | N/A | N/A | CGGAGCACTCAGTCTC | ekkddddddddddkke | 38 | 8985 | 9000 | 1133 |
| 612779 | N/A | N/A | GTCCTCAGTCCTCGGA | ekkddddddddddkke | 8 | 8997 | 9012 | 1134 |
| 612780 | N/A | N/A | CGTCCTCAGTCCTCGG | ekkddddddddddkke | 53 | 8998 | 9013 | 1135 |
| 612781 | N/A | N/A | GCAGTGGCAGACCTGG | ekkddddddddddkke | 23 | 9023 | 9038 | 1136 |
| 612782 | N/A | N/A | TAGAGATGGTTCAGAA | ekkddddddddddkke | 13 | 9166 | 9181 | 1137 |

TABLE 7-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612783 | N/A | N/A | TGAGTAGAGATGGTTC | ekkddddddddddkke | 25 | 9170 | 9185 | 1138 |
| 612784 | N/A | N/A | GGAGTCTGAGTAGAGA | ekkddddddddddkke | 21 | 9176 | 9191 | 1139 |
| 612785 | N/A | N/A | GCCCTCGGCTGTCCTC | ekkddddddddddkke | 24 | 9294 | 9309 | 1140 |
| 612786 | N/A | N/A | CTCGACCTTACACTAG | ekkddddddddddkke | 29 | 9319 | 9334 | 1141 |
| 612787 | N/A | N/A | CCTCTGCCTCGACCTT | ekkddddddddddkke | 49 | 9326 | 9341 | 1142 |
| 612788 | N/A | N/A | AACTCGGGAGAGCCCG | ekkddddddddddkke | 41 | 9410 | 9425 | 1143 |
| 612789 | N/A | N/A | AACGAGGGCTCCATTC | ekkddddddddddkke | 22 | 9557 | 9572 | 1144 |
| 612790 | N/A | N/A | GACACACTCACTTTTT | ekkddddddddddkke | 25 | 9999 | 10014 | 1145 |
| 612791 | N/A | N/A | CTGCCAGGTCAACTCA | ekkddddddddddkke | 39 | 10050 | 10065 | 1146 |
| 612792 | N/A | N/A | GTACCTGCCAGGTCAA | ekkddddddddddkke | 25 | 10054 | 10069 | 1147 |
| 612793 | N/A | N/A | CTGGTACCTGCCAGGT | ekkddddddddddkke | 32 | 10057 | 10072 | 1148 |
| 612794 | N/A | N/A | AGTTCACTGAGGCAGC | ekkddddddddddkke | 37 | 10156 | 10171 | 1149 |
| 612795 | N/A | N/A | CCATTTGAGTTCACTG | ekkddddddddddkke | 61 | 10163 | 10178 | 1150 |
| 612796 | N/A | N/A | GCAGCCATTTGAGTTC | ekkddddddddddkke | 42 | 10167 | 10182 | 1151 |
| 612797 | N/A | N/A | AAGGCCCAGATCCTGC | ekkddddddddddkke | 0 | 10286 | 10301 | 1152 |
| 612798 | N/A | N/A | GAAATCCAGACAGGAG | ekkddddddddddkke | 11 | 10358 | 10373 | 1153 |
| 612821 | N/A | N/A | GGTCAGGCACAGACAC | ekkddddddddddkke | 0 | 12398 | 12413 | 1026 |
| 612822 | N/A | N/A | ATCCCGGTTTCAACTC | ekkddddddddddkke | 14 | 12671 | 12686 | 1027 |
| 612823 | N/A | N/A | TCCCGCTGGCCCCCGT | ekkddddddddddkke | 36 | 12866 | 12881 | 1028 |
| 612824 | N/A | N/A | CTAACTTAGCACAGAG | ekkddddddddddkke | 22 | 12888 | 12903 | 1029 |
| 612825 | N/A | N/A | CCATGGCCCACCAGTG | ekkddddddddddkke | 35 | 12915 | 12930 | 1030 |
| 612826 | N/A | N/A | TTGGCCATGGCCCACC | ekkddddddddddkke | 23 | 12919 | 12934 | 1031 |
| 612827 | N/A | N/A | GGCAGAATTCCTGGCT | ekkddddddddddkke | 0 | 12938 | 12953 | 1032 |
| 612828 | N/A | N/A | GCAAGGGTGTGTCTGT | ekkddddddddddkke | 23 | 13059 | 13074 | 1033 |
| 612829 | N/A | N/A | GGCAAGGGTGTGTCTG | ekkddddddddddkke | 29 | 13060 | 13075 | 1034 |
| 612830 | N/A | N/A | CTCAGTGTAGGCAAGG | ekkddddddddddkke | 37 | 13069 | 13084 | 1035 |
| 612831 | N/A | N/A | GAGGATGCACAGTGTA | ekkddddddddddkke | 15 | 13094 | 13109 | 1036 |
| 612832 | N/A | N/A | GCTCAGGACCTCTGTG | ekkddddddddddkke | 20 | 13151 | 13166 | 1037 |
| 612833 | N/A | N/A | GGCTCAGGACCTCTGT | ekkddddddddddkke | 48 | 13152 | 13167 | 1038 |
| 612834 | N/A | N/A | GGCGCACTGGGTGACC | ekkddddddddddkke | 32 | 13198 | 13213 | 1039 |
| 612835 | N/A | N/A | TCTGAGGGCGCACTGG | ekkddddddddddkke | 24 | 13204 | 13219 | 1040 |
| 612836 | N/A | N/A | TCATTCTGAGGGCGCA | ekkddddddddddkke | 18 | 13208 | 13223 | 1041 |
| 612837 | N/A | N/A | TGCCTTACCTTGGAAG | ekkddddddddddkke | 1 | 6574 | 6589 | 1154 |
| 612839 | N/A | N/A | ACACATACCTCCCCCA | ekkddddddddddkke | 4 | 12376 | 12391 | 1043 |
| 612840 | N/A | N/A | CGCATACCCTGAAATA | ekkddddddddddkke | 1 | 5715 | 5730 | 1044 |
| 612841 | N/A | N/A | CATCTTCCCTGAAATC | ekkddddddddddkke | 0 | 10368 | 10383 | 1155 |

TABLE 7-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 612843 | N/A | N/A | TTCAGCACCTGCAAAG | ekkddddddddddkke | 0 | 13239 | 13254 | 1046 |
| 612844 | N/A | N/A | CCGGCTTACCTTCTGC | ekkddddddddddkke | 21 | 2484 | 2499 | 1047 |
| 612845 | N/A | N/A | CCCCCGGCTTACCTTC | ekkddddddddddkke | 0 | 2487 | 2502 | 1048 |
| 612846 | N/A | N/A | GGGCCCCCGGCTTACC | ekkddddddddddkke | 9 | 2490 | 2505 | 1049 |
| 612847 | N/A | N/A | GTGAATGTGAGCCCCG | ekkddddddddddkke | 9 | 3361 | 3376 | 1050 |
| 612848 | N/A | N/A | TCCCTCCTTATAACCC | ekkddddddddddkke | 5 | 3435 | 3450 | 1051 |
| 612849 | N/A | N/A | CCGGGCACTCTCAACT | ekkddddddddddkke | 6 | 3471 | 3486 | 1052 |
| 612850 | N/A | N/A | AGTAATGGTGCTCTGG | ekkddddddddddkke | 13 | 3752 | 3767 | 1053 |
| 612851 | N/A | N/A | TCCTGGGAGTAATGGT | ekkddddddddddkke | 16 | 3759 | 3774 | 1054 |
| 612852 | N/A | N/A | TCTCAGTTGTGATCTG | ekkddddddddddkke | 19 | 3817 | 3832 | 1055 |
| 612853 | N/A | N/A | TCCAGAGACGCAATTC | ekkddddddddddkke | 0 | 3868 | 3883 | 1056 |
| 612854 | N/A | N/A | TCTCCAGAGACGCAAT | ekkddddddddddkke | 15 | 3870 | 3885 | 1057 |
| 612855 | N/A | N/A | ACCTGTGGGAACCGAC | ekkddddddddddkke | 17 | 3983 | 3998 | 1058 |
| 612856 | N/A | N/A | AAACCTGTGGGAACCG | ekkddddddddddkke | 7 | 3985 | 4000 | 1059 |
| 612857 | N/A | N/A | CCTAGATTTTCTGCT | ekkddddddddddkke | 15 | 4340 | 4355 | 1060 |
| 612858 | N/A | N/A | GCCTTTTCTGTCCCCC | ekkddddddddddkke | 24 | 4420 | 4435 | 1061 |
| 612859 | N/A | N/A | CATTTCTTGTGGAGGG | ekkddddddddddkke | 3 | 4464 | 4479 | 1062 |
| 612860 | N/A | N/A | TGGGCTGGCCCTGCTA | ekkddddddddddkke | 0 | 4569 | 4584 | 1063 |
| 612861 | N/A | N/A | GAGCCCCAAAGGCATG | ekkddddddddddkke | 0 | 4822 | 4837 | 1064 |
| 612862 | N/A | N/A | TCTAATATGACCTGTG | ekkddddddddddkke | 25 | 5357 | 5372 | 1065 |
| 612863 | N/A | N/A | TGATCTAATATGACCT | ekkddddddddddkke | 6 | 5360 | 5375 | 1066 |
| 612864 | N/A | N/A | GTCCTCAACCCCAGGA | ekkddddddddddkke | 9 | 5455 | 5470 | 1067 |
| 612865 | N/A | N/A | GCTCCATGGAAAATAT | ekkddddddddddkke | 0 | 5553 | 5568 | 1068 |
| 612866 | N/A | N/A | TCCATTCATGTCTACA | ekkddddddddddkke | 11 | 5593 | 5608 | 1069 |
| 612867 | N/A | N/A | TTAAGTGCCATCTAAC | ekkddddddddddkke | 23 | 5660 | 5675 | 1070 |
| 612868 | N/A | N/A | GCATACCCTGAAATAT | ekkddddddddddkke | 0 | 5714 | 5729 | 1071 |
| 612869 | N/A | N/A | AGGTATGTCCGCAGGG | ekkddddddddddkke | 35 | 6679 | 6694 | 1156 |
| 612870 | N/A | N/A | TAGTAGGGCAGCAGGT | ekkddddddddddkke | 7 | 6765 | 6780 | 1157 |
| 612871 | N/A | N/A | TTGTTTCTCCGAGTCT | ekkddddddddddkke | 42 | 6879 | 6894 | 1158 |
| 612872 | N/A | N/A | AGGCACTTTGTTTCTC | ekkddddddddddkke | 5 | 6886 | 6901 | 1159 |
| 612873 | N/A | N/A | CAAGGCACTTTGTTTC | ekkddddddddddkke | 0 | 6888 | 6903 | 1160 |
| 612874 | N/A | N/A | TAGAACTGGGCTGTGG | ekkddddddddddkke | 0 | 6962 | 6977 | 1161 |
| 612875 | N/A | N/A | CCCTCCTAACATGAAA | ekkddddddddddkke | 0 | 7071 | 7086 | 1162 |
| 612876 | N/A | N/A | CTTACAAGTAGCAAAT | ekkddddddddddkke | 11 | 7332 | 7347 | 1163 |
| 612877 | N/A | N/A | GCCAGGCTTAAAGTCT | ekkddddddddddkke | 10 | 7346 | 7361 | 1164 |
| 612878 | N/A | N/A | ATTGACCTTTAAAAGC | ekkddddddddddkke | 5 | 7407 | 7422 | 1165 |

TABLE 7-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 612879 | N/A | N/A | TCTGGTTCAACACTCA | ekkddddddddddkke | 39 | 7640 | 7655 | 1166 |
| 612880 | N/A | N/A | TTCCCGTGACTGTGTG | ekkddddddddddkke | 25 | 7813 | 7828 | 1167 |
| 612881 | N/A | N/A | CGAGCTGCTCCCTGAG | ekkddddddddddkke | 15 | 7835 | 7850 | 1168 |
| 612882 | N/A | N/A | CACCCCACCCATGGAT | ekkddddddddddkke | 0 | 7855 | 7870 | 1169 |
| 612883 | N/A | N/A | TCTCTGTCCCTCACGA | ekkddddddddddkke | 20 | 7925 | 7940 | 1170 |
| 612884 | N/A | N/A | TTTCGAAGGGAGACCC | ekkddddddddddkke | 9 | 8273 | 8288 | 1171 |
| 612885 | N/A | N/A | CATCTAGCTGCCTGCT | ekkddddddddddkke | 0 | 8572 | 8587 | 1172 |
| 612886 | N/A | N/A | TGGGACACATCTAGCT | ekkddddddddddkke | 9 | 8579 | 8594 | 1173 |
| 612887 | N/A | N/A | ATCCTCAGGTCCTCTC | ekkddddddddddkke | 14 | 8598 | 8613 | 1174 |
| 612888 | N/A | N/A | ATGGTTCAGAAACAGT | ekkddddddddddkke | 28 | 9161 | 9176 | 1175 |
| 612889 | N/A | N/A | GATTTGCACACTGGGC | ekkddddddddddkke | 0 | 9489 | 9504 | 1176 |
| 612890 | N/A | N/A | CCCCGTGATCAACATC | ekkddddddddddkke | 0 | 9874 | 9889 | 1177 |
| 612891 | N/A | N/A | ATCGAGCAGAAAGTAC | ekkddddddddddkke | 24 | 9932 | 9947 | 1178 |
| 612892 | N/A | N/A | ACTGGTACCTGCCAGG | ekkddddddddddkke | 0 | 10058 | 10073 | 1179 |
| 612907 | N/A | N/A | TTAGCTAACTTAGCAC | ekkddddddddddkke | 10 | 12892 | 12907 | 1086 |
| 612908 | N/A | N/A | CATGGCCCACCAGTGC | ekkddddddddddkke | 13 | 12914 | 12929 | 1087 |
| 612909 | N/A | N/A | CACAGTGTATGCCTGC | ekkddddddddddkke | 15 | 13087 | 13102 | 1088 |
| 612910 | N/A | N/A | GCACTGGGTGACCCAG | ekkddddddddddkke | 0 | 13195 | 13210 | 1089 |
| 612911 | N/A | N/A | TCAGCACCTGCAAAGC | ekkddddddddddkke | 0 | 13238 | 13253 | 1090 |

Table 8 shows inhibition of AGT mRNA in HepG2 cells cultured at a density of 20,000 cells per well which were transfected using electroporation with 4000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 8

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610015 | 2049 | 2068 | GACACATCGCTGATTTGTCC | eeeeeddddddddddeeeee | 91 | 13518 | 13537 | 239 |
| 610015 | 2049 | 2068 | GACACATCGCTGATTTGTCC | eeeeeddddddddddeeeee | 87 | 13518 | 13537 | 239 |
| 610015 | 2049 | 2068 | GACACATCGCTGATTTGTCC | eeeeeddddddddddeeeee | 81 | 13518 | 13537 | 239 |
| 610015 | 2049 | 2068 | GACACATCGCTGATTTGTCC | eeeeeddddddddddeeeee | 43 | 13518 | 13537 | 239 |
| 610015 | 2049 | 2068 | GACACATCGCTGATTTGTCC | eeeeeddddddddddeeeee | 91 | 13518 | 13537 | 239 |
| 610015 | 2049 | 2068 | GACACATCGCTGATTTGTCC | eeeeeddddddddddeeeee | 88 | 13518 | 13537 | 239 |
| 610015 | 2049 | 2068 | GACACATCGCTGATTTGTCC | eeeeeddddddddddeeeee | 91 | 13518 | 13537 | 239 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610015 | 2049 | 2068 | GACACATCGCTGATTTGTCC | eeeeddddddddddeeeee | 87 | 13518 | 13537 | 239 |
| 619461 | 1 | 20 | CTGCTGCCCGCTCATGGGAT | eeeeddddddddddeeeee | 5 | 1986 | 2005 | 1180 |
| 619462 | 7 | 26 | CTGACCCTGCTGCCCGCTCA | eeeeddddddddddeeeee | 30 | 1992 | 2011 | 1181 |
| 619463 | 13 | 32 | CCACTTCTGACCCTGCTGCC | eeeeddddddddddeeeee | 31 | 1998 | 2017 | 1182 |
| 619464 | 35 | 54 | TCTTGCTTAGGCAACACGGG | eeeeddddddddddeeeee | 31 | 2020 | 2039 | 1183 |
| 619465 | 41 | 60 | GGAGAGTCTTGCTTAGGCAA | eeeeddddddddddeeeee | 16 | 2026 | 2045 | 1184 |
| 619466 | 66 | 85 | GGAGGTGCAGAGGGCAGAGG | eeeeddddddddddeeeee | 5 | 2051 | 2070 | 1185 |
| 619467 | 72 | 91 | CAGGCCGGAGGTGCAGAGGG | eeeeddddddddddeeeee | 11 | 2057 | 2076 | 1186 |
| 619468 | 78 | 97 | GACATGCAGGCCGGAGGTGC | eeeeddddddddddeeeee | 15 | 2063 | 2082 | 1187 |
| 619469 | 84 | 103 | CACAGGGACATGCAGGCCGG | eeeeddddddddddeeeee | 19 | 2069 | 2088 | 1188 |
| 619470 | 90 | 109 | AGAGGCCACAGGGACATGCA | eeeeddddddddddeeeee | 26 | 2075 | 2094 | 1189 |
| 619471 | 96 | 115 | CCCCCAAGAGGCCACAGGGA | eeeeddddddddddeeeee | 10 | 2081 | 2100 | 1190 |
| 619472 | 102 | 121 | GATGTACCCCCAAGAGGCCA | eeeeddddddddddeeeee | 31 | 2087 | 2106 | 1191 |
| 619473 | 108 | 127 | CCGGGAGATGTACCCCCAAG | eeeeddddddddddeeeee | 34 | 2093 | 2112 | 1192 |
| 619474 | 114 | 133 | CCAGCCCCGGGAGATGTACC | eeeeddddddddddeeeee | 11 | 2099 | 2118 | 1193 |
| 619475 | 120 | 139 | TCTGACCCAGCCCCGGGAGA | eeeeddddddddddeeeee | 35 | 2105 | 2124 | 1194 |
| 619476 | 126 | 145 | AGGCCTTCTGACCCAGCCCC | eeeeddddddddddeeeee | 21 | 2111 | 2130 | 1195 |
| 619477 | 132 | 151 | CCACCCAGGCCTTCTGACCC | eeeeddddddddddeeeee | 0 | 2117 | 2136 | 1196 |
| 619478 | 138 | 157 | GGCCAACCACCCAGGCCTTC | eeeeddddddddddeeeee | 31 | 2123 | 2142 | 1197 |
| 619479 | 144 | 163 | GCCTGAGGCCAACCACCCAG | eeeeddddddddddeeeee | 36 | 2129 | 2148 | 1198 |
| 619480 | 150 | 169 | GTGACAGCCTGAGGCCAACC | eeeeddddddddddeeeee | 8 | 2135 | 2154 | 1199 |
| 619481 | 156 | 175 | AGGTGTGTGACAGCCTGAGG | eeeeddddddddddeeeee | 45 | 2141 | 2160 | 1200 |
| 619482 | 162 | 181 | CTCCCTAGGTGTGTGACAGC | eeeeddddddddddeeeee | 27 | 2147 | 2166 | 1201 |
| 619483 | 168 | 187 | GAGCATCTCCCTAGGTGTGT | eeeeddddddddddeeeee | 21 | 2153 | 2172 | 1202 |
| 619484 | 174 | 193 | AAACGGGAGCATCTCCCTAG | eeeeddddddddddeeeee | 27 | 2159 | 2178 | 1203 |
| 619485 | 180 | 199 | TCCCAGAAACGGGAGCATCT | eeeeddddddddddeeeee | 29 | 2165 | 2184 | 1204 |
| 619486 | 186 | 205 | CAAGGTTCCCAGAAACGGGA | eeeeddddddddddeeeee | 0 | 2171 | 2190 | 1205 |
| 619487 | 208 | 227 | CGAAGTTTGCAGGAGTCGGG | eeeeddddddddddeeeee | 27 | 2193 | 2212 | 1206 |
| 619488 | 214 | 233 | ATTTACCGAAGTTTGCAGGA | eeeeddddddddddeeeee | 40 | 2199 | 2218 | 1207 |
| 619489 | 220 | 239 | TTACACATTTACCGAAGTTT | eeeeddddddddddeeeee | 10 | 2205 | 2224 | 1208 |
| 619490 | 226 | 245 | GTCGAGTTACACATTTACCG | eeeeddddddddddeeeee | 29 | 2211 | 2230 | 1209 |
| 619491 | 232 | 251 | TGCAGGGTCGAGTTACACAT | eeeeddddddddddeeeee | 24 | 2217 | 2236 | 1210 |
| 619492 | 238 | 257 | AGCCGGTGCAGGGTCGAGTT | eeeeddddddddddeeeee | 20 | 2223 | 2242 | 1211 |
| 619493 | 244 | 263 | AGAGTGAGCCGGTGCAGGGT | eeeeddddddddddeeeee | 20 | 2229 | 2248 | 1212 |
| 619494 | 250 | 269 | CTGAACAGAGTGAGCCGGTG | eeeeddddddddddeeeee | 25 | 2235 | 2254 | 1213 |
| 619495 | 256 | 275 | TCACTGCTGAACAGAGTGAG | eeeeddddddddddeeeee | 41 | 2241 | 2260 | 1214 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619496 | 262 | 281 | AGAGTTTCACTGCTGAACAG | eeeeddddddddddeeeee | 13 | 2247 | 2266 | 1215 |
| 619497 | 268 | 287 | CGATGCAGAGTTTCACTGCT | eeeeddddddddddeeeee | 29 | 2253 | 2272 | 1216 |
| 619498 | 274 | 293 | AGTGATCGATGCAGAGTTTC | eeeeddddddddddeeeee | 28 | 2259 | 2278 | 1217 |
| 619499 | 280 | 299 | AGTCTTAGTGATCGATGCAG | eeeeddddddddddeeeee | 26 | 2265 | 2284 | 1218 |
| 619500 | 286 | 305 | CCAGGAAGTCTTAGTGATCG | eeeeddddddddddeeeee | 26 | 2271 | 2290 | 1219 |
| 619501 | 292 | 311 | CCTCTTCCAGGAAGTCTTAG | eeeeddddddddddeeeee | 28 | 2277 | 2296 | 1220 |
| 619502 | 298 | 317 | CTGGGACCTCTTCCAGGAAG | eeeeddddddddddeeeee | 20 | 2283 | 2302 | 1221 |
| 619503 | 304 | 323 | CTCACGCTGGGACCTCTTCC | eeeeddddddddddeeeee | 12 | 2289 | 2308 | 1222 |
| 619504 | 310 | 329 | GCGACACTCACGCTGGGACC | eeeeddddddddddeeeee | 25 | 2295 | 2314 | 1223 |
| 619505 | 316 | 335 | CCAGAAGCGACACTCACGCT | eeeeddddddddddeeeee | 13 | 2301 | 2320 | 1224 |
| 619506 | 322 | 341 | CAGATGCCAGAAGCGACACT | eeeeddddddddddeeeee | 24 | 2307 | 2326 | 1225 |
| 619507 | 328 | 347 | GAAGGACAGATGCCAGAAGC | eeeeddddddddddeeeee | 40 | 2313 | 2332 | 1226 |
| 619508 | 334 | 353 | TGGCCAGAAGGACAGATGCC | eeeeddddddddddeeeee | 3 | 2319 | 2338 | 1227 |
| 619509 | 340 | 359 | ACAGGCTGGCCAGAAGGACA | eeeeddddddddddeeeee | 31 | 2325 | 2344 | 1228 |
| 619510 | 346 | 365 | CAGACCACAGGCTGGCCAGA | eeeeddddddddddeeeee | 17 | 2331 | 2350 | 1229 |
| 619511 | 352 | 371 | CTTGGCCAGACCACAGGCTG | eeeeddddddddddeeeee | 20 | 2337 | 2356 | 1230 |
| 619512 | 358 | 377 | ACATCACTTGGCCAGACCAC | eeeeddddddddddeeeee | 7 | 2343 | 2362 | 1231 |
| 619513 | 364 | 383 | AGGGTTACATCACTTGGCCA | eeeeddddddddddeeeee | 19 | 2349 | 2368 | 1232 |
| 619514 | 370 | 389 | GAGAGGAGGGTTACATCACT | eeeeddddddddddeeeee | 28 | 2355 | 2374 | 1233 |
| 619515 | 376 | 395 | AGGCTGGAGAGGAGGGTTAC | eeeeddddddddddeeeee | 31 | 2361 | 2380 | 1234 |
| 619516 | 382 | 401 | GTGCACAGGCTGGAGAGGAG | eeeeddddddddddeeeee | 5 | 2367 | 2386 | 1235 |
| 619517 | 388 | 407 | CTGCCTGTGCACAGGCTGGA | eeeeddddddddddeeeee | 15 | 2373 | 2392 | 1236 |
| 619518 | 394 | 413 | CCCAGGCTGCCTGTGCACAG | eeeeddddddddddeeeee | 23 | 2379 | 2398 | 1237 |
| 619519 | 400 | 419 | GCTGTTCCCAGGCTGCCTGT | eeeeddddddddddeeeee | 40 | 2385 | 2404 | 1238 |
| 619520 | 406 | 425 | GATGGAGCTGTTCCCAGGCT | eeeeddddddddddeeeee | 12 | 2391 | 2410 | 1239 |
| 619521 | 431 | 450 | GCCCTATTTATAGCTGAGGG | eeeeddddddddddeeeee | 23 | 2416 | 2435 | 1240 |
| 619522 | 437 | 456 | CACGATGCCCTATTTATAGC | eeeeddddddddddeeeee | 10 | 2422 | 2441 | 1241 |
| 619523 | 443 | 462 | CCGGGTCACGATGCCCTATT | eeeeddddddddddeeeee | 24 | 2428 | 2447 | 1242 |
| 619524 | 449 | 468 | CCCCGGCCGGGTCACGATGC | eeeeddddddddddeeeee | 37 | 2434 | 2453 | 1243 |
| 619525 | 452 | 471 | TTCCCCCGGCCGGGTCACGA | eeeeddddddddddeeeee | 24 | 2437 | 2456 | 1244 |
| 619526 | 455 | 474 | TTCTTCCCCCGGCCGGGTCA | eeeeddddddddddeeeee | 19 | 2440 | 2459 | 1245 |
| 619527 | 458 | 477 | AGCTTCTTCCCCCGGCCGGG | eeeeddddddddddeeeee | 7 | 2443 | 2462 | 1246 |
| 619528 | 461 | 480 | GGCAGCTTCTTCCCCCGGCC | eeeeddddddddddeeeee | 38 | 2446 | 2465 | 1247 |
| 619529 | 464 | 483 | AACGGCAGCTTCTTCCCCCG | eeeeddddddddddeeeee | 31 | 2449 | 2468 | 1248 |
| 619530 | 467 | 486 | AACAACGGCAGCTTCTTCCC | eeeeddddddddddeeeee | 40 | 2452 | 2471 | 1249 |
| 619531 | 470 | 489 | CAGAACAACGGCAGCTTCTT | eeeeddddddddddeeeee | 53 | 2455 | 2474 | 1250 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619532 | 473 | 492 | ACCCAGAACAACGGCAGCTT | eeeeedddddddddddeeeee | 56 | 2458 | 2477 | 1251 |
| 619533 | 476 | 495 | AGTACCCAGAACAACGGCAG | eeeeedddddddddddeeeee | 50 | 2461 | 2480 | 1252 |
| 619534 | 479 | 498 | TGTAGTACCCAGAACAACGG | eeeeedddddddddddeeeee | 31 | 2464 | 2483 | 1253 |
| 619535 | 482 | 501 | TGCTGTAGTACCCAGAACAA | eeeeedddddddddddeeeee | 39 | 2467 | 2486 | 1254 |
| 619536 | 485 | 504 | TTCTGCTGTAGTACCCAGAA | eeeeedddddddddddeeeee | 52 | 2470 | 2489 | 1255 |
| 619537 | 488 | 507 | CCCTTCTGCTGTAGTACCCA | eeeeedddddddddddeeeee | 55 | N/A | N/A | 1256 |
| 619538 | 491 | 510 | ATACCCTTCTGCTGTAGTAC | eeeeedddddddddddeeeee | 39 | N/A | N/A | 1257 |
| 619539 | 494 | 513 | CGCATACCCTTCTGCTGTAG | eeeeedddddddddddeeeee | 69 | N/A | N/A | 1258 |
| 619540 | 497 | 516 | TTCCGCATACCCTTCTGCTG | eeeeedddddddddddeeeee | 65 | N/A | N/A | 1259 |
| 619541 | 500 | 519 | CGCTTCCGCATACCCTTCTG | eeeeedddddddddddeeeee | 60 | N/A | N/A | 1260 |
| 619542 | 503 | 522 | GCTCGCTTCCGCATACCCTT | eeeeedddddddddddeeeee | 78 | N/A | N/A | 1261 |
| 619543 | 506 | 525 | GGTGCTCGCTTCCGCATACC | eeeeedddddddddddeeeee | 69 | 5723 | 5742 | 1262 |
| 619544 | 525 | 544 | AGGAGCCATCTCAGACTGGG | eeeeedddddddddddeeeee | 53 | 5742 | 5761 | 1263 |
| 619545 | 528 | 547 | GGCAGGAGCCATCTCAGACT | eeeeedddddddddddeeeee | 56 | 5745 | 5764 | 1264 |
| 619546 | 531 | 550 | ACCGGCAGGAGCCATCTCAG | eeeeedddddddddddeeeee | 47 | 5748 | 5767 | 1265 |
| 619547 | 534 | 553 | CACACCGGCAGGAGCCATCT | eeeeedddddddddddeeeee | 39 | 5751 | 5770 | 1266 |
| 619548 | 537 | 556 | GCTCACACCGGCAGGAGCCA | eeeeedddddddddddeeeee | 47 | 5754 | 5773 | 1267 |
| 619549 | 540 | 559 | CAGGCTCACACCGGCAGGAG | eeeeedddddddddddeeeee | 42 | 5757 | 5776 | 1268 |
| 619550 | 543 | 562 | CCTCAGGCTCACACCGGCAG | eeeeedddddddddddeeeee | 58 | 5760 | 5779 | 1269 |
| 619551 | 546 | 565 | GGCCCTCAGGCTCACACCGG | eeeeedddddddddddeeeee | 53 | 5763 | 5782 | 1270 |
| 619552 | 549 | 568 | GGTGGCCCTCAGGCTCACAC | eeeeedddddddddddeeeee | 31 | 5766 | 5785 | 1271 |
| 619553 | 552 | 571 | GATGGTGGCCCTCAGGCTCA | eeeeedddddddddddeeeee | 8 | 5769 | 5788 | 1272 |
| 619554 | 555 | 574 | GAGGATGGTGGCCCTCAGGC | eeeeedddddddddddeeeee | 35 | 5772 | 5791 | 1273 |
| 619555 | 558 | 577 | GCAGAGGATGGTGGCCCTCA | eeeeedddddddddddeeeee | 54 | 5775 | 5794 | 1274 |
| 619556 | 561 | 580 | GAGGCAGAGGATGGTGGCCC | eeeeedddddddddddeeeee | 37 | 5778 | 5797 | 1275 |
| 619557 | 564 | 583 | CAGGAGGCAGAGGATGGTGG | eeeeedddddddddddeeeee | 13 | 5781 | 5800 | 1276 |
| 619558 | 572 | 591 | GCCCAGGCCAGGAGGCAGAG | eeeeedddddddddddeeeee | 43 | 5789 | 5808 | 1277 |
| 619559 | 575 | 594 | CCAGCCCAGGCCAGGAGGCA | eeeeedddddddddddeeeee | 44 | 5792 | 5811 | 1278 |
| 619560 | 578 | 597 | AGGCCAGCCCAGGCCAGGAG | eeeeedddddddddddeeeee | 50 | 5795 | 5814 | 1279 |
| 619561 | 581 | 600 | GCCAGGCCAGCCCAGGCCAG | eeeeedddddddddddeeeee | 55 | 5798 | 5817 | 1280 |
| 619562 | 584 | 603 | GCAGCCAGGCCAGCCCAGGC | eeeeedddddddddddeeeee | 43 | 5801 | 5820 | 1281 |
| 619563 | 587 | 606 | CCTGCAGCCAGGCCAGCCCA | eeeeedddddddddddeeeee | 38 | 5804 | 5823 | 1282 |
| 619564 | 590 | 609 | TCACCTGCAGCCAGGCCAGC | eeeeedddddddddddeeeee | 33 | 5807 | 5826 | 1283 |
| 619565 | 593 | 612 | CGGTCACCTGCAGCCAGGCC | eeeeedddddddddddeeeee | 45 | 5810 | 5829 | 1284 |
| 619566 | 596 | 615 | ACCCGGTCACCTGCAGCCAG | eeeeedddddddddddeeeee | 42 | 5813 | 5832 | 1285 |
| 619567 | 599 | 618 | TACACCCGGTCACCTGCAGC | eeeeedddddddddddeeeee | 22 | 5816 | 5835 | 1286 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619568 | 602 | 621 | ATGTACACCCGGTCACCTGC | eeeeedddddddddddeeeee | 37 | 5819 | 5838 | 1287 |
| 619569 | 605 | 624 | TGTATGTACACCCGGTCACC | eeeeedddddddddddeeeee | 18 | 5822 | 5841 | 1288 |
| 619570 | 608 | 627 | GGGTGTATGTACACCCGGTC | eeeeedddddddddddeeeee | 26 | 5825 | 5844 | 1289 |
| 619571 | 626 | 645 | TGGATGACGAGGTGGAAGGG | eeeeedddddddddddeeeee | 44 | 5843 | 5862 | 1290 |
| 619572 | 629 | 648 | TTGTGGATGACGAGGTGGAA | eeeeedddddddddddeeeee | 35 | 5846 | 5865 | 1291 |
| 619573 | 632 | 651 | TCATTGTGGATGACGAGGTG | eeeeedddddddddddeeeee | 39 | 5849 | 5868 | 1292 |
| 619574 | 635 | 654 | CTCTCATTGTGGATGACGAG | eeeeedddddddddddeeeee | 68 | 5852 | 5871 | 1293 |
| 619575 | 638 | 657 | GTACTCTCATTGTGGATGAC | eeeeedddddddddddeeeee | 65 | 5855 | 5874 | 1294 |
| 619576 | 641 | 660 | CAGGTACTCTCATTGTGGAT | eeeeedddddddddddeeeee | 54 | 5858 | 5877 | 1295 |
| 619577 | 644 | 663 | TCACAGGTACTCTCATTGTG | eeeeedddddddddddeeeee | 42 | 5861 | 5880 | 1296 |
| 619578 | 647 | 666 | TGCTCACAGGTACTCTCATT | eeeeedddddddddddeeeee | 59 | 5864 | 5883 | 1297 |
| 619579 | 650 | 669 | AGCTGCTCACAGGTACTCTC | eeeeedddddddddddeeeee | 57 | 5867 | 5886 | 1298 |
| 619580 | 653 | 672 | GCCAGCTGCTCACAGGTACT | eeeeedddddddddddeeeee | 70 | 5870 | 5889 | 1299 |
| 619581 | 656 | 675 | TTTGCCAGCTGCTCACAGGT | eeeeedddddddddddeeeee | 47 | 5873 | 5892 | 1300 |
| 619582 | 659 | 678 | GCCTTTGCCAGCTGCTCACA | eeeeedddddddddddeeeee | 49 | 5876 | 5895 | 1301 |
| 619583 | 662 | 681 | TTGGCCTTTGCCAGCTGCTC | eeeeedddddddddddeeeee | 58 | 5879 | 5898 | 1302 |
| 619584 | 665 | 684 | GCATTGGCCTTTGCCAGCTG | eeeeedddddddddddeeeee | 56 | 5882 | 5901 | 1303 |
| 619585 | 668 | 687 | CCGGCATTGGCCTTTGCCAG | eeeeedddddddddddeeeee | 45 | 5885 | 5904 | 1304 |
| 619586 | 671 | 690 | TTCCCGGCATTGGCCTTTGC | eeeeedddddddddddeeeee | 46 | 5888 | 5907 | 1305 |
| 619587 | 674 | 693 | GGCTTCCCGGCATTGGCCTT | eeeeedddddddddddeeeee | 39 | 5891 | 5910 | 1306 |
| 619588 | 677 | 696 | TTGGGCTTCCCGGCATTGGC | eeeeedddddddddddeeeee | 41 | 5894 | 5913 | 1307 |
| 619589 | 680 | 699 | TCTTTGGGCTTCCCGGCATT | eeeeedddddddddddeeeee | 28 | 5897 | 5916 | 1308 |
| 619590 | 701 | 720 | GGAGCAGGTATGAAGGTGGG | eeeeedddddddddddeeeee | 35 | 5918 | 5937 | 1309 |
| 619591 | 704 | 723 | ATTGGAGCAGGTATGAAGGT | eeeeedddddddddddeeeee | 49 | 5921 | 5940 | 1310 |
| 619592 | 707 | 726 | TGAATTGGAGCAGGTATGAA | eeeeedddddddddddeeeee | 32 | 5924 | 5943 | 1311 |
| 619593 | 710 | 729 | GCCTGAATTGGAGCAGGTAT | eeeeedddddddddddeeeee | 57 | 5927 | 5946 | 1312 |
| 619594 | 713 | 732 | TTGGCCTGAATTGGAGCAGG | eeeeedddddddddddeeeee | 51 | 5930 | 5949 | 1313 |
| 619595 | 716 | 735 | GTCTTGGCCTGAATTGGAGC | eeeeedddddddddddeeeee | 42 | 5933 | 5952 | 1314 |
| 619596 | 719 | 738 | GATGTCTTGGCCTGAATTGG | eeeeedddddddddddeeeee | 24 | 5936 | 5955 | 1315 |
| 619597 | 740 | 759 | AGGGCCTTTTCATCCACAGG | eeeeedddddddddddeeeee | 17 | 5957 | 5976 | 1316 |
| 619598 | 743 | 762 | TGTAGGGCCTTTTCATCCAC | eeeeedddddddddddeeeee | 33 | 5960 | 5979 | 1317 |
| 619599 | 746 | 765 | TCCTGTAGGGCCTTTTCATC | eeeeedddddddddddeeeee | 6 | 5963 | 5982 | 1318 |
| 619600 | 749 | 768 | TGGTCCTGTAGGGCCTTTTC | eeeeedddddddddddeeeee | 42 | 5966 | 5985 | 1319 |
| 619601 | 752 | 771 | AGCTGGTCCTGTAGGGCCTT | eeeeedddddddddddeeeee | 51 | 5969 | 5988 | 1320 |
| 619602 | 755 | 774 | ACCAGCTGGTCCTGTAGGGC | eeeeedddddddddddeeeee | 37 | 5972 | 5991 | 1321 |
| 619603 | 758 | 777 | AGCACCAGCTGGTCCTGTAG | eeeeedddddddddddeeeee | 44 | 5975 | 5994 | 1322 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619604 | 761 | 780 | ACTAGCACCAGCTGGTCCTG | eeeeedddddddddddeeeee | 37 | 5978 | 5997 | 1323 |
| 619605 | 764 | 783 | GCGACTAGCACCAGCTGGTC | eeeeedddddddddddeeeee | 52 | 5981 | 6000 | 1324 |
| 619606 | 767 | 786 | GCAGCGACTAGCACCAGCTG | eeeeedddddddddddeeeee | 67 | 5984 | 6003 | 1325 |
| 619607 | 770 | 789 | TTTGCAGCGACTAGCACCAG | eeeeedddddddddddeeeee | 60 | 5987 | 6006 | 1326 |
| 619608 | 773 | 792 | AGTTTTGCAGCGACTAGCAC | eeeeedddddddddddeeeee | 43 | 5990 | 6009 | 1327 |
| 619609 | 776 | 795 | TCAAGTTTTGCAGCGACTAG | eeeeedddddddddddeeeee | 38 | 5993 | 6012 | 1328 |
| 619610 | 779 | 798 | GTGTCAAGTTTTGCAGCGAC | eeeeedddddddddddeeeee | 57 | 5996 | 6015 | 1329 |
| 619611 | 782 | 801 | TCGGTGTCAAGTTTTGCAGC | eeeeedddddddddddeeeee | 55 | 5999 | 6018 | 1330 |
| 619612 | 785 | 804 | TCTTCGGTGTCAAGTTTTGC | eeeeedddddddddddeeeee | 45 | 6002 | 6021 | 1331 |
| 619613 | 788 | 807 | TTGTCTTCGGTGTCAAGTTT | eeeeedddddddddddeeeee | 50 | 6005 | 6024 | 1332 |
| 619614 | 791 | 810 | AACTTGTCTTCGGTGTCAAG | eeeeedddddddddddeeeee | 48 | 6008 | 6027 | 1333 |
| 619615 | 794 | 813 | CTCAACTTGTCTTCGGTGTC | eeeeedddddddddddeeeee | 59 | 6011 | 6030 | 1334 |
| 619616 | 797 | 816 | GCCCTCAACTTGTCTTCGGT | eeeeedddddddddddeeeee | 41 | 6014 | 6033 | 1335 |
| 619617 | 800 | 819 | GCGGCCCTCAACTTGTCTTC | eeeeedddddddddddeeeee | 42 | 6017 | 6036 | 1336 |
| 619618 | 803 | 822 | ATTGCGGCCCTCAACTTGTC | eeeeedddddddddddeeeee | 32 | 6020 | 6039 | 1337 |
| 619619 | 806 | 825 | ACCATTGCGGCCCTCAACTT | eeeeedddddddddddeeeee | 34 | 6023 | 6042 | 1338 |
| 619620 | 809 | 828 | CCGACCATTGCGGCCCTCAA | eeeeedddddddddddeeeee | 55 | 6026 | 6045 | 1339 |
| 619621 | 812 | 831 | ATCCCGACCATTGCGGCCCT | eeeeedddddddddddeeeee | 37 | 6029 | 6048 | 1340 |
| 619622 | 815 | 834 | AGCATCCCGACCATTGCGGC | eeeeedddddddddddeeeee | 50 | 6032 | 6051 | 1341 |
| 619623 | 818 | 837 | GCCAGCATCCCGACCATTGC | eeeeedddddddddddeeeee | 58 | 6035 | 6054 | 1342 |
| 619624 | 821 | 840 | TTGGCCAGCATCCCGACCAT | eeeeedddddddddddeeeee | 38 | 6038 | 6057 | 1343 |
| 619625 | 824 | 843 | AAGTTGGCCAGCATCCCGAC | eeeeedddddddddddeeeee | 46 | 6041 | 6060 | 1344 |
| 619626 | 827 | 846 | AAGAAGTTGGCCAGCATCCC | eeeeedddddddddddeeeee | 24 | 6044 | 6063 | 1345 |
| 619627 | 830 | 849 | CCCAAGAAGTTGGCCAGCAT | eeeeedddddddddddeeeee | 55 | 6047 | 6066 | 1346 |
| 619628 | 833 | 852 | AAGCCCAAGAAGTTGGCCAG | eeeeedddddddddddeeeee | 48 | 6050 | 6069 | 1347 |
| 619629 | 836 | 855 | CGGAAGCCCAAGAAGTTGGC | eeeeedddddddddddeeeee | 36 | 6053 | 6072 | 1348 |
| 619630 | 839 | 858 | ATACGGAAGCCCAAGAAGTT | eeeeedddddddddddeeeee | 40 | 6056 | 6075 | 1349 |
| 619631 | 842 | 861 | TATATACGGAAGCCCAAGAA | eeeeedddddddddddeeeee | 29 | 6059 | 6078 | 1350 |
| 619632 | 845 | 864 | CCATATACGGAAGCCCAA | eeeeedddddddddddeeeee | 48 | 6062 | 6081 | 1351 |
| 619633 | 848 | 867 | ATGCCATATATACGGAAGCC | eeeeedddddddddddeeeee | 58 | 6065 | 6084 | 1352 |
| 619634 | 851 | 870 | TGCATGCCATATATACGGAA | eeeeedddddddddddeeeee | 59 | 6068 | 6087 | 1353 |
| 619635 | 854 | 873 | CTGTGCATGCCATATATACG | eeeeedddddddddddeeeee | 66 | 6071 | 6090 | 1354 |
| 619636 | 857 | 876 | TCACTGTGCATGCCATATAT | eeeeedddddddddddeeeee | 72 | 6074 | 6093 | 1355 |
| 619637 | 860 | 879 | AGCTCACTGTGCATGCCATA | eeeeedddddddddddeeeee | 74 | 6077 | 6096 | 1356 |
| 619638 | 863 | 882 | CATAGCTCACTGTGCATGCC | eeeeedddddddddddeeeee | 69 | 6080 | 6099 | 1357 |
| 619639 | 866 | 885 | CCCCATAGCTCACTGTGCAT | eeeeedddddddddddeeeee | 43 | 6083 | 6102 | 1358 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619640 | 869 | 888 | ACGCCCCATAGCTCACTGTG | eeeeedddddddddddeeeee | 48 | 6086 | 6105 | 1359 |
| 619641 | 872 | 891 | ACCACGCCCCATAGCTCACT | eeeeedddddddddddeeeee | 56 | 6089 | 6108 | 1360 |
| 619642 | 875 | 894 | TGGACCACGCCCCATAGCTC | eeeeedddddddddddeeeee | 40 | 6092 | 6111 | 1361 |
| 619643 | 878 | 897 | CCATGGACCACGCCCCATAG | eeeeedddddddddddeeeee | 24 | 6095 | 6114 | 1362 |
| 619644 | 881 | 900 | GCCCCATGGACCACGCCCCA | eeeeedddddddddddeeeee | 40 | 6098 | 6117 | 1363 |
| 619645 | 884 | 903 | GTGGCCCCATGGACCACGCC | eeeeedddddddddddeeeee | 26 | 6101 | 6120 | 1364 |
| 619646 | 887 | 906 | ACGGTGGCCCCATGGACCAC | eeeeedddddddddddeeeee | 35 | 6104 | 6123 | 1365 |
| 619647 | 890 | 909 | AGGACGGTGGCCCCATGGAC | eeeeedddddddddddeeeee | 35 | 6107 | 6126 | 1366 |
| 619648 | 893 | 912 | GAGAGGACGGTGGCCCCATG | eeeeedddddddddddeeeee | 44 | 6110 | 6129 | 1367 |
| 619649 | 913 | 932 | TGCCAAAGACAGCCGTTGGG | eeeeedddddddddddeeeee | 53 | 6130 | 6149 | 1368 |
| 619650 | 916 | 935 | GGGTGCCAAAGACAGCCGTT | eeeeedddddddddddeeeee | 40 | 6133 | 6152 | 1369 |
| 619651 | 919 | 938 | CCAGGGTGCCAAAGACAGCC | eeeeedddddddddddeeeee | 62 | 6136 | 6155 | 1370 |
| 619652 | 922 | 941 | AGGCCAGGGTGCCAAAGACA | eeeeedddddddddddeeeee | 44 | 6139 | 6158 | 1371 |
| 619653 | 925 | 944 | GAGAGGCCAGGGTGCCAAAG | eeeeedddddddddddeeeee | 58 | 6142 | 6161 | 1372 |
| 619654 | 928 | 947 | AGAGAGAGGCCAGGGTGCCA | eeeeedddddddddddeeeee | 34 | 6145 | 6164 | 1373 |
| 619655 | 931 | 950 | GATAGAGAGAGGCCAGGGTG | eeeeedddddddddddeeeee | 16 | 6148 | 6167 | 1374 |
| 619656 | 934 | 953 | CCAGATAGAGAGAGGCCAGG | eeeeedddddddddddeeeee | 41 | 6151 | 6170 | 1375 |
| 619657 | 937 | 956 | CTCCCAGATAGAGAGAGGCC | eeeeedddddddddddeeeee | 58 | 6154 | 6173 | 1376 |
| 619658 | 940 | 959 | AGGCTCCCAGATAGAGAGAG | eeeeedddddddddddeeeee | 21 | 6157 | 6176 | 1377 |
| 619659 | 943 | 962 | CCAAGGCTCCCAGATAGAGA | eeeeedddddddddddeeeee | 21 | 6160 | 6179 | 1378 |
| 619660 | 946 | 965 | GGTCCAAGGCTCCCAGATAG | eeeeedddddddddddeeeee | 43 | 6163 | 6182 | 1379 |
| 619661 | 949 | 968 | TGTGGTCCAAGGCTCCCAGA | eeeeedddddddddddeeeee | 45 | 6166 | 6185 | 1380 |
| 619662 | 952 | 971 | CTGTGTGGTCCAAGGCTCCC | eeeeedddddddddddeeeee | 33 | 6169 | 6188 | 1381 |
| 619663 | 955 | 974 | CAGCTGTGTGGTCCAAGGCT | eeeeedddddddddddeeeee | 52 | 6172 | 6191 | 1382 |
| 619664 | 958 | 977 | TGTCAGCTGTGTGGTCCAAG | eeeeedddddddddddeeeee | 44 | 6175 | 6194 | 1383 |
| 619665 | 961 | 980 | GCCTGTCAGCTGTGTGGTCC | eeeeedddddddddddeeeee | 66 | 6178 | 6197 | 1384 |
| 619666 | 964 | 983 | GTAGCCTGTCAGCTGTGTGG | eeeeedddddddddddeeeee | 47 | 6181 | 6200 | 1385 |
| 619667 | 967 | 986 | CCTGTAGCCTGTCAGCTGTG | eeeeedddddddddddeeeee | 59 | 6184 | 6203 | 1386 |
| 619668 | 970 | 989 | TTGCCTGTAGCCTGTCAGCT | eeeeedddddddddddeeeee | 57 | 6187 | 6206 | 1387 |
| 619669 | 973 | 992 | GGATTGCCTGTAGCCTGTCA | eeeeedddddddddddeeeee | 53 | 6190 | 6209 | 1388 |
| 619670 | 976 | 995 | CCAGGATTGCCTGTAGCCTG | eeeeedddddddddddeeeee | 57 | 6193 | 6212 | 1389 |
| 619671 | 979 | 998 | CACCCAGGATTGCCTGTAGC | eeeeedddddddddddeeeee | 52 | 6196 | 6215 | 1390 |
| 619672 | 982 | 1001 | GAACACCCAGGATTGCCTGT | eeeeedddddddddddeeeee | 63 | 6199 | 6218 | 1391 |
| 619673 | 985 | 1004 | AAGGAACACCCAGGATTGCC | eeeeedddddddddddeeeee | 47 | 6202 | 6221 | 1392 |
| 619674 | 988 | 1007 | TCCAAGGAACACCCAGGATT | eeeeedddddddddddeeeee | 63 | 6205 | 6224 | 1393 |
| 619675 | 991 | 1010 | CCTTCCAAGGAACACCCAGG | eeeeedddddddddddeeeee | 60 | 6208 | 6227 | 1394 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619676 | 994 | 1013 | TGTCCTTCCAAGGAACACCC | eeeeeddddddddddeeeee | 62 | 6211 | 6230 | 1395 |
| 619677 | 997 | 1016 | TCTTGTCCTTCCAAGGAACA | eeeeeddddddddddeeeee | 48 | 6214 | 6233 | 1396 |
| 619678 | 1000 | 1019 | AGTTCTTGTCCTTCCAAGGA | eeeeeddddddddddeeeee | 35 | 6217 | 6236 | 1397 |
| 619679 | 1003 | 1022 | TGCAGTTCTTGTCCTTCCAA | eeeeeddddddddddeeeee | 56 | 6220 | 6239 | 1398 |
| 619680 | 1006 | 1025 | AGGTGCAGTTCTTGTCCTTC | eeeeeddddddddddeeeee | 41 | 6223 | 6242 | 1399 |
| 619681 | 1009 | 1028 | GGGAGGTGCAGTTCTTGTCC | eeeeeddddddddddeeeee | 26 | 6226 | 6245 | 1400 |
| 619682 | 1012 | 1031 | GCCGGGAGGTGCAGTTCTTG | eeeeeddddddddddeeeee | 44 | 6229 | 6248 | 1401 |
| 619683 | 1015 | 1034 | CCAGCCGGGAGGTGCAGTTC | eeeeeddddddddddeeeee | 36 | 6232 | 6251 | 1402 |
| 619684 | 1018 | 1037 | CATCCAGCCGGGAGGTGCAG | eeeeeddddddddddeeeee | 32 | 6235 | 6254 | 1403 |
| 619685 | 1021 | 1040 | GCGCATCCAGCCGGGAGGTG | eeeeeddddddddddeeeee | 21 | 6238 | 6257 | 1404 |
| 619686 | 1024 | 1043 | TGTGCGCATCCAGCCGGGAG | eeeeeddddddddddeeeee | 44 | 6241 | 6260 | 1405 |
| 619687 | 1027 | 1046 | CCTTGTGCGCATCCAGCCGG | eeeeeddddddddddeeeee | 60 | 6244 | 6263 | 1406 |
| 619688 | 1030 | 1049 | GGACCTTGTGCGCATCCAGC | eeeeeddddddddddeeeee | 61 | 6247 | 6266 | 1407 |
| 619689 | 1033 | 1052 | ACAGGACCTTGTGCGCATCC | eeeeeddddddddddeeeee | 65 | 6250 | 6269 | 1408 |
| 619690 | 1036 | 1055 | CAGACAGGACCTTGTGCGCA | eeeeeddddddddddeeeee | 59 | 6253 | 6272 | 1409 |
| 619691 | 1039 | 1058 | GGGCAGACAGGACCTTGTGC | eeeeeddddddddddeeeee | 45 | 6256 | 6275 | 1410 |
| 619692 | 1042 | 1061 | GCAGGGCAGACAGGACCTTG | eeeeeddddddddddeeeee | 46 | 6259 | 6278 | 1411 |
| 619693 | 1045 | 1064 | CCTGCAGGGCAGACAGGACC | eeeeeddddddddddeeeee | 38 | 6262 | 6281 | 1412 |
| 619694 | 1048 | 1067 | CAGCCTGCAGGGCAGACAGG | eeeeeddddddddddeeeee | 41 | 6265 | 6284 | 1413 |
| 619695 | 1051 | 1070 | GTACAGCCTGCAGGGCAGAC | eeeeeddddddddddeeeee | 43 | 6268 | 6287 | 1414 |
| 619696 | 1054 | 1073 | CCTGTACAGCCTGCAGGGCA | eeeeeddddddddddeeeee | 48 | 6271 | 6290 | 1415 |
| 619697 | 1057 | 1076 | GGCCCTGTACAGCCTGCAGG | eeeeeddddddddddeeeee | 35 | 6274 | 6293 | 1416 |
| 619698 | 1060 | 1079 | GCAGGCCCTGTACAGCCTGC | eeeeeddddddddddeeeee | 22 | 6277 | 6296 | 1417 |
| 619699 | 1063 | 1082 | CTAGCAGGCCCTGTACAGCC | eeeeeddddddddddeeeee | 1 | 6280 | 6299 | 1418 |
| 619700 | 1066 | 1085 | CCACTAGCAGGCCCTGTACA | eeeeeddddddddddeeeee | 29 | 6283 | 6302 | 1419 |
| 619701 | 1069 | 1088 | GGGCCACTAGCAGGCCCTGT | eeeeeddddddddddeeeee | 2 | 6286 | 6305 | 1420 |
| 619702 | 1072 | 1091 | CCTGGGCCACTAGCAGGCCC | eeeeeddddddddddeeeee | 25 | 6289 | 6308 | 1421 |
| 619703 | 1075 | 1094 | TGCCCTGGGCCACTAGCAGG | eeeeeddddddddddeeeee | 23 | 6292 | 6311 | 1422 |
| 619704 | 1078 | 1097 | CCCTGCCCTGGGCCACTAGC | eeeeeddddddddddeeeee | 46 | 6295 | 6314 | 1423 |
| 619705 | 1081 | 1100 | CAGCCCTGCCCTGGGCCACT | eeeeeddddddddddeeeee | 59 | 6298 | 6317 | 1424 |
| 619706 | 1084 | 1103 | TATCAGCCCTGCCCTGGGCC | eeeeeddddddddddeeeee | 36 | 6301 | 6320 | 1425 |
| 619707 | 1087 | 1106 | GGCTATCAGCCCTGCCCTGG | eeeeeddddddddddeeeee | 51 | 6304 | 6323 | 1426 |
| 619708 | 1090 | 1109 | CCTGGCTATCAGCCCTGCCC | eeeeeddddddddddeeeee | 34 | 6307 | 6326 | 1427 |
| 619709 | 1093 | 1112 | GGGCCTGGCTATCAGCCCTG | eeeeeddddddddddeeeee | 17 | 6310 | 6329 | 1428 |
| 619710 | 1096 | 1115 | GCTGGGCCTGGCTATCAGCC | eeeeeddddddddddeeeee | 31 | 6313 | 6332 | 1429 |
| 619711 | 1099 | 1118 | GCAGCTGGGCCTGGCTATCA | eeeeeddddddddddeeeee | 44 | 6316 | 6335 | 1430 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619712 | 1102 | 1121 | GCAGCAGCTGGGCCTGGCTA | eeeeedddddddddddeeeee | 38 | 6319 | 6338 | 1431 |
| 619713 | 1105 | 1124 | ACAGCAGCAGCTGGGCCTGG | eeeeedddddddddddeeeee | 29 | 6322 | 6341 | 1432 |
| 619714 | 1108 | 1127 | TGGACAGCAGCAGCTGGGCC | eeeeedddddddddddeeeee | 50 | 6325 | 6344 | 1433 |
| 619715 | 1111 | 1130 | CCGTGGACAGCAGCAGCTGG | eeeeedddddddddddeeeee | 53 | 6328 | 6347 | 1434 |
| 619716 | 1114 | 1133 | CCACCGTGGACAGCAGCAGC | eeeeedddddddddddeeeee | 24 | 6331 | 6350 | 1435 |
| 619717 | 1117 | 1136 | CCACCACCGTGGACAGCAGC | eeeeedddddddddddeeeee | 34 | 6334 | 6353 | 1436 |
| 619718 | 1120 | 1139 | CGCCCACCACCGTGGACAGC | eeeeedddddddddddeeeee | 56 | 6337 | 6356 | 1437 |
| 619719 | 1123 | 1142 | ACACGCCCACCACCGTGGAC | eeeeedddddddddddeeeee | 27 | 6340 | 6359 | 1438 |
| 619720 | 1126 | 1145 | TGAACACGCCCACCACCGTG | eeeeedddddddddddeeeee | 16 | 6343 | 6362 | 1439 |
| 619721 | 1129 | 1148 | CTGTGAACACGCCCACCACC | eeeeedddddddddddeeeee | 40 | 6346 | 6365 | 1440 |
| 619722 | 1132 | 1151 | GGGCTGTGAACACGCCCACC | eeeeedddddddddddeeeee | 25 | 6349 | 6368 | 1441 |
| 619723 | 1150 | 1169 | GCTTCAGGTGCAGGCCTGGG | eeeeedddddddddddeeeee | 36 | 6367 | 6386 | 1442 |
| 619724 | 1153 | 1172 | GCTGCTTCAGGTGCAGGCCT | eeeeedddddddddddeeeee | 47 | 6370 | 6389 | 1443 |
| 619725 | 1156 | 1175 | ACGGCTGCTTCAGGTGCAGG | eeeeedddddddddddeeeee | 14 | 6373 | 6392 | 1444 |
| 619726 | 1159 | 1178 | CAAACGGCTGCTTCAGGTGC | eeeeedddddddddddeeeee | 37 | 6376 | 6395 | 1445 |
| 619727 | 1162 | 1181 | GCACAAACGGCTGCTTCAGG | eeeeedddddddddddeeeee | 19 | 6379 | 6398 | 1446 |
| 619728 | 1165 | 1184 | CCTGCACAAACGGCTGCTTC | eeeeedddddddddddeeeee | 33 | 6382 | 6401 | 1447 |
| 619729 | 1168 | 1187 | GGCCCTGCACAAACGGCTGC | eeeeedddddddddddeeeee | 48 | 6385 | 6404 | 1448 |
| 619730 | 1171 | 1190 | CCAGGCCCTGCACAAACGGC | eeeeedddddddddddeeeee | 27 | 6388 | 6407 | 1449 |
| 619731 | 1174 | 1193 | GAGCCAGGCCCTGCACAAAC | eeeeedddddddddddeeeee | 35 | 6391 | 6410 | 1450 |
| 619732 | 1177 | 1196 | AGAGAGCCAGGCCCTGCACA | eeeeedddddddddddeeeee | 51 | 6394 | 6413 | 1451 |
| 619733 | 1180 | 1199 | TATAGAGAGCCAGGCCCTGC | eeeeedddddddddddeeeee | 27 | 6397 | 6416 | 1452 |
| 619734 | 1183 | 1202 | GGGTATAGAGAGCCAGGCCC | eeeeedddddddddddeeeee | 41 | 6400 | 6419 | 1453 |
| 619735 | 1217 | 1236 | TCTGTGAAGTCCAGAGAGCG | eeeeedddddddddddeeeee | 22 | 6434 | 6453 | 1454 |
| 619736 | 1220 | 1239 | AGTTCTGTGAAGTCCAGAGA | eeeeedddddddddddeeeee | 48 | 6437 | 6456 | 1455 |
| 619737 | 1223 | 1242 | TCCAGTTCTGTGAAGTCCAG | eeeeedddddddddddeeeee | 26 | 6440 | 6459 | 1456 |
| 619738 | 1226 | 1245 | ACATCCAGTTCTGTGAAGTC | eeeeedddddddddddeeeee | 35 | 6443 | 6462 | 1457 |
| 619739 | 1229 | 1248 | GCAACATCCAGTTCTGTGAA | eeeeedddddddddddeeeee | 28 | 6446 | 6465 | 1458 |
| 619740 | 1232 | 1251 | GCAGCAACATCCAGTTCTGT | eeeeedddddddddddeeeee | 40 | 6449 | 6468 | 1459 |
| 619741 | 1235 | 1254 | TCAGCAGCAACATCCAGTTC | eeeeedddddddddddeeeee | 41 | 6452 | 6471 | 1460 |
| 619742 | 1238 | 1257 | TTCTCAGCAGCAACATCCAG | eeeeedddddddddddeeeee | 29 | 6455 | 6474 | 1461 |
| 619743 | 1241 | 1260 | ATCTTCTCAGCAGCAACATC | eeeeedddddddddddeeeee | 32 | 6458 | 6477 | 1462 |
| 619744 | 1244 | 1263 | TCAATCTTCTCAGCAGCAAC | eeeeedddddddddddeeeee | 38 | 6461 | 6480 | 1463 |
| 619745 | 1247 | 1266 | CTGTCAATCTTCTCAGCAGC | eeeeedddddddddddeeeee | 39 | 6464 | 6483 | 1464 |
| 619746 | 1250 | 1269 | AACCTGTCAATCTTCTCAGC | eeeeedddddddddddeeeee | 20 | 6467 | 6486 | 1465 |
| 619747 | 1253 | 1272 | ATGAACCTGTCAATCTTCTC | eeeeedddddddddddeeeee | 50 | 6470 | 6489 | 1466 |

TABLE 8-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619748 | 1256 | 1275 | TGCATGAACCTGTCAATCTT | eeeeedddddddddeeeee | 61 | 6473 | 6492 | 1467 |
| 619749 | 1259 | 1278 | GCCTGCATGAACCTGTCAAT | eeeeedddddddddeeeee | 62 | 6476 | 6495 | 1468 |
| 619750 | 1262 | 1281 | ACAGCCTGCATGAACCTGTC | eeeeedddddddddeeeee | 56 | 6479 | 6498 | 1469 |
| 619751 | 1265 | 1284 | GTCACAGCCTGCATGAACCT | eeeeedddddddddeeeee | 75 | 6482 | 6501 | 1470 |
| 619752 | 1268 | 1287 | CCTGTCACAGCCTGCATGAA | eeeeedddddddddeeeee | 46 | 6485 | 6504 | 1471 |
| 619753 | 1271 | 1290 | CATCCTGTCACAGCCTGCAT | eeeeedddddddddeeeee | 74 | 6488 | 6507 | 1472 |
| 619754 | 1274 | 1293 | TTCCATCCTGTCACAGCCTG | eeeeedddddddddeeeee | 71 | 6491 | 6510 | 1473 |
| 619755 | 1277 | 1296 | GTCTTCCATCCTGTCACAGC | eeeeedddddddddeeeee | 65 | 6494 | 6513 | 1474 |
| 619756 | 1280 | 1299 | CCAGTCTTCCATCCTGTCAC | eeeeedddddddddeeeee | 56 | 6497 | 6516 | 1475 |
| 619757 | 1283 | 1302 | CAGCCAGTCTTCCATCCTGT | eeeeedddddddddeeeee | 63 | 6500 | 6519 | 1476 |

Table 9 shows inhibition of AGT mRNA in HepG2 cells cultured at a density of 20,000 cells per well which were transfected using electroporation with 4000 nM antisense oligonucleotide. After a treatment period of approximately 24 hours, RNA was isolated from the cells and AGT mRNA levels were measured by quantitative real-time PCR. Human primer probe set RTS4039 was used to measure mRNA levels. AGT mRNA levels were adjusted according to total RNA content, as measured by RIBOGREEN®. Results are presented as percent inhibition of AGT, relative to untreated control cells.

TABLE 9

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610015 | 2049 | 2068 | GACACATCGCTGATTTGTCC | eeeeedddddddddeeeee | 91 | 13518 | 13537 | 239 |
| 610015 | 2049 | 2068 | GACACATCGCTGATTTGTCC | eeeeedddddddddeeeee | 86 | 13518 | 13537 | 239 |
| 610015 | 2049 | 2068 | GACACATCGCTGATTTGTCC | eeeeedddddddddeeeee | 88 | 13518 | 13537 | 239 |
| 610015 | 2049 | 2068 | GACACATCGCTGATTTGTCC | eeeeedddddddddeeeee | 85 | 13518 | 13537 | 239 |
| 619692 | 1042 | 1061 | GCAGGGCAGACAGGACCTTG | eeeeedddddddddeeeee | 17 | 6259 | 6278 | 1411 |
| 619693 | 1045 | 1064 | CCTGCAGGGCAGACAGGACC | eeeeedddddddddeeeee | 25 | 6262 | 6281 | 1412 |
| 619694 | 1048 | 1067 | CAGCCTGCAGGGCAGACAGG | eeeeedddddddddeeeee | 32 | 6265 | 6284 | 1413 |
| 619695 | 1051 | 1070 | GTACAGCCTGCAGGGCAGAC | eeeeedddddddddeeeee | 25 | 6268 | 6287 | 1414 |
| 619696 | 1054 | 1073 | CCTGTACAGCCTGCAGGGCA | eeeeedddddddddeeeee | 48 | 6271 | 6290 | 1415 |
| 619697 | 1057 | 1076 | GGCCCTGTACAGCCTGCAGG | eeeeedddddddddeeeee | 32 | 6274 | 6293 | 1416 |
| 619698 | 1060 | 1079 | GCAGGCCCTGTACAGCCTGC | eeeeedddddddddeeeee | 17 | 6277 | 6296 | 1417 |
| 619699 | 1063 | 1082 | CTAGCAGGCCCTGTACAGCC | eeeeedddddddddeeeee | 13 | 6280 | 6299 | 1418 |
| 619700 | 1066 | 1085 | CCACTAGCAGGCCCTGTACA | eeeeedddddddddeeeee | 36 | 6283 | 6302 | 1419 |
| 619701 | 1069 | 1088 | GGGCCACTAGCAGGCCCTGT | eeeeedddddddddeeeee | 6 | 6286 | 6305 | 1420 |
| 619702 | 1072 | 1091 | CCTGGGCCACTAGCAGGCCC | eeeeedddddddddeeeee | 16 | 6289 | 6308 | 1421 |

TABLE 9-continued

Inhibition of AGT mRNA by MOE containing gapmers targeting
SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619703 | 1075 | 1094 | TGCCCTGGGCCACTAGCAGG | eeeeddddddddddeeeee | 26 | 6292 | 6311 | 1422 |
| 619704 | 1078 | 1097 | CCCTGCCCTGGGCCACTAGC | eeeeddddddddddeeeee | 41 | 6295 | 6314 | 1423 |
| 619705 | 1081 | 1100 | CAGCCCTGCCCTGGGCCACT | eeeeddddddddddeeeee | 36 | 6298 | 6317 | 1424 |
| 619706 | 1084 | 1103 | TATCAGCCCTGCCCTGGGCC | eeeeddddddddddeeeee | 21 | 6301 | 6320 | 1425 |
| 619707 | 1087 | 1106 | GGCTATCAGCCCTGCCCTGG | eeeeddddddddddeeeee | 27 | 6304 | 6323 | 1426 |
| 619708 | 1090 | 1109 | CCTGGCTATCAGCCCTGCCC | eeeeddddddddddeeeee | 30 | 6307 | 6326 | 1427 |
| 619709 | 1093 | 1112 | GGGCCTGGCTATCAGCCCTG | eeeeddddddddddeeeee | 9 | 6310 | 6329 | 1428 |
| 619710 | 1096 | 1115 | GCTGGGCCTGGCTATCAGCC | eeeeddddddddddeeeee | 15 | 6313 | 6332 | 1429 |
| 619711 | 1099 | 1118 | GCAGCTGGGCCTGGCTATCA | eeeeddddddddddeeeee | 26 | 6316 | 6335 | 1430 |
| 619712 | 1102 | 1121 | GCAGCAGCTGGGCCTGGCTA | eeeeddddddddddeeeee | 61 | 6319 | 6338 | 1431 |
| 619713 | 1105 | 1124 | ACAGCAGCAGCTGGGCCTGG | eeeeddddddddddeeeee | 44 | 6322 | 6341 | 1432 |
| 619714 | 1108 | 1127 | TGGACAGCAGCAGCTGGGCC | eeeeddddddddddeeeee | 47 | 6325 | 6344 | 1433 |
| 619715 | 1111 | 1130 | CCGTGGACAGCAGCAGCTGG | eeeeddddddddddeeeee | 41 | 6328 | 6347 | 1434 |
| 619716 | 1114 | 1133 | CCACCGTGGACAGCAGCAGC | eeeeddddddddddeeeee | 35 | 6331 | 6350 | 1435 |
| 619717 | 1117 | 1136 | CCACCACCGTGGACAGCAGC | eeeeddddddddddeeeee | 34 | 6334 | 6353 | 1436 |
| 619718 | 1120 | 1139 | CGCCCACCACCGTGGACAGC | eeeeddddddddddeeeee | 37 | 6337 | 6356 | 1437 |
| 619719 | 1123 | 1142 | ACACGCCCACCACCGTGGAC | eeeeddddddddddeeeee | 17 | 6340 | 6359 | 1438 |
| 619720 | 1126 | 1145 | TGAACACGCCCACCACCGTG | eeeeddddddddddeeeee | 20 | 6343 | 6362 | 1439 |
| 619721 | 1129 | 1148 | CTGTGAACACGCCCACCACC | eeeeddddddddddeeeee | 36 | 6346 | 6365 | 1440 |
| 619722 | 1132 | 1151 | GGGCTGTGAACACGCCCACC | eeeeddddddddddeeeee | 14 | 6349 | 6368 | 1441 |
| 619723 | 1150 | 1169 | GCTTCAGGTGCAGGCCTGGG | eeeeddddddddddeeeee | 32 | 6367 | 6386 | 1442 |
| 619724 | 1153 | 1172 | GCTGCTTCAGGTGCAGGCCT | eeeeddddddddddeeeee | 47 | 6370 | 6389 | 1443 |
| 619725 | 1156 | 1175 | ACGGCTGCTTCAGGTGCAGG | eeeeddddddddddeeeee | 27 | 6373 | 6392 | 1444 |
| 619726 | 1159 | 1178 | CAAACGGCTGCTTCAGGTGC | eeeeddddddddddeeeee | 20 | 6376 | 6395 | 1445 |
| 619727 | 1162 | 1181 | GCACAAACGGCTGCTTCAGG | eeeeddddddddddeeeee | 13 | 6379 | 6398 | 1446 |
| 619728 | 1165 | 1184 | CCTGCACAAACGGCTGCTTC | eeeeddddddddddeeeee | 25 | 6382 | 6401 | 1447 |
| 619729 | 1168 | 1187 | GGCCCTGCACAAACGGCTGC | eeeeddddddddddeeeee | 29 | 6385 | 6404 | 1448 |
| 619730 | 1171 | 1190 | CCAGGCCCTGCACAAACGGC | eeeeddddddddddeeeee | 27 | 6388 | 6407 | 1449 |
| 619731 | 1174 | 1193 | GAGCCAGGCCCTGCACAAAC | eeeeddddddddddeeeee | 18 | 6391 | 6410 | 1450 |
| 619732 | 1177 | 1196 | AGAGAGCCAGGCCCTGCACA | eeeeddddddddddeeeee | 33 | 6394 | 6413 | 1451 |
| 619733 | 1180 | 1199 | TATAGAGAGCCAGGCCCTGC | eeeeddddddddddeeeee | 0 | 6397 | 6416 | 1452 |
| 619734 | 1183 | 1202 | GGGTATAGAGAGCCAGGCCC | eeeeddddddddddeeeee | 14 | 6400 | 6419 | 1453 |
| 619735 | 1217 | 1236 | TCTGTGAAGTCCAGAGAGCG | eeeeddddddddddeeeee | 17 | 6434 | 6453 | 1454 |
| 619736 | 1220 | 1239 | AGTTCTGTGAAGTCCAGAGA | eeeeddddddddddeeeee | 41 | 6437 | 6456 | 1455 |
| 619737 | 1223 | 1242 | TCCAGTTCTGTGAAGTCCAG | eeeeddddddddddeeeee | 31 | 6440 | 6459 | 1456 |
| 619738 | 1226 | 1245 | ACATCCAGTTCTGTGAAGTC | eeeeddddddddddeeeee | 35 | 6443 | 6462 | 1457 |

TABLE 9-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619739 | 1229 | 1248 | GCAACATCCAGTTCTGTGAA | eeeeddddddddddeeeee | 29 | 6446 | 6465 | 1458 |
| 619740 | 1232 | 1251 | GCAGCAACATCCAGTTCTGT | eeeeddddddddddeeeee | 35 | 6449 | 6468 | 1459 |
| 619741 | 1235 | 1254 | TCAGCAGCAACATCCAGTTC | eeeeddddddddddeeeee | 35 | 6452 | 6471 | 1460 |
| 619742 | 1238 | 1257 | TTCTCAGCAGCAACATCCAG | eeeeddddddddddeeeee | 5 | 6455 | 6474 | 1461 |
| 619743 | 1241 | 1260 | ATCTTCTCAGCAGCAACATC | eeeeddddddddddeeeee | 22 | 6458 | 6477 | 1462 |
| 619744 | 1244 | 1263 | TCAATCTTCTCAGCAGCAAC | eeeeddddddddddeeeee | 45 | 6461 | 6480 | 1463 |
| 619745 | 1247 | 1266 | CTGTCAATCTTCTCAGCAGC | eeeeddddddddddeeeee | 21 | 6464 | 6483 | 1464 |
| 619746 | 1250 | 1269 | AACCTGTCAATCTTCTCAGC | eeeeddddddddddeeeee | 8 | 6467 | 6486 | 1465 |
| 619747 | 1253 | 1272 | ATGAACCTGTCAATCTTCTC | eeeeddddddddddeeeee | 43 | 6470 | 6489 | 1466 |
| 619748 | 1256 | 1275 | TGCATGAACCTGTCAATCTT | eeeeddddddddddeeeee | 31 | 6473 | 6492 | 1467 |
| 619749 | 1259 | 1278 | GCCTGCATGAACCTGTCAAT | eeeeddddddddddeeeee | 44 | 6476 | 6495 | 1468 |
| 619750 | 1262 | 1281 | ACAGCCTGCATGAACCTGTC | eeeeddddddddddeeeee | 41 | 6479 | 6498 | 1469 |
| 619751 | 1265 | 1284 | GTCACAGCCTGCATGAACCT | eeeeddddddddddeeeee | 69 | 6482 | 6501 | 1470 |
| 619752 | 1268 | 1287 | CCTGTCACAGCCTGCATGAA | eeeeddddddddddeeeee | 43 | 6485 | 6504 | 1471 |
| 619753 | 1271 | 1290 | CATCCTGTCACAGCCTGCAT | eeeeddddddddddeeeee | 59 | 6488 | 6507 | 1472 |
| 619754 | 1274 | 1293 | TTCCATCCTGTCACAGCCTG | eeeeddddddddddeeeee | 49 | 6491 | 6510 | 1473 |
| 619755 | 1277 | 1296 | GTCTTCCATCCTGTCACAGC | eeeeddddddddddeeeee | 42 | 6494 | 6513 | 1474 |
| 619756 | 1280 | 1299 | CCAGTCTTCCATCCTGTCAC | eeeeddddddddddeeeee | 20 | 6497 | 6516 | 1475 |
| 619757 | 1283 | 1302 | CAGCCAGTCTTCCATCCTGT | eeeeddddddddddeeeee | 41 | 6500 | 6519 | 1476 |
| 619758 | 1286 | 1305 | GAGCAGCCAGTCTTCCATCC | eeeeddddddddddeeeee | 41 | 6503 | 6522 | 1477 |
| 619759 | 1289 | 1308 | AGGGAGCAGCCAGTCTTCCA | eeeeddddddddddeeeee | 29 | 6506 | 6525 | 1478 |
| 619760 | 1292 | 1311 | ATCAGGGAGCAGCCAGTCTT | eeeeddddddddddeeeee | 29 | 6509 | 6528 | 1479 |
| 619761 | 1295 | 1314 | CCCATCAGGGAGCAGCCAGT | eeeeddddddddddeeeee | 7 | 6512 | 6531 | 1480 |
| 619762 | 1298 | 1317 | GCTCCCATCAGGGAGCAGCC | eeeeddddddddddeeeee | 4 | 6515 | 6534 | 1481 |
| 619763 | 1301 | 1320 | CTGGCTCCCATCAGGGAGCA | eeeeddddddddddeeeee | 8 | 6518 | 6537 | 1482 |
| 619764 | 1304 | 1323 | ACACTGGCTCCCATCAGGGA | eeeeddddddddddeeeee | 0 | 6521 | 6540 | 1483 |
| 619765 | 1307 | 1326 | TCCACACTGGCTCCCATCAG | eeeeddddddddddeeeee | 27 | 6524 | 6543 | 1484 |
| 619766 | 1310 | 1329 | CTGTCCACACTGGCTCCCAT | eeeeddddddddddeeeee | 27 | 6527 | 6546 | 1485 |
| 619767 | 1313 | 1332 | GTGCTGTCCACACTGGCTCC | eeeeddddddddddeeeee | 42 | 6530 | 6549 | 1486 |
| 619768 | 1316 | 1335 | AGGGTGCTGTCCACACTGGC | eeeeddddddddddeeeee | 39 | 6533 | 6552 | 1487 |
| 619769 | 1319 | 1338 | GCCAGGGTGCTGTCCACACT | eeeeddddddddddeeeee | 65 | 6536 | 6555 | 1488 |
| 619770 | 1322 | 1341 | AAAGCCAGGGTGCTGTCCAC | eeeeddddddddddeeeee | 65 | 6539 | 6558 | 1489 |
| 619771 | 1325 | 1344 | TTGAAAGCCAGGGTGCTGTC | eeeeddddddddddeeeee | 48 | 6542 | 6561 | 1490 |
| 619772 | 1328 | 1347 | GTGTTGAAAGCCAGGGTGCT | eeeeddddddddddeeeee | 44 | 6545 | 6564 | 1491 |
| 619773 | 1331 | 1350 | TAGGTGTTGAAAGCCAGGGT | eeeeddddddddddeeeee | 16 | 6548 | 6567 | 1492 |
| 619774 | 1351 | 1370 | TCTTCCCTTGGAAGTGGACG | eeeeddddddddddeeeee | 40 | N/A | N/A | 1493 |

TABLE 9-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619775 | 1354 | 1373 | TCATCTTCCCTTGGAAGTGG | eeeeddddddddddeeeee | 41 | N/A | N/A | 1494 |
| 619776 | 1357 | 1376 | CCTTCATCTTCCCTTGGAAG | eeeeddddddddddeeeee | 30 | N/A | N/A | 1495 |
| 619777 | 1360 | 1379 | AGCCCTTCATCTTCCCTTGG | eeeeddddddddddeeeee | 53 | N/A | N/A | 1496 |
| 619778 | 1363 | 1382 | AGAAGCCCTTCATCTTCCCT | eeeeddddddddddeeeee | 33 | 10374 | 10393 | 1497 |
| 619779 | 1366 | 1385 | GGGAGAAGCCCTTCATCTTC | eeeeddddddddddeeeee | 56 | 10377 | 10396 | 1498 |
| 619780 | 1369 | 1388 | GCAGGGAGAAGCCCTTCATC | eeeeddddddddddeeeee | 42 | 10380 | 10399 | 1499 |
| 619781 | 1372 | 1391 | CCAGCAGGGAGAAGCCCTTC | eeeeddddddddddeeeee | 63 | 10383 | 10402 | 1500 |
| 619782 | 1375 | 1394 | CGGCCAGCAGGGAGAAGCCC | eeeeddddddddddeeeee | 52 | 10386 | 10405 | 1501 |
| 619783 | 1378 | 1397 | GCTCGGCCAGCAGGGAGAAG | eeeeddddddddddeeeee | 37 | 10389 | 10408 | 1502 |
| 619784 | 1398 | 1417 | GTCCACCCAGAACTCCTGGG | eeeeddddddddddeeeee | 67 | 10409 | 10428 | 1503 |
| 619785 | 1401 | 1420 | GTTGTCCACCCAGAACTCCT | eeeeddddddddddeeeee | 65 | 10412 | 10431 | 1504 |
| 619786 | 1404 | 1423 | GCTGTTGTCCACCCAGAACT | eeeeddddddddddeeeee | 43 | 10415 | 10434 | 1505 |
| 619787 | 1407 | 1426 | GGTGCTGTTGTCCACCCAGA | eeeeddddddddddeeeee | 49 | 10418 | 10437 | 1506 |
| 619788 | 1410 | 1429 | TGAGGTGCTGTTGTCCACCC | eeeeddddddddddeeeee | 50 | 10421 | 10440 | 1507 |
| 619789 | 1413 | 1432 | CACTGAGGTGCTGTTGTCCA | eeeeddddddddddeeeee | 47 | 10424 | 10443 | 1508 |
| 619790 | 1416 | 1435 | AGACACTGAGGTGCTGTTGT | eeeeddddddddddeeeee | 50 | 10427 | 10446 | 1509 |
| 619791 | 1419 | 1438 | AACAGACACTGAGGTGCTGT | eeeeddddddddddeeeee | 58 | 10430 | 10449 | 1510 |
| 619792 | 1422 | 1441 | GGGAACAGACACTGAGGTGC | eeeeddddddddddeeeee | 56 | 10433 | 10452 | 1511 |
| 619793 | 1425 | 1444 | CATGGGAACAGACACTGAGG | eeeeddddddddddeeeee | 45 | 10436 | 10455 | 1512 |
| 619794 | 1428 | 1447 | GAGCATGGGAACAGACACTG | eeeeddddddddddeeeee | 49 | 10439 | 10458 | 1513 |
| 619795 | 1431 | 1450 | AGAGAGCATGGGAACAGACA | eeeeddddddddddeeeee | 32 | 10442 | 10461 | 1514 |
| 619796 | 1434 | 1453 | GCCAGAGAGCATGGGAACAG | eeeeddddddddddeeeee | 32 | 10445 | 10464 | 1515 |
| 619797 | 1437 | 1456 | CATGCCAGAGAGCATGGGAA | eeeeddddddddddeeeee | 35 | 10448 | 10467 | 1516 |
| 619798 | 1440 | 1459 | GCCCATGCCAGAGAGCATGG | eeeeddddddddddeeeee | 23 | 10451 | 10470 | 1517 |
| 619799 | 1443 | 1462 | GGTGCCCATGCCAGAGAGCA | eeeeddddddddddeeeee | 48 | 10454 | 10473 | 1518 |
| 619800 | 1446 | 1465 | GAAGGTGCCCATGCCAGAGA | eeeeddddddddddeeeee | 46 | 10457 | 10476 | 1519 |
| 619801 | 1449 | 1468 | CTGGAAGGTGCCCATGCCAG | eeeeddddddddddeeeee | 55 | 10460 | 10479 | 1520 |
| 619802 | 1452 | 1471 | GTGCTGGAAGGTGCCCATGC | eeeeddddddddddeeeee | 43 | 10463 | 10482 | 1521 |
| 619803 | 1455 | 1474 | CCAGTGCTGGAAGGTGCCCA | eeeeddddddddddeeeee | 58 | 10466 | 10485 | 1522 |
| 619804 | 1458 | 1477 | ACTCCAGTGCTGGAAGGTGC | eeeeddddddddddeeeee | 50 | 10469 | 10488 | 1523 |
| 619805 | 1461 | 1480 | GTCACTCCAGTGCTGGAAGG | eeeeddddddddddeeeee | 53 | 10472 | 10491 | 1524 |
| 619806 | 1464 | 1483 | GATGTCACTCCAGTGCTGGA | eeeeddddddddddeeeee | 46 | 10475 | 10494 | 1525 |
| 619807 | 1467 | 1486 | CTGGATGTCACTCCAGTGCT | eeeeddddddddddeeeee | 70 | 10478 | 10497 | 1526 |
| 619808 | 1470 | 1489 | GTCCTGGATGTCACTCCAGT | eeeeddddddddddeeeee | 49 | 10481 | 10500 | 1527 |
| 619809 | 1473 | 1492 | GTTGTCCTGGATGTCACTCC | eeeeddddddddddeeeee | 51 | 10484 | 10503 | 1528 |
| 619810 | 1476 | 1495 | GAAGTTGTCCTGGATGTCAC | eeeeddddddddddeeeee | 51 | 10487 | 10506 | 1529 |

TABLE 9-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619811 | 1479 | 1498 | CGAGAAGTTGTCCTGGATGT | eeeeddddddddddeeeee | 33 | 10490 | 10509 | 1530 |
| 619812 | 1482 | 1501 | CACCGAGAAGTTGTCCTGGA | eeeeddddddddddeeeee | 49 | 10493 | 10512 | 1531 |
| 619813 | 1485 | 1504 | AGTCACCGAGAAGTTGTCCT | eeeeddddddddddeeeee | 53 | 10496 | 10515 | 1532 |
| 619814 | 1488 | 1507 | TTGAGTCACCGAGAAGTTGT | eeeeddddddddddeeeee | 41 | 10499 | 10518 | 1533 |
| 619815 | 1491 | 1510 | CACTTGAGTCACCGAGAAGT | eeeeddddddddddeeeee | 32 | 10502 | 10521 | 1534 |
| 619816 | 1494 | 1513 | GGGCACTTGAGTCACCGAGA | eeeeddddddddddeeeee | 69 | 10505 | 10524 | 1535 |
| 619817 | 1497 | 1516 | GAAGGGCACTTGAGTCACCG | eeeeddddddddddeeeee | 63 | 10508 | 10527 | 1536 |
| 619818 | 1500 | 1519 | AGTGAAGGGCACTTGAGTCA | eeeeddddddddddeeeee | 37 | 10511 | 10530 | 1537 |
| 619819 | 1503 | 1522 | CTCAGTGAAGGGCACTTGAG | eeeeddddddddddeeeee | 35 | 10514 | 10533 | 1538 |
| 619820 | 1506 | 1525 | GCTCTCAGTGAAGGGCACTT | eeeeddddddddddeeeee | 65 | 10517 | 10536 | 1539 |
| 619821 | 1524 | 1543 | GATCAGCAGCAGGCAGGCGC | eeeeddddddddddeeeee | 58 | 10535 | 10554 | 1540 |
| 619822 | 1527 | 1546 | CTGGATCAGCAGCAGGCAGG | eeeeddddddddddeeeee | 55 | 10538 | 10557 | 1541 |
| 619823 | 1530 | 1549 | AGGCTGGATCAGCAGCAGGC | eeeeddddddddddeeeee | 72 | 10541 | 10560 | 1542 |
| 619824 | 1533 | 1552 | GTGAGGCTGGATCAGCAGCA | eeeeddddddddddeeeee | 70 | 10544 | 10563 | 1543 |
| 619825 | 1536 | 1555 | ATAGTGAGGCTGGATCAGCA | eeeeddddddddddeeeee | 17 | 10547 | 10566 | 1544 |
| 619826 | 1539 | 1558 | GGCATAGTGAGGCTGGATCA | eeeeddddddddddeeeee | 67 | 10550 | 10569 | 1545 |
| 619827 | 1542 | 1561 | AGAGGCATAGTGAGGCTGGA | eeeeddddddddddeeeee | 51 | 10553 | 10572 | 1546 |
| 619828 | 1545 | 1564 | GTCAGAGGCATAGTGAGGCT | eeeeddddddddddeeeee | 46 | 10556 | 10575 | 1547 |

Table 10 shows inhibition of AGT mRNA in HepG2 cells cultured at a density of 20,000 cells per well which were transfected using electroporation with 4000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 10

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 610015 | 2049 | 2068 | GACACATCGCTGATTTGTCC | eeeeddddddddddeeeee | 91 | 13518 | 13537 | 239 |
| 610015 | 2049 | 2068 | GACACATCGCTGATTTGTCC | eeeeddddddddddeeeee | 84 | 13518 | 13537 | 239 |
| 610015 | 2049 | 2068 | GACACATCGCTGATTTGTCC | eeeeddddddddddeeeee | 91 | 13518 | 13537 | 239 |
| 610015 | 2049 | 2068 | GACACATCGCTGATTTGTCC | eeeeddddddddddeeeee | 78 | 13518 | 13537 | 239 |
| 610015 | 2049 | 2068 | GACACATCGCTGATTTGTCC | eeeeddddddddddeeeee | 89 | 13518 | 13537 | 239 |
| 610015 | 2049 | 2068 | GACACATCGCTGATTTGTCC | eeeeddddddddddeeeee | 81 | 13518 | 13537 | 239 |
| 610015 | 2049 | 2068 | GACACATCGCTGATTTGTCC | eeeeddddddddddeeeee | 92 | 13518 | 13537 | 239 |
| 610015 | 2049 | 2068 | GACACATCGCTGATTTGTCC | eeeeddddddddddeeeee | 90 | 13518 | 13537 | 239 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619784 | 1398 | 1417 | GTCCACCCAGAACTCCTGGG | eeeeedddddddddddeeeee | 73 | 10409 | 10428 | 1503 |
| 619785 | 1401 | 1420 | GTTGTCCACCCAGAACTCCT | eeeeedddddddddddeeeee | 76 | 10412 | 10431 | 1504 |
| 619786 | 1404 | 1423 | GCTGTTGTCCACCCAGAACT | eeeeedddddddddddeeeee | 54 | 10415 | 10434 | 1505 |
| 619787 | 1407 | 1426 | GGTGCTGTTGTCCACCCAGA | eeeeedddddddddddeeeee | 55 | 10418 | 10437 | 1506 |
| 619788 | 1410 | 1429 | TGAGGTGCTGTTGTCCACCC | eeeeedddddddddddeeeee | 51 | 10421 | 10440 | 1507 |
| 619789 | 1413 | 1432 | CACTGAGGTGCTGTTGTCCA | eeeeedddddddddddeeeee | 46 | 10424 | 10443 | 1508 |
| 619790 | 1416 | 1435 | AGACACTGAGGTGCTGTTGT | eeeeedddddddddddeeeee | 51 | 10427 | 10446 | 1509 |
| 619791 | 1419 | 1438 | AACAGACACTGAGGTGCTGT | eeeeedddddddddddeeeee | 36 | 10430 | 10449 | 1510 |
| 619792 | 1422 | 1441 | GGGAACAGACACTGAGGTGC | eeeeedddddddddddeeeee | 57 | 10433 | 10452 | 1511 |
| 619793 | 1425 | 1444 | CATGGGAACAGACACTGAGG | eeeeedddddddddddeeeee | 42 | 10436 | 10455 | 1512 |
| 619794 | 1428 | 1447 | GAGCATGGGAACAGACACTG | eeeeedddddddddddeeeee | 45 | 10439 | 10458 | 1513 |
| 619795 | 1431 | 1450 | AGAGAGCATGGGAACAGACA | eeeeedddddddddddeeeee | 25 | 10442 | 10461 | 1514 |
| 619796 | 1434 | 1453 | GCCAGAGAGCATGGGAACAG | eeeeedddddddddddeeeee | 45 | 10445 | 10464 | 1515 |
| 619797 | 1437 | 1456 | CATGCCAGAGAGCATGGGAA | eeeeedddddddddddeeeee | 38 | 10448 | 10467 | 1516 |
| 619798 | 1440 | 1459 | GCCCATGCCAGAGAGCATGG | eeeeedddddddddddeeeee | 27 | 10451 | 10470 | 1517 |
| 619799 | 1443 | 1462 | GGTGCCCATGCCAGAGAGCA | eeeeedddddddddddeeeee | 50 | 10454 | 10473 | 1518 |
| 619800 | 1446 | 1465 | GAAGGTGCCCATGCCAGAGA | eeeeedddddddddddeeeee | 39 | 10457 | 10476 | 1519 |
| 619801 | 1449 | 1468 | CTGGAAGGTGCCCATGCCAG | eeeeedddddddddddeeeee | 54 | 10460 | 10479 | 1520 |
| 619802 | 1452 | 1471 | GTGCTGGAAGGTGCCCATGC | eeeeedddddddddddeeeee | 42 | 10463 | 10482 | 1521 |
| 619803 | 1455 | 1474 | CCAGTGCTGGAAGGTGCCCA | eeeeedddddddddddeeeee | 83 | 10466 | 10485 | 1522 |
| 619804 | 1458 | 1477 | ACTCCAGTGCTGGAAGGTGC | eeeeedddddddddddeeeee | 42 | 10469 | 10488 | 1523 |
| 619805 | 1461 | 1480 | GTCACTCCAGTGCTGGAAGG | eeeeedddddddddddeeeee | 66 | 10472 | 10491 | 1524 |
| 619806 | 1464 | 1483 | GATGTCACTCCAGTGCTGGA | eeeeedddddddddddeeeee | 55 | 10475 | 10494 | 1525 |
| 619807 | 1467 | 1486 | CTGGATGTCACTCCAGTGCT | eeeeedddddddddddeeeee | 68 | 10478 | 10497 | 1526 |
| 619808 | 1470 | 1489 | GTCCTGGATGTCACTCCAGT | eeeeedddddddddddeeeee | 49 | 10481 | 10500 | 1527 |
| 619809 | 1473 | 1492 | GTTGTCCTGGATGTCACTCC | eeeeedddddddddddeeeee | 61 | 10484 | 10503 | 1528 |
| 619810 | 1476 | 1495 | GAAGTTGTCCTGGATGTCAC | eeeeedddddddddddeeeee | 47 | 10487 | 10506 | 1529 |
| 619811 | 1479 | 1498 | CGAGAAGTTGTCCTGGATGT | eeeeedddddddddddeeeee | 44 | 10490 | 10509 | 1530 |
| 619812 | 1482 | 1501 | CACCGAGAAGTTGTCCTGGA | eeeeedddddddddddeeeee | 56 | 10493 | 10512 | 1531 |
| 619813 | 1485 | 1504 | AGTCACCGAGAAGTTGTCCT | eeeeedddddddddddeeeee | 48 | 10496 | 10515 | 1532 |
| 619814 | 1488 | 1507 | TTGAGTCACCGAGAAGTTGT | eeeeedddddddddddeeeee | 45 | 10499 | 10518 | 1533 |
| 619815 | 1491 | 1510 | CACTTGAGTCACCGAGAAGT | eeeeedddddddddddeeeee | 33 | 10502 | 10521 | 1534 |
| 619816 | 1494 | 1513 | GGGCACTTGAGTCACCGAGA | eeeeedddddddddddeeeee | 70 | 10505 | 10524 | 1535 |
| 619817 | 1497 | 1516 | GAAGGGCACTTGAGTCACCG | eeeeedddddddddddeeeee | 72 | 10508 | 10527 | 1536 |
| 619818 | 1500 | 1519 | AGTGAAGGGCACTTGAGTCA | eeeeedddddddddddeeeee | 41 | 10511 | 10530 | 1537 |
| 619819 | 1503 | 1522 | CTCAGTGAAGGGCACTTGAG | eeeeedddddddddddeeeee | 39 | 10514 | 10533 | 1538 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619820 | 1506 | 1525 | GCTCTCAGTGAAGGGCACTT | eeeeddddddddddeeeee | 57 | 10517 | 10536 | 1539 |
| 619821 | 1524 | 1543 | GATCAGCAGCAGGCAGGCGC | eeeeddddddddddeeeee | 58 | 10535 | 10554 | 1540 |
| 619822 | 1527 | 1546 | CTGGATCAGCAGCAGGCAGG | eeeeddddddddddeeeee | 59 | 10538 | 10557 | 1541 |
| 619823 | 1530 | 1549 | AGGCTGGATCAGCAGCAGGC | eeeeddddddddddeeeee | 82 | 10541 | 10560 | 1542 |
| 619824 | 1533 | 1552 | GTGAGGCTGGATCAGCAGCA | eeeeddddddddddeeeee | 65 | 10544 | 10563 | 1543 |
| 619825 | 1536 | 1555 | ATAGTGAGGCTGGATCAGCA | eeeeddddddddddeeeee | 7 | 10547 | 10566 | 1544 |
| 619826 | 1539 | 1558 | GGCATAGTGAGGCTGGATCA | eeeeddddddddddeeeee | 71 | 10550 | 10569 | 1545 |
| 619827 | 1542 | 1561 | AGAGGCATAGTGAGGCTGGA | eeeeddddddddddeeeee | 58 | 10553 | 10572 | 1546 |
| 619828 | 1545 | 1564 | GTCAGAGGCATAGTGAGGCT | eeeeddddddddddeeeee | 57 | 10556 | 10575 | 1547 |
| 619829 | 1548 | 1567 | CAGGTCAGAGGCATAGTGAG | eeeeddddddddddeeeee | 46 | 10559 | 10578 | 1548 |
| 619830 | 1551 | 1570 | GTCCAGGTCAGAGGCATAGT | eeeeddddddddddeeeee | 6 | 10562 | 10581 | 1549 |
| 619831 | 1554 | 1573 | CTTGTCCAGGTCAGAGGCAT | eeeeddddddddddeeeee | 54 | 10565 | 10584 | 1550 |
| 619832 | 1557 | 1576 | CACCTTGTCCAGGTCAGAGG | eeeeddddddddddeeeee | 47 | 10568 | 10587 | 1551 |
| 619833 | 1560 | 1579 | CTCCACCTTGTCCAGGTCAG | eeeeddddddddddeeeee | 33 | 10571 | 10590 | 1552 |
| 619834 | 1563 | 1582 | ACCCTCCACCTTGTCCAGGT | eeeeddddddddddeeeee | 59 | 10574 | 10593 | 1553 |
| 619835 | 1566 | 1585 | GAGACCCTCCACCTTGTCCA | eeeeddddddddddeeeee | 47 | 10577 | 10596 | 1554 |
| 619836 | 1569 | 1588 | AGTGAGACCCTCCACCTTGT | eeeeddddddddddeeeee | 52 | 10580 | 10599 | 1555 |
| 619837 | 1572 | 1591 | GAAAGTGAGACCCTCCACCT | eeeeddddddddddeeeee | 40 | 10583 | 10602 | 1556 |
| 619838 | 1575 | 1594 | CTGGAAAGTGAGACCCTCCA | eeeeddddddddddeeeee | 55 | 10586 | 10605 | 1557 |
| 619839 | 1578 | 1597 | TTGCTGGAAAGTGAGACCCT | eeeeddddddddddeeeee | 44 | 10589 | 10608 | 1558 |
| 619840 | 1581 | 1600 | GTTTTGCTGGAAAGTGAGAC | eeeeddddddddddeeeee | 50 | 10592 | 10611 | 1559 |
| 619841 | 1584 | 1603 | GGAGTTTTGCTGGAAAGTGA | eeeeddddddddddeeeee | 54 | 10595 | 10614 | 1560 |
| 619842 | 1587 | 1606 | GAGGGAGTTTTGCTGGAAAG | eeeeddddddddddeeeee | 35 | 10598 | 10617 | 1561 |
| 619843 | 1590 | 1609 | GTTGAGGGAGTTTTGCTGGA | eeeeddddddddddeeeee | 40 | 10601 | 10620 | 1562 |
| 619844 | 1593 | 1612 | CCAGTTGAGGGAGTTTTGCT | eeeeddddddddddeeeee | 32 | 10604 | 10623 | 1563 |
| 619845 | 1596 | 1615 | CATCCAGTTGAGGGAGTTTT | eeeeddddddddddeeeee | 52 | 10607 | 10626 | 1564 |
| 619846 | 1599 | 1618 | CTTCATCCAGTTGAGGGAGT | eeeeddddddddddeeeee | 56 | 10610 | 10629 | 1565 |
| 619847 | 1602 | 1621 | TTTCTTCATCCAGTTGAGGG | eeeeddddddddddeeeee | 38 | 10613 | 10632 | 1566 |
| 619848 | 1605 | 1624 | TAGTTTCTTCATCCAGTTGA | eeeeddddddddddeeeee | 29 | 10616 | 10635 | 1567 |
| 619849 | 1608 | 1627 | AGATAGTTTCTTCATCCAGT | eeeeddddddddddeeeee | 12 | 10619 | 10638 | 1568 |
| 619850 | 1611 | 1630 | GGGAGATAGTTTCTTCATCC | eeeeddddddddddeeeee | 32 | 10622 | 10641 | 1569 |
| 619851 | 1629 | 1648 | GGTCAGGTGGATGGTCCGGG | eeeeddddddddddeeeee | 43 | N/A | N/A | 1570 |
| 619852 | 1632 | 1651 | CATGGTCAGGTGGATGGTCC | eeeeddddddddddeeeee | 41 | 12238 | 12257 | 1571 |
| 619853 | 1635 | 1654 | GGGCATGGTCAGGTGGATGG | eeeeddddddddddeeeee | 57 | 12241 | 12260 | 1572 |
| 619854 | 1653 | 1672 | TCCTTGCAGCACCAGTTGGG | eeeeddddddddddeeeee | 46 | 12259 | 12278 | 1573 |
| 619855 | 1656 | 1675 | AGATCCTTGCAGCACCAGTT | eeeeddddddddddeeeee | 36 | 12262 | 12281 | 1574 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
| --- | --- | --- | --- | --- | --- | --- | --- | --- |
| 619856 | 1659 | 1678 | ATAAGATCCTTGCAGCACCA | eeeeedddddddddddeeeee | 37 | 12265 | 12284 | 1575 |
| 619857 | 1662 | 1681 | GTCATAAGATCCTTGCAGCA | eeeeedddddddddddeeeee | 35 | 12268 | 12287 | 1576 |
| 619858 | 1665 | 1684 | CAGGTCATAAGATCCTTGCA | eeeeedddddddddddeeeee | 41 | 12271 | 12290 | 1577 |
| 619859 | 1668 | 1687 | CTGCAGGTCATAAGATCCTT | eeeeedddddddddddeeeee | 32 | 12274 | 12293 | 1578 |
| 619860 | 1671 | 1690 | GTCCTGCAGGTCATAAGATC | eeeeedddddddddddeeeee | 47 | 12277 | 12296 | 1579 |
| 619861 | 1674 | 1693 | CAGGTCCTGCAGGTCATAAG | eeeeedddddddddddeeeee | 33 | 12280 | 12299 | 1580 |
| 619862 | 1677 | 1696 | GAGCAGGTCCTGCAGGTCAT | eeeeedddddddddddeeeee | 53 | 12283 | 12302 | 1581 |
| 619863 | 1680 | 1699 | GGCGAGCAGGTCCTGCAGGT | eeeeedddddddddddeeeee | 51 | 12286 | 12305 | 1582 |
| 619864 | 1683 | 1702 | CTGGGCGAGCAGGTCCTGCA | eeeeedddddddddddeeeee | 50 | 12289 | 12308 | 1583 |
| 619865 | 1686 | 1705 | AGCCTGGGCGAGCAGGTCCT | eeeeedddddddddddeeeee | 49 | 12292 | 12311 | 1584 |
| 619866 | 1689 | 1708 | CTCAGCCTGGGCGAGCAGGT | eeeeedddddddddddeeeee | 63 | 12295 | 12314 | 1585 |
| 619867 | 1692 | 1711 | CAGCTCAGCCTGGGCGAGCA | eeeeedddddddddddeeeee | 45 | 12298 | 12317 | 1586 |
| 619868 | 1699 | 1718 | TGGCGGGCAGCTCAGCCTGG | eeeeedddddddddddeeeee | 46 | 12305 | 12324 | 1587 |
| 619869 | 1702 | 1721 | GAATGGCGGGCAGCTCAGCC | eeeeedddddddddddeeeee | 46 | 12308 | 12327 | 1588 |
| 619870 | 1705 | 1724 | GCAGAATGGCGGGCAGCTCA | eeeeedddddddddddeeeee | 41 | 12311 | 12330 | 1589 |
| 619871 | 1708 | 1727 | TGTGCAGAATGGCGGGCAGC | eeeeedddddddddddeeeee | 44 | 12314 | 12333 | 1590 |
| 619872 | 1711 | 1730 | CGGTGTGCAGAATGGCGGGC | eeeeedddddddddddeeeee | 36 | 12317 | 12336 | 1591 |
| 619873 | 1714 | 1733 | GCTCGGTGTGCAGAATGGCG | eeeeedddddddddddeeeee | 63 | 12320 | 12339 | 1592 |
| 619874 | 1717 | 1736 | TCAGCTCGGTGTGCAGAATG | eeeeedddddddddddeeeee | 42 | 12323 | 12342 | 1593 |
| 619875 | 1720 | 1739 | GGTTCAGCTCGGTGTGCAGA | eeeeedddddddddddeeeee | 62 | 12326 | 12345 | 1594 |
| 619876 | 1723 | 1742 | GCAGGTTCAGCTCGGTGTGC | eeeeedddddddddddeeeee | 73 | 12329 | 12348 | 1595 |
| 619877 | 1726 | 1745 | TTTGCAGGTTCAGCTCGGTG | eeeeedddddddddddeeeee | 52 | 12332 | 12351 | 1596 |
| 619878 | 1729 | 1748 | ATTTTGCAGGTTCAGCTCG | eeeeedddddddddddeeeee | 43 | 12335 | 12354 | 1597 |
| 619879 | 1732 | 1751 | TCAATTTTTGCAGGTTCAGC | eeeeedddddddddddeeeee | 29 | 12338 | 12357 | 1598 |
| 619880 | 1735 | 1754 | TGCTCAATTTTTGCAGGTTC | eeeeedddddddddddeeeee | 72 | 12341 | 12360 | 1599 |
| 619881 | 1738 | 1757 | CATTGCTCAATTTTTGCAGG | eeeeedddddddddddeeeee | 36 | 12344 | 12363 | 1600 |
| 619882 | 1741 | 1760 | GGTCATTGCTCAATTTTTGC | eeeeedddddddddddeeeee | 56 | 12347 | 12366 | 1601 |
| 619883 | 1744 | 1763 | TGCGGTCATTGCTCAATTTT | eeeeedddddddddddeeeee | 45 | 12350 | 12369 | 1602 |
| 619884 | 1747 | 1766 | TGATGCGGTCATTGCTCAAT | eeeeedddddddddddeeeee | 51 | 12353 | 12372 | 1603 |
| 619885 | 1750 | 1769 | CCCTGATGCGGTCATTGCTC | eeeeedddddddddddeeeee | 77 | 12356 | 12375 | 1604 |
| 619886 | 1753 | 1772 | CCACCCTGATGCGGTCATTG | eeeeedddddddddddeeeee | 56 | 12359 | 12378 | 1605 |
| 619887 | 1756 | 1775 | CCCCCACCCTGATGCGGTCA | eeeeedddddddddddeeeee | 52 | 12362 | 12381 | 1606 |
| 619888 | 1759 | 1778 | CCTCCCCCACCCTGATGCGG | eeeeedddddddddddeeeee | 36 | 12365 | 12384 | 1607 |
| 619889 | 1762 | 1781 | GCACCTCCCCCACCCTGATG | eeeeedddddddddddeeeee | 36 | N/A | N/A | 1608 |
| 619890 | 1765 | 1784 | TCAGCACCTCCCCCACCCTG | eeeeedddddddddddeeeee | 57 | N/A | N/A | 1609 |
| 619891 | 1768 | 1787 | TGTTCAGCACCTCCCCCACC | eeeeedddddddddddeeeee | 60 | N/A | N/A | 1610 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619892 | 1771 | 1790 | TGCTGTTCAGCACCTCCCCC | eeeeddddddddddeeeee | 65 | N/A | N/A | 1611 |
| 619893 | 1774 | 1793 | AAATGCTGTTCAGCACCTCC | eeeeddddddddddeeeee | 68 | N/A | N/A | 1612 |
| 619894 | 1777 | 1796 | AAAAAATGCTGTTCAGCACC | eeeeddddddddddeeeee | 41 | 13246 | 13265 | 1613 |
| 619895 | 1780 | 1799 | CAAAAAAAATGCTGTTCAGC | eeeeddddddddddeeeee | 40 | 13249 | 13268 | 1614 |
| 619896 | 1783 | 1802 | GCTCAAAAAAAATGCTGTTC | eeeeddddddddddeeeee | 64 | 13252 | 13271 | 1615 |
| 619897 | 1786 | 1805 | CAAGCTCAAAAAAAATGCTG | eeeeddddddddddeeeee | 44 | 13255 | 13274 | 1616 |
| 619898 | 1789 | 1808 | CTTCAAGCTCAAAAAAAATG | eeeeddddddddddeeeee | 15 | 13258 | 13277 | 1617 |
| 619899 | 1792 | 1811 | CCGCTTCAAGCTCAAAAAAA | eeeeddddddddddeeeee | 62 | 13261 | 13280 | 1618 |
| 619900 | 1795 | 1814 | CATCCGCTTCAAGCTCAAAA | eeeeddddddddddeeeee | 62 | 13264 | 13283 | 1619 |
| 619901 | 1798 | 1817 | TCTCATCCGCTTCAAGCTCA | eeeeddddddddddeeeee | 72 | 13267 | 13286 | 1620 |
| 619902 | 1801 | 1820 | CTCTCTCATCCGCTTCAAGC | eeeeddddddddddeeeee | 66 | 13270 | 13289 | 1621 |
| 619903 | 1804 | 1823 | GCTCTCTCTCATCCGCTTCA | eeeeddddddddddeeeee | 68 | 13273 | 13292 | 1622 |
| 619904 | 1807 | 1826 | TGGGCTCTCTCTCATCCGCT | eeeeddddddddddeeeee | 83 | 13276 | 13295 | 1623 |
| 619905 | 1810 | 1829 | CTGTGGGCTCTCTCTCATCC | eeeeddddddddddeeeee | 80 | 13279 | 13298 | 1624 |
| 619906 | 1813 | 1832 | ACTCTGTGGGCTCTCTCTCA | eeeeddddddddddeeeee | 54 | 13282 | 13301 | 1625 |
| 619907 | 1816 | 1835 | TAGACTCTGTGGGCTCTCTC | eeeeddddddddddeeeee | 75 | 13285 | 13304 | 1626 |
| 619908 | 1824 | 1843 | CTGTTGGGTAGACTCTGTGG | eeeeddddddddddeeeee | 46 | 13293 | 13312 | 1627 |
| 619909 | 1827 | 1846 | AAGCTGTTGGGTAGACTCTG | eeeeddddddddddeeeee | 63 | 13296 | 13315 | 1628 |
| 619910 | 1830 | 1849 | GTTAAGCTGTTGGGTAGACT | eeeeddddddddddeeeee | 61 | 13299 | 13318 | 1629 |
| 619911 | 1833 | 1852 | CTTGTTAAGCTGTTGGGTAG | eeeeddddddddddeeeee | 47 | 13302 | 13321 | 1630 |
| 619912 | 1836 | 1855 | AGGCTTGTTAAGCTGTTGGG | eeeeddddddddddeeeee | 69 | 13305 | 13324 | 1631 |
| 619913 | 1839 | 1858 | CTCAGGCTTGTTAAGCTGTT | eeeeddddddddddeeeee | 62 | 13308 | 13327 | 1632 |
| 619914 | 1842 | 1861 | GACCTCAGGCTTGTTAAGCT | eeeeddddddddddeeeee | 55 | 13311 | 13330 | 1633 |
| 619915 | 1845 | 1864 | CAAGACCTCAGGCTTGTTAA | eeeeddddddddddeeeee | 50 | 13314 | 13333 | 1634 |
| 619916 | 1848 | 1867 | CTCCAAGACCTCAGGCTTGT | eeeeddddddddddeeeee | 60 | 13317 | 13336 | 1635 |
| 619917 | 1851 | 1870 | CACCTCCAAGACCTCAGGCT | eeeeddddddddddeeeee | 61 | 13320 | 13339 | 1636 |
| 619918 | 1854 | 1873 | GGTCACCTCCAAGACCTCAG | eeeeddddddddddeeeee | 67 | 13323 | 13342 | 1637 |
| 619919 | 1857 | 1876 | CAGGGTCACCTCCAAGACCT | eeeeddddddddddeeeee | 54 | 13326 | 13345 | 1638 |
| 619920 | 1860 | 1879 | GTTCAGGGTCACCTCCAAGA | eeeeddddddddddeeeee | 54 | 13329 | 13348 | 1639 |
| 619921 | 1863 | 1882 | GCGGTTCAGGGTCACCTCCA | eeeeddddddddddeeeee | 70 | 13332 | 13351 | 1640 |
| 619922 | 1873 | 1892 | ACAGGAATGGGCGGTTCAGG | eeeeddddddddddeeeee | 34 | 13342 | 13361 | 1641 |
| 619926 | 1876 | 1895 | CAAACAGGAATGGGCGGTTC | eeeeddddddddddeeeee | 40 | 13345 | 13364 | 1642 |
| 619927 | 1879 | 1898 | CAGCAAACAGGAATGGGCGG | eeeeddddddddddeeeee | 49 | 13348 | 13367 | 1643 |
| 619928 | 1882 | 1901 | ACACAGCAAACAGGAATGGG | eeeeddddddddddeeeee | 28 | 13351 | 13370 | 1644 |
| 619929 | 1885 | 1904 | CATACACAGCAAACAGGAAT | eeeeddddddddddeeeee | 29 | 13354 | 13373 | 1645 |
| 619930 | 1888 | 1907 | GATCATACACAGCAAACAGG | eeeeddddddddddeeeee | 49 | 13357 | 13376 | 1646 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 619931 | 1891 | 1910 | TTTGATCATACACAGCAAAC | eeeeedddddddddeeeee | 22 | 13360 | 13379 | 1647 |
| 619932 | 1894 | 1913 | CGCTTTGATCATACACAGCA | eeeeedddddddddeeeee | 56 | 13363 | 13382 | 1648 |
| 619933 | 1911 | 1930 | GAAGTGCAGGGCAGTGGCGC | eeeeedddddddddeeeee | 44 | 13380 | 13399 | 1649 |
| 619934 | 1914 | 1933 | CAGGAAGTGCAGGGCAGTGG | eeeeedddddddddeeeee | 39 | 13383 | 13402 | 1650 |
| 619935 | 1917 | 1936 | GCCCAGGAAGTGCAGGGCAG | eeeeedddddddddeeeee | 20 | 13386 | 13405 | 1651 |
| 619936 | 1920 | 1939 | GCGGCCCAGGAAGTGCAGGG | eeeeedddddddddeeeee | 19 | 13389 | 13408 | 1652 |
| 619937 | 1923 | 1942 | CACGCGGCCCAGGAAGTGCA | eeeeedddddddddeeeee | 34 | 13392 | 13411 | 1653 |
| 619938 | 1926 | 1945 | GGCCACGCGGCCCAGGAAGT | eeeeedddddddddeeeee | 21 | 13395 | 13414 | 1654 |
| 619939 | 1929 | 1948 | GTTGGCCACGCGGCCCAGGA | eeeeedddddddddeeeee | 34 | 13398 | 13417 | 1655 |
| 619940 | 1932 | 1951 | CGGGTTGGCCACGCGGCCCA | eeeeedddddddddeeeee | 38 | 13401 | 13420 | 1656 |
| 619941 | 1935 | 1954 | CAGCGGGTTGGCCACGCGGC | eeeeedddddddddeeeee | 42 | 13404 | 13423 | 1657 |
| 619942 | 1938 | 1957 | GCTCAGCGGGTTGGCCACGC | eeeeedddddddddeeeee | 64 | 13407 | 13426 | 1658 |
| 619943 | 1941 | 1960 | TGTGCTCAGCGGGTTGGCCA | eeeeedddddddddeeeee | 43 | 13410 | 13429 | 1659 |
| 619944 | 1944 | 1963 | TGCTGTGCTCAGCGGGTTGG | eeeeedddddddddeeeee | 29 | 13413 | 13432 | 1660 |
| 619945 | 1947 | 1966 | TCATGCTGTGCTCAGCGGGT | eeeeedddddddddeeeee | 49 | 13416 | 13435 | 1661 |
| 619946 | 1950 | 1969 | GCCTCATGCTGTGCTCAGCG | eeeeedddddddddeeeee | 74 | 13419 | 13438 | 1662 |
| 619947 | 1953 | 1972 | CTGGCCTCATGCTGTGCTCA | eeeeedddddddddeeeee | 56 | 13422 | 13441 | 1663 |
| 619948 | 1956 | 1975 | GCCCTGGCCTCATGCTGTGC | eeeeedddddddddeeeee | 44 | 13425 | 13444 | 1664 |
| 619949 | 1976 | 1995 | GCCAGGCACTGTGTTCTGGG | eeeeedddddddddeeeee | 65 | 13445 | 13464 | 1665 |
| 619950 | 1979 | 1998 | CTTGCCAGGCACTGTGTTCT | eeeeedddddddddeeeee | 71 | 13448 | 13467 | 1666 |
| 619951 | 1982 | 2001 | GGCCTTGCCAGGCACTGTGT | eeeeedddddddddeeeee | 80 | 13451 | 13470 | 1667 |
| 619952 | 2114 | 2133 | AGGAGAAACGGCTGCTTTCC | eeeeedddddddddeeeee | 61 | 13583 | 13602 | 1668 |
| 619953 | 2117 | 2136 | CCAAGGAGAAACGGCTGCTT | eeeeedddddddddeeeee | 75 | 13586 | 13605 | 1669 |
| 619954 | 2120 | 2139 | AGACCAAGGAGAAACGGCTG | eeeeedddddddddeeeee | 76 | 13589 | 13608 | 1670 |
| 619955 | 2123 | 2142 | CTTAGACCAAGGAGAAACGG | eeeeedddddddddeeeee | 67 | 13592 | 13611 | 1671 |
| 619956 | 2126 | 2145 | ACACTTAGACCAAGGAGAAA | eeeeedddddddddeeeee | 45 | 13595 | 13614 | 1672 |
| 619957 | 2129 | 2148 | AGCACACTTAGACCAAGGAG | eeeeedddddddddeeeee | 74 | 13598 | 13617 | 1673 |
| 619958 | 2132 | 2151 | TGCAGCACACTTAGACCAAG | eeeeedddddddddeeeee | 55 | 13601 | 13620 | 1674 |
| 619959 | 2135 | 2154 | CCATGCAGCACACTTAGACC | eeeeedddddddddeeeee | 56 | 13604 | 13623 | 1675 |
| 619960 | 2138 | 2157 | ACTCCATGCAGCACACTTAG | eeeeedddddddddeeeee | 66 | 13607 | 13626 | 1676 |
| 619961 | 2141 | 2160 | CTCACTCCATGCAGCACACT | eeeeedddddddddeeeee | 63 | 13610 | 13629 | 1677 |
| 619962 | 2159 | 2178 | CGCTGCAGGCTTCTACTGCT | eeeeedddddddddeeeee | 64 | 13628 | 13647 | 1678 |
| 619963 | 2162 | 2181 | TGCCGCTGCAGGCTTCTACT | eeeeedddddddddeeeee | 60 | 13631 | 13650 | 1679 |
| 619964 | 2165 | 2184 | TTGTGCCGCTGCAGGCTTCT | eeeeedddddddddeeeee | 45 | 13634 | 13653 | 1680 |
| 619965 | 2168 | 2187 | CATTTGTGCCGCTGCAGGCT | eeeeedddddddddeeeee | 62 | 13637 | 13656 | 1681 |
| 619966 | 2171 | 2190 | GTGCATTTGTGCCGCTGCAG | eeeeedddddddddeeeee | 85 | 13640 | 13659 | 1682 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 619967 | 2174 | 2193 | GAGGTGCATTTGTGCCGCTG | eeeeeddddddddddeeeee | 80 | 13643 | 13662 | 1683 |
| 619968 | 2177 | 2196 | TGGGAGGTGCATTTGTGCCG | eeeeeddddddddddeeeee | 53 | 13646 | 13665 | 1684 |
| 619969 | 2180 | 2199 | AACTGGGAGGTGCATTTGTG | eeeeeddddddddddeeeee | 34 | 13649 | 13668 | 1685 |
| 619970 | 2183 | 2202 | GCAAACTGGGAGGTGCATTT | eeeeeddddddddddeeeee | 62 | 13652 | 13671 | 1686 |
| 619971 | 2186 | 2205 | CCAGCAAACTGGGAGGTGCA | eeeeeddddddddddeeeee | 76 | 13655 | 13674 | 1687 |
| 619972 | 2189 | 2208 | AACCCAGCAAACTGGGAGGT | eeeeeddddddddddeeeee | 56 | 13658 | 13677 | 1688 |
| 619973 | 2192 | 2211 | ATAAACCCAGCAAACTGGGA | eeeeeddddddddddeeeee | 56 | 13661 | 13680 | 1689 |
| 619974 | 2195 | 2214 | AAAATAAACCCAGCAAACTG | eeeeeddddddddddeeeee | 33 | 13664 | 13683 | 1690 |
| 619975 | 2198 | 2217 | TCTAAAATAAACCCAGCAAA | eeeeeddddddddddeeeee | 29 | 13667 | 13686 | 1691 |
| 619976 | 2201 | 2220 | TTCTCTAAAATAAACCCAGC | eeeeeddddddddddeeeee | 58 | 13670 | 13689 | 1692 |
| 619977 | 2204 | 2223 | CCATTCTCTAAAATAAACCC | eeeeeddddddddddeeeee | 55 | 13673 | 13692 | 1693 |
| 619978 | 2207 | 2226 | CCCCCATTCTCTAAAATAAA | eeeeeddddddddddeeeee | 49 | 13676 | 13695 | 1694 |
| 619979 | 2210 | 2229 | CCACCCCCATTCTCTAAAAT | eeeeeddddddddddeeeee | 19 | 13679 | 13698 | 1695 |
| 619980 | 2213 | 2232 | TCCCCACCCCCATTCTCTAA | eeeeeddddddddddeeeee | 41 | 13682 | 13701 | 1696 |
| 619981 | 2216 | 2235 | GCCTCCCCACCCCCATTCTC | eeeeeddddddddddeeeee | 53 | 13685 | 13704 | 1697 |
| 619982 | 2219 | 2238 | CTTGCCTCCCCACCCCCATT | eeeeeddddddddddeeeee | 56 | 13688 | 13707 | 1698 |
| 619983 | 2222 | 2241 | GTTCTTGCCTCCCCACCCCC | eeeeeddddddddddeeeee | 72 | 13691 | 13710 | 1699 |
| 619984 | 2225 | 2244 | CTGGTTCTTGCCTCCCCACC | eeeeeddddddddddeeeee | 82 | 13694 | 13713 | 1700 |
| 619985 | 2228 | 2247 | ACACTGGTTCTTGCCTCCCC | eeeeeddddddddddeeeee | 74 | 13697 | 13716 | 1701 |
| 619986 | 2231 | 2250 | TAAACACTGGTTCTTGCCTC | eeeeeddddddddddeeeee | 72 | 13700 | 13719 | 1702 |
| 619987 | 2234 | 2253 | CGCTAAACACTGGTTCTTGC | eeeeeddddddddddeeeee | 93 | 13703 | 13722 | 1703 |
| 619988 | 2237 | 2256 | CCGCGCTAAACACTGGTTCT | eeeeeddddddddddeeeee | 82 | 13706 | 13725 | 1704 |
| 619989 | 2240 | 2259 | GTCCCGCGCTAAACACTGGT | eeeeeddddddddddeeeee | 75 | 13709 | 13728 | 1705 |
| 619990 | 2243 | 2262 | GTAGTCCCGCGCTAAACACT | eeeeeddddddddddeeeee | 73 | 13712 | 13731 | 1706 |
| 619991 | 2246 | 2265 | ACAGTAGTCCCGCGCTAAAC | eeeeeddddddddddeeeee | 64 | 13715 | 13734 | 1707 |
| 619992 | 2249 | 2268 | GGAACAGTAGTCCCGCGCTA | eeeeeddddddddddeeeee | 85 | 13718 | 13737 | 1708 |
| 619993 | 2252 | 2271 | TTTGGAACAGTAGTCCCGCG | eeeeeddddddddddeeeee | 65 | 13721 | 13740 | 1709 |
| 619994 | 2255 | 2274 | CTTTTTGGAACAGTAGTCCC | eeeeeddddddddddeeeee | 69 | 13724 | 13743 | 1710 |
| 619995 | 2258 | 2277 | ATTCTTTTTGGAACAGTAGT | eeeeeddddddddddeeeee | 53 | 13727 | 13746 | 1711 |
| 619996 | 2261 | 2280 | GGAATTCTTTTTGGAACAGT | eeeeeddddddddddeeeee | 70 | 13730 | 13749 | 1712 |
| 619997 | 2264 | 2283 | GTTGGAATTCTTTTTGGAAC | eeeeeddddddddddeeeee | 57 | 13733 | 13752 | 1713 |
| 619998 | 2267 | 2286 | TCGGTTGGAATTCTTTTTGG | eeeeeddddddddddeeeee | 83 | 13736 | 13755 | 1714 |
| 619999 | 2270 | 2289 | TGGTCGGTTGGAATTCTTTT | eeeeeddddddddddeeeee | 74 | 13739 | 13758 | 1715 |
| 620000 | 2273 | 2292 | AGCTGGTCGGTTGGAATTCT | eeeeeddddddddddeeeee | 78 | 13742 | 13761 | 1716 |
| 620001 | 2276 | 2295 | ACAAGCTGGTCGGTTGGAAT | eeeeeddddddddddeeeee | 61 | 13745 | 13764 | 1717 |
| 620002 | 2279 | 2298 | CAAACAAGCTGGTCGGTTGG | eeeeeddddddddddeeeee | 61 | 13748 | 13767 | 1718 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 620003 | 2282 | 2301 | TCACAAACAAGCTGGTCGGT | eeeeddddddddddeeeee | 88 | 13751 | 13770 | 1719 |
| 620004 | 2285 | 2304 | GTTTCACAAACAAGCTGGTC | eeeeddddddddddeeeee | 91 | 13754 | 13773 | 1720 |
| 620005 | 2288 | 2307 | TTTGTTTCACAAACAAGCTG | eeeeddddddddddeeeee | 73 | 13757 | 13776 | 1721 |
| 620006 | 2304 | 2323 | GAAAAGGGAACACTTTTTTG | eeeeddddddddddeeeee | 59 | 13773 | 13792 | 1722 |
| 620007 | 2307 | 2326 | CTTGAAAAGGGAACACTTTT | eeeeddddddddddeeeee | 57 | 13776 | 13795 | 1723 |
| 620008 | 2310 | 2329 | CAACTTGAAAAGGGAACACT | eeeeddddddddddeeeee | 88 | 13779 | 13798 | 1724 |
| 620009 | 2313 | 2332 | TCTCAACTTGAAAAGGGAAC | eeeeddddddddddeeeee | 88 | 13782 | 13801 | 1725 |
| 620010 | 2316 | 2335 | TGTTCTCAACTTGAAAAGGG | eeeeddddddddddeeeee | 93 | 13785 | 13804 | 1726 |
| 620011 | 2319 | 2338 | TTTTGTTCTCAACTTGAAAA | eeeeddddddddddeeeee | 49 | 13788 | 13807 | 1727 |
| 620012 | 2322 | 2341 | AATTTTTGTTCTCAACTTGA | eeeeddddddddddeeeee | 63 | 13791 | 13810 | 1728 |
| 620013 | 2325 | 2344 | CCCAATTTTTGTTCTCAACT | eeeeddddddddddeeeee | 89 | 13794 | 13813 | 1729 |
| 620014 | 2328 | 2347 | AAACCCAATTTTTGTTCTCA | eeeeddddddddddeeeee | 78 | 13797 | 13816 | 1730 |
| 620015 | 2331 | 2350 | TTAAAACCCAATTTTTGTTC | eeeeddddddddddeeeee | 68 | 13800 | 13819 | 1731 |
| 620016 | 2334 | 2353 | ATTTTAAAACCCAATTTTTG | eeeeddddddddddeeeee | 15 | 13803 | 13822 | 1732 |
| 620017 | 2337 | 2356 | TTAATTTTAAAACCCAATTT | eeeeddddddddddeeeee | 15 | 13806 | 13825 | 1733 |
| 620018 | 2353 | 2372 | TGCAAAAATGTATACTTTAA | eeeeddddddddddeeeee | 32 | 13822 | 13841 | 1734 |
| 620019 | 2356 | 2375 | CAATGCAAAAATGTATACTT | eeeeddddddddddeeeee | 64 | 13825 | 13844 | 1735 |
| 620020 | 2359 | 2378 | AGGCAATGCAAAAATGTATA | eeeeddddddddddeeeee | 76 | 13828 | 13847 | 1736 |
| 620021 | 2362 | 2381 | CGAAGGCAATGCAAAAATGT | eeeeddddddddddeeeee | 50 | 13831 | 13850 | 1737 |
| 620022 | 2365 | 2384 | AACCGAAGGCAATGCAAAAA | eeeeddddddddddeeeee | 55 | 13834 | 13853 | 1738 |
| 620023 | 2368 | 2387 | ACAAACCGAAGGCAATGCAA | eeeeddddddddddeeeee | 68 | 13837 | 13856 | 1739 |
| 620024 | 2371 | 2390 | AATACAAACCGAAGGCAATG | eeeeddddddddddeeeee | 68 | 13840 | 13859 | 1740 |
| 620025 | 2374 | 2393 | CTAAATACAAACCGAAGGCA | eeeeddddddddddeeeee | 64 | 13843 | 13862 | 1741 |
| 620026 | 2377 | 2396 | ACACTAAATACAAACCGAAG | eeeeddddddddddeeeee | 49 | 13846 | 13865 | 1742 |
| 620027 | 2380 | 2399 | AAGACACTAAATACAAACCG | eeeeddddddddddeeeee | 53 | 13849 | 13868 | 1743 |
| 620028 | 2383 | 2402 | TTCAAGACACTAAATACAAA | eeeeddddddddddeeeee | 31 | 13852 | 13871 | 1744 |
| 620029 | 2386 | 2405 | ACATTCAAGACACTAAATAC | eeeeddddddddddeeeee | 35 | 13855 | 13874 | 1745 |
| 620030 | 2389 | 2408 | CTTACATTCAAGACACTAAA | eeeeddddddddddeeeee | 57 | 13858 | 13877 | 1746 |
| 620031 | 2392 | 2411 | GTTCTTACATTCAAGACACT | eeeeddddddddddeeeee | 54 | 13861 | 13880 | 1747 |
| 620032 | 2395 | 2414 | CATGTTCTTACATTCAAGAC | eeeeddddddddddeeeee | 39 | 13864 | 13883 | 1748 |
| 620033 | 2398 | 2417 | GGTCATGTTCTTACATTCAA | eeeeddddddddddeeeee | 58 | 13867 | 13886 | 1749 |
| 620034 | 2401 | 2420 | GGAGGTCATGTTCTTACATT | eeeeddddddddddeeeee | 51 | 13870 | 13889 | 1750 |
| 620035 | 2404 | 2423 | CACGGAGGTCATGTTCTTAC | eeeeddddddddddeeeee | 61 | 13873 | 13892 | 1751 |
| 620036 | 2407 | 2426 | CTACACGGAGGTCATGTTCT | eeeeddddddddddeeeee | 53 | 13876 | 13895 | 1752 |
| 620037 | 2410 | 2429 | ACACTACACGGAGGTCATGT | eeeeddddddddddeeeee | 44 | 13879 | 13898 | 1753 |
| 620038 | 2413 | 2432 | CAGACACTACACGGAGGTCA | eeeeddddddddddeeeee | 50 | 13882 | 13901 | 1754 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 620039 | 2416 | 2435 | TTACAGACACTACACGGAGG | eeeeedddddddddddeeeee | 66 | 13885 | 13904 | 1755 |
| 620040 | 2419 | 2438 | GTATTACAGACACTACACGG | eeeeedddddddddddeeeee | 53 | 13888 | 13907 | 1756 |
| 620041 | 2422 | 2441 | AAGGTATTACAGACACTACA | eeeeedddddddddddeeeee | 57 | 13891 | 13910 | 1757 |
| 620042 | 2425 | 2444 | ACTAAGGTATTACAGACACT | eeeeedddddddddddeeeee | 50 | 13894 | 13913 | 1758 |
| 620043 | 2428 | 2447 | AAAACTAAGGTATTACAGAC | eeeeedddddddddddeeeee | 28 | 13897 | 13916 | 1759 |
| 620044 | 2431 | 2450 | GAAAAAACTAAGGTATTACA | eeeeedddddddddddeeeee | 19 | 13900 | 13919 | 1760 |
| 620045 | 2434 | 2453 | GTGGAAAAAACTAAGGTATT | eeeeedddddddddddeeeee | 36 | 13903 | 13922 | 1761 |
| 620046 | 2437 | 2456 | TCTGTGGAAAAAACTAAGGT | eeeeedddddddddddeeeee | 38 | 13906 | 13925 | 1762 |
| 620047 | 2440 | 2459 | GCATCTGTGGAAAAAACTAA | eeeeedddddddddddeeeee | 29 | 13909 | 13928 | 1763 |
| 620048 | 2443 | 2462 | CAAGCATCTGTGGAAAAAAC | eeeeedddddddddddeeeee | 21 | 13912 | 13931 | 1764 |
| 620049 | 2446 | 2465 | TCACAAGCATCTGTGGAAAA | eeeeedddddddddddeeeee | 30 | 13915 | 13934 | 1765 |
| 620050 | 2449 | 2468 | AAATCACAAGCATCTGTGGA | eeeeedddddddddddeeeee | 36 | 13918 | 13937 | 1766 |
| 620051 | 2452 | 2471 | CAAAAATCACAAGCATCTGT | eeeeedddddddddddeeeee | 19 | 13921 | 13940 | 1767 |
| 620052 | 2455 | 2474 | GTTCAAAAATCACAAGCATC | eeeeedddddddddddeeeee | 32 | 13924 | 13943 | 1768 |
| 620053 | 2458 | 2477 | ATTGTTCAAAAATCACAAGC | eeeeedddddddddddeeeee | 16 | 13927 | 13946 | 1769 |
| 620054 | 2461 | 2480 | CGTATTGTTCAAAAATCACA | eeeeedddddddddddeeeee | 30 | 13930 | 13949 | 1770 |
| 620055 | 2479 | 2498 | AGGTGCTTGCATCTTTCACG | eeeeedddddddddddeeeee | 61 | 13948 | 13967 | 1771 |
| 620056 | 2482 | 2501 | TTCAGGTGCTTGCATCTTTC | eeeeedddddddddddeeeee | 58 | 13951 | 13970 | 1772 |
| 620057 | 2485 | 2504 | AAATTCAGGTGCTTGCATCT | eeeeedddddddddddeeeee | 35 | 13954 | 13973 | 1773 |
| 620058 | 2488 | 2507 | CAGAAATTCAGGTGCTTGCA | eeeeedddddddddddeeeee | 58 | 13957 | 13976 | 1774 |
| 620059 | 2491 | 2510 | AAACAGAAATTCAGGTGCTT | eeeeedddddddddddeeeee | 51 | 13960 | 13979 | 1775 |
| 620060 | 2494 | 2513 | TTCAAACAGAAATTCAGGTG | eeeeedddddddddddeeeee | 46 | 13963 | 13982 | 1776 |
| 620061 | 2497 | 2516 | GCATTCAAACAGAAATTCAG | eeeeedddddddddddeeeee | 40 | 13966 | 13985 | 1777 |
| 620062 | 2500 | 2519 | TCCGCATTCAAACAGAAATT | eeeeedddddddddddeeeee | 73 | 13969 | 13988 | 1778 |
| 620063 | 2503 | 2522 | GGTTCCGCATTCAAACAGAA | eeeeedddddddddddeeeee | 54 | 13972 | 13991 | 1779 |
| 620064 | 2506 | 2525 | TATGGTTCCGCATTCAAACA | eeeeedddddddddddeeeee | 44 | 13975 | 13994 | 1780 |
| 620065 | 2509 | 2528 | AGCTATGGTTCCGCATTCAA | eeeeedddddddddddeeeee | 67 | 13978 | 13997 | 1781 |
| 620066 | 2512 | 2531 | ACCAGCTATGGTTCCGCATT | eeeeedddddddddddeeeee | 60 | 13981 | 14000 | 1782 |
| 620067 | 2515 | 2534 | ATAACCAGCTATGGTTCCGC | eeeeedddddddddddeeeee | 70 | 13984 | 14003 | 1783 |
| 620068 | 2518 | 2537 | GAAATAACCAGCTATGGTTC | eeeeedddddddddddeeeee | 50 | 13987 | 14006 | 1784 |
| 620069 | 2521 | 2540 | GGAGAAATAACCAGCTATGG | eeeeedddddddddddeeeee | 50 | 13990 | 14009 | 1785 |
| 620070 | 2524 | 2543 | AAGGGAGAAATAACCAGCTA | eeeeedddddddddddeeeee | 56 | 13993 | 14012 | 1786 |
| 620071 | 2527 | 2546 | CACAAGGGAGAAATAACCAG | eeeeedddddddddddeeeee | 53 | 13996 | 14015 | 1787 |
| 620072 | 2530 | 2549 | TAACACAAGGGAGAAATAAC | eeeeedddddddddddeeeee | 27 | 13999 | 14018 | 1788 |
| 620073 | 2533 | 2552 | TACTAACACAAGGGAGAAAT | eeeeedddddddddddeeeee | 39 | 14002 | 14021 | 1789 |
| 620074 | 2536 | 2555 | TATTACTAACACAAGGGAGA | eeeeedddddddddddeeeee | 52 | 14005 | 14024 | 1790 |

TABLE 10-continued

Inhibition of AGT mRNA by MOE containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 620075 | 2539 | 2558 | GTTTATTACTAACACAAGGG | eeeeeddddddddddeeeee | 56 | 14008 | 14027 | 1791 |
| 620076 | 2558 | 2577 | AGGCTTATTGTGGCAAGACG | eeeeeddddddddddeeeee | 50 | 14027 | 14046 | 1792 |
| 620077 | 2561 | 2580 | TGGAGGCTTATTGTGGCAAG | eeeeeddddddddddeeeee | 38 | 14030 | 14049 | 1793 |
| 620078 | 2564 | 2583 | TTTTGGAGGCTTATTGTGGC | eeeeeddddddddddeeeee | 22 | 14033 | 14052 | 1794 |
| 620079 | 2567 | 2586 | TTTTTTTGGAGGCTTATTGT | eeeeeddddddddddeeeee | 48 | N/A | N/A | 1795 |

Table 11 shows inhibition of AGT mRNA in HepG2 cells cultured at a density of 20,000 cells per well which were transfected using electroporation with 500 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 11

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 62 | 13515 | 13530 | 129 |
| 594621 | 2022 | 2037 | CTGCTGCTGGCCTTTG | kkkddddddddddkkk | 16 | 13491 | 13506 | 162 |
| 594622 | 2027 | 2042 | GTTATCTGCTGCTGGC | kkkddddddddddkkk | 44 | 13496 | 13511 | 163 |
| 594623 | 2032 | 2047 | GGGTTGTTATCTGCTG | kkkddddddddddkkk | 32 | 13501 | 13516 | 164 |
| 594624 | 2046 | 2061 | CGCTGATTTGTCCGGG | kkkddddddddddkkk | 62 | 13515 | 13530 | 129 |
| 594625 | 2047 | 2062 | TCGCTGATTTGTCCGG | kkkddddddddddkkk | 49 | 13516 | 13531 | 165 |
| 594626 | 2049 | 2064 | CATCGCTGATTTGTCC | kkkddddddddddkkk | 36 | 13518 | 13533 | 166 |
| 594627 | 2053 | 2068 | GACACATCGCTGATTT | kkkddddddddddkkk | 0 | 13522 | 13537 | 167 |
| 594628 | 2073 | 2088 | AAAGGTGGGAGACTGG | kkkddddddddddkkk | 51 | 13542 | 13557 | 168 |
| 609078 | 2020 | 2035 | GCTGCTGGCCTTTGCC | kkkddddddddddkkk | 26 | 13489 | 13504 | 173 |
| 609079 | 2021 | 2036 | TGCTGCTGGCCTTTGC | kkkddddddddddkkk | 31 | 13490 | 13505 | 174 |
| 609080 | 2023 | 2038 | TCTGCTGCTGGCCTTT | kkkddddddddddkkk | 41 | 13492 | 13507 | 175 |
| 609081 | 2024 | 2039 | ATCTGCTGCTGGCCTT | kkkddddddddddkkk | 29 | 13493 | 13508 | 176 |
| 609082 | 2025 | 2040 | TATCTGCTGCTGGCCT | kkkddddddddddkkk | 43 | 13494 | 13509 | 177 |
| 609083 | 2026 | 2041 | TTATCTGCTGCTGGCC | kkkddddddddddkkk | 19 | 13495 | 13510 | 178 |
| 609084 | 2028 | 2043 | TGTTATCTGCTGCTGG | kkkddddddddddkkk | 0 | 13497 | 13512 | 179 |
| 609085 | 2029 | 2044 | TTGTTATCTGCTGCTG | kkkddddddddddkkk | 40 | 13498 | 13513 | 180 |
| 609086 | 2030 | 2045 | GTTGTTATCTGCTGCT | kkkddddddddddkkk | 67 | 13499 | 13514 | 181 |
| 609087 | 2031 | 2046 | GGTTGTTATCTGCTGC | kkkddddddddddkkk | 73 | 13500 | 13515 | 182 |
| 609088 | 2048 | 2063 | ATCGCTGATTTGTCCG | kkkddddddddddkkk | 59 | 13517 | 13532 | 183 |

TABLE 11-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 609089 | 2050 | 2065 | ACATCGCTGATTTGTC | kkkddddddddddkkk | 47 | 13519 | 13534 | 184 |
| 609090 | 2051 | 2066 | CACATCGCTGATTTGT | kkkddddddddddkkk | 34 | 13520 | 13535 | 185 |
| 609091 | 2052 | 2067 | ACACATCGCTGATTTG | kkkddddddddddkkk | 59 | 13521 | 13536 | 186 |
| 609092 | 2054 | 2069 | TGACACATCGCTGATT | kkkddddddddddkkk | 27 | 13523 | 13538 | 187 |
| 609093 | 2055 | 2070 | GTGACACATCGCTGAT | kkkddddddddddkkk | 38 | 13524 | 13539 | 188 |
| 609094 | 2056 | 2071 | GGTGACACATCGCTGA | kkkddddddddddkkk | 51 | 13525 | 13540 | 130 |
| 609095 | 2057 | 2072 | GGGTGACACATCGCTG | kkkddddddddddkkk | 59 | 13526 | 13541 | 189 |
| 609096 | 2074 | 2089 | AAAAGGTGGGAGACTG | kkkddddddddddkkk | 20 | 13543 | 13558 | 190 |
| 609097 | 2075 | 2090 | GAAAAGGTGGGAGACT | kkkddddddddddkkk | 19 | 13544 | 13559 | 131 |
| 609098 | 2076 | 2091 | AGAAAAGGTGGGAGAC | kkkddddddddddkkk | 12 | 13545 | 13560 | 191 |
| 622201 | 2020 | 2035 | GCTGCTGGCCTTTGCC | ekkddddddddddkke | 29 | 13489 | 13504 | 173 |
| 622202 | 2021 | 2036 | TGCTGCTGGCCTTTGC | ekkddddddddddkke | 17 | 13490 | 13505 | 174 |
| 622203 | 2022 | 2037 | CTGCTGCTGGCCTTTG | ekkddddddddddkke | 28 | 13491 | 13506 | 162 |
| 622204 | 2023 | 2038 | TCTGCTGCTGGCCTTT | ekkddddddddddkke | 23 | 13492 | 13507 | 175 |
| 622205 | 2024 | 2039 | ATCTGCTGCTGGCCTT | ekkddddddddddkke | 0 | 13493 | 13508 | 176 |
| 622206 | 2025 | 2040 | TATCTGCTGCTGGCCT | ekkddddddddddkke | 22 | 13494 | 13509 | 177 |
| 622207 | 2026 | 2041 | TTATCTGCTGCTGGCC | ekkddddddddddkke | 16 | 13495 | 13510 | 178 |
| 622208 | 2027 | 2042 | GTTATCTGCTGCTGGC | ekkddddddddddkke | 29 | 13496 | 13511 | 163 |
| 622209 | 2028 | 2043 | TGTTATCTGCTGCTGG | ekkddddddddddkke | 37 | 13497 | 13512 | 179 |
| 622210 | 2029 | 2044 | TTGTTATCTGCTGCTG | ekkddddddddddkke | 44 | 13498 | 13513 | 180 |
| 622211 | 2030 | 2045 | GTTGTTATCTGCTGCT | ckkddddddddddkke | 61 | 13499 | 13514 | 181 |
| 622212 | 2031 | 2046 | GGTTGTTATCTGCTGC | ekkddddddddddkke | 51 | 13500 | 13515 | 182 |
| 622213 | 2032 | 2047 | GGGTTGTTATCTGCTG | ekkddddddddddkke | 44 | 13501 | 13516 | 164 |
| 622214 | 2046 | 2061 | CGCTGATTTGTCCGGG | ekkddddddddddkke | 62 | 13515 | 13530 | 129 |
| 622215 | 2047 | 2062 | TCGCTGATTTGTCCGG | ekkddddddddddkke | 47 | 13516 | 13531 | 165 |
| 622216 | 2048 | 2063 | ATCGCTGATTTGTCCG | ekkddddddddddkke | 55 | 13517 | 13532 | 183 |
| 622217 | 2049 | 2064 | CATCGCTGATTTGTCC | ekkddddddddddkke | 11 | 13518 | 13533 | 166 |
| 622218 | 2050 | 2065 | ACATCGCTGATTTGTC | ekkddddddddddkke | 33 | 13519 | 13534 | 184 |
| 622219 | 2051 | 2066 | CACATCGCTGATTTGT | ekkddddddddddkke | 41 | 13520 | 13535 | 185 |
| 622220 | 2052 | 2067 | ACACATCGCTGATTTG | ekkddddddddddkke | 49 | 13521 | 13536 | 186 |
| 622221 | 2053 | 2068 | GACACATCGCTGATTT | ekkddddddddddkke | 52 | 13522 | 13537 | 167 |
| 622222 | 2054 | 2069 | TGACACATCGCTGATT | ekkddddddddddkke | 34 | 13523 | 13538 | 187 |
| 622223 | 2055 | 2070 | GTGACACATCGCTGAT | ekkddddddddddkke | 32 | 13524 | 13539 | 188 |
| 622224 | 2056 | 2071 | GGTGACACATCGCTGA | ekkddddddddddkke | 45 | 13525 | 13540 | 130 |
| 622225 | 2057 | 2072 | GGGTGACACATCGCTG | ekkddddddddddkke | 58 | 13526 | 13541 | 189 |
| 622226 | 2073 | 2088 | AAAGGTGGGAGACTGG | ekkddddddddddkke | 18 | 13542 | 13557 | 168 |

TABLE 11-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 622227 | 2074 | 2089 | AAAAGGTGGGAGACTG | ekkddddddddddkke | 0 | 13543 | 13558 | 190 |
| 622228 | 2075 | 2090 | GAAAAGGTGGGAGACT | ekkddddddddddkke | 0 | 13544 | 13559 | 131 |
| 622229 | 2076 | 2091 | AGAAAAGGTGGGAGAC | ekkddddddddddkke | 0 | 13545 | 13560 | 191 |
| 622230 | 2080 | 2095 | TAGAAGAAAAGGTGGG | ekkddddddddddkke | 12 | 13549 | 13564 | 192 |
| 622231 | 2081 | 2096 | TTAGAAGAAAAGGTGG | ekkddddddddddkke | 22 | 13550 | 13565 | 193 |
| 622232 | 2082 | 2097 | ATTAGAAGAAAAGGTG | ekkddddddddddkke | 7 | 13551 | 13566 | 169 |
| 622233 | 2083 | 2098 | CATTAGAAGAAAAGGT | ekkddddddddddkke | 0 | 13552 | 13567 | 194 |
| 622234 | 2084 | 2099 | TCATTAGAAGAAAAGG | ekkddddddddddkke | 20 | 13553 | 13568 | 195 |
| 622235 | 2085 | 2100 | CTCATTAGAAGAAAAG | ekkddddddddddkke | 4 | 13554 | 13569 | 196 |
| 622236 | 2086 | 2101 | ACTCATTAGAAGAAAA | ekkddddddddddkke | 0 | 13555 | 13570 | 197 |
| 622237 | 2087 | 2102 | GACTCATTAGAAGAAA | ekkddddddddddkke | 22 | 13556 | 13571 | 198 |
| 622238 | 2088 | 2103 | CGACTCATTAGAAGAA | ekkddddddddddkke | 46 | 13557 | 13572 | 132 |
| 622239 | 2089 | 2104 | TCGACTCATTAGAAGA | ekkddddddddddkke | 33 | 13558 | 13573 | 199 |
| 622240 | 2090 | 2105 | GTCGACTCATTAGAAG | ekkddddddddddkke | 6 | 13559 | 13574 | 170 |
| 622241 | 2091 | 2106 | AGTCGACTCATTAGAA | ekkddddddddddkke | 33 | 13560 | 13575 | 200 |
| 622242 | 2092 | 2107 | AAGTCGACTCATTAGA | ekkddddddddddkke | 31 | 13561 | 13576 | 201 |
| 622243 | 2093 | 2108 | AAAGTCGACTCATTAG | ekkddddddddddkke | 16 | 13562 | 13577 | 202 |
| 622244 | 2094 | 2109 | CAAAGTCGACTCATTA | ekkddddddddddkke | 28 | 13563 | 13578 | 203 |
| 622245 | 2095 | 2110 | TCAAAGTCGACTCATT | ekkddddddddddkke | 16 | 13564 | 13579 | 171 |
| 622246 | 2096 | 2111 | CTCAAAGTCGACTCAT | ekkddddddddddkke | 25 | 13565 | 13580 | 204 |
| 622247 | 2097 | 2112 | GCTCAAAGTCGACTCA | ekkddddddddddkke | 43 | 13566 | 13581 | 205 |
| 622248 | 2098 | 2113 | AGCTCAAAGTCGACTC | ekkddddddddddkke | 39 | 13567 | 13582 | 206 |
| 622249 | 2099 | 2114 | CAGCTCAAAGTCGACT | ekkddddddddddkke | 17 | 13568 | 13583 | 172 |

Table 12 shows the percent inhibition of AGT mRNA by antisense oligonucleotides. Cultured HepG2 cells at a density of about 20,000 cells per well were transfected using electroporation with 3,000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 12

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 88 | 13515 | 13530 | 129 |
| 610006 | 2023 | 2042 | GTTATCTGCTGCTGGCCTTT | eeeeddddddddddeeee | 60 | 13492 | 13511 | 230 |
| 610009 | 2026 | 2045 | GTTGTTATCTGCTGCTGGCC | eeeeddddddddddeeee | 38 | 13495 | 13514 | 233 |

TABLE 12-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 610010 | 2027 | 2046 | GGTTGTTATCTGCTGCTGGC | eeeeddddddddddeeeee | 66 | 13496 | 13515 | 234 |
| 610015 | 2049 | 2068 | GACACATCGCTGATTTGTCC | eeeeddddddddddeeeee | 72 | 13518 | 13537 | 239 |
| 610015 | 2049 | 2068 | GACACATCGCTGATTTGTCC | eeeeddddddddddeeeee | 25 | 13518 | 13537 | 239 |
| 654354 | 636 | 655 | ACTCTCATTGTGGATGACGA | eeeeddddddddddeeeee | 41 | 5853 | 5872 | 1796 |
| 654355 | 640 | 659 | AGGTACTCTCATTGTGGATG | eeeeddddddddddeeeee | 26 | 5857 | 5876 | 1797 |
| 654356 | 642 | 661 | ACAGGTACTCTCATTGTGGA | eeeeddddddddddeeeee | 16 | 5859 | 5878 | 1798 |
| 654357 | 646 | 665 | GCTCACAGGTACTCTCATTG | eeeeddddddddddeeeee | 18 | 5863 | 5882 | 1799 |
| 654358 | 757 | 776 | GCACCAGCTGGTCCTGTAGG | eeeeddddddddddeeeee | 10 | 5974 | 5993 | 1800 |
| 654359 | 759 | 778 | TAGCACCAGCTGGTCCTGTA | eeeeddddddddddeeeee | 24 | 5976 | 5995 | 1801 |
| 654360 | 760 | 779 | CTAGCACCAGCTGGTCCTGT | eeeeddddddddddeeeee | 13 | 5977 | 5996 | 1802 |
| 654361 | 763 | 782 | CGACTAGCACCAGCTGGTCC | eeeeddddddddddeeeee | 1 | 5980 | 5999 | 1803 |
| 654362 | 765 | 784 | AGCGACTAGCACCAGCTGGT | eeeeddddddddddeeeee | 28 | 5982 | 6001 | 1804 |
| 654363 | 769 | 788 | TTGCAGCGACTAGCACCAGC | eeeeddddddddddeeeee | 18 | 5986 | 6005 | 1805 |
| 654364 | 771 | 790 | TTTTGCAGCGACTAGCACCA | eeeeddddddddddeeeee | 9 | 5988 | 6007 | 1806 |
| 654365 | 775 | 794 | CAAGTTTTGCAGCGACTAGC | eeeeddddddddddeeeee | 0 | 5992 | 6011 | 1807 |
| 654366 | 1267 | 1286 | CTGTCACAGCCTGCATGAAC | eeeeddddddddddeeeee | 15 | 6484 | 6503 | 1808 |
| 654367 | 1269 | 1288 | TCCTGTCACAGCCTGCATGA | eeeeddddddddddeeeee | 34 | 6486 | 6505 | 1809 |
| 654368 | 1270 | 1289 | ATCCTGTCACAGCCTGCATG | eeeeddddddddddeeeee | 34 | 6487 | 6506 | 1810 |
| 654369 | 1273 | 1292 | TCCATCCTGTCACAGCCTGC | eeeeddddddddddeeeee | 32 | 6490 | 6509 | 1811 |
| 654370 | 1275 | 1294 | CTTCCATCCTGTCACAGCCT | eeeeddddddddddeeeee | 50 | 6492 | 6511 | 1812 |
| 654371 | 1460 | 1479 | TCACTCCAGTGCTGGAAGGT | eeeeddddddddddeeeee | 0 | 10471 | 10490 | 1813 |
| 654372 | 1462 | 1481 | TGTCACTCCAGTGCTGGAAG | eeeeddddddddddeeeee | 18 | 10473 | 10492 | 1814 |
| 654373 | 1463 | 1482 | ATGTCACTCCAGTGCTGGAA | eeeeddddddddddeeeee | 6 | 10474 | 10493 | 1815 |
| 654374 | 1466 | 1485 | TGGATGTCACTCCAGTGCTG | eeeeddddddddddeeeee | 26 | 10477 | 10496 | 1816 |
| 654375 | 1468 | 1487 | CCTGGATGTCACTCCAGTGC | eeeeddddddddddeeeee | 20 | 10479 | 10498 | 1817 |
| 654376 | 2115 | 2134 | AAGGAGAAACGGCTGCTTTC | eeeeddddddddddeeeee | 19 | 13584 | 13603 | 1818 |
| 654377 | 2116 | 2135 | CAAGGAGAAACGGCTGCTTT | eeeeddddddddddeeeee | 40 | 13585 | 13604 | 1819 |
| 654378 | 2118 | 2137 | ACCAAGGAGAAACGGCTGCT | eeeeddddddddddeeeee | 48 | 13587 | 13606 | 1820 |
| 654379 | 2119 | 2138 | GACCAAGGAGAAACGGCTGC | eeeeddddddddddeeeee | 57 | 13588 | 13607 | 1821 |
| 654380 | 2121 | 2140 | TAGACCAAGGAGAAACGGCT | eeeeddddddddddeeeee | 46 | 13590 | 13609 | 1822 |
| 654381 | 2122 | 2141 | TTAGACCAAGGAGAAACGGC | eeeeddddddddddeeeee | 32 | 13591 | 13610 | 1823 |
| 654382 | 2124 | 2143 | ACTTAGACCAAGGAGAAACG | eeeeddddddddddeeeee | 42 | 13593 | 13612 | 1824 |
| 654383 | 2125 | 2144 | CACTTAGACCAAGGAGAAAC | eeeeddddddddddeeeee | 29 | 13594 | 13613 | 1825 |
| 654384 | 2127 | 2146 | CACACTTAGACCAAGGAGAA | eeeeddddddddddeeeee | 21 | 13596 | 13615 | 1826 |
| 654385 | 2128 | 2147 | GCACACTTAGACCAAGGAGA | eeeeddddddddddeeeee | 65 | 13597 | 13616 | 1827 |
| 654386 | 2130 | 2149 | CAGCACACTTAGACCAAGGA | eeeeddddddddddeeeee | 39 | 13599 | 13618 | 1828 |
| 654387 | 2131 | 2150 | GCAGCACACTTAGACCAAGG | eeeeddddddddddeeeee | 39 | 13600 | 13619 | 1829 |

TABLE 12-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 654388 | 2133 | 2152 | ATGCAGCACACTTAGACCAA | eeeeddddddddddeeeee | 27 | 13602 | 13621 | 1830 |
| 654389 | 2134 | 2153 | CATGCAGCACACTTAGACCA | eeeeddddddddddeeeee | 26 | 13603 | 13622 | 1831 |
| 654390 | 2136 | 2155 | TCCATGCAGCACACTTAGAC | eeeeddddddddddeeeee | 2 | 13605 | 13624 | 1832 |
| 654391 | 2137 | 2156 | CTCCATGCAGCACACTTAGA | eeeeddddddddddeeeee | 48 | 13606 | 13625 | 1833 |
| 654392 | 2139 | 2158 | CACTCCATGCAGCACACTTA | eeeeddddddddddeeeee | 60 | 13608 | 13627 | 1834 |
| 654393 | 2140 | 2159 | TCACTCCATGCAGCACACTT | eeeeddddddddddeeeee | 45 | 13609 | 13628 | 1835 |
| 654394 | 2142 | 2161 | GCTCACTCCATGCAGCACAC | eeeeddddddddddeeeee | 72 | 13611 | 13630 | 1836 |
| 654395 | 2160 | 2179 | CCGCTGCAGGCTTCTACTGC | eeeeddddddddddeeeee | 34 | 13629 | 13648 | 1837 |
| 654396 | 2161 | 2180 | GCCGCTGCAGGCTTCTACTG | eeeeddddddddddeeeee | 32 | 13630 | 13649 | 1838 |
| 654397 | 2163 | 2182 | GTGCCGCTGCAGGCTTCTAC | eeeeddddddddddeeeee | 38 | 13632 | 13651 | 1839 |
| 654398 | 2164 | 2183 | TGTGCCGCTGCAGGCTTCTA | eeeeddddddddddeeeee | 17 | 13633 | 13652 | 1840 |
| 654399 | 2166 | 2185 | TTTGTGCCGCTGCAGGCTTC | eeeeddddddddddeeeee | 16 | 13635 | 13654 | 1841 |
| 654400 | 2167 | 2186 | ATTTGTGCCGCTGCAGGCTT | eeeeddddddddddeeeee | 27 | 13636 | 13655 | 1842 |
| 654401 | 2169 | 2188 | GCATTTGTGCCGCTGCAGGC | eeeeddddddddddeeeee | 75 | 13638 | 13657 | 1843 |
| 654402 | 2170 | 2189 | TGCATTTGTGCCGCTGCAGG | eeeeddddddddddeeeee | 64 | 13639 | 13658 | 1844 |
| 654403 | 2172 | 2191 | GGTGCATTTGTGCCGCTGCA | eeeeddddddddddeeeee | 64 | 13641 | 13660 | 1845 |
| 654404 | 2173 | 2192 | AGGTGCATTTGTGCCGCTGC | eeeeddddddddddeeeee | 68 | 13642 | 13661 | 1846 |
| 654405 | 2175 | 2194 | GGAGGTGCATTTGTGCCGCT | eeeeddddddddddeeeee | 42 | 13644 | 13663 | 1847 |
| 654406 | 2176 | 2195 | GGGAGGTGCATTTGTGCCGC | eeeeddddddddddeeeee | 36 | 13645 | 13664 | 1848 |
| 654407 | 2178 | 2197 | CTGGGAGGTGCATTTGTGCC | eeeeddddddddddeeeee | 26 | 13647 | 13666 | 1849 |
| 654408 | 2179 | 2198 | ACTGGGAGGTGCATTTGTGC | eeeeddddddddddeeeee | 10 | 13648 | 13667 | 1850 |
| 654409 | 2181 | 2200 | AAACTGGGAGGTGCATTTGT | eeeeddddddddddeeeee | 15 | 13650 | 13669 | 1851 |
| 654410 | 2182 | 2201 | CAAACTGGGAGGTGCATTTG | eeeeddddddddddeeeee | 7 | 13651 | 13670 | 1852 |
| 654411 | 2184 | 2203 | AGCAAACTGGGAGGTGCATT | eeeeddddddddddeeeee | 34 | 13653 | 13672 | 1853 |
| 654412 | 2185 | 2204 | CAGCAAACTGGGAGGTGCAT | eeeeddddddddddeeeee | 33 | 13654 | 13673 | 1854 |
| 654413 | 2187 | 2206 | CCCAGCAAACTGGGAGGTGC | eeeeddddddddddeeeee | 57 | 13656 | 13675 | 1855 |
| 654414 | 2188 | 2207 | ACCCAGCAAACTGGGAGGTG | eeeeddddddddddeeeee | 53 | 13657 | 13676 | 1856 |
| 654415 | 2193 | 2212 | AATAAACCCAGCAAACTGGG | eeeeddddddddddeeeee | 17 | 13662 | 13681 | 1857 |
| 654416 | 2194 | 2213 | AAATAAACCCAGCAAACTGG | eeeeddddddddddeeeee | 20 | 13663 | 13682 | 1858 |
| 654417 | 2196 | 2215 | TAAAATAAACCCAGCAAACT | eeeeddddddddddeeeee | 13 | 13665 | 13684 | 1859 |
| 654418 | 2197 | 2216 | CTAAAATAAACCCAGCAAAC | eeeeddddddddddeeeee | 2 | 13666 | 13685 | 1860 |
| 654419 | 2199 | 2218 | CTCTAAAATAAACCCAGCAA | eeeeddddddddddeeeee | 12 | 13668 | 13687 | 1861 |
| 654420 | 2200 | 2219 | TCTCTAAAATAAACCCAGCA | eeeeddddddddddeeeee | 47 | 13669 | 13688 | 1862 |
| 654421 | 2202 | 2221 | ATTCTCTAAAATAAACCCAG | eeeeddddddddddeeeee | 23 | 13671 | 13690 | 1863 |
| 654422 | 2203 | 2222 | CATTCTCTAAAATAAACCCA | eeeeddddddddddeeeee | 22 | 13672 | 13691 | 1864 |
| 654423 | 2205 | 2224 | CCCATTCTCTAAAATAAACC | eeeeddddddddddeeeee | 12 | 13674 | 13693 | 1865 |

TABLE 12-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 654424 | 2206 | 2225 | CCCCATTCTCTAAAATAAAC | eeeeddddddddddeeeee | 20 | 13675 | 13694 | 1866 |
| 654425 | 2208 | 2227 | ACCCCATTCTCTAAAATAA | eeeeddddddddddeeeee | 21 | 13677 | 13696 | 1867 |
| 654426 | 2209 | 2228 | CACCCCATTCTCTAAAATA | eeeeddddddddddeeeee | 32 | 13678 | 13697 | 1868 |
| 654427 | 2211 | 2230 | CCCACCCCATTCTCTAAAA | eeeeddddddddddeeeee | 18 | 13680 | 13699 | 1869 |

Table 13 shows inhibition of AGT mRNA in HepG2 cells cultured at a density of 20,000 cells per well which were transfected using electroporation with 4000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 13

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 568637 | 2046 | 2061 | CGCTGATTTGTCCGGG | eekddddddddddkke | 95 | 13515 | 13530 | 129 |
| 568637 | 2046 | 2061 | CGCTGATTTGTCCGGG | eekddddddddddkke | 98 | 13515 | 13530 | 129 |
| 610012 | 2046 | 2065 | ACATCGCTGATTTGTCCGGG | eeeeddddddddddeeeee | 74 | 13515 | 13534 | 236 |
| 610013 | 2047 | 2066 | CACATCGCTGATTTGTCCGG | eeeeddddddddddeeeee | 76 | 13516 | 13535 | 237 |
| 610014 | 2048 | 2067 | ACACATCGCTGATTTGTCCG | eeeeddddddddddeeeee | 85 | 13517 | 13536 | 238 |
| 610015 | 2049 | 2068 | GACACATCGCTGATTTGTCC | eeeeddddddddddeeeee | 85 | 13518 | 13537 | 239 |
| 610015 | 2049 | 2068 | GACACATCGCTGATTTGTCC | eeeeddddddddddeeeee | 3 | 13518 | 13537 | 239 |
| 610015 | 2049 | 2068 | GACACATCGCTGATTTGTCC | eeeeddddddddddeeeee | 17 | 13518 | 13537 | 239 |
| 610043 | 2096 | 2115 | CCAGCTCAAAGTCGACTCAT | eeeeddddddddddeeeee | 87 | 13565 | 13584 | 267 |
| 619998 | 2267 | 2286 | TCGGTTGGAATTCTTTTTGG | eeeeddddddddddeeeee | 80 | 13736 | 13755 | 1714 |
| 620000 | 2273 | 2292 | AGCTGGTCGGTTGGAATTCT | eeeeddddddddddeeeee | 69 | 13742 | 13761 | 1716 |
| 654428 | 2212 | 2231 | CCCCACCCCATTCTCTAAA | eeeeddddddddddeeeee | 49 | 13681 | 13700 | 1870 |
| 654429 | 2214 | 2233 | CTCCCCACCCCATTCTCTA | eeeeddddddddddeeeee | 58 | 13683 | 13702 | 1871 |
| 654430 | 2217 | 2236 | TGCCTCCCCACCCCATTCT | eeeeddddddddddeeeee | 61 | 13686 | 13705 | 1872 |
| 654431 | 2218 | 2237 | TTGCCTCCCCACCCCATTC | eeeeddddddddddeeeee | 51 | 13687 | 13706 | 1873 |
| 654432 | 2220 | 2239 | TCTTGCCTCCCCACCCCAT | eeeeddddddddddeeeee | 67 | 13689 | 13708 | 1874 |
| 654433 | 2223 | 2242 | GGTTCTTGCCTCCCCACCCC | eeeeddddddddddeeeee | 84 | 13692 | 13711 | 1875 |
| 654434 | 2224 | 2243 | TGGTTCTTGCCTCCCCACCC | eeeeddddddddddeeeee | 83 | 13693 | 13712 | 1876 |
| 654435 | 2226 | 2245 | ACTGGTTCTTGCCTCCCCAC | eeeeddddddddddeeeee | 75 | 13695 | 13714 | 1877 |
| 654436 | 2227 | 2246 | CACTGGTTCTTGCCTCCCCA | eeeeddddddddddeeeee | 84 | 13696 | 13715 | 1878 |
| 654437 | 2229 | 2248 | AACACTGGTTCTTGCCTCCC | eeeeddddddddddeeeee | 76 | 13698 | 13717 | 1879 |
| 654438 | 2230 | 2249 | AAACACTGGTTCTTGCCTCC | eeeeddddddddddeeeee | 75 | 13699 | 13718 | 1880 |
| 654439 | 2232 | 2251 | CTAAACACTGGTTCTTGCCT | eeeeddddddddddeeeee | 70 | 13701 | 13720 | 1881 |

TABLE 13-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654440 | 2233 | 2252 | GCTAAACACTGGTTCTTGCC | eeeeddddddddddeeeee | 79 | 13702 | 13721 | 1882 |
| 654441 | 2235 | 2254 | GCGCTAAACACTGGTTCTTG | eeeeddddddddddeeeee | 79 | 13704 | 13723 | 1883 |
| 654442 | 2236 | 2255 | CGCGCTAAACACTGGTTCTT | eeeeddddddddddeeeee | 81 | 13705 | 13724 | 1884 |
| 654443 | 2238 | 2257 | CCCGCGCTAAACACTGGTTC | eeeeddddddddddeeeee | 80 | 13707 | 13726 | 1885 |
| 654444 | 2239 | 2258 | TCCCGCGCTAAACACTGGTT | eeeeddddddddddeeeee | 89 | 13708 | 13727 | 1886 |
| 654445 | 2241 | 2260 | AGTCCCGCGCTAAACACTGG | eeeeddddddddddeeeee | 75 | 13710 | 13729 | 1887 |
| 654446 | 2242 | 2261 | TAGTCCCGCGCTAAACACTG | eeeeddddddddddeeeee | 73 | 13711 | 13730 | 1888 |
| 654447 | 2244 | 2263 | AGTAGTCCCGCGCTAAACAC | eeeeddddddddddeeeee | 59 | 13713 | 13732 | 1889 |
| 654448 | 2245 | 2264 | CAGTAGTCCCGCGCTAAACA | eeeeddddddddddeeeee | 67 | 13714 | 13733 | 1890 |
| 654449 | 2247 | 2266 | AACAGTAGTCCCGCGCTAAA | eeeeddddddddddeeeee | 60 | 13716 | 13735 | 1891 |
| 654450 | 2248 | 2267 | GAACAGTAGTCCCGCGCTAA | eeeeddddddddddeeeee | 69 | 13717 | 13736 | 1892 |
| 654451 | 2250 | 2269 | TGGAACAGTAGTCCCGCGCT | eeeeddddddddddeeeee | 87 | 13719 | 13738 | 1893 |
| 654452 | 2251 | 2270 | TTGGAACAGTAGTCCCGCGC | eeeeddddddddddeeeee | 87 | 13720 | 13739 | 1894 |
| 654453 | 2253 | 2272 | TTTTGGAACAGTAGTCCCGC | eeeeddddddddddeeeee | 73 | 13722 | 13741 | 1895 |
| 654454 | 2254 | 2273 | TTTTTGGAACAGTAGTCCCG | eeeeddddddddddeeeee | 51 | 13723 | 13742 | 1896 |
| 654455 | 2256 | 2275 | TCTTTTTGGAACAGTAGTCC | eeeeddddddddddeeeee | 74 | 13725 | 13744 | 1897 |
| 654456 | 2257 | 2276 | TTCTTTTTGGAACAGTAGTC | eeeeddddddddddeeeee | 66 | 13726 | 13745 | 1898 |
| 654457 | 2259 | 2278 | AATTCTTTTTGGAACAGTAG | eeeeddddddddddeeeee | 46 | 13728 | 13747 | 1899 |
| 654458 | 2260 | 2279 | GAATTCTTTTTGGAACAGTA | eeeeddddddddddeeeee | 74 | 13729 | 13748 | 1900 |
| 654459 | 2262 | 2281 | TGGAATTCTTTTTGGAACAG | eeeeddddddddddeeeee | 41 | 13731 | 13750 | 1901 |
| 654460 | 2263 | 2282 | TTGGAATTCTTTTTGGAACA | eeeeddddddddddeeeee | 34 | 13732 | 13751 | 1902 |
| 654461 | 2265 | 2284 | GGTTGGAATTCTTTTTGGAA | eeeeddddddddddeeeee | 58 | 13734 | 13753 | 1903 |
| 654462 | 2266 | 2285 | CGGTTGGAATTCTTTTTGGA | eeeeddddddddddeeeee | 77 | 13735 | 13754 | 1904 |
| 654463 | 2268 | 2287 | GTCGGTTGGAATTCTTTTTG | eeeeddddddddddeeeee | 74 | 13737 | 13756 | 1905 |
| 654464 | 2269 | 2288 | GGTCGGTTGGAATTCTTTTT | eeeeddddddddddeeeee | 81 | 13738 | 13757 | 1906 |
| 654465 | 2271 | 2290 | CTGGTCGGTTGGAATTCTTT | eeeeddddddddddeeeee | 78 | 13740 | 13759 | 1907 |
| 654466 | 2272 | 2291 | GCTGGTCGGTTGGAATTCTT | eeeeddddddddddeeeee | 81 | 13741 | 13760 | 1908 |
| 654467 | 2274 | 2293 | AAGCTGGTCGGTTGGAATTC | eeeeddddddddddeeeee | 61 | 13743 | 13762 | 1909 |
| 654468 | 2275 | 2294 | CAAGCTGGTCGGTTGGAATT | eeeeddddddddddeeeee | 62 | 13744 | 13763 | 1910 |
| 654469 | 2277 | 2296 | AACAAGCTGGTCGGTTGGAA | eeeeddddddddddeeeee | 70 | 13746 | 13765 | 1911 |
| 654470 | 2278 | 2297 | AAACAAGCTGGTCGGTTGGA | eeeeddddddddddeeeee | 62 | 13747 | 13766 | 1912 |
| 654471 | 2280 | 2299 | ACAAACAAGCTGGTCGGTTG | eeeeddddddddddeeeee | 62 | 13749 | 13768 | 1913 |
| 654472 | 2281 | 2300 | CACAAACAAGCTGGTCGGTT | eeeeddddddddddeeeee | 88 | 13750 | 13769 | 1914 |
| 654473 | 2283 | 2302 | TTCACAAACAAGCTGGTCGG | eeeeddddddddddeeeee | 76 | 13752 | 13771 | 1915 |
| 654474 | 2284 | 2303 | TTTCACAAACAAGCTGGTCG | eeeeddddddddddeeeee | 77 | 13753 | 13772 | 1916 |
| 654475 | 2286 | 2305 | TGTTTCACAAACAAGCTGGT | eeeeddddddddddeeeee | 80 | 13755 | 13774 | 1917 |

TABLE 13-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 654476 | 2287 | 2306 | TTGTTTCACAAACAAGCTGG | eeeeddddddddddeeeee | 83 | 13756 | 13775 | 1918 |
| 654477 | 2289 | 2308 | TTTTGTTTCACAAACAAGCT | eeeeddddddddddeeeee | 66 | 13758 | 13777 | 1919 |
| 654478 | 2290 | 2309 | TTTTTGTTTCACAAACAAGC | eeeeddddddddddeeeee | 70 | 13759 | 13778 | 1920 |
| 654479 | 2309 | 2328 | AACTTGAAAAGGGAACACTT | eeeeddddddddddeeeee | 69 | 13778 | 13797 | 1921 |
| 654480 | 2311 | 2330 | TCAACTTGAAAAGGGAACAC | eeeeddddddddddeeeee | 84 | 13780 | 13799 | 1922 |
| 654481 | 2312 | 2331 | CTCAACTTGAAAAGGGAACA | eeeeddddddddddeeeee | 90 | 13781 | 13800 | 1923 |
| 654482 | 2314 | 2333 | TTCTCAACTTGAAAAGGGAA | eeeeddddddddddeeeee | 67 | 13783 | 13802 | 1924 |
| 654483 | 2315 | 2334 | GTTCTCAACTTGAAAAGGGA | eeeeddddddddddeeeee | 92 | 13784 | 13803 | 1925 |
| 654484 | 2317 | 2336 | TTGTTCTCAACTTGAAAAGG | eeeeddddddddddeeeee | 82 | 13786 | 13805 | 1926 |
| 654485 | 2318 | 2337 | TTTGTTCTCAACTTGAAAAG | eeeeddddddddddeeeee | 61 | 13787 | 13806 | 1927 |
| 654486 | 2320 | 2339 | TTTTTGTTCTCAACTTGAAA | eeeeddddddddddeeeee | 35 | 13789 | 13808 | 1928 |
| 654487 | 2321 | 2340 | ATTTTTGTTCTCAACTTGAA | eeeeddddddddddeeeee | 44 | 13790 | 13809 | 1929 |
| 654488 | 2323 | 2342 | CAATTTTTGTTCTCAACTTG | eeeeddddddddddeeeee | 54 | 13792 | 13811 | 1930 |
| 654489 | 2324 | 2343 | CCAATTTTTGTTCTCAACTT | eeeeddddddddddeeeee | 79 | 13793 | 13812 | 1931 |
| 654490 | 2326 | 2345 | ACCCAATTTTTGTTCTCAAC | eeeeddddddddddeeeee | 85 | 13795 | 13814 | 1932 |
| 654491 | 2327 | 2346 | AACCCAATTTTTGTTCTCAA | eeeeddddddddddeeeee | 82 | 13796 | 13815 | 1933 |
| 654492 | 2330 | 2349 | TAAAACCCAATTTTTGTTCT | eeeeddddddddddeeeee | 52 | 13799 | 13818 | 1934 |
| 654493 | 2332 | 2351 | TTTAAAACCCAATTTTTGTT | eeeeddddddddddeeeee | 13 | 13801 | 13820 | 1935 |
| 654494 | 2355 | 2374 | AATGCAAAAATGTATACTTT | eeeeddddddddddeeeee | 53 | 13824 | 13843 | 1936 |
| 654495 | 2357 | 2376 | GCAATGCAAAAATGTATACT | eeeeddddddddddeeeee | 73 | 13826 | 13845 | 1937 |
| 654496 | 2360 | 2379 | AAGGCAATGCAAAAATGTAT | eeeeddddddddddeeeee | 56 | 13829 | 13848 | 1938 |
| 654497 | 2361 | 2380 | GAAGGCAATGCAAAAATGTA | eeeeddddddddddeeeee | 70 | 13830 | 13849 | 1939 |
| 654498 | 2363 | 2382 | CCGAAGGCAATGCAAAAATG | eeeeddddddddddeeeee | 60 | 13832 | 13851 | 1940 |
| 654521 | 495 | 511 | CATACCCTTCTGCTGTA | eeeddddddddddeeee | 46 | N/A | N/A | 1941 |
| 654522 | 498 | 514 | CCGCATACCCTTCTGCT | eeeddddddddddeeee | 44 | N/A | N/A | 1942 |
| 654523 | 504 | 520 | TCGCTTCCGCATACCCT | eeeddddddddddeeee | 69 | 5721 | 5737 | 1943 |
| 654524 | 507 | 523 | TGCTCGCTTCCGCATAC | eeeddddddddddeeee | 58 | 5724 | 5740 | 1944 |
| 654525 | 636 | 652 | CTCATTGTGGATGACGA | eeeddddddddddeeee | 53 | 5853 | 5869 | 1945 |
| 654526 | 639 | 655 | ACTCTCATTGTGGATGA | eeeddddddddddeeee | 48 | 5856 | 5872 | 1946 |
| 654527 | 654 | 670 | CAGCTGCTCACAGGTAC | eeeddddddddddeeee | 47 | 5871 | 5887 | 1947 |
| 654528 | 768 | 784 | AGCGACTAGCACCAGCT | eeeddddddddddeeee | 56 | 5985 | 6001 | 1948 |
| 654529 | 1266 | 1282 | CACAGCCTGCATGAACC | eeeddddddddddeeee | 48 | 6483 | 6499 | 1949 |
| 654530 | 1272 | 1288 | TCCTGTCACAGCCTGCA | eeeddddddddddeeee | 68 | 6489 | 6505 | 1950 |
| 654531 | 1275 | 1291 | CCATCCTGTCACAGCCT | eeeddddddddddeeee | 65 | 6492 | 6508 | 1951 |
| 654532 | 1456 | 1472 | AGTGCTGGAAGGTGCCC | eeeddddddddddeeee | 41 | 10467 | 10483 | 1952 |
| 654533 | 1531 | 1547 | GCTGGATCAGCAGCAGG | eeeddddddddddeeee | 61 | 10542 | 10558 | 1953 |
| 654534 | 1751 | 1767 | CTGATGCGGTCATTGCT | eeeddddddddddeeee | 52 | 12357 | 12373 | 1954 |

TABLE 13-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID: 2 Stop Site | SEQ ID NO |
|---|---|---|---|---|---|---|---|---|
| 654535 | 1808 | 1824 | GGCTCTCTCTCATCCGC | eeedddddddddeeee | 74 | 13277 | 13293 | 1955 |
| 654536 | 1811 | 1827 | GTGGGCTCTCTCTCATC | eeedddddddddeeee | 60 | 13280 | 13296 | 1956 |
| 654537 | 1983 | 1999 | CCTTGCCAGGCACTGTG | eeedddddddddeeee | 69 | 13452 | 13468 | 1957 |
| 654538 | 1984 | 2000 | GCCTTGCCAGGCACTGT | eeedddddddddeeee | 77 | 13453 | 13469 | 1958 |
| 654539 | 1986 | 2002 | AGGCCTTGCCAGGCACT | eeedddddddddeeee | 78 | 13455 | 13471 | 1959 |
| 654540 | 1987 | 2003 | GAGGCCTTGCCAGGCAC | eeedddddddddeeee | 44 | 13456 | 13472 | 1960 |
| 654541 | 2019 | 2035 | GCTGCTGGCCTTTGCCT | eeedddddddddeeee | 54 | 13488 | 13504 | 1961 |
| 654542 | 2024 | 2040 | TATCTGCTGCTGGCCTT | eeedddddddddeeee | 59 | 13493 | 13509 | 1962 |
| 654543 | 2025 | 2041 | TTATCTGCTGCTGGCCT | eeedddddddddeeee | 4 | 13494 | 13510 | 1963 |
| 654544 | 2027 | 2043 | TGTTATCTGCTGCTGGC | eeedddddddddeeee | 67 | 13496 | 13512 | 1964 |
| 654545 | 2028 | 2044 | TTGTTATCTGCTGCTGG | eeedddddddddeeee | 56 | 13497 | 13513 | 1965 |
| 654546 | 2029 | 2045 | GTTGTTATCTGCTGCTG | eeedddddddddeeee | 77 | 13498 | 13514 | 1966 |
| 654547 | 2047 | 2063 | ATCGCTGATTTGTCCGG | eeedddddddddeeee | 80 | 13516 | 13532 | 1967 |
| 654548 | 2048 | 2064 | CATCGCTGATTTGTCCG | eeedddddddddeeee | 59 | 13517 | 13533 | 1968 |
| 654549 | 2049 | 2065 | ACATCGCTGATTTGTCC | eeedddddddddeeee | 65 | 13518 | 13534 | 1969 |
| 654550 | 2050 | 2066 | CACATCGCTGATTTGTC | eeedddddddddeeee | 81 | 13519 | 13535 | 1970 |
| 654551 | 2051 | 2067 | ACACATCGCTGATTTGT | eeedddddddddeeee | 74 | 13520 | 13536 | 1971 |
| 654552 | 2053 | 2069 | TGACACATCGCTGATTT | eeedddddddddeeee | 53 | 13522 | 13538 | 1972 |
| 654553 | 2054 | 2070 | GTGACACATCGCTGATT | eeedddddddddeeee | 74 | 13523 | 13539 | 1973 |
| 654554 | 2082 | 2098 | CATTAGAAGAAAAGGTG | eeedddddddddeeee | 18 | 13551 | 13567 | 1974 |
| 654555 | 2083 | 2099 | TCATTAGAAGAAAAGGT | eeedddddddddeeee | 23 | 13552 | 13568 | 1975 |
| 654556 | 2087 | 2103 | CGACTCATTAGAAGAAA | eeedddddddddeeee | 51 | 13556 | 13572 | 1976 |
| 654557 | 2096 | 2112 | GCTCAAAGTCGACTCAT | eeedddddddddeeee | 70 | 13565 | 13581 | 1977 |
| 654558 | 2097 | 2113 | AGCTCAAAGTCGACTCA | eeedddddddddeeee | 82 | 13566 | 13582 | 1978 |
| 654559 | 2098 | 2114 | CAGCTCAAAGTCGACTC | eeedddddddddeeee | 88 | 13567 | 13583 | 1979 |
| 654560 | 2099 | 2115 | CCAGCTCAAAGTCGACT | eeedddddddddeeee | 84 | 13568 | 13584 | 1980 |
| 654561 | 2100 | 2116 | TCCAGCTCAAAGTCGAC | eeedddddddddeeee | 81 | 13569 | 13585 | 1981 |
| 654562 | 2103 | 2119 | CTTTCCAGCTCAAAGTC | eeedddddddddeeee | 53 | 13572 | 13588 | 1982 |
| 654563 | 2114 | 2130 | AGAAACGGCTGCTTTCC | eeedddddddddeeee | 54 | 13583 | 13599 | 1983 |
| 654564 | 2121 | 2137 | ACCAAGGAGAAACGGCT | eeedddddddddeeee | 66 | 13590 | 13606 | 1984 |
| 654565 | 2172 | 2188 | GCATTTGTGCCGCTGCA | eeedddddddddeeee | 82 | 13641 | 13657 | 1985 |
| 654566 | 2175 | 2191 | GGTGCATTTGTGCCGCT | eeedddddddddeeee | 85 | 13644 | 13660 | 1986 |
| 654567 | 2187 | 2203 | AGCAAACTGGGAGGTGC | eeedddddddddeeee | 70 | 13656 | 13672 | 1987 |
| 654568 | 2226 | 2242 | GGTTCTTGCCTCCCCAC | eeedddddddddeeee | 88 | 13695 | 13711 | 1988 |
| 654569 | 2235 | 2251 | CTAAACACTGGTTCTTG | eeedddddddddeeee | 64 | 13704 | 13720 | 1989 |
| 654570 | 2238 | 2254 | GCGCTAAACACTGGTTC | eeedddddddddeeee | 85 | 13707 | 13723 | 1990 |

TABLE 13-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654571 | 2250 | 2266 | AACAGTAGTCCCGCGCT | eeedddddddddddeeee | 83 | 13719 | 13735 | 1991 |
| 654572 | 2268 | 2284 | GGTTGGAATTCTTTTTG | eeedddddddddddeeee | 38 | 13737 | 13753 | 1992 |
| 654573 | 2274 | 2290 | CTGGTCGGTTGGAATTC | eeedddddddddddeeee | 67 | 13743 | 13759 | 1993 |
| 654574 | 2283 | 2299 | ACAAACAAGCTGGTCGG | eeedddddddddddeeee | 70 | 13752 | 13768 | 1994 |
| 654575 | 2286 | 2302 | TTCACAAACAAGCTGGT | eeedddddddddddeeee | 67 | 13755 | 13771 | 1995 |
| 654576 | 2311 | 2327 | ACTTGAAAAGGGAACAC | eeedddddddddddeeee | 72 | 13780 | 13796 | 1996 |
| 654577 | 2314 | 2330 | TCAACTTGAAAAGGGAA | eeedddddddddddeeee | 29 | 13783 | 13799 | 1997 |
| 654578 | 2317 | 2333 | TTCTCAACTTGAAAAGG | eeedddddddddddeeee | 46 | 13786 | 13802 | 1998 |
| 654579 | 2326 | 2342 | CAATTTTGTTCTCAAC | eeedddddddddddeeee | 11 | 13795 | 13811 | 1999 |
| 654580 | 2329 | 2345 | ACCCAATTTTGTTCTC | eeedddddddddddeeee | 70 | 13798 | 13814 | 2000 |
| 654582 | 2024 | 2040 | TATCTGCTGCTGGCCTT | eeedddddddddeeeeee | 58 | 13493 | 13509 | 1962 |
| 654585 | 2027 | 2043 | TGTTATCTGCTGCTGGC | eeedddddddddeeeeee | 66 | 13496 | 13512 | 1964 |
| 654586 | 2028 | 2044 | TTGTTATCTGCTGCTGG | eeedddddddddeeeeee | 66 | 13497 | 13513 | 1965 |
| 654609 | 2024 | 2040 | TATCTGCTGCTGGCCTT | eeedddddddddddeeee | 62 | 13493 | 13509 | 1962 |
| 654612 | 2027 | 2043 | TGTTATCTGCTGCTGGC | eeedddddddddddeeee | 61 | 13496 | 13512 | 1964 |
| 654636 | 2024 | 2040 | TATCTGCTGCTGGCCTT | eeeedddddddddeeeee | 70 | 13493 | 13509 | 1962 |
| 654639 | 2027 | 2043 | TGTTATCTGCTGCTGGC | eeeedddddddddeeeee | 69 | 13496 | 13512 | 1964 |
| 654689 | 2023 | 2039 | ATCTGCTGCTGGCCTTT | eeedddddddddddeeee | 60 | 13492 | 13508 | 2001 |
| 654690 | 2026 | 2042 | GTTATCTGCTGCTGGCC | eeedddddddddddeeee | 77 | 13495 | 13511 | 2002 |
| 654691 | 2046 | 2062 | TCGCTGATTTGTCCGGG | eeedddddddddddeeee | 90 | 13515 | 13531 | 2003 |
| 654692 | 2249 | 2265 | ACAGTAGTCCCGCGCTA | eeedddddddddddeeee | 76 | 13718 | 13734 | 2004 |
| 654693 | 2251 | 2267 | GAACAGTAGTCCCGCGC | eeedddddddddddeeee | 74 | 13720 | 13736 | 2005 |
| 654694 | 2267 | 2283 | GTTGGAATTCTTTTTGG | eeedddddddddddeeee | 41 | 13736 | 13752 | 2006 |
| 654695 | 2269 | 2285 | CGGTTGGAATTCTTTTT | eeedddddddddddeeee | 65 | 13738 | 13754 | 2007 |
| 654696 | 2273 | 2289 | TGGTCGGTTGGAATTCT | eeedddddddddddeeee | 61 | 13742 | 13758 | 2008 |
| 654697 | 2275 | 2291 | GCTGGTCGGTTGGAATT | eeedddddddddddeeee | 61 | 13744 | 13760 | 2009 |
| 654698 | 2282 | 2298 | CAAACAAGCTGGTCGGT | eeedddddddddddeeee | 84 | 13751 | 13767 | 2010 |
| 654699 | 2284 | 2300 | CACAAACAAGCTGGTCG | eeedddddddddddeeee | 78 | 13753 | 13769 | 2011 |

Table 14 shows inhibition of AGT mRNA in HepG2 cells cultured at a density of 20,000 cells per well which were transfected using electroporation with 4000 nM antisense oligonucleotide. After a treatment period of approximately 24 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells.

TABLE 14

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 568637 | 2046 | 2061 | CGCTGATTTGTCCGGG | eekddddddddddkke | 96 | 13515 | 13530 | 129 |
| 568637 | 2046 | 2061 | CGCTGATTTGTCCGGG | eekddddddddddkke | 98 | 13515 | 13530 | 129 |
| 568637 | 2046 | 2061 | CGCTGATTTGTCCGGG | eekddddddddddkke | 97 | 13515 | 13530 | 129 |
| 610006 | 2023 | 2042 | GTTATCTGCTGCTGGCCTTT | eeeeddddddddddeeeee | 77 | 13492 | 13511 | 230 |
| 610009 | 2026 | 2045 | GTTGTTATCTGCTGCTGGCC | eeeeddddddddddeeeee | 73 | 13495 | 13514 | 233 |
| 610010 | 2027 | 2046 | GGTTGTTATCTGCTGCTGGC | eeeeddddddddddeeeee | 82 | 13496 | 13515 | 234 |
| 610012 | 2046 | 2065 | ACATCGCTGATTTGTCCGGG | eeeeddddddddddeeeee | 84 | 13515 | 13534 | 236 |
| 610013 | 2047 | 2066 | CACATCGCTGATTTGTCCGG | eeeeddddddddddeeeee | 76 | 13516 | 13535 | 237 |
| 610014 | 2048 | 2067 | ACACATCGCTGATTTGTCCG | eeeeddddddddddeeeee | 89 | 13517 | 13536 | 238 |
| 610015 | 2049 | 2068 | GACACATCGCTGATTTGTCC | eeeeddddddddddeeeee | 35 | 13518 | 13537 | 239 |
| 610015 | 2049 | 2068 | GACACATCGCTGATTTGTCC | eeeeddddddddddeeeee | 28 | 13518 | 13537 | 239 |
| 610015 | 2049 | 2068 | GACACATCGCTGATTTGTCC | eeeeddddddddddeeeee | 89 | 13518 | 13537 | 239 |
| 610015 | 2049 | 2068 | GACACATCGCTGATTTGTCC | eeeeddddddddddeeeee | 22 | 13518 | 13537 | 239 |
| 610043 | 2096 | 2115 | CCAGCTCAAAGTCGACTCAT | eeeeddddddddddeeeee | 82 | 13565 | 13584 | 267 |
| 619992 | 2249 | 2268 | GGAACAGTAGTCCCGCGCTA | eeeeddddddddddeeeee | 88 | 13718 | 13737 | 1708 |
| 619998 | 2267 | 2286 | TCGGTTGGAATTCTTTTTGG | eeeeddddddddddeeeee | 69 | 13736 | 13755 | 1714 |
| 620000 | 2273 | 2292 | AGCTGGTCGGTTGGAATTCT | eeeeddddddddddeeeee | 76 | 13742 | 13761 | 1716 |
| 620003 | 2282 | 2301 | TCACAAACAAGCTGGTCGGT | eeeeddddddddddeeeee | 85 | 13751 | 13770 | 1719 |
| 654701 | 2024 | 2041 | TTATCTGCTGCTGGCCTT | eeeddddddddddeeee | 50 | 13493 | 13510 | 2012 |
| 654704 | 2027 | 2044 | TTGTTATCTGCTGCTGGC | eeeddddddddddeeee | 46 | 13496 | 13513 | 2013 |
| 654705 | 2028 | 2045 | GTTGTTATCTGCTGCTGG | eeeddddddddddeeee | 60 | 13497 | 13514 | 2014 |
| 654707 | 2046 | 2063 | ATCGCTGATTTGTCCGGG | eeeddddddddddeeee | 91 | 13515 | 13532 | 2015 |
| 654708 | 2047 | 2064 | CATCGCTGATTTGTCCGG | eeeddddddddddeeee | 78 | 13516 | 13533 | 2016 |
| 654709 | 2048 | 2065 | ACATCGCTGATTTGTCCG | eeeddddddddddeeee | 66 | 13517 | 13534 | 2017 |
| 654710 | 2049 | 2066 | CACATCGCTGATTTGTCC | eeeddddddddddeeee | 80 | 13518 | 13535 | 2018 |
| 654711 | 2050 | 2067 | ACACATCGCTGATTTGTC | eeeddddddddddeeee | 77 | 13519 | 13536 | 2019 |
| 654713 | 2097 | 2114 | CAGCTCAAAGTCGACTCA | eeeddddddddddeeee | 77 | 13566 | 13583 | 2020 |
| 654716 | 2250 | 2267 | GAACAGTAGTCCCGCGCT | eeeddddddddddeeee | 80 | 13719 | 13736 | 2021 |
| 654719 | 2268 | 2285 | CGGTTGGAATTCTTTTTG | eeeddddddddddeeee | 65 | 13737 | 13754 | 2022 |
| 654722 | 2274 | 2291 | GCTGGTCGGTTGGAATTC | eeeddddddddddeeee | 74 | 13743 | 13760 | 2023 |
| 654724 | 2282 | 2299 | ACAAACAAGCTGGTCGGT | eeeddddddddddeeee | 81 | 13751 | 13768 | 2024 |
| 654725 | 2283 | 2300 | CACAAACAAGCTGGTCGG | eeeddddddddddeeee | 80 | 13752 | 13769 | 2025 |
| 654728 | 2024 | 2041 | TTATCTGCTGCTGGCCTT | eeeeddddddddeeeeee | 53 | 13493 | 13510 | 2012 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654731 | 2027 | 2044 | TTGTTATCTGCTGCTGGC | eeeedddddddddeeeee | 56 | 13496 | 13513 | 2013 |
| 654732 | 2028 | 2045 | GTTGTTATCTGCTGCTGG | eeeedddddddddeeeee | 71 | 13497 | 13514 | 2014 |
| 654735 | 2047 | 2064 | CATCGCTGATTTGTCCGG | eeeedddddddddeeeee | 71 | 13516 | 13533 | 2016 |
| 654736 | 2048 | 2065 | ACATCGCTGATTTGTCCG | eeeedddddddddeeeee | 72 | 13517 | 13534 | 2017 |
| 654737 | 2049 | 2066 | CACATCGCTGATTTGTCC | eeeedddddddddeeeee | 82 | 13518 | 13535 | 2018 |
| 654740 | 2097 | 2114 | CAGCTCAAAGTCGACTCA | eeeedddddddddeeeee | 88 | 13566 | 13583 | 2020 |
| 654743 | 2250 | 2267 | GAACAGTAGTCCCGCGCT | eeeedddddddddeeeee | 75 | 13719 | 13736 | 2021 |
| 654745 | 2267 | 2284 | GGTTGGAATTCTTTTTGG | eeeedddddddddeeeee | 49 | 13736 | 13753 | 2026 |
| 654746 | 2268 | 2285 | CGGTTGGAATTCTTTTTG | eeeedddddddddeeeee | 62 | 13737 | 13754 | 2022 |
| 654749 | 2274 | 2291 | GCTGGTCGGTTGGAATTC | eeeedddddddddeeeee | 55 | 13743 | 13760 | 2023 |
| 654752 | 2283 | 2300 | CACAAACAAGCTGGTCGG | eeeedddddddddeeeee | 74 | 13752 | 13769 | 2025 |
| 654755 | 2024 | 2041 | TTATCTGCTGCTGGCCTT | eeeeedddddddddeeeee | 47 | 13493 | 13510 | 2012 |
| 654758 | 2027 | 2044 | TTGTTATCTGCTGCTGGC | eeeeedddddddddeeeee | 51 | 13496 | 13513 | 2013 |
| 654759 | 2028 | 2045 | GTTGTTATCTGCTGCTGG | eeeeedddddddddeeeee | 56 | 13497 | 13514 | 2014 |
| 654761 | 2046 | 2063 | ATCGCTGATTTGTCCGGG | eeeeedddddddddeeeee | 74 | 13515 | 13532 | 2015 |
| 654762 | 2047 | 2064 | CATCGCTGATTTGTCCGG | eeeeedddddddddeeeee | 62 | 13516 | 13533 | 2016 |
| 654763 | 2048 | 2065 | ACATCGCTGATTTGTCCG | eeeeedddddddddeeeee | 61 | 13517 | 13534 | 2017 |
| 654764 | 2049 | 2066 | CACATCGCTGATTTGTCC | eeeeedddddddddeeeee | 68 | 13518 | 13535 | 2018 |
| 654765 | 2050 | 2067 | ACACATCGCTGATTTGTC | eeeeedddddddddeeeee | 72 | 13519 | 13536 | 2019 |
| 654767 | 2097 | 2114 | CAGCTCAAAGTCGACTCA | eeeeedddddddddeeeee | 63 | 13566 | 13583 | 2020 |
| 654768 | 2098 | 2115 | CCAGCTCAAAGTCGACTC | eeeeedddddddddeeeee | 86 | 13567 | 13584 | 2027 |
| 654770 | 2250 | 2267 | GAACAGTAGTCCCGCGCT | eeeeedddddddddeeeee | 55 | 13719 | 13736 | 2021 |
| 654771 | 2251 | 2268 | GGAACAGTAGTCCCGCGC | eeeeedddddddddeeeee | 82 | 13720 | 13737 | 2028 |
| 654773 | 2268 | 2285 | CGGTTGGAATTCTTTTTG | eeeeedddddddddeeeee | 58 | 13737 | 13754 | 2022 |
| 654776 | 2274 | 2291 | GCTGGTCGGTTGGAATTC | eeeeedddddddddeeeee | 37 | 13743 | 13760 | 2023 |
| 654778 | 2282 | 2299 | ACAAACAAGCTGGTCGGT | eeeeedddddddddeeeee | 71 | 13751 | 13768 | 2024 |
| 654779 | 2283 | 2300 | CACAAACAAGCTGGTCGG | eeeeedddddddddeeeee | 63 | 13752 | 13769 | 2025 |
| 654781 | 2023 | 2040 | TATCTGCTGCTGGCCTTT | eeeeeddddddddddeeee | 56 | 13492 | 13509 | 2029 |
| 654782 | 2024 | 2041 | TTATCTGCTGCTGGCCTT | eeeeeddddddddddeeee | 63 | 13493 | 13510 | 2012 |
| 654784 | 2026 | 2043 | TGTTATCTGCTGCTGGCC | eeeeeddddddddddeeee | 65 | 13495 | 13512 | 2030 |
| 654785 | 2027 | 2044 | TTGTTATCTGCTGCTGGC | eeeeeddddddddddeeee | 55 | 13496 | 13513 | 2013 |
| 654786 | 2028 | 2045 | GTTGTTATCTGCTGCTGG | eeeeeddddddddddeeee | 48 | 13497 | 13514 | 2014 |
| 654789 | 2047 | 2064 | CATCGCTGATTTGTCCGG | eeeeeddddddddddeeee | 73 | 13516 | 13533 | 2016 |
| 654790 | 2048 | 2065 | ACATCGCTGATTTGTCCG | eeeeeddddddddddeeee | 69 | 13517 | 13534 | 2017 |
| 654791 | 2049 | 2066 | CACATCGCTGATTTGTCC | eeeeeddddddddddeeee | 61 | 13518 | 13535 | 2018 |
| 654794 | 2097 | 2114 | CAGCTCAAAGTCGACTCA | eeeeeddddddddddeeee | 79 | 13566 | 13583 | 2020 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654797 | 2250 | 2267 | GAACAGTAGTCCCGCGCT | eeeeeedddddddddeeee | 37 | 13719 | 13736 | 2021 |
| 654800 | 2268 | 2285 | CGGTTGGAATTCTTTTTG | eeeeeedddddddddeeee | 63 | 13737 | 13754 | 2022 |
| 654801 | 2269 | 2286 | TCGGTTGGAATTCTTTTT | eeeeeedddddddddeeee | 59 | 13738 | 13755 | 2031 |
| 654803 | 2274 | 2291 | GCTGGTCGGTTGGAATTC | eeeeeedddddddddeeee | 61 | 13743 | 13760 | 2023 |
| 654806 | 2283 | 2300 | CACAAACAAGCTGGTCGG | eeeeeedddddddddeeee | 54 | 13752 | 13769 | 2025 |
| 654809 | 2023 | 2041 | TTATCTGCTGCTGGCCTTT | eeeedddddddddddeeee | 45 | 13492 | 13510 | 2032 |
| 654812 | 2026 | 2044 | TTGTTATCTGCTGCTGGCC | eeeedddddddddddeeee | 57 | 13495 | 13513 | 2033 |
| 654813 | 2027 | 2045 | GTTGTTATCTGCTGCTGGC | eeeedddddddddddeeee | 64 | 13496 | 13514 | 2034 |
| 654815 | 2046 | 2064 | CATCGCTGATTTGTCCGGG | eeeedddddddddddeeee | 83 | 13515 | 13533 | 2035 |
| 654816 | 2047 | 2065 | ACATCGCTGATTTGTCCGG | eeeedddddddddddeeee | 68 | 13516 | 13534 | 2036 |
| 654817 | 2048 | 2066 | CACATCGCTGATTTGTCCG | eeeedddddddddddeeee | 82 | 13517 | 13535 | 2037 |
| 654818 | 2049 | 2067 | ACACATCGCTGATTTGTCC | eeeedddddddddddeeee | 44 | 13518 | 13536 | 2038 |
| 654820 | 2096 | 2114 | CAGCTCAAAGTCGACTCAT | eeeedddddddddddeeee | 80 | 13565 | 13583 | 2039 |
| 654822 | 2248 | 2266 | AACAGTAGTCCCGCGCTAA | eeeedddddddddddeeee | 63 | 13717 | 13735 | 2040 |
| 654823 | 2249 | 2267 | GAACAGTAGTCCCGCGCTA | eeeedddddddddddeeee | 77 | 13718 | 13736 | 2041 |
| 654826 | 2267 | 2285 | CGGTTGGAATTCTTTTTGG | eeeedddddddddddeeee | 76 | 13736 | 13754 | 2042 |
| 654829 | 2273 | 2291 | GCTGGTCGGTTGGAATTCT | eeeedddddddddddeeee | 78 | 13742 | 13760 | 2043 |
| 654832 | 2282 | 2300 | CACAAACAAGCTGGTCGGT | eeeedddddddddddeeee | 82 | 13751 | 13769 | 2044 |
| 654833 | 2283 | 2301 | TCACAAACAAGCTGGTCGG | eeeedddddddddddeeee | 28 | 13752 | 13770 | 2045 |
| 654834 | 2022 | 2040 | TATCTGCTGCTGGCCTTTG | eeedddddddddeeeeeee | 3 | 13491 | 13509 | 2046 |
| 654835 | 2023 | 2041 | TTATCTGCTGCTGGCCTTT | eeedddddddddeeeeeee | 48 | 13492 | 13510 | 2032 |
| 654837 | 2025 | 2043 | TGTTATCTGCTGCTGGCCT | eeedddddddddeeeeeee | 64 | 13494 | 13512 | 2047 |
| 654838 | 2026 | 2044 | TTGTTATCTGCTGCTGGCC | eeedddddddddeeeeeee | 38 | 13495 | 13513 | 2033 |
| 654839 | 2027 | 2045 | GTTGTTATCTGCTGCTGGC | eeedddddddddeeeeeee | 60 | 13496 | 13514 | 2034 |
| 654841 | 2046 | 2064 | CATCGCTGATTTGTCCGGG | eeedddddddddeeeeeee | 72 | 13515 | 13533 | 2035 |
| 654842 | 2047 | 2065 | ACATCGCTGATTTGTCCGG | eeedddddddddeeeeeee | 70 | 13516 | 13534 | 2036 |
| 654843 | 2048 | 2066 | CACATCGCTGATTTGTCCG | eeedddddddddeeeeeee | 85 | 13517 | 13535 | 2037 |
| 654845 | 2095 | 2113 | AGCTCAAAGTCGACTCATT | eeedddddddddeeeeeee | 44 | 13564 | 13582 | 2048 |
| 654846 | 2096 | 2114 | CAGCTCAAAGTCGACTCAT | eeedddddddddeeeeeee | 84 | 13565 | 13583 | 2039 |
| 654849 | 2249 | 2267 | GAACAGTAGTCCCGCGCTA | eeedddddddddeeeeeee | 43 | 13718 | 13736 | 2041 |
| 654852 | 2267 | 2285 | CGGTTGGAATTCTTTTTGG | eeedddddddddeeeeeee | 73 | 13736 | 13754 | 2042 |
| 654855 | 2273 | 2291 | GCTGGTCGGTTGGAATTCT | eeedddddddddeeeeeee | 59 | 13742 | 13760 | 2043 |
| 654858 | 2282 | 2300 | CACAAACAAGCTGGTCGGT | eeedddddddddeeeeeee | 72 | 13751 | 13769 | 2044 |
| 654861 | 2023 | 2041 | TTATCTGCTGCTGGCCTTT | eeeedddddddddeeeeee | 40 | 13492 | 13510 | 2032 |
| 654864 | 2026 | 2044 | TTGTTATCTGCTGCTGGCC | eeeedddddddddeeeeee | 57 | 13495 | 13513 | 2033 |
| 654865 | 2027 | 2045 | GTTGTTATCTGCTGCTGGC | eeeedddddddddeeeeee | 52 | 13496 | 13514 | 2034 |
| 654867 | 2046 | 2064 | CATCGCTGATTTGTCCGGG | eeeedddddddddeeeeee | 71 | 13515 | 13533 | 2035 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654868 | 2047 | 2065 | ACATCGCTGATTTGTCCGG | eeeeedddddddddeeeee | 69 | 13516 | 13534 | 2036 |
| 654869 | 2048 | 2066 | CACATCGCTGATTTGTCCG | eeeeedddddddddeeeee | 69 | 13517 | 13535 | 2037 |
| 654872 | 2096 | 2114 | CAGCTCAAAGTCGACTCAT | eeeeedddddddddeeeee | 63 | 13565 | 13583 | 2039 |
| 654875 | 2249 | 2267 | GAACAGTAGTCCCGCGCTA | eeeeedddddddddeeeee | 55 | 13718 | 13736 | 2041 |
| 654877 | 2266 | 2284 | GGTTGGAATTCTTTTTGGA | eeeeedddddddddeeeee | 43 | 13735 | 13753 | 2049 |
| 654878 | 2267 | 2285 | CGGTTGGAATTCTTTTTGG | eeeeedddddddddeeeee | 61 | 13736 | 13754 | 2042 |
| 654881 | 2273 | 2291 | GCTGGTCGGTTGGAATTCT | eeeeedddddddddeeeee | 49 | 13742 | 13760 | 2043 |
| 654883 | 2281 | 2299 | ACAAACAAGCTGGTCGGTT | eeeeedddddddddeeeee | 40 | 13750 | 13768 | 2050 |
| 654884 | 2282 | 2300 | CACAAACAAGCTGGTCGGT | eeeeedddddddddeeeee | 73 | 13751 | 13769 | 2044 |
| 654887 | 2023 | 2041 | TTATCTGCTGCTGGCCTTT | eeeeeedddddddddeeeee | 60 | 13492 | 13510 | 2032 |
| 654890 | 2026 | 2044 | TTGTTATCTGCTGCTGGCC | eeeeeedddddddddeeeee | 44 | 13495 | 13513 | 2033 |
| 654891 | 2027 | 2045 | GTTGTTATCTGCTGCTGGC | eeeeeedddddddddeeeee | 60 | 13496 | 13514 | 2034 |
| 654893 | 2046 | 2064 | CATCGCTGATTTGTCCGGG | eeeeeedddddddddeeeee | 74 | 13515 | 13533 | 2035 |
| 654894 | 2047 | 2065 | ACATCGCTGATTTGTCCGG | eeeeeedddddddddeeeee | 64 | 13516 | 13534 | 2036 |
| 654895 | 2048 | 2066 | CACATCGCTGATTTGTCCG | eeeeeedddddddddeeeee | 62 | 13517 | 13535 | 2037 |
| 654898 | 2096 | 2114 | CAGCTCAAAGTCGACTCAT | eeeeeedddddddddeeeee | 67 | 13565 | 13583 | 2039 |
| 654899 | 2097 | 2115 | CCAGCTCAAAGTCGACTCA | eeeeeedddddddddeeeee | 63 | 13566 | 13584 | 2051 |
| 654901 | 2249 | 2267 | GAACAGTAGTCCCGCGCTA | eeeeeedddddddddeeeee | 55 | 13718 | 13736 | 2041 |
| 654904 | 2267 | 2285 | CGGTTGGAATTCTTTTTGG | eeeeeedddddddddeeeee | 45 | 13736 | 13754 | 2042 |
| 654907 | 2273 | 2291 | GCTGGTCGGTTGGAATTCT | eeeeeedddddddddeeeee | 51 | 13742 | 13760 | 2043 |
| 654910 | 2282 | 2300 | CACAAACAAGCTGGTCGGT | eeeeeedddddddddeeeee | 47 | 13751 | 13769 | 2044 |
| 654911 | 2283 | 2301 | TCACAAACAAGCTGGTCGG | eeeeeedddddddddeeeee | 72 | 13752 | 13770 | 2045 |
| 654917 | 2027 | 2045 | GTTGTTATCTGCTGCTGGC | eeeeeeedddddddddeeee | 45 | 13496 | 13514 | 2034 |
| 654920 | 2047 | 2065 | ACATCGCTGATTTGTCCGG | eeeeeeedddddddddeeee | 77 | 13516 | 13534 | 2036 |
| 654939 | 2023 | 2042 | GTTATCTGCTGCTGGCCTTT | eeeeeedddddddddeeeeee | 65 | 13492 | 13511 | 230 |
| 654941 | 2025 | 2044 | TTGTTATCTGCTGCTGGCCT | eeeeeedddddddddeeeeee | 55 | 13494 | 13513 | 232 |
| 654942 | 2026 | 2045 | GTTGTTATCTGCTGCTGGCC | eeeeeedddddddddeeeeee | 48 | 13495 | 13514 | 233 |
| 654943 | 2027 | 2046 | GGTTGTTATCTGCTGCTGGC | eeeeeedddddddddeeeeee | 67 | 13496 | 13515 | 234 |
| 654944 | 2028 | 2047 | GGGTTGTTATCTGCTGCTGG | eeeeeedddddddddeeeeee | 56 | 13497 | 13516 | 235 |
| 654945 | 2046 | 2065 | ACATCGCTGATTTGTCCGGG | eeeeeedddddddddeeeeee | 77 | 13515 | 13534 | 236 |
| 654946 | 2047 | 2066 | CACATCGCTGATTTGTCCGG | eeeeeedddddddddeeeeee | 67 | 13516 | 13535 | 237 |
| 654947 | 2048 | 2067 | ACACATCGCTGATTTGTCCG | eeeeeedddddddddeeeeee | 56 | 13517 | 13536 | 238 |
| 654950 | 2096 | 2115 | CCAGCTCAAAGTCGACTCAT | eeeeeedddddddddeeeeee | 75 | 13565 | 13584 | 267 |
| 654951 | 2097 | 2116 | TCCAGCTCAAAGTCGACTCA | eeeeeedddddddddeeeeee | 50 | 13566 | 13585 | 268 |
| 654952 | 2248 | 2267 | GAACAGTAGTCCCGCGCTAA | eeeeeedddddddddeeeeee | 53 | 13717 | 13736 | 1892 |
| 654953 | 2249 | 2268 | GGAACAGTAGTCCCGCGCTA | eeeeeedddddddddeeeeee | 44 | 13718 | 13737 | 1708 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 654955 | 2266 | 2285 | CGGTTGGAATTCTTTTTGGA | eeeeeeedddddddddeeeee | 58 | 13735 | 13754 | 1904 |
| 654956 | 2267 | 2286 | TCGGTTGGAATTCTTTTTGG | eeeeeeedddddddddeeeee | 66 | 13736 | 13755 | 1714 |
| 654959 | 2273 | 2292 | AGCTGGTCGGTTGGAATTCT | eeeeeeedddddddddeeeee | 56 | 13742 | 13761 | 1716 |
| 654962 | 2282 | 2301 | TCACAAACAAGCTGGTCGGT | eeeeeeedddddddddeeeee | 55 | 13751 | 13770 | 1719 |
| 654963 | 2283 | 2302 | TTCACAAACAAGCTGGTCGG | eeeeeeedddddddddeeeee | 63 | 13752 | 13771 | 1915 |
| 654964 | 2022 | 2041 | TTATCTGCTGCTGGCCTTTG | eeeeeeedddddddddeeeee | 43 | 13491 | 13510 | 229 |
| 654965 | 2023 | 2042 | GTTATCTGCTGCTGGCCTTT | eeeeeeedddddddddeeeee | 65 | 13492 | 13511 | 230 |
| 654968 | 2026 | 2045 | GTTGTTATCTGCTGCTGGCC | eeeeeeedddddddddeeeee | 44 | 13495 | 13514 | 233 |
| 654969 | 2027 | 2046 | GGTTGTTATCTGCTGCTGGC | eeeeeeedddddddddeeeee | 64 | 13496 | 13515 | 234 |
| 654970 | 2028 | 2047 | GGGTTGTTATCTGCTGCTGG | eeeeeeedddddddddeeeee | 76 | 13497 | 13516 | 235 |
| 654971 | 2046 | 2065 | ACATCGCTGATTTGTCCGGG | eeeeeeedddddddddeeeee | 60 | 13515 | 13534 | 236 |
| 654972 | 2047 | 2066 | CACATCGCTGATTTGTCCGG | eeeeeeedddddddddeeeee | 74 | 13516 | 13535 | 237 |
| 654973 | 2048 | 2067 | ACACATCGCTGATTTGTCCG | eeeeeeedddddddddeeeee | 54 | 13517 | 13536 | 238 |
| 654974 | 2049 | 2068 | GACACATCGCTGATTTGTCC | eeeeeeedddddddddeeeee | 78 | 13518 | 13537 | 239 |
| 654976 | 2096 | 2115 | CCAGCTCAAAGTCGACTCAT | eeeeeeedddddddddeeeee | 62 | 13565 | 13584 | 267 |
| 654979 | 2249 | 2268 | GGAACAGTAGTCCCGCGCTA | eeeeeeedddddddddeeeee | 59 | 13718 | 13737 | 1708 |
| 654982 | 2267 | 2286 | TCGGTTGGAATTCTTTTTGG | eeeeedddddddddeeeeee | 63 | 13736 | 13755 | 1714 |
| 654985 | 2273 | 2292 | AGCTGGTCGGTTGGAATTCT | eeeeedddddddddeeeeee | 57 | 13742 | 13761 | 1716 |
| 654988 | 2282 | 2301 | TCACAAACAAGCTGGTCGGT | eeeeedddddddddeeeeee | 70 | 13751 | 13770 | 1719 |
| 654989 | 2283 | 2302 | TTCACAAACAAGCTGGTCGG | eeeeedddddddddeeeeee | 77 | 13752 | 13771 | 1915 |
| 654990 | 2022 | 2041 | TTATCTGCTGCTGGCCTTTG | eeeeedddddddddeeeeee | 41 | 13491 | 13510 | 229 |
| 654991 | 2023 | 2042 | GTTATCTGCTGCTGGCCTTT | eeeeedddddddddeeeeee | 70 | 13492 | 13511 | 230 |
| 654994 | 2026 | 2045 | GTTGTTATCTGCTGCTGGCC | eeeeedddddddddeeeeee | 33 | 13495 | 13514 | 233 |
| 654995 | 2027 | 2046 | GGTTGTTATCTGCTGCTGGC | eeeeedddddddddeeeeee | 79 | 13496 | 13515 | 234 |
| 654997 | 2046 | 2065 | ACATCGCTGATTTGTCCGGG | eeeeedddddddddeeeeee | 64 | 13515 | 13534 | 236 |
| 654998 | 2047 | 2066 | CACATCGCTGATTTGTCCGG | eeeeedddddddddeeeeee | 70 | 13516 | 13535 | 237 |
| 654999 | 2048 | 2067 | ACACATCGCTGATTTGTCCG | eeeeedddddddddeeeeee | 85 | 13517 | 13536 | 238 |
| 655002 | 2096 | 2115 | CCAGCTCAAAGTCGACTCAT | eeeeedddddddddeeeeee | 85 | 13565 | 13584 | 267 |
| 655005 | 2249 | 2268 | GGAACAGTAGTCCCGCGCTA | eeeeedddddddddeeeeee | 73 | 13718 | 13737 | 1708 |
| 655008 | 2267 | 2286 | TCGGTTGGAATTCTTTTTGG | eeeeedddddddddeeeeee | 67 | 13736 | 13755 | 1714 |
| 655011 | 2273 | 2292 | AGCTGGTCGGTTGGAATTCT | eeeeedddddddddeeeeee | 31 | 13742 | 13761 | 1716 |
| 655014 | 2282 | 2301 | TCACAAACAAGCTGGTCGGT | eeeeedddddddddeeeeee | 76 | 13751 | 13770 | 1719 |
| 655044 | 2024 | 2041 | TTATCTGCTGCTGGCCTT | eeeddddddddddeeeee | 55 | 13493 | 13510 | 2012 |
| 655045 | 2027 | 2044 | TTGTTATCTGCTGCTGGC | eeeddddddddddeeeee | 46 | 13496 | 13513 | 2013 |
| 655046 | 2028 | 2045 | GTTGTTATCTGCTGCTGG | eeeddddddddddeeeee | 54 | 13497 | 13514 | 2014 |
| 655047 | 2047 | 2064 | CATCGCTGATTTGTCCGG | eeeddddddddddeeeee | 61 | 13516 | 13533 | 2016 |
| 655048 | 2048 | 2065 | ACATCGCTGATTTGTCCG | eeeddddddddddeeeee | 59 | 13517 | 13534 | 2017 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 655049 | 2049 | 2066 | CACATCGCTGATTTGTCC | eeeedddddddddeeeee | 84 | 13518 | 13535 | 2018 |
| 655050 | 2097 | 2114 | CAGCTCAAAGTCGACTCA | eeeedddddddddeeeee | 75 | 13566 | 13583 | 2020 |
| 655051 | 2250 | 2267 | GAACAGTAGTCCCGCGCT | eeeedddddddddeeeee | 74 | 13719 | 13736 | 2021 |
| 655052 | 2268 | 2285 | CGGTTGGAATTCTTTTTG | eeeedddddddddeeeee | 58 | 13737 | 13754 | 2022 |
| 655053 | 2274 | 2291 | GCTGGTCGGTTGGAATTC | eeeedddddddddeeeee | 58 | 13743 | 13760 | 2023 |
| 655054 | 2283 | 2300 | CACAAACAAGCTGGTCGG | eeeedddddddddeeeee | 76 | 13752 | 13769 | 2025 |
| 655055 | 2024 | 2041 | TTATCTGCTGCTGGCCTT | eeeeddddddddddeeee | 57 | 13493 | 13510 | 2012 |
| 655056 | 2027 | 2044 | TTGTTATCTGCTGCTGGC | eeeeddddddddddeeee | 50 | 13496 | 13513 | 2013 |
| 655057 | 2028 | 2045 | GTTGTTATCTGCTGCTGG | eeeeddddddddddeeee | 63 | 13497 | 13514 | 2014 |
| 655058 | 2047 | 2064 | CATCGCTGATTTGTCCGG | eeeeddddddddddeeee | 80 | 13516 | 13533 | 2016 |
| 655059 | 2048 | 2065 | ACATCGCTGATTTGTCCG | eeeeddddddddddeeee | 60 | 13517 | 13534 | 2017 |
| 655060 | 2049 | 2066 | CACATCGCTGATTTGTCC | eeeeddddddddddeeee | 68 | 13518 | 13535 | 2018 |
| 655061 | 2097 | 2114 | CAGCTCAAAGTCGACTCA | eeeeddddddddddeeee | 79 | 13566 | 13583 | 2020 |
| 655062 | 2250 | 2267 | GAACAGTAGTCCCGCGCT | eeeeddddddddddeeee | 51 | 13719 | 13736 | 2021 |
| 655063 | 2268 | 2285 | CGGTTGGAATTCTTTTTG | eeeeddddddddddeeee | 74 | 13737 | 13754 | 2022 |
| 655064 | 2274 | 2291 | GCTGGTCGGTTGGAATTC | eeeeddddddddddeeee | 65 | 13743 | 13760 | 2023 |
| 655065 | 2283 | 2300 | CACAAACAAGCTGGTCGG | eeeeddddddddddeeee | 69 | 13752 | 13769 | 2025 |
| 655066 | 2023 | 2041 | TTATCTGCTGCTGGCCTTT | eeeedddddddddddeeeee | 50 | 13492 | 13510 | 2032 |
| 655067 | 2026 | 2044 | TTGTTATCTGCTGCTGGCC | eeeedddddddddddeeeee | 60 | 13495 | 13513 | 2033 |
| 655068 | 2027 | 2045 | GTTGTTATCTGCTGCTGGC | eeeedddddddddddeeeee | 65 | 13496 | 13514 | 2034 |
| 655069 | 2046 | 2064 | CATCGCTGATTTGTCCGGG | eeeedddddddddddeeeee | 71 | 13515 | 13533 | 2035 |
| 655070 | 2047 | 2065 | ACATCGCTGATTTGTCCGG | eeeedddddddddddeeeee | 65 | 13516 | 13534 | 2036 |
| 655071 | 2048 | 2066 | CACATCGCTGATTTGTCCG | eeeedddddddddddeeeee | 87 | 13517 | 13535 | 2037 |
| 655072 | 2096 | 2114 | CAGCTCAAAGTCGACTCAT | eeeedddddddddddeeeee | 75 | 13565 | 13583 | 2039 |
| 655073 | 2249 | 2267 | GAACAGTAGTCCCGCGCTA | eeeedddddddddddeeeee | 73 | 13718 | 13736 | 2041 |
| 655074 | 2267 | 2285 | CGGTTGGAATTCTTTTTGG | eeeedddddddddddeeeee | 70 | 13736 | 13754 | 2042 |
| 655075 | 2273 | 2291 | GCTGGTCGGTTGGAATTCT | eeeedddddddddddeeeee | 65 | 13742 | 13760 | 2043 |
| 655076 | 2282 | 2300 | CACAAACAAGCTGGTCGGT | eeeedddddddddddeeeee | 65 | 13751 | 13769 | 2044 |
| 655077 | 2023 | 2041 | TTATCTGCTGCTGGCCTTT | eeeeddddddddddddeeeee | 40 | 13492 | 13510 | 2032 |
| 655078 | 2026 | 2044 | TTGTTATCTGCTGCTGGCC | eeeeddddddddddddeeeee | 57 | 13495 | 13513 | 2033 |
| 655079 | 2027 | 2045 | GTTGTTATCTGCTGCTGGC | eeeeddddddddddddeeeee | 66 | 13496 | 13514 | 2034 |
| 655080 | 2046 | 2064 | CATCGCTGATTTGTCCGGG | eeeeddddddddddddeeeee | 70 | 13515 | 13533 | 2035 |
| 655081 | 2047 | 2065 | ACATCGCTGATTTGTCCGG | eeeeddddddddddddeeeee | 66 | 13516 | 13534 | 2036 |
| 655082 | 2048 | 2066 | CACATCGCTGATTTGTCCG | eeeeddddddddddddeeeee | 73 | 13517 | 13535 | 2037 |
| 655083 | 2096 | 2114 | CAGCTCAAAGTCGACTCAT | eeeeddddddddddddeeeee | 81 | 13565 | 13583 | 2039 |
| 655084 | 2249 | 2267 | GAACAGTAGTCCCGCGCTA | eeeeddddddddddddeeeee | 65 | 13718 | 13736 | 2041 |

TABLE 14-continued

Inhibition of AGT mRNA by MOE and/or cEt containing gapmers targeting SEQ ID NO: 1 and/or 2

| ISIS NO | SEQ ID: 1 Start Site | SEQ ID: 1 Stop Site | Sequence | Chemistry | % Inhibition | SEQ ID: 2 Start Site | SEQ ID 2: Stop Site | SEQ ID NO |
|---|---|---|---|---|---|---|---|---|
| 655085 | 2267 | 2285 | CGGTTGGAATTCTTTTTGG | eeeeedddddddddeeeee | 70 | 13736 | 13754 | 2042 |
| 655086 | 2273 | 2291 | GCTGGTCGGTTGGAATTCT | eeeeedddddddddeeeee | 69 | 13742 | 13760 | 2043 |
| 655087 | 2282 | 2300 | CACAAACAAGCTGGTCGGT | eeeeedddddddddeeeee | 79 | 13751 | 13769 | 2044 |
| 655088 | 2023 | 2042 | GTTATCTGCTGCTGGCCTTT | eeeeeddddddddddeeeee | 70 | 13492 | 13511 | 230 |
| 655089 | 2026 | 2045 | GTTGTTATCTGCTGCTGGCC | eeeeeddddddddddeeeee | 42 | 13495 | 13514 | 233 |
| 655090 | 2027 | 2046 | GGTTGTTATCTGCTGCTGGC | eeeeeddddddddddeeeee | 82 | 13496 | 13515 | 234 |
| 655091 | 2046 | 2065 | ACATCGCTGATTTGTCCGGG | eeeeeddddddddddeeeee | 66 | 13515 | 13534 | 236 |
| 655092 | 2047 | 2066 | CACATCGCTGATTTGTCCGG | eeeeeddddddddddeeeee | 78 | 13516 | 13535 | 237 |
| 655093 | 2048 | 2067 | ACACATCGCTGATTTGTCCG | eeeeeddddddddddeeeee | 90 | 13517 | 13536 | 238 |
| 655094 | 2096 | 2115 | CCAGCTCAAAGTCGACTCAT | eeeeeddddddddddeeeee | 80 | 13565 | 13584 | 267 |
| 655095 | 2249 | 2268 | GGAACAGTAGTCCCGCGCTA | eeeeeddddddddddeeeee | 84 | 13718 | 13737 | 1708 |
| 655096 | 2267 | 2286 | TCGGTTGGAATTCTTTTTGG | eeeeeddddddddddeeeee | 76 | 13736 | 13755 | 1714 |
| 655097 | 2273 | 2292 | AGCTGGTCGGTTGGAATTCT | eeeeeddddddddddeeeee | 63 | 13742 | 13761 | 1716 |
| 655098 | 2282 | 2301 | TCACAAACAAGCTGGTCGGT | eeeeeddddddddddeeeee | 79 | 13751 | 13770 | 1719 |
| 655099 | 2023 | 2042 | GTTATCTGCTGCTGGCCTTT | eeeeeddddddddddeeeee | 75 | 13492 | 13511 | 230 |
| 655100 | 2026 | 2045 | GTTGTTATCTGCTGCTGGCC | eeeeeddddddddddeeeee | 67 | 13495 | 13514 | 233 |
| 655101 | 2027 | 2046 | GGTTGTTATCTGCTGCTGGC | eeeeeddddddddddeeeee | 78 | 13496 | 13515 | 234 |
| 655102 | 2046 | 2065 | ACATCGCTGATTTGTCCGGG | eeeeeddddddddddeeeee | 82 | 13515 | 13534 | 236 |
| 655103 | 2047 | 2066 | CACATCGCTGATTTGTCCGG | eeeeeddddddddddeeeee | 74 | 13516 | 13535 | 237 |
| 655104 | 2048 | 2067 | ACACATCGCTGATTTGTCCG | eeeeeddddddddddeeeee | 71 | 13517 | 13536 | 238 |
| 655105 | 2096 | 2115 | CCAGCTCAAAGTCGACTCAT | eeeeeddddddddddeeeee | 82 | 13565 | 13584 | 267 |
| 655106 | 2249 | 2268 | GGAACAGTAGTCCCGCGCTA | eeeeeddddddddddeeeee | 68 | 13718 | 13737 | 1708 |
| 655107 | 2267 | 2286 | TCGGTTGGAATTCTTTTTGG | eeeeeddddddddddeeeee | 79 | 13736 | 13755 | 1714 |
| 655108 | 2273 | 2292 | AGCTGGTCGGTTGGAATTCT | eeeeeddddddddddeeeee | 65 | 13742 | 13761 | 1716 |
| 655109 | 2282 | 2301 | TCACAAACAAGCTGGTCGGT | eeeeeddddddddddeeeee | 82 | 13751 | 13770 | 1719 |

Example 2: Dose-Dependent Antisense Inhibition of Human Angiotensinogen (AGT) in HepG2 Cells Of over 2000 antisense oligonucleotides designed and tested in single dose in vitro assays described in Example 1, several of those exhibiting significant inhibition of AGT mRNA were selected and further tested at various doses in HepG2 cells. The results for exemplary antisense oligonucleotides tested in several series of experiment are presented in tables shown below.

Cells were plated at a density of 20,000 cells per well and transfected using electroporation with 0.406 µM, 0.813 µM, 1.63 µM, 3.25 µM, 6.5 µM and 13.0 µM concentrations of antisense oligonucleotide, as specified in Table 15 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells. The half maximal inhibitory concentration ($IC_{50}$) of each oligonucleotide is also presented. AGT mRNA levels were significantly reduced in a dose-dependent manner in antisense oligonucleotide treated cells.

TABLE 15

| ISIS NO | 0.406 µM | 0.813 µM | 1.63 µM | 3.25 µM | 6.5 µM | 13.0 µM | $IC_{50}$ (µM) | SEQ ID NO |
|---|---|---|---|---|---|---|---|---|
| 568550 | 34 | 36 | 55 | 68 | 78 | 83 | 1.3 | 46 |
| 568557 | 32 | 42 | 61 | 71 | 69 | 72 | 1.2 | 53 |
| 568558 | 30 | 31 | 54 | 67 | 72 | 80 | 1.6 | 54 |
| 568565 | 19 | 32 | 45 | 60 | 72 | 75 | 2.2 | 61 |
| 568572 | 29 | 17 | 56 | 53 | 65 | 63 | 2.9 | 68 |
| 568580 | 13 | 12 | 51 | 56 | 67 | 69 | 3 | 76 |

TABLE 15-continued

| ISIS NO | 0.406 μM | 0.813 μM | 1.63 μM | 3.25 μM | 6.5 μM | 13.0 μM | IC$_{50}$ (μM) | SEQ ID NO |
|---|---|---|---|---|---|---|---|---|
| 568589 | 32 | 46 | 61 | 69 | 78 | 88 | 1.1 | 85 |
| 568601 | 23 | 16 | 40 | 56 | 71 | 73 | 2.8 | 93 |
| 568605 | 37 | 45 | 61 | 68 | 76 | 77 | 1 | 97 |
| 568617 | 12 | 28 | 52 | 57 | 76 | 76 | 2.3 | 109 |
| 568635 | 21 | 27 | 40 | 61 | 82 | 90 | 2 | 127 |
| 568637 | 69 | 82 | 95 | 94 | 98 | 97 | <0.4 | 129 |
| 568637 | 15 | 9 | 35 | 43 | 59 | 67 | 4.6 | 129 |
| 568638 | 31 | 60 | 74 | 86 | 93 | 90 | 0.6 | 130 |
| 568640 | 41 | 47 | 61 | 84 | 90 | 97 | 0.8 | 132 |
| 568642 | 30 | 41 | 71 | 83 | 94 | 97 | 0.9 | 134 |
| 568643 | 33 | 51 | 74 | 83 | 92 | 93 | 0.7 | 135 |
| 568645 | 26 | 38 | 55 | 74 | 88 | 92 | 1.3 | 137 |
| 568646 | 15 | 37 | 57 | 72 | 88 | 94 | 1.4 | 138 |
| 568647 | 32 | 50 | 71 | 85 | 94 | 96 | 0.8 | 139 |
| 568650 | 44 | 51 | 70 | 79 | 87 | 90 | 0.6 | 142 |

Cells were plated at a density of 20,000 cells per well and transfected using electroporation with 39.1 nM, 156.3 nM, 625.0 nM, 2500 nM and 10,000 nM concentrations of antisense oligonucleotide, as specified in Table 16 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells, and are an average of two trials. The half maximal inhibitory concentration (IC$_{50}$) of each oligonucleotide is also presented. AGT mRNA levels were significantly reduced in a dose-dependent manner in antisense oligonucleotide treated cells.

TABLE 16

| ISIS NO | 39.1 nM | 156.3 nM | 625.0 nM | 2500 nM | 10,000 nM | IC$_{50}$ (μM) | SEQ ID NO |
|---|---|---|---|---|---|---|---|
| 568637 | -2 | 33 | 77 | 92 | 98 | 0.4 | 129 |
| 594622 | 15 | 52 | 84 | 96 | 97 | 0.3 | 163 |
| 594623 | 16 | 30 | 65 | 87 | 96 | 0.4 | 164 |
| 594624 | 13 | 37 | 74 | 92 | 96 | 0.4 | 129 |
| 594625 | 14 | 31 | 74 | 90 | 95 | 0.4 | 165 |
| 594626 | 11 | 20 | 58 | 84 | 94 | 0.6 | 166 |
| 594627 | 11 | 36 | 72 | 93 | 95 | 0.3 | 167 |
| 594628 | -30 | 4 | 51 | 78 | 87 | 1.1 | 168 |
| 594629 | -20 | -1 | 39 | 67 | 94 | 1.4 | 169 |
| 594630 | -10 | 13 | 35 | 52 | 78 | 2.4 | 170 |
| 594631 | 13 | 13 | 49 | 81 | 94 | 0.6 | 171 |
| 594632 | 2 | 27 | 60 | 85 | 97 | 0.6 | 172 |

Cells were plated at a density of 20,000 cells per well and transfected using electroporation with 312.5 nM, 625 nM, 1250 nM, 2500 nM and 5000 nM concentrations of antisense oligonucleotide, as specified in Tables 17 and 18 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells, and are an average of two trials. The half maximal inhibitory concentration (IC$_{50}$) of each oligonucleotide is also presented. AGT mRNA levels were significantly reduced in a dose-dependent manner in antisense oligonucleotide treated cells.

TABLE 17

| ISIS NO | 312.5 nM | 625 nM | 1250 nM | 2500 nM | 5000 nM | IC$_{50}$ (μM) | SEQ ID NO |
|---|---|---|---|---|---|---|---|
| 568637 | 51 | 71 | 84 | 89 | 93 | 0.2 | 129 |
| 594625 | 52 | 73 | 84 | 92 | 95 | 0.2 | 165 |
| 611933 | -7 | 7 | 5 | 1 | -2 | >5 | 313 |
| 612024 | 22 | 39 | 48 | 73 | 80 | 1.1 | 46 |
| 612025 | 21 | 15 | 36 | 59 | 64 | 2.2 | 654 |
| 612058 | 49 | 52 | 53 | 72 | 74 | 0.5 | 53 |
| 612063 | 22 | 38 | 56 | 63 | 65 | 1.3 | 689 |
| 612077 | 35 | 37 | 45 | 67 | 74 | 1.1 | 702 |
| 612101 | 32 | 59 | 68 | 83 | 93 | 0.6 | 725 |
| 612102 | 53 | 67 | 80 | 85 | 91 | 0.2 | 726 |
| 612104 | 41 | 51 | 50 | 72 | 83 | 0.7 | 728 |
| 612117 | 25 | 47 | 56 | 68 | 73 | 1.0 | 738 |
| 612134 | 40 | 43 | 49 | 67 | 79 | 0.9 | 894 |
| 612147 | 30 | 48 | 74 | 76 | 82 | 0.7 | 905 |
| 612151 | 33 | 38 | 51 | 71 | 81 | 1.0 | 909 |
| 612202 | 33 | 49 | 62 | 83 | 87 | 0.7 | 954 |
| 612315 | 7 | 33 | 55 | 72 | 76 | 1.3 | 779 |
| 612322 | 29 | 48 | 61 | 78 | 87 | 0.8 | 786 |
| 612323 | 42 | 60 | 82 | 87 | 91 | 0.4 | 787 |
| 612336 | 31 | 59 | 72 | 83 | 89 | 0.5 | 800 |
| 612344 | 31 | 39 | 69 | 76 | 85 | 0.8 | 808 |
| 612346 | 13 | 42 | 55 | 74 | 86 | 1.1 | 810 |
| 612347 | 29 | 46 | 71 | 83 | 90 | 0.7 | 811 |
| 612448 | 15 | 26 | 59 | 76 | 86 | 1.1 | 411 |
| 612491 | 16 | 14 | 33 | 29 | 49 | 8.0 | 452 |
| 612502 | 28 | 37 | 58 | 75 | 89 | 0.9 | 463 |
| 612503 | 44 | 55 | 75 | 83 | 91 | 0.4 | 464 |
| 612504 | 17 | 44 | 63 | 68 | 88 | 1.0 | 465 |
| 612505 | 43 | 50 | 66 | 76 | 90 | 0.5 | 466 |
| 612506 | 32 | 44 | 70 | 81 | 91 | 0.7 | 467 |
| 612507 | 24 | 45 | 49 | 70 | 81 | 1.0 | 468 |
| 612509 | 25 | 43 | 60 | 77 | 88 | 0.9 | 470 |
| 612514 | 44 | 41 | 59 | 79 | 92 | 0.6 | 475 |
| 612515 | 21 | 38 | 48 | 61 | 78 | 1.3 | 476 |
| 612516 | 38 | 47 | 74 | 79 | 93 | 0.6 | 477 |
| 612517 | 33 | 37 | 60 | 75 | 86 | 0.8 | 478 |
| 612519 | 14 | 16 | 38 | 54 | 64 | 2.4 | 480 |
| 612540 | 38 | 53 | 76 | 80 | 91 | 0.5 | 500 |
| 612541 | 38 | 51 | 58 | 83 | 90 | 0.6 | 501 |
| 612542 | 43 | 61 | 73 | 83 | 94 | 0.4 | 502 |
| 612543 | 34 | 53 | 64 | 81 | 91 | 0.6 | 503 |
| 612553 | 44 | 64 | 78 | 87 | 91 | 0.3 | 512 |
| 612559 | 36 | 59 | 74 | 89 | 95 | 0.5 | 517 |
| 612560 | 49 | 57 | 68 | 80 | 95 | 0.4 | 518 |
| 612567 | 38 | 50 | 57 | 83 | 85 | 0.6 | 524 |
| 612568 | 32 | 67 | 73 | 86 | 92 | 0.5 | 525 |
| 612569 | 27 | 54 | 71 | 78 | 93 | 0.7 | 526 |
| 612615 | 44 | 64 | 65 | 70 | 75 | 0.3 | 825 |
| 612658 | 19 | 23 | 43 | 57 | 58 | 2.3 | 865 |
| 612662 | 39 | 47 | 62 | 77 | 75 | 0.6 | 868 |

TABLE 18

| ISIS NO | 312.5 nM | 625 nM | 1250 nM | 2500 nM | 5000 nM | IC$_{50}$ (μM) | SEQ ID NO |
|---|---|---|---|---|---|---|---|
| 568637 | 57 | 79 | 89 | 95 | 97 | <0.3 | 129 |
| 594625 | 72 | 80 | 91 | 97 | 97 | <0.3 | 165 |
| 610015 | 41 | 70 | 72 | 84 | 92 | 0.3 | 239 |
| 612129 | 28 | 40 | 67 | 71 | 84 | 0.9 | 889 |
| 612135 | 41 | 40 | 47 | 62 | 73 | 1.0 | 68 |
| 612145 | 22 | 48 | 54 | 61 | 65 | 1.3 | 903 |
| 612185 | 16 | 29 | 36 | 45 | 62 | 2.7 | 83 |
| 612239 | 42 | 57 | 65 | 66 | 72 | 0.5 | 966 |
| 612252 | 23 | 22 | 30 | 61 | 60 | 2.4 | 96 |
| 612806 | 52 | 73 | 67 | 76 | 73 | <0.3 | 1011 |
| 612810 | 24 | 36 | 57 | 73 | 79 | 1.1 | 1015 |
| 612816 | 14 | 30 | 24 | 51 | 61 | 2.9 | 1021 |
| 612819 | 31 | 40 | 53 | 64 | 67 | 1.2 | 1024 |
| 612901 | 40 | 44 | 54 | 72 | 80 | 0.8 | 1080 |
| 612906 | 4 | 9 | 21 | 37 | 39 | 8.8 | 1085 |

Cells were plated at a density of 20,000 cells per well and transfected using electroporation with 37 nM, 111 nM, 333 nM, 1,000 nM and 3,000 nM concentrations of antisense oligonucleotide, as specified in Table 19 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells, and are an average of two trials. The half maximal inhibitory concentration ($IC_{50}$) of each oligonucleotide is also presented. AGT mRNA levels were significantly reduced in a dose-dependent manner in antisense oligonucleotide treated cells.

TABLE 19

| ISIS NO | 37 nM | 111 nM | 333 nM | 1000 nM | 3000 nM | $IC_{50}$ (µM) | SEQ ID NO |
|---|---|---|---|---|---|---|---|
| 568637 | 10 | 59 | 74 | 88 | 98 | 0.1 | 129 |
| 594622 | 46 | 58 | 65 | 89 | 96 | 0.1 | 163 |
| 594625 | 24 | 46 | 68 | 85 | 94 | 0.1 | 165 |
| 594628 | 13 | 48 | 53 | 74 | 91 | 0.2 | 168 |
| 609089 | 44 | 27 | 61 | 72 | 92 | 0.2 | 184 |
| 609094 | −3 | 41 | 67 | 87 | 96 | 0.2 | 130 |
| 622210 | 18 | 36 | 51 | 74 | 95 | 0.3 | 180 |
| 622212 | 38 | 51 | 85 | 88 | 97 | 0.1 | 182 |
| 622213 | 41 | 51 | 69 | 89 | 97 | 0.1 | 164 |
| 622215 | 36 | 40 | 61 | 84 | 89 | 0.1 | 165 |
| 622216 | 18 | 51 | 60 | 85 | 96 | 0.2 | 183 |
| 622220 | 48 | 51 | 63 | 81 | 90 | 0.1 | 186 |
| 622221 | 28 | 46 | 62 | 76 | 88 | 0.2 | 167 |
| 622224 | 8 | 32 | 55 | 77 | 91 | 0.3 | 130 |
| 622238 | 45 | 33 | 60 | 67 | 91 | 0.2 | 132 |

Cells were plated at a density of 20,000 cells per well and transfected using electroporation with 12.3 nM, 37 nM, 111 nM, 333 nM, 1,000 nM and 3,000 nM concentrations of antisense oligonucleotide, as specified in Table 20 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells, and are an average of two trials. The half maximal inhibitory concentration ($IC_{50}$) of each oligonucleotide is also presented. AGT mRNA levels were significantly reduced in a dose-dependent manner in antisense oligonucleotide treated cells.

TABLE 20

| ISIS NO | 12.3 nM | 37 nM | 111 nM | 333 nM | 1000 nM | 3000 nM | $IC_{50}$ (µM) | SEQ ID NO |
|---|---|---|---|---|---|---|---|---|
| 568637 | −5 | 6 | 24 | 69 | 86 | 95 | 0.2 | 129 |
| 594622 | 1 | −1 | 32 | 63 | 88 | 97 | 0.2 | 163 |
| 594624 | 9 | 0 | 54 | 57 | 87 | 92 | 0.2 | 129 |
| 594625 | 14 | 11 | 6 | 47 | 81 | 93 | 0.3 | 165 |
| 609086 | 26 | 3 | 35 | 72 | 92 | 97 | 0.1 | 181 |
| 609087 | −9 | 16 | 38 | 63 | 81 | 90 | 0.2 | 182 |
| 609088 | 11 | 9 | 44 | 61 | 86 | 97 | 0.2 | 183 |
| 609091 | 3 | 7 | 27 | 58 | 75 | 92 | 0.3 | 186 |
| 609095 | −4 | −15 | 20 | 67 | 88 | 98 | 0.3 | 189 |
| 622211 | 21 | 7 | 3 | 50 | 85 | 94 | 0.3 | 181 |
| 622214 | 8 | 19 | 39 | 69 | 89 | 96 | 0.1 | 129 |
| 622225 | 5 | 19 | 30 | 59 | 82 | 97 | 0.2 | 189 |

Cells were plated at a density of 20,000 cells per well and transfected using electroporation with 0.33 µM, 1.0 µM, 3.0 µM and 9.0 µM concentrations of antisense oligonucleotide, as specified in Table 21 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells. The half maximal inhibitory concentration ($IC_{50}$) of each oligonucleotide is also presented. AGT mRNA levels were significantly reduced in a dose-dependent manner in antisense oligonucleotide treated cells.

TABLE 21

| ISIS NO | 0.33 µM | 1.0 µM | 3.0 µM | 9.0 µM | $IC_{50}$ (µM) | SEQ ID NO |
|---|---|---|---|---|---|---|
| 568637 | 74 | 74 | 95 | 97 | 0.03 | 129 |
| 568637 | 52 | 80 | 89 | 95 | 0.2 | 129 |
| 610015 | 47 | 64 | 90 | 92 | 0.4 | 239 |
| 610015 | 25 | 51 | 79 | 92 | 1 | 239 |
| 654385 | 2 | 38 | 71 | 82 | 1.9 | 1827 |
| 654394 | 24 | 47 | 80 | 90 | 1.1 | 1836 |
| 654401 | 27 | 57 | 85 | 89 | 0.8 | 1843 |
| 654402 | 11 | 38 | 72 | 90 | 1.5 | 1844 |
| 654404 | 16 | 47 | 79 | 82 | 1.3 | 1846 |
| 654444 | 18 | 48 | 78 | 91 | 1.2 | 1886 |
| 654451 | 34 | 59 | 83 | 93 | 0.7 | 1893 |
| 654452 | 35 | 50 | 82 | 92 | 0.8 | 1894 |
| 654472 | 23 | 49 | 79 | 93 | 1 | 1914 |
| 654481 | 22 | 53 | 79 | 93 | 1 | 1923 |
| 654483 | 28 | 63 | 80 | 95 | 0.8 | 1925 |
| 654490 | 31 | 55 | 68 | 95 | 0.9 | 1932 |
| 654559 | 16 | 44 | 75 | 92 | 1.3 | 1979 |
| 654566 | 20 | 40 | 78 | 84 | 1.3 | 1986 |
| 654568 | 37 | 58 | 81 | 92 | 0.6 | 1988 |
| 654570 | 19 | 39 | 71 | 89 | 1.4 | 1990 |
| 654691 | 31 | 57 | 86 | 92 | 0.7 | 2003 |
| 654707 | 32 | 72 | 90 | 95 | 0.5 | 2015 |
| 654737 | 31 | 69 | 83 | 96 | 0.6 | 2018 |
| 654740 | 36 | 67 | 82 | 94 | 0.5 | 2020 |
| 654768 | 29 | 64 | 82 | 95 | 0.7 | 2027 |
| 654771 | 43 | 72 | 84 | 89 | 0.3 | 2028 |
| 654815 | 25 | 51 | 78 | 91 | 1 | 2035 |
| 654817 | 23 | 55 | 89 | 95 | 0.9 | 2037 |
| 654832 | 12 | 46 | 75 | 94 | 1.3 | 2044 |
| 654843 | 20 | 57 | 85 | 87 | 1 | 2037 |
| 654846 | 26 | 57 | 84 | 92 | 0.8 | 2039 |
| 654999 | 48 | 63 | 82 | 93 | 0.4 | 238 |
| 655002 | 29 | 64 | 86 | 94 | 0.7 | 267 |
| 655049 | 38 | 67 | 88 | 95 | 0.5 | 2018 |
| 655071 | 47 | 64 | 84 | 96 | 0.4 | 2037 |
| 655093 | 35 | 71 | 86 | 93 | 0.5 | 238 |
| 655095 | 28 | 54 | 80 | 86 | 0.9 | 1708 |
| 655102 | 42 | 54 | 77 | 90 | 0.6 | 236 |

Cells were plated at a density of 20,000 cells per well and transfected using electroporation with 0.44 µM, 1.33 µM, 4.0 µM and 12.0 µM concentrations of antisense oligonucleotide, as specified in Table 22 below. After a treatment period of approximately 16 hours, RNA was isolated from the cells and AGT mRNA levels were measured by quantitative real-time PCR. Human primer probe set RTS3721 was used to measure mRNA levels. AGT mRNA levels were adjusted according to total RNA content, as measured by RIBOGREEN®. Results are presented as percent inhibition of AGT, relative to untreated control cells. The half maximal inhibitory concentration ($IC_{50}$) of each oligonucleotide is also presented. AGT mRNA levels were significantly reduced in a dose-dependent manner in antisense oligonucleotide treated cells.

TABLE 22

| ISIS NO | 0.44 µM | 1.33 µM | 4.0 µM | 12.0 µM | IC$_{50}$ (µM) | SEQ ID NO |
|---|---|---|---|---|---|---|
| 610010 | 15 | 67 | 84 | 96 | 1.2 | 234 |
| 610010 | 20 | 64 | 85 | 97 | 1.1 | 234 |
| 610015 | 39 | 76 | 90 | 94 | 0.5 | 239 |
| 610015 | 43 | 73 | 91 | 98 | 0.5 | 239 |
| 619539 | 21 | 33 | 45 | 74 | 3.5 | 1258 |
| 619540 | 7 | 22 | 40 | 70 | 5.3 | 1259 |
| 619542 | 22 | 34 | 69 | 84 | 2.1 | 1261 |
| 619543 | 29 | 33 | 59 | 70 | 2.8 | 1262 |
| 619574 | 34 | 43 | 56 | 80 | 1.8 | 1293 |
| 619575 | 20 | 35 | 59 | 74 | 2.8 | 1294 |
| 619580 | 19 | 37 | 53 | 79 | 2.8 | 1299 |
| 619606 | 24 | 39 | 48 | 57 | 5.1 | 1325 |
| 619751 | 2 | 20 | 49 | 77 | 4.0 | 1470 |
| 619753 | 6 | 23 | 57 | 83 | 3.2 | 1472 |
| 619754 | 7 | 22 | 52 | 72 | 4.1 | 1473 |
| 619803 | 74 | 82 | 87 | 92 | <0.4 | 1522 |
| 619823 | 47 | 64 | 72 | 86 | 0.5 | 1542 |
| 619885 | 20 | 34 | 61 | 80 | 2.4 | 1604 |
| 619904 | 30 | 45 | 70 | 87 | 1.5 | 1623 |
| 619905 | 11 | 34 | 65 | 78 | 2.7 | 1624 |
| 619951 | 49 | 68 | 94 | 99 | 0.4 | 1667 |
| 619954 | 7 | 68 | 82 | 95 | 1.4 | 1670 |
| 619966 | 33 | 73 | 90 | 96 | 0.7 | 1682 |
| 619967 | 42 | 67 | 89 | 92 | 0.6 | 1683 |
| 619971 | 1 | 44 | 76 | 90 | 2.1 | 1687 |
| 619984 | 35 | 63 | 91 | 95 | 0.8 | 1700 |
| 619987 | 73 | 84 | 96 | 98 | <0.4 | 1703 |
| 619988 | 40 | 71 | 92 | 95 | 0.6 | 1704 |
| 619992 | 42 | 71 | 90 | 97 | 0.5 | 1708 |
| 619998 | 31 | 64 | 90 | 98 | 0.8 | 1714 |
| 620000 | 29 | 61 | 82 | 94 | 1.0 | 1716 |
| 620003 | 45 | 77 | 93 | 98 | 0.4 | 1719 |
| 620004 | 52 | 78 | 93 | 98 | 0.3 | 1720 |
| 620008 | 46 | 72 | 88 | 96 | 0.4 | 1724 |
| 620009 | 61 | 82 | 96 | 98 | <0.4 | 1725 |
| 620010 | 58 | 83 | 97 | 96 | <0.4 | 1726 |
| 620013 | 46 | 77 | 90 | 98 | 0.4 | 1729 |
| 620014 | 26 | 31 | 76 | 92 | 1.7 | 1730 |

Example 3: Tolerability and Efficacy of Single Dose Treatment of Antisense Oligonucleotides Targeting Human AGT in Transgenic Mouse Model A transgenic (Tg) mouse model "huAGT" was generated and the efficacy of antisense oligonucleotides was evaluated in this huAGT Tg model. Selected AGT antisense oligonucleotides from the in vitro studies were assessed in huAGT mice.

The huAGT transgenic mice were maintained on a 12-hour light/dark cycle and were fed ad libitum normal mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Treatment #1

Transgenic huAGT female mice, 10 weeks old, were divided into groups of 4 mice each. Eight groups received subcutaneous injections of antisense oligonucleotide at a dose of 20 mg/kg once per week over a course of 2.5 weeks (for three treatments). One group of mice received subcutaneous injections of PBS once per week for 2.5 weeks. The saline-injected group served as the control group to which oligonucleotide-treated groups were compared.

RNA Analysis, Treatment #1

On day 17, total RNA was extracted from liver and kidney of the transgenic mice for real-time PCR analysis and measurement of human AGT mRNA expression. Results are presented as percent inhibition, relative to PBS control, normalized with RIBOGREEN®. As shown in Table 23, treatment with most antisense oligonucleotides resulted in significant reduction of human AGT mRNA in comparison to the PBS control.

TABLE 23

Percent inhibition of huAGT mRNA in transgenic mouse liver and kidney relative to PBS control

| ISIS NO | liver | kidney | SEQ ID NO |
|---|---|---|---|
| 568605 | 42 | 20 | 97 |
| 568637 | 77 | 39 | 129 |
| 568638 | 56 | 11 | 130 |
| 568640 | 38 | 49 | 132 |
| 568642 | 0 | 7 | 134 |
| 568643 | 41 | 8 | 135 |
| 568647 | 49 | 32 | 139 |
| 568650 | 34 | 13 | 142 |

Plasma Chemistry Markers, Treatment #1

To evaluate the effect of antisense oligonucleotides on liver and kidney function, plasma levels of transaminases, total bilirubin and blood urea nitrogen (BUN) were measured using an automated clinical chemistry analyzer (Hitachi Olympus AU400e, Melville, N.Y.). The results are presented in Table 24. Antisense oligonucleotides causing changes in the levels of any of the liver or kidney function markers outside the expected range for antisense oligonucleotides were excluded from further studies.

TABLE 24

Plasma chemistry markers in female transgenic huAGT mice

| ISIS NO | ALT (U/L) | AST (U/L) | T. Bilirubin (mg/dL) | BUN (mg/dL) |
|---|---|---|---|---|
| PBS | 22 | 54 | 0.18 | 28 |
| 568605 | 40 | 82 | 0.19 | 28 |
| 568637 | 30 | 57 | 0.19 | 30 |
| 568638 | 39 | 67 | 0.21 | 27 |
| 568640 | 78 | 141 | 0.28 | 31 |
| 568642 | 127 | 227 | 0.39 | 25 |
| 568643 | 35 | 66 | 0.16 | 31 |
| 568647 | 26 | 46 | 0.18 | 27 |
| 568650 | 71 | 105 | 0.18 | 27 |

Body and Organ Weights, Treatment #1

Body weights of transgenic mice were measured at day 15 and the average body weight for each group is presented in the table below. Liver, spleen and kidney weights were measured at the end of the study, and are presented in Table 25. Antisense oligonucleotides that caused any changes in organ weights outside the expected range for antisense oligonucleotides were excluded from further studies.

TABLE 25

Body and organ weights (in grams)

| ISIS NO | body (g) | kidney (g) | liver (g) | spleen (g) |
|---|---|---|---|---|
| PBS | 18.8 | 0.3 | 0.9 | 0.08 |
| 568605 | 19.0 | 0.2 | 1.0 | 0.09 |
| 568637 | 19.3 | 0.3 | 1.0 | 0.08 |
| 568638 | 20.5 | 0.3 | 0.9 | 0.11 |
| 568640 | 19.7 | 0.3 | 1.0 | 0.09 |
| 568642 | 19.3 | 0.3 | 1.0 | 0.08 |
| 568643 | 19.9 | 0.3 | 1.0 | 0.09 |

TABLE 25-continued

Body and organ weights (in grams)

| ISIS NO | body (g) | kidney (g) | liver (g) | spleen (g) |
|---|---|---|---|---|
| 568647 | 20.6 | 0.3 | 1.0 | 0.09 |
| 568650 | 20.0 | 0.3 | 1.0 | 0.09 |

Treatment #2

Groups of two huAGT mice each received subcutaneous injections of antisense oligonucleotide at doses of 25 mg/kg/wk over the course of two weeks. One group of huAGT mice received subcutaneous injections of PBS as the control group to which oligonucleotide-treated groups were compared.

RNA Analysis, Treatment #2

On day 10, total RNA was extracted from livers of the transgenic mice for real-time PCR analysis and measurement of human AGT mRNA expression. The results were averaged for each group of two mice, and are presented as percent inhibition, relative to PBS control, normalized with RIBOGREEN®. As shown in Table 26, treatment with most antisense antisense oligonucleotides resulted in significant reduction of human AGT mRNA in comparison to the PBS control.

TABLE 26

Percent inhibition of human AGT mRNA in the transgenic mouse liver relative to the PBS control

| ISIS NO | % inhibit | SEQ ID NO |
|---|---|---|
| 568637 | 96 | 129 |
| 610010 | 66 | 234 |
| 610015 | 29 | 239 |
| 619967 | 59 | 1683 |
| 619984 | 56 | 1700 |
| 619987 | 25 | 1703 |
| 619988 | 38 | 1704 |
| 619992 | 70 | 1708 |
| 619998 | 75 | 1714 |
| 620000 | 75 | 1716 |
| 620003 | 56 | 1719 |
| 620004 | 27 | 1720 |
| 620008 | 4 | 1724 |
| 620009 | 41 | 1725 |
| 620010 | 72 | 1726 |
| 620013 | 65 | 1729 |

Plasma Chemistry Markers, Treatment #2

To evaluate the effect of antisense oligonucleotides on liver function, plasma levels of transaminases were measured using an automated clinical chemistry analyzer (Hitachi Olympus AU400e, Melville, N.Y.). The results were averaged for each group of two mice, and are presented in Table 27. Antisense oligonucleotides causing changes in the levels of any of the liver function markers outside the expected range for antisense oligonucleotides were excluded from further studies.

TABLE 27

Plasma chemistry markers in female transgenic huAGT mice

| ISIS NO | ALT (U/L) | AST (U/L) |
|---|---|---|
| PBS | 29 | 58 |
| 568637 | 29 | 82 |
| 610010 | 28 | 72 |
| 610015 | 71 | 103 |
| 619967 | 58 | 179 |
| 619984 | 23 | 41 |
| 619987 | 24 | 39 |
| 619988 | 29 | 107 |
| 619992 | 26 | 43 |
| 619998 | 25 | 71 |
| 620000 | 31 | 106 |
| 620003 | 24 | 46 |
| 620004 | 24 | 105 |
| 620008 | 24 | 51 |
| 620009 | 28 | 53 |
| 620010 | 24 | 38 |
| 620013 | 41 | 130 |

Body and Organ Weights, Treatment #2

Body weights of all treatment groups of huAGT mice were measured at day 1 and day 8, and animals were sacrificed and their livers harvested and weighed at day 10. The results were averaged for each group of two mice, and are presented in Table 28. Antisense oligonucleotides that caused any changes in organ weights outside the expected range for antisense oligonucleotides were excluded from further studies.

TABLE 28

Body and liver weights (in grams)

| ISIS NO | Day 1 body (g) | Day 8 body (g) | liver (g) |
|---|---|---|---|
| PBS | 18.3 | 18.8 | 1.0 |
| 568637 | 20.0 | 20.5 | 1.1 |
| 610010 | 19.0 | 19.4 | 1.1 |
| 610015 | 19.9 | 20.7 | 1.2 |
| 619967 | 19.8 | 19.9 | 1.0 |
| 619984 | 18.9 | 19.3 | 1.0 |
| 619987 | 20.2 | 20.5 | 1.2 |
| 619988 | 17.3 | 18.2 | 0.9 |
| 619992 | 18.3 | 19.4 | 1.0 |
| 619998 | 18.8 | 19.0 | 1.0 |
| 620000 | 19.7 | 20.4 | 1.1 |
| 620003 | 19.8 | 20.2 | 1.0 |
| 620004 | 21.0 | 21.6 | 1.1 |
| 620008 | 20.0 | 19.8 | 1.0 |
| 620009 | 18.9 | 19.0 | 1.0 |
| 620010 | 18.9 | 19.6 | 1.0 |
| 620013 | 19.7 | 20.3 | 1.1 |

Treatment #3

Groups of two huAGT mice each received subcutaneous injections of antisense oligonucleotide at doses of 25 mg/kg/wk over the course of two weeks. One group of four huAGT mice received subcutaneous injections of PBS as the control group to which oligonucleotide-treated groups were compared.

RNA Analysis, Treatment #3

On day 10, total RNA was extracted from livers of the transgenic mice for real-time PCR analysis and measurement of human AGT mRNA expression. The results were averaged for each group of two mice, and are presented as percent inhibition, relative to PBS control, normalized with RIBOGREEN®. As shown in Table 29, treatment with most antisense antisense oligonucleotides resulted in significant reduction of human AGT mRNA in comparison to the PBS control.

TABLE 29

Percent inhibition of human AGT mRNA in the transgenic mouse liver relative to the PBS control

| ISIS NO | % inhibit | SEQ ID NO |
|---|---|---|
| 568637 | 93 | 129 |
| 654401 | 63 | 1843 |
| 654451 | 43 | 1893 |
| 654452 | 48 | 1894 |
| 654472 | 69 | 1914 |
| 654481 | 0 | 1923 |
| 654483 | 58 | 1925 |
| 654490 | 80 | 1932 |
| 654568 | 70 | 1988 |
| 654691 | 81 | 2003 |
| 654707 | 32 | 2015 |
| 654740 | 0 | 2020 |
| 654771 | 0 | 2028 |
| 654999 | 76 | 238 |
| 655049 | 75 | 2018 |
| 655071 | 81 | 2037 |
| 655093 | 59 | 238 |

Plasma Chemistry Markers, Treatment #3

To evaluate the effect of antisense oligonucleotides on liver function, plasma levels of transaminases were measured using an automated clinical chemistry analyzer (Hitachi Olympus AU400e, Melville, N.Y.). The results were averaged for each group of two mice, and are presented in Table 30. Antisense oligonucleotides causing changes in the levels of any of the liver function markers outside the expected range for antisense oligonucleotides were excluded from further studies.

TABLE 30

Plasma chemistry markers in female transgenic huAGT mice

| ISIS NO | ALT (U/L) | AST (U/L) |
|---|---|---|
| PBS | 32 | 44 |
| 568637 | 36 | 41 |
| 654401 | 34 | 44 |
| 654451 | 52 | 82 |
| 654452 | 29 | 54 |
| 654472 | 50 | 78 |
| 654481 | 35 | 43 |
| 654483 | 28 | 62 |
| 654490 | 28 | 75 |
| 654568 | 35 | 60 |
| 654691 | 32 | 54 |
| 654707 | 48 | 65 |
| 654740 | 43 | 55 |
| 654771 | 59 | 166 |
| 654999 | 31 | 60 |
| 655049 | 27 | 61 |
| 655071 | 42 | 67 |
| 655093 | 26 | 50 |

Body and Organ Weights, Treatment #3

Body weights of all treatment groups of huAGT mice were measured at day 1 and day 8, and animals were sacrificed and their livers harvested and weighed at day 10. The results were averaged for each group of two mice, and are presented in Table 31. Antisense oligonucleotides that caused any changes in weights outside the expected range for antisense oligonucleotides were excluded from further studies.

TABLE 31

Body and liver weights

| ISIS NO | Day 1 body (g) | Day 8 body (g) | liver (g) |
|---|---|---|---|
| PBS | 26.7 | 27.4 | 1.5 |
| 568637 | 28.6 | 29.9 | 1.7 |
| 654401 | 29.1 | 30.9 | 1.9 |
| 654451 | 27.0 | 27.4 | 1.4 |
| 654452 | 26.6 | 27.2 | 1.4 |
| 654472 | 29.7 | 30.8 | 1.8 |
| 654481 | 28.3 | 29.4 | 1.6 |
| 654483 | 25.8 | 26.4 | 1.3 |
| 654490 | 28.6 | 28.7 | 1.5 |
| 654568 | 28.6 | 29.6 | 1.7 |
| 654691 | 29.6 | 31.1 | 1.7 |
| 654707 | 29.3 | 30.4 | 1.9 |
| 654740 | 29.1 | 29.8 | 1.7 |
| 654771 | 29.1 | 30.3 | 1.7 |
| 654999 | 28.2 | 29.0 | 1.6 |
| 655049 | 29.8 | 32.2 | 1.8 |
| 655071 | 28.5 | 30.4 | 1.8 |
| 655093 | 28.0 | 29.7 | 1.6 |

Treatment #4

Transgenic huAGT male mice, six weeks old, were divided into groups of 3-4 mice each. Eight groups received subcutaneous injections of antisense oligonucleotide at a dose of 5 mg/kg once per week over a course of 2 weeks. One group of mice received subcutaneous injections of PBS once per week for 2 weeks. The saline-injected group served as the control group to which oligonucleotide-treated groups were compared.

RNA Analysis, Treatment #4

On day 17, total RNA was extracted from liver and kidney of the transgenic mice for real-time PCR analysis and measurement of human AGT mRNA expression. Results are presented as percent inhibition, relative to PBS control, normalized with RIBOGREEN®. As shown in Table 32, treatment with most antisense oligonucleotides resulted in significant reduction of human AGT mRNA in comparison to the PBS control.

TABLE 32

Percent inhibition of huAGT mRNA in transgenic mouse liver and kidney relative to PBS control

| ISIS NO | liver | kidney | SEQ ID NO |
|---|---|---|---|
| 594622 | 81 | 90 | 163 |
| 594623 | 32 | 55 | 164 |
| 594624 | 79 | 67 | 129 |
| 594625 | 91 | 70 | 165 |
| 594626 | 76 | 81 | 166 |
| 594627 | 82 | 88 | 167 |
| 594628 | 28 | 22 | 168 |
| 594629 | 17 | 20 | 169 |
| 594630 | 37 | 35 | 170 |
| 594631 | 45 | 75 | 171 |
| 594632 | 50 | 51 | 172 |
| 568637 | 67 | 54 | 129 |

Plasma Chemistry Markers, Treatment #4

On day 15, to evaluate the effect of antisense oligonucleotides on liver and kidney function, plasma levels of transaminases, total bilirubin and blood urea nitrogen (BUN) were measured using an automated clinical chemistry analyzer (Hitachi Olympus AU400e, Melville, N.Y.). The results are presented in Table 33. Antisense oligonucleotides causing changes in the levels of any of the liver function markers outside the expected range for antisense oligonucleotides were excluded from further studies.

TABLE 33

Plasma chemistry markers in female transgenic huAGT mice

| ISIS NO | ALT (U/L) | AST (U/L) | T. Bilirubin (mg/dL) | BUN (mg/dL) |
|---|---|---|---|---|
| PBS | 77 | 118 | 0.18 | 40 |
| 594622 | 71 | 152 | 0.24 | 34 |
| 594623 | 57 | 92 | 0.18 | 36 |
| 594624 | 53 | 72 | 0.14 | 40 |
| 594625 | 92 | 116 | 0.17 | 36 |
| 594626 | 43 | 68 | 0.15 | 37 |
| 594627 | 50 | 67 | 0.17 | 35 |
| 594628 | 86 | 210 | 0.24 | 34 |
| 594629 | 55 | 68 | 0.16 | 31 |
| 594630 | 55 | 59 | 0.16 | 32 |
| 594631 | 32 | 44 | 0.15 | 36 |
| 594632 | 58 | 59 | 0.15 | 35 |
| 568637 | 110 | 371 | 0.22 | 31 |

Body and Organ Weights, Treatment #4

Body weights of transgenic mice were measured at days 1, 8 and 13 and the averages for each group are presented in the table below. On day 15, liver, spleen and kidney weights were also measured, and are presented in Table 34. Antisense oligonucleotides that caused any changes in weights outside the expected range for antisense oligonucleotides were excluded from further studies.

TABLE 34

Body and organ weights (in grams)

| ISIS NO | body (g) Day 1 | body (g) Day 8 | body (g) Day 13 | kidney (g) | liver (g) | spleen (g) |
|---|---|---|---|---|---|---|
| PBS | 20.4 | 21.6 | 21.5 | 0.3 | 1.2 | 0.08 |
| 594622 | 18.5 | 21.6 | 21.6 | 0.3 | 1.5 | 0.11 |
| 594623 | 18.1 | 20.4 | 20.3 | 0.3 | 1.2 | 0.06 |
| 594624 | 19.8 | 22.8 | 22.6 | 0.3 | 1.3 | 0.08 |
| 594625 | 20.3 | 22.2 | 22.1 | 0.3 | 1.3 | 0.06 |
| 594626 | 21.6 | 22.9 | 22.7 | 0.3 | 1.2 | 0.07 |
| 594627 | 21.9 | 22.8 | 22.7 | 0.3 | 1.2 | 0.07 |
| 594628 | 20.6 | 22.2 | 21.9 | 0.3 | 1.2 | 0.07 |
| 594629 | 20.8 | 22.1 | 22.0 | 0.3 | 1.2 | 0.07 |
| 594630 | 22.2 | 24.0 | 23.7 | 0.3 | 1.2 | 0.08 |
| 594631 | 20.2 | 21.9 | 21.6 | 0.3 | 1.1 | 0.07 |
| 594632 | 21.3 | 22.5 | 22.4 | 0.3 | 1.3 | 0.07 |
| 568637 | 20.1 | 21.4 | 21.5 | 0.3 | 1.2 | 0.05 |

Example 4: Tolerability and Efficacy of Multiple Dose Treatment of Antisense Oligonucleotides Targeting Human AGT in Transgenic Mouse Model Selected AGT antisense oligonucleotides from the single dose studies in huAGT transgenic mice were further assessed in dose response studies in huAGT transgenic mice.

The huAGT transgenic mice were maintained on a 12-hour light/dark cycle and were fed ad libitum normal mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Treatment #1

For a four point dose-response study, male huAGT mice were divided into 37 groups of four mice each. 36 groups received subcutaneous injections of antisense oligonucleotide at doses of 5, 10, 25 and 50 mg/kg/week for 2.5 weeks (three doses in total). One group of huAGT mice received subcutaneous injections of saline as a control group, to which oligonucleotide-treated groups were compared.

RNA Analysis, Treatment #1

On day 17, the huAGT mice were sacrificed, and total RNA was extracted from liver and kidney for real-time PCR analysis and measurement of human AGT mRNA expression. RT-PCR results are presented as average percent inhibition relative to the saline-treated control group, and normalized with RIBOGREEN®. As shown in Table 35, treatment with the selected antisense oligonucleotides resulted in significant reduction of human AGT mRNA in comparison to the saline control.

TABLE 35

Percent inhibition of human AGT mRNA in organs of huAGT mice treated with nine lead ASOs

| ISIS NO | mg/kg/wk | ED50 | Liver | Kidney | SEQ ID NO |
|---|---|---|---|---|---|
| 619998 | 50 | 7 | 96 | 71 | 1714 |
|  | 25 |  | 89 | 59 |  |
|  | 10 |  | 80 | 69 |  |
|  | 5 |  | 45 | 47 |  |
| 620003 | 50 | 10 | 80 | 69 | 1719 |
|  | 25 |  | 91 | 68 |  |
|  | 10 |  | 51 | 52 |  |
|  | 5 |  | 35 | 58 |  |
| 654451 | 50 | 9 | 94 | 56 | 1893 |
|  | 25 |  | 81 | 48 |  |
|  | 10 |  | 36 | 43 |  |
|  | 5 |  | 11 | 48 |  |
| 654452 | 50 | 8 | 82 | 53 | 1894 |
|  | 25 |  | 77 | 59 |  |
|  | 10 |  | 69 | 62 |  |
|  | 5 |  | 0 | 54 |  |
| 654472 | 50 | 5 | 81 | 41 | 1914 |
|  | 25 |  | 82 | 62 |  |
|  | 10 |  | 51 | 50 |  |
|  | 5 |  | 46 | 51 |  |
| 654481 | 50 | ~47 | 84 | 70 | 1923 |
|  | 25 |  | 31 | 54 |  |
|  | 10 |  | 47 | 59 |  |
|  | 5 |  | 52 | 67 |  |
| 654483 | 50 | 18 | 78 | 33 | 1925 |
|  | 25 |  | 77 | 45 |  |
|  | 10 |  | 84 | 73 |  |
|  | 5 |  | 11 | 41 |  |
| 654691 | 50 | 6 | 93 | 70 | 2003 |
|  | 25 |  | 87 | 78 |  |
|  | 10 |  | 43 | 70 |  |
|  | 5 |  | 54 | 70 |  |
| 654999 | 50 | 1 | 99 | 87 | 238 |
|  | 25 |  | 95 | 76 |  |
|  | 10 |  | 74 | 78 |  |
|  | 5 |  | 69 | 81 |  |

Body and Organ Weights, Treatment #1

Body weights of all treatment groups of huAGT mice were measured at days 1, 8 and 15 of the experiment. The results were averaged for each group of mice, and are presented in Table 36.

TABLE 36

Body Weight (BW) of huAGT mice treated with nine lead ASOs

| ISIS NO | mg/kg/wk | BW (grams) day 1 | day 8 | day 15 |
|---|---|---|---|---|
| saline | n/a | 28 | 29 | 29 |
| 619998 | 50 | 30 | 30 | 31 |
|  | 25 | 29 | 29 | 30 |
|  | 10 | 32 | 32 | 32 |
|  | 5 | 32 | 32 | 31 |
| 620003 | 50 | 31 | 32 | 32 |
|  | 25 | 32 | 32 | 33 |
|  | 10 | 30 | 30 | 30 |
|  | 5 | 32 | 32 | 32 |
| 654451 | 50 | 27 | 28 | 28 |
|  | 25 | 28 | 28 | 28 |
|  | 10 | 26 | 27 | 27 |
|  | 5 | 27 | 28 | 29 |
| 654452 | 50 | 28 | 29 | 28 |
|  | 25 | 27 | 28 | 28 |
|  | 10 | 27 | 28 | 27 |
|  | 5 | 28 | 28 | 29 |
| 654472 | 50 | 26 | 27 | 28 |
|  | 25 | 27 | 27 | 28 |
|  | 10 | 25 | 26 | 27 |
|  | 5 | 27 | 27 | 28 |
| 654481 | 50 | 28 | 29 | 29 |
|  | 25 | 33 | 34 | 34 |
|  | 10 | 32 | 33 | 33 |
|  | 5 | 30 | 32 | 32 |
| 654483 | 50 | 34 | 36 | 36 |
|  | 25 | 31 | 31 | 32 |
|  | 10 | 29 | 30 | 30 |
|  | 5 | 31 | 32 | 32 |
| 654691 | 50 | 29 | 30 | 30 |
|  | 25 | 30 | 31 | 31 |
|  | 10 | 30 | 31 | 32 |
|  | 5 | 30 | 30 | 30 |
| 654999 | 50 | 33 | 33 | 34 |
|  | 25 | 33 | 32 | 32 |
|  | 10 | 31 | 31 | 31 |
|  | 5 | 31 | 31 | 31 |

Treatment #2

Five potent antisense oligonucleotides targeting human AGT from previous studies (ISIS NOs. 620003, 654451, 654472, 654691 and 654999) were selected for another four point dose-response study and compared to ISIS 568637 which had been potent in vitro and potent and tolerable in single dose huAGT transgenic mice studies. In this study, huAGT mice were divided into 25 groups of three mice each. Groups received subcutaneous injections of antisense oligonucleotide at doses of 1, 4, 10 and 40 mg/kg for two injections over ten days. One group of three huAGT mice received subcutaneous injections of saline as a control group, to which oligonucleotide-treated groups were compared.

RNA Analysis, Treatment #2

On day 10, the antisense oligonucleotide treated huAGT mice were sacrificed, and total RNA was extracted from liver and kidney for real-time PCR analysis and measurement of human AGT mRNA expression. Results are presented as average percent inhibition of mRNA, relative to the PBS control group, and normalized with RIBOGREEN®. As shown in Table 37, treatment with the antisense oligonucleotides resulted in significant reduction of human AGT mRNA in comparison to the saline control.

TABLE 37

Percent inhibition of human AGT mRNA in organs of huAGT mice treated with five lead ASOs

| ISIS NO | mg/kg | ED50 AGT mRNA | Liver | Kidney | SEQ ID NO |
|---|---|---|---|---|---|
| 568637 | 1 | 4.1 | 16 | 54 | 129 |
|  | 4 |  | 42 | 69 |  |
|  | 10 |  | 82 | 82 |  |
|  | 40 |  | 96 | 90 |  |
| 620003 | 1 | 9.5 | 22 | 25 | 1719 |
|  | 4 |  | 29 | 32 |  |
|  | 10 |  | 54 | 50 |  |
|  | 40 |  | 81 | 49 |  |
| 654451 | 1 | 8.0 | 18 | 31 | 1893 |
|  | 4 |  | 24 | 32 |  |
|  | 10 |  | 59 | 49 |  |
|  | 40 |  | 87 | 58 |  |
| 654472 | 1 | 5.6 | 15 | 13 | 1914 |
|  | 4 |  | 26 | 38 |  |
|  | 10 |  | 64 | 59 |  |
|  | 40 |  | 82 | 66 |  |
| 654691 | 1 | 7.2 | 10 | 18 | 2003 |
|  | 4 |  | 28 | 53 |  |
|  | 10 |  | 63 | 61 |  |
|  | 40 |  | 95 | 65 |  |
| 654999 | 1 | 3.4 | 0 | 13 | 238 |
|  | 4 |  | 37 | 62 |  |
|  | 10 |  | 70 | 65 |  |
|  | 40 |  | 93 | 67 |  |

Plasma Chemistry Markers, Treatment #2

On day 10, plasma levels of transaminases, bilirubin and BUN were measured using an automated clinical chemistry analyzer (Hitachi Olympus AU400e, Melville, N.Y.) to evaluate the effect of antisense oligonucleotides on liver and kidney function. The results are presented in Table 38.

TABLE 38

Plasma chemistry markers in transgenic huAGT mice

| ISIS NO | mg/kg | ALT (U/L) | AST (U/L) | BUN (mg/dL) | T. Bil (mg/dL) |
|---|---|---|---|---|---|
| PBS | n/a | 34 | 62 | 29 | 0.12 |
| 568637 | 1 | 29 | 50 | 25 | 0.08 |
|  | 4 | 37 | 54 | 31 | 0.11 |
|  | 10 | 44 | 54 | 29 | 0.12 |
|  | 40 | 39 | 52 | 27 | 0.12 |
| 620003 | 1 | 32 | 59 | 27 | 0.16 |
|  | 4 | 44 | 53 | 34 | 0.10 |
|  | 10 | 40 | 60 | 29 | 0.14 |
|  | 40 | 33 | 34 | 26 | 0.11 |
| 654451 | 1 | 38 | 49 | 30 | 0.12 |
|  | 4 | 33 | 49 | 30 | 0.13 |
|  | 10 | 35 | 45 | 29 | 0.11 |
|  | 40 | 33 | 38 | 29 | 0.12 |
| 654472 | 1 | 39 | 69 | 28 | 0.17 |
|  | 4 | 31 | 54 | 30 | 0.11 |
|  | 10 | 30 | 70 | 30 | 0.15 |
|  | 40 | 33 | 41 | 30 | 0.10 |
| 654691 | 1 | 39 | 79 | 32 | 0.11 |
|  | 4 | 35 | 54 | 29 | 0.12 |
|  | 10 | 34 | 44 | 32 | 0.12 |
|  | 40 | 37 | 43 | 30 | 0.14 |
| 654999 | 1 | 34 | 56 | 31 | 0.11 |
|  | 4 | 38 | 51 | 32 | 0.13 |
|  | 10 | 29 | 53 | 33 | 0.09 |
|  | 40 | 30 | 42 | 28 | 0.09 |

Treatment #3

Five potent antisense oligonucleotides targeting human AGT from a previous dose response study (ISIS NOs. 568637, 594622, 594624, 594625 and 594627) were selected for a three-point dose-response study. In this study, huAGT mice were divided into 16 groups of three mice each. Groups received subcutaneous injections of antisense oligonucleotide at doses of 1, 5 and 15 mg/kg for two injections over the course of a week. One group of three huAGT mice received subcutaneous injections of saline as a control group, to which oligonucleotide-treated groups were compared.

RNA Analysis, Treatment #3

On day 8, total RNA was extracted from liver and kidneys of the transgenic mice for real-time PCR analysis and measurement of human AGT mRNA expression. Results are presented as percent inhibition, relative to PBS control, normalized with RIBOGREEN®. As shown in Table 39, treatment with most antisense oligonucleotides resulted in significant reduction of human AGT mRNA in comparison to the PBS control.

TABLE 39

Percent inhibition of huAGT mRNA in transgenic mouse liver and kidney relative to PBS control

|  | ISIS NO | Liver ED50 AGT mRNA | mg/kg | liver | kidney | SEQ ID NO |
|---|---|---|---|---|---|---|
| males | 594622 | 2.4 | 1 | 35 | 76 | 163 |
|  |  |  | 5 | 84 | 89 |  |
|  |  |  | 15 | 98 | 92 |  |
|  | 594624 | 3.9 | 1 | 23 | 10 | 129 |
|  |  |  | 5 | 84 | 70 |  |
|  |  |  | 15 | 96 | 83 |  |
|  | 594625 | 1.8 | 1 | 34 | 15 | 165 |
|  |  |  | 5 | 82 | 59 |  |
|  |  |  | 15 | 96 | 76 |  |
|  | 594627 | 1.4 | 1 | 17 | 71 | 167 |
|  |  |  | 5 | 78 | 87 |  |
|  |  |  | 15 | 91 | 91 |  |
|  | 568637 | 3.8 | 1 | 21 | 10 | 129 |
|  |  |  | 5 | 75 | 49 |  |
|  |  |  | 15 | 91 | 74 |  |
| females | 594625 | 1.7 | 1 | 45 | 77 | 165 |
|  |  |  | 5 | 86 | 88 |  |
|  |  |  | 15 | 98 | 96 |  |

Plasma Chemistry Markers, Treatment #3

On day 8, to evaluate the effect of antisense oligonucleotides on liver and kidney function, plasma levels of transaminases, total bilirubin and blood urea nitrogen (BUN) were measured using an automated clinical chemistry analyzer (Hitachi Olympus AU400e, Melville, N.Y.). The results are presented in Table 40.

TABLE 40

Plasma chemistry markers in male and female transgenic huAGT mice

|  | ISIS NO | mg/kg | ALT (U/L) | AST (U/L) | BUN (mg/dL) | T. Bilirubin (mg/dL) |
|---|---|---|---|---|---|---|
| males |  | PBS | 67 | 101 | 34 | 0.26 |
|  | 594622 | 1 | 34 | 43 | 36 | 0.14 |
|  |  | 5 | 92 | 151 | 32 | 0.29 |
|  |  | 15 | 132 | 167 | 30 | 0.30 |
|  | 594624 | 1 | 40 | 57 | 31 | 0.15 |
|  |  | 5 | 46 | 83 | 35 | 0.12 |
|  |  | 15 | 37 | 74 | 32 | 0.15 |
|  | 594625 | 1 | 74 | 166 | 33 | 0.23 |
|  |  | 5 | 55 | 67 | 34 | 0.18 |
|  |  | 15 | 63 | 89 | 34 | 0.15 |
|  | 594627 | 1 | 36 | 96 | 34 | 0.12 |
|  |  | 5 | 40 | 67 | 33 | 0.13 |
|  |  | 15 | 57 | 62 | 30 | 0.13 |

TABLE 40-continued

Plasma chemistry markers in male and female transgenic huAGT mice

|  | ISIS NO | mg/kg | ALT (U/L) | AST (U/L) | BUN (mg/dL) | T. Bilirubin (mg/dL) |
|---|---|---|---|---|---|---|
|  | 568637 | 1 | 38 | 69 | 33 | 0.14 |
|  |  | 5 | 33 | 48 | 32 | 0.15 |
|  |  | 15 | 74 | 81 | 28 | 0.14 |
| females |  | PBS | 39 | 61 | 33 | 0.17 |
|  | 594625 | 1 | 53 | 91 | 29 | 0.22 |
|  |  | 5 | 276 | 304 | 28 | 0.25 |
|  |  | 15 | 60 | 77 | 29 | 0.21 |

Body and Organ Weights, Treatment #3

Body weights of transgenic mice were measured at days 1, 8 and 13 and the averages for each group are presented in the table below. On day 15, liver, spleen and kidney weights were also measured, and are presented in Table 41.

TABLE 41

Body and organ weights (in grams)

|  | ISIS NO | mg/kg | body (g) Day 1 | body (g) Day 6 | kidney (g) | liver (g) | spleen (g) |
|---|---|---|---|---|---|---|---|
| males |  | PBS | 23.6 | 23.9 | 0.33 | 1.3 | 0.08 |
|  | 594622 | 1 | 23.3 | 23.7 | 0.30 | 1.3 | 0.07 |
|  |  | 5 | 22.7 | 23.5 | 0.34 | 1.4 | 0.09 |
|  |  | 15 | 23.9 | 24.4 | 0.33 | 1.8 | 0.08 |
|  | 594624 | 1 | 24.9 | 26.0 | 0.35 | 1.4 | 0.08 |
|  |  | 5 | 23.8 | 24.6 | 0.33 | 1.4 | 0.09 |
|  |  | 15 | 23.7 | 24.2 | 0.33 | 1.4 | 0.07 |
|  | 594625 | 1 | 23.3 | 23.7 | 0.31 | 1.3 | 0.07 |
|  |  | 5 | 22.1 | 23.0 | 0.30 | 1.4 | 0.08 |
|  |  | 15 | 23.8 | 24.6 | 0.32 | 1.6 | 0.09 |
|  | 594627 | 1 | 22.8 | 23.8 | 0.31 | 1.3 | 0.07 |
|  |  | 5 | 23.8 | 23.9 | 0.32 | 1.4 | 0.08 |
|  |  | 15 | 21.2 | 21.7 | 0.29 | 1.4 | 0.07 |
|  | 568637 | 1 | 22.6 | 23.3 | 0.30 | 1.3 | 0.08 |
|  |  | 5 | 22.7 | 22.9 | 0.31 | 1.2 | 0.07 |
|  |  | 15 | 23.0 | 23.6 | 0.31 | 1.4 | 0.08 |
| females |  | PBS | 17.6 | 18.0 | 0.25 | 1.0 | 0.07 |
|  | 594625 | 1 | 18.2 | 18.4 | 0.24 | 1.0 | 0.08 |
|  |  | 5 | 18.0 | 18.8 | 0.25 | 1.1 | 0.08 |
|  |  | 15 | 19.2 | 19.7 | 0.28 | 1.2 | 0.09 |

Example 5: Viscosity Assessment of Nine Lead Antisense Oligonucleotides Targeting AGT The viscosity of the 9 antisense oligonucleotides was measured with the aim of screening out antisense oligonucleotides which have a viscosity more than 40 cP. Oligonucleotides having a viscosity greater than 40 cP are considered too viscous to be administered to any subject.

Antisense oligonucleotides (32-35 mg) were weighed into a glass vial, 120 µL of water was added and the antisense oligonucleotide was dissolved into solution by heating the vial at 50° C. Part of (75 µL) the pre-heated sample was pipetted to a micro-viscometer (Cambridge). The temperature of the micro-viscometer was set to 25° C. and the viscosity of the sample was measured. Another part (20 µL) of the pre-heated sample was pipetted into 10 mL of water for UV reading at 260 nM at 85° C. (Cary UV instrument). The results are presented in Table 42 and indicate that the antisense oligonucleotides tested do not exceed a viscosity of 40 cP.

TABLE 42

Viscosity Data for ASOs targeting AGT

| ISIS NO | Chemistry | cP |
|---|---|---|
| 619998 | 5-10-5 MOE | 29 |
| 620003 | 5-10-5 MOE | 12 |
| 654451 | 5-10-5 MOE | 25 |
| 654452 | 5-10-5 MOE | 13 |
| 654472 | 5-10-5 MOE | 11 |
| 654481 | 5-10-5 MOE | 12 |
| 654483 | 5-10-5 MOE | 28 |
| 654691 | 3-10-4 MOE | 23 |
| 654999 | 5-8-7 MOE | 34 |

Example 6: Tolerability of Nine Lead Antisense Oligonucleotides (ASOs) Targeting Human AGT in CD1 Mice CD1® mice (Charles River, Mass.) are a multipurpose mice model, frequently utilized for safety and efficacy testing. The mice were treated with antisense oligonucleotides selected from studies described above and evaluated for changes in the levels of various plasma chemistry markers.

The 9 antisense oligonucleotides identified in the examples, above, were tested in CD1 mice for tolerability. The mice were divided into groups of four mice per group, and were injected subcutaneously twice a week for six weeks with 50 mg/kg of antisense oligonucleotides (100 mg/kg/week dose). One group of male CD1 mice was injected subcutaneously twice a week for six weeks with PBS. Mice were euthanized 48 hours after the last dose, and organs and plasma were harvested for further analysis.

Body and Organ Weights

Body weights of ASO-treated CD1 mice were measured weekly. On day 43, the mice were sacrificed and organs harvested and weighed. The body and organ weights in grams (g) at the end of the study are shown in Table 43.

TABLE 43

Body and organ weights (grams) of CD1 mice treated with nine lead ASOs

| ISIS NO | body day 41 | liver | kidney | spleen |
|---|---|---|---|---|
| PBS | 39.1 | 2.2 | 0.7 | 0.2 |
| 619998 | 42.5 | 2.5 | 0.6 | 0.3 |
| 620003 | 38.9 | 2.5 | 0.6 | 0.2 |
| 654451 | 31.6 | 1.8 | 0.5 | 0.1 |
| 654452 | 37.1 | 2.3 | 0.6 | 0.2 |
| 654472 | 37.2 | 2.3 | 0.6 | 0.1 |
| 654481 | 37.7 | 2.2 | 0.6 | 0.2 |
| 654483 | 35.1 | 2.3 | 0.6 | 0.2 |
| 654691 | 37.5 | 2.3 | 0.7 | 0.3 |
| 654999 | 35.9 | 2.2 | 0.5 | 0.5 |

Plasma Chemistry Markers

To evaluate the effect of the oligonucleotides on liver and kidney function, plasma levels of ALT (alanine transaminase) and AST (aspartate transaminase), bilirubin, creatinine, and BUN were measured using an automated clinical chemistry analyzer (Hitachi Olympus AU400e, Melville, N.Y.).

The results were averaged for each group, and a selection of these is presented in Table 44.

TABLE 44

Plasma chemistry markers in CD1 mice

| ISIS NO | Compound | ALT (U/L) | AST (U/L) | BUN (mg/dL) | Cre (mg/dL) | T. Bilirubin (mg/dL) |
|---|---|---|---|---|---|---|
| PBS | N/A | 25 | 41 | 28 | 0.15 | 0.14 |
| 619998 | 5-10-5 MOE | 79 | 124 | 28 | 0.16 | 0.12 |
| 620003 | 5-10-5 MOE | 30 | 46 | 29 | 0.16 | 0.14 |
| 654451 | 5-10-5 MOE | 46 | 84 | 22 | 0.08 | 0.16 |
| 654452 | 5-10-5 MOE | 122 | 182 | 25 | 0.10 | 0.11 |
| 654472 | 5-10-5 MOE | 50 | 65 | 29 | 0.11 | 0.11 |
| 654481 | 5-10-5 MOE | 35 | 50 | 25 | 0.08 | 0.14 |
| 654483 | 5-10-5 MOE | 107 | 108 | 25 | 0.09 | 0.17 |
| 654691 | 3-10-4 MOE | 95 | 109 | 25 | 0.11 | 0.13 |
| 654999 | 5-8-7 MOE | 71 | 135 | 28 | 0.11 | 0.10 |

In a separate study antisense compounds ISIS 568637, 594622, 594624, 594625 and 594627 were also tested in CD1 mice, but exhibited some tolerability issues and the study was terminated early.

Example 7: Tolerability of Nine Lead Antisense Oligonucleotides (ASOs) Targeting Human AGT in Sprague-Dawley Rats Sprague-Dawley (SD) rats are a multipurpose model used for safety and efficacy evaluations. The SD rats were treated with 9 antisense oligonucleotides selected from the studies described in the Examples above and evaluated for changes in the levels of various plasma chemistry markers.

Treatment

Male SD rats were maintained on a 12-hour light/dark cycle and fed ad libitum with Purina normal rat chow. The rats were divided into groups of four rats per group, and each group was injected subcutaneously with 100 mg/kg/week for six weeks. Forty eight hours after the last dose, rats were euthanized and organs and plasma were harvested for further analysis.

Organ Weights

Liver, spleen and kidney weights of antisense oligonucleotide treated rats were measured at the end of the study. The body and organ weights are shown in grams in Table 45.

TABLE 45

Body and organ weights (grams) of Sprague-Dawley rats treated with nine lead ASOs

| ISIS NO | body | kidney | liver | spleen |
|---|---|---|---|---|
| 619998 | 333 | 3.0 | 12.1 | 2.6 |
| 620003 | 361 | 2.9 | 11.7 | 1.4 |
| 654451 | 316 | 2.7 | 13.4 | 1.5 |
| 654452 | 320 | 2.5 | 11.6 | 0.9 |
| 654472 | 361 | 3.0 | 13.1 | 1.5 |
| 654481 | 370 | 3.2 | 11.4 | 1.3 |
| 654483 | 366 | 3.3 | 13.5 | 1.2 |
| 654691 | 288 | 3.1 | 14.3 | 2.1 |
| 654999 | 344 | 2.7 | 11.5 | 2.0 |

Liver and Kidney Function

To evaluate the effect of the 9 antisense oligonucleotides on liver and kidney function, plasma levels of ALT (alanine transaminase) and AST (aspartate transaminase), albumin, BUN, creatinine and bilirubin were measured using an automated clinical chemistry analyzer (Hitachi Olympus AU400e, Melville, N.Y.), and total urine protein and urine creatinine levels were measured, and the ratio of total urine protein to creatinine (P/C Ratio) was determined.

Results of each group were averaged, and a selection of these is presented in Table 46.

TABLE 46

Liver and kidney function markers in Sprague-Dawley rats

| | | plasma | | | | | | urine | | |
|---|---|---|---|---|---|---|---|---|---|---|
| ISIS NO | Compound | ALT (U/L) | AST (U/L) | Albumin (g/dL) | BUN (mg/dL) | Cre (mg/dL) | T. bil (mg/dL) | Cre (mg/dL) | Total protein (mg/dL) | Urine P/C Ratio |
| PBS | N/A | 28 | 72 | 3.2 | 19 | 0.28 | 0.08 | 86 | 88 | 1 |
| 619998 | 5-10-5 MOE | 57 | 125 | 2.8 | 28 | 0.31 | 0.10 | 76 | 251 | 3 |
| 620003 | 5-10-5 MOE | 54 | 106 | 3.1 | 25 | 0.30 | 0.09 | 81 | 356 | 4 |
| 654401 | 5-10-5 MOE | 69 | 136 | 3.3 | 25 | 0.36 | 0.12 | 64 | 343 | 6 |
| 654451 | 5-10-5 MOE | 62 | 149 | 2.8 | 28 | 0.28 | 0.10 | 37 | 209 | 6 |
| 654452 | 5-10-5 MOE | 159 | 196 | 3.0 | 30 | 0.34 | 0.11 | 44 | 356 | 8 |
| 654472 | 5-10-5 MOE | 44 | 98 | 3.1 | 28 | 0.36 | 0.09 | 69 | 413 | 6 |
| 654481 | 5-10-5 MOE | 43 | 101 | 3.2 | 26 | 0.37 | 0.09 | 56 | 323 | 6 |
| 654483 | 5-10-5 MOE | 42 | 87 | 3.0 | 28 | 0.30 | 0.08 | 54 | 360 | 6 |
| 654691 | 3-10-4 MOE | 41 | 94 | 2.7 | 31 | 0.31 | 0.08 | 40 | 237 | 6 |
| 654999 | 5-8-7 MOE | 40 | 120 | 2.8 | 28 | 0.30 | 0.09 | 47 | 335 | 7 |

Histology

Liver and kidney from antisense oligonucleotide-treated rats were microscopically examined, and no remarkable treatment-related adverse finding was observed.

In a separate study, antisense compounds ISIS 568637, 594622, 594624, 594625 and 594627 were also tested in SD rats, but exhibited some tolerability issues and the study was terminated early.

Example 8: Potency in Cynomolgus Monkey Hepatocytes of Nine Lead Antisense Oligonucleotides (ASOs) Targeting Human AGT At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the antisense oligonucleotides used in the cynomolgus monkeys were compared to a rhesus monkey sequence for complementarity. It is expected that antisense oligonucleotides with complementarity to the rhesus monkey sequence are fully cross-reactive with the cynomolgus monkey sequence as well.

The human antisense oligonucleotides tested had at most 3 mismatches with the rhesus genomic sequence (GENBANK Accession NW_001109259.1 truncated from nucleotide 16090000 to Ser. No. 16/106,000, designated herein as SEQ ID NO: 7). The greater the complementarity between the human oligonucleotide and the rhesus monkey sequence, the more likely the human oligonucleotide can cross-react with the rhesus monkey sequence and the cynomolgus monkey sequence. The start and stop sites of each oligonucleotide to SEQ ID NO: 7 is presented in Table 47. "Start site" indicates the 5'-most nucleotide to which the gapmer is targeted in the rhesus monkey gene sequence.

Nine antisense oligonucleotides exhibiting significant inhibition of AGT mRNA and tolerability in previous studies were selected and tested at various doses in cryopreserved individual male cynomolgus monkey primary hepatocytes. These 9 lead antisense oligonucleotides are described in the table below.

TABLE 47

ASO complementarity to the rhesus AGT genomic sequence (SEQ ID NO: 7)

| ISIS NO | Target Start Site | Target Stop Site | Sequence | Chemistry | # mismatches in Rhesus | SEQ ID NO |
|---|---|---|---|---|---|---|
| 619998 | 13777 | 13796 | TCGGTTGGAATTCTTTTTGG | 5-10-5 MOE | 0 | 1714 |
| 620003 | 13792 | 13811 | TCACAAACAAGCTGGTCGGT | 5-10-5 MOE | 0 | 1719 |
| 654451 | N/A | N/A | TGGAACAGTAGTCCCGCGCT | 5-10-5 MOE | 2 | 1893 |
| 654452 | N/A | N/A | TTGGAACAGTAGTCCCGCGC | 5-10-5 MOE | 2 | 1894 |
| 654472 | 13791 | 13810 | CACAAACAAGCTGGTCGGTT | 5-10-5 MOE | 0 | 1914 |
| 654481 | 13822 | 13841 | CTCAACTTGAAAAGGGAACA | 5-10-5 MOE | 0 | 1923 |
| 654483 | 13825 | 13844 | GTTCTCAACTTGAAAAGGGA | 5-10-5 MOE | 0 | 1925 |
| 654691 | N/A | N/A | TCGCTGATTTGTCCGGG | 3-10-4 MOE | 3 | 2003 |
| 654999 | N/A | N/A | ACACATCGCTGATTTGTCCG | 5-8-7 MOE | 3 | 238 |

Cynomolgus monkey primary hepatocytes were plated at a density of 35,000 cells per well and transfected using electroporation with 0.156 µM, 0.313 µM, 0.625 µM, 1.25 µM, 2.5 µM, 5.0 µM, 10.0 µM and 20.0 µM concentrations of antisense oligonucleotide, as specified in Table 48 below. After a treatment period of approximately 24 hours, the cells were washed and lysed, and RNA was isolated. Monkey AGT mRNA levels were measured by quantitative real-time PCR, using primer probe set RTS4039. AGT mRNA target levels were adjusted according to total RNA content, as measured by RIBOGREEN®. Results are presented as percent inhibition of AGT, relative to untreated control cells.

TABLE 48

Dose response in primary hepatocytes from cynomolgus monkeys

| ISIS NO | 0.156 µM | 0.313 µM | 0.625 µM | 1.25 µM | 2.5 µM | 5.0 µM | 10.0 µM | 20.0 µM | IC50 (µM) | SEQ ID NO |
|---|---|---|---|---|---|---|---|---|---|---|
| 619998 | 3 | 1 | 0 | 13 | 20 | 31 | 36 | 64 | 13.9 | 1714 |
| 620003 | 9 | 7 | 15 | 27 | 30 | 62 | 76 | 80 | 3.0 | 1719 |
| 654451 | 13 | 24 | 20 | 30 | 38 | 42 | 47 | 29 | 10.6 | 1893 |
| 654452 | 13 | 13 | 25 | 47 | 44 | 41 | 62 | 35 | >20 | 1894 |
| 654472 | 12 | 24 | 22 | 37 | 39 | 55 | 74 | 78 | 3.4 | 1914 |
| 654481 | 0 | 14 | 27 | 26 | 43 | 48 | 53 | 45 | >20 | 1923 |
| 654483 | 25 | 24 | 39 | 46 | 61 | 50 | 56 | 61 | 3.2 | 1925 |
| 654691 | 0 | 12 | 18 | 0 | 23 | 18 | 19 | 24 | >20 | 2003 |
| 654999 | 0 | 19 | 0 | 0 | 9 | 17 | 37 | 42 | >20 | 238 |

Most monkey AGT mRNA levels were significantly reduced in a dose-dependent manner in antisense oligonucleotide treated cells.

Example 9: Effect of Antisense Oligonucleotides Targeting Human AGT in Cynomolgus Monkeys In a 12-week dose response study, cynomolgus monkeys were treated with the nine antisense oligonucleotides selected from studies described in the Examples above. Antisense oligonucleotide efficacy and tolerability, as well as their pharmacokinetic profile in the liver and kidney, were evaluated.

Treatment

Prior to the study, the monkeys were kept in quarantine during which the animals were observed daily for general health. The monkeys were two to four years old and weighed 2-4 kg. Ten groups of five randomly assigned male cynomolgus monkeys each were injected subcutaneously with antisense oligonucleotide or PBS. The monkeys were dosed once a week for 12 weeks with 40 mg/kg/wk of antisense oligonucleotide for a total of 15 doses (monkeys received a loading treatment of two doses of 40 mg/kg in weeks 1 and 2). A control group of cynomolgus monkeys was injected with PBS in a similar manner and served as the control group.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. At the end of the 12-week study, the monkeys were sacrificed and organs removed. The protocols described in the Example were approved by the Institutional Animal Care and Use Committee (IACUC).

Body and Organ Weights

Body weight was assessed weekly, and no remarkable effects of the antisense oligonucleotides on body weight were observed. Body weight at day 77 and organ weights at day 79 were measured and are presented in Table 49 below

TABLE 49

Body and organ weights (grams) of cynomolgus monkeys treated with nine lead ASOs

| | Weight (g) | | | | |
|---|---|---|---|---|---|
| ISIS NO | body (day 77) | heart | kidney | liver | spleen |
| PBS | 2524 | 10.2 | 12.2 | 51.8 | 2.7 |
| 619998 | 2520 | 9.3 | 23.4 | 73.9 | 4.4 |
| 620003 | 2638 | 9.5 | 14.5 | 67.8 | 3.3 |
| 654451 | 2488 | 9.4 | 15.9 | 68.5 | 3.0 |
| 654452 | 2510 | 9.8 | 14.2 | 60.8 | 3.1 |
| 654472 | 2623 | 9.8 | 14.8 | 62.1 | 4.0 |
| 654481 | 2549 | 9.6 | 14.2 | 59.8 | 4.0 |
| 654483 | 2525 | 10.0 | 15.8 | 68.6 | 4.0 |
| 654691 | 2497 | 8.8 | 15.3 | 67.9 | 4.3 |
| 654999 | 2590 | 10.1 | 16.6 | 69.1 | 5.7 |

Pharmacodynamics

Plasma, serum and urine were collected for analysis during the study. To evaluate the effect of the nine lead antisense oligonucleotides on liver and kidney function, on day 79, plasma levels of ALT (alanine transaminase) and AST (aspartate transaminase), BUN and bilirubin were measured using an automated clinical chemistry analyzer (Hitachi Olympus AU400e, Melville, N.Y.). As shown in Table 50, no significant effects on ALT, AST, BUN and bilirubin were observed.

TABLE 50

Plasma chemistry markers in monkeys treated with antisense oligonucleotides

| ISIS NO | ALT (U/L) | AST (U/L) | BUN (mg/dL) | T. Bil (mg/dL) |
|---|---|---|---|---|
| PBS | 54 | 87 | 25.1 | 0.20 |
| 619998 | 74 | 98 | 36.6 | 0.16 |
| 620003 | 53 | 87 | 24.9 | 0.16 |
| 654451 | 61 | 74 | 30.1 | 0.13 |
| 654452 | 63 | 100 | 25.8 | 0.20 |
| 654472 | 62 | 77 | 27.1 | 0.16 |
| 654481 | 58 | 63 | 21.7 | 0.16 |
| 654483 | 70 | 78 | 25.0 | 0.14 |
| 654691 | 57 | 97 | 26.4 | 0.14 |
| 654999 | 62 | 111 | 23.2 | 0.14 |

In addition, no significant changes in ECG, blood pressure, plasma electrolytes, proteinuria, inflammatory response (e.g., CRP levels) or renal accumulation were observed. In general, the antisense oligonucleotides were well tolerated.

RNA Analysis

At the end of the study, RNA was extracted from monkey livers and kidneys for real-time PCR analysis of measurement of mRNA expression of AGT. Primer probe set RTS4039 was used, and the results for each group were averaged and presented as percent inhibition of mRNA, relative to the PBS control, normalized with RIBOGREEN®. As shown in Table 51, treatment with antisense oligonucleotides resulted in variable effects on AGT mRNA levels.

TABLE 51

Percent inhibition of AGT mRNA in the cynomolgus monkey liver relative to the PBS control

| ISIS NO | % inhibit | SEQ ID NO |
|---|---|---|
| 619998 | 75 | 1714 |
| 620003 | 40 | 1719 |
| 654451 | 33 | 1893 |
| 654452 | 0 | 1894 |
| 654472 | 9 | 1914 |
| 654481 | 1 | 1923 |
| 654483 | 38 | 1925 |
| 654691 | 36 | 2003 |
| 654999 | 3 | 238 |

Example 10: Tolerability of GalNAc Conjugated Antisense Oligonucleotides in CD-1 Mice A lead candidate (ISIS 654472) 5-10-5 full phosphorothioate MOE gapmer was chosen from studies above and used as the basis for design of six 5'-Trishexylamino-(THA)-C6 GalNAc$_3$ (a.k.a. "GalNAc")-conjugated 5-10-5 MOE gapmers having the same nucleotide sequence but differences in the backbone structure, as described in Table 52 below. "s" is a phosphorothioate internucleoside linkage. "o" is a phosphodiester internucleoside linkage. "A" is an adenine nucleobase. "mC" is a 5'-methylcytosine nucleobase. "G" is a guanine nucleobase. "T" is a thymine nucleobase. "e" indicates a MOE modification. "d" indicates deoxyribose.

TABLE 52

GalNAc-conjugated ASOs and unconjugated parent ASO

| ISIS NO | Chemistry notation | | SEQ ID NO |
|---|---|---|---|
| 654472 (parent) | mCes Aes mCes Aes Aes Ads mCds Ads Ads Gds mCds Tds Gds Gds Tds mCes Ges Ges Tes Te | (PS) | 1914 |
| 757456 | mCes Aes mCes Aes Aes Ads mCds Ads Ads Gds mCds Tds Gds Gds Tds mCes Ges Ges Tes Te | (PS) GalNAc | 1914 |
| 757457 | mCes Aeo mCeo Aeo Aeo Ads mCds Ads Ads Gds mCds Tds Gds Gds Tds mCeo Geo Ges Tes Te | (mixed backbone) GalNAc | 1914 |
| 775493 | mCes Aeo mCeo Aeo Aes Ads mCds Ads Ads Gds mCds Tds Gds Gds Tds mCeo Geo Ges Tes Te | (mixed backbone) GalNAc | 1914 |
| 775494 | mCes Aes mCeo Aeo Aes Ads mCds Ads Ads Gds mCds Tds Gds Gds Tds mCeo Geo Ges Tes Te | (mixed backbone) GalNAc | 1914 |
| 775495 | mCes Aeo mCes Aeo Aes Ads mCds Ads Ads Gds mCds Tds Gds Gds Tds mCeo Ges Geo Tes Te | (mixed backbone) GalNAc | 1914 |
| 775496 | mCes Aes mCeo Aes Aes Ads mCds Ads Ads Gds mCds Tds Gds Gds Tds mCes Geo Ges Tes Te | (mixed backbone) GalNAc | 1914 |

For a three-point dose response study, sixteen groups of four CD1 mice each were subcutaneously injected with 10 mg/kg/week of GalNAc-conjugated antisense oligonucleotide over the course of four weeks. One group of mice was injected subcutaneously twice a week for six weeks with PBS. Body weights of ASO-treated CD1 mice were measured weekly. Mice were euthanized 48 hours after the last dose, and organs and plasma were harvested for further analysis. Plasma and urine were collected and plasma levels of transaminases, bilirubin and BUN were measured using an automated clinical chemistry analyzer (Hitachi Olympus AU400e, Melville, N.Y.) to evaluate the effect of antisense oligonucleotides on liver and kidney function. At the end of the experiment, the livers, kidneys and spleens were harvested and weighed.

The results were averaged for each group is presented in Table 53.

TABLE 53

Plasma chemistry markers in CD1 mice treated with GalNAc-conjugated ASOs

| ISIS NO | mg/ kg | Weight (g) | | | | ALT (U/L) | AST (U/L) | BUN (mg/ dL) | T. Bil (mg/ dL) |
|---|---|---|---|---|---|---|---|---|---|
| | | body (day 29) | kidney | liver | spleen | | | | |
| PBS | n/a | 36.1 | 0.58 | 2.1 | 0.1 | 31 | 41 | 25.8 | 0.14 |
| 757456 | 20 | 39.3 | 0.64 | 2.5 | 0.1 | 28 | 31 | 24.2 | 0.18 |
| | 10 | 38.1 | 0.56 | 2.3 | 0.1 | 38 | 74 | 24.8 | 0.22 |
| | 5 | 36.1 | 0.54 | 2.1 | 0.1 | 39 | 59 | 27.7 | 0.21 |
| 757457 | 20 | 40.6 | 0.59 | 2.4 | 0.2 | 34 | 38 | 26.2 | 0.23 |
| | 10 | 38.7 | 0.60 | 2.2 | 0.1 | 24 | 29 | 23.1 | 0.26 |
| | 5 | 39.1 | 0.58 | 2.2 | 0.2 | 39 | 46 | 29.0 | 0.20 |
| 775493 | 20 | 36.3 | 0.59 | 2.0 | 0.1 | 36 | 51 | 28.3 | 0.21 |
| | 10 | 38.6 | 0.58 | 2.2 | 0.1 | 30 | 45 | 25.0 | 0.34 |
| | 5 | 37.1 | 0.58 | 2.3 | 0.1 | 23 | 32 | 26.5 | 0.15 |
| 775494 | 20 | 37.9 | 0.56 | 2.0 | 0.2 | 47 | 55 | 29.1 | 0.31 |
| | 10 | 36.4 | 0.59 | 2.1 | 0.3 | 25 | 34 | 25.4 | 0.20 |
| | 5 | 38.4 | 0.59 | 2.0 | 0.1 | 35 | 69 | 24.9 | 0.21 |
| 775495 | 20 | 39.3 | 0.67 | 2.3 | 0.2 | 42 | 86 | 23.7 | 0.19 |
| | 10 | 37.0 | 0.55 | 2.1 | 0.1 | 34 | 44 | 25.1 | 0.21 |
| | 5 | 38.1 | 0.62 | 2.2 | 0.1 | 20 | 28 | 22.5 | 0.28 |
| 775496 | 20 | 37.0 | 0.58 | 2.1 | 0.2 | 32 | 38 | 24.7 | 0.15 |
| | 10 | 36.4 | 0.59 | 1.9 | 0.2 | 38 | 42 | 25.0 | 0.24 |
| | 5 | 36.7 | 0.56 | 2.1 | 0.1 | 23 | 28 | 25.6 | 0.34 |

Example 11: Tolerability of GalNAc Conjugated ASOs in SD Rats

Twenty-eight male SD rats were divided into seven groups, four rats per group. Rats were subcutaneously injected with PBS as an untreated control or 10 mg/kg/week of a GalNAc conjugated antisense oligonucleotide over the course of four weeks.

Plasma and urine were collected and analyzed using an automated clinical chemistry analyzer (Hitachi Olympus AU400e, Melville, N.Y.) to evaluate the effect of antisense oligonucleotides on liver and kidney function. At the end of the experiment, the livers, kidneys and spleens were harvested and weighed.

Results are presented as average of 4 animals in each group and presented in Table 54.

TABLE 54

Tolerability of GalNAc-conjugated ASOs in SD rats

| | plasma | | | | urine | | | Weight (g) | | |
|---|---|---|---|---|---|---|---|---|---|---|
| Tx | ALT | AST | BUN | T. Bil | Cre | MTP | MTP/ Cre | body (day 30) | kidney | liver | spleen |
| PBS | 29 | 76 | 17 | 0.08 | 95.8 | 106.8 | 0.99 | 395 | 3.1 | 11.2 | 0.70 |
| 757456 | 42 | 103 | 19 | 0.12 | 55.5 | 65.3 | 1.24 | 387 | 3.0 | 11.1 | 0.84 |
| 757457 | 36 | 84 | 18 | 0.08 | 82.8 | 103.0 | 1.13 | 396 | 3.0 | 11.2 | 0.69 |
| 775493 | 42 | 102 | 16 | 0.14 | 66.0 | 85.3 | 1.29 | 407 | 3.3 | 12.3 | 0.78 |
| 775494 | 43 | 84 | 17 | 0.09 | 91.3 | 119.0 | 1.34 | 396 | 2.8 | 10.7 | 0.89 |
| 775495 | 37 | 92 | 17 | 0.10 | 65.0 | 70.3 | 1.01 | 387 | 3.0 | 10.4 | 0.81 |
| 775496 | 36 | 90 | 16 | 0.08 | 58.3 | 92.8 | 1.39 | 397 | 3.1 | 11.7 | 0.91 |

Example 12: Dose Response Comparison of Unconjugated and GalNAc Conjugated Antisense Oligonucleotides in Male and Female huAGT Mice As described in previous examples, huAGT mice are useful in testing the potency of antisense oligonucleotdies. A dose response comparison of the parent 5-10-5 MOE gapmer (ISIS 654472) to a GalNAc conjugated compound with the same sequence (ISIS 757456) was performed. The GalNAc conjugated antisense oligonucleotide is 8-fold more potent than the unconjugated antisense oligonucleotide as shown in Table 55.

TABLE 55

Dose response of conjugated versus unconjugated ASO

| | | mg/kg | ED50 AGT mRNA | Liver % inhib | Kidney % inhib | % reduction plasma AGT protein |
|---|---|---|---|---|---|---|
| Females | Saline | n/a | | 0 | 0 | 0 |
| 654472 (parent) | | 2.5 8 | 24 | 15 17 | 4 26 | 0 8 |

TABLE 55-continued

Dose response of conjugated versus unconjugated ASO

| | | mg/kg | ED50 AGT mRNA | Liver % inhib | Kidney % inhib | % reduction plasma AGT protein |
|---|---|---|---|---|---|---|
| | | 25 | | 48 | 38 | 31 |
| | | 80 | | 76 | 51 | 70 |
| 757456 (GalNAc) | | 0.3 | 3 | 10 | 0 | 0 |
| | | 1 | | 19 | 12 | 15 |
| | | 3 | | 47 | 0 | 53 |
| | | 10 | | 79 | 7 | 75 |
| Males | Saline | n/a | | 0 | 0 | 2 |
| 654472 (parent) | | 8 | 24 | 35 | 23 | 33 |
| | | 25 | | 48 | 36 | 39 |
| | | 80 | | 79 | 49 | 78 |
| 757456 (GalNAc) | | 1 | 3 | 19 | 1 | 17 |
| | | 3 | | 50 | 10 | 39 |
| | | 10 | | 78 | 20 | 71 |

What is claimed is:

1. A compound comprising a single-stranded modified oligonucleotide consisting of 20 linked nucleosides and having the nucleobase sequence of SEQ IP NO: 1914, wherein the modified oligonucleotide comprises:
   a. a gap segment consisting of ten linked 2'-deoxynucleosides;
   b. a 5' wing segment consisting of five linked nucleosides; and
   c. a 3' wing segment consisting of five linked nucleosides;
   wherein the gap segment is positioned immediately adjacent to and between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

2. The compound of claim 1, comprising a conjugate group.

3. The compound of claim 2, wherein the conjugate group comprises a GalNac moiety.

4. A composition comprising the compound of claim 1, or a salt thereof, and a pharmaceutically acceptable carrier or diluent.

5. A method of treating a disease in a human, wherein the disease is hypertension, comprising administering to the human a therapeutically effective amount of the compound of claim 1, thereby treating the hypertension.

6. The method of claim 5, wherein the disease is resistant hypertension.
7. A compound, wherein the anion form of the compound has the following chemical structure:
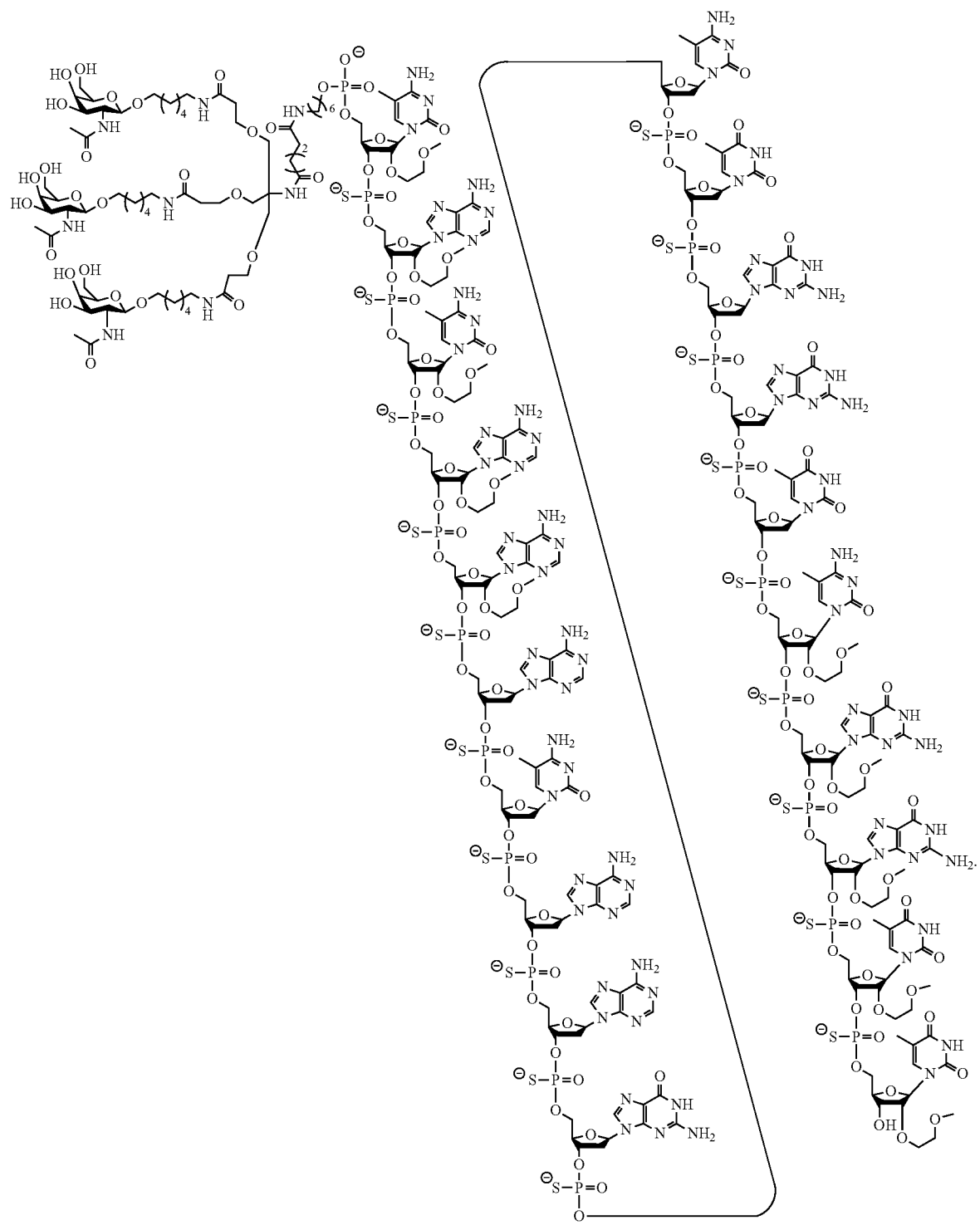

8. The compound of claim 7, wherein the compound is a salt, and wherein the cation of the salt is sodium.

9. A composition comprising the compound of claim 7, or a salt thereof, and a pharmaceutically acceptable carrier or diluent.

10. A method of treating a disease in a human, wherein the disease is hypertension, comprising adminsitering to the human a therapeutically effective amount of the compound of claim 7, thereby treating the hypertension.

11. The method of claim 10, wherein the disease is resistant hypertension.

* * * * *

SEQUENCE LISTING

<160> NUMBER OF SEQ ID NOS: 2051

<210> SEQ ID NO 1
<211> LENGTH: 2587
<212> TYPE: DNA
<213> ORGANISM: Homo sapiens

<400> SEQUENCE: 1

```
atcccatgag cgggcagcag ggtcagaagt ggcccccgtg ttgcctaagc aagactctcc      60
cctgccctct gccctctgca cctccggcct gcatgtccct gtggcctctt gggggtacat     120
ctcccggggc tgggtcagaa ggcctgggtg gttggcctca ggctgtcaca cacctaggga     180
gatgctcccg tttctgggaa ccttggcccc gactcctgca aacttcggta aatgtgtaac     240
tcgaccctgc accggctcac tctgttcagc agtgaaactc tgcatcgatc actaagactt     300
cctggaagag gtcccagcgt gagtgtcgct tctggcatct gtccttctgg ccagcctgtg     360
gtctggccaa gtgatgtaac cctcctctcc agcctgtgca caggcagcct gggaacagct     420
ccatccccac ccctcagcta taaatagggc atcgtgaccc ggccggggga agaagctgcc     480
gttgttctgg gtactacagc agaagggtat gcggaagcga gcacccccagt ctgagatggc     540 tcctgccggt gtgagcctga gggccaccat cctctgcctc ctggcctggg ctggcctggc     600
```

```
tgcaggtgac cgggtgtaca tacacccctt ccacctcgtc atccacaatg agagtacctg    660
tgagcagctg gcaaaggcca atgccgggaa gcccaaagac cccaccttca tacctgctcc    720
aattcaggcc aagacatccc ctgtggatga aaaggcccta caggaccagc tggtgctagt    780
cgctgcaaaa cttgacaccg aagacaagtt gagggccgca atggtcggga tgctggccaa    840
cttcttgggc ttccgtatat atggcatgca cagtgagcta tggggcgtgg tccatggggc    900
caccgtcctc tccccaacgg ctgtctttgg caccctggcc tctctctatc tgggagcctt    960
ggaccacaca gctgacaggc tacaggcaat cctgggtgtt ccttggaagg acaagaactg   1020
cacctcccgg ctggatgcgc acaaggtcct gtctgccctg caggctgtac agggcctgct   1080
agtggcccag ggcagggctg atagccaggc ccagctgctg ctgtccacgg tggtgggcgt   1140
gttcacagcc ccaggcctgc acctgaagca gccgtttgtg cagggcctgg ctctctatac   1200
ccctgtggtc ctcccacgct ctctggactt cacagaactg gatgttgctg ctgagaagat   1260
tgacaggttc atgcaggctg tgacaggatg gaagactggc tgctccctga tgggagccag   1320
tgtggacagc accctggctt tcaacaccta cgtccacttc aagggaagat gaagggcttc   1380
ctccctgctg gccgagcccc aggagttctg ggtggacaac agcacctcag tgtctgttcc   1440
catgctctct ggcatgggca ccttccagca ctggagtgac atccaggaca acttctcggt   1500
gactcaagtg ccccttcactg agagcgcctg cctgctgctg atccagcctc actatgcctc   1560
tgacctggac aaggtggagg gtctcacttt ccagcaaaac tccctcaact ggatgaagaa   1620
actatctccc cggaccatcc acctgaccat gccccaactg gtgctgcaag gatcttatga   1680
cctgcaggac ctgctcgccc aggctgagct gcccgccatt ctgcacaccg agctgaacct   1740
gcaaaaattg agcaatgacc gcatcagggt gggggaggtg ctgaacagca ttttttttga   1800
gcttgaagcg gatgagagag agcccacaga gtctacccaa cagcttaaca agcctgaggt   1860
cttggaggtg accctgaacc gcccattcct gtttgctgtg tatgatcaaa gcgccactgc   1920
cctgcacttc ctgggccgcg tggccaaccc gctgagcaca gcatgaggcc agggccccag   1980
aacacagtgc ctggcaaggc ctctgcccct ggccttgtag gcaaaggcca gcagcagata   2040
acaaccccgg acaaatcagc gatgtgtcac ccccagtctc ccacctttc ttctaatgag   2100 tcgactttga gctggaaagc agccgttct ccttggtcta agtgtgctgc atggagtgag   2160
cagtagaagc ctgcagcggc acaaatgcac ctcccagttt gctgggttta ttttagaaa   2220 tgggggtggg gaggcaagaa ccagtgttta gcgcgggact actgttccaa aaagaattcc   2280
aaccgaccag cttgtttgtg aaacaaaaa gtgttccctt ttcaagttga gaacaaaaat   2340
tgggttttaa aattaaagta tacattttg cattgccttc ggtttgtatt tagtgtcttg   2400
aatgtaagaa catgacctcc gtgtagtgtc tgtaatacct tagtttttc cacagatgct   2460 tgtgattttt gaacaatacg tgaaagatgc aagcacctga atttctgttt gaatgcggaa   2520
ccatagctgg ttatttctcc cttgtgttag taataaacgt cttgccacaa taagcctcca   2580
aaaaaaa                                                             2587
```

<210> SEQ ID NO 2
<211> LENGTH: 16101
<212> TYPE: DNA
<213> ORGANISM: Homo sapiens

<400> SEQUENCE: 2

```
catcagaaag atccaccctc atgattcaat tacctcccac tgggtccctc ccatgacaca    60
```

```
tgggaattat gggagctaca attggagatt tgggtgggga cacagccaaa ccatatcaga    120
tggcttattt ggtttctatg tagaacctct gcttttcatt caacagtctt catttagcca    180
cagataagct ctgtccctaa cttccactga tggaatgtac acataagaaa cttccactga    240
tggaatgaac acagaaggtg cctactggga agaaaactgg cctgaatctg agctgggtca    300
aatgtctgca gtcagtttga atggctgctc cttatgggaa taatttacat tctcaataaa    360
attctctagc aattttctga ttgattttaa tgagctttaa agccttacgt agaagatccc    420
ccagctgata gtcagccttg ggcatggatt aagggctttt aaccaatctt gcaacaagtt    480
taagcagata ttctttattg ggtccaatct aaccaaaatt attttcttat gttctcccca    540
gtaacgtgtc attattaaga gaagtttggc ttgcttagag gccaaattta gagggtcctg    600
aaattttatt ttcttttaca ccactttcca gcatgttacc tgatcagttg tttattatct    660
ttgctgttga atggagtgat cattccaagg gcccgaggca ggaggccag gcacagtgga    720
aactctccca aagaccagga tctttgtttt gttccctgac atatgctgag caccaggaat    780
agtgagtgaa tgaaacaaat tgtgaggctt taaagagccg aaatatttaa acactgggca    840
caaggttgtt gcttaatcag tgctagatcc ttacctcccc cttgtgtcca ggtggacttg    900
ttactgcagt taaaccactt gctgatcctc aaacaactag ttagtggcac agccaggcct    960
aggaccccag tctctactgt tccaactaac ccattcgcag gcaggagcac tttgaatggt   1020
ctcttatttt aaaaaaatta aattaaaatt gtctatttat ttagagacag agtcttactc   1080
tgtagcccag gctcgagtgc agtggtgcaa tcatagctca ctgtaacctc catctcctgg   1140
cctcaaaaag tgtttgaatt acagatgcga ggcactgtac ctggcccgaa tgttctgttc   1200
agacaaagcc acctctaagt cgctgtgggg ccccagacaa gtgattttg aggagtccct   1260
atctatagga acaaagtaat taaaaaaatg tatttcagaa tttacaggcc catgtgagat   1320
atgattttt taaatgaaga tttagagtaa tgggtaaaaa agaggtattt gtgtgtttgt   1380
tgattgttca gtcagtgaat gtacagcttc tgcctcatat ccaggcacca tctcttcctg   1440
ctctttgttg ttaaatgttc cattcctggg taatttcatg tctgccatcg tggatatgcc   1500
gtggctcctt gaacctgctt gtgttgaagc aggatcttcc ttcctgtccc ttcagtgccc   1560
taataccatg tatttaaggc tggacacatc accactccca acctgcctca cccactgcgt   1620
cacttgtgat cactggcttc tggcgactct caccaaggtc tctgtcatgc cctgttataa   1680
tgactacaaa agcaagtctt acctatagga aaataagaat tataacccTT ttactggtca   1740
tgtgaaactt accatttgca atttgtacag cataaacaca gaacagcaca tctttcaatg   1800
cctgcatcct gaaggcattt tgtttgtgtc tttcaatctg gctgtgctat tgttggtgtt   1860
taacagtctc cccagctaca ctggaaactt ccagaaggca cttttcactt gcttgtgtgt   1920
tttccccagt gtctattaga ggcctttgca cagggtaggc tctttggagc agctgaaggt   1980
cacacatccc atgagcgggc agcagggtca gaagtggccc ccgtgttgcc taagcaagac   2040
tctcccctgc cctctgccct ctgcacctcc ggcctgcatg tccctgtggc ctcttggggg   2100
tacatctccc ggggctgggt cagaaggcct gggtggttgg cctcaggctg tcacacacct   2160
agggagatgc tcccgtttct gggaaccttg gccccgactc ctgcaaactt cggtaaatgt   2220
gtaactcgac cctgcaccgg ctcactctgt tcagcagtga aactctgcat cgatcactaa   2280
gacttcctgg aagaggtccc agcgtgagtg tcgcttctgg catctgtcct tctggccagc   2340
ctgtggtctg gccaagtgat gtaaccctcc tctccagcct gtgcacaggc agcctgggaa   2400
cagctccatc cccaccectc agctataaat agggcatcgt gacccggccg ggggaagaag   2460
```

```
ctgccgttgt tctgggtact acagcagaag gtaagccggg ggccccctca gctccttctc    2520
ggtcttgtct ctctcagatg taactgagct gtgggctagg aggaaaaggc cgggaggagg    2580
cacggtgatg actgaaaaac ctctcccctc tcataagacc agtcatccgg acgcgggctt    2640
tcccccactc ggtgcccacc tggggtctta caggaggagc tgctcctcct cagcaatagg    2700
acaagatggt caggtcttcc tgcttccgct gagaaaagtt agggtcctca ggaacggagc    2760
agactggtac aggaacagag tcatcatggc caagagtcca ccgggtcctc ttgccatcag    2820
gaggaatagc agggcttgtg caggaattgg ggctggaggg aagggccggg ctcggtcagt    2880
ctccagctgg gatccccaga gtggtcaccc tacccctccc tcgagacaga ctgcctgact    2940
gtgtgtcatc aggctggtca ccatctccct gaacctcgat ttgctcacct ataaaatgga    3000
actaataacg atgcctgggc tccctgtctc aggggctctg gtatagctga agagaactaa    3060
tataacatga aagtgctttc taagctttgg gataagctaa aaggcagatt ccaattttat    3120
tcgagggcag cgtagattgg tgcttcagct cgtggatgac agagtcaggg ggcctggttc    3180
tgagtcctag ttctgtctct cccagctgt gtgacgttga acaagtcact ggacctctct    3240
gttcctctgc aaaacagcat gaaccaattc attaactact tctccaggat gcagtaggtc    3300
ccagggacta tcctaggaat gtgggctgta ttagtaaaca caacagcggg aaccctgttc    3360
cggggctcac attcacatca gagcaaacag acaaagacgc tggacagaat aagtgcataa    3420
ctacatggta cagagggtta taaggaggga aaggggagc tggatgagag agttgagagt    3480
gcccggtgtg gtggggaaag ctgcagggtg aaatactgca tcagggaaac ctcagggaag    3540
gtgaggacta tggtgaggtc agaggggttg atatgagaac agtgccctgc aaatggcagg    3600
caccacagga gcatgagccg tcatcttcac ctttagcatt cagcccggga gaagtaggga    3660
gacatagaag gggcaggtgc tggccaagag gcaggggcag gagaggagaa ggcggagggg    3720
cactcagggc gagggtgtca ggcccgccac cccagcagca cattactccc aggacgcggc    3780
tgcgtgcaga cctggaacca gcctagggag cagccgcaga tcacaactga gaacaaacga    3840
cagtctctgc ctcaaaaatg gcccatggaa ttgcgtctct ggagacgctg cctgagcagg    3900
agcagcacag tgagcgggct gcatcgacca gcgccatcca aaccccgaac agttggcgct    3960
tgtcaggcag gacttcccag cagtcggttc ccacaggttt ccctgttga cctgattga    4020 tgtgactgtc tagattaggt gtgaactggt ggcttaggct tctctgcaca gaaaggcctg    4080
caagcagcag agagagttt tctgttccatt tttccatgtc atgtggctct tcctgagaac    4140
agcggatgga gtcaaatgca tgggagtgg ggtgagatgg tagctgaggt cagaatttgg    4200
catttgaatg actgaagcag aacaaaacac accaggtact tcagcagctg caccgtgttg    4260
agggcaggtc ctggttacgg gtctgggtga gggaagccag ctgccaatgt aagaagaatg    4320
actgggtatg cttagatgaa gcagaaaat ctaggcatca aggtggcctt gagtcagtga    4380
tgacacgcta cagctccaag gaagcctggc ctagccctgg ggggacagaa aaggccaaga    4440
agtgacgata ttgcagtaca ccccctcca caagaaatga gtgagatgtg gtacaaaatg    4500
ttagaattga atgaatcaat agaataaacg ttcatcccctt caatcaagaa gagtcagatg    4560
aaatgaatta gcagggccag cccaagaacc tcttctgggg gtctcagggt agctttcatt    4620
tgtagcagct gaggctgaag cccagctgca aggcctttga gagaacgtgg tgctggaccc    4680
gtgtctaggg cagggttct aaaccctgct tacatatcag agtcacctga gaattttcta    4740
tttttttttt ttttttttta tacgtggtcc cagcacagac taaggaatcc aactatcatt    4800
```

-continued

```
gggcaagcca tgctaggtat gcatgccttt ggggctctgc aggggatagc gctatgcagg    4860
gatggttgag agctggtttt ggggttgaga cacgtgggaa atacttggac tttgggctga    4920
gcctgtggtg ctcaatcccg gctgcatgtt gggaccacag ggagatgaca aaaccatccc    4980
cagccctcac cctagggccc tcgaatgagc atctcagggg tctaggaggc ctccacaaag    5040
acctactgat tggcacacac ttgtttctct aggaagagaa cttacagctg caggcaggag    5100
catgtcttaa tctgcttggg ctgccataag taccacagac tgggagggtt taacaacaga    5160
aatgtgttat ctcacagttc tggaagctag aagcctggga gccagccatc agcagagttg    5220
gtttcctctg gtcctctat ccttggcttg tagatggccg tcttctctct gtgtccccac     5280
atggtcttcc ctctgtgtcc ccacatggtc ttccctctgt gtgtgtccat gtcctcatct    5340
cctcttctca taaggacaca ggtcatatta gatcagggct caccctcatg gcctcatttt    5400
aacttaatca tctctttaaa gatcctgtct ccaaataatg gtcacattct gaggtcctgg    5460
ggttgaggac ttcaacacgg gcattatggc cgttggggga ggtaggacat aattcagctg    5520
atattggtgc attttgcact tggatcatgt agatattttc catggagctt tgaatccatt    5580
tcttcttttt tttgtagaca tgaatggatt tattctgggc taaatggtga cagggaatat    5640
tgagacaatg aaagatctgg ttagatggca cttaaaggtc agttaataac cacctttcac    5700
cctttgcaaa atgatatttc agggtatgcg gaagcgagca ccccagtctg agatggctcc    5760
tgccggtgtg agcctgaggg ccaccatcct ctgcctcctg gctgggctg gcctggctgc    5820
aggtgaccgg gtgtacatac accccttcca cctcgtcatc cacaatgaga gtacctgtga    5880
gcagctggca aaggccaatg ccgggaagcc caaagacccc accttcatac ctgctccaat    5940
tcaggccaag acatcccctg tggatgaaaa ggccctacag gaccagctgg tgctagtcgc    6000
tgcaaaactt gacaccgaag acaagttgag ggccgcaatg gtcgggatgc tggccaactt    6060
cttgggcttc cgtatatatg gcatgcacag tgagctatgg ggcgtggtcc atggggccac    6120
cgtcctctcc ccaacggctg tctttggcac cctggcctct ctctatctgg gagccttgga    6180
ccacacagct gacaggctac aggcaatcct gggtgttcct tggaaggaca agaactgcac    6240
ctcccggctg gatgcgcaca aggtcctgtc tgccctgcag gctgtacagg gcctgctagt    6300
ggcccagggc agggctgata gccaggccca gctgctgctg tccacggtgg tgggcgtgtt    6360
cacagcccca ggcctgcacc tgaagcagcc gtttgtgcag ggcctggctc tctataccc     6420
tgtggtcctc ccacgctctc tggacttcac agaactggat gttgctgctg agaagattga    6480
caggttcatg caggctgtga caggatgaaa gactggctgc tccctgatgg gagccagtgt    6540
ggacagcacc ctggctttca cacctacgt ccacttccaa ggtaaggcaa acctctctgc     6600
tggctctggc cctaggactt agtatccaat gtgtagctga gatcagccag tcaggccttg    6660
gagatgggca gggggcagcc ctgcggacat acctggtgac cacccttgag aagtggggaa    6720
gtggctgctc cgctgggtcc ctggatgggc cgtccacctc ctggacctgc tgccctacta    6780
tgtgcacgac tatacaacat ccttttttctt acatcattta atcccttat gatgtggtga    6840
agaggtattt gtgcctttgt ttaccagtga agaaatagag actcggagaa acaaagtgcc    6900
ttgctcaaga tggcacagcc accagtgggg gtcctgggat tgaaacccac atctcctggc    6960
cccacagccc agttctacac tcagaagggt caggttcata tctcttgaga aggtcaggaa    7020
ctggggtccc tggcccatgc agaaataagc aattggcttg cttaaatccc tttcatgtta    7080
ggaggggcat tactgaaaac cctctactac aaagattgtt gattttttt tttttttta     7140
ttgagacagg gtcttgttct gtcacccagg ctgcagtgta gtggtgccat cattgctcac    7200
```

```
tgtagccttg aactcctggc ctcaagcgat cctcccacct ctgccttcca aagtgttggg     7260
attaaaggtg tgagccactg cacccagcca cagattgctt aaagcattca tttaacaaat     7320
acttgttgag gatttgctac ttgtaagact ttaagcctgg catctcagag gaggccagag     7380
gagggctgta taggccctgc ctccaggctt ttaaaggtca atgggcaaat gcctaggatt     7440
tggagctgca gggaaacgtg ctccacaagg taactcaggg aagcctcggg gctctcagag     7500
gacagaggtc actggggagc ggagagcagg ccttgcctgg cagtgagggc aacagggctg     7560
gtgaagctag gagcaagcat gatgagccca gcctgcagag tttggggcaa ggaacgagga     7620
tggggcggtt ggcttggcat gagtgttgaa ccagaaaatg ggcctgggga gggcagagct     7680
ggagacactt tgaacgccat gcttggtagg tgtgggaatg gggacgcgtt ctgttcagag     7740
gtcatcccgg aagcctgccg tgtgcagact ggaggcaggg aggattgttt gaaggttacg     7800
caagagtcca ggcacacagt cacgggaaca cgtgctcagg gagcagctcg gcaaatccat     7860
gggtggggtg gggctgaggg gtgtgtctaa gagacactga ggaggctctg tcaagatgtt     7920
aacctcgtga gggacagaga gccaggcggg aggtgaaaga caagactgtg gagaagagg      7980 ttcagtggcg catagtgatt tttcttacca caacaacctc cttgaggtct ttcccttcgg     8040
gttcagggag aggtgataga tgggggggatt gctcagccct ggcactgact ggtcacaggg     8100
gcagaggcca gcccgagggt tgcccggttg agggtggcag cacactgtgc agggcagagc     8160
agggacacat ggacttagcc tgctgtccct aggagaagtg ctgggaggag cgctcactga     8220
gaaggagggg cctgcagaag gcaaaggcaa gaaagccagt ggcatctgaa atgggtctcc     8280
cttcgaaaga gagcacatcc acctgaccca gaccgcagag ccaggccagg aggaagagga     8340
ggaagaataa aaaagccaac cacatcggga ctcaaaggaa gcccaggatc ctcgccggcc     8400
tccaccgcat gctgccctga ccctgcccca cttcctaact ttgctggcct cagtttccgt     8460
caaaggaggc agccacttcc tgcccacatg gtctgtccag tgaggagatc ggggctgtc      8520 tcgggacctc taggtttccc tttagcaatg atgttctatt tacatgacct cagcaggcag     8580
ctagatgtgt cccactagag aggacctgag gatctggggc ctgatgggct ccagggtacc     8640
gtctgcccag tgcttgctgt gctcctgagc atggggcgcg ggccctggtg gtttccatga     8700
caccaggtcc tgacttgacc tcgacagatt tacctagcct ccggatgaga atggtgagct     8760
gtgcatgtca gacgagcaga gggaagacgg cagccactct catgtcaaat cccagcgtct     8820
tttgggaggc agcttccctt ttttagttta gtttgttgga agaaaagaat tgtccctttc     8880 cccctctaa actaaaagcc ttgccagccc aggtgggcag caccgaggtc cctgcaggga      8940
acgtgcaagg ggaaccctgc agtttcccgc tcacatgccc ttccgagact gagtgctccg     9000
aggactgagg acgagaaata tgccaggtct gccactgcct tcttacgaga cccggaccca     9060
ggggaggcac agccatgccc agctcctgcc tgccagttct gtcctcccag ctgccctact     9120
ttcatgctgg gacctccaat tcagtacaaa gggagacctc actgtttctg aaccatctct     9180
actcagactc caagtgcca cgtgcccagg ggactgttct gtgacaaact tatacacaac      9240
ttcaccctat tctcctaaga acaaccgcag aataggcctt tcaggatgag tgggaggaca     9300
gccgagggca gggatgtgct agtgtaaggt cgaggcagag ggtgggctgc tgtcatggaa     9360 agacccccagg taactgcgtc acacacaaat ttgtgtcctt ctcccacaac gggctctccc    9420
gagttctctg tcatctgcac ggccctgtga gcaggagggg aaacagaggg ctcacccctg     9480
cccccaaggc ccagtgtgca aatccattca tcacaacgag gttgtgtgag tctccccagt     9540
```

```
agcaagggct gctgaggaat ggagccctcg tttccggggc ctgcgtggcc cactctgtat    9600
tctatgactg tgatggggga gggtgggggc cacaggacag ctggtgggct ctgccatggc    9660
tggggctaga catggattaa aaagtgagta tgagcagggg cctctaggag tggtgggata    9720
gtgcggtggt ggccacatgt cattctacgt gcgtccaaac ctacagaatg taaaacacca    9780
ggagggagac tcaaagaaaa ctatcaactt tgagtgctga ggacgtgtca gtgtaggttc    9840
gtcagttgca acaaatgggc cacgctggtg tgagatgttg atcacggggg aggctgtgta    9900
gtgggggaca agagttatat gggaactttc tgtactttct gctcgatttt gctgtgaacc    9960
taaagtcact ctaaaaaata acatctctta aattttttaa aaagtgagtg tgtcaaacca   10020
cagcctttgg gtcaggacag ttctaggttt gagttgacct ggcaggtacc agtggcttat   10080
gtccctaaag gtgacagatg caaaaccccc ggtttggtgc ctggcatgtt gtgtgtcttg   10140
caggtggcgg ttagggctgc ctcagtgaac tcaaatggct gcattttaca ggagaaatat   10200
ttgagccaca cttgcggtcc tgtgccagg agaatgcaga gtggcctggg gggggccaag    10260
gaaggaggct gaggcagggc gagggcagg atctgggcct ttggtgtctg ccagccctca   10320
ttcctgcccc tgtcttgggt gactcttccc tccctgtctc ctgtctggat ttcagggaag   10380
atgaagggct tctccctgct ggccgagccc caggagttct gggtggacaa cagcacctca   10440
gtgtctgttc ccatgctctc tggcatgggc accttccagc actggagtga catccaggac   10500
aacttctcgg tgactcaagt gcccttcact gagagcgcct gctgctgct gatccagcct    10560
cactatgcct ctgacctgga caaggtggag ggtctcactt tccagcaaaa ctccctcaac   10620
tggatgaaga aactatctcc ccggtaggag cctcccggtc tccccttgaa tgtgggagcc   10680
acactgtcct gcccaggctg ggggcggggt ggggagtaga cacacctgag ctgagccttg   10740
ggtgcagagc agggcagggc cgcggtggca cggggctggg caggcggcct gtgtgtctgt   10800
ctaccagtcc tctatccagc cagcacccag ctctccagtt agtgtctgtc tttcaagtgc   10860
aggcaaggta aaggaggaga ggaagaatgc ttttctaca cttacacttg cctggtagtt    10920
ttggaggggg agaaaacatt gcaatccgcc ctctgagaga ggaccatttt ggtcccacac   10980
ctgacacaca gcacacctgt gacatccaag agcttcttgg aactgacttg ccaggagggt   11040
tcggacttcg cgtgagcggg ggtgggggcct tctcagggag cgtcccttga ctccagaacg   11100
cccttgctgg cggctggcgg ctgggtgggg ataggtgttg ttagctcctc tttcctgctg   11160
caattccttt ccacagagcc ctggactcaa actacacatc accccagatc atcgaggcct   11220
ggaaatctgc tccagaggc aggcattgag tgacacgatg gcttgacatc aactctgggt    11280
gtttttatg ttttaaaaat tgtgatggta aaatatacgt aacaaaattt gccatcgtaa    11340
ccattttcga gtgcacagtt cagtggtact aggcccattc acactgttgt gcagccatca   11400
cccccgtcca tctccattta tcttctcaac ttcccaaact gaagctctgt cctgctgaaa   11460
cactaactct ccatttcccc ttcccctggg ccccggcaac caccacgatg tcctcgaggt   11520
tcacccatgt tgtagcacat gtcagaatgt ccttcctttt gaaggctgaa taatattcca   11580
ttgcatgtgg ttaccacctt ttgtgtatcc actcatccat cgatggacac gtgggttgct   11640
tccacctttg agctgctgtg aatagtgcag tgtaccctgt aaacatgggt gtactgtcag   11700
ctcttataag tgcttgatac atcactggaa atgtccatgg gctctgaagg atgccaaaag   11760
atggaagagg ctctatacga agatcaatcg agttgacata gcaacgtgtc cagcacgagg   11820
ttgacactgt accctcctgc ctctctcctt ttcatgggtg tcatgtcatc aagaacactg   11880
ctgtggcagt agtaagacac agtgcattat ttcagagaat agcatttaaa aattacccaa   11940
```

```
gtaacacacc ttcaatgcag ccaacctaaa aacagaatgc accaaaggac aaccattcct   12000
aggtcctcat cggtaaatct tctatgtccc tcacatagta ttgcaaatga catgaaggat   12060
ttttattgta ggttttgctg aaattttccc caaggggag gatgacttag ttgggtgatg    12120
gggggagcaa acatccctgt cgtcagggtt gggtgcaagg agcataagcc tgcctggcct   12180
ctgggagagc cctcactgtg tggcctggag ccttcctaac tgtgcatcat ctccccagga   12240
ccatccacct gaccatgccc caactggtgc tgcaaggatc ttatgacctg caggacctgc   12300
tcgcccaggc tgagctgccc gccattctgc acaccgagct gaacctgcaa aaattgagca   12360
atgaccgcat cagggtgggg gaggtatgtg tgagcctgtg tctgtgcctg acctgggttc   12420
caagtgtgca cagggtggga ggcatggatg taagggacac agaggaggct atgggtgggg   12480
ccagcagggc aagagggagc ggagagtagg gccaaaggtg ggagagaagt agccagagca   12540
ttctggggcc ttccaggtgc agagcagcaa atccctcccc atccctgctg tgcctcctcc   12600
tgctaggtgt gtgttccatg gtcctgcttg gccttgcctt gctcagggt cctccagggt    12660 tcctatagtg gagttgaaac cgggatgaag acagcaagca cccctggacc tggtgccctg   12720
ggcccagccc cttcttcagg gaaatgctga gcagcagaca gaatgtcccc ctgccatgtg   12780
gcaccatgca catctgcagc taccaaggat gtgccttgat gttctgggcc ctgtgctcag   12840
tgctggggag aaagtgggag ttcttacggg ggccagcggg aagagccctc tgtgctaagt   12900
tagctaagcc ctggcactgg tgggccatgg ccaagggagc caggaattct gcctgggaca   12960
tcagggcaga atgtgaagat gggaggatgt aaggggtgtg ttaggagga gccggcatgt    13020 gagtttggcc attgtggcca attaacggtc atctacacac agacacaccc ttgcctacac   13080
tgaggggcag gcatacactg tgcatcctcc tggcaggctg gaaaatgtcc ccctccagga   13140
cagtgcacag cacagaggtc ctgagcccac cccggccctc tagccctcag caccctgggt   13200
cacccagtgc gccctcagaa tgatcctgat gtctgctgct ttgcaggtgc tgaacagcat   13260
tttttttgag cttgaagcgg atgagagaga gcccacagag tctacccaac agcttaacaa   13320
gcctgaggtc ttggaggtga ccctgaaccg cccattcctg tttgctgtgt atgatcaaag   13380
cgccactgcc ctgcacttcc tgggccgcgt ggccaacccg ctgagcacag catgaggcca   13440
gggcccagaa acacagtgcc tggcaaggcc tctgccctg gcctttgagg caaaggccag    13500
cagcagataa caacccccgga caaatcagcg atgtgtcacc cccagtctcc cacctttct    13560 tctaatgagt cgactttgag ctggaaagca gccgtttctc cttggtctaa gtgtgctgca   13620
tggagtgagc agtagaagcc tgcagcggca caaatgcacc tcccagtttg ctgggtttat   13680
tttagagaat gggggtgggg aggcaagaac cagtgtttag cgcgggacta ctgttccaaa   13740
aagaattcca accgaccagc ttgtttgtga acaaaaaag tgttcccttt tcaagttgag    13800
aacaaaaatt gggttttaaa attaaagtat acattttgc attgccttcg gtttgtattt    13860
agtgtcttga atgtaagaac atgacctccg tgtagtgtct gtaataccttt agttttttcc   13920 acagatgctt gtgatttttg aacaatacgt gaaagatgca agcacctgaa tttctgtttg   13980
aatgcggaac catagctggt tatttctccc ttgtgttagt aataaacgtc ttgccacaat   14040
aagcctccaa aaatttttatc tttcatttag cagccaaaca gatgtataca attcagcaga   14100
tagactgtgc aaacgaaagt gctttcctgg actttggatg gaatttccat gggaggtctg   14160
agccagtact tagcagtcct ttgaagtttt aggtgatgct tttctctgga cacttccatt   14220
ggtaagcagt ggtggccatc tgtgtgatgg acagggggcg ggaagagggt gacagggaag   14280
```

```
gccccatacc ccatgtggca cctgggaaag gaaccaggca gatgggactt cttccgtcct    14340
ggtgacacag ggccagactg ctgctggtat tgtgccccgg gagtggaagg tagagaaata    14400
aatcttcaca aataaatatt tgcaattttc ccccatctgt tgagtgcctc tgcctgctcc    14460
tcctcgatgg gattaggccc acagttcgga atcttgggga gagccaagga agcggtaggc    14520
acccagtagg cccacggccg tcggctgata gcaatggtga tgctgtccta cctacttgtg    14580
taaggcattc gatcttcctc ccttccatac atattgaaat aaataagccg cgcaatgtgt    14640
tagctattga tcagaactaa agtgaagtca gccacgggga ttacaaatct cggcttctcc    14700
cctcatgttc ctgagagtct tcccctggtt ttgaacacat ctcccctagct cgatgtcaag    14760 gtgagggatt ctgtcggcaa cagcagtgcc cttagttgct tcgtcgtaac tccccgtcac    14820
cggttttatt cagttacctt ccagtcccac tctcagagct tcctggcttg ttctgctctc    14880
aaagcgggta gagctggcac acatggactc tccgaaacgg ctgcaagatg ccaagtttct    14940
cggaagaact ggaagcacag agaccagaag tgccttaagg tctcgctatt cagtgtggcg    15000
cttagaccgg cagtggcggc agctgccctg ggagcttgtt agaatgtggc ttctcacgcc    15060
cctcctggac ctacagagtc agaatctgca gttttacagg aggtccaggc ttggaagttg    15120
ctcgtagaga cctgagacag cgcagccacg tgctggaaac aaagcattta agtttgtgac    15180
tttattttaa aaggcagcag gcagtcgaca aaccaatttc ttctacttag aggcggcttc    15240
ggcttctgga agtcgctagg agtataaagt tgccaaccag cgctgttctc ccgctgtttt    15300
ctgtgcactt ataaatggga agttaggtca ggatagatct ctcagctatt acaaggatac    15360
aaaatacgaa cattctacaa gttacttaac acacacacac acacacacac acacacacac    15420
acacacaaaa ttaattccac aggtcagttt ctctgaaaca ttttttcact aaattctaag    15480
tcttcctgga gttgcaagtg cctatctcct agacaaggca attactcacc aactaaaatc    15540
actgtcaatc tgagatttcg gctgggcatg agaccatggt caggggatgc tttgaacagc    15600
ctctgaggaa attagtgagt ttgaaaaatg gaaagatttt tattactcac ttggcagtaa    15660
aacctgatgg ggacagacgt caggctgttt aagatcctca gaagaaaaag ttgatagtgt    15720
gaatattcct aaatttgcca cacgaagatg tacatgtgat tataaggtgc tgttgcagaa    15780 gccccctgggg gtgttatggg atatacacta tatgggccac tttaccttcc taaaatctga    15840
aaaacttcaa ctactgaaac atggactgaa ggttttgaat agtggatggt gaatttgaat    15900
accatcccgt gtgatttttt tttctagcag actttagttt tttagagcag ttttaagccc    15960
acaccaaaac tgagaggaag atacagcaat ttctcatata cccctacta ccttccagtc    16020 tcccccatta ttgacatccc ccacccagag tggtccattt cttacaaccc acgaacctac    16080
attgacacat cattattact c                                              16101
```

<210> SEQ ID NO 3
<211> LENGTH: 1399
<212> TYPE: DNA
<213> ORGANISM: Homo sapiens

<400> SEQUENCE: 3

```
agaagctgcc gttgttctgg gtactacagc agaagggtat gcggaagcga gcaccccagt      60
ctgagatggc tcctgccggt gtgagcctga ggaccaccat cctctgcctc ctggcctggg     120
ctggcctggc tgcaggtgac cgggtgtaca tacccccctt ccacctcgtc atccacaatg     180
agagtacctg tgagcagctg gccctacagg accagctggt gctagtcgct gcaaaacttg     240
acaccgaaga caagttgagg gccgcaatgg tcgggatgct ggccaacttc ttgggcttcc     300
```

```
gtatatatgg catgcacagt gagctatggg gcgtggtcca tggggccacc gtcctctccc    360
caacggctgt ctttggcacc ctggcctctc tctatctggg agccttggac cacacagctg    420
acaggctaca ggcaatcctg ggtgttcctt ggaaggacaa gaactgcacc tcccggctgg    480
atgcgcacaa ggtcctgtct gccctgcagg ctgtacaggg cctgctagtg cccagggca     540 gggctgatag ccaggcccag ctgctgctgt ccacggtggt gggcgtgttc acagccccag    600
gcctgcacct gaagcagccg tttgtgcagg gcctggctct ctatacccct gtggtcctcc    660
cacgctctct ggacttcaca gaactggatg ttgctgctga aagattgaca aggttcatgc    720
aggctgtgac aggatggaag actggctgct ccctgatggg agccagtgtg acagcaccc     780 tggctttcaa cacctacgtc cacttccaag ggaagatgaa gggcttctcc ctgctggccg    840
agccccagga gttctgggtg acaacagca  cctcagtgtc tgttcccatg ctctctggca    900
tgggcacctt ccagcactgg agtgacatcc aggacaactt ctcggtgact caagtgccct    960
tcactgagag cgcctgcctg ctgctgatcc agcctcacta tgcctctgac ctggacaagg   1020
tggagggtct cactttccag caaaactccc tcaactggat gaagaaactg tctccccgga   1080
ccatccacct gaccatgccc caactggtgc tgcaaggatc ttatgacctg caggacctgc   1140
tcgcccaggc tgagctgccc gccattctgc acaccgagct gaacctgcaa aaattgagca   1200
atgaccgcat cagggtgggg gaggtgctga acagcatttt tttgagcttg aagcggatga   1260
gagagagccc acagagtcta cccaacagct taacaagcct gaggtcttgg aggtgaccct   1320
gaaccgccca ttcctgtttg ctgtgtatga tcaaagcgcc actgccctgc acttcctggg   1380
ccgcgtggcc aacccgctg                                                1399

<210> SEQ ID NO 4
<211> LENGTH: 1584
<212> TYPE: DNA
<213> ORGANISM: Homo sapiens

<400> SEQUENCE: 4
agaagctgcc gttgttctgg gtactacagc agaagggtat gcggaagcga gcacccagt      60 ctgagatggc tcctgccggt gtgagcctga gggccaccat cctctgcctc gtcatccaca    120
atgagagtac ctgtgagcag ctggcaaagg ccaatgccgg gaagcccaaa gaccccacct    180
tcatacctgc tccaattcag gccaagacat cccctgtgga tgaaaaggcc ctacaggacc    240
agctggtgct agtcgctgca aaacttgaca ccgaagacaa gttgagggcc gcaatggtcg    300
ggatgctggc caacttcttg ggcttccgta tatatggcat gcacagtgag ctatggggcg    360
tggtccatgg ggccaccgtc ctctccccaa cggctgtctt tggcaccctg cctctctct     420 atctgggagc cttggaccac acagctgaca ggctacaggc aatcctgggt gttccttgga    480
aggacaagaa ctgcacctcc cggctggatg cgcacaaggt cctgtctgcc ctgcaggctg    540
tacagggcct gctagtggcc cagggcaggg ctgatagcca ggcccagctg ctgctgtcca    600
cggtggtggg cgtgttcaca gccccaggcc tgcacctgaa gcagccgttt gtgcagggcc    660
tggctctcta tacccctgtg gtcctcccac gctctctgga cttcacagaa ctggatgttg    720
ctgctgagaa gattgacagg ttcatgcagg ctgtgacagg atggaagact ggctgctccc    780
tgacgggagc cagtgtggac agcaccctgg ctttcaacac ctacgtccac ttccaaggga    840
ggatgaaggg cttctcccctg ctggccgagc cccaggagtt ctgggtggac aacagcacct    900
cagtgtctgt tcccatgctc tctggcatgg gcaccttcca gcactggagt gacatccagg    960
```

```
acaacttctc ggtgactcaa gtgcccttca ctgagagcgc ctgcctgctg ctgatccagc    1020
ctcactatgc ctctgacctg gacaaggtgg agggtctcac tttccagcaa aactccctca    1080
actggatgaa gaaactgtct ccccggacca tccacctgac catgccccaa ctggtgctgc    1140
aaggatctta tgacctgcag gacctgctcg cccaggctga gctgcccgcc attctgcaca    1200
ccgagctgaa cctgcaaaaa ttgagcaatg accgcatcag ggtgggggag gtgctgaaca    1260
gcattttttt tgagcttgaa gcggatgaga gagagcccac agagtctacc caacagctta    1320
acaagcctga ggtcttggag gtgaccctga accgcccatt cctgtttgct gtgtatgatc    1380
aaagcgccac tgccctgcac ttcctgggcc gcgtggccaa cccgctgagc acagcatgag    1440
gccagggccc cagaacacag tgcctggcaa ggcctctgcc cctggccttt gaggcaaagg    1500
ccagcagcag ataacaaccc cggacaaatc agcgatgtgt cacccccagt ctcccacctt    1560
ttcttctaat gagtcgactt tgag                                          1584

<210> SEQ ID NO 5
<211> LENGTH: 1691
<212> TYPE: DNA
<213> ORGANISM: Homo sapiens

<400> SEQUENCE: 5
aagaagctgc cgttgttctg ggtactacag cagaagggta tgcggaagcg agcaccccag      60
tctgagatgc ctcctgccgg tgtgagcctg agggccacca tcctctgcct cctggcctgg     120
gctggcctgg ctgcaggtga ccgggtgtac atacacccct ccacctcgt catccacaat      180 gagagtacct gtgagcagct ggcaaaggcc aatgccggga gcccaaaga ccccaccttc      240 atacctgctc caattcaggc caagacatcc cctgtggatg aaaaggccct acaggaccag     300
ctggtgctag tcgctgcaaa acttgacacc gaagacaagt tgagggccgc aatggtcggg     360
atgctggcca acttcttggg cttccgtata tatggcatgc acagtgagct atggggcgtg     420
gtccatgggg ccaccgtcct ctccccaacg gctgtctttg gcaccctggc ctctctctat     480
ctgggagcct tggaccacac agctgacagg ctacaggcaa tcctggatgt tgctgctgag     540
aagattgaca ggttcatgca ggctgtgaca ggatggaaga ctggctgctc cctgatggga     600
gccagtgtgg acagcaccct ggctttcaac acctacgtcc acttccaagg gaagatgaag     660
ggcttctccc tgctggccga gcccaggag ttctgggtgg acaacagcac ctcagtgtct     720
gttcccatgc tctctggcat gggcaccttc agcactgga gtgacatcca ggacaacttc     780
tcggtgactc aagtgccctt cactgagagc cctgcctgc tgctgatcca gcctcactat     840
gcctctgacc tggacaaggt ggagggtctc actttccagc aaaactccct caactggatg     900
aagaaactgt ctccccggac catccacctg accatgccccc aactggtgct gcaaggatct     960
tatgacctgc aggacctgct cgcccaggct gagctgcccg ccattctgca caccgagctg    1020
aacctgcaaa aattgagcaa tgaccgcatc agggtggggg aggtgctgaa cagcatttttt   1080 tttgagcttg aagcggatga gagagagccc acagagtcta cccaacggct taacaagcct    1140
gaggtcttgg aggtgaccct gaaccgccca ttcctgtttg ctgtgtatga tcaaagcgcc    1200
actgccctgc acttcctggg ccgcgtggcc aacccgctga gcacagcatg aggccagggc    1260
cccagaacac agtgcctggc aaggcctctg cccctggcct tgaggcaaa ggccagcagc     1320 agataacaac cccggacaaa tcagcgatgt gtcaccccca gtctcccacc ttttcttcta   1380
atgagtcgac tttgagctgg aaagcagccg tttctccttg gtctaagtgt gctgcatgga    1440
gtgagcagta gaagcctgca gcggcgcaaa tgcacctccc agtttgctgg gtttatttta    1500
```

```
gagaatgggg gtgggaggc aagaaccagt gtttagcgcg ggactactgt tccaaaaaga    1560
attccaaccg accagcttgt ttgtgaaaca aaaaagtgtt ccctttcaa gttgagaaca    1620 aaaattgggt tttaaaatta aagtatacat ttttgcattg ccttcggttt gtatttagtg    1680
tcttgaatgt a                                                         1691

<210> SEQ ID NO 6
<211> LENGTH: 1670
<212> TYPE: DNA
<213> ORGANISM: Homo sapiens

<400> SEQUENCE: 6
agggtatgcg gaagcgagca ccccagtctg agatggctcc tgccggtgtg agcctgaggg      60
ccaccatcct ctgcctcctg gcctgggctg gctggctgc aggtgaccgg gtgtacatac     120
accccttcca cctcgtcatc cacaatgaga gtacctgtga gcagctggca aaggccaatg     180
ccgggaagcc caaagacccc accttcatac ctgctccaat tcaggccaag acatccctg     240 tggatgaaaa ggccctacag gaccagctgg tgctagtcgc tgcaaaactt gacaccgaag     300
acaagttgag ggccgcaatg gtcgggatgc tggccaactt cttgggcttc cgtatatatg     360
gcatgcacag tgagctatgg ggcgtggtcc atggggccac cgtcctctcc ccaacggctg     420
tctttggcac cctggcctct ctctatctgg gagccttgga ccacacagct gacaggctac     480
aggcaatcct gggtgttcct tggaaggaca agaactgcac ctcccggctg gatgcgcaca     540
aggtcctgtc tgccctgcag gctgtacagg gcctgctagt ggcccaggc agggctgata     600 gccaggccca gctgctgctg tccacggtgg tgggcgtgtt cacagcccca ggcctgcacc     660
tgaagcagcc gtttgtgcag ggcctggctc tctataccc tgtggtcctc ccacgctctc     720
tggacttcac agaactggat gttgctgctg agaagattga caggttcatg caggctgtga     780
caggatggaa gactggctgc tccctgatgg gagccagtgt ggacagcacc ctggcttca     840 acacctacgt ccacttccaa gggaagatga agggcttctc cctgctggcc gagccccagg     900
agttctgggt ggacaacagc acctcagtgt ctgttcccat gctctctggc atgggcacct     960
tccagcactg gagtgacatc caggacaact tctcggtgac tcaagtgccc ttcactgaga    1020
gcgcctgcct gctgctgatc cagcctcact atgcctctga cctggacaag gtggagggtc    1080 tcacttcca gcaaaactcc ctcaactgga tgaagaaact atctccccgg tgctgaacag    1140
catttttttt gagcttgaag cggatgagag agagcccaca gagtctaccc aacagcttaa    1200
caagcctgag gtcttggagg tgaccctgaa ccgcccattc ctgtttgctg tgtatgatca    1260
aagcgccact gccctgcact tcctgggccg cgtggccaac ccgctgagca cagcatgagg    1320
ccagggcccc agaacacagt gcctggcaag gcctctgccc ctggcctttg aggcaaaggc    1380
cagcagcaga taacaacccc ggacaaatca gcgatgtgtc accccagtc tcccacctt    1440 tcttctaatg agtcgacttt gagctggaaa gcagccgttt ctccttggtc taagtgtgct    1500
gcatggagtg agcagtagaa gcctgcagcg gcacaaatgc acctcccagt ttgctgggtt    1560
tattttagag aatggggtg gggaggcaag aaccagtgtt tagcgcggga ctactgttcc    1620
aaaaagaatt ccaaccgacc agcttgtttg tgaaacaaaa agtgttccc               1670

<210> SEQ ID NO 7
<211> LENGTH: 16001
<212> TYPE: DNA
<213> ORGANISM: Macaca mulatta
```

<400> SEQUENCE: 7

```
gaagacagtg tggcaattct tcaaggatct agaactagaa ataccatttg acccagccat      60
cccattactg ggtatatacc caaggattta taaatcatgc tgctataaag acacatgcac     120
acatatgttt attgcggcac tattcacaac agcgaagact tggaaccaac ccaaatgtcc     180
aacaaggata gactggatta agaaaatgtg gcacatatac accatggaat actatgtagc     240
cataaaaaag gatgagttca cgtcctttgt agggacatgg atgaagctgg aaaccataat     300
tctcagcaaa ctaatacaag aacagaaaac taaacaccgc atgttctcac tcataggtgg     360
gaattaacaa tgagaacact tggacacagg aaggggaaca tcacacacca gggcctgtcg     420
tggggtgggg agaggggga gggatagcat taggagatat acctaatgta aatgacgagt     480
tattgggtgc agcacaccaa catggcacat gtatatacat gcaacaaacc tgcaagtttg     540
tgcacatgtg ccctagaact taaagtgtac taaatttaaa aaaaaaaaa aaaagaaat      600
ttacttgttt aaaaaaaat ccaaatcctg gcattgtcca gaaaatata acaagtttat       660
ttataattat cataaagttg aattgctgaa acttgttcac tgaaacattt tgatttgcat     720
taatgcctta tgtttccaca tttatattaa aaattcacac acaataaaa atggaaaaac     780
tgccaaaaaa aaatcaagga gacatttat ttacatttac tggttaatta taaggaatac      840
aaaagaacag ccagaagaag agacacaaag cgtgaggtcc acagggtcc ttttaagag       900
acagagtctc tgtcattcag gctggagtgc agcggtgtga gcatagctca ctacagcctc     960
aaacttctgg gctcaagtga tcctcctgcc ccagcctccc aagcagctag gactaccagt    1020
gcatatcacc atatccagtt agttttattt tttgcacaga tgggggtctt gctatgttgc    1080
ctaggctggt ctcaaactct tggcctcaaa ctatcttcct gcctcagttt tccagagtac    1140
ttgggttata aatgtgggcc actgcacctg gcccccaatc ttgatgggga gcaggtttct    1200
gcatgtgtgt caaccccagc tccttgagag tgcggcctga agtccttggt cccggaggct    1260
cagcaggaaa taggacagtg actgcataag cttgtgagaa cctgtggcca ggcagcagca    1320
gccgtttggc cagggcttgt ctcctgcagc cctcctgccc agtacccggg cctgcttgta    1380
ttcccctaca cgcgccccc atgctctccc tcttgttggt gagtgtcact caagcctctg     1440
cctcagaaaa gcccttctgc agcttccaag tcagaccagc tcctcctcca ggtgcaggcc    1500
cagtgatatc tgtccctcgc ccctcgccag cttgcacagg tgaatgcttt ctgcatcctg    1560
aaggcatttc gtttgtgtct tttaatctgg ctgtgctact gttggtgttt aacagtctcc    1620
ccagctacac tggaagcgac cagaaggcac ttttcacttg ctcgtgtgtt tttcccagtg    1680
tctattagag gcctttgcac agggtaggcg ccaaatggct gttgggagca gctgaaggtc    1740
acacatccca tgagcgggca gcagggtcag aagtggcccc cgtgttgcct gagcgagacg    1800
ctcccctgcc ctctgccctc cgcgcctccg gcctgcatgt cccgtggcc tcttagggc     1860
acatcccggg gctgggtcag gaggtctggg cggttggcct taagctgtca cacacccagg    1920
gagatgctgc tgtttctggg aaccttggcc cccactcctg caaacttcgg taaatgtgta    1980
actcgaccct gcaccggctc actctgttca gcagtgaaac tgtgcatcga tcactaagac    2040
ttcctggaag gggtcccagc gtgagtgtcc cttctggcgt ctgtctttct ggccagcctg    2100
tggtctggcc acatgatgta accccctcc agcctgtgca caggcagcct gggaacggct    2160
ccatccccac ccctcagata taaataggc ctcatgacgc ggccagggga agaagctgcc     2220
attgttctgg gtactacagc agaaggtaag ccggggccc cctcagctcc ttctcagcct     2280
tgtccctctc agacgtaact gagctgtggg ccggaaggaa aaggccggga ggggcactgg    2340
```

```
tgatggctga agcatctctc ccctcccata agaccagtca tctggacgca ggctttctcc    2400
gctcagtgcc cacccagggg tctcccagga ggagctgctc ctccttagca ataggaccag    2460
atggtcaggt cttcctgctt cggctgagaa gagttagggt cctcagggat ggagcagact    2520
ggcacaggag cagagtcatc atggtcaaga gtccaccagg tcctcttgcc atgaggagga    2580
acagcagggc ttgtacagga agtggggcca cagggaaggg ctgggccggg tcagtcccca    2640
gctgggatcc ccagagtggt cacccctaccc ctccctcgag acagattccc tgactgtgtc    2700
atcaggctgg tcaccatctc tctgaacctc gatttgctca cctataaaat gggactagta    2760
acgatgcctg ggctccctct ctcaggggct gtggtgcagc tgaagagaac taatacaaca    2820
tgaaagtact ttctaagctt tgggataagc taaaaggcag attccaattt cattcaaggg    2880
cagcgtagat tggtgcttaa acttgtggat gacagagtca gagggcctgg ttctgagtcc    2940
tagttctgtc tcttcccagc tgtgtgactt tgcacaagtc actggacctc tttgttcctc    3000
tggaaaacag caggaaccaa ttcattaact acttctccag gatgcattag gtcccgggga    3060
ctgtcctggg aatgtgggct gtattaggaa acatagcagt gggaaccctg ctccggggct    3120
cacattcacg tcagggcaaa cagacaaaga cgctggacag cacaagtgcg taactacatg    3180
gtacaggggt tataaggagg gaaaagggga gccggatgag agagttgaga gtgcccggtg    3240
tggtggggaa agctgcaggg tgaaatacgg caccaaggaa acctcaggga aggtgaggac    3300
tatgatgagg tcagagcggt tgatataaga acgatgccct gcaaatcaca ggcaccacgg    3360
gagcgtgagc cgtcatcttc acctgtagca ttcagcctgg gggaagtagg gagacataga    3420
aggggcaggt gctggcaaag aggcaggggc aggagggag aaggcggagg ggcgctccag    3480
gcaagggtgt caggcccgcc accccagagc accattactc ccaggacgcg gctgggtgca    3540
gacctggaaa cagcctaggg agcagctgca gatcacaact gagaacaaac gacagtctct    3600
gccttaaaaa tggcccaagg aattgcgtct ctggagatgg tacctgcgca ggagcagcac    3660
agtgagtggg ctgcaccgac cagcgccatc caaaccccga acaggtggcg cttgtcaggc    3720
aggacttccc agcagtcggt tcccacaggt ttcccctgac gacctgatgt gatgtgactg    3780
tctagattag gtgagaactg gtggctcagg cttctctgca cagacaggcc tgcaagcagc    3840
agggagagtt ttctgttctg ttttttccatg tcgtgtggct cttcctgaga acagcggatg    3900
gagtcaacgc atggggagtg gggtgaggcg gtagctgagg tcagaagtca aagtctcttt    3960
ggcatttgaa tgactgaagc agaacgaaac acaccaggta cttcagcagt tgcaccgtgt    4020
tgagggcagg tgctggttac cggtctgggg ggaagccagc tgctaatgta agaagaatga    4080
ctgggtgtgc ttaggtgaag cagaaaaatc taggcatcaa ggtggcctcg agtcagtgat    4140
gacctgctac agctccaagg aagcctgcg tagccctggg gggacagaaa aggctaagca    4200
gtgacgatat tgcagtacac cccctccaca agaaatgagt gagatgtggt acaaactgtt    4260
agaattgaat gaatcaatag aatcaacgtt catcccgtca atcaggaaga gtcagatgaa    4320
atgaattagc agggccagcc caagaacctt gtcttctggg gtctcggggt agtcttcatt    4380
tgcagcagct gaggctgaag cccagtggca aggcctttga gagaacatgg tgccggaccc    4440
gtgtctaagg caggggttct aaaccctgct tacatatcag agccacctga gaaattttt    4500 ttttttttaat ttttattttt ttaatctaag gaatccaagt atcagtgggc aaaccatgct    4560
aggtgtgcat gcctttgggg ctctgcaggg gatagcacta tggagggatg gttgagagct    4620
ggttttgggg ttgagacacg tggaaaatac ttgggctttg ggttgagcct gtggtgctca    4680
```

```
tcctggctgc atattaggac cacaaggaga tgagaaaacc attcccaacc ctcaccctag    4740
ggcccttgaa tgagcatctc aggggtctag gagtcctccg caaagaccta ctgattggca    4800
cgtatgtgtt tttctaggag agaacttaca gccgcaggca ggagcatgtc ttagtgtgct    4860
tgggctgcca taagtaccac agactgggag gcttcaacaa cagaaatgta ttatctcaca    4920
gttctggaag ctagaagccc gggagcaagc catcggcaga gttggtttcc tctggggcct    4980
ctatccttgc cttgtagatg gctgtcttct ctctctgtcc tcacatggtc ttccctctgt    5040
gtgtgtccat gtcctcatct ccccttctca taaggacaca ggtcatatta gatcagggct    5100
cactctcatg gcctcatttt aacttaatca tctctttaaa gattctgtct ccaaataatg    5160
gtcacattct gaggtcctgg ggttgaggac ttcaacatat gcattgtggc cattggggga    5220
gttaggacat gattcagcct atattggtgc attttgcact tggatcatgt agatattttc    5280
catggagctt agaatccatt tcttttcttt ttttgtagac atgaatggac ttattctggg    5340
ctaaatggtg acagagaata ttgagacaat gaaaaatctg gttagatggc acttaacgat    5400
cagttaatag taatcacctt tcacccttg caaaatgata tttcagggta tgcagaagcg    5460
agcaccccag tccgagatgg ctcctgccag cgtgagcctg agggccacca tcctctgcct    5520
cctggctgg gctggcctgg ccacaggtga ccgggtgtac atacaccct tccacctcgt    5580
catccacaat gagagtacct gtgagcagct ggcaaaggcc gatgctggga agcccaaaga    5640
tcccaccttc acacctgttc cgatacaggc caagacgtcc cctgtggatg aaaaggccct    5700
gcaggaccag ctagtgctgg tcgctgcaaa actcgacacc gaggacaagt tgagagccgc    5760
gatggttggg atgctggcca acttcttggg cttccgtata tatggcatgc acagtgagct    5820
atgggcgtg gtccatgggg ccaccatcct ctccccaacg gctgtctttg gcaccctggc    5880
ctctctctac ctgggagcgt tggaccacac agccgacagg ctacaggcaa tcctgggcgt    5940
cccttggaag gacaagaact gcacctcccg gctggatgcg cacaaggtcc tctctgccct    6000
gcaggctgta cagggcctgc tggtggccca gggcagggct gacggccagt cccagctgct    6060
gttgtccaca gtggtgggtc tcttcacagc cccagatctg cacctgaagc agccgtttgt    6120
gcagggcctg gctctctatg cccctgtggt cctcccacgc tctctggact tcacagacct    6180
ggaagtcgct gctgagaaga ttgacaggtt catgcaggct gtgacaggat ggaagattag    6240
cagcccctg acgggagcca gtgcggacag caccctggtt ttcaacacct acgtccattt    6300
ccaaggtagg gcaaacccct ctgccggctc tgccctagga cttagttcc aatgcatagc    6360
tgagctcagc aggtcaggcc ttggagatgg gcaggggcag ccctgcggac atacctggtg    6420
gccaccctcg aggagtgggg aagtggctgc tctgctgggt cctggatgg atgtccacct    6480
cccggacctg ctgccctact atgcacgact acactacatc cttttctta catcatttaa    6540
tccccttatg atgtgatgca gaggtatttg tgcctttgtt tactggtaaa gaaatagaga    6600
ctcgagaaa caaagtgcct tgctcaagat ggcactgcca ccagtggggg tcctgggatt    6660
tcagcccaca tctcctggcc ccacagccca gttctacgct cagagggtac gggttcttgt    6720
ctctggagat ggtcaggagc tggggtccct ggcctatgca gaaataagca attggcttgc    6780
ttaaatccct tcatgttag gaggggcatt actgaaaacc cgtactacaa agatcgttgg    6840
gtttttttt tttttttt tttaattga cacagggtct cgctctgtcc cccaggctga    6900
agtgcagtgg tgcaatcatt gttcactgta tccttgaact cctggctgca agcgatcctc    6960
ccacctcagc cttccaaagt gttgggatta caggcatgag ccactgcacc cagccaaaga    7020
ttgcttaaag cattctttta acaaatactc attgaggatt tgctacttgt aagactttaa    7080
```

```
gcctggcatc tcagaggagg ccagaggagg gttgtagagg ccctgactcc aggcttttaa   7140
aggtcaatgg gcaaacgcct aggatatgga gctgcaggga acgtgctgt acaaggtact    7200 cagggagggc tcggagccct cagaggacag aggtcactgg ggagtggaga gcaggcctca   7260
cctggcagtg aggggaacgg ggctggtgaa gccaggagca agcatgatgg gcccagcctg   7320
cagagtttgg ggcaaggaat gaggatgggg tgtttggctt ggcatgagtg ttgaaccaga   7380
aaatgggcct ggggagggca gagctggaga cactttgaat gccatgccag gtaggtgtgg   7440
gaacggggac gcattcgttc agaggtcgtc ccggaagccc gccgtgtgtg gactggaggc   7500 agggaggggtt gtttgaaggt tacgcaagag tccaggcaca cagtcacggg aacacgcgct   7560
cagggagcag ctcggcgaat ccatgggtgg ggtggggctg aggggtgtgt ctgagagaca   7620
ttgatgaggc tccgtcaaga tgtgtaacct cgtgagggac agagagccag gcgggcggtg   7680
aaagacagga cggtggagaa agaggttcag tggcgcgtgg tgattttctc accatggcaa   7740
cattcttgag gtctctcccc gcgggttcag gggaggtgat agacggggga ttgctcagcc   7800
ctggcactga ctggtcacag gggcagaggc cagcctgagg gttgcccggc tgagggtggc   7860
agcacgctgt gcagggcaga gcggggacac gtgggctcag cctgctgaac ctaggaggag   7920
tgctgggagg agcgctcact gagaaggagg gtcctgcaga aggcaaaggc aagaaagcca   7980
gtggcatctg aaatgggtct cccttcgaaa gacagcccat ccactcacc cagacctcag   8040 agccaggcca tgaggaagag gagaaagaag aaaaaaacca gtgacatcag gactcaaagg   8100
aagcccggca tcctccctgg cctccaccac atgctgccct gaccctgccc cacttcctaa   8160
cctttgctgg tctcagtttc catgaaagga gacagcccct tcctgcccac atggcctgtc   8220
cagtgaggag atcgggggct gtctcgggac ctctagattc ccctttagca atgatgttct   8280
atgtacatga cctcagcagg cagctagatg tgtcccacta gagaggacct gaggatctgg   8340
ggcccgatgg gctccagggc acccttttgcc cagcacctgc tgtgctgctg agcatgggac   8400
tctggccccg gcagttacca caatgccagc tgacttgagc tcgagagatt tacctagcct   8460
tcggatgaga atggtgagct atgtgtgtgt cagacgaaca gagggaagag ggcagccact   8520
ctcatgtcaa attccaacat cttttgggaa gcagcttcct ttttttggtt tagtttgttg   8580
gaagaaaaga attgtccctt tcctcccctct aaactaaaag ccttgctagc ctgggtgggc   8640
ggcaccgagg tccctgtagg gaatgtgcaa ggaggatcct gcagtttccc gctcacatgc   8700 cctccccgaga ctgagtgctc cgaggactga ggacgaggaa tatgccaggt ctgccactgc   8760
cttctcacaa gacccagacc caggggaggc acagccatgc ccagctccca cctgccagtt   8820
ctgtcctccc agcttcccta cttccctgct ggaagctcca attgagtaca aagggagacc   8880
ccactgtttc tgaaccatct ctactcagac tcccaagcgt cacgtgccca gaggactgct   8940
ctgtgacaaa ctcatataca atttcaccct cttctcctaa aaactaccac aaaatgggcc   9000
tttcaaggtg agtgggagga cagccgaggg catcctgtga tgcactagtg taaggtcgag   9060
gcagagggcg agctgccgtc atggagagac cccgggtaac tgcttcacac acaagtttgt   9120
gtccttctcc cacgccgggc tctcccgagt tctctgtctt ctccacggcc ctgtgagcgg   9180
ggcagggggt ggggagaaca gagggctcac ccctgccccc agggcccagt gtgcaaatcc   9240
attcgtcaca gcgaggtctt gtgagtctcc tcagtagcaa gggctgctga agaatggagc   9300
cctcgttccc ggagcctgcg tggccagctc tgtattccgt gactgtgatg ggggagggtg   9360
ggggccacag gacagccggc aggctctgcc actgctgcgg ctggacatgg attaaaagt    9420
```

| | |
|---|---|
| gagcatgagc agggcctct aggagcagtg ggatactgca gtggtggctg cgcgtcattc | 9480 |
| tacatgcatg caaacccaca gaatgtaaaa caccaggacg gagccccaaa gaaaaccatc | 9540 |
| aactttgggt gctgaggatg tgtcaatgca ggttcatcaa ctgcaataaa tgggccactc | 9600 |
| tggtgtgaga tgttgatcac ggggaaggct gtgtgtgggg ggacaggagt tatatgggaa | 9660 |
| cttttttgtac tttctgctcg attttgctgt gaacgtagtc actctaaaaa agagtatctc | 9720 |
| ttaaaatttt taaaaagtga gtgtgtcaaa tcacagcctc tgtgtcagga cagatgtagg | 9780 |
| tttgagttga cctggcaggt accagtggca tatgtccctt aaaatgacag acgcaaacct | 9840 |
| ccggttcagt gcctagcatg ttacatgtct tcagcaggtg gcagttaggg ctgcctcagt | 9900 |
| gaactcaaat ggctgcattt tgcaggaaga tatgagctac atttggggtc ctgtggccag | 9960 |
| gagaatacag agtggcctgg ggcggaccag ggaaggaggc tgtggcaggg agaggggcag | 10020 |
| gatctgggcc ttcggtgtct gccagccctc gtccctgccc ctgtcccggc tgactcttcc | 10080 |
| ctccccgtct cctgtctgga tttcagggaa gatgagggac ttcttcctgc tggctgagcc | 10140 |
| ccaggagttc tgggtggaca acagcacctc agtgtctgtc cccatgctgt ctggcgtggg | 10200 |
| caccttccag cactggagcg acgcccagga caacttctca gtgactcaag tgcccttttac | 10260 |
| tgagagcgcc tgcttgctgc tgattcagcc tcactacgcc tctgacctgg acaaggtgga | 10320 |
| gggtctcact ttccagcaaa actccctcaa ctggatgaag aaactgtctc cccggtagga | 10380 |
| gcctcctggt ctcccctgga atgtgggagc cgagctgtcc ttctgccccc actggggtg | 10440 |
| gggtggggag tagacacaca tgaactgagc cttgggtgca gagcagggca gggccgcagt | 10500 |
| ggcatggggc tgggcaggcg gcctgtgtgt ctatccacca gctctccatc cacccagcac | 10560 |
| ccagctctcc agttagtgtc tgtctttcag gtgcaggcaa ggtaaagcag gggaggaaga | 10620 |
| atgcttttc tatgcttata tttgcttggt ggttttggag ggaaagaata cattgcaatc | 10680 |
| cgccctctga gagaggaaca ttttggcccc acacctgaca cacagcacat ctgtggcatc | 10740 |
| caagagcttc ttggaactga cttgccagga gggtttggac tccatgtgag cggggtgga | 10800 |
| gccttctcag ggagcatgcc ttgactccag aacgtccttg ctggcggctg gcggctgggc | 10860 |
| ggggacaggt gtcgttagca cctctttcct gctgcaattc ccttccatag gccttggat | 10920 |
| tcaacctaca catccccca gatcatcaag gcctggaaat ctgatcccag aggcaggcat | 10980 |
| ggagtgacac gatggcttct tgacatcagc tctggatgct ttttatgttt taaaaattat | 11040 |
| ggtgataaaa tatacataac aaaatttgcc atcgtaacca ttttcgagtg cacagttcag | 11100 |
| tagcactagg cacattcaca ctgttgtgca gccatcaccg ccatccatct ccatttacct | 11160 |
| tctcatcttc ccagaccgaa gctctgccct gctgaaacac taactctcca tttccccttc | 11220 |
| ccctgggttc ctggcaagca ccacgatgtc ctcgaggttt acccatgttg tagcacgtgt | 11280 |
| cagaatttcc ttccttttga aggctgaata atattcccct gcatgtggtt accaccttt | 11340 |
| gtctatccac tcgtccatca atggacacgt gggttgcttt cacctttgag ctgctgtgac | 11400 |
| tagtgcagtg tacattgtaa acatggatgt actgtcagct cttataagtg cttgatatat | 11460 |
| cactggaaat gtccatgcgc tctgaaggat gccagaagat ggaagaggcc cttacaaaga | 11520 |
| tcaattgagt tgacatagca acgtgtccag cacgagttga cactgtaccc tcctgtctcc | 11580 |
| ctccttttca tgggtgtctt gtcatcaaga acactgctgt tgcagtagta agacacagtg | 11640 |
| cattatttag agaatagcat tttaaaatta cccaagtaac acaccttcag tgcagccaat | 11700 |
| ctaaaaacag aatgcaccaa aggacaacca ttcctaggtc ctcatcggta aatgttctat | 11760 |
| gtccctgtca tagtatttca aatgacatga acgttttta ttgtaggttt tgctgaaatt | 11820 |

```
ttccccaagg gggaggatga cctagttggg tgggagggg  acaaacatcc ctgtcgtcag  11880
gattgggtac aaggagcata tgcccacctg gcctctggga gagccctctc tgtgtggcct  11940
ggagccttcc taactgtgcc tcatctcccc agggccatcc acctgaccat gccccgactg  12000
gtgctgcgag gatcttatga cctgcaggac ctgcttgccc aggctgagct gcccgccatt  12060
ctgggcaccg agctgaacct gcaaaaattg agcaatgacg acctcagggt ggggaaggta  12120
tgcgcgagcc tgtgtctgtg cctgacctgg gttccgagtg ttcacagggt gggggggcatg 12180
gatggaaggg acacagagga ggctgtgggt ggggccagca gggcaagagg gagaggagag  12240
tagggccaaa ggtgggagag aagtggccag agcattgtga ggcttttccag gtgcacagca  12300
gcaaatccct cccctgctcc gcctcctcct gctgggggtg tgttccatgg tctcgcctgc  12360
tccgcctcct cctgctgggg gtgtgtttca tggtcctgct ccgcctcctc ctgctggggg  12420
tgtgttccat gtcctgctcc gcctcctcct gctgggggtg tgttccatgg ttctgctccg  12480
cctccacctg ctgggagtgt gttccatggt cctgctccgc tcctcctgc  tggggggtgt  12540
ttccatggac ctgctccgcc tcctcctgct ggggtgtgt  tccatggacc tgctccgcct  12600
catcctgctg ggggtgtgtt ccatgtcctg ctccgcctcc tcctgctaga agtgtgttcc  12660
atggtcctgc tcggccttgc cttgcctcag ggtcctccag ggatcctgca gtggagttga  12720
aaccgggatg aagagagtga gcacccttgg acctggtgcc ctgggtccag ccccttcttt  12780
agggaaatgc tgagcgcaga cagaatgtcc cctgccatgc ggcaccatgc acatctgtgg  12840
ctaccaagga tgcgcctgga tgctctgggc cctgtgctcg gtgctgggga gaaagtggaa  12900
gttcctacgg gggccagcgg gatgagctct ctgtgctaag ttagctaagc cctggcactg  12960
gtgggccatg gccaagggag ccaggaattc tgcccggaac agccgggcgg aacgtgaaga  13020
tgggaggacg tgagggggcgt ggtagggagg agccggtacg tgagtttggc cactgtggcc  13080
aagtaagggt catctacaca gacacaccct tgcctacact gaggagcagg catacactgt  13140
gcatcctcct ggcagactgg acaatgtctc cctccaggac agtgcacatc acagaggtcc  13200
tgagccctcc ccggccctct agccctcagc ccctgggtc  acccagtgcg ccctcagaat  13260
gaccctgatg tctgccgctt tgcaggtgct gaacagcatt ttttttgaac tcgaagcgga  13320
tgagagagag cccacagagt ctacccgaca gctgaacagg cctgagttct tggaggtgac  13380
cctggaccgc ccattcctgt ttgctgtgta tgatcaaagt gccactgccc tgcacttcct  13440
gggccgtgtg gccaacccgc tgagcccagc atgaggccag ggcccagaa  cacagcgcct  13500
ggcaaggcct ctgcccctgg cctttgaggc gaaggccagc ggcagatagt aactctggac  13560
aaaccagcga tttgtcaccc ccagtctccc acctttctt  ctaatgagtc aacttcgagc  13620
tggaaagcag tcgtttctcc ttggtctacg tggtgctgcg tggagtgagc agtaagaaac  13680
ctgtggcagc acaaatgcgc ctcccaggtt gctgggttta ttttagagaa tgggggtggg  13740
gaggcaagaa ccagtgttta gcgcgggacc accgttccaa aaagaattcc aaccgaccag  13800
cttgtttgtg aaacaaaaaa gtgttccctt ttcaagttga gaacaaaaat tgggttttaa  13860
aattaaagta tacattttg  cattgccttc ggtttgtatt tagtgtcttg aatgtaagaa  13920
catgacctcc gtgtagtgtc tacagtagct tagttttttc cacagatgct tgtgattttt  13980
ttgaataaca cgtgaaagat gcaagcatct gaatttctgt ttgaatgtgg aaaccatagc  14040
tggttatttc tcctttgtgt tagtaataaa cgtcttgcaa caataagcct cccaaaattc  14100
tatctttcat ttagcagcca aacagatgta tacaatttag cagatagact gtgcaaacca  14160
```

```
aagtgctttc ctggactttg gatggaattt ccattggaag cctgagccag tacttagcag    14220
tcctttgaag ttttaggtga tgcttttctc tggacacttc cattggtaag cagtggtggc    14280
catctgtgtg acggacaggg ggtgggaaga gggtgacagg gaaggcccca taccccacat    14340
ggcacctggg aaaggaacca ggcggacagg acttcttcca tcctggtgac acagggccag    14400
actgctgctg gtattgtgct ccgggagtgg aaggtagaga aataaatctt cacaaataaa    14460
tatttgccat ttttccccat ctgttgagtg cctccacctg ctcctcctcg atgggattag    14520
gcccacagtt tggaatcttg gggagagcca aggaggcggt aggcacccag caggcccatg    14580
gccatcagct gatagcaatg gtgatcctgt cctacctatg tgtgtaaggc actcaatctt    14640
cctcccttcc atacatattg caataaataa gcaagccgta caatgtgtta gctattgatc    14700
agaacgaaag tgaaatctgc cacggggatt acaaatcttg gcttctcccc tcacatttct    14760
gagagtcttc ccctgatttt gaacacatct ccctagctcg atgtcaagat gaggggattc    14820
tgtcggtgac agcagtgccc ttagttgctt cgttgtaact ccccgtcacc agttttattc    14880
agttaccctc cagtcccact ctcagcgctt cctggcttgt tctgccctca aagtgcgtag    14940
aactggcaca catggactct ccgaaacagc tgaaggacgc caagtttctc aggagtactg    15000
gaagtacaga gagcagaagt gccttaaggt ctcactattc aaagtgtggc gcttggacct    15060
gcagtggcag cagctgccct gggagcttgt tagaaggcag cttctcacgc ccctcctgga    15120
cctacagagt cagaatctgc aattttacgg gaggtccagg cttggaagtt gcttgtaatg    15180
acctgagaca gcgcagccaa gtgctggaaa aatagagcat ttaagtttgt gactttattt    15240
taaaaggcag ctggcagtcg acgaaccaaa tttcttctac ttagtggcgg cttcggcttc    15300
tggaagtcgc taggagtatg aagttgccaa acagcactgt tctcctgctg ttctctgtgc    15360
acttgtaaat gggaagctgg gtcaggatag atctctcagc tattagaaag atacaaaata    15420
ctaacatttt gcaggttact taacacacac acacacaaaa ttcattccac aggtcagttt    15480
ctctgaaaca ttttttcact aaattctaag tgttcctgga gttgcaagtg cctgtctcct    15540
agactaggca attactcagc aactacaatc actgtcaatc cgagatttca gctgcgcatg    15600
agaccatggt caggggatgc tttgaacagt ctctgaggaa atgagtttga aaaatggaaa    15660 gattttttt acgcacttgg cagtaaaacc tgatggggac agacatcagg ctgtttaaga    15720
tcctcagaag aaaaaattga tagtgtgaat attcctcaat ttgctgcaca agatgtacg    15780 tgtgattata aggtgttatt ccggaagccc ctgggggggt tatgggatat acactatatg    15840
ggccacttta ccttcctaaa atctgaaaaa ttccaacgac tgaaacatgg actgaaggtt    15900
ttgaatcgtg tatggtgaat gtgaatacca ttccatgtga tttttttttc tagcagactt    15960
tagtttttta gagcagtttt aagcccacac caaaacggag a                       16001
```

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
ccctgatggg agccagtgt                                                 19

<210> SEQ ID NO 9
<211> LENGTH: 19
<212> TYPE: DNA
<213> ORGANISM: Artificial sequence

```
<220> FEATURE:
<223> OTHER INFORMATION: Primer

<400> SEQUENCE: 9
agcagggaga agcccttca                                                    19

<210> SEQ ID NO 10
<211> LENGTH: 27
<212> TYPE: DNA
<213> ORGANISM: Artificial sequence
<220> FEATURE:
<223> OTHER INFORMATION: Probe

<400> SEQUENCE: 10
ccctggcttt caacacctac gtccact                                           27

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
ggacaaggtg gagggtctca                                                   20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
agatccttgc agcaccagtt g                                                 21

<210> SEQ ID NO 13
<211> LENGTH: 29
<212> TYPE: DNA
<213> ORGANISM: Artificial sequence
<220> FEATURE:
<223> OTHER INFORMATION: Probe

<400> SEQUENCE: 13
atgaagaaac tatctccccg gaccatcca                                         29

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
tgcccgctca tgggat                                                       16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
gggccacttc tgaccc                                                       16
```

```
<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
gcttaggcaa cacggg                                                         16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
ggagagtctt gcttag                                                         16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
catgcaggcc ggaggt                                                         16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
gccacaggga catgca                                                         16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
tgacccagcc ccggga                                                         16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
tgtgacagcc tgaggc                                                         16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 22
tccctaggtg tgtgac                                                     16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
gaaacgggag catctc                                                     16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
aaggttccca gaaacg                                                     16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
agtttgcagg agtcgg                                                     16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
tcgagttaca cattta                                                     16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
agagtgagcc ggtgca                                                     16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
actgctgaac agagtg                                                     16

<210> SEQ ID NO 29
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
gcagagtttc actgct                                                    16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
agtgatcgat gcagag                                                    16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
aggaagtctt agtgat                                                    16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
tgggacctct tccagg                                                    16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
ggccagacca caggct                                                    16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
tacatcactt ggccag                                                    16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
```
agaggagggt tacatc                                                  16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
gtgcacaggc tggaga                                                  16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
tatttatagc tgaggg                                                  16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
cacgatgccc tattta                                                  16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
tacccagaac aacggc                                                  16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gccatctcag actggg                                                  16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
accggcagga gccatc                                                  16

<210> SEQ ID NO 42
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 42
tcaggctcac accggc                                                      16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
atggtggccc tcaggc                                                      16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
ggtcacctgc agccag                                                      16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
atgtacaccc ggtcac                                                      16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ggtactctca ttgtgg                                                      16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
agctgctcac aggtac                                                      16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
cttcccggca ttggcc                                                      16
```

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
agcaggtatg aaggtg                                                     16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
cctgaattgg agcagg                                                     16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
gatgtcttgg cctgaa                                                     16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cttttcatcc acaggg                                                     16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
agcaccagct ggtcct                                                     16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
tgcagcgact agcacc                                                     16

<210> SEQ ID NO 55
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 55
tgtcaagttt tgcagc                                                         16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
cggccctcaa cttgtc                                                         16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
tcccgaccat tgcggc                                                         16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
ttggccagca tcccga                                                         16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
gcccaagaag ttggcc                                                         16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
atatacggaa gcccaa                                                         16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
tgcatgccat atatac                                                         16

```
<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
gccccatagc tcactg                                                      16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
ggccccatgg accacg                                                      16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
aaagacagcc gttggg                                                      16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
ccagggtgcc aaagac                                                      16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
cagatagaga gaggcc                                                      16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
gtgtggtcca aggctc                                                      16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 68
cacccaggat tgcctg                                                    16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
ttccaaggaa caccca                                                    16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
agccgggagg tgcagt                                                    16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
tccagccggg aggtgc                                                    16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
acagcctgca gggcag                                                    16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
ccactagcag gccctg                                                    16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
tatcagccct gccctg                                                    16

<210> SEQ ID NO 75
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 75
tgggcctggc tatcag                                                    16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
cgtggacagc agcagc                                                    16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
gtgaacacgc ccacca                                                    16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
tcaggtgcag gcctgg                                                    16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
gccctgcaca aacggc                                                    16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
tagagagcca ggccct                                                    16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
```
cgtgggagga ccacag                                                        16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
tgaagtccag agagcg                                                        16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
gcaacatcca gttctg                                                        16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
tcttctcagc agcaac                                                        16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
cctgtcacag cctgca                                                        16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
ttccatcctg tcacag                                                        16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tgtccaccca gaactc                                                        16

<210> SEQ ID NO 88
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 88
tgttgtccac ccagaa                                                       16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
tgctgttgtc caccca                                                       16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
aggtgctgtt gtccac                                                       16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
ctgaggtgct gttgtc                                                       16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
acactgaggt gctgtt                                                       16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
cagacactga ggtgct                                                       16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
agcatgggaa cagaca                                                       16
```

```
<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
cccatgccag agagca                                                   16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
actccagtgc tggaag                                                   16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gtcactccag tgctgg                                                   16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
gtcctggatg tcactc                                                   16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
ccgagaagtt gtcctg                                                   16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
acttgagtca ccgaga                                                   16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 101
agtgaagggc acttga                                                    16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
ctggatcagc agcagg                                                    16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
ggtcagaggc atagtg                                                    16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
tggaaagtga gaccct                                                    16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
ggagttttgc tggaaa                                                    16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
tccagttgag ggagtt                                                    16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
ggagatagtt tcttca                                                    16

<210> SEQ ID NO 108
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
tcaggtggat ggtccg                                                    16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
tgcagcacca gttggg                                                    16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
ataagatcct tgcagc                                                    16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
agcaggtcct gcaggt                                                    16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
cgggcagctc agcctg                                                    16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
tgcagaatgg cgggca                                                    16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
```
cagctcggtg tgcaga                                                        16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
tttgcaggtt cagctc                                                        16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
ggtcattgct caattt                                                        16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
accctgatgc ggtcat                                                        16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
gcttcaagct caaaaa                                                        16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
tgttgggtag actctg                                                        16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
caggcttgtt aagctg                                                        16

<210> SEQ ID NO 121
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 121
tccaagacct caggct                                               16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
aggaatgggc ggttca                                               16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
cggcccagga agtgca                                               16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
gttggccacg cggccc                                               16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
tgctcagcgg gttggc                                               16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
ggccctggcc tcatgc                                               16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ggccttgcca ggcact                                               16
```

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
gcctcaaagg ccaggg                                                    16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
cgctgatttg tccggg                                                    16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
ggtgacacat cgctga                                                    16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
gaaaaggtgg gagact                                                    16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
cgactcatta gaagaa                                                    16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
acggctgctt tccagc                                                    16

<210> SEQ ID NO 134
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 134
ccaaggagaa acggct 16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
cacacttaga ccaagg 16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
tgccgctgca ggcttc 16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
ggtgcatttg tgccgc 16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
tggtcggttg gaattc 16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
acaaacaagc tggtcg 16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
cttgaaaagg gaacac 16

```
<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141 aacccaatttt ttgttc                                                  16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ggcaatgcaa aaatgt                                                   16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
tacattcaag acacta                                                   16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
ggtcatgttc ttacat                                                   16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
actacacgga ggtcat                                                   16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
tattacagac actaca                                                   16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 147
ggtgcttgca tctttc                                                    16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
cagaaattca ggtgct                                                    16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
ccgcattcaa acagaa                                                    16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
agctatggtt ccgcat                                                    16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
tactaacaca agggag                                                    16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
ttattgtggc aagacg                                                    16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
ttactaatac agccca                                                    16

<210> SEQ ID NO 154
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 154
ggtttccctg atgcag                                                     16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
tgatagttgg attcct                                                     16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
tgtggtccca acatgc                                                     16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
ttgaagtcct caaccc                                                     16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
ctcttggatg tcacag                                                     16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
gatggcaaat tttgtt                                                     16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
```
tgtgttactt gggtaa                                            16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gccacacagt gagggc                                            16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
ctgctgctgg cctttg                                            16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
gttatctgct gctggc                                            16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
gggttgttat ctgctg                                            16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
tcgctgattt gtccgg                                            16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
catcgctgat ttgtcc                                            16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
gacacatcgc tgattt                          16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
aaaggtggga gactgg                          16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
attagaagaa aaggtg                          16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
gtcgactcat tagaag                          16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
tcaaagtcga ctcatt                          16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
cagctcaaag tcgact                          16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
gctgctggcc tttgcc                          16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
tgctgctggc ctttgc                                                   16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
tctgctgctg gcctttt                                                  16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
atctgctgct ggcctt                                                   16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
tatctgctgc tggcct                                                   16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
ttatctgctg ctggcc                                                   16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
tgttatctgc tgctgg                                                   16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 180
ttgttatctg ctgctg                                                    16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
gttgttatct gctgct                                                    16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
ggttgttatc tgctgc                                                    16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
atcgctgatt tgtccg                                                    16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
acatcgctga tttgtc                                                    16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
cacatcgctg atttgt                                                    16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
acacatcgct gatttg                                                    16

<210> SEQ ID NO 187
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
tgacacatcg ctgatt                                                     16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
gtgacacatc gctgat                                                     16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
gggtgacaca tcgctg                                                     16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
aaaaggtggg agactg                                                     16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
agaaaaggtg ggagac                                                     16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
tagaagaaaa ggtggg                                                     16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
```
ttagaagaaa aggtgg                                                   16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
cattagaaga aaaggt                                                   16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
tcattagaag aaaagg                                                   16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
ctcattagaa gaaaag                                                   16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
actcattaga agaaaa                                                   16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
gactcattag aagaaa                                                   16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
tcgactcatt agaaga                                                   16

<210> SEQ ID NO 200
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 200
agtcgactca ttagaa        16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
aagtcgactc attaga        16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
aaagtcgact cattag        16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
caaagtcgac tcatta        16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
ctcaaagtcg actcat        16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
gctcaaagtc gactca        16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
agctcaaagt cgactc        16

```
<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
aggccttgcc aggcactgtg                                                  20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
gaggccttgc caggcactgt                                                  20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
agaggccttg ccaggcactg                                                  20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
cagaggcctt gccaggcact                                                  20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
gcagaggcct tgccaggcac                                                  20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
ggcagaggcc ttgccaggca                                                  20

<210> SEQ ID NO 213
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 213
gggcagaggc cttgccaggc                                              20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
ctttgcctca aaggccaggg                                              20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
cctttgcctc aaaggccagg                                              20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
gcctttgcct caaaggccag                                              20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
ggcctttgcc tcaaaggcca                                              20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
tggcctttgc ctcaaaggcc                                              20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
ctggcctttg cctcaaaggc                                              20

```
<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
gctggccttt gcctcaaagg                                                  20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
tgctggcctt tgcctcaaag                                                  20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
ctgctggcct ttgcctcaaa                                                  20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
gctgctggcc tttgcctcaa                                                  20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
tgctgctggc ctttgcctca                                                  20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
ctgctgctgg cctttgcctc                                                  20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 226
tctgctgctg gcctttgcct                                           20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
atctgctgct ggcctttgcc                                           20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
tatctgctgc tggcctttgc                                           20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
ttatctgctg ctggcctttg                                           20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
gttatctgct gctggccttt                                           20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
tgttatctgc tgctggcctt                                           20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
ttgttatctg ctgctggcct                                           20

<210> SEQ ID NO 233
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 233
gttgttatct gctgctggcc                                          20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
ggttgttatc tgctgctggc                                          20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
gggttgttat ctgctgctgg                                          20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
acatcgctga tttgtccggg                                          20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
cacatcgctg atttgtccgg                                          20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
acacatcgct gatttgtccg                                          20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
```
gacacatcgc tgatttgtcc                                          20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
tgacacatcg ctgatttgtc                                          20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
gtgacacatc gctgatttgt                                          20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
ggtgacacat cgctgatttg                                          20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
gggtgacaca tcgctgattt                                          20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
aagaaaaggt gggagactgg                                          20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
gaagaaaagg tgggagactg                                          20

<210> SEQ ID NO 246
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 246
agaagaaaag gtgggagact                                              20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
tagaagaaaa ggtgggagac                                              20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
ttagaagaaa aggtgggaga                                              20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
attagaagaa aaggtgggag                                              20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
cattagaaga aaaggtggga                                              20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
tcattagaag aaaaggtggg                                              20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
ctcattagaa gaaaaggtgg                                              20
```

```
<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
actcattaga agaaaaggtg                                               20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
gactcattag aagaaaaggt                                               20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
cgactcatta gaagaaaagg                                               20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
tcgactcatt agaagaaaag                                               20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
gtcgactcat tagaagaaaa                                               20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
agtcgactca ttagaagaaa                                               20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 259
aagtcgactc attagaagaa                                          20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
aaagtcgact cattagaaga                                          20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
caaagtcgac tcattagaag                                          20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
tcaaagtcga ctcattagaa                                          20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
ctcaaagtcg actcattaga                                          20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gctcaaagtc gactcattag                                          20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
agctcaaagt cgactcatta                                          20

<210> SEQ ID NO 266
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
cagctcaaag tcgactcatt                                               20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
ccagctcaaa gtcgactcat                                               20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
tccagctcaa agtcgactca                                               20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
ttccagctca aagtcgactc                                               20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
tttccagctc aaagtcgact                                               20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
ctttccagct caaagtcgac                                               20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
```
gctttccagc tcaaagtcga                                                20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
tgctttccag ctcaaagtcg                                                20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ctgctttcca gctcaaagtc                                                20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
gctgctttcc agctcaaagt                                                20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
ggctgctttc cagctcaaag                                                20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
cggctgcttt ccagctcaaa                                                20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
acggctgctt tccagctcaa                                                20

<210> SEQ ID NO 279
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 279
aacggctgct ttccagctca                                                    20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
aaacggctgc tttccagctc                                                    20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
gaaacggctg ctttccagct                                                    20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
agaaacggct gctttccagc                                                    20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
gagaaacggc tgctttccag                                                    20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
ggagaaacgg ctgctttcca                                                    20

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
cctgctgccc gctcat                                                        16
```

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
ctgaccctgc tgcccg                                                        16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
cacttctgac cctgct                                                        16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
gtcttgctta ggcaac                                                        16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
ggtgcagagg gcagag                                                        16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
ccggaggtgc agaggg                                                        16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
gcaggccgga ggtgca                                                        16

<210> SEQ ID NO 292
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 292
gacatgcagg ccggag                                                        16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
acagggacat gcaggc                                                        16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
aggccacagg gacatg                                                        16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295
ccaagaggcc acaggg                                                        16

<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 296
tacccccaag aggcca                                                        16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297
agatgtaccc ccaaga                                                        16

<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298
ccgggagatg tacccc                                                        16

```
<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299
cagccccggg agatgt                                                     16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 300
ccttctgacc cagccc                                                     16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 301
ccaggccttc tgaccc                                                     16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 302
accacccagg ccttct                                                     16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
ggccaaccac ccaggc                                                     16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
cctgaggcca accacc                                                     16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 305
gacagcctga ggccaa                                                   16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306
tgtgtgacag cctgag                                                   16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 307
ctaggtgtgt gacagc                                                   16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
tctccctagg tgtgtg                                                   16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 309
gagcatctcc ctaggt                                                   16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
aacgggagca tctccc                                                   16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
ccagaaacgg gagcat                                                   16

<210> SEQ ID NO 312
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 312
ggttcccaga aacggg                                                    16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313
gccaaggttc ccagaa                                                    16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
gtttgcagga gtcggg                                                    16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 315
ccgaagtttg caggag                                                    16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 316
atttaccgaa gtttgc                                                    16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
tacacattta ccgaag                                                    16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318

```
cgagttacac atttac                                              16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
agggtcgagt tacaca                                              16

<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 320
ggtgcagggt cgagtt                                              16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
gagccggtgc agggtc                                              16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
tgaacagagt gagccg                                              16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323
gtttcactgc tgaaca                                              16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324
tcgatgcaga gtttca                                              16

<210> SEQ ID NO 325
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 325
gtcttagtga tcgatg                                                       16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326
cttccaggaa gtctta                                                       16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327
ggacctcttc caggaa                                                       16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 328
cgctgggacc tcttcc                                                       16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 329
actcacgctg ggacct                                                       16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
gcgacactca cgctgg                                                       16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
cagaagcgac actcac                                                       16
```

```
<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
gatgccagaa gcgaca                                                     16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
ggacagatgc cagaag                                                     16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
cagaaggaca gatgcc                                                     16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
ctggccagaa ggacag                                                     16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
acaggctggc cagaag                                                     16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
agaccacagg ctggcc                                                     16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 338
tggccagacc acaggc                                                    16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
tcacttggcc agacca                                                    16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
ttacatcact tggcca                                                    16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
gagggttaca tcactt                                                    16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
gagaggaggg ttacat                                                    16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
tgcctgtgca caggct                                                    16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
caggctgcct gtgcac                                                    16

<210> SEQ ID NO 345
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
gttcccaggc tgcctg                                                    16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
gagctgttcc caggct                                                    16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
ggatggagct gttccc                                                    16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
tgccctattt atagct                                                    16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
ctccaagacc tcaggc                                                    16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
cacctccaag acctca                                                    16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
```
ggtcacctcc aagacc                                                     16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
cagggtcacc tccaag                                                     16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
gttcagggtc acctcc                                                     16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
gcggttcagg gtcacc                                                     16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
gaatgggcgg ttcagg                                                     16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
caggaatggg cggttc                                                     16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
aaacaggaat gggcgg                                                     16

<210> SEQ ID NO 358
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 358
cagcaaacag gaatgg                                                         16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
tacacagcaa acagga                                                         16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
gatcatacac agcaaa                                                         16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
tttgatcata cacagc                                                         16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
cgctttgatc atacac                                                         16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
ggaagtgcag ggcagt                                                         16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
acgcggccca ggaagt                                                         16
```

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
gccacgcggc ccagga                                                      16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
ttggccacgc ggccca                                                      16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
gggttggcca cgcggc                                                      16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
agcgggttgg ccacgc                                                      16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
ctcagcgggt tggcca                                                      16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
gtgctcagcg ggttgg                                                      16

<210> SEQ ID NO 371
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 371
gctgtgctca gcgggt                                                    16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
atgctgtgct cagcgg                                                    16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
catgctgtgc tcagcg                                                    16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
tcatgctgtg ctcagc                                                    16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
ctcatgctgt gctcag                                                    16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
gcctcatgct gtgctc                                                    16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
tggcctcatg ctgtgc                                                    16

```
<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ctggcctcat gctgtg                                                   16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
ccctggcctc atgctg                                                   16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
gccctggcct catgct                                                   16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
ggcactgtgt tctggg                                                   16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
aggccttgcc aggcac                                                   16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
ggcagaggcc ttgcca                                                   16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 384
tgcctcaaag gccagg    16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
ttgcctcaaa ggccag    16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
tttgcctcaa aggcca    16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
ctttgcctca aaggcc    16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
cctttgcctc aaaggc    16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
gcctttgcct caaagg    16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
ggcctttgcc tcaaag    16

<210> SEQ ID NO 391
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 391
tggcctttgc ctcaaa                                                   16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
ctggcctttg cctcaa                                                   16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
gctggccttt gcctca                                                   16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
ccagctcaaa gtcgac                                                   16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
tccagctcaa agtcga                                                   16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
ttccagctca aagtcg                                                   16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
```

```
tttccagctc aaagtc                                                  16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
gctttccagc tcaaag                                                  16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
cggctgcttt ccagct                                                  16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
aacggctgct ttccag                                                  16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
aaacggctgc tttcca                                                  16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
gaaacggctg ctttcc                                                  16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
agaaacggct gctttc                                                  16

<210> SEQ ID NO 404
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 404
gagaaacggc tgcttt                                                        16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
ggagaaacgg ctgctt                                                        16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
aggagaaacg gctgct                                                        16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
aaggagaaac ggctgc                                                        16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
caaggagaaa cggctg                                                        16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
accaaggaga aacggc                                                        16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
gaccaaggag aaacgg                                                        16
```

```
<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
agaccaagga gaaacg                                                        16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 412
tagaccaagg agaaac                                                        16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
ttagaccaag gagaaa                                                        16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
acttagacca aggaga                                                        16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
cacttagacc aaggag                                                        16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
acacttagac caagga                                                        16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 417
agcacactta gaccaa                                                          16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
cagcacactt agacca                                                          16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
gcagcacact tagacc                                                          16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
tgcagcacac ttagac                                                          16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
atgcagcaca cttaga                                                          16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
catgcagcac acttag                                                          16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
ccatgcagca cactta                                                          16

<210> SEQ ID NO 424

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
tccatgcagc acactt                                                     16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
ctccatgcag cacact                                                     16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
actccatgca gcacac                                                     16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
cactccatgc agcaca                                                     16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
tcactccatg cagcac                                                     16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
gctgcaggct tctact                                                     16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
```
cgctgcaggc ttctac 16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
ccgctgcagg cttcta 16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432
gccgctgcag gcttct 16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
gtgccgctgc aggctt 16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
tgtgccgctg caggct 16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
ttgtgccgct gcaggc 16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
tttgtgccgc tgcagg 16

<210> SEQ ID NO 437
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 437
atttgtgccg ctgcag                                                   16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
catttgtgcc gctgca                                                   16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
gcatttgtgc cgctgc                                                   16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
tgcatttgtg ccgctg                                                   16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
gtgcatttgt gccgct                                                   16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
aggtgcattt gtgccg                                                   16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
gaggtgcatt tgtgcc                                                   16
```

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
ggaggtgcat ttgtgc                                                      16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 445
gggaggtgca tttgtg                                                      16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
tgggaggtgc atttgt                                                      16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
ctgggaggtg catttg                                                      16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
actgggaggt gcattt                                                      16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
aactgggagg tgcatt                                                      16

<210> SEQ ID NO 450
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 450
aaactgggag gtgcat                                                        16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
caaactggga ggtgca                                                        16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
gcaaactggg aggtgc                                                        16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
agcaaactgg gaggtg                                                        16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
acccagcaaa ctggga                                                        16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
aacccagcaa actggg                                                        16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
taaacccagc aaactg                                                        16
```

```
<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
ataaacccag caaact                                                    16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
ccccattctc taaaat                                                    16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
cccccattct ctaaaa                                                    16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
acccccattc tctaaa                                                    16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461 caccccatt ctctaa                                                     16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462 ccaccccat tctcta                                                     16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 463
gttcttgcct ccccac                                                      16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
ggttcttgcc tcccca                                                      16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
tggttcttgc ctcccc                                                      16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
ctggttcttg cctccc                                                      16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
actggttctt gcctcc                                                      16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
cactggttct tgcctc                                                      16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
acactggttc ttgcct                                                      16

<210> SEQ ID NO 470
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 470
aacactggtt cttgcc                                                    16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
aaacactggt tcttgc                                                    16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
taaacactgg ttcttg                                                    16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
ctaaacactg gttctt                                                    16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
gctaaacact ggttct                                                    16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
cgctaaacac tggttc                                                    16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
```

```
gcgctaaaca ctggtt                                                    16
```

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477

```
cgcgctaaac actggt                                                    16
```

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478

```
ccgcgctaaa cactgg                                                    16
```

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479

```
cccgcgctaa acactg                                                    16
```

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480

```
tcccgcgcta aacact                                                    16
```

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481

```
gtcccgcgct aaacac                                                    16
```

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482

```
agtcccgcgc taaaca                                                    16
```

<210> SEQ ID NO 483
<211> LENGTH: 16
<212> TYPE: DNA
<213> ORGANISM: Artificial sequence -continued

```
<220> FEATURE:
<223> OTHER INFORMATION: Synthetic oligonucleotide

<400> SEQUENCE: 483
tagtcccgcg ctaaac                                                  16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
agtagtcccg cgctaa                                                  16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
cagtagtccc gcgcta                                                  16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
acagtagtcc cgcgct                                                  16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
aacagtagtc ccgcgc                                                  16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
gaacagtagt cccgcg                                                  16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
ggaacagtag tcccgc                                                  16
```

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
tggaacagta gtcccg                                                     16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
ttggaacagt agtccc                                                     16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
tttggaacag tagtcc                                                     16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
ttttggaaca gtagtc                                                     16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
tttttggaac agtagt                                                     16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495 cttttttggaa cagtag                                                    16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 496
gaattctttt tggaac                                                   16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
ggaattcttt ttggaa                                                   16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
tggaattctt tttgga                                                   16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
ttggaattct ttttgg                                                   16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
cggttggaat tctttt                                                   16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
tcggttggaa ttcttt                                                   16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
gtcggttgga attctt                                                   16

<210> SEQ ID NO 503
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
ggtcggttgg aattct                                                   16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
ctggtcggtt ggaatt                                                   16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
gctggtcggt tggaat                                                   16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
agctggtcgg ttggaa                                                   16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
aagctggtcg gttgga                                                   16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
caagctggtc ggttgg                                                   16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
```
acaagctggt cggttg                                                         16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
aacaagctgg tcggtt                                                         16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
aaacaagctg gtcggt                                                         16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
caaacaagct ggtcgg                                                         16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
cacaaacaag ctggtc                                                         16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
tcacaaacaa gctggt                                                         16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
ttcacaaaca agctgg                                                         16

<210> SEQ ID NO 516
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 516
tttcacaaac aagctg                                                   16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
gtttcacaaa caagct                                                   16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
tgtttcacaa acaagc                                                   16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
ttgtttcaca aacaag                                                   16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
agggaacact tttttg                                                   16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
acttgaaaag ggaaca                                                   16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
aacttgaaaa gggaac                                                   16
```

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
ctcaacttga aaaggg                                              16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 524
ttgttctcaa cttgaa                                              16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
tttgttctca acttga                                              16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
cccaattttt gttctc                                              16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
acccaatttt tgttct                                              16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
cgaaggcaat gcaaaa                                              16

<210> SEQ ID NO 529
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 529
ccgaaggcaa tgcaaa                                                      16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
accgaaggca atgcaa                                                      16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
aaccgaaggc aatgca                                                      16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
aaaccgaagg caatgc                                                      16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
caaaccgaag gcaatg                                                      16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
acaaaccgaa ggcaat                                                      16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
tacaaaccga aggcaa                                                      16

```
<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
atacaaaccg aaggca                                                    16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
aatacaaacc gaaggc                                                    16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
aaatacaaac cgaagg                                                    16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
taaatacaaa ccgaag                                                    16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
ctaaatacaa accgaa                                                    16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
actaaataca aaccga                                                    16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 542
cactaaatac aaaccg                                                     16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
gacactaaat acaaac                                                     16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
caagacacta aataca                                                     16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
tcaagacact aaatac                                                     16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
ttcaagacac taaata                                                     16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
attcaagaca ctaaat                                                     16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
cattcaagac actaaa                                                     16

<210> SEQ ID NO 549
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 549
acattcaaga cactaa                                              16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
ttacattcaa gacact                                              16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
cttacattca agacac                                              16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
tcttacattc aagaca                                              16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
ttcttacatt caagac                                              16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
atgttcttac attcaa                                              16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
```

```
gtcatgttct tacatt                                              16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
aggtcatgtt cttaca                                              16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
gaggtcatgt tcttac                                              16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
ggaggtcatg ttctta                                              16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
cggaggtcat gttctt                                              16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
acggaggtca tgttct                                              16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
cacggaggtc atgttc                                              16

<210> SEQ ID NO 562
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 562
tggaggctta ttgtgg                                                    16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
ttggaggctt attgtg                                                    16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
tttggaggct tattgt                                                    16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
cggcttacct tctgct                                                    16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
cctcccggcc ttttcc                                                    16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
tagggtgacc actctg                                                    16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
agcaaatcga ggttca                                                    16
```

```
<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
tattagttct cttcag                                                    16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570 cctttagct tatccc                                                     16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
aatctgcctt ttagct                                                    16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
caatctacgc tgccct                                                    16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
agcaccaatc tacgct                                                    16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
catcctggag aagtag                                                    16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 575
gcatcctgga gaagta                                                        16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
atacagccca cattcc                                                        16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
ctgtaccatg tagtta                                                        16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
ccacaccggg cactct                                                        16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
cccaccacac cgggca                                                        16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
ttccccacca caccgg                                                        16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
ttcaccctgc agcttt                                                        16

<210> SEQ ID NO 582
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
catagtcctc accttc                                                         16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
gtgaagatga cggctc                                                         16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
tatgtctccc tacttc                                                         16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
gggagtaatg gtgctc                                                         16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
gtcctgggag taatgg                                                         16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
gggaaccgac tgctgg                                                         16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
```
cctgtgggaa ccgact                                                   16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
cctaatctag acagtc                                                   16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
catccgctgt tctcag                                                   16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
ctccatccgc tgttct                                                   16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
gactccatcc gctgtt                                                   16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
tgactccatc cgctgt                                                   16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
gctgaagtac ctggtg                                                   16

<210> SEQ ID NO 595
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 595
gccctcaaca cggtgc                                                    16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
tgccctcaac acggtg                                                    16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
gtcattcttc ttacat                                                    16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
gcttccttgg agctgt                                                    16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
gtgtactgca atatcg                                                    16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
cactcatttc ttgtgg                                                    16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
ttgtaccaca tctcac                                                    16
```

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
gttctctcaa aggcct                                                         16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
gcagggttta gaaccc                                                         16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
tatgtaagca gggttt                                                         16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
aaaccagctc tcaacc                                                         16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
taagacatgc tcctgc                                                         16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
acttatggca gcccaa                                                         16

<210> SEQ ID NO 608
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 608
tacttatggc agccca     16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
ccattatttg gagaca     16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
tgccatctaa ccagat     16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
gttttcagta atgccc     16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
cgggtcacga tgccct     16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
ccggccgggt cacgat     16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
cccccggccg ggtcac     16

```
<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615 cttccccgg ccgggt                                              16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
cttcttcccc cggccg                                             16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
cagcttcttc ccccgg                                             16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
cggcagcttc ttcccc                                             16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
caacggcagc ttcttc                                             16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
gaacaacggc agcttc                                             16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 621
ccagaacaac ggcagc                                                  16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
tagtacccag aacaac                                                  16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623
ctgtagtacc cagaac                                                  16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
ctgctgtagt acccag                                                  16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
cttctgctgt agtacc                                                  16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
acccttctgc tgtagt                                                  16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
catacccttc tgctgt                                                  16

<210> SEQ ID NO 628
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 628
ccgcataccc ttctgc                                                   16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
cttccgcata cccttc                                                   16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
tcgcttccgc ataccc                                                   16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
tgctcgcttc cgcata                                                   16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
gggtgctcgc ttccgc                                                   16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
cggcaggagc catctc                                                   16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
```
caccggcagg agccat 16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
tcacaccggc aggagc 16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
ggctcacacc ggcagg 16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
gccctcaggc tcacac 16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
gtggccctca ggctca 16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
cagaggatgg tggccc 16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
cccggtcacc tgcagc 16

<210> SEQ ID NO 641
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 641
acacccggtc acctgc                                                  16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
tgtacacccg gtcacc                                                  16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
gtatgtacac ccggtc                                                  16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
ggtgtatgta cacccg                                                  16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
tgacgaggtg gaaggg                                                  16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
ggatgacgag gtggaa                                                  16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
tgtggatgac gaggtg                                                  16
```

```
<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
cattgtggat gacgag                                                   16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 649
tctcattgtg gatgac                                                   16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
ctctcattgt ggatga                                                   16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
actctcattg tggatg                                                   16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
tactctcatt gtggat                                                   16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
gtactctcat tgtgga                                                   16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 654
caggtactct cattgt                                                        16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
acaggtactc tcattg                                                        16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
cacaggtact ctcatt                                                        16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
tcacaggtac tctcat                                                        16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
ctcacaggta ctctca                                                        16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
ctgctcacag gtactc                                                        16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
ttgccagctg ctcaca                                                        16

<210> SEQ ID NO 661

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
cctttgccag ctgctc                                                   16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
tggcctttgc cagctg                                                   16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
cattggcctt tgccag                                                   16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
cggcattggc ctttgc                                                   16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
tcccggcatt ggcctt                                                   16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
gcttcccggc attggc                                                   16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
```
tgggcttccc ggcatt                                                     16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
ctttgggctt cccggc                                                     16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
ggtctttggg cttccc                                                     16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
caggtatgaa ggtggg                                                     16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
gagcaggtat gaaggt                                                     16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
ttggagcagg tatgaa                                                     16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
gaattggagc aggtat                                                     16

<210> SEQ ID NO 674
<211> LENGTH: 16
<212> TYPE: DNA

-continued

<213> ORGANISM: Artificial sequence
<220> FEATURE:
<223> OTHER INFORMATION: Synthetic oligonucleotide

<400> SEQUENCE: 674
tggcctgaat tggagc                                                         16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
tcttggcctg aattgg                                                         16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
atgtcttggc ctgaat                                                         16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
gggatgtctt ggcctg                                                         16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
ggccttttca tccaca                                                         16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
tagggccttt tcatcc                                                         16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
ctgtagggcc ttttca                                                         16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
gtcctgtagg gccttt                                                    16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 682
ctggtcctgt agggcc                                                    16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
ccagctggtc ctgtag                                                    16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
accagctggt cctgta                                                    16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
tagcaccagc tggtcc                                                    16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
ctagcaccag ctggtc                                                    16

<210> SEQ ID NO 687
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 687
actagcacca gctggt                                                         16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
gactagcacc agctgg                                                         16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
cgactagcac cagctg                                                         16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
gcgactagca ccagct                                                         16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
agcgactagc accagc                                                         16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
cagcgactag caccag                                                         16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
gcagcgacta gcacca                                                         16

```
<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
ttgcagcgac tagcac                                              16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
tttgcagcga ctagca                                              16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
ttttgcagcg actagc                                              16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
gttttgcagc gactag                                              16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
agttttgcag cgacta                                              16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
aagttttgca gcgact                                              16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 700
gtcaagtttt gcagcg					16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
ggtgtcaagt tttgca					16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702
ttcggtgtca agtttt					16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
gtcttcggtg tcaagt					16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704
cttgtcttcg gtgtca					16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
caacttgtct tcggtg					16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
cctcaacttg tcttcg					16

<210> SEQ ID NO 707
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 707
ggccctcaac ttgtct                                                     16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
tgcggccctc aacttg                                                     16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
cattgcggcc ctcaac                                                     16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
gaccattgcg gccctc                                                     16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
cccgaccatt gcggcc                                                     16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
catcccgacc attgcg                                                     16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
```
cagcatcccg accatt                                              16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
ggccagcatc ccgacc                                              16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
gttggccagc atcccg                                              16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
gaagttggcc agcatc                                              16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
caagaagttg gccagc                                              16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
gaagcccaag aagttg                                              16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
acggaagccc aagaag                                              16

<210> SEQ ID NO 720
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 720
tatacggaag cccaag                                                    16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
atatatacgg aagccc                                                    16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
gccatatata cggaag                                                    16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
catgccatat atacgg                                                    16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
gtgcatgcca tatata                                                    16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
actgtgcatg ccatat                                                    16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
ctcactgtgc atgcca                                                    16
```

```
<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
tagctcactg tgcatg                                                    16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 728
ccatagctca ctgtgc                                                    16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
gaccacgccc catagc                                                    16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
atggaccacg ccccat                                                    16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
ccccatggac cacgcc                                                    16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
tggccccatg gaccac                                                    16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 733
cggtggcccc atggac                                                16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
ggacggtggc cccatg                                                16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
agaggacggt ggcccc                                                16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
gggagaggac ggtggc                                                16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
gccaaagaca gccgtt                                                16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
ggtgccaaag acagcc                                                16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
cagggtgcca aagaca                                                16

<210> SEQ ID NO 740
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
aggccagggt gccaaa                                               16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
tcccagatag agagag                                               16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
ggctcccaga tagaga                                               16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
caaggctccc agatag                                               16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
gtccaaggct cccaga                                               16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
gtggtccaag gctccc                                               16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
```
tgtgtggtcc aaggct                                                        16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
agctgtgtgg tccaag                                                        16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
gtcagctgtg tggtcc                                                        16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
cagaggcata gtgagg                                                        16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
ccaggtcaga ggcata                                                        16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
ttgtccaggt cagagg                                                        16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
accttgtcca ggtcag                                                        16

<210> SEQ ID NO 753
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 753
ccctccacct tgtcca                                                        16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
gagaccctcc accttg                                                        16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
aagtgagacc ctccac                                                        16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
tgctggaaag tgagac                                                        16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
ttttgctgga aagtga                                                        16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
gagttttgct ggaaag                                                        16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
agggagtttt gctgga                                                        16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
gttgagggag ttttgc                                                   16

<210> SEQ ID NO 761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 761
ccagttgagg gagttt                                                   16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
catccagttg agggag                                                   16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
cttcatccag ttgagg                                                   16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
agatagtttc ttcatc                                                   16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
aggtggatgg tccggg                                                   16

<210> SEQ ID NO 766
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 766
gtcaggtgga tggtcc                                                       16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
catggtcagg tggatg                                                       16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
gggcatggtc aggtgg                                                       16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
ccttgcagca ccagtt                                                       16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
gatccttgca gcacca                                                       16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
taagatcctt gcagca                                                       16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
tcataagatc cttgca                                                       16

```
<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
caggtcataa gatcct                                              16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
ctgcaggtca taagat                                              16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
gtcctgcagg tcataa                                              16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
cgagcaggtc ctgcag                                              16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
gggcgagcag gtcctg                                              16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
cctgggcgag caggtc                                              16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 779
tggcgggcag ctcagc                                               16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
gaatggcggg cagctc                                               16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
gcagaatggc gggcag                                               16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
tgtgcagaat ggcggg                                               16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
cggtgtgcag aatggc                                               16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
gctcggtgtg cagaat                                               16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
tcagctcggt gtgcag                                               16

<210> SEQ ID NO 786
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 786
ggttcagctc ggtgtg                                                    16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
gcaggttcag ctcggt                                                    16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
tttttgcagg ttcagc                                                    16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789 caattttgc aggttc                                                     16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
gctcaatttt tgcagg                                                    16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
attgctcaat ttttgc                                                    16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
```
gtcattgctc aatttt                                          16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
gcggtcattg ctcaat                                          16

<210> SEQ ID NO 794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
gatgcggtca ttgctc                                          16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
cctgatgcgg tcattg                                          16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
caccctgatg cggtca                                          16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
ccccaccctg atgcgg                                          16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
ctcccccacc ctgatg                                          16

<210> SEQ ID NO 799
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 799
gttcagcacc tcccccc                                                     16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
gctgttcagc acctcc                                                      16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
aatgctgttc agcacc                                                      16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
aaaaatgctg ttcagc                                                      16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
cttcaagctc aaaaaa                                                      16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
ccgcttcaag ctcaaa                                                      16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
catccgcttc aagctc                                                      16
```

```
<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
tctcatccgc ttcaag                                                    16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 807
ctctctcatc cgcttc                                                    16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
gctctctctc atccgc                                                    16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
gtgggctctc tctcat                                                    16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
actctgtggg ctctct                                                    16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
tagactctgt gggctc                                                    16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 812
tgggtagact ctgtgg    16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
agctgttggg tagact    16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
ttaagctgtt gggtag    16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
ttgttaagct gttggg    16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
ggcttgttaa gctgtt    16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
tcaggcttgt taagct    16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
acctcaggct tgttaa    16

<210> SEQ ID NO 819

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
aagacctcag gcttgt                                                       16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
acacggaggt catgtt                                                       16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
tacacggagg tcatgt                                                       16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
ctacacggag gtcatg                                                       16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
cactacacgg aggtca                                                       16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
acactacacg gaggtc                                                       16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
```
gacactacac ggaggt                                              16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
agacactaca cggagg                                              16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
cagacactac acggag                                              16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
acagacacta cacgga                                              16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
tacagacact acacgg                                              16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
ttacagacac tacacg                                              16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
attacagaca ctacac                                              16

<210> SEQ ID NO 832
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 832
gtattacaga cactac                                                      16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
ctaaggtatt acagac                                                      16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
actaaggtat tacaga                                                      16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
aactaaggta ttacag                                                      16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
aaactaaggt attaca                                                      16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
aaaactaagg tattac                                                      16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
gtggaaaaaa ctaagg                                                      16
```

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
caagcatctg tggaaa                                                        16

<210> SEQ ID NO 840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 840
cacaagcatc tgtgga                                                        16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841
tcacaagcat ctgtgg                                                        16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
atcacaagca tctgtg                                                        16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
aatcacaagc atctgt                                                        16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
gtattgttca aaaatc                                                        16

<210> SEQ ID NO 845
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 845
cgtattgttc aaaaat                                                     16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
aggtgcttgc atcttt                                                     16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
caggtgcttg catctt                                                     16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
tcaggtgctt gcatct                                                     16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
ttcaggtgct tgcatc                                                     16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
attcaggtgc ttgcat                                                     16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
aattcaggtg cttgca                                                     16
```

```
<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
aaattcaggt gcttgc                                               16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
gaaattcagg tgcttg                                               16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
agaaattcag gtgctt                                               16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
acagaaattc aggtgc                                               16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
cgcattcaaa cagaaa                                               16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
tccgcattca aacaga                                               16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 858
ttccgcattc aaacag                                                       16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
gttccgcatt caaaca                                                       16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
ggttccgcat tcaaac                                                       16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
tggttccgca ttcaaa                                                       16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
atggttccgc attcaa                                                       16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
tatggttccg cattca                                                       16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
ctatggttcc gcattc                                                       16

<210> SEQ ID NO 865
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 865
gctatggttc cgcatt                                                    16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
cagctatggt tccgca                                                    16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
ccagctatgg ttccgc                                                    16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
accagctatg gttccg                                                    16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
aaccagctat ggttcc                                                    16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
taaccagcta tggttc                                                    16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
```

```
ataaccagct atggtt                                                   16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
aaataaccag ctatgg                                                   16

<210> SEQ ID NO 873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873
gaaataacca gctatg                                                   16

<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
agaaataacc agctat                                                   16

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
ctaacacaag ggagaa                                                   16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
actaacacaa gggaga                                                   16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
ttactaacac aaggga                                                   16

<210> SEQ ID NO 878
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 878
attactaaca caaggg                                                        16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
tattactaac acaagg                                                        16

<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
ttattactaa cacaag                                                        16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 881
gtttattact aacaca                                                        16

<210> SEQ ID NO 882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 882
cgtttattac taacac                                                        16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
cttattgtgg caagac                                                        16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
gcttattgtg gcaaga                                                        16
```

<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
ggcttattgt ggcaag                                                       16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 886
aggcttattg tggcaa                                                       16

<210> SEQ ID NO 887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 887
gaggcttatt gtggca                                                       16

<210> SEQ ID NO 888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
ggaggcttat tgtggc                                                       16

<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
gcctgtcagc tgtgtg                                                       16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
gtagcctgtc agctgt                                                       16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 891
cctgtagcct gtcagc                                                       16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
ttgcctgtag cctgtc                                                       16

<210> SEQ ID NO 893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
ggattgcctg tagcct                                                       16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
ccaggattgc ctgtag                                                       16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 895
gaacacccag gattgc                                                       16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
gtccttccaa ggaaca                                                       16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
cttgtccttc caagga                                                       16

<210> SEQ ID NO 898

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 898
gttcttgtcc ttccaa                                              16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
gcagttcttg tccttc                                              16

<210> SEQ ID NO 900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 900
ggtgcagttc ttgtcc                                              16

<210> SEQ ID NO 901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 901
ggaggtgcag ttcttg                                              16

<210> SEQ ID NO 902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
ccgggaggtg cagttc                                              16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
cagccgggag gtgcag                                              16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
```
atccagccgg gaggtg    16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
cgcatccagc cgggag    16

<210> SEQ ID NO 906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 906
gtgcgcatcc agccgg    16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
cttgtgcgca tccagc    16

<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
gaccttgtgc gcatcc    16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
caggaccttg tgcgca    16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
agacaggacc ttgtgc    16

<210> SEQ ID NO 911
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 911
ggcagacagg accttg                                                    16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
gccctgtaca gcctgc                                                    16

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
gcaggccctg tacagc                                                    16

<210> SEQ ID NO 914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 914
ctagcaggcc ctgtac                                                    16

<210> SEQ ID NO 915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 915
gccactagca ggccct                                                    16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
tgggccacta gcaggc                                                    16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
ccctgggcca ctagca                                                    16
```

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
ctgccctggg ccacta                                                    16

<210> SEQ ID NO 919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 919
ggctatcagc cctgcc                                                    16

<210> SEQ ID NO 920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 920
cctggctatc agccct                                                    16

<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
gggcctggct atcagc                                                    16

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
gctgggcctg gctatc                                                    16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
ccgtggacag cagcag                                                    16

<210> SEQ ID NO 924
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 924
ccaccgtgga cagcag                                                        16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
ccaccaccgt ggacag                                                        16

<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
cgcccaccac cgtgga                                                        16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 927
acacgcccac caccgt                                                        16

<210> SEQ ID NO 928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 928
tgaacacgcc caccac                                                        16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
ctgtgaacac gcccac                                                        16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
gggctgtgaa cacgcc                                                        16

```
<210> SEQ ID NO 931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
gcttcaggtg caggcc                                                   16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 932
gctgcttcag gtgcag                                                   16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
acggctgctt caggtg                                                   16

<210> SEQ ID NO 934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 934
caaacggctg cttcag                                                   16

<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
gcacaaacgg ctgctt                                                   16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
cctgcacaaa cggctg                                                   16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 937
ggccctgcac aaacgg                                                     16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
gtatagagag ccaggc                                                     16

<210> SEQ ID NO 939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 939
ctgtgaagtc cagaga                                                     16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940
gttctgtgaa gtccag                                                     16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 941
ccagttctgt gaagtc                                                     16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
catccagttc tgtgaa                                                     16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
caacatccag ttctgt                                                     16

<210> SEQ ID NO 944
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 944
cagcaacatc cagttc                                                     16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
caatcttctc agcagc                                                     16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
tgtcaatctt ctcagc                                                     16

<210> SEQ ID NO 947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 947
acctgtcaat cttctc                                                     16

<210> SEQ ID NO 948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 948
tgaacctgtc aatctt                                                     16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
gcatgaacct gtcaat                                                     16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
```
cctgcatgaa cctgtc                                              16

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
cagcctgcat gaacct                                              16

<210> SEQ ID NO 952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 952
cacagcctgc atgaac                                              16

<210> SEQ ID NO 953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
tcacagcctg catgaa                                              16

<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
atcctgtcac agcctg                                              16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
ccatcctgtc acagcc                                              16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
tccatcctgt cacagc                                              16

<210> SEQ ID NO 957
<211> LENGTH: 16
<212> TYPE: DNA
<213> ORGANISM: Artificial sequence -continued

```
<220> FEATURE:
<223> OTHER INFORMATION: Synthetic oligonucleotide

<400> SEQUENCE: 957
cttccatcct gtcaca                                                    16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
agtcttccat cctgtc                                                    16

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
agccagtctt ccatcc                                                    16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 960
cacccagaac tcctgg                                                    16

<210> SEQ ID NO 961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 961
gtccacccag aactcc                                                    16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
gttgtccacc cagaac                                                    16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
gctgttgtcc acccag                                                    16
```

<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
ggtgctgttg tccacc                                                       16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 965
tgaggtgctg ttgtcc                                                       16

<210> SEQ ID NO 966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 966
cactgaggtg ctgttg                                                       16

<210> SEQ ID NO 967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
catgggaaca gacact                                                       16

<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
gagcatggga acagac                                                       16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
agagagcatg ggaaca                                                       16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 970
gccagagagc atggga                                              16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
catgccagag agcatg                                              16

<210> SEQ ID NO 972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
gcccatgcca gagagc                                              16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
ggtgcccatg ccagag                                              16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 974
gaaggtgccc atgcca                                              16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
ctggaaggtg cccatg                                              16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
agtgctggaa ggtgcc                                              16

<210> SEQ ID NO 977

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 977
tccagtgctg gaaggt                                                    16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
cactccagtg ctggaa                                                    16

<210> SEQ ID NO 979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 979
tgtcactcca gtgctg                                                    16

<210> SEQ ID NO 980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 980
atgtcactcc agtgct                                                    16

<210> SEQ ID NO 981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
gatgtcactc cagtgc                                                    16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
ggatgtcact ccagtg                                                    16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
```
tggatgtcac tccagt                                                    16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
cctggatgtc actcca                                                    16

<210> SEQ ID NO 985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 985
tgtcctggat gtcact                                                    16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
agttgtcctg gatgtc                                                    16

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
agaagttgtc ctggat                                                    16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
tcaccgagaa gttgtc                                                    16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
gagtcaccga gaagtt                                                    16

<210> SEQ ID NO 990
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 990
cttgagtcac cgagaa                                                 16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
gcacttgagt caccga                                                 16

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
agggcacttg agtcac                                                 16

<210> SEQ ID NO 993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 993
tgaagggcac ttgagt                                                 16

<210> SEQ ID NO 994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 994
cagtgaaggg cacttg                                                 16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
tctcagtgaa gggcac                                                 16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
cgctctcagt gaaggg                                                 16
```

<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
agcagcaggc aggcgc                                                    16

<210> SEQ ID NO 998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 998
gatcagcagc aggcag                                                    16

<210> SEQ ID NO 999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 999
gctggatcag cagcag                                                    16

<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
gaggctggat cagcag                                                    16

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
agtgaggctg gatcag                                                    16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
catagtgagg ctggat                                                    16

<210> SEQ ID NO 1003
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1003
aggcatagtg aggctg                                                        16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004
agacacacag gccgcc                                                        16

<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
acactaactg gagagc                                                        16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1006
agagggcgga ttgcaa                                                        16

<210> SEQ ID NO 1007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1007
cagagggcgg attgca                                                        16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008
tctcagaggg cggatt                                                        16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
ctctcagagg gcggat                                                        16

```
<210> SEQ ID NO 1010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
tctctcagag ggcgga                                               16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1011
gctgtgtgtc aggtgt                                               16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
aagaagctct tggatg                                               16

<210> SEQ ID NO 1013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1013
tccaagaagc tcttgg                                               16

<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
ccagccgcca gccgcc                                               16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
ttagtgtttc agcagg                                               16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1016
agttagtgtt tcagca                                               16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
aacctcgagg acatcg                                               16

<210> SEQ ID NO 1018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1018
acttataaga gctgac                                               16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
agcacttata agagct                                               16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1020
gcagtgttct tgatga                                               16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
acagcagtgt tcttga                                               16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
ataatgcact gtgtct                                               16

<210> SEQ ID NO 1023
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1023
gatgaggacc taggaa                                                       16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
ccgatgagga cctagg                                                       16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
acgacaggga tgtttg                                                       16

<210> SEQ ID NO 1026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1026
ggtcaggcac agacac                                                       16

<210> SEQ ID NO 1027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1027
atcccggttt caactc                                                       16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
tcccgctggc ccccgt                                                       16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
```
ctaacttagc acagag					16

<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
ccatggccca ccagtg					16

<210> SEQ ID NO 1031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1031
ttggccatgg cccacc					16

<210> SEQ ID NO 1032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
ggcagaattc ctggct					16

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
gcaagggtgt gtctgt					16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
ggcaagggtg tgtctg					16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
ctcagtgtag gcaagg					16

<210> SEQ ID NO 1036
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1036
gaggatgcac agtgta                                                   16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
gctcaggacc tctgtg                                                   16

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
ggctcaggac ctctgt                                                   16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
ggcgcactgg gtgacc                                                   16

<210> SEQ ID NO 1040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1040
tctgagggcg cactgg                                                   16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
tcattctgag ggcgca                                                   16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
gctcctaccg gggaga                                                   16
```

```
<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
acacatacct cccca                                                  16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1044
cgcataccct gaaata                                                 16

<210> SEQ ID NO 1045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1045
ggatggtcct ggggag                                                 16

<210> SEQ ID NO 1046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
ttcagcacct gcaaag                                                 16

<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
ccggcttacc ttctgc                                                 16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
cccccggctt accttc                                                 16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1049
gggcccccgg cttacc            16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
gtgaatgtga gccccg            16

<210> SEQ ID NO 1051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
tccctcctta taaccc            16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
ccgggcactc tcaact            16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1053
agtaatggtg ctctgg            16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
tcctgggagt aatggt            16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
tctcagttgt gatctg            16

<210> SEQ ID NO 1056

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1056
tccagagacg caattc                                                    16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
tctccagaga cgcaat                                                    16

<210> SEQ ID NO 1058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1058
acctgtggga accgac                                                    16

<210> SEQ ID NO 1059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1059
aaacctgtgg gaaccg                                                    16

<210> SEQ ID NO 1060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
cctagatttt tctgct                                                    16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
gcctttnctg tccccc                                                    16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
```
catttcttgt ggaggg					16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
tgggctggcc ctgcta					16

<210> SEQ ID NO 1064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1064
gagccccaaa ggcatg					16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
tctaatatga cctgtg					16

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
tgatctaata tgacct					16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067
gtcctcaacc ccagga					16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
gctccatgga aaatat					16

<210> SEQ ID NO 1069
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1069
tccattcatg tctaca                                                    16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
ttaagtgcca tctaac                                                    16

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
gcataccctg aaatat                                                    16

<210> SEQ ID NO 1072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1072
tgtctactcc ccaccc                                                    16

<210> SEQ ID NO 1073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1073
acagacacta actgga                                                    16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
gtgtgtcagg tgtggg                                                    16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
gcaagtcagt tccaag                                                    16
```

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
ctcgaaaatg gttacg                                                    16

<210> SEQ ID NO 1077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1077
ggtggtaacc acatgc                                                    16

<210> SEQ ID NO 1078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1078
atgcactgtg tcttac                                                    16

<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
aataatgcac tgtgtc                                                    16

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
gttacttggg taattt                                                    16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
tcctttggtg cattct                                                    16

<210> SEQ ID NO 1082
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1082
ctaggaatgg ttgtcc                                                        16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
gacgacaggg atgttt                                                        16

<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
ctgacgacag ggatgt                                                        16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1085
gcacagttag gaaggc                                                        16

<210> SEQ ID NO 1086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1086
ttagctaact tagcac                                                        16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
catggcccac cagtgc                                                        16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
cacagtgtat gcctgc                                                        16

```
<210> SEQ ID NO 1089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
gcactgggtg acccag                                                         16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1090
tcagcacctg caaagc                                                         16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
gagcagccag tcttcc                                                         16

<210> SEQ ID NO 1092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1092
agggagcagc cagtct                                                         16

<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
atcagggagc agccag                                                         16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
tcccatcagg gagcag                                                         16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1095
ggctcccatc agggag				16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
actggctccc atcagg				16

<210> SEQ ID NO 1097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1097
ccacactggc tcccat				16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
gctgtccaca ctggct				16

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1099
ggtgctgtcc acactg				16

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100
cagggtgctg tccaca				16

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101
agccagggtg ctgtcc				16

<210> SEQ ID NO 1102
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1102
gaaagccagg gtgctg                                                   16

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103
gttgaaagcc agggtg                                                   16

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104
ggtgttgaaa gccagg                                                   16

<210> SEQ ID NO 1105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1105
gtaggtgttg aaagcc                                                   16

<210> SEQ ID NO 1106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1106
cccttggaag tggacg                                                   16

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107
cttcccttgg aagtgg                                                   16

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108
```

```
catcttccct tggaag                                                          16

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109
cttcatcttc ccttgg                                                          16

<210> SEQ ID NO 1110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1110
agcccttcat cttccc                                                          16

<210> SEQ ID NO 1111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
agaagccctt catctt                                                          16

<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
gggagaagcc cttcat                                                          16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
gcagggagaa gccctt                                                          16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
tcggccagca gggaga                                                          16

<210> SEQ ID NO 1115
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1115
ggctcggcca gcaggg                                                    16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
cgaagggaga cccatt                                                    16

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117
ttcgaaggga gaccca                                                    16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1118
ctttcgaagg gagacc                                                    16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
ccgatctcct cactgg                                                    16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
ccccgatctc ctcact                                                    16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121 acagccccg atctcc                                                     16
```

<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
gagacagccc ccgatc                                                     16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1123
ccgagacagc ccccga                                                     16

<210> SEQ ID NO 1124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1124
ctagctgcct gctgag                                                     16

<210> SEQ ID NO 1125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
tctagctgcc tgctga                                                     16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
gtgggacaca tctagc                                                     16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
tctagtggga cacatc                                                     16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1128
tctctagtgg gacaca                                                    16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
catgagagtg gctgcc                                                    16

<210> SEQ ID NO 1130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
cttttagttt agaggg                                                    16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
atgtgagcgg gaaact                                                    16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1132
catgtgagcg ggaaac                                                    16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
cggagcactc agtctc                                                    16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
gtcctcagtc ctcgga                                                    16

<210> SEQ ID NO 1135
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1135
cgtcctcagt cctcgg                                              16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
gcagtggcag acctgg                                              16

<210> SEQ ID NO 1137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1137
tagagatggt tcagaa                                              16

<210> SEQ ID NO 1138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1138
tgagtagaga tggttc                                              16

<210> SEQ ID NO 1139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
ggagtctgag tagaga                                              16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
gccctcggct gtcctc                                              16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
``` ctcgaccttacactag 16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142 cctctgcctcgacctt 16

<210> SEQ ID NO 1143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1143 aactcgggagagcccg 16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144 aacgagggctccattc 16

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145 gacacactcacttttt 16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146 ctgccaggtcaactca 16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147 gtacctgccaggtcaa 16

<210> SEQ ID NO 1148
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1148
ctggtacctg ccaggt                                                  16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
agttcactga ggcagc                                                  16

<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
ccatttgagt tcactg                                                  16

<210> SEQ ID NO 1151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1151
gcagccattt gagttc                                                  16

<210> SEQ ID NO 1152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1152
aaggcccaga tcctgc                                                  16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
gaaatccaga caggag                                                  16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
tgccttacct tggaag                                                  16
```

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
catcttccct gaaatc                                                    16

<210> SEQ ID NO 1156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1156
aggtatgtcc gcaggg                                                    16

<210> SEQ ID NO 1157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1157
tagtagggca gcaggt                                                    16

<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
ttgtttctcc gagtct                                                    16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
aggcactttg tttctc                                                    16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
caaggcactt tgtttc                                                    16

<210> SEQ ID NO 1161
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1161
tagaactggg ctgtgg                                                    16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
ccctcctaac atgaaa                                                    16

<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
cttacaagta gcaaat                                                    16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1164
gccaggctta aagtct                                                    16

<210> SEQ ID NO 1165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1165
attgaccttt aaaagc                                                    16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
tctggttcaa cactca                                                    16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
ttcccgtgac tgtgtg                                                    16

```
<210> SEQ ID NO 1168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
cgagctgctc cctgag                                                      16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1169 cacccaccc atggat                                                       16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
tctctgtccc tcacga                                                      16

<210> SEQ ID NO 1171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1171
tttcgaaggg agaccc                                                      16

<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
catctagctg cctgct                                                      16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
tgggacacat ctagct                                                      16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1174
atcctcaggt cctctc                                                   16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
atggttcaga aacagt                                                   16

<210> SEQ ID NO 1176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1176
gatttgcaca ctgggc                                                   16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
ccccgtgatc aacatc                                                   16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1178
atcgagcaga aagtac                                                   16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
actggtacct gccagg                                                   16

<210> SEQ ID NO 1180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1180
ctgctgcccg ctcatgggat                                               20

<210> SEQ ID NO 1181
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1181
ctgaccctgc tgcccgctca                                              20

<210> SEQ ID NO 1182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1182
ccacttctga ccctgctgcc                                              20

<210> SEQ ID NO 1183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1183
tcttgcttag gcaacacggg                                              20

<210> SEQ ID NO 1184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1184
ggagagtctt gcttaggcaa                                              20

<210> SEQ ID NO 1185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1185
ggaggtgcag agggcagagg                                              20

<210> SEQ ID NO 1186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1186
caggccggag gtgcagaggg                                              20

<210> SEQ ID NO 1187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1187
```

-continued gacatgcagg ccggaggtgc                                           20

<210> SEQ ID NO 1188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1188
cacagggaca tgcaggccgg                                           20

<210> SEQ ID NO 1189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1189
agaggccaca gggacatgca                                           20

<210> SEQ ID NO 1190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1190
cccccaagag gccacaggga                                           20

<210> SEQ ID NO 1191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1191
gatgtacccc caagaggcca                                           20

<210> SEQ ID NO 1192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1192
ccgggagatg taccccaag                                            20

<210> SEQ ID NO 1193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1193
ccagccccgg gagatgtacc                                           20

<210> SEQ ID NO 1194
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1194
tctgacccag ccccgggaga                                               20

<210> SEQ ID NO 1195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1195
aggccttctg acccagcccc                                               20

<210> SEQ ID NO 1196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1196
ccacccaggc cttctgaccc                                               20

<210> SEQ ID NO 1197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1197
ggccaaccac ccaggccttc                                               20

<210> SEQ ID NO 1198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1198
gcctgaggcc aaccacccag                                               20

<210> SEQ ID NO 1199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1199
gtgacagcct gaggccaacc                                               20

<210> SEQ ID NO 1200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1200
aggtgtgtga cagcctgagg                                               20
```

```
<210> SEQ ID NO 1201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1201
ctccctaggt gtgtgacagc                                                    20

<210> SEQ ID NO 1202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1202
gagcatctcc ctaggtgtgt                                                    20

<210> SEQ ID NO 1203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1203
aaacgggagc atctccctag                                                    20

<210> SEQ ID NO 1204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1204
tcccagaaac gggagcatct                                                    20

<210> SEQ ID NO 1205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1205
caaggttccc agaaacggga                                                    20

<210> SEQ ID NO 1206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1206
cgaagtttgc aggagtcggg                                                    20

<210> SEQ ID NO 1207
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1207
atttaccgaa gtttgcagga                                               20

<210> SEQ ID NO 1208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1208
ttacacattt accgaagttt                                               20

<210> SEQ ID NO 1209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1209
gtcgagttac acatttaccg                                               20

<210> SEQ ID NO 1210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1210
tgcagggtcg agttacacat                                               20

<210> SEQ ID NO 1211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1211
agccggtgca gggtcgagtt                                               20

<210> SEQ ID NO 1212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1212
agagtgagcc ggtgcagggt                                               20

<210> SEQ ID NO 1213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1213
ctgaacagag tgagccggtg                                               20

<210> SEQ ID NO 1214
```

-continued

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1214
tcactgctga acagagtgag                                          20

<210> SEQ ID NO 1215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1215
agagtttcac tgctgaacag                                          20

<210> SEQ ID NO 1216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1216
cgatgcagag tttcactgct                                          20

<210> SEQ ID NO 1217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1217
agtgatcgat gcagagtttc                                          20

<210> SEQ ID NO 1218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1218
agtcttagtg atcgatgcag                                          20

<210> SEQ ID NO 1219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1219
ccaggaagtc ttagtgatcg                                          20

<210> SEQ ID NO 1220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1220
cctcttccag gaagtcttag                                          20

<210> SEQ ID NO 1221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1221
ctgggacctc ttccaggaag                                          20

<210> SEQ ID NO 1222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1222
ctcacgctgg gacctcttcc                                          20

<210> SEQ ID NO 1223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1223
gcgacactca cgctgggacc                                          20

<210> SEQ ID NO 1224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1224
ccagaagcga cactcacgct                                          20

<210> SEQ ID NO 1225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1225
cagatgccag aagcgacact                                          20

<210> SEQ ID NO 1226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1226
gaaggacaga tgccagaagc                                          20

<210> SEQ ID NO 1227
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 1227
tggccagaag gacagatgcc					20

<210> SEQ ID NO 1228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1228
acaggctggc cagaaggaca					20

<210> SEQ ID NO 1229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1229
cagaccacag gctggccaga					20

<210> SEQ ID NO 1230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1230
cttggccaga ccacaggctg					20

<210> SEQ ID NO 1231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1231
acatcacttg gccagaccac					20

<210> SEQ ID NO 1232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1232
agggttacat cacttggcca					20

<210> SEQ ID NO 1233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1233
gagaggaggg ttacatcact					20

<210> SEQ ID NO 1234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1234
aggctggaga ggagggttac                                              20

<210> SEQ ID NO 1235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1235
gtgcacaggc tggagaggag                                              20

<210> SEQ ID NO 1236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1236
ctgcctgtgc acaggctgga                                              20

<210> SEQ ID NO 1237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1237
cccaggctgc ctgtgcacag                                              20

<210> SEQ ID NO 1238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1238
gctgttccca ggctgcctgt                                              20

<210> SEQ ID NO 1239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1239
gatggagctg ttcccaggct                                              20

<210> SEQ ID NO 1240
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1240
gccctattta tagctgaggg                                                       20

<210> SEQ ID NO 1241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1241
cacgatgccc tatttatagc                                                       20

<210> SEQ ID NO 1242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1242
ccgggtcacg atgccctatt                                                       20

<210> SEQ ID NO 1243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1243
ccccggccgg gtcacgatgc                                                       20

<210> SEQ ID NO 1244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1244
ttcccccggc cgggtcacga                                                       20

<210> SEQ ID NO 1245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1245
ttcttccccc ggccgggtca                                                       20

<210> SEQ ID NO 1246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1246
agcttcttcc cccggccggg                                                       20

```
<210> SEQ ID NO 1247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1247
ggcagcttct tcccccggcc                                                   20

<210> SEQ ID NO 1248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1248
aacggcagct tcttcccccg                                                   20

<210> SEQ ID NO 1249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1249
aacaacggca gcttcttccc                                                   20

<210> SEQ ID NO 1250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1250
cagaacaacg gcagcttctt                                                   20

<210> SEQ ID NO 1251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1251
acccagaaca acggcagctt                                                   20

<210> SEQ ID NO 1252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1252
agtacccaga acaacggcag                                                   20

<210> SEQ ID NO 1253
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1253
tgtagtaccc agaacaacgg                                              20

<210> SEQ ID NO 1254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1254
tgctgtagta cccagaacaa                                              20

<210> SEQ ID NO 1255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1255
ttctgctgta gtacccagaa                                              20

<210> SEQ ID NO 1256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1256
cccttctgct gtagtaccca                                              20

<210> SEQ ID NO 1257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1257 ataccettct gctgtagtac                                              20

<210> SEQ ID NO 1258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1258
cgcataccct tctgctgtag                                              20

<210> SEQ ID NO 1259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1259
ttccgcatac ccttctgctg                                              20

<210> SEQ ID NO 1260
<211> LENGTH: 20

-continued

```
<212> TYPE: DNA
<213> ORGANISM: Artificial sequence
<220> FEATURE:
<223> OTHER INFORMATION: Synthetic oligonucleotide

<400> SEQUENCE: 1260
cgcttccgca tacccttctg                                                   20

<210> SEQ ID NO 1261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1261
gctcgcttcc gcataccctt                                                   20

<210> SEQ ID NO 1262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1262
ggtgctcgct tccgcatacc                                                   20

<210> SEQ ID NO 1263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1263
aggagccatc tcagactggg                                                   20

<210> SEQ ID NO 1264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1264
ggcaggagcc atctcagact                                                   20

<210> SEQ ID NO 1265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1265
accggcagga gccatctcag                                                   20

<210> SEQ ID NO 1266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1266
```
cacaccggca ggagccatct                                              20

<210> SEQ ID NO 1267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1267
gctcacaccg gcaggagcca                                              20

<210> SEQ ID NO 1268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1268
caggctcaca ccggcaggag                                              20

<210> SEQ ID NO 1269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1269
cctcaggctc acaccggcag                                              20

<210> SEQ ID NO 1270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1270
ggccctcagg ctcacaccgg                                              20

<210> SEQ ID NO 1271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1271
ggtggccctc aggctcacac                                              20

<210> SEQ ID NO 1272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1272
gatggtggcc ctcaggctca                                              20

<210> SEQ ID NO 1273
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1273
gaggatggtg gccctcaggc                                                    20

<210> SEQ ID NO 1274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1274
gcagaggatg gtggccctca                                                    20

<210> SEQ ID NO 1275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1275
gaggcagagg atggtggccc                                                    20

<210> SEQ ID NO 1276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1276
caggaggcag aggatggtgg                                                    20

<210> SEQ ID NO 1277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1277
gcccaggcca ggaggcagag                                                    20

<210> SEQ ID NO 1278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1278
ccagcccagg ccaggaggca                                                    20

<210> SEQ ID NO 1279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1279
aggccagccc aggccaggag                                                    20
```

<210> SEQ ID NO 1280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1280
gccaggccag cccaggccag         20

<210> SEQ ID NO 1281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1281
gcagccaggc cagcccaggc         20

<210> SEQ ID NO 1282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1282
cctgcagcca ggccagccca         20

<210> SEQ ID NO 1283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1283
tcacctgcag ccaggccagc         20

<210> SEQ ID NO 1284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1284
cggtcacctg cagccaggcc         20

<210> SEQ ID NO 1285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1285
acccggtcac ctgcagccag         20

<210> SEQ ID NO 1286
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1286
tacacccggt cacctgcagc                                              20

<210> SEQ ID NO 1287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1287
atgtacaccc ggtcacctgc                                              20

<210> SEQ ID NO 1288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1288
tgtatgtaca cccggtcacc                                              20

<210> SEQ ID NO 1289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1289
gggtgtatgt acacccggtc                                              20

<210> SEQ ID NO 1290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1290
tggatgacga ggtggaaggg                                              20

<210> SEQ ID NO 1291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1291
ttgtggatga cgaggtggaa                                              20

<210> SEQ ID NO 1292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1292
tcattgtgga tgacgaggtg                                              20

<210> SEQ ID NO 1293
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1293
ctctcattgt ggatgacgag                                            20

<210> SEQ ID NO 1294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1294
gtactctcat tgtggatgac                                            20

<210> SEQ ID NO 1295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1295
caggtactct cattgtggat                                            20

<210> SEQ ID NO 1296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1296
tcacaggtac tctcattgtg                                            20

<210> SEQ ID NO 1297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1297
tgctcacagg tactctcatt                                            20

<210> SEQ ID NO 1298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1298
agctgctcac aggtactctc                                            20

<210> SEQ ID NO 1299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1299
```
gccagctgct cacaggtact                                               20

<210> SEQ ID NO 1300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1300
tttgccagct gctcacaggt                                               20

<210> SEQ ID NO 1301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1301
gcctttgcca gctgctcaca                                               20

<210> SEQ ID NO 1302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1302
ttggcctttg ccagctgctc                                               20

<210> SEQ ID NO 1303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1303
gcattggcct ttgccagctg                                               20

<210> SEQ ID NO 1304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1304
ccggcattgg cctttgccag                                               20

<210> SEQ ID NO 1305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1305
ttcccggcat tggcctttgc                                               20

<210> SEQ ID NO 1306
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1306
ggcttcccgg cattggcctt                                                  20

<210> SEQ ID NO 1307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1307
ttgggcttcc cggcattggc                                                  20

<210> SEQ ID NO 1308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1308
tctttgggct tcccggcatt                                                  20

<210> SEQ ID NO 1309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1309
ggagcaggta tgaaggtggg                                                  20

<210> SEQ ID NO 1310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1310
attggagcag gtatgaaggt                                                  20

<210> SEQ ID NO 1311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1311
tgaattggag caggtatgaa                                                  20

<210> SEQ ID NO 1312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1312
gcctgaattg gagcaggtat                                                  20
```

<210> SEQ ID NO 1313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1313
ttggcctgaa ttggagcagg                                          20

<210> SEQ ID NO 1314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1314
gtcttggcct gaattggagc                                          20

<210> SEQ ID NO 1315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1315
gatgtcttgg cctgaattgg                                          20

<210> SEQ ID NO 1316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1316
agggcctttt catccacagg                                          20

<210> SEQ ID NO 1317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1317
tgtagggcct tttcatccac                                          20

<210> SEQ ID NO 1318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1318
tcctgtaggg ccttttcatc                                          20

<210> SEQ ID NO 1319
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1319
tggtcctgta gggccttttc                                                 20

<210> SEQ ID NO 1320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1320
agctggtcct gtagggcctt                                                 20

<210> SEQ ID NO 1321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1321
accagctggt cctgtagggc                                                 20

<210> SEQ ID NO 1322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1322
agcaccagct ggtcctgtag                                                 20

<210> SEQ ID NO 1323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1323
actagcacca gctggtcctg                                                 20

<210> SEQ ID NO 1324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1324
gcgactagca ccagctggtc                                                 20

<210> SEQ ID NO 1325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1325
gcagcgacta gcaccagctg                                                 20

```
<210> SEQ ID NO 1326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1326
tttgcagcga ctagcaccag                                               20

<210> SEQ ID NO 1327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1327
agttttgcag cgactagcac                                               20

<210> SEQ ID NO 1328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1328
tcaagttttg cagcgactag                                               20

<210> SEQ ID NO 1329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1329
gtgtcaagtt ttgcagcgac                                               20

<210> SEQ ID NO 1330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1330
tcggtgtcaa gttttgcagc                                               20

<210> SEQ ID NO 1331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1331
tcttcggtgt caagttttgc                                               20

<210> SEQ ID NO 1332
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1332
ttgtcttcgg tgtcaagttt                                          20

<210> SEQ ID NO 1333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1333
aacttgtctt cggtgtcaag                                          20

<210> SEQ ID NO 1334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1334
ctcaacttgt cttcggtgtc                                          20

<210> SEQ ID NO 1335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1335
gccctcaact tgtcttcggt                                          20

<210> SEQ ID NO 1336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1336
gcggccctca acttgtcttc                                          20

<210> SEQ ID NO 1337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1337
attgcggccc tcaacttgtc                                          20

<210> SEQ ID NO 1338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1338
accattgcgg ccctcaactt                                          20

<210> SEQ ID NO 1339
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1339
ccgaccattg cggccctcaa                                             20

<210> SEQ ID NO 1340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1340
atcccgacca ttgcggccct                                             20

<210> SEQ ID NO 1341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1341
agcatcccga ccattgcggc                                             20

<210> SEQ ID NO 1342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1342
gccagcatcc cgaccattgc                                             20

<210> SEQ ID NO 1343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1343
ttggccagca tcccgaccat                                             20

<210> SEQ ID NO 1344
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1344
aagttggcca gcatcccgac                                             20

<210> SEQ ID NO 1345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1345
```
aagaagttgg ccagcatccc                                              20

<210> SEQ ID NO 1346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1346
cccaagaagt tggccagcat                                              20

<210> SEQ ID NO 1347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1347
aagcccaaga agttggccag                                              20

<210> SEQ ID NO 1348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1348
cggaagccca agaagttggc                                              20

<210> SEQ ID NO 1349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1349
atacggaagc ccaagaagtt                                              20

<210> SEQ ID NO 1350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1350
tatatacgga agcccaagaa                                              20

<210> SEQ ID NO 1351
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1351
ccatatatac ggaagcccaa                                              20

<210> SEQ ID NO 1352
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1352
atgccatata tacggaagcc                                                     20

<210> SEQ ID NO 1353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1353
tgcatgccat atatacggaa                                                     20

<210> SEQ ID NO 1354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1354
ctgtgcatgc catatatacg                                                     20

<210> SEQ ID NO 1355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1355
tcactgtgca tgccatatat                                                     20

<210> SEQ ID NO 1356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1356
agctcactgt gcatgccata                                                     20

<210> SEQ ID NO 1357
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1357
catagctcac tgtgcatgcc                                                     20

<210> SEQ ID NO 1358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1358
ccccatagct cactgtgcat                                                     20
```

<210> SEQ ID NO 1359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1359
acgccccata gctcactgtg                                              20

<210> SEQ ID NO 1360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1360
accacgcccc atagctcact                                              20

<210> SEQ ID NO 1361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1361
tggaccacgc cccatagctc                                              20

<210> SEQ ID NO 1362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1362
ccatggacca cgccccatag                                              20

<210> SEQ ID NO 1363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1363
gccccatgga ccacgcccca                                              20

<210> SEQ ID NO 1364
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1364
gtggccccat ggaccacgcc                                              20

<210> SEQ ID NO 1365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1365
acggtggccc catggaccac                                              20

<210> SEQ ID NO 1366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1366
aggacggtgg ccccatggac                                              20

<210> SEQ ID NO 1367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1367
gagaggacgg tggccccatg                                              20

<210> SEQ ID NO 1368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1368
tgccaaagac agccgttggg                                              20

<210> SEQ ID NO 1369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1369
gggtgccaaa gacagccgtt                                              20

<210> SEQ ID NO 1370
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1370
ccagggtgcc aaagacagcc                                              20

<210> SEQ ID NO 1371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1371
aggccagggt gccaaagaca                                              20

<210> SEQ ID NO 1372

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1372
gagaggccag ggtgccaaag                                               20

<210> SEQ ID NO 1373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1373
agagagaggc cagggtgcca                                               20

<210> SEQ ID NO 1374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1374
gatagagaga ggccagggtg                                               20

<210> SEQ ID NO 1375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1375
ccagatagag agaggccagg                                               20

<210> SEQ ID NO 1376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1376
ctcccagata gagagaggcc                                               20

<210> SEQ ID NO 1377
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1377
aggctcccag atagagagag                                               20

<210> SEQ ID NO 1378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1378
```
ccaaggctcc cagatagaga                                              20

<210> SEQ ID NO 1379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1379
ggtccaaggc tcccagatag                                              20

<210> SEQ ID NO 1380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1380
tgtggtccaa ggctcccaga                                              20

<210> SEQ ID NO 1381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1381
ctgtgtggtc caaggctccc                                              20

<210> SEQ ID NO 1382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1382
cagctgtgtg gtccaaggct                                              20

<210> SEQ ID NO 1383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1383
tgtcagctgt gtggtccaag                                              20

<210> SEQ ID NO 1384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1384
gcctgtcagc tgtgtggtcc                                              20

<210> SEQ ID NO 1385
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1385
gtagcctgtc agctgtgtgg                                              20

<210> SEQ ID NO 1386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1386
cctgtagcct gtcagctgtg                                              20

<210> SEQ ID NO 1387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1387
ttgcctgtag cctgtcagct                                              20

<210> SEQ ID NO 1388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1388
ggattgcctg tagcctgtca                                              20

<210> SEQ ID NO 1389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1389
ccaggattgc ctgtagcctg                                              20

<210> SEQ ID NO 1390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1390
cacccaggat tgcctgtagc                                              20

<210> SEQ ID NO 1391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1391
gaacacccag gattgcctgt                                              20
```

```
<210> SEQ ID NO 1392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1392
aaggaacacc caggattgcc                                                 20

<210> SEQ ID NO 1393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1393
tccaaggaac acccaggatt                                                 20

<210> SEQ ID NO 1394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1394
ccttccaagg aacacccagg                                                 20

<210> SEQ ID NO 1395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1395
tgtccttcca aggaacaccc                                                 20

<210> SEQ ID NO 1396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1396
tcttgtcctt ccaaggaaca                                                 20

<210> SEQ ID NO 1397
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1397
agttcttgtc cttccaagga                                                 20

<210> SEQ ID NO 1398
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 1398
tgcagttctt gtccttccaa                                            20

<210> SEQ ID NO 1399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1399
aggtgcagtt cttgtccttc                                            20

<210> SEQ ID NO 1400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1400
gggaggtgca gttcttgtcc                                            20

<210> SEQ ID NO 1401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1401
gccgggaggt gcagttcttg                                            20

<210> SEQ ID NO 1402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1402
ccagccggga ggtgcagttc                                            20

<210> SEQ ID NO 1403
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1403
catccagccg ggaggtgcag                                            20

<210> SEQ ID NO 1404
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1404
gcgcatccag ccgggaggtg                                            20

```
<210> SEQ ID NO 1405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1405
tgtgcgcatc cagccgggag                                          20

<210> SEQ ID NO 1406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1406
ccttgtgcgc atccagccgg                                          20

<210> SEQ ID NO 1407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1407
ggaccttgtg cgcatccagc                                          20

<210> SEQ ID NO 1408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1408
acaggacctt gtgcgcatcc                                          20

<210> SEQ ID NO 1409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1409
cagacaggac cttgtgcgca                                          20

<210> SEQ ID NO 1410
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1410
gggcagacag gaccttgtgc                                          20

<210> SEQ ID NO 1411
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1411
gcagggcaga caggaccttg                                               20

<210> SEQ ID NO 1412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1412
cctgcagggc agacaggacc                                               20

<210> SEQ ID NO 1413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1413
cagcctgcag ggcagacagg                                               20

<210> SEQ ID NO 1414
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1414
gtacagcctg cagggcagac                                               20

<210> SEQ ID NO 1415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1415
cctgtacagc ctgcagggca                                               20

<210> SEQ ID NO 1416
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1416
ggccctgtac agcctgcagg                                               20

<210> SEQ ID NO 1417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1417
gcaggccctg tacagcctgc                                               20

<210> SEQ ID NO 1418
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1418
ctagcaggcc ctgtacagcc                                           20

<210> SEQ ID NO 1419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1419
ccactagcag gccctgtaca                                           20

<210> SEQ ID NO 1420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1420
gggccactag caggccctgt                                           20

<210> SEQ ID NO 1421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1421
cctgggccac tagcaggccc                                           20

<210> SEQ ID NO 1422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1422
tgccctgggc cactagcagg                                           20

<210> SEQ ID NO 1423
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1423
ccctgccctg ggccactagc                                           20

<210> SEQ ID NO 1424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1424
```
cagccctgcc ctgggccact                                              20

<210> SEQ ID NO 1425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1425
tatcagccct gccctgggcc                                              20

<210> SEQ ID NO 1426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1426
ggctatcagc cctgccctgg                                              20

<210> SEQ ID NO 1427
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1427
cctggctatc agccctgccc                                              20

<210> SEQ ID NO 1428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1428
gggcctggct atcagccctg                                              20

<210> SEQ ID NO 1429
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1429
gctgggcctg gctatcagcc                                              20

<210> SEQ ID NO 1430
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1430
gcagctgggc ctggctatca                                              20

<210> SEQ ID NO 1431
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1431
gcagcagctg ggcctggcta                                                   20

<210> SEQ ID NO 1432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1432
acagcagcag ctgggcctgg                                                   20

<210> SEQ ID NO 1433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1433
tggacagcag cagctgggcc                                                   20

<210> SEQ ID NO 1434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1434
ccgtggacag cagcagctgg                                                   20

<210> SEQ ID NO 1435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1435
ccaccgtgga cagcagcagc                                                   20

<210> SEQ ID NO 1436
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1436
ccaccaccgt ggacagcagc                                                   20

<210> SEQ ID NO 1437
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1437
cgcccaccac cgtggacagc                                                   20
```

<210> SEQ ID NO 1438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1438
acacgcccac caccgtggac                                           20

<210> SEQ ID NO 1439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1439
tgaacacgcc caccaccgtg                                           20

<210> SEQ ID NO 1440
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1440
ctgtgaacac gcccaccacc                                           20

<210> SEQ ID NO 1441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1441
gggctgtgaa cacgcccacc                                           20

<210> SEQ ID NO 1442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1442
gcttcaggtg caggcctggg                                           20

<210> SEQ ID NO 1443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1443
gctgcttcag gtgcaggcct                                           20

<210> SEQ ID NO 1444
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 1444
acggctgctt caggtgcagg                                               20

<210> SEQ ID NO 1445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1445
caaacggctg cttcaggtgc                                               20

<210> SEQ ID NO 1446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1446
gcacaaacgg ctgcttcagg                                               20

<210> SEQ ID NO 1447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1447
cctgcacaaa cggctgcttc                                               20

<210> SEQ ID NO 1448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1448
ggccctgcac aaacggctgc                                               20

<210> SEQ ID NO 1449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1449
ccaggccctg cacaaacggc                                               20

<210> SEQ ID NO 1450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1450
gagccaggcc ctgcacaaac                                               20

<210> SEQ ID NO 1451

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1451
agagagccag gccctgcaca                                                     20

<210> SEQ ID NO 1452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1452
tatagagagc caggccctgc                                                     20

<210> SEQ ID NO 1453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1453
gggtatagag agccaggccc                                                     20

<210> SEQ ID NO 1454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1454
tctgtgaagt ccagagagcg                                                     20

<210> SEQ ID NO 1455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1455
agttctgtga agtccagaga                                                     20

<210> SEQ ID NO 1456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1456
tccagttctg tgaagtccag                                                     20

<210> SEQ ID NO 1457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1457
```
acatccagtt ctgtgaagtc                                              20

<210> SEQ ID NO 1458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1458
gcaacatcca gttctgtgaa                                              20

<210> SEQ ID NO 1459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1459
gcagcaacat ccagttctgt                                              20

<210> SEQ ID NO 1460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1460
tcagcagcaa catccagttc                                              20

<210> SEQ ID NO 1461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1461
ttctcagcag caacatccag                                              20

<210> SEQ ID NO 1462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1462
atcttctcag cagcaacatc                                              20

<210> SEQ ID NO 1463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1463
tcaatcttct cagcagcaac                                              20

<210> SEQ ID NO 1464
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1464
ctgtcaatct tctcagcagc                                                  20

<210> SEQ ID NO 1465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1465
aacctgtcaa tcttctcagc                                                  20

<210> SEQ ID NO 1466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1466
atgaacctgt caatcttctc                                                  20

<210> SEQ ID NO 1467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1467
tgcatgaacc tgtcaatctt                                                  20

<210> SEQ ID NO 1468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1468
gcctgcatga acctgtcaat                                                  20

<210> SEQ ID NO 1469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1469
acagcctgca tgaacctgtc                                                  20

<210> SEQ ID NO 1470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1470
gtcacagcct gcatgaacct                                                  20
```

<210> SEQ ID NO 1471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1471
cctgtcacag cctgcatgaa                                           20

<210> SEQ ID NO 1472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1472
catcctgtca cagcctgcat                                           20

<210> SEQ ID NO 1473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1473
ttccatcctg tcacagcctg                                           20

<210> SEQ ID NO 1474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1474
gtcttccatc ctgtcacagc                                           20

<210> SEQ ID NO 1475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1475
ccagtcttcc atcctgtcac                                           20

<210> SEQ ID NO 1476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1476
cagccagtct tccatcctgt                                           20

<210> SEQ ID NO 1477
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1477
gagcagccag tcttccatcc                                                   20

<210> SEQ ID NO 1478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1478
agggagcagc cagtcttcca                                                   20

<210> SEQ ID NO 1479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1479
atcagggagc agccagtctt                                                   20

<210> SEQ ID NO 1480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1480
cccatcaggg agcagccagt                                                   20

<210> SEQ ID NO 1481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1481
gctcccatca gggagcagcc                                                   20

<210> SEQ ID NO 1482
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1482
ctggctccca tcagggagca                                                   20

<210> SEQ ID NO 1483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1483
acactggctc ccatcaggga                                                   20

```
<210> SEQ ID NO 1484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1484
tccacactgg ctcccatcag                                                     20

<210> SEQ ID NO 1485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1485
ctgtccacac tggctcccat                                                     20

<210> SEQ ID NO 1486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1486
gtgctgtcca cactggctcc                                                     20

<210> SEQ ID NO 1487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1487
agggtgctgt ccacactggc                                                     20

<210> SEQ ID NO 1488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1488
gccagggtgc tgtccacact                                                     20

<210> SEQ ID NO 1489
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1489
aaagccaggg tgctgtccac                                                     20

<210> SEQ ID NO 1490
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1490
ttgaaagcca gggtgctgtc                                               20

<210> SEQ ID NO 1491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1491
gtgttgaaag ccagggtgct                                               20

<210> SEQ ID NO 1492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1492
taggtgttga agccagggt                                                20

<210> SEQ ID NO 1493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1493
tcttcccttg gaagtggacg                                               20

<210> SEQ ID NO 1494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1494
tcatcttccc ttggaagtgg                                               20

<210> SEQ ID NO 1495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1495
ccttcatctt cccttggaag                                               20

<210> SEQ ID NO 1496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1496
agcccttcat cttcccttgg                                               20

<210> SEQ ID NO 1497
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1497
agaagccctt catcttccct                                               20

<210> SEQ ID NO 1498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1498
gggagaagcc cttcatcttc                                               20

<210> SEQ ID NO 1499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1499
gcagggagaa gcccttcatc                                               20

<210> SEQ ID NO 1500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1500
ccagcaggga gaagcccttc                                               20

<210> SEQ ID NO 1501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1501
cggccagcag ggagaagccc                                               20

<210> SEQ ID NO 1502
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1502
gctcggccag cagggagaag                                               20

<210> SEQ ID NO 1503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1503
```

```
gtccacccag aactcctggg                                              20

<210> SEQ ID NO 1504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1504
gttgtccacc cagaactcct                                              20

<210> SEQ ID NO 1505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1505
gctgttgtcc acccagaact                                              20

<210> SEQ ID NO 1506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1506
ggtgctgttg tccacccaga                                              20

<210> SEQ ID NO 1507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1507
tgaggtgctg ttgtccaccc                                              20

<210> SEQ ID NO 1508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1508
cactgaggtg ctgttgtcca                                              20

<210> SEQ ID NO 1509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1509
agacactgag gtgctgttgt                                              20

<210> SEQ ID NO 1510
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1510
aacagacact gaggtgctgt                                               20

<210> SEQ ID NO 1511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1511
gggaacagac actgaggtgc                                               20

<210> SEQ ID NO 1512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1512
catgggaaca gacactgagg                                               20

<210> SEQ ID NO 1513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1513
gagcatggga acagacactg                                               20

<210> SEQ ID NO 1514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1514
agagagcatg ggaacagaca                                               20

<210> SEQ ID NO 1515
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1515
gccagagagc atgggaacag                                               20

<210> SEQ ID NO 1516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1516
catgccagag agcatgggaa                                               20
```

<210> SEQ ID NO 1517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1517
gcccatgcca gagagcatgg                                                    20

<210> SEQ ID NO 1518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1518
ggtgcccatg ccagagagca                                                    20

<210> SEQ ID NO 1519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1519
gaaggtgccc atgccagaga                                                    20

<210> SEQ ID NO 1520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1520
ctggaaggtg cccatgccag                                                    20

<210> SEQ ID NO 1521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1521
gtgctggaag gtgcccatgc                                                    20

<210> SEQ ID NO 1522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1522
ccagtgctgg aaggtgccca                                                    20

<210> SEQ ID NO 1523
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1523
actccagtgc tggaaggtgc                                          20

<210> SEQ ID NO 1524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1524
gtcactccag tgctggaagg                                          20

<210> SEQ ID NO 1525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1525
gatgtcactc cagtgctgga                                          20

<210> SEQ ID NO 1526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1526
ctggatgtca ctccagtgct                                          20

<210> SEQ ID NO 1527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1527
gtcctggatg tcactccagt                                          20

<210> SEQ ID NO 1528
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1528
gttgtcctgg atgtcactcc                                          20

<210> SEQ ID NO 1529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1529
gaagttgtcc tggatgtcac                                          20

<210> SEQ ID NO 1530
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1530
cgagaagttg tcctggatgt                                               20

<210> SEQ ID NO 1531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1531
caccgagaag ttgtcctgga                                               20

<210> SEQ ID NO 1532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1532
agtcaccgag aagttgtcct                                               20

<210> SEQ ID NO 1533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1533
ttgagtcacc gagaagttgt                                               20

<210> SEQ ID NO 1534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1534
cacttgagtc accgagaagt                                               20

<210> SEQ ID NO 1535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1535
gggcacttga gtcaccgaga                                               20

<210> SEQ ID NO 1536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1536
```
gaagggcact tgagtcaccg                                        20

<210> SEQ ID NO 1537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1537
agtgaagggc acttgagtca                                        20

<210> SEQ ID NO 1538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1538
ctcagtgaag ggcacttgag                                        20

<210> SEQ ID NO 1539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1539
gctctcagtg aagggcactt                                        20

<210> SEQ ID NO 1540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1540
gatcagcagc aggcaggcgc                                        20

<210> SEQ ID NO 1541
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1541
ctggatcagc agcaggcagg                                        20

<210> SEQ ID NO 1542
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1542
aggctggatc agcagcaggc                                        20

<210> SEQ ID NO 1543
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1543
gtgaggctgg atcagcagca                                                   20

<210> SEQ ID NO 1544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1544
atagtgaggc tggatcagca                                                   20

<210> SEQ ID NO 1545
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1545
ggcatagtga ggctggatca                                                   20

<210> SEQ ID NO 1546
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1546
agaggcatag tgaggctgga                                                   20

<210> SEQ ID NO 1547
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1547
gtcagaggca tagtgaggct                                                   20

<210> SEQ ID NO 1548
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1548
caggtcagag gcatagtgag                                                   20

<210> SEQ ID NO 1549
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1549
gtccaggtca gaggcatagt                                                   20
```

<210> SEQ ID NO 1550
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1550
cttgtccagg tcagaggcat                                              20

<210> SEQ ID NO 1551
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1551
caccttgtcc aggtcagagg                                              20

<210> SEQ ID NO 1552
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1552
ctccaccttg tccaggtcag                                              20

<210> SEQ ID NO 1553
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1553
accctccacc ttgtccaggt                                              20

<210> SEQ ID NO 1554
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1554
gagaccctcc accttgtcca                                              20

<210> SEQ ID NO 1555
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1555
agtgagaccc tccaccttgt                                              20

<210> SEQ ID NO 1556
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 1556
gaaagtgaga ccctccacct                                              20

<210> SEQ ID NO 1557
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1557
ctggaaagtg agaccctcca                                              20

<210> SEQ ID NO 1558
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1558
ttgctggaaa gtgagaccct                                              20

<210> SEQ ID NO 1559
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1559
gttttgctgg aaagtgagac                                              20

<210> SEQ ID NO 1560
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1560
ggagttttgc tggaaagtga                                              20

<210> SEQ ID NO 1561
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1561
gagggagttt tgctggaaag                                              20

<210> SEQ ID NO 1562
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1562
gttgagggag ttttgctgga                                              20

```
<210> SEQ ID NO 1563
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1563
ccagttgagg gagttttgct                                                     20

<210> SEQ ID NO 1564
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1564
catccagttg agggagtttt                                                     20

<210> SEQ ID NO 1565
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1565
cttcatccag ttgagggagt                                                     20

<210> SEQ ID NO 1566
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1566
tttcttcatc cagttgaggg                                                     20

<210> SEQ ID NO 1567
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1567
tagtttcttc atccagttga                                                     20

<210> SEQ ID NO 1568
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1568
agatagtttc ttcatccagt                                                     20

<210> SEQ ID NO 1569
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1569
gggagatagt ttcttcatcc                                          20

<210> SEQ ID NO 1570
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1570
ggtcaggtgg atggtccggg                                          20

<210> SEQ ID NO 1571
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1571
catggtcagg tggatggtcc                                          20

<210> SEQ ID NO 1572
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1572
gggcatggtc aggtggatgg                                          20

<210> SEQ ID NO 1573
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1573
tccttgcagc accagttggg                                          20

<210> SEQ ID NO 1574
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1574
agatccttgc agcaccagtt                                          20

<210> SEQ ID NO 1575
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1575
ataagatcct tgcagcacca                                          20

<210> SEQ ID NO 1576
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1576
gtcataagat ccttgcagca                                              20

<210> SEQ ID NO 1577
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1577
caggtcataa gatccttgca                                              20

<210> SEQ ID NO 1578
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1578
ctgcaggtca taagatcctt                                              20

<210> SEQ ID NO 1579
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1579
gtcctgcagg tcataagatc                                              20

<210> SEQ ID NO 1580
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1580
caggtcctgc aggtcataag                                              20

<210> SEQ ID NO 1581
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1581
gagcaggtcc tgcaggtcat                                              20

<210> SEQ ID NO 1582
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1582
```
ggcgagcagg tcctgcaggt                                               20

<210> SEQ ID NO 1583
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1583
ctgggcgagc aggtcctgca                                               20

<210> SEQ ID NO 1584
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1584
agcctgggcg agcaggtcct                                               20

<210> SEQ ID NO 1585
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1585
ctcagcctgg gcgagcaggt                                               20

<210> SEQ ID NO 1586
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1586
cagctcagcc tgggcgagca                                               20

<210> SEQ ID NO 1587
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1587
tggcgggcag ctcagcctgg                                               20

<210> SEQ ID NO 1588
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1588
gaatggcggg cagctcagcc                                               20

<210> SEQ ID NO 1589
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1589
gcagaatggc gggcagctca                                              20

<210> SEQ ID NO 1590
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1590
tgtgcagaat ggcgggcagc                                              20

<210> SEQ ID NO 1591
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1591
cggtgtgcag aatggcgggc                                              20

<210> SEQ ID NO 1592
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1592
gctcggtgtg cagaatggcg                                              20

<210> SEQ ID NO 1593
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1593
tcagctcggt gtgcagaatg                                              20

<210> SEQ ID NO 1594
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1594
ggttcagctc ggtgtgcaga                                              20

<210> SEQ ID NO 1595
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1595
gcaggttcag ctcggtgtgc                                              20
```

<210> SEQ ID NO 1596
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1596
tttgcaggtt cagctcggtg                                                 20

<210> SEQ ID NO 1597
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1597
atttttgcag gttcagctcg                                                 20

<210> SEQ ID NO 1598
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1598 tcaattttg caggttcagc                                                  20

<210> SEQ ID NO 1599
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1599
tgctcaattt ttgcaggttc                                                 20

<210> SEQ ID NO 1600
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1600
cattgctcaa tttttgcagg                                                 20

<210> SEQ ID NO 1601
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1601
ggtcattgct caattttgc                                                  20

<210> SEQ ID NO 1602
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 1602
tgcggtcatt gctcaatttt                                          20

<210> SEQ ID NO 1603
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1603
tgatgcggtc attgctcaat                                          20

<210> SEQ ID NO 1604
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1604
ccctgatgcg gtcattgctc                                          20

<210> SEQ ID NO 1605
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1605
ccaccctgat gcggtcattg                                          20

<210> SEQ ID NO 1606
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1606
cccccaccct gatgcggtca                                          20

<210> SEQ ID NO 1607
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1607
cctcccccac cctgatgcgg                                          20

<210> SEQ ID NO 1608
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1608
gcacctcccc caccctgatg                                          20

<210> SEQ ID NO 1609

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1609
tcagcacctc ccccaccctg                                               20

<210> SEQ ID NO 1610
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1610
tgttcagcac ctcccccacc                                               20

<210> SEQ ID NO 1611
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1611
tgctgttcag cacctccccc                                               20

<210> SEQ ID NO 1612
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1612
aaatgctgtt cagcacctcc                                               20

<210> SEQ ID NO 1613
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1613
aaaaaatgct gttcagcacc                                               20

<210> SEQ ID NO 1614
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1614
caaaaaaaat gctgttcagc                                               20

<210> SEQ ID NO 1615
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1615
```
gctcaaaaaa aatgctgttc                                               20

<210> SEQ ID NO 1616
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1616
caagctcaaa aaaatgctg                                                20

<210> SEQ ID NO 1617
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1617
cttcaagctc aaaaaaaatg                                               20

<210> SEQ ID NO 1618
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1618
ccgcttcaag ctcaaaaaaa                                               20

<210> SEQ ID NO 1619
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1619
catccgcttc aagctcaaaa                                               20

<210> SEQ ID NO 1620
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1620
tctcatccgc ttcaagctca                                               20

<210> SEQ ID NO 1621
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1621
ctctctcatc cgcttcaagc                                               20

<210> SEQ ID NO 1622
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1622
gctctctctc atccgcttca                                              20

<210> SEQ ID NO 1623
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1623
tgggctctct ctcatccgct                                              20

<210> SEQ ID NO 1624
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1624
ctgtgggctc tctctcatcc                                              20

<210> SEQ ID NO 1625
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1625
actctgtggg ctctctctca                                              20

<210> SEQ ID NO 1626
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1626
tagactctgt gggctctctc                                              20

<210> SEQ ID NO 1627
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1627
ctgttgggta gactctgtgg                                              20

<210> SEQ ID NO 1628
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1628
aagctgttgg gtagactctg                                              20
```

<210> SEQ ID NO 1629
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1629
gttaagctgt tgggtagact                                           20

<210> SEQ ID NO 1630
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1630
cttgttaagc tgttgggtag                                           20

<210> SEQ ID NO 1631
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1631
aggcttgtta agctgttggg                                           20

<210> SEQ ID NO 1632
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1632
ctcaggcttg ttaagctgtt                                           20

<210> SEQ ID NO 1633
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1633
gacctcaggc ttgttaagct                                           20

<210> SEQ ID NO 1634
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1634
caagacctca ggcttgttaa                                           20

<210> SEQ ID NO 1635
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1635
ctccaagacc tcaggcttgt                                                    20

<210> SEQ ID NO 1636
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1636
cacctccaag acctcaggct                                                    20

<210> SEQ ID NO 1637
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1637
ggtcacctcc aagacctcag                                                    20

<210> SEQ ID NO 1638
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1638
cagggtcacc tccaagacct                                                    20

<210> SEQ ID NO 1639
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1639
gttcagggtc acctccaaga                                                    20

<210> SEQ ID NO 1640
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1640
gcggttcagg gtcacctcca                                                    20

<210> SEQ ID NO 1641
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1641
acaggaatgg gcggttcagg                                                    20

```
<210> SEQ ID NO 1642
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1642
caaacaggaa tgggcggttc                                                  20

<210> SEQ ID NO 1643
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1643
cagcaaacag gaatgggcgg                                                  20

<210> SEQ ID NO 1644
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1644
acacagcaaa caggaatggg                                                  20

<210> SEQ ID NO 1645
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1645
catacacagc aaacaggaat                                                  20

<210> SEQ ID NO 1646
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1646
gatcatacac agcaaacagg                                                  20

<210> SEQ ID NO 1647
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1647
tttgatcata cacagcaaac                                                  20

<210> SEQ ID NO 1648
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1648
cgctttgatc atacacagca                                                   20

<210> SEQ ID NO 1649
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1649
gaagtgcagg gcagtggcgc                                                   20

<210> SEQ ID NO 1650
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1650
caggaagtgc agggcagtgg                                                   20

<210> SEQ ID NO 1651
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1651
gcccaggaag tgcagggcag                                                   20

<210> SEQ ID NO 1652
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1652
gcggcccagg aagtgcaggg                                                   20

<210> SEQ ID NO 1653
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1653
cacgcggccc aggaagtgca                                                   20

<210> SEQ ID NO 1654
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1654
ggccacgcgg cccaggaagt                                                   20

<210> SEQ ID NO 1655
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1655
gttggccacg cggcccagga                                              20

<210> SEQ ID NO 1656
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1656
cgggttggcc acgcggccca                                              20

<210> SEQ ID NO 1657
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1657
cagcgggttg gccacgcggc                                              20

<210> SEQ ID NO 1658
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1658
gctcagcggg ttggccacgc                                              20

<210> SEQ ID NO 1659
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1659
tgtgctcagc gggttggcca                                              20

<210> SEQ ID NO 1660
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1660
tgctgtgctc agcgggttgg                                              20

<210> SEQ ID NO 1661
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1661
```

```
tcatgctgtg ctcagcgggt                                              20

<210> SEQ ID NO 1662
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1662
gcctcatgct gtgctcagcg                                              20

<210> SEQ ID NO 1663
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1663
ctggcctcat gctgtgctca                                              20

<210> SEQ ID NO 1664
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1664
gccctggcct catgctgtgc                                              20

<210> SEQ ID NO 1665
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1665
gccaggcact gtgttctggg                                              20

<210> SEQ ID NO 1666
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1666
cttgccaggc actgtgttct                                              20

<210> SEQ ID NO 1667
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1667
ggccttgcca ggcactgtgt                                              20

<210> SEQ ID NO 1668
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1668
aggagaaacg gctgctttcc                                               20

<210> SEQ ID NO 1669
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1669
ccaaggagaa acggctgctt                                               20

<210> SEQ ID NO 1670
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1670
agaccaagga gaaacggctg                                               20

<210> SEQ ID NO 1671
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1671
cttagaccaa ggagaaacgg                                               20

<210> SEQ ID NO 1672
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1672
acacttagac caaggagaaa                                               20

<210> SEQ ID NO 1673
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1673
agcacactta gaccaaggag                                               20

<210> SEQ ID NO 1674
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1674
tgcagcacac ttagaccaag                                               20
```

<210> SEQ ID NO 1675
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1675
ccatgcagca cacttagacc                                               20

<210> SEQ ID NO 1676
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1676
actccatgca gcacacttag                                               20

<210> SEQ ID NO 1677
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1677
ctcactccat gcagcacact                                               20

<210> SEQ ID NO 1678
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1678
cgctgcaggc ttctactgct                                               20

<210> SEQ ID NO 1679
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1679
tgccgctgca ggcttctact                                               20

<210> SEQ ID NO 1680
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1680
ttgtgccgct gcaggcttct                                               20

<210> SEQ ID NO 1681
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1681
catttgtgcc gctgcaggct                                               20

<210> SEQ ID NO 1682
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1682
gtgcatttgt gccgctgcag                                               20

<210> SEQ ID NO 1683
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1683
gaggtgcatt tgtgccgctg                                               20

<210> SEQ ID NO 1684
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1684
tgggaggtgc atttgtgccg                                               20

<210> SEQ ID NO 1685
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1685
aactgggagg tgcatttgtg                                               20

<210> SEQ ID NO 1686
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1686
gcaaactggg aggtgcattt                                               20

<210> SEQ ID NO 1687
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1687
ccagcaaact gggaggtgca                                               20

<210> SEQ ID NO 1688

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1688
aacccagcaa actgggaggt                                              20

<210> SEQ ID NO 1689
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1689
ataaacccag caaactggga                                              20

<210> SEQ ID NO 1690
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1690
aaaataaacc cagcaaactg                                              20

<210> SEQ ID NO 1691
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1691
tctaaaataa acccagcaaa                                              20

<210> SEQ ID NO 1692
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1692
ttctctaaaa taaacccagc                                              20

<210> SEQ ID NO 1693
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1693
ccattctcta aaataaaccc                                              20

<210> SEQ ID NO 1694
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1694
``` ccccccattct ctaaaataaa                                              20

<210> SEQ ID NO 1695
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1695
ccacccccat tctctaaaat                                               20

<210> SEQ ID NO 1696
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1696
tccccacccc cattctctaa                                               20

<210> SEQ ID NO 1697
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1697
gcctccccac ccccattctc                                               20

<210> SEQ ID NO 1698
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1698
cttgcctccc cacccccatt                                               20

<210> SEQ ID NO 1699
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1699
gttcttgcct ccccaccccc                                               20

<210> SEQ ID NO 1700
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1700
ctggttcttg cctccccacc                                               20

<210> SEQ ID NO 1701
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1701
acactggttc ttgcctcccc                                                    20

<210> SEQ ID NO 1702
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1702
taaacactgg ttcttgcctc                                                    20

<210> SEQ ID NO 1703
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1703
cgctaaacac tggttcttgc                                                    20

<210> SEQ ID NO 1704
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1704
ccgcgctaaa cactggttct                                                    20

<210> SEQ ID NO 1705
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1705
gtcccgcgct aaacactggt                                                    20

<210> SEQ ID NO 1706
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1706
gtagtcccgc gctaaacact                                                    20

<210> SEQ ID NO 1707
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1707
acagtagtcc cgcgctaaac                                                    20
```

<210> SEQ ID NO 1708
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1708
ggaacagtag tcccgcgcta                                          20

<210> SEQ ID NO 1709
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1709
tttggaacag tagtcccgcg                                          20

<210> SEQ ID NO 1710
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1710 cttttttggaa cagtagtccc                                         20

<210> SEQ ID NO 1711
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1711 attcttttg gaacagtagt                                           20

<210> SEQ ID NO 1712
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1712
ggaattcttt ttggaacagt                                          20

<210> SEQ ID NO 1713
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1713
gttggaattc ttttggaac                                           20

<210> SEQ ID NO 1714
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1714
tcggttggaa ttctttttgg       20

<210> SEQ ID NO 1715
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1715
tggtcggttg gaattctttt       20

<210> SEQ ID NO 1716
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1716
agctggtcgg ttggaattct       20

<210> SEQ ID NO 1717
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1717
acaagctggt cggttggaat       20

<210> SEQ ID NO 1718
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1718
caaacaagct ggtcggttgg       20

<210> SEQ ID NO 1719
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1719
tcacaaacaa gctggtcggt       20

<210> SEQ ID NO 1720
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1720
gtttcacaaa caagctggtc       20

```
<210> SEQ ID NO 1721
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1721
tttgtttcac aaacaagctg                                                   20

<210> SEQ ID NO 1722
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1722
gaaaagggaa cacttttttg                                                   20

<210> SEQ ID NO 1723
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1723
cttgaaaagg gaacactttt                                                   20

<210> SEQ ID NO 1724
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1724
caacttgaaa agggaacact                                                   20

<210> SEQ ID NO 1725
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1725
tctcaacttg aaaagggaac                                                   20

<210> SEQ ID NO 1726
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1726
tgttctcaac ttgaaaaggg                                                   20

<210> SEQ ID NO 1727
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1727
ttttgttctc aacttgaaaa                                               20

<210> SEQ ID NO 1728
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1728
aatttttgtt ctcaacttga                                               20

<210> SEQ ID NO 1729
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1729
cccaattttt gttctcaact                                               20

<210> SEQ ID NO 1730
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1730
aaacccaatt tttgttctca                                               20

<210> SEQ ID NO 1731
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1731
ttaaaaccca attttttgttc                                              20

<210> SEQ ID NO 1732
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1732
attttaaaac ccaattttg                                                20

<210> SEQ ID NO 1733
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1733
ttaattttaa aacccaattt                                               20

<210> SEQ ID NO 1734
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1734
tgcaaaaatg tatactttaa                                              20

<210> SEQ ID NO 1735
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1735
caatgcaaaa atgtatactt                                              20

<210> SEQ ID NO 1736
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1736
aggcaatgca aaatgtata                                               20

<210> SEQ ID NO 1737
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1737
cgaaggcaat gcaaaaatgt                                              20

<210> SEQ ID NO 1738
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1738
aaccgaaggc aatgcaaaaa                                              20

<210> SEQ ID NO 1739
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1739
acaaaccgaa ggcaatgcaa                                              20

<210> SEQ ID NO 1740
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1740
```
aatacaaacc gaaggcaatg                                        20

<210> SEQ ID NO 1741
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1741
ctaaatacaa accgaaggca                                        20

<210> SEQ ID NO 1742
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1742
acactaaata caaaccgaag                                        20

<210> SEQ ID NO 1743
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1743
aagacactaa atacaaaccg                                        20

<210> SEQ ID NO 1744
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1744
ttcaagacac taaatacaaa                                        20

<210> SEQ ID NO 1745
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1745
acattcaaga cactaaatac                                        20

<210> SEQ ID NO 1746
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1746
cttacattca agacactaaa                                        20

<210> SEQ ID NO 1747
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1747
gttcttacat tcaagacact                                                    20

<210> SEQ ID NO 1748
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1748
catgttctta cattcaagac                                                    20

<210> SEQ ID NO 1749
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1749
ggtcatgttc ttacattcaa                                                    20

<210> SEQ ID NO 1750
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1750
ggaggtcatg ttcttacatt                                                    20

<210> SEQ ID NO 1751
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1751
cacggaggtc atgttcttac                                                    20

<210> SEQ ID NO 1752
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1752
ctacacggag gtcatgttct                                                    20

<210> SEQ ID NO 1753
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1753
acactacacg gaggtcatgt                                                    20
```

```
<210> SEQ ID NO 1754
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1754
cagacactac acggaggtca                                              20

<210> SEQ ID NO 1755
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1755
ttacagacac tacacggagg                                              20

<210> SEQ ID NO 1756
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1756
gtattacaga cactacacgg                                              20

<210> SEQ ID NO 1757
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1757
aaggtattac agacactaca                                              20

<210> SEQ ID NO 1758
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1758
actaaggtat tacagacact                                              20

<210> SEQ ID NO 1759
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1759
aaaactaagg tattacagac                                              20

<210> SEQ ID NO 1760
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1760
gaaaaaacta aggtattaca                                              20

<210> SEQ ID NO 1761
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1761
gtggaaaaaa ctaaggtatt                                              20

<210> SEQ ID NO 1762
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1762
tctgtggaaa aaactaaggt                                              20

<210> SEQ ID NO 1763
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1763
gcatctgtgg aaaaaactaa                                              20

<210> SEQ ID NO 1764
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1764
caagcatctg tggaaaaaac                                              20

<210> SEQ ID NO 1765
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1765
tcacaagcat ctgtggaaaa                                              20

<210> SEQ ID NO 1766
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1766
aaatcacaag catctgtgga                                              20

<210> SEQ ID NO 1767
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1767
caaaaatcac aagcatctgt                                           20

<210> SEQ ID NO 1768
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1768
gttcaaaaat cacaagcatc                                           20

<210> SEQ ID NO 1769
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1769
attgttcaaa aatcacaagc                                           20

<210> SEQ ID NO 1770
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1770
cgtattgttc aaaaatcaca                                           20

<210> SEQ ID NO 1771
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1771
aggtgcttgc atctttcacg                                           20

<210> SEQ ID NO 1772
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1772
ttcaggtgct tgcatctttc                                           20

<210> SEQ ID NO 1773
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1773
```
aaattcaggt gcttgcatct 20

<210> SEQ ID NO 1774
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1774
cagaaattca ggtgcttgca 20

<210> SEQ ID NO 1775
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1775
aaacagaaat tcaggtgctt 20

<210> SEQ ID NO 1776
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1776
ttcaaacaga aattcaggtg 20

<210> SEQ ID NO 1777
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1777
gcattcaaac agaaattcag 20

<210> SEQ ID NO 1778
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1778
tccgcattca aacagaaatt 20

<210> SEQ ID NO 1779
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1779
ggttccgcat tcaaacagaa 20

<210> SEQ ID NO 1780
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1780
tatggttccg cattcaaaca                                              20

<210> SEQ ID NO 1781
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1781
agctatggtt ccgcattcaa                                              20

<210> SEQ ID NO 1782
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1782
accagctatg gttccgcatt                                              20

<210> SEQ ID NO 1783
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1783
ataaccagct atggttccgc                                              20

<210> SEQ ID NO 1784
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1784
gaaataacca gctatggttc                                              20

<210> SEQ ID NO 1785
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1785
ggagaaataa ccagctatgg                                              20

<210> SEQ ID NO 1786
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1786
aagggagaaa taaccagcta                                              20
```

<210> SEQ ID NO 1787
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1787
cacaagggag aaataaccag                                              20

<210> SEQ ID NO 1788
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1788
taacacaagg gagaaataac                                              20

<210> SEQ ID NO 1789
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1789
tactaacaca agggagaaat                                              20

<210> SEQ ID NO 1790
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1790
tattactaac acaagggaga                                              20

<210> SEQ ID NO 1791
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1791
gtttattact aacacaaggg                                              20

<210> SEQ ID NO 1792
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1792
aggcttattg tggcaagacg                                              20

<210> SEQ ID NO 1793
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1793
tggaggctta ttgtggcaag                                                  20

<210> SEQ ID NO 1794
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1794
ttttggaggc ttattgtggc                                                  20

<210> SEQ ID NO 1795
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1795
tttttttgga ggcttattgt                                                  20

<210> SEQ ID NO 1796
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1796
actctcattg tggatgacga                                                  20

<210> SEQ ID NO 1797
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1797
aggtactctc attgtggatg                                                  20

<210> SEQ ID NO 1798
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1798
acaggtactc tcattgtgga                                                  20

<210> SEQ ID NO 1799
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1799
gctcacaggt actctcattg                                                  20

```
<210> SEQ ID NO 1800
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1800
gcaccagctg gtcctgtagg                                                   20

<210> SEQ ID NO 1801
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1801
tagcaccagc tggtcctgta                                                   20

<210> SEQ ID NO 1802
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1802
ctagcaccag ctggtcctgt                                                   20

<210> SEQ ID NO 1803
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1803
cgactagcac cagctggtcc                                                   20

<210> SEQ ID NO 1804
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1804
agcgactagc accagctggt                                                   20

<210> SEQ ID NO 1805
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1805
ttgcagcgac tagcaccagc                                                   20

<210> SEQ ID NO 1806
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1806
ttttgcagcg actagcacca                                              20

<210> SEQ ID NO 1807
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1807
caagttttgc agcgactagc                                              20

<210> SEQ ID NO 1808
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1808
ctgtcacagc ctgcatgaac                                              20

<210> SEQ ID NO 1809
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1809
tcctgtcaca gcctgcatga                                              20

<210> SEQ ID NO 1810
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1810
atcctgtcac agcctgcatg                                              20

<210> SEQ ID NO 1811
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1811
tccatcctgt cacagcctgc                                              20

<210> SEQ ID NO 1812
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1812
cttccatcct gtcacagcct                                              20

<210> SEQ ID NO 1813
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1813
tcactccagt gctggaaggt                                              20

<210> SEQ ID NO 1814
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1814
tgtcactcca gtgctggaag                                              20

<210> SEQ ID NO 1815
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1815
atgtcactcc agtgctggaa                                              20

<210> SEQ ID NO 1816
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1816
tggatgtcac tccagtgctg                                              20

<210> SEQ ID NO 1817
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1817
cctggatgtc actccagtgc                                              20

<210> SEQ ID NO 1818
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1818
aaggagaaac ggctgctttc                                              20

<210> SEQ ID NO 1819
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1819
```

-continued caaggagaaa cggctgcttt    20

<210> SEQ ID NO 1820
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1820
accaaggaga aacggctgct    20

<210> SEQ ID NO 1821
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1821
gaccaaggag aaacggctgc    20

<210> SEQ ID NO 1822
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1822
tagaccaagg agaaacggct    20

<210> SEQ ID NO 1823
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1823
ttagaccaag gagaaacggc    20

<210> SEQ ID NO 1824
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1824
acttagacca aggagaaacg    20

<210> SEQ ID NO 1825
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1825
cacttagacc aaggagaaac    20

<210> SEQ ID NO 1826
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1826
cacacttaga ccaaggagaa                                                  20

<210> SEQ ID NO 1827
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1827
gcacacttag accaaggaga                                                  20

<210> SEQ ID NO 1828
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1828
cagcacactt agaccaagga                                                  20

<210> SEQ ID NO 1829
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1829
gcagcacact tagaccaagg                                                  20

<210> SEQ ID NO 1830
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1830
atgcagcaca cttagaccaa                                                  20

<210> SEQ ID NO 1831
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1831
catgcagcac acttagacca                                                  20

<210> SEQ ID NO 1832
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1832
tccatgcagc acacttagac                                                  20
```

```
<210> SEQ ID NO 1833
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1833
ctccatgcag cacacttaga                                                   20

<210> SEQ ID NO 1834
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1834
cactccatgc agcacactta                                                   20

<210> SEQ ID NO 1835
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1835
tcactccatg cagcacactt                                                   20

<210> SEQ ID NO 1836
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1836
gctcactcca tgcagcacac                                                   20

<210> SEQ ID NO 1837
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1837
ccgctgcagg cttctactgc                                                   20

<210> SEQ ID NO 1838
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1838
gccgctgcag gcttctactg                                                   20

<210> SEQ ID NO 1839
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1839
gtgccgctgc aggcttctac                                           20

<210> SEQ ID NO 1840
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1840
tgtgccgctg caggcttcta                                           20

<210> SEQ ID NO 1841
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1841
tttgtgccgc tgcaggcttc                                           20

<210> SEQ ID NO 1842
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1842
atttgtgccg ctgcaggctt                                           20

<210> SEQ ID NO 1843
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1843
gcatttgtgc cgctgcaggc                                           20

<210> SEQ ID NO 1844
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1844
tgcatttgtg ccgctgcagg                                           20

<210> SEQ ID NO 1845
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1845
ggtgcatttg tgccgctgca                                           20

<210> SEQ ID NO 1846

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1846
aggtgcattt gtgccgctgc                                              20

<210> SEQ ID NO 1847
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1847
ggaggtgcat ttgtgccgct                                              20

<210> SEQ ID NO 1848
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1848
gggaggtgca tttgtgccgc                                              20

<210> SEQ ID NO 1849
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1849
ctgggaggtg catttgtgcc                                              20

<210> SEQ ID NO 1850
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1850
actgggaggt gcatttgtgc                                              20

<210> SEQ ID NO 1851
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1851
aaactgggag gtgcatttgt                                              20

<210> SEQ ID NO 1852
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1852
```
caaactggga ggtgcatttg 20

<210> SEQ ID NO 1853
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1853
agcaaactgg gaggtgcatt 20

<210> SEQ ID NO 1854
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1854
cagcaaactg ggaggtgcat 20

<210> SEQ ID NO 1855
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1855
cccagcaaac tgggaggtgc 20

<210> SEQ ID NO 1856
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1856
acccagcaaa ctgggaggtg 20

<210> SEQ ID NO 1857
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1857
aataaaccca gcaaactggg 20

<210> SEQ ID NO 1858
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1858
aaataaaccc agcaaactgg 20

<210> SEQ ID NO 1859
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1859
taaaataaac ccagcaaact                                                  20

<210> SEQ ID NO 1860
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1860
ctaaaataaa cccagcaaac                                                  20

<210> SEQ ID NO 1861
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1861
ctctaaaata aacccagcaa                                                  20

<210> SEQ ID NO 1862
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1862
tctctaaaat aaacccagca                                                  20

<210> SEQ ID NO 1863
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1863
attctctaaa ataaacccag                                                  20

<210> SEQ ID NO 1864
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1864
cattctctaa aataaaccca                                                  20

<210> SEQ ID NO 1865
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1865
cccattctct aaaataaacc                                                  20
```

<210> SEQ ID NO 1866
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1866
ccccattctc taaaataaac                                          20

<210> SEQ ID NO 1867
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1867
acccccattc tctaaaataa                                          20

<210> SEQ ID NO 1868
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1868 caccccatt ctctaaaata                                           20

<210> SEQ ID NO 1869
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1869 cccacccca ttctctaaaa                                           20

<210> SEQ ID NO 1870
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1870
ccccaccccc attctctaaa                                          20

<210> SEQ ID NO 1871
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1871
ctccccaccc ccattctcta                                          20

<210> SEQ ID NO 1872
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1872
tgcctcccca cccccattct                                                   20

<210> SEQ ID NO 1873
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1873
ttgcctcccc acccccattc                                                   20

<210> SEQ ID NO 1874
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1874
tcttgcctcc ccacccccat                                                   20

<210> SEQ ID NO 1875
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1875
ggttcttgcc tccccacccc                                                   20

<210> SEQ ID NO 1876
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1876
tggttcttgc ctccccaccc                                                   20

<210> SEQ ID NO 1877
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1877
actggttctt gcctccccac                                                   20

<210> SEQ ID NO 1878
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1878
cactggttct tgcctcccca                                                   20

```
<210> SEQ ID NO 1879
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1879
aacactggtt cttgcctccc                                                   20

<210> SEQ ID NO 1880
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1880
aaacactggt tcttgcctcc                                                   20

<210> SEQ ID NO 1881
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1881
ctaaacactg gttcttgcct                                                   20

<210> SEQ ID NO 1882
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1882
gctaaacact ggttcttgcc                                                   20

<210> SEQ ID NO 1883
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1883
gcgctaaaca ctggttcttg                                                   20

<210> SEQ ID NO 1884
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1884
cgcgctaaac actggttctt                                                   20

<210> SEQ ID NO 1885
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1885
cccgcgctaa acactggttc            20

<210> SEQ ID NO 1886
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1886
tcccgcgcta aacactggtt            20

<210> SEQ ID NO 1887
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1887
agtcccgcgc taaacactgg            20

<210> SEQ ID NO 1888
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1888
tagtcccgcg ctaaacactg            20

<210> SEQ ID NO 1889
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1889
agtagtcccg cgctaaacac            20

<210> SEQ ID NO 1890
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1890
cagtagtccc gcgctaaaca            20

<210> SEQ ID NO 1891
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1891
aacagtagtc ccgcgctaaa            20

<210> SEQ ID NO 1892
<211> LENGTH: 20

-continued

```
<212> TYPE: DNA
<213> ORGANISM: Artificial sequence
<220> FEATURE:
<223> OTHER INFORMATION: Synthetic oligonucleotide

<400> SEQUENCE: 1892
gaacagtagt cccgcgctaa                                                20

<210> SEQ ID NO 1893
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1893
tggaacagta gtcccgcgct                                                20

<210> SEQ ID NO 1894
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1894
ttggaacagt agtcccgcgc                                                20

<210> SEQ ID NO 1895
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1895
ttttggaaca gtagtcccgc                                                20

<210> SEQ ID NO 1896
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1896
tttttggaac agtagtcccg                                                20

<210> SEQ ID NO 1897
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1897
tctttttgga acagtagtcc                                                20

<210> SEQ ID NO 1898
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1898
``` ttcttttttgg aacagtagtc                                              20

<210> SEQ ID NO 1899
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1899 aattctttttt ggaacagtag                                              20

<210> SEQ ID NO 1900
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1900
gaattctttt tggaacagta                                               20

<210> SEQ ID NO 1901
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1901
tggaattctt tttggaacag                                               20

<210> SEQ ID NO 1902
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1902
ttggaattct ttttggaaca                                               20

<210> SEQ ID NO 1903
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1903
ggttggaatt cttttttggaa                                              20

<210> SEQ ID NO 1904
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1904
cggttggaat tcttttttgga                                              20

<210> SEQ ID NO 1905
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1905
gtcggttgga attcttttg                                            20

<210> SEQ ID NO 1906
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1906
ggtcggttgg aattctttt                                            20

<210> SEQ ID NO 1907
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1907
ctggtcggtt ggaattcttt                                           20

<210> SEQ ID NO 1908
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1908
gctggtcggt tggaattctt                                           20

<210> SEQ ID NO 1909
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1909
aagctggtcg gttggaattc                                           20

<210> SEQ ID NO 1910
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1910
caagctggtc ggttggaatt                                           20

<210> SEQ ID NO 1911
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1911
aacaagctgg tcggttggaa                                           20
```

<210> SEQ ID NO 1912
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1912
aaacaagctg gtcggttgga                                              20

<210> SEQ ID NO 1913
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1913
acaaacaagc tggtcggttg                                              20

<210> SEQ ID NO 1914
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1914
cacaaacaag ctggtcggtt                                              20

<210> SEQ ID NO 1915
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1915
ttcacaaaca agctggtcgg                                              20

<210> SEQ ID NO 1916
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1916
tttcacaaac aagctggtcg                                              20

<210> SEQ ID NO 1917
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1917
tgtttcacaa acaagctggt                                              20

<210> SEQ ID NO 1918
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 1918
ttgtttcaca aacaagctgg                                              20

<210> SEQ ID NO 1919
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1919
ttttgtttca caacaagct                                               20

<210> SEQ ID NO 1920
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1920
tttttgtttc acaaacaagc                                              20

<210> SEQ ID NO 1921
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1921
aacttgaaaa gggaacactt                                              20

<210> SEQ ID NO 1922
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1922
tcaacttgaa aagggaacac                                              20

<210> SEQ ID NO 1923
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1923
ctcaacttga aagggaaca                                               20

<210> SEQ ID NO 1924
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1924
ttctcaactt gaaagggaa                                               20

<210> SEQ ID NO 1925
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1925
gttctcaact tgaaaaggga                                              20

<210> SEQ ID NO 1926
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1926
ttgttctcaa cttgaaaagg                                              20

<210> SEQ ID NO 1927
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1927
tttgttctca acttgaaaag                                              20

<210> SEQ ID NO 1928
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1928
tttttgttct caacttgaaa                                              20

<210> SEQ ID NO 1929
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1929
atttttgttc tcaacttgaa                                              20

<210> SEQ ID NO 1930
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1930 caattttgt tctcaacttg                                               20

<210> SEQ ID NO 1931
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1931
```
ccaatttttg ttctcaactt                                              20

<210> SEQ ID NO 1932
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1932 acccaattttt tgttctcaac                                             20

<210> SEQ ID NO 1933
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1933
aacccaattt ttgttctcaa                                              20

<210> SEQ ID NO 1934
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1934
taaaacccaa tttttgttct                                              20

<210> SEQ ID NO 1935
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1935
tttaaaaccc aattttttgtt                                             20

<210> SEQ ID NO 1936
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1936
aatgcaaaaa tgtatacttt                                              20

<210> SEQ ID NO 1937
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1937
gcaatgcaaa aatgtatact                                              20

<210> SEQ ID NO 1938
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1938
aaggcaatgc aaaaatgtat                                           20

<210> SEQ ID NO 1939
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1939
gaaggcaatg caaaaatgta                                           20

<210> SEQ ID NO 1940
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1940
ccgaaggcaa tgcaaaaatg                                           20

<210> SEQ ID NO 1941
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1941
catacccttc tgctgta                                              17

<210> SEQ ID NO 1942
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1942
ccgcataccc ttctgct                                              17

<210> SEQ ID NO 1943
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1943
tcgcttccgc ataccct                                              17

<210> SEQ ID NO 1944
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1944
tgctcgcttc cgcatac                                              17
```

<210> SEQ ID NO 1945
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1945
ctcattgtgg atgacga                                              17

<210> SEQ ID NO 1946
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1946
actctcattg tggatga                                              17

<210> SEQ ID NO 1947
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1947
cagctgctca caggtac                                              17

<210> SEQ ID NO 1948
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1948
agcgactagc accagct                                              17

<210> SEQ ID NO 1949
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1949
cacagcctgc atgaacc                                              17

<210> SEQ ID NO 1950
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1950
tcctgtcaca gcctgca                                              17

<210> SEQ ID NO 1951
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1951
ccatcctgtc acagcct                                                          17

<210> SEQ ID NO 1952
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1952
agtgctggaa ggtgccc                                                          17

<210> SEQ ID NO 1953
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1953
gctggatcag cagcagg                                                          17

<210> SEQ ID NO 1954
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1954
ctgatgcggt cattgct                                                          17

<210> SEQ ID NO 1955
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1955
ggctctctct catccgc                                                          17

<210> SEQ ID NO 1956
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1956
gtgggctctc tctcatc                                                          17

<210> SEQ ID NO 1957
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1957
ccttgccagg cactgtg                                                          17

```
<210> SEQ ID NO 1958
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1958
gccttgccag gcactgt                                                  17

<210> SEQ ID NO 1959
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1959
aggccttgcc aggcact                                                  17

<210> SEQ ID NO 1960
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1960
gaggccttgc caggcac                                                  17

<210> SEQ ID NO 1961
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1961
gctgctggcc tttgcct                                                  17

<210> SEQ ID NO 1962
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1962
tatctgctgc tggcctt                                                  17

<210> SEQ ID NO 1963
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1963
ttatctgctg ctggcct                                                  17

<210> SEQ ID NO 1964
<211> LENGTH: 17
<212> TYPE: DNA
<213> ORGANISM: Artificial sequence
<220> FEATURE:
<223> OTHER INFORMATION: Synthetic oligonucleotide
```

<400> SEQUENCE: 1964
tgttatctgc tgctggc        17

<210> SEQ ID NO 1965
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1965
ttgttatctg ctgctgg        17

<210> SEQ ID NO 1966
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1966
gttgttatct gctgctg        17

<210> SEQ ID NO 1967
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1967
atcgctgatt tgtccgg        17

<210> SEQ ID NO 1968
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1968
catcgctgat ttgtccg        17

<210> SEQ ID NO 1969
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1969
acatcgctga tttgtcc        17

<210> SEQ ID NO 1970
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1970
cacatcgctg atttgtc        17

<210> SEQ ID NO 1971
<211> LENGTH: 17

```
<212> TYPE: DNA
<213> ORGANISM: Artificial sequence
<220> FEATURE:
<223> OTHER INFORMATION: Synthetic oligonucleotide

<400> SEQUENCE: 1971
acacatcgct gatttgt                                                    17

<210> SEQ ID NO 1972
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1972
tgacacatcg ctgattt                                                    17

<210> SEQ ID NO 1973
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1973
gtgacacatc gctgatt                                                    17

<210> SEQ ID NO 1974
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1974
cattagaaga aaaggtg                                                    17

<210> SEQ ID NO 1975
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1975
tcattagaag aaaaggt                                                    17

<210> SEQ ID NO 1976
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1976
cgactcatta gaagaaa                                                    17

<210> SEQ ID NO 1977
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1977
```

-continued gctcaaagtc gactcat                                              17

<210> SEQ ID NO 1978
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1978
agctcaaagt cgactca                                              17

<210> SEQ ID NO 1979
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1979
cagctcaaag tcgactc                                              17

<210> SEQ ID NO 1980
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1980
ccagctcaaa gtcgact                                              17

<210> SEQ ID NO 1981
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1981
tccagctcaa agtcgac                                              17

<210> SEQ ID NO 1982
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1982
ctttccagct caaagtc                                              17

<210> SEQ ID NO 1983
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1983
agaaacggct gctttcc                                              17

<210> SEQ ID NO 1984
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 1984
accaaggaga aacggct                                                   17

<210> SEQ ID NO 1985
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1985
gcatttgtgc cgctgca                                                   17

<210> SEQ ID NO 1986
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1986
ggtgcatttg tgccgct                                                   17

<210> SEQ ID NO 1987
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1987
agcaaactgg gaggtgc                                                   17

<210> SEQ ID NO 1988
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1988
ggttcttgcc tccccac                                                   17

<210> SEQ ID NO 1989
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1989
ctaaacactg gttcttg                                                   17

<210> SEQ ID NO 1990
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1990
gcgctaaaca ctggttc                                                   17
```

<210> SEQ ID NO 1991
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1991
aacagtagtc ccgcgct                                                  17

<210> SEQ ID NO 1992
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1992
ggttggaatt ctttttg                                                  17

<210> SEQ ID NO 1993
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1993
ctggtcggtt ggaattc                                                  17

<210> SEQ ID NO 1994
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1994
acaaacaagc tggtcgg                                                  17

<210> SEQ ID NO 1995
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1995
ttcacaaaca agctggt                                                  17

<210> SEQ ID NO 1996
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1996
acttgaaaag ggaacac                                                  17

<210> SEQ ID NO 1997
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1997
tcaacttgaa aagggaa 17

<210> SEQ ID NO 1998
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1998
ttctcaactt gaaaagg 17

<210> SEQ ID NO 1999
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1999
caatttttgt tctcaac 17

<210> SEQ ID NO 2000
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2000
acccaatttt tgttctc 17

<210> SEQ ID NO 2001
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2001
atctgctgct ggccttt 17

<210> SEQ ID NO 2002
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2002
gttatctgct gctggcc 17

<210> SEQ ID NO 2003
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2003
tcgctgattt gtccggg 17

<210> SEQ ID NO 2004

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2004
acagtagtcc cgcgcta                                              17

<210> SEQ ID NO 2005
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2005
gaacagtagt cccgcgc                                              17

<210> SEQ ID NO 2006
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2006
gttggaattc tttttgg                                              17

<210> SEQ ID NO 2007
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2007
cggttggaat tctttttt                                             17

<210> SEQ ID NO 2008
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2008
tggtcggttg gaattct                                              17

<210> SEQ ID NO 2009
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2009
gctggtcggt tggaatt                                              17

<210> SEQ ID NO 2010
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2010
```
caaacaagct ggtcggt 17

<210> SEQ ID NO 2011
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2011
cacaaacaag ctggtcg 17

<210> SEQ ID NO 2012
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2012
ttatctgctg ctggcctt 18

<210> SEQ ID NO 2013
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2013
ttgttatctg ctgctggc 18

<210> SEQ ID NO 2014
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2014
gttgttatct gctgctgg 18

<210> SEQ ID NO 2015
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2015
atcgctgatt tgtccggg 18

<210> SEQ ID NO 2016
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2016
catcgctgat ttgtccgg 18

<210> SEQ ID NO 2017
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 2017
acatcgctga tttgtccg                                                   18

<210> SEQ ID NO 2018
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2018
cacatcgctg atttgtcc                                                   18

<210> SEQ ID NO 2019
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2019
acacatcgct gatttgtc                                                   18

<210> SEQ ID NO 2020
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2020
cagctcaaag tcgactca                                                   18

<210> SEQ ID NO 2021
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2021
gaacagtagt cccgcgct                                                   18

<210> SEQ ID NO 2022
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2022
cggttggaat tctttttg                                                   18

<210> SEQ ID NO 2023
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2023
gctggtcggt tggaattc                                                   18
```

<210> SEQ ID NO 2024
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2024
acaaacaagc tggtcggt                                                 18

<210> SEQ ID NO 2025
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2025
cacaaacaag ctggtcgg                                                 18

<210> SEQ ID NO 2026
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2026
ggttggaatt ctttttgg                                                 18

<210> SEQ ID NO 2027
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2027
ccagctcaaa gtcgactc                                                 18

<210> SEQ ID NO 2028
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2028
ggaacagtag tcccgcgc                                                 18

<210> SEQ ID NO 2029
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2029
tatctgctgc tggccttt                                                 18

<210> SEQ ID NO 2030
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 2030
tgttatctgc tgctggcc                                                 18

<210> SEQ ID NO 2031
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2031
tcggttggaa ttcttttt                                                 18

<210> SEQ ID NO 2032
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2032
ttatctgctg ctggccttt                                                19

<210> SEQ ID NO 2033
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2033
ttgttatctg ctgctggcc                                                19

<210> SEQ ID NO 2034
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2034
gttgttatct gctgctggc                                                19

<210> SEQ ID NO 2035
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2035
catcgctgat ttgtccggg                                                19

<210> SEQ ID NO 2036
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2036
acatcgctga tttgtccgg                                                19

```
<210> SEQ ID NO 2037
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2037
cacatcgctg atttgtccg                                               19

<210> SEQ ID NO 2038
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2038
acacatcgct gatttgtcc                                               19

<210> SEQ ID NO 2039
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2039
cagctcaaag tcgactcat                                               19

<210> SEQ ID NO 2040
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2040
aacagtagtc ccgcgctaa                                               19

<210> SEQ ID NO 2041
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2041
gaacagtagt cccgcgcta                                               19
```

```
<210> SEQ ID NO 2042
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2042
cggttggaat tcttttttgg                                              19

<210> SEQ ID NO 2043
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2043
gctggtcggt tggaattct                                               19

<210> SEQ ID NO 2044
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2044
cacaaacaag ctggtcggt                                               19

<210> SEQ ID NO 2045
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2045
tcacaaacaa gctggtcgg                                               19

<210> SEQ ID NO 2046
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2046
tatctgctgc tggcctttg                                               19
```

```
<210> SEQ ID NO 2047
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2047
tgttatctgc tgctggcct                                                19

<210> SEQ ID NO 2048
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2048
agctcaaagt cgactcatt                                                19

<210> SEQ ID NO 2049
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2049
ggttggaatt cttttttgga                                               19

<210> SEQ ID NO 2050
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2050
acaaacaagc tggtcggtt                                                19

<210> SEQ ID NO 2051
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2051
ccagctcaaa gtcgactca                                                19
```